(12) United States Patent
Xie et al.

(10) Patent No.: US 12,209,085 B2
(45) Date of Patent: Jan. 28, 2025

(54) RET INHIBITORS, PHARMACEUTICAL COMPOSITIONS AND USES THEREOF

(71) Applicant: SUNSHINE LAKE PHARMA CO., LTD., Guangdong (CN)

(72) Inventors: Hongming Xie, Dongguan (CN); Ming Luo, Dongguan (CN); Jianli Wu, Dongguan (CN); Yingjun Zhang, Dongguan (CN); Yingchao Cheng, Dongguan (CN)

(73) Assignee: SUNSHINE LAKE PHARMA CO., LTD., Guangdong (CN)

( * ) Notice: Subject to any disclaimer, the term of this patent is extended or adjusted under 35 U.S.C. 154(b) by 881 days.

(21) Appl. No.: 17/288,328

(22) PCT Filed: Dec. 6, 2019

(86) PCT No.: PCT/CN2019/123668
§ 371 (c)(1),
(2) Date: Apr. 23, 2021

(87) PCT Pub. No.: WO2020/114487
PCT Pub. Date: Jun. 11, 2020

(65) Prior Publication Data
US 2022/0135557 A1    May 5, 2022

(30) Foreign Application Priority Data

| Dec. 7, 2018 | (CN) | 201811495053.X |
|---|---|---|
| Mar. 28, 2019 | (CN) | 201910245827.1 |
| Mar. 29, 2019 | (CN) | 201910248377.1 |

(51) Int. Cl.

| C07D 471/04 | (2006.01) |
|---|---|
| C07D 519/00 | (2006.01) |
| A61K 31/444 | (2006.01) |
| A61K 31/4545 | (2006.01) |
| A61K 31/496 | (2006.01) |
| A61K 31/497 | (2006.01) |
| A61K 31/499 | (2006.01) |
| A61K 31/4995 | (2006.01) |
| A61K 31/506 | (2006.01) |
| A61K 31/519 | (2006.01) |
| A61K 31/541 | (2006.01) |
| A61P 1/00 | (2006.01) |
| A61P 29/00 | (2006.01) |
| A61P 35/00 | (2006.01) |
| A61P 37/00 | (2006.01) |
| C07D 471/10 | (2006.01) |
| C07D 487/04 | (2006.01) |
| C07D 487/10 | (2006.01) |

(52) U.S. Cl.
CPC ......... *C07D 471/04* (2013.01); *C07D 519/00* (2013.01)

(58) Field of Classification Search
CPC .. C07D 471/04; C07D 519/00; C07D 471/10; C07D 487/04; C07D 487/10; A61P 1/00; A61P 29/00; A61P 35/00; A61P 37/00; A61K 31/496; A61K 31/444; A61K 31/4545; A61K 31/497; A61K 31/499; A61K 31/4995; A61K 31/506; A61K 31/519; A61K 31/541
See application file for complete search history.

(56) References Cited

U.S. PATENT DOCUMENTS

| 10,023,570 B2 | 7/2018 | Andrews et al. |
|---|---|---|
| 10,112,942 B2 | 10/2018 | Andrews et al. |
| 10,144,734 B2 | 12/2018 | Andrews et al. |
| 10,174,027 B2 | 1/2019 | Andrews et al. |

(Continued)

FOREIGN PATENT DOCUMENTS

| WO | 2012/146657 A1 | 11/2012 |
|---|---|---|
| WO | 2012/171337 A1 | 12/2012 |

OTHER PUBLICATIONS

Fura A. Role of pharmacologically active metabolites in drug discovery and development. Drug Discov Today. Feb. 2006;11(3-4):133-42. doi: 10.1016/S1359-6446(05)03681-0. PMID: 16533711. (Year: 2006).*

(Continued)

*Primary Examiner* — Bruck Kifle
*Assistant Examiner* — Kevin S Martin
(74) *Attorney, Agent, or Firm* — Oliff PLC

(57) ABSTRACT

A RET inhibitor, a pharmaceutical composition thereof and uses thereof including a compound having Formula (I) or a stereoisomer, a geometric isomer, a tautomer, an N-oxide, a solvate, a metabolite, a pharmaceutically acceptable salt or a prodrug thereof. Furthermore, a pharmaceutical composition including the compound, and uses of the compound and pharmaceutical composition thereof in the manufacture of a medicament for treatment and prevention of RET-related diseases and conditions, including cancer, irritable bowel syndrome, and/or pain associated with irritable bowel syndrome.

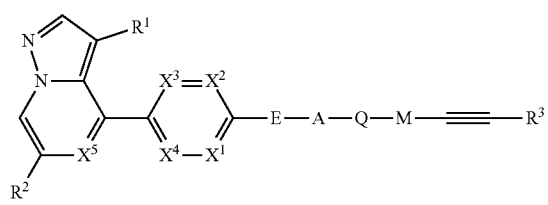

(I)

19 Claims, No Drawings

(56) References Cited

U.S. PATENT DOCUMENTS

| | | | |
|---|---|---|---|
| 10,555,944 | B2 | 2/2020 | Andrews et al. |
| 10,881,652 | B2 | 1/2021 | Andrews et al. |
| 2020/0055860 | A1 | 2/2020 | Andrews et al. |

OTHER PUBLICATIONS

Bundgaard, Design of Prodrugs, 1985, CH 1 (Year: 1985).*
Di Martino RMC, Maxwell BD, Pirali T. Deuterium in drug discovery: progress, opportunities and challenges. Nat Rev Drug Discov. Jul. 2023;22(7):562-584. doi: 10.1038/s41573-023-00703-8. Epub Jun. 5, 2023. PMID: 37277503; PMCID: PMC10241557. (Year: 2023).*
Addeo A, et al. RET aberrant cancers and RET inhibitor therapies: Current state-of-the-art and future perspectives. Pharmacol Ther. Feb. 2023;242:108344. doi: 10.1016/j.pharmthera.2023.108344. Epub Jan. 9, 2023. PMID: 36632846; PMCID: PMC10141525. (Year: 2023).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
Cecil Textbook of Medicine, 1997, 20th Ed, Oncology (Year: 1997).*
Eidam et al., Discovery of a First-in-Class Gut-Restricted RET Kinase Inhibitor as a Clinical Candidate for the Treatment of IBS. ACS Med Chem Lett. May 24, 2018;9(7):623-628. doi: 10.1021/acsmedchemlett.8b00035. PMID: 30034590; PMCID: PMC6047170. (Year: 2018).*
Russell et al., Exploring the Potential of RET Kinase Inhibition for Irritable Bowel Syndrome: A Preclinical Investigation in Rodent Models of Colonic Hypersensitivity. J Pharmacol Exp Ther. Feb. 2019;368(2):299-307. doi: 10.1124/jpet.118.252973. Epub Nov. 9, 2018. PMID: 30413627; PMCID: PMC6346376. (Year: 2018).*
Merriam-Webster, definition of Prevent, 2024, https://www.merriam-webster.com/dictionary/prevent (Year: 2024).*
Mar. 12, 2020 Search Report issued in International Patent Application No. PCT/CN2019/123668.
Mar. 12, 2020 Written Opinion of the International Searching Authority issued in International Patent Application No. PCT/CN2019/123668.

* cited by examiner

RET INHIBITORS, PHARMACEUTICAL COMPOSITIONS AND USES THEREOF

CROSS-REFERENCE TO RELATED APPLICATIONS

This application claims priorities and benefits of Chinese Patent Application Serial No 201811495053.X, filed on Dec. 7, 2018; Chinese Patent Application Serial No 201910245827.1, filed on Mar. 28, 2019; and Chinese Patent Application Serial No 201910248377.1, filed on Mar. 29, 2019, all of which are hereby incorporated by reference in their entireties.

FIELD OF THE INVENTION

The invention belongs to the field of medicine, specifically, the present invention relates to novel compounds which exhibit inhibition for re-aranged during transfection (RET) kinase, pharmaceutical compositions comprising the compounds and uses of the compounds or pharmaceutical compositions thereof in the preparation of a medicament. The medicament is particularly useful for the treatment and prevention of RET-related diseases and conditions, including cancer, irritable bowel syndrome and/or pain associated with irritable bowel syndrome.

BACKGROUND ART

Re-arranged during transfection (RET) is one of the receptor-type tyrosine kinases belonging to the cadherin superfamily, which activates multiple downstream pathways involved in cell proliferation and survival.

The results of abnormalities in RET genes (point mutations, chromosomal translocations, chromosomal inversions, gene amplification) have been reported to be involved in canceration. RET fusion proteins are associated with several cancers, including papillary thyroid cancer and non-small cell lung cancer. Identification of RET fusion proteins as a driver of certain cancers has driven the use of multi-kinase inhibitors with RET inhibitory activity to treat patients whose tumors express RET fusion proteins. It has been reported that multi-kinase inhibitors such as Sorafenib, sunitinib, vandetanib and punatinib exhibit cell proliferation inhibition in KIF5B-RET-expressing cell lines (*J Clin Oncol* 30, 2012, suppl; Abstract no: 7510). In addition, it has been reported that the multi-kinase inhibitor cabozantini showed partial efficacy in two patients with non-small cell lung cancer positive for RET fusion gene (Cancer Discov, 3(6), June 2013, p. 630-5). However, these drugs cannot always be administered at a level sufficient to inhibit RET due to toxicity caused by inhibition of targets other than RET. In addition, one of the biggest challenges in treating cancer is the ability of tumor cells to develop resistance to treatment. Reactivation of kinases via mutations is a common mechanism of resistance. When resistance develops, the patient's treatment options are usually very limited, and in most cases cancer progression is not inhibited. WO 2017011776 discloses a single-targeted RET kinase inhibitor that has a good prophylactic or therapeutic effect on RET-associated and RET mutation-associated cancer. There is still a need to further develop compounds that inhibit RET and its resistant mutants in response to cancers with abnormal RET genes.

SUMMARY OF THE INVENTION

The present invention provides a novel compound exhibiting inhibition of Re-arranged during transfection (RET) kinase, which has a good inhibitory effect on RET wild type and RET gene mutants, and has a good inhibition selectivity on RET wild type and RET gene mutants.

The excellent properties of certain parameters of the compounds of the present invention, such as half-life, clearance, selectivity, bioavailability, chemical stability, metabolic stability, membrane permeability, solubility, etc., can promote the reduction of side effects, the expansion of the treatment index or the improvement of tolerance.

In one aspect, the present invention provides a compound having Formula (I) or a stereoisomer, a geometric isomer, a tautomer, an N-oxide, a solvate, a metabolite, a pharmaceutically acceptable salt or a prodrug thereof,

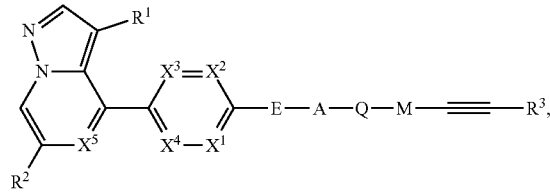

(I)

wherein, each of $X^1$, $X^2$, $X^3$, $X^4$ and $X^5$ is independently $CR^4$ or N, wherein 0, 1, or 2 of $X^1$, $X^2$, $X^3$ and $X^4$ are N;

E is a bond, —$NR^6$— or —O—;

A is Cyc or hetCyc, wherein each of Cyc and hetCyc is independently and optionally substituted by 1, 2, 3 or 4 substituents selected from F, Cl, Br, oxo, $NR^5R^6$, $R^5O$—, $R^5(C═O)NR^6$—, $NR^5R^6$ alkyl, $NR^5R^6(C═O)$ alkoxyalkyl, $NR^6R^7$ alkoxy, $NR^6R^7$ alkoxyalkyl, alkyl, haloalkyl, hydroxyalkyl, Cyc, hetCyc, hetCyc-alkyl, alkoxyalkyl, hetCyc-alkoxyalkyl, cycloalkylidene and heterocyclylidene;

Q is —(C═O)—, —O—, —(C═O)$NR^5$—, —(C═S)$NR^5$—, —S(═O)$_2$—, —S(═O)$_2NR^5$—, —$NR^5$(C═O)—, —$NR^5$(C═O)O—, —$NR^5$(C═O)$NR^5$—, —$NR^5$—, —(C═O)O— or a bond;

M is —(C═O)—, alkyl, alkenyl, alkynyl, alkylaryl, alkylheteroaryl, alkenylaryl, alkynylaryl, alkenylheteroaryl, alkynylheteroaryl, aryl, heteroaryl, Cyc, hetCyc, arylalkyl, heteroarylalkyl, Cyc-alkyl or hetCyc-alkyl, wherein each of alkyl, alkenyl, alkynyl, alkylaryl, alkylheteroaryl, alkenylaryl, alkynylaryl, alkenylheteroaryl, alkynylheteroaryl, aryl, heteroaryl, Cyc, hetCyc, arylalkyl, heteroarylalkyl, Cyc-alkyl and hetCyc-alkyl is independently and optionally substituted by 1, 2, 3 or 4 substituents selected from F, Cl, Br, OH, $CF_3$, $NR^5R^6$, oxo, alkoxy, cycloalkylidene, heterocyclylidene, hydroxyalkyl, alkyl, cycloalkyl and heterocyclyl;

$R^1$ is H, D, CN, F, Cl, Br, alkyl or cycloalkyl, wherein each of alkyl and cycloalkyl is independently and optionally substituted by 1, 2, 3 or 4 substituents selected from F, Cl, Br, CN, $NH_2$, OH and $NO_2$;

$R^2$ is a 5-membered heteroaryl group, wherein the 5-membered heteroaryl group can be independently and optionally substituted by 1, 2, 3 or 4 substituents selected from F, Cl, Br, alkyl, Cyc, hetCyc, arylalkyl, heteroarylalkyl and alkyl hetCyc; wherein each of alkyl, Cyc, hetCyc, arylalkyl and alkyl hetCyc can be further independently and optionally substituted by 1, 2, 3 or 4 substituents selected from F, Cl, Br, CN, $R^5O-$, $R^5(C=O)-$, $R^5O(C=O)-$, $NR^5R^6$, $NR^5R^6(C=O)-$, $R^5S(=O)_2-$, alkyl, Cyc, hetCyc and alkoxy;

$R^3$ is H, D, alkyl, alkynyl, Cyc, hetCyc, aryl, heteroaryl, Cyc-alkyl, hetCyc-alkyl, alkoxyalkyl, arylalkyl, heteroarylalkyl or aminoalkyl, wherein each of alkyl, alkynyl, Cyc, hetCyc, aryl, heteroaryl, Cyc-alkyl, hetCyc-alkyl, alkoxyalkyl, arylalkyl, heteroarylalkyl and aminoalkyl is independently and optionally substituted by 1, 2, 3 or 4 substituents selected from F, Cl, Br, $NR^5R^6$, $R^5O-$, $R^5O(C=O)-$, $R^5(C=O)-$, $NR^5R^6(C=O)NR^5-$, $R^5S(=O)_2-$, $NO_2$, CN, $CF_3$, alkyl and cycloalkyl;

$R^4$ is H, D, alkyl, F, Cl, Br or alkoxy, wherein each of alkyl and alkoxy is independently and optionally substituted by 1, 2, 3 or 4 substituents selected from F, Cl, Br, CN, $NH_2$, OH and $NO_2$;

$R^5$ is H, D, alkyl, Cyc, hetCyc, aryl, heteroaryl, arylalkyl, heteroarylalkyl, alkoxyalkyl, aryloxyalkyl, aminoalkyl, alkylaminoalkyl, dialkylaminoalkyl, Cyc-alkyl or hetCyc-alkyl, wherein each of alkyl, Cyc, hetCyc, aryl, heteroaryl, arylalkyl, heteroarylalkyl, alkoxyalkyl, aryloxyalkyl, aminoalkyl, alkylaminoalkyl, dialkylaminoalkyl, Cyc-alkyl and hetCyc-alkyl is independently and optionally substituted by 1, 2, 3 or 4 substituents selected from F, Cl, Br, OH, $NR^6R^7$, alkyl, alkylsulfonyl, alkoxy, aryl and heteroaryl;

$R^6$ is H or alkyl;

$R^7$ is alkyl, arylalkyl or heteroarylalkyl;

each Cyc is independently cycloalkyl, bridged carbocyclyl or spirocarbocyclyl; and each hetCyc is independently heterocyclyl, bridged heterocyclyl or spiroheterocyclyl.

In some embodiments, $R^2$ is one of the following sub-formulae:

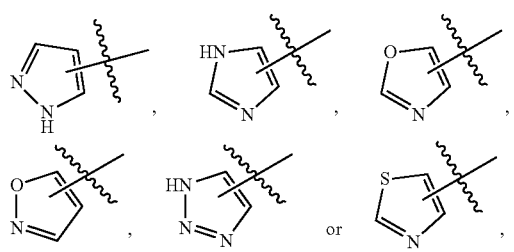

wherein each sub-formula of $R^2$ can be independently and optionally substituted by F, Cl, Br, $C_{1-6}$ alkyl, 3-12 membered Cyc, 3-12 membered hetCyc, $C_{6-12}$ aryl $C_{1-6}$ alkyl, (5-10 membered heteroaryl)-$C_{1-6}$ alkyl and $C_{1-6}$ alkyl-(3-12 membered hetCyc); wherein each of $C_{1-6}$ alkyl, 3-12 membered Cyc, 3-12 membered hetCyc, $C_{6-12}$ aryl $C_{1-6}$ alkyl, (5-10 membered heteroaryl)-$C_{1-6}$ alkyl and $C_{1-6}$ alkyl-(3-12 membered hetCyc) can be further independently and optionally substituted by 1, 2, 3 or 4 substituents selected from F, Cl, Br, CN, $R^5O-$, $R^5(C=O)-$, $R^5O(C=O)-$, $NR^5R^6$, $NR^5R^6(C=O)-$, $R^5S(=O)_2-$, $C_{1-6}$ alkyl, 3-12 membered Cyc, 3-12 membered hetCyc and $C_{1-6}$ alkoxy.

In some embodiments, $R^2$ is one of the following sub-formulae:

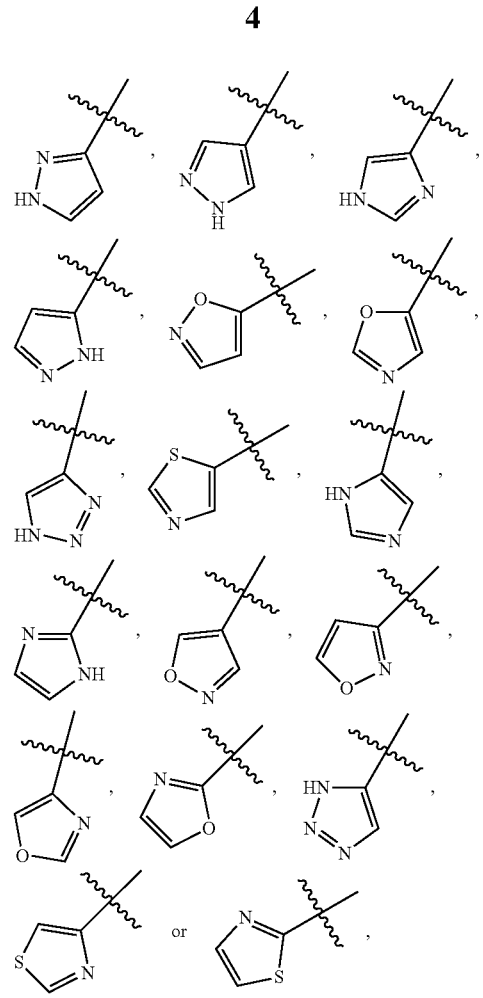

wherein each sub-formula of $R^2$ can be independently and optionally substituted by F, Cl, Br, $C_{1-4}$ alkyl, 3-10 membered Cyc, 3-10 membered hetCyc, phenyl $C_{1-4}$ alkyl, (5-10 membered heteroaryl)-$C_{1-4}$ alkyl and $C_{1-4}$ alkyl-(3-10 membered hetCyc); wherein each of $C_{1-4}$ alkyl, 3-10 membered Cyc, 3-10 membered hetCyc, phenyl $C_{1-4}$ alkyl, (5-10 membered heteroaryl)-$C_{1-4}$ alkyl and $C_{1-4}$ alkyl-(3-10 membered hetCyc) can be further independently and optionally substituted by 1, 2, 3 or 4 substituents selected from F, Cl, Br, CN, $R^5O-$, $R^5(C=O)-$, $R^5O(C=O)-$, $NR^5R^6$, $NR^5R^6(C=O)-$, $R^5S(=O)_2-$, $C_{1-4}$ alkyl, 3-10 membered Cyc, 3-10 membered hetCyc and $C_{1-4}$ alkoxy.

In some embodiments, $R^2$ is one of the following sub-formula:

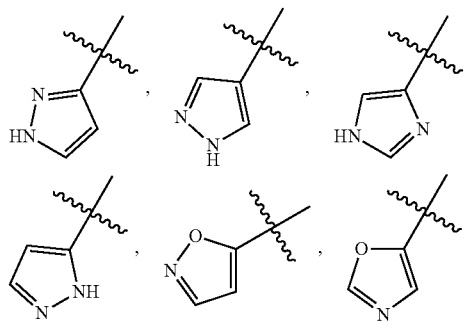

-continued

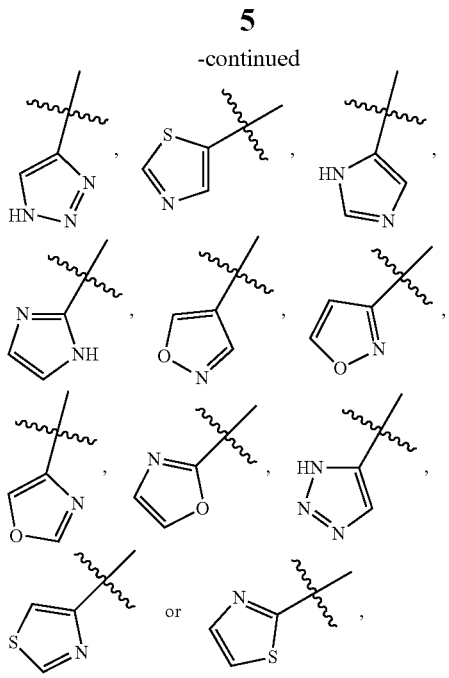

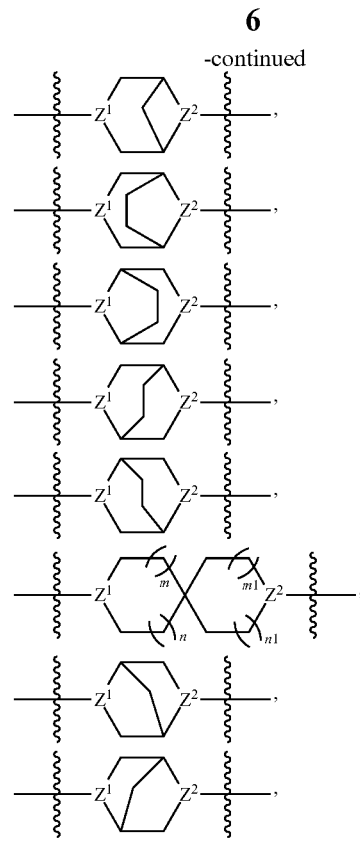

wherein each substructure of R[2] can be independently and optionally substituted by 1, 2, 3 or 4 substituents selected from F, Cl, Br, methyl, ethyl, n-propyl, isopropyl trifluoromethyl, difluoromethyl, 2-methylpropyl, 2-hydroxypropyl, benzyl, cyclopropyl, tert-butoxy carbonylazetidinyl, isopropylazetidinyl, 2-hydroxymethylpropyl, methoxymethyl, methoxyethyl, ethoxymethyl, piperidinyl, methoxybenzyl, isopropylsulfonylethyl, isopropylsulfonylmethyl, tetrahydropyranyl, aminocarbonylethyl, dimethylaminocarbonylethyl, 2-methoxypropyl, ethoxymethylpiperidinyl.

In some embodiments, A is 3-12 membered Cyc or 3-12 membered hetCyc, wherein each of 3-12 membered Cyc and 3-12 membered hetCyc is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-12 membered Cyc, 3-12 membered hetCyc, 3-12 membered hetCyc-$C_{1-6}$ alkyl, $C_{1-6}$ alkoxy $C_{1-6}$ alkyl, 3-12 membered hetCyc-$C_{1-6}$ alkoxy $C_{1-6}$ alkyl, $C_{3-6}$ cycloalkylidene, 3-6 membered heterocyclidene.

In some embodiments, A is one of the following sub-formulae:

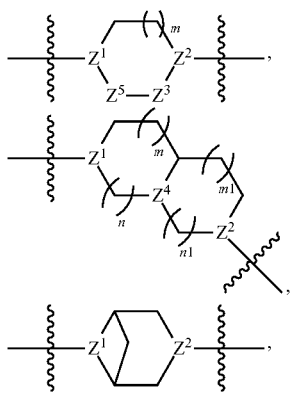

wherein each $Z^1$, $Z^2$ and $Z^4$ is independently CH or N;
each of $Z^3$, $Z^5$ is independently a bond, $CH_2$, O, S, NH, C=O, S=O or $S(=O)_2$;
each m is 0, 1, or 2;
each n, m1 and n1 is independently 0 or 1;
each sub-formula of A is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene, 3-6 membered heterocyclidene.

In some embodiments, each sub-formula of A is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-4}$ alkyl, $NR^5R^6(C=O)C_{1-4}$ alkoxy $C_{1-4}$ alkyl, $NR^6R^7C_{1-4}$ alkoxy, $NR^6R^7C_{1-4}$ alkoxy $C_{1-4}$ alkyl, $C_{1-4}$ alkyl, $C_{1-4}$ haloalkyl, $C_{1-4}$ hydroxyalkyl, 3-10 membered Cyc, 3-10 membered hetCyc, 3-10 membered hetCyc-$C_{1-4}$ alkyl, $C_{1-4}$ alkoxy $C_{1-4}$ alkyl, 3-10 membered hetCyc-$C_{1-4}$ alkoxy $C_{1-4}$ alkyl, $C_{3-6}$ cycloalkylidene, 3-6 membered heterocyclidene.

In some embodiments, A is one of the following sub-formulae:

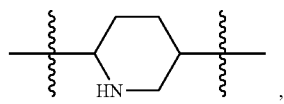

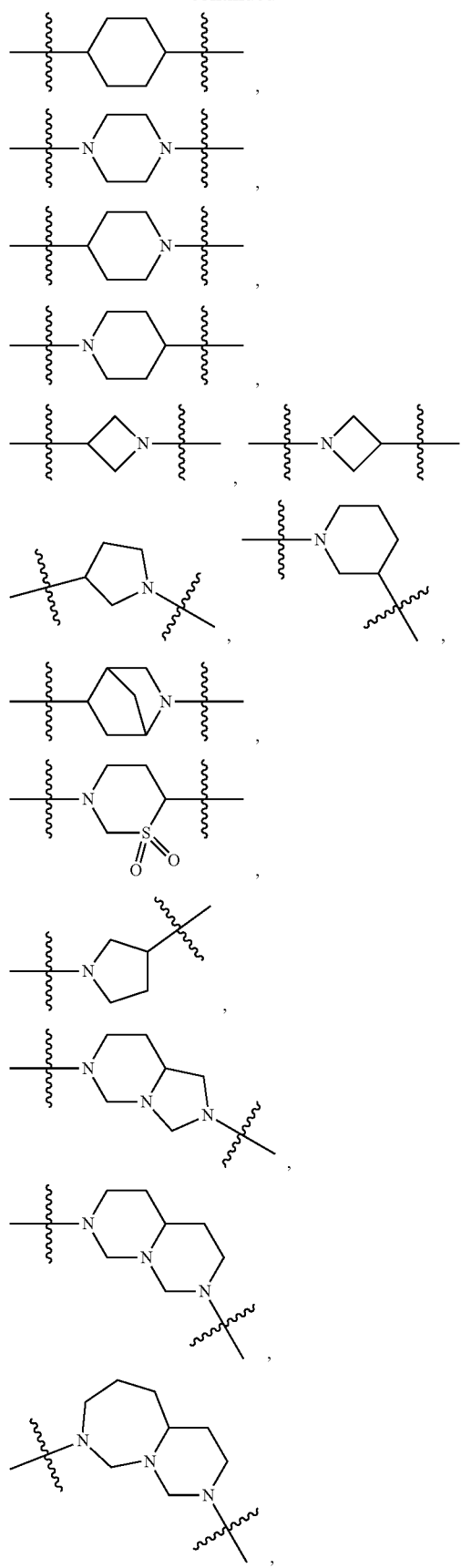
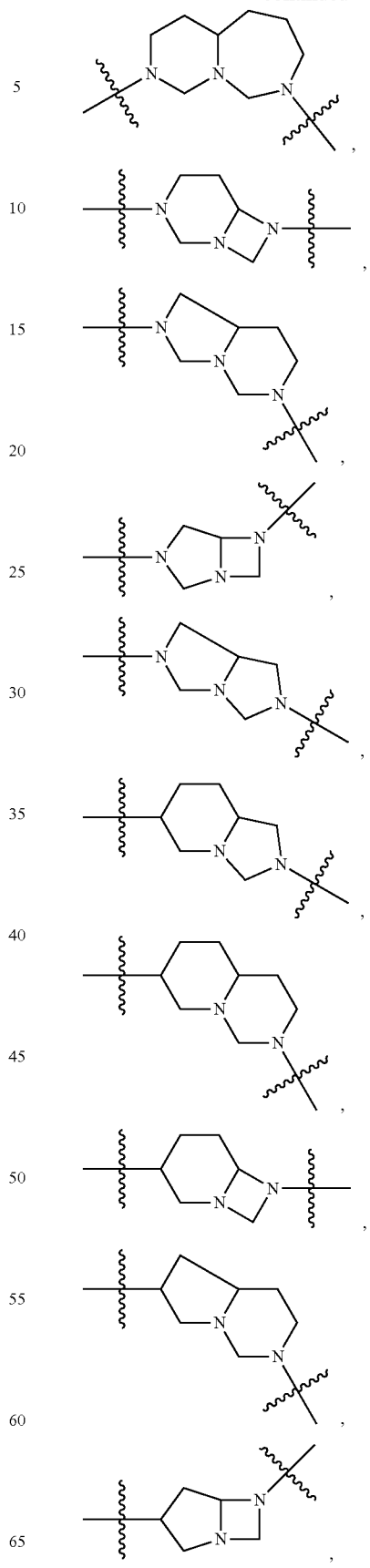

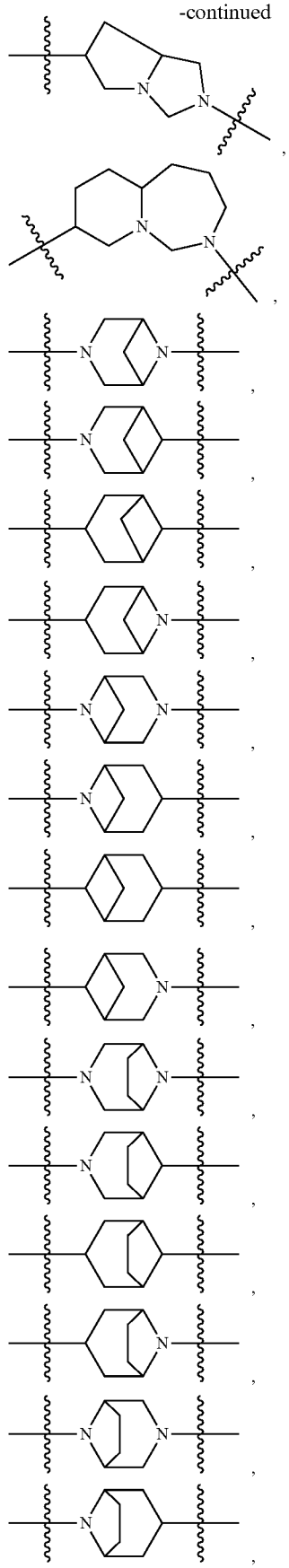
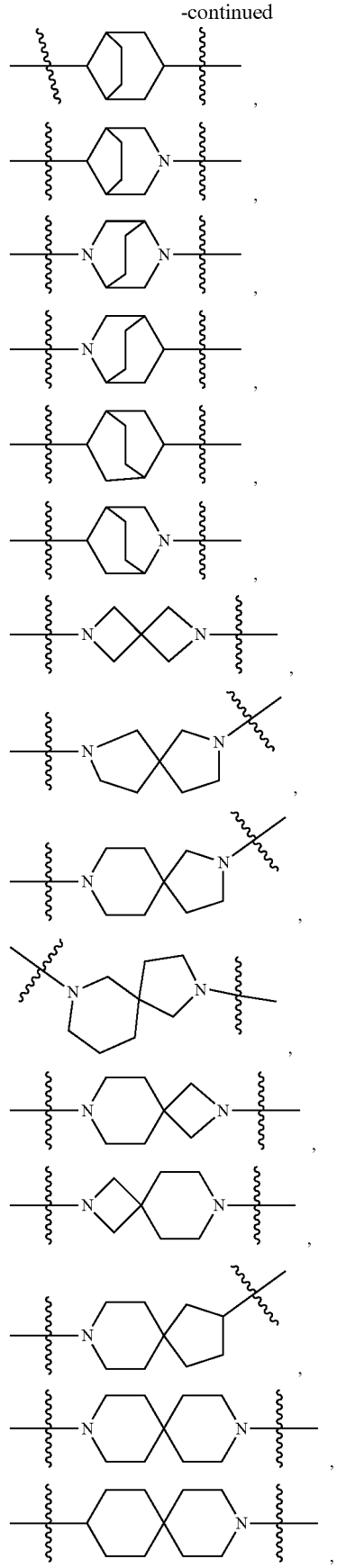

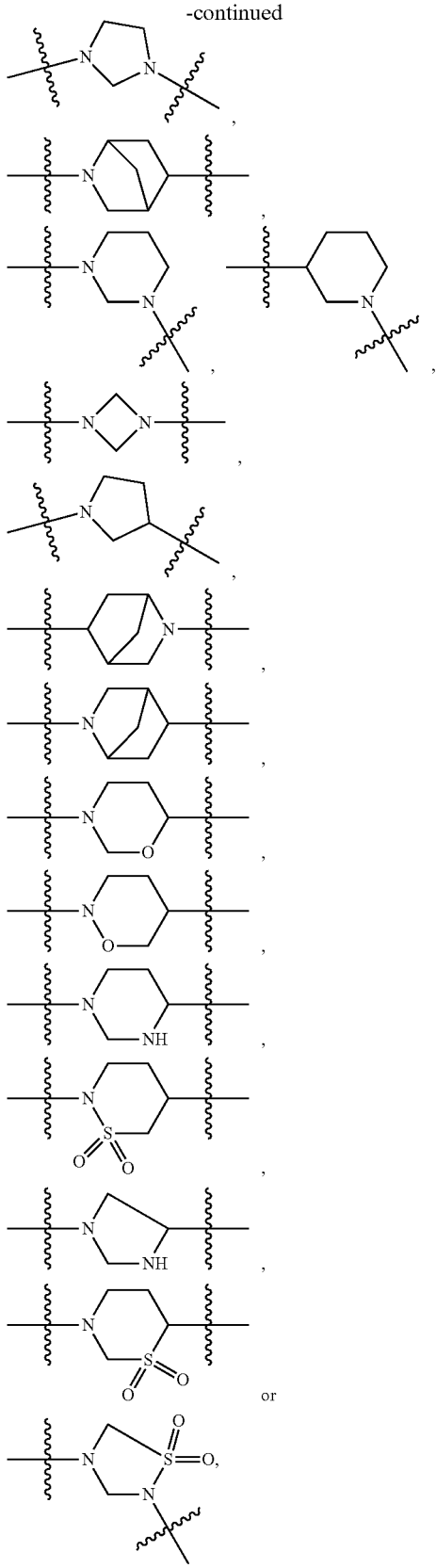

wherein each sub-formula of A is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-4}$ alkyl, $NR^6R^7C_{1-4}$ alkoxy, $C_{1-4}$ alkyl, $C_{1-4}$ haloalkyl, 3-10 membered Cyc, 3-10 membered hetCyc, 3-10 membered hetCyc-$C_{1-4}$ alkyl, 3-10 membered hetCyc-$C_{1-4}$ alkoxy $C_{1-4}$ alkyl, $C_{3-6}$ cycloalkylidene and 3-6 membered heterocyclylidene.

In some embodiments, each sub-formula of A is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl $(C=O)NH-$, pyridylmethyl $(C=O)NH-$, $CH_3CH_2(C=O)NH-$, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2$ $O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, methoxymethyl, methoxyethyl, ethoxymethyl, cyclopropylidene, cyclobutylidene, cyclopentylidene, cyclohexylidene, azetidinylidene, oxetanylidene, pyrrolidinylidene and pyrazolidinylidene.

In some embodiments, M is $-(C=O)-$, $C_{1-6}$ alkyl, $C_{2-6}$ alkenyl, $C_{2-6}$ alkynyl, $C_{1-6}$ alkyl-$C_{6-10}$ aryl, $C_{1-6}$ alkyl-(5-10 membered heteroaryl), $C_{2-6}$ alkenyl-$C_{6-10}$ aryl, $C_{2-6}$ alkynyl-$C_{6-10}$ aryl, $C_{2-6}$ alkenyl-(5-10 membered heteroaryl), $C_{2-6}$ alkynyl-(5-10 membered heteroaryl), $C_{6-10}$ aryl, 5-10 membered heteroaryl, 3-12 membered hetCyc, 3-12 membered Cyc, $C_{6-10}$ aryl-$C_{1-6}$ alkyl, (5-10 membered heteroaryl)-$C_{1-6}$ alkyl, (3-12 membered hetCyc)-$C_{1-6}$ alkyl or (3-12 membered Cyc)-$C_{1-6}$ alkyl, wherein each of $C_{1-6}$ alkyl, $C_{2-6}$ alkenyl, $C_{2-6}$ alkynyl, $C_{1-6}$ alkyl-$C_{6-10}$ aryl, $C_{1-6}$ alkyl-(5-10 membered heteroaryl), $C_{2-6}$ alkenyl-$C_{6-10}$ aryl, $C_{2-6}$ alkynyl-$C_{6-10}$ aryl, $C_{2-6}$ alkenyl-(5-10 membered heteroaryl), $C_{2-6}$ alkynyl-(5-10 membered heteroaryl), $C_{6-10}$ aryl, 5-10 membered heteroaryl, 3-12 membered hetCyc, 3-12 membered Cyc, $C_{6-10}$ aryl-$C_{1-6}$ alkyl, (5-10 membered heteroaryl)-$C_{1-6}$ alkyl, (3-12 membered hetCyc)-$C_{1-6}$ alkyl and (3-12 membered Cyc)-$C_{1-6}$ alkyl is independently and optionally substituted by 1, 2, 3 or 4 substituents selected from F, Cl, Br, OH, $CF_3$, $NR^5R^6$, oxo, $C_{1-6}$ alkoxy, $C_{3-6}$ cycloalkylidene, 3-6 membered heterocyclylidene, hydroxy $C_{1-6}$ alkyl, $C_{1-6}$ alkyl, $C_{3-6}$ cycloalkyl and 3-7 membered heterocyclyl.

In some embodiments, M is $-(C=O)-$, $C_{1-4}$ alkyl, $C_{2-4}$ alkenyl, $C_{2-4}$ alkynyl, $C_{1-4}$ alkylphenyl, $C_{1-4}$ alkyl-(5-10 membered heteroaryl), $C_{2-4}$ alkenylphenyl, $C_{2-4}$ alkynylphenyl, $C_{2-4}$ alkenyl-(5-10 membered heteroaryl), $C_{2-4}$ alkynyl-(5-10 membered heteroaryl), phenyl, 5-10 membered heteroaryl, 3-10 membered hetCyc, 3-10 membered Cyc, phenyl-$C_{1-4}$ alkyl, (5-10 membered heteroaryl)-$C_{1-4}$ alkyl, (3-10 membered hetCyc)-$C_{1-4}$-alkyl or (3-10 membered Cyc)-$C_{1-4}$ alkyl, wherein each of $C_{1-4}$ alkyl, $C_{2-4}$ alkenyl, $C_{2-4}$ alkynyl, $C_{1-4}$ alkylphenyl, $C_{1-4}$ alkyl-(5-10 membered heteroaryl), $C_{2-4}$ alkenylphenyl, $C_{2-4}$ alkynylphenyl, $C_{2-4}$ alkenyl-(5-10 membered heteroaryl), $C_{2-4}$ alkynyl-(5-10 membered heteroaryl), phenyl, 5-10 membered heteroaryl, 3-10 membered hetCyc, 3-10 membered Cyc, phenyl-$C_{1-4}$ alkyl, (5-10 membered heteroaryl)-$C_{1-4}$ alkyl, (3-10 membered hetCyc)-$C_{1-4}$-alkyl and (3-10 membered Cyc)-$C_{1-4}$ alkyl is independently and optionally substituted by 1, 2, 3 or 4 substituents selected from F, Cl, Br, OH, $CF_3$, $NR^5R^6$, oxo, $C_{1-4}$ alkoxy, $C_{3-6}$ cycloalkylidene, 3-6 membered heterocyclylidene, hydroxy $C_{1-4}$ alkyl, $C_{1-4}$ alkyl, $C_{3-6}$ cycloalkyl and 3-6 membered heterocyclyl.

In some embodiments, M is $-(C=O)-$, $-CH_2-$, $-(CH_2)_2-$, $-(CH_2)_3-$, $-(CH_2)_4-$, $-CH=CH-$, —CH₂CH═CH—, —CH₂CH═CHCH₂—, —C≡C—, —CH₂CH≡CH—, —CH₂CH≡CCH₂—, —CH═CH-phenyl, —CH₂CH═CH-phenyl, —CH₂CH═CH—CH₂-phenyl, —C≡C-phenyl, —CH₂C≡C-phenyl, —CH₂C≡C—CH₂-phenyl, —CH═CH-pyridyl, —CH₂CH═CH-pyridyl, —CH₂CH═CH—CH₂-pyridyl, —CH═CH-pyrazolyl, —CH₂CH═CH-pyrazolyl, —CH═CH-pyrimidinyl, —CH═CH-pyrazinyl, —CH═CH-benzimidazolyl, —CH═CH-benzopyrazolyl, —C≡C-pyridyl, —CH₂C≡C-pyridyl, —CH₂C≡C—CH₂-pyridyl, —C≡C-pyrazolyl, —CH₂C≡C-pyrazolyl, —C≡C-pyrimidinyl, —C≡C-pyrazinyl, —C≡C-benzimidazolyl, —C≡C-benzopyrazolyl, phenyl, pyridyl, pyrimidinyl, pyrazinyl, imidazolyl, pyrazolyl, —CH₂-pyridyl, —CH₂CH₂-pyridyl, —CH₂-phenyl, —CH₂CH₂-phenyl, —CH₂-pyrimidinyl, —CH₂-pyrazinyl, —CH₂-imidazolyl, —CH₂-pyrazolyl, phenyl-CH₂—, phenyl-CH₂CH₂—, pyridyl-CH₂—, pyridyl-CH₂CH₂—, pyrimidinyl-CH₂—, pyrazinyl-CH₂—, imidazolyl-CH₂— or pyrazolyl-CH₂—, wherein each of —CH₂—, —(CH₂)₂—, —(CH₂)₃-, —(CH₂)₄-, —CH═CH—, —CH₂CH═CH—, —CH₂CH═CHCH₂—, —C≡C—, —CH₂CH≡CH—, —CH₂CH≡CCH₂—, —CH═CH-phenyl, —CH₂CH═CH-phenyl, —CH₂CH═CH—CH₂-phenyl, —C≡C-phenyl, —CH₂C≡C-phenyl, —CH₂C≡C—CH₂-phenyl, —CH═CH-pyridyl, —CH₂CH═CH-pyridyl, —CH₂CH═CH—CH₂-pyridyl, —CH═CH-pyrazolyl, —CH₂CH═CH-pyrazolyl, —CH═CH-pyrimidinyl, —CH═CH-pyrazinyl, —CH═CH-benzimidazolyl, —CH═CH-benzopyrazolyl, —C≡C-pyridyl, —CH₂C≡C-pyridyl, —CH₂C≡C—CH₂-pyridyl, —C≡C-pyrazolyl, —CH₂C≡C-pyrazolyl, —C≡C-pyrimidinyl, —C≡C-pyrazinyl, —C≡C-benzimidazolyl, —C≡C-benzopyrazolyl, phenyl, pyridyl, pyrimidinyl, pyrazinyl, imidazolyl, pyrazolyl, —CH₂-pyridyl, —CH₂CH₂-pyridyl, —CH₂-phenyl, —CH₂CH₂-phenyl, —CH₂-pyrimidinyl, —CH₂-pyrazinyl, —CH₂-imidazolyl, —CH₂-pyrazolyl, phenyl-CH₂—, phenyl-CH₂CH₂—, pyridyl-CH₂—, pyridyl-CH₂CH₂—, pyrimidinyl-CH₂—, pyrazinyl-CH₂—, imidazolyl-CH₂— and pyrazolyl-CH₂— is independently and optionally substituted by 1, 2, 3 or 4 substituents selected from F, Cl, Br, OH, CF₃, NH2, oxo, methoxy, ethoxy, n-propoxy, isopropoxy, cyclopropylidene, cyclobutylidene, cyclopentylidene, azetidinylidene, hydroxymethyl, hydroxyethyl, 2-hydroxy-2-propyl, methyl, ethyl, n-propyl, isopropyl, n-butyl, isobutyl, tert-butyl, cyclopropyl, cyclobutyl, cyclopentyl, pyrrolidinyl and morpholinyl.

In some embodiments, $R^3$ is H, D, $C_{1-6}$ alkyl, $C_{2-6}$ alkynyl, 3-12 membered Cyc, 3-12 membered hetCyc, $C_{6-10}$ aryl, 5-10 membered heteroaryl, (3-12 membered Cyc)-$C_{1-6}$ alkyl, (3-12 membered hetCyc)-$C_{1-6}$ alkyl, $C_{1-6}$ alkoxy $C_{1-6}$ alkyl, $C_{6-10}$ aryl $C_{1-6}$ alkyl, (5-10 membered heteroaryl) $C_{1-6}$ alkyl or amino $C_{1-6}$ alkyl, wherein each of $C_{1-6}$ alkyl, $C_{2-6}$ alkynyl, 3-12 membered Cyc, 3-12 membered hetCyc, $C_{6-10}$ aryl, 5-10 membered heteroaryl, (3-12 membered Cyc)-$C_{1-6}$ alkyl, (3-12 membered hetCyc)-$C_{1-6}$ alkyl, $C_{1-6}$ alkoxy $C_{1-6}$ alkyl, $C_{6-10}$ aryl $C_{1-6}$ alkyl, (5-10 membered heteroaryl) $C_{1-6}$ alkyl and amino $C_{1-6}$ alkyl is independently and optionally substituted by 1, 2, 3 or 4 substituents selected from F, Cl, Br, NR⁵R⁶, R⁵O—, R⁵O(C═O)—, R⁵(C═O)—, NR⁵R⁶(C═O)NR⁵—, R⁵S(═O)₂—, NO₂, CN, CF₃, $C_{1-6}$ alkyl and $C_{3-6}$ cycloalkyl.

In some embodiments, $R^3$ is H, D, $C_{1-4}$ alkyl, $C_{2-4}$ alkynyl, 3-10 membered Cyc, 3-10 membered hetCyc, phenyl, 5-10 membered heteroaryl, (3-10 membered Cyc)-$C_{1-4}$ alkyl, (3-10 membered hetCyc)-$C_{1-4}$ alkyl, $C_{1-4}$ alkoxy $C_{1-4}$ alkyl, phenyl $C_{1-4}$ alkyl, (5-10 membered heteroaryl)-$C_{1-4}$ alkyl or amino $C_{1-4}$ alkyl, wherein each of $C_{1-4}$ alkyl, $C_{2-4}$ alkynyl, 3-10 membered Cyc, 3-10 membered hetCyc, phenyl, 5-10 membered heteroaryl, (3-10 membered Cyc)-$C_{1-4}$ alkyl, (3-10 membered hetCyc)-$C_{1-4}$ alkyl, $C_{1-4}$ alkoxy $C_{1-4}$ alkyl, phenyl $C_{1-4}$ alkyl, (5-10 membered heteroaryl)-$C_{1-4}$ alkyl or amino $C_{1-4}$ alkyl is independently and optionally substituted by 1, 2, 3 or 4 substituents selected from F, Cl, Br, NR⁵R⁶, R⁵O—, R⁵O(C═O)—, R⁵(C═O)—, NR⁵R⁶(C═O)NR⁵—, R⁵S(═O)₂—, NO₂, CN, CF₃, $C_{1-4}$ alkyl and $C_{3-6}$ cycloalkyl.

In some embodiments, $R^3$ is H, D, methyl, ethyl, n-propyl, isopropyl, n-butyl, isobutyl, tert-butyl, ethynyl, trifluoromethyl, cyclopropyl, cyclobutyl, cyclopentyl, cyclohexyl, cyclopentylmethyl, cyclopropylmethyl, cyclobutylmethyl, cyclohexylmethyl, spiro[4.4]decylmethyl, bicyclo[3.3.0]octyl, pyrrolidinyl, azetidinyl, piperidinyl, morpholinyl, azetidinylmethyl, piperidinylmethyl, morpholinylmethyl, methoxymethyl, methoxyethyl, ethoxymethyl, ethoxyethyl, n-propoxymethyl, isopropoxymethyl, isopropoxyethyl, n-butoxymethyl, isobutoxymethyl, tert-butoxymethyl, tert-butoxyethyl, phenyl, pyridyl, imidazolyl, pyrazolyl, pyrimidinyl, 3H-indolyl, indolyl, benzimidazolyl, 3,8a-dihydroindolizinyl, phenylmethyl, 3,8a-dihydroindolizinylmethyl, pyridylmethyl, imidazolylmethyl, pyrazolylmethyl, pyrimidinylmethyl, 3H-indolylmethyl, indolylmethyl, benzimidazolylmethyl, NH₂CH₂—, NH(CH₃)CH₂—, N(CH₃)₂CH₂—, NH₂(CH₂)₂—, NH(CH₃)CH₂—, NH(CH₃)(CH₂)₂— or N(CH₃)₂(CH₂)₂—, wherein each of methyl, ethyl, n-propyl, isopropyl, n-butyl, isobutyl, tert-butyl, ethynyl, trifluoromethyl, cyclopropyl, cyclobutyl, cyclopentyl, cyclohexyl, cyclopentylmethyl, cyclopropylmethyl, cyclobutylmethyl, cyclohexylmethyl, spiro[4.4]decylmethyl, bicyclo[3.3.0]octyl, pyrrolidinyl, azetidinyl, piperidinyl, morpholinyl, azetidinylmethyl, piperidinylmethyl, morpholinylmethyl, methoxymethyl, methoxyethyl, ethoxymethyl, ethoxyethyl, n-propoxymethyl, isopropoxymethyl, isopropoxyethyl, n-butoxymethyl, isobutoxymethyl, tert-butoxy methyl, tert-butoxy ethyl, phenyl, pyridyl, imidazolyl, pyrazolyl, pyrimidinyl, 3H-indolyl, indolyl, benzimidazolyl, 3,8a-dihydroindolizinyl, phenylmethyl, 3,8a-dihydroindolizinylmethyl, pyridylmethyl, imidazolylmethyl, pyrazolylmethyl, pyrimidinylmethyl, 3H-indolylmethyl, indolylmethyl, benzimidazolylmethyl, NH₂CH₂—, NH(CH₃)CH₂—, N(CH₃)₂CH₂—, NH₂(CH₂)₂—, NH(CH₃)CH₂—, NH(CH₃)(CH₂)₂— and N(CH₃)₂(CH₂)₂— is independently and optionally substituted by 1, 2, 3 or 4 substituents selected from F, Cl, Br, OH, NH₂, NO₂, CN, CF₃, C(CH₃)₃O(C═O)—, CH₃(C═O)—, NH₂(C═O)NH—, NHCH₃(C═O)NH—, CH₃S(═O)₂—, methyl, methoxy, ethoxy, n-propoxy, isopropoxy, phenoxy, pyridyloxy, cyclopropyl, cyclobutyl, cyclopentyl and cyclohexyl.

In some embodiments, $R^1$ is H, D, CN, F, Cl, Br, methyl, ethyl, n-propyl, isopropyl, n-butyl, isobutyl, tert-butyl, cyclopropyl, cyclobutyl, cyclopentyl or cyclohexyl, wherein each of methyl, ethyl, n-propyl, isopropyl, n-butyl, isobutyl, tert-butyl, cyclopropyl, cyclobutyl, cyclopentyl and cyclohexyl is independently and optionally substituted by 1, 2, 3 or 4 substituents selected from F, Cl, Br, CN, NH₂, OH and NO₂; and $R^4$ is H, D, F, Cl, Br, CN, methyl, ethyl, n-propyl, isopropyl, n-butyl, isobutyl, tert-butylmethoxy, ethoxy, n-propoxy, isopropoxy, n-butoxy, isobutoxy or tert-butoxy, wherein each of methyl, ethyl, n-propyl, isopropyl, n-butyl, isobutyl, tert-butylmethoxy, ethoxy, n-propoxy, isopropoxy, n-butoxy, isobutoxy and tert-butoxy is independently and optionally substituted by 1, 2, 3 or 4 substituents selected from F, Cl, Br, CN, NH₂, OH and NO₂.

In some embodiments, $R^5$ is H, D, $C_{1-6}$ alkyl, 3-12 membered Cyc, 3-12 membered hetCyc, $C_{6-10}$ aryl, 5-10 membered heteroaryl, $C_{6-10}$ aryl $C_{1-6}$ alkyl, (5-10 membered heteroaryl)-$C_{1-6}$ alkyl, $C_{1-6}$ alkoxy $C_{1-6}$ alkyl, $C_{6-10}$ aryloxy $C_{1-6}$ alkyl, amino $C_{1-6}$ alkyl, $C_{1-6}$ alkylamino $C_{1-6}$ alkyl, di($C_{1-6}$ alkyl)amino $C_{1-6}$ alkyl, (3-12 membered Cyc)-$C_{1-6}$ alkyl or (3-12 membered hetCyc)-$C_{1-6}$ alkyl, wherein each of $C_{1-6}$ alkyl, 3-12 membered Cyc, 3-12 membered hetCyc, $C_{6-10}$ aryl, 5-10 membered heteroaryl, $C_{6-10}$ aryl $C_{1-6}$ alkyl, (5-10 membered heteroaryl)-$C_{1-6}$ alkyl, $C_{1-6}$ alkoxy $C_{1-6}$ alkyl, $C_{6-10}$ aryloxy $C_{1-6}$ alkyl, amino $C_{1-6}$ alkyl, $C_{1-6}$ alkylamino $C_{1-6}$ alkyl, di($C_{1-6}$ alkyl)amino $C_{1-6}$ alkyl, (3-12 membered Cyc)-$C_{1-6}$ alkyl and (3-12 membered hetCyc)-$C_{1-6}$ alkyl is independently and optionally substituted by 1, 2, 3 or 4 substituents selected from F, Cl, Br, OH, $NR^6R^7$, $C_{1-6}$ alkyl, $C_{1-6}$ alkylsulfonyl, $C_{1-6}$ alkoxy, $C_{6-10}$ aryl and 5-10 membered heteroaryl;

$R^6$ is H, D or $C_{1-6}$ alkyl; and $R^7$ is H, D, $C_{1-6}$ alkyl, $C_{6-10}$ aryl $C_{1-6}$ alkyl or (5-10 membered heteroaryl) $C_{1-6}$ alkyl.

In some embodiments, $R^5$ is H, D, $C_{1-4}$ alkyl, 3-10 membered Cyc, 3-10 membered hetCyc, phenyl, 5-10 membered heteroaryl, phenyl $C_{1-4}$ alkyl, (5-10 membered heteroaryl)-$C_{1-4}$ alkyl, $C_{1-4}$ alkoxy $C_{1-4}$ alkyl, phenoxy $C_{1-4}$ alkyl, amino $C_{1-4}$ alkyl, $C_{1-4}$ alkylamino $C_{1-4}$ alkyl, di($C_{1-4}$ alkyl)amino $C_{1-4}$ alkyl, (3-10 membered Cyc)-$C_{1-4}$ alkyl or hetCyc-$C_{1-4}$ alkyl, wherein each of $C_{1-4}$ alkyl, 3-10 membered Cyc, 3-10 membered hetCyc, phenyl, 5-10 membered heteroaryl, phenyl $C_{1-4}$ alkyl, (5-10 membered heteroaryl)-$C_{1-4}$ alkyl, $C_{1-4}$ alkoxy $C_{1-4}$ alkyl, phenoxy $C_{1-4}$ alkyl, amino $C_{1-4}$ alkyl, $C_{1-4}$ alkylamino $C_{1-4}$ alkyl, di($C_{1-4}$ alkyl)amino $C_{1-4}$ alkyl, (3-10 membered Cyc)-$C_{1-4}$ alkyl and hetCyc-$C_{1-4}$ alkyl is independently and optionally substituted by 1, 2, 3 or 4 substituents selected from F, Cl, Br, OH, $NR^6R^7$, $C_{1-6}$ alkyl, $C_{1-4}$ alkylsulfonyl, $C_{1-4}$ alkoxy, phenyl and 5-10 membered heteroaryl;

$R^6$ is H, D or $C_{1-4}$ alkyl; and $R^7$ is H, D, $C_{1-4}$ alkyl, phenyl $C_{1-4}$ alkyl or (5-10 membered heteroaryl) $C_{1-4}$ alkyl.

In some embodiments, $R^5$ is H, D, $NH_2CH_2$—, $NH_2(CH_2)_2$—, $NH(CH_3)CH_2$—, $NH(CH_3)(CH_2)_2$—, $N(CH_3)_2CH_2$—, $NH(CH_3)_2(CH_2)_2$—, methyl, ethyl, n-propyl, isopropyl, n-butyl, isobutyl, tert-butyl, cyclopropyl, cyclobutyl, cyclopentyl, cyclohexyl, cyclopropylmethyl, cyclopropylethyl, cyclobutylmethyl, cyclopentylmethyl, cyclopentylmethyl, cyclopentylethyl, cyclohexylmethyl, cyclohexylethyl, methoxymethyl, methoxyethyl, ethoxyethyl, phenylmethyl, phenylethyl, phenyl-n-propyl, pyridylmethyl, pyridylethyl, pyridyl-n-propyl, phenoxymethyl, phenoxyethyl, phenoxy-n-propyl, azetidinyl, oxetanyl or tetrahydropyranyl, wherein each of $NH_2CH_2$—, $NH_2(CH_2)_2$—, $NH(CH_3)CH_2$—, $NH(CH_3)(CH_2)_2$—, $N(CH_3)_2CH_2$—, $NH(CH_3)_2(CH_2)_2$—, methyl, ethyl, n-propyl, isopropyl, n-butyl, isobutyl, tert-butyl, cyclopropyl, cyclobutyl, cyclopentyl, cyclohexyl, cyclopropylmethyl, cyclopropylethyl, cyclobutylethyl, cyclobutylmethyl, cyclopentylmethyl, cyclopentylethyl, cyclohexylmethyl, cyclohexylethyl, methoxymethyl, methoxyethyl, ethoxyethyl, phenylmethyl, phenylethyl, phenyl-/z-propyl, pyridylmethyl, pyridylethyl, pyridyl-n-propyl, phenoxymethyl, phenoxyethyl, phenoxy-n-propyl, azetidinyl, oxetanyl and tetrahydropyranyl is independently and optionally substituted by 1, 2, 3 or 4 substituents selected from F, Cl, Br, OH, $NH_2$, $NH(CH_3)$, $CH_3S(=O)_2$—, $CH_3CH_2S(=O)_2$—, $CH(CH_3)_2S(=O)_2$—, $C(CH_3)_3S(=O)_2$—, methyl, ethyl, n-propyl, isopropyl, n-butyl, isobutyl, tert-butyl, methoxy, ethoxy, n-propoxy, phenyl, pyridyl, pyrazolyl and pyrimidinyl;

$R^6$ is H, D, methyl, ethyl, n-propyl, isopropyl, n-butyl, isobutyl or tert-butyl; and $R^7$ is H, D, methyl, ethyl, n-propyl, isopropyl, n-butyl, isobutyl, tert-butyl, phenylmethyl, phenylethyl, phenyl-n-propyl, imidazolylmethyl, pyrazolylmethyl, pyridylmethyl, pyridylethyl, pyrimidinylmethyl or pyrimidinylethyl.

In some embodiments, the present invention provides a compound having Formula (I-1), or a stereoisomer, a geometric isomer, a tautomer, an N-oxide, a solvate, a metabolite, a pharmaceutically acceptable salt or a prodrug thereof,

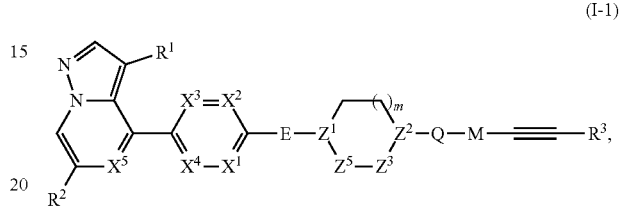

(I-1)

wherein each of $R^1$, $R^2$, $X^1$, $X^2$, $X^3$, $X^4$, $X^5$, E, Q, M and $R^3$ is as defined herein;

each of $Z^1$ and $Z^2$ is independently CH or N;

each of $Z^3$, $Z^5$ is independently a bond, $CH_2$, O, S, NH, C=O, S=O or $S(=O)_2$;

m is 0, 1 or 2;

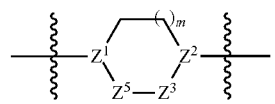

is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene and 3-6 membered heterocyclylidene.

In some embodiments,

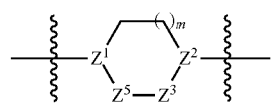

is one of the following sub-formulae:

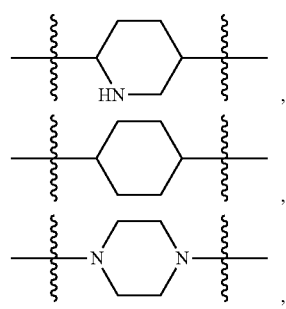

-continued

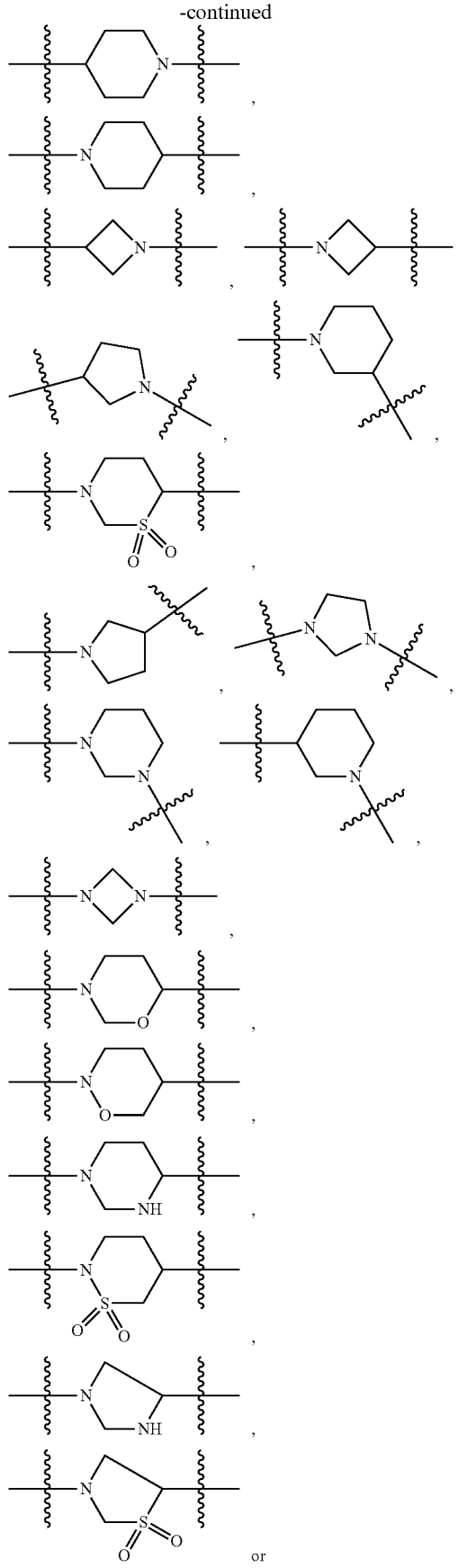

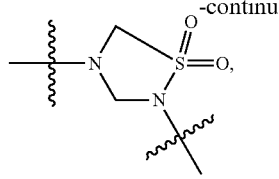

wherein each sub-formula of

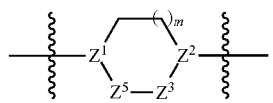

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl $(C=O)NH-$, pyridylmethyl$(C=O)NH-$, $CH_3CH_2(C=O)NH-$, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxy methyl, methoxy ethyl, ethoxymethyl, cyclopropylidene, cyclobutylidene, cyclopentylidene, cyclohexylidene, azetidinylidene, oxetanylidene and pyrazolylidene.

In some embodiments, the present invention provides a compound having Formula (I-2), or a stereoisomer, a geometric isomer, a tautomer, an N-oxide, a solvate, a metabolite, a pharmaceutically acceptable salt or a prodrug thereof,

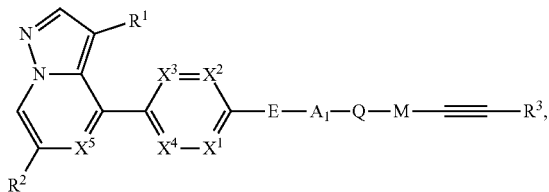

(I-2)

wherein each of $R^1$, $R^2$, $X^1$, $X^2$, $X^3$, $X^4$, $X^5$, E, Q, M and $R^3$ is as defined herein:

$A_1$ is one of the following sub-formulae:

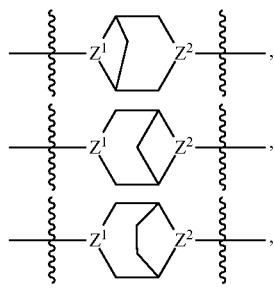

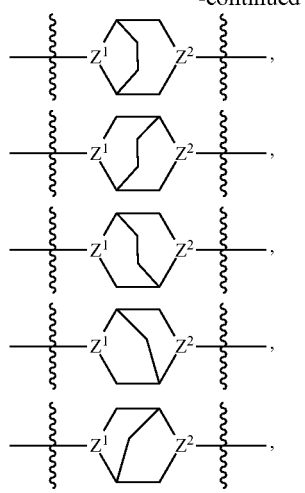

each $Z^1$ and $Z^2$ is independently CH or N;

each sub-formula of $A_1$ is independently and optionally substituted by 1, 2, 3 or 4 substituents selected from F, Cl, Br, oxo, $NR^5R^6$, $R^5O-$, $R^5(C=O)NR^6-$, $NR^5R^6 C_{1-6}$ alkyl, $NR^5R^6(C=O)C_{1-6}$ alkoxy $C_{1-6}$ alkyl, $NR^6R^7 C_{1-6}$ alkoxy, $NR^6R^7 C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene and 3-6 membered heterocyclylidene.

In some embodiments, $A_1$ is one of the following sub-formulae:

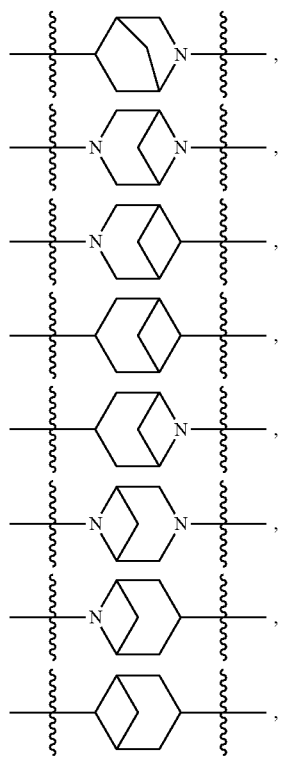

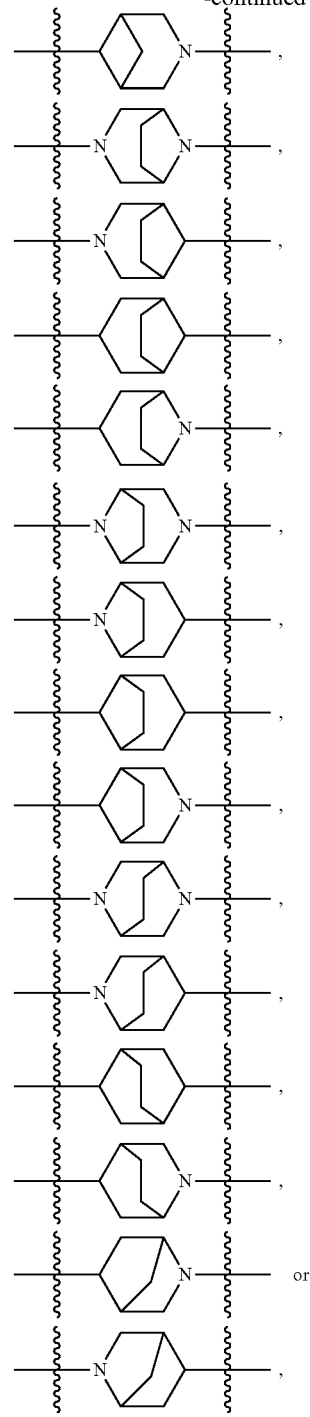

wherein each sub-formula of $A_1$ is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl $(C=O)NH-$, pyridylmethyl $(C=O)NH-$, $CH_3CH_2(C=O)NH-$, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, methoxymethyl, methoxyethyl, ethoxymethyl, cyclopropylidene, cyclobutylidene, cyclopentylidene, cyclohexylidene, azetidinylidene, oxetanylidene, pyrrolidinylidene and pyrazolidinylidene.

In some embodiments, the present invention provides a compound having Formula (I-3) or (I-4), or a stereoisomer, a geometric isomer, a tautomer, an N-oxide, a solvate, a metabolite, a pharmaceutically acceptable salt or a prodrug thereof,

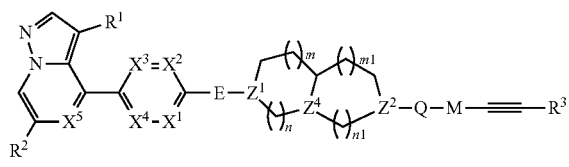

(I-3)

or

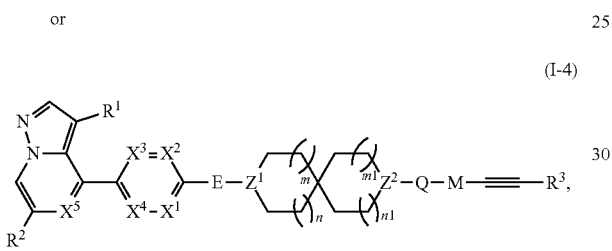

(I-4)

wherein each $R^1$, $R^2$, $X^1$, $X^2$, $X^3$, $X^4$, $X^5$, E, Q, M and $R^3$ is as defined herein;

wherein each $Z^1$, $Z^2$ and $Z^4$ is independently CH or N;

each m is 0, 1, or 2;

each n, m1 and n1 is independently 0 or 1;

each of

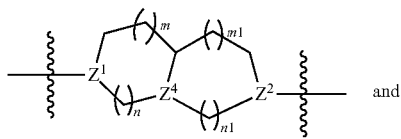 and

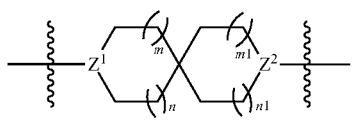

is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene and 3-6 membered heterocyclylidene.

In some embodiments,

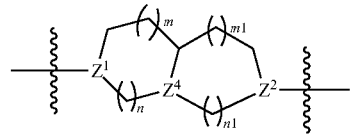

is one of the following sub-formulae:

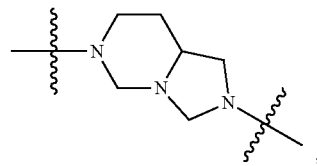,

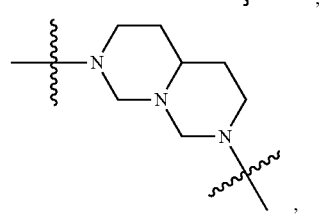,

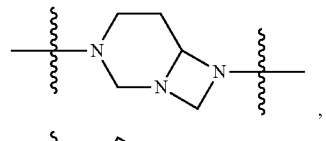,

,

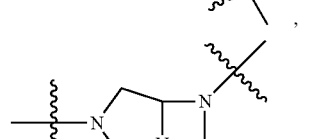,

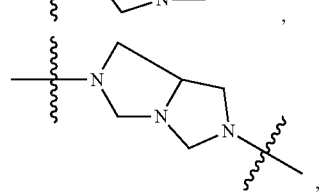,

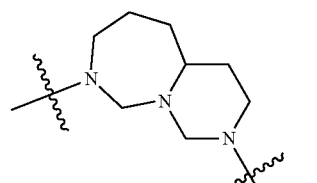,

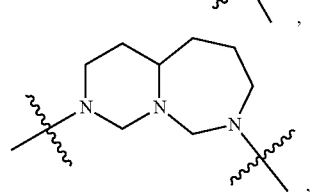,

-continued

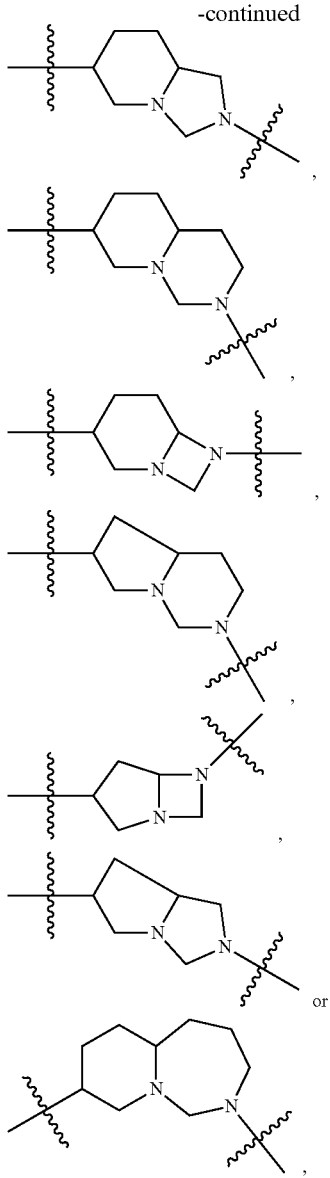

or wherein each sub-formula of

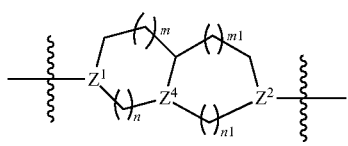

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl $(C=O)NH-$, pyridylmethyl $(C=O)NH-$, $CH_3CH_2(C=O)NH-$, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene or pyrazolylidene;

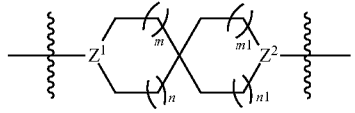

is one of the following sub-formulae:

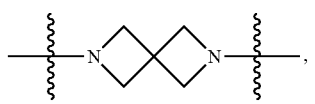

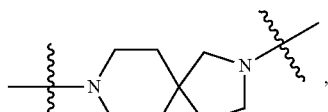

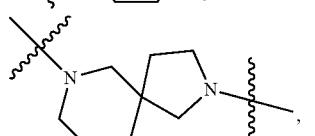

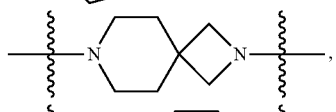

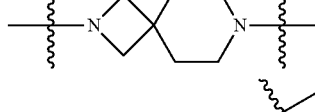

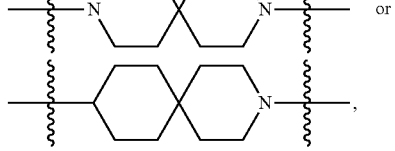 or

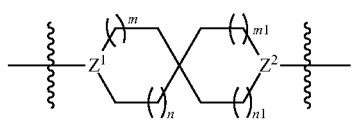

wherein each sub-formula of

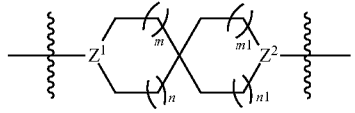

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl (C=O)NH—, pyridylmethyl (C=O)NH—, CH₃CH₂ (C=O)NH—, methoxy, ethoxy, n-propoxy, isopropoxy, n-butoxy, isobutoxy, phenoxy-(CH₂)₂O—, NH₂(CH₂)₂O—, N(CH₃)₂(CH₂)₂O—, 1-ethylcyclopropylmethyl, fluoropyridyl ethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene and pyrazolylidene.

In another aspect, the invention provides a pharmaceutical composition comprising a compound of the invention, and a pharmaceutically acceptable adjuvant.

In other aspect, provided herein is use of the compound or the pharmaceutical composition disclosed herein in the manufacture a medicament for preventing or treating a RET-related disease.

In some embodiments, the RET-related diseases include cancer, irritable bowel syndrome, and/or pain associated with irritable bowel syndrome.

In other aspect, provided herein is the compound or the pharmaceutical composition disclosed herein for use in preventing or treating a RET-related disease.

In some embodiments, the RET-related diseases include cancer, irritable bowel syndrome, and/or pain associated with irritable bowel syndrome.

In another aspect, the invention provides a method of preventing or treating a RET-related disease, wherein the method comprises administering to a patient a therapeutically effective amount of a compound of the invention or a pharmaceutical composition thereof.

In some embodiments, the RET-related diseases include cancer, irritable bowel syndrome, and/or pain associated with irritable bowel syndrome.

In other aspect, provided herein is a compound for preparing the compound of Formula (I), (I-1), (I-2), (I-3) or (I-4).

In another aspect, provided herein are a method for preparing, separating, and purifying the compound of Formula (I), (I-1), (I-2), (I-3) or (I-4).

In another aspect, the invention provides a pharmaceutical composition comprising a compound of the invention, and a pharmaceutically acceptable adjuvant. In some embodiments, adjuvants described herein include, but are not limited to, carriers, excipients, diluents, vehicles, or combinations thereof. In some embodiments, the pharmaceutical composition can be in the form of a liquid, solid, semi-solid, gel or spray.

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention.

In particular, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

Salts of the compounds disclosed herein also include salts of the compounds which are not necessarily pharmaceutically acceptable salts, and which may be useful as intermediates for preparing and/or purifying compounds of Formula (I), (I-1), (I-2), (I-3) or (I-4) and/or for separating enantiomers of compounds of Formula (I), (I-1), (I-2), (I-3) or (I-4).

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In some embodiments, "patient" refers to a human.

The term "comprise" is an open expression, it means comprising the contents disclosed herein, but don't exclude other contents.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Cis and trans isomers are diastereomer.

The term "tautomer" or "tautomeric form" refers to structural isomers of different energies which are interconvertible via a low energy barrier. Where tautomerization is possible (e.g. in solution), a chemical equilibrium of tautomers can be reached. For example, protontautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is the interconversion of pyridin-4-ol and pyridin-4(1H)-one tautomers. Unless otherwise stated, all tautomeric forms of the compounds disclosed herein are within the scope of the invention.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, individual stereochemical isomers, enantiomers, diastereomers, or mixtures of geometric isomers (or conformational isomers) are within the scope disclosed herein.

Unless otherwise stated, the structural formula and the compounds described include all isomeric (e.g., enantiomeric, diastereomeric, and geometric or conformational) forms, N-oxides, hydrates, solvates, metabolites, pharmaceutically acceptable salts and prodrugs. Therefore, individual stereochemical isomers, enantiomers, diastereomers, geometric isomers, conformational isomers, N-oxides, hydrates, solvates, metabolites, pharmaceutically acceptable salts and prodrugs are also within the scope disclosed herein. Additionally, unless otherwise stated, the formula of the compounds described herein include enriched isotopes of one or more different atoms.

As described herein, compounds disclosed herein may be independently and optionally substituted with one or more substituents, such as are illustrated generally above, or as exemplified by particular classes, subclasses, and species of the invention. It should be understood that the phrase "independently optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention includes each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl", then it is understood that the "alkyl" or "aryl" represents a linking alkylene group or arylene group, respectively.

The term "alkyl" or "alkyl group" refers to a saturated linear or branched-chain monovalent hydrocarbon group of 1-20 carbon atoms, wherein the alkyl group is optionally substituted with one or more substituents described herein. Unless otherwise stated, the alkyl group contains 1-20 carbon atoms. In some embodiments, the alkyl group contains 1-12 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms. Some non-limiting examples of the alkyl group include, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl and n-octyl, etc.

When an alkyl group is a linking group, and an "alkyl group" is recited for the definition of the Markush group, then "alkyl" means a linked alkylene group. For example, when M is an alkyl group as defined in the present invention, it means that M is a linked alkylene group. The term "alkylene" refers to a saturated divalent hydrocarbon group derived from a straight or branched chain saturated hydrocarbon by the removal of two hydrogen atoms. Some non-limiting examples of the alkyl group represented as the linked alkylene group include —CH$_2$—, —CH$_2$CH$_2$—, —CH(CH$_3$)CH$_2$—, and the like.

The term "alkenyl" refers to linear or branched-chain monovalent hydrocarbon radical of 2 to 12 carbon atoms with at least one site of unsaturation, i.e., a carbon-carbon sp2 double bond, wherein the alkenyl radical may be optionally substituted with one or more substituents described herein, and includes radicals having "cis" and "trans" orientations, or alternatively, "E" and "Z" orientations. In some embodiments, the alkenyl contains 2-10 carbon atoms. In other embodiments, the alkenyl contains 2-6 carbon atoms. In still other embodiments, the alkenyl contains 2-4 carbon atoms. Some non-limiting examples of the alkenyl group include ethenyl or vinyl (—CH=CH$_2$), allyl (—CH$_2$CH=CH$_2$), propenyl (—C=CHCH$_3$), isopropenyl (—C(CH$_3$)=CH$_2$) and the like.

When an alkenyl group is a linking group, and an "alkenyl group" is recited for the definition of the Markush group, then "alkenyl" means a linked alkenylene group. For example, when M is an alkenyl group as defined in the present invention, it means that M is a linked alkenylene group. Some non-limiting examples of the alkenyl group represented as the linked alkenylene group include —CH=CH$_2$—, —CH$_2$CH=CH—, —CH$_2$CH=CHCH$_2$—, and the like.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted by one or more substituents described herein. In some embodiments, the alkynyl contains 2-6 carbon atoms. In other embodiments, the alkynyl contains 2-10 carbon atoms. In still other embodiments, the alkynyl contains 2-4 carbon atoms. Examples of such groups include, but are not limited to, ethynyl (—C≡CH), propargyl (—CH$_2$C≡CH), 1-propynyl (—C≡C—CH$_3$), and the like. When an alkynyl group is a linking group, and an "alkynyl group" is recited for the definition of the Markush group, then "alkynyl" means a linked alkynylene group. Some non-limiting examples of the alkynyl group represented as the linked alkynylene group include —C≡C—, —CH$_2$CH≡CH—, —CH$_2$CH≡CHCH$_2$—, and the like.

The term "cycloalkylidene" means a divalent saturated monocyclic carbon system formed by the removal of two hydrogen atoms from the same carbon atom in a 3-7 membered saturated monocyclic carbocycle. In some embodiments, the cycloalkylidene group represents a $C_{3-6}$ cycloalkylidene group. In other embodiments, the cycloalkylidene group represents a $C_{3-5}$ cycloalkylidene group. Examples of the cycloalkylidene group include, but are not limited to, cyclopropylidene, cyclopentylidene, cyclobutylidene, cyclohexylidene, and the like.

The term "heterocyclylidene" means a divalent saturated monocyclic heterocyclic system formed by the removal of two hydrogen atoms from the same carbon atom in a 3-7 membered saturated monocyclic heterocycle, wherein the system contains at least one carbon atom and contains one, two or three heteroatoms selected from O, N and S. In some embodiments, the heterocyclylidene group represents a $C_{3-6}$ heterocyclylidene group. In other embodiments, the heterocyclylidene group represents a $C_{3-5}$ heterocyclylidene group. Examples of the heterocyclylidene group include, but are not limited to, oxiranylidene, aziridinylidene, oxetanylidene, oxolanylidene, azetidinylidene, and the like.

The term "hydroxyalkyl" refers to an alkyl group substituted by one or more hydroxy groups. In some embodiments, hydroxyalkyl means an alkyl group substituted by 1, 2, 3 or 4 hydroxy groups. In some embodiments, hydroxyalkyl refers to an alkyl group substituted by 1 or 2 hydroxy groups. In some embodiments, hydroxyalkyl means hydroxy $C_{1-6}$ alkyl, i.e., $C_{1-6}$ alkyl in which the alkyl is substituted by one or more hydroxy groups, preferably, hydroxy $C_{1-6}$ alkyl refers to $C_{1-6}$ alkyl in which the alkyl is substituted by one hydroxy group. In some embodiments, hydroxyalkyl refers to a hydroxy $C_{1-4}$ alkyl group. In some embodiments, hydroxyalkyl refers to a hydroxy $C_{1-3}$ alkyl group. Some non-limiting examples of hydroxyalkyl include CH$_2$OH—, CH$_2$OHCH$_2$CH$_2$CH$_2$—, CH$_2$OHCH$_2$—, CH$_2$OHCH$_2$CHOHCH$_2$—, CH(CH$_3$)OHCH$_2$CHOHCH$_2$—, and the like.

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted by one or more substituents disclosed herein. Some non-limiting examples of the alkoxy group include, but not limited to, methoxy (MeO, —OCH$_3$), ethoxy (EtO, —OCH$_2$CH$_3$), 1-propoxy (n-PrO, n-propoxy, —OCH$_2$CH$_2$CEE), 2-propoxy (i-PrO, i-propoxy, —OCH(CH$_3$)$_2$), 1-butoxy (n-BuO, n-butoxy, —OCH$_2$CH$_2$CH$_2$CEE), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (i-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "alkoxyalkyl" refers to an alkyl group substituted by an alkoxy group, wherein the alkoxy group and the alkyl group have the definitions as described herein. In some embodiments, alkoxyalkyl is $C_{1-6}$ alkoxy $C_{1-6}$ alkyl; in other embodiments, alkoxyalkyl is $C_{1-4}$ alkoxy $C_{1-4}$ alkyl; in still other embodiments, the alkoxyalkyl is $C_{1-4}$ alkoxy $C_{1-3}$ alkyl; in yet other embodiments, the alkoxyalkyl is $C_{1-3}$ alkoxy $C_{1-3}$ alkyl. Such examples include, but are not limited to, methoxymethyl, ethoxymethyl, propoxy methyl, methoxyethyl, methoxypropyl, ethoxyethyl, ethoxypropyl, propoxyethyl, propoxypropyl, and the like.

The term "halogen" means F (fluoro), Cl (chloro), Br (bromine) or I (iodine).

The term "haloalkyl" refers to an alkyl group substituted by one or more halogen atoms, examples of which include, but are not limited to, monofluoromethyl, difluoromethyl, trifluoromethyl, monofluoroethyl, 1,2-difluoroethyl, 1,1-difluoroethyl, 2,2-difluoroethyl, monochloromethyl, dichloromethyl, trichloromethyl, monochloroethyl, 1,2-dichloroethyl, 1,1-dichloroethyl, 2,2-dichloroethyl, 1,1-dibromoethyl, and the like.

The terms "cycloalkyl" or "cycloalkane" are used interchangeably and all denote a monovalent saturated monocyclic carbocyclic ring system of 3-7 carbon atoms. The —CH$_2$— group in the carbocyclic ring can be optionally replaced by —C(O)—. In some embodiments, the cycloalkyl group contains 3-6 carbon atoms, ie, a $C_{3-6}$ cycloalkyl group; in other embodiments, the cycloalkyl group contains 3-5 carbon atoms, ie, a $C_{3-5}$ cycloalkyl group; Examples of the cycloalkyl group include, but are not limited to, cyclopropyl, cyclobutyl, cyclopentyl, cyclohexyl and the like. Some non-limiting examples of that the —CH$_2$— group in the carbocyclic ring may be replaced by —C(O)— include cyclopentanone, cyclobutanone, and the like. When a cycloalkyl group is a linking group, and a "cycloalkyl group" is recited for the definition of the Markush group, then "cycloalkyl" means a linked cycloalkylene group. The term "cycloalkylene" means a divalent cycloalkane group formed by removing two hydrogen atoms from a ring carbon atom of a cycloalkyl group. The cycloalkyl group or cycloalkane may be independently and optionally substituted by one or more substituents described herein.

The term "aromatic ring" or "aromatic hydrocarbon" refers to monocyclic, bicyclic and tricyclic carbocyclic ring systems having a total of 6-14 ring members, or 6-12 ring members, or 6-10 ring members, wherein at least one ring in the system is aromatic, wherein each ring in the system contains 3-7 ring atoms. Examples of the aromatic ring may include benzene, naphthalene, and anthracene.

The term "aryl" means a monovalent aromatic ring group formed by removing a hydrogen atom from a ring carbon atom of an aromatic ring. Examples of aryl may include phenyl, naphthyl and anthracenyl. When an aryl group is a linking group, and an "aryl group" is recited for the definition of the Markush group, then "aryl" means a linked arylene group. For example, when M is an aryl group as defined in the present invention, it means that M is a linked arylene group. The term "arylene" means a divalent aromatic ring group formed by removing two hydrogen atoms from a ring carbon atom of an aromatic ring. Examples of that an aryl group represents a arylene group may include phenylene, naphthylene and anthranylene. The aryl group may be independently and optionally substituted by one or more substituents disclosed herein.

The term "heteroaromatic ring" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from heteroatom, and wherein each ring in the system contains 5 to 7 ring atoms.

The term "heteroaryl" means a monovalent aromatic ring group formed by removing a hydrogen atom from the ring atom of the heteroaryl ring. The heteroaryl group is optionally substituted by one or more substituents disclosed herein. In one embodiment, a heteroaryl consisting of 5-10 atoms or a 5-10 membered heteroaryl comprises 1, 2, 3 or 4 heteroatoms independently selected from O, S and N. In some embodiments, the term "heteroaryl" means a heteroaryl consisting of 5 ring atoms or a 5-membered heteroaryl, which comprises 1, 2, 3 or 4 heteroatoms independently selected from O, S and N. Some non-limiting examples of heteroaryl include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, etc. When a heteroaryl group is a linking group, and a "heteroaryl group" is recited for the definition of the Markush group, then "heteroaryl" means a linked heteroarylene group. For example, when M is a heteroaryl group as defined in the present invention, it means that M is a linked heteroarylene group. The term "heteroarylene" means a divalent heteroaryl ring group formed by removing two hydrogen atoms from a ring atom of a heteroaryl group. The heteroaryl group may be independently and optionally substituted with one or more substituents disclosed herein.

The term "aryloxy" refers to aryl-O—, i.e., an aryl group, as previously defined, attached to the parent molecular moiety via an oxygen atom. Examples of aryloxy include, but are not limited to, phenoxy, naphthyloxy, and the like.

The term "aryloxyalkyl" refers to an alkyl group substituted with an aryloxy group, wherein the aryloxy group and the alkyl group have the definitions as described herein. In some embodiments, aryloxyalkyl is $C_{6-10}$ aryloxy $C_{1-6}$ alkyl; in other embodiments, aryloxyalkyl is phenoxy $C_{1-6}$ alkyl; in still some embodiments, aryloxyalkyl is phenoxy $C_{1-4}$ alkyl. Examples of the aryloxyalkyl group include, but are not limited to, phenoxymethyl, phenoxyethyl, phenoxy-n-propyl, phenoxyisopropyl, phenoxy-n-butyl, phenoxy-isobutyl, phenoxy-tert-butyl, and the like.

The term "arylalkyl" refers to an alkyl group substituted with an aryl group, wherein the aryl group and the alkyl group have the definitions as described herein. In some embodiments, arylalkyl is $C_{6-10}$ aryl $C_{1-6}$ alkyl; in other embodiments, arylalkyl is phenyl $C_{1-6}$ alkyl; in still other embodiments, arylalkyl is phenyl $C_{1-4}$ alkyl. Examples of arylalkyl include, but are not limited to, phenylmethyl, phenylethyl, phenyl-n-propyl, phenylisopropyl, phenyl-n-butyl, phenylisobutyl, phenyl-tert-butyl, and the like.

The term "heteroarylalkyl" refers to an alkyl group substituted by a heteroaryl group, wherein the heteroaryl group and the alkyl group have the definitions as described herein. In some embodiments, heteroarylalkyl is (5-10 membered heteroaryl)-$C_{1-6}$ alkyl; in other embodiments, heteroarylalkyl is (5-10 membered heteroaryl)-$C_{1-4}$ alkyl; in still other embodiments, heteroarylalkyl is (5-6 membered heteroaryl)-$C_{1-4}$ alkyl. Examples of heteroarylalkyl include, but are not limited to, imidazolylmethyl, imidazolylethyl, pyrazolylmethyl, pyrazolyl ethyl, oxazolylmethyl, oxazolylethyl, imidazolylpropyl, pyridylpropyl, pyridylmethyl, pyridylethyl, pyrimidinylmethyl, furylmethyl, furylethyl, indolylmethyl, pyrazolo[1,5-a]pyrimidinylmethyl, etc.

The terms "bridged carbocycle" and "bridged carbocyclyl" are used interchangeably and both refer to a non-aromatic saturated or partially unsaturated bicyclic or polycyclic ring system that shares two or more carbon atoms, and the ring atom is carbon atom. The —$CH_2$— group in the bridged carbocycle can be optionally replaced by —C(O)—. In some embodiments, the bridged carbocycle contains 6-12 ring carbon atoms, i.e., represents a 6-12 membered bridged carbocycle; in other embodiments, the bridged carbocycle contains 6-10 ring carbon atoms, i.e., represents a 6-10 membered bridged carbocycle. Examples of bridged carbocycle include, but are not limited to, bicyclo[3.1.1] heptane, bicyclo[3.2.1] octane, bicyclo[2.2.2] octane, bicyclo[2.2.0] hexane, octahydro-1H-indene, etc. When a bridged carbocycle or a bridged carbocyclyl is a linking group, and a bridged carbocycle or a bridged carbocyclyl is recited for the definition of the Markush group, then the bridged carbocycle or the bridged carbocyclyl means a linked bridged carbocyclylene. The term "bridged carbocyclylene" means a divalent bridged carbocyclic group formed by the removal of two hydrogen atoms from the ring atom of a bridged carbocycle. The bridged carbocycle or bridged carbocyclyl may be independently and optionally substituted by one or more substituents disclosed herein.

The terms "spiro carbocycle" and "spiro carbocyclyl" are used interchangeably and both refer to a non-aromatic saturated or partially unsaturated ring system in which two carbon rings share a carbon atom. The —$CH_2$— group in the spiro carbocyclic ring can be optionally replaced by —C(O)—. In some embodiments, the spiro carbocycle contains 7-12 ring carbon atoms, i.e., represents a 7-12 membered spiro carbocycle; in other embodiments, the spiro carbocycle contains 7-10 ring carbon atoms, i.e., represents a 7-10 membered spiro carbocycle. Examples of spiro carbocycle include, but are not limited to, spiro[4.4]decane, spiro[3.4]octane, spiro[4.5]decane, and the like. When a spiro carbocycle or a spiro carbocyclyl is a linking group, and a spiro carbocycle or a spiro carbocyclyl is recited for the definition of the Markush group, then the spiro carbocycle or the spiro carbocyclyl means a linked spiro carbocyclylene. The term "spiro carbocyclylene" means a divalent spiro carbocyclic group formed by the removal of two hydrogen atoms from the ring atom of a spiro carbocycle.

The spiro carbocycle or spiro carbocyclyl may be independently and optionally substituted by one or more substituents disclosed herein.

The terms "heterocycle" or "heterocyclyl" are used interchangeably and all denote a monovalent, non-aromatic, saturated or partially unsaturated monocyclic ring system having 3-12 ring atoms, wherein the system contains at least one carbon atom and one, two or three heteroatoms selected from O, N, S. Unless otherwise specified, the heterocyclyl group may be carbon or nitrogen linked, and a —$CH_2$— group can be optionally replaced by a —C(=O)— group. Ring sulfur atoms may be optionally oxidized to form S-oxides, and ring nitrogen atoms may be optionally oxidized to form N-oxides. In some embodiments, the heterocycle contains 4-7 ring atoms, i.e., represents a 4-7 membered heterocycle; in other embodiments, the heterocycle contains 4-7 ring atoms, i.e., represents a 4-7 membered heterocycle. Examples of the heterocyclyl group include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxocyclopentyl, dithiocyclopentyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, 1,1-dioxo-1,3-thiomorpholine, and the like. Some non-limiting examples of heterocyclyl wherein —$CH_2$— group is replaced by —C(O)— moiety include 2-oxopyrrolidinyl, oxo-1,3-thiazolidinyl, 2-piperidinonyl and 3,5-dioxopiperidinyl. Some non-limited examples of heterocyclyl wherein the ring nitrogen atom is oxidized is 1,1-dioxo-1,3-thiomorpholine. When a heterocycle or a heterocyclyl is a linking group, and a heterocycle or a heterocyclyl is recited for the definition of the Markush group, then the heterocycle or the heterocyclyl means a linked heterocyclylene group. The term "heterocyclylene" means a divalent heterocyclyl group formed by removing two hydrogen atoms from a ring atom of a heterocyclic ring. The heterocycle or heterocyclyl may be independently and optionally substituted by one or more substituents disclosed herein.

The term "bridged heterocycle" or "bridged heterocyclyl" can be used interchangeably and all denote a non-aromatic saturated or partially unsaturated bicyclic or polycyclic ring system that shares two or more carbon atoms, wherein the system contains at least one carbon atom and 1, 2 or 3 heteroatoms selected from O, N, S. The —$CH_2$— group in the bridged heterocycle can be optionally replaced by —C(O)—. Ring sulfur atoms may be optionally oxidized to form S-oxides, and ring nitrogen atoms may be optionally oxidized to form N-oxides. In some embodiments, the bridged heterocycle contains 6-12 ring atoms, i.e., represents a 6-12 membered bridged heterocycle; in other embodiments, the bridged heterocycle contains 6-10 ring atoms, i.e., represents a 6-10 membered bridged heterocycle. Examples of the bridged heterocycle include, but are not limited to, 3,6-diazabicyclo[3.1.1]heptane, 3,8-diazabicyclo[3.2.1]octane, 2-azabicyclo[2.2.1] heptane, octahydroimidazo[1,5-c]pyrimidine, 6-azabicyclo[3.1.1]heptane, 3-azabicyclo[3.1.1]heptane, 8-azabicyclo[3.2.1]octane, 3-azabicyclo[3.2.1]octane, 2-diazabicyclo[2.2.2]octane, and the like. When a bridged heterocycle or a bridged heterocyclyl is a linking group, and a bridged heterocycle or a bridged heterocyclyl is recited for the definition of the Markush group, then the bridged heterocycle or the bridged heterocyclyl means a linked bridged heterocyclylene group. The term "bridged heterocyclylene" means a divalent bridged heterocyclyl group formed by removing two hydrogen atoms from a ring atom of a bridged heterocyclic ring. The bridged heterocycle or bridged heterocyclyl may be independently and optionally substituted by one or more substituents disclosed herein.

The term "spiroheterocycle" or "spiroheterocyclyl" can be used interchangeably and all denote a non-aromatic saturated or partially unsaturated ring system in which two rings share a carbon atom, and the system contains one, two or three heteroatoms selected from O, N, S. The —$CH_2$— group in the spiroheterocycle can be optionally replaced by —C(O)—. Ring sulfur atoms may be optionally oxidized to form S-oxides, and ring nitrogen atoms may be optionally oxidized to form N-oxides. In some embodiments, the spiroheterocycle contains 7-12 ring atoms, i.e., represents a 7-12 membered spiroheterocycle; in other embodiments, the spiroheterocycle contains 7-10 ring atoms, i.e., represents a 7-10 membered spiroheterocycle. Examples of the spiroheterocycle include, but are not limited to, 4,7-diazaspiro[2.5]octane, 2,8-diazaspiro[4.5]decane, 2,7-diazaspiro[4.5]decane, 2,7-diazaspiro[3.5]decane, 2,6-diazaspiro[3.3]heptane, 2,7-diazaspiro[4.4]nonane, 3-azaspiro[5.5]undecane, 2,7-diazaspiro[4.4]nonane-1-one, and the like. When a spiroheterocycle or a spiroheterocyclyl is a linking group, and a spiroheterocycle or a spiroheterocyclyl is recited for the definition of the Markush group, then the spiroheterocycle or spiroheterocyclyl means a linked spiroheterocyclylene group. The term "spiroheterocyclylene" means a divalent spiroheterocyclyl group formed by removing two hydrogen atoms from a ring atom of a spiroheterocyclic ring. The spiroheterocycle or spiroheterocyclyl may be independently and optionally substituted by one or more substituents disclosed herein.

The term "alkylaryl" refers to an aryl group substituted with an alkyl group, wherein the alkyl group and the aryl group have the definitions as described herein. In some embodiments, "alkylaryl" refers to $C_{1-6}$ alkyl-$C_{6-10}$ aryl, i.e., $C_{6-10}$ aryl substituted by $C_{1-6}$ alkyl; in other embodiments, "alkylaryl" refers to $C_{1-4}$ alkylphenyl, i.e., phenyl substituted by $C_{1-4}$ alkyl. Examples of the alkylaryl group include, but are not limited to, methylphenyl, ethylphenyl, propylphenyl, methylnaphthyl, and the like. When an alkylaryl group is a linking group, and an alkylaryl is recited for the definition of the Markush group, then alkylaryl means a linked alkylarylene group. For example, when M is an alkylaryl group as defined in the present invention, it means that M is a linked alkylarylene group. The term "alkylarylene" means a divalent alkylaryl group formed by removing a hydrogen atom from the alkyl group of the alkylaryl group and removing a hydrogen atom from the ring atom of the aryl group. The alkylaryl group may be independently and optionally substituted by one or more substituents disclosed herein.

The term "alkenylaryl" refers to an aryl group substituted by an alkenyl group, wherein the alkenyl group and the aryl group have the definitions as described herein. In some embodiments, "alkenylaryl" refers to $C_{2-6}$ alkenyl-$C_{6-10}$ aryl, i.e., $C_{6-10}$ aryl substituted by $C_{2-6}$ alkenyl; in other embodiments, "alkenylaryl" refers to $C_{2-4}$ alkenylphenyl, i.e., phenyl substituted by $C_{2-4}$ alkenyl. Examples of the alkenylaryl group include, but are not limited to, $CH_2$=CH-phenyl, $CH_3CH$=CH-phenyl, $CH_3CH$=CH—$CH_2$-phenyl, and the like. When an alkenylaryl group is a linking group, and an alkenylaryl is recited for the definition of the Markush group, then alkenylaryl means a linked alkenylarylene group. For example, when M is an alkenylaryl group as defined in the present invention, it means that M is a linked alkenylarylene group. Examples of the alkenylarylene group include, but are not limited to, —CH═CH-phenyl, —CH$_2$CH═CH-phenyl, —CH$_2$CH═CH—CH$_2$-phenyl, etc. The alkenylarylene group may be independently and optionally substituted by one or more substituents described herein.

The term "alkynylaryl" refers to an aryl group substituted with an alkynyl group, wherein the alkynyl group and the aryl group have the definitions as described herein. In some embodiments, "alkynylaryl" refers to C$_{2-6}$ alkynyl-C$_{6-10}$ aryl, i.e., C$_{6-10}$ aryl substituted by C$_{2-6}$ alkynyl; in other embodiments, "alkynylaryl" refers to C$_{2-4}$ alkynylphenyl, i.e., phenyl substituted by C$_{2-4}$ alkynyl. Examples of the alkynylaryl group include, but are not limited to, CH≡C-phenyl, CH$_3$C≡C-phenyl, CH$_3$C≡C—CH$_2$-phenyl, and the like. When an alkynylaryl group is a linking group, and an alkynylaryl is recited for the definition of the Markush group, then alkynylaryl means a linked alkynylarylene group. For example, when M is an alkynylaryl group as defined in the present invention, it means that M is a linked alkynylarylene group. Examples of the alkynylarylene group include, but are not limited to, —C≡C-phenyl, —CH$_2$C≡C-phenyl, —CH$_2$C≡C—CH$_2$-phenyl, and the like. The alkynylaryl group may be independently and optionally substituted with one or more substituents disclosed herein.

The term "alkylheteroaryl" refers to a heteroaryl group substituted with an alkyl group. The alkyl and heteroaryl are as defined herein. In some embodiments, "alkylheteroaryl" means C$_{1-6}$ alkyl-(5-10 membered heteroaryl), i.e., 5-10 membered heteroaryl substituted with C$_{1-6}$ alkyl; in other embodiments, "alkylheteroaryl" means C$_{1-4}$ alkyl-(5-6 membered heteroaryl), i.e., 5-6 membered heteroaryl substituted with C$_{1-4}$ alkyl. Examples of the alkylheteroaryl group include, but are not limited to, methylpyridyl, ethylpyridyl, propylpyridyl, methylpyrazolyl, ethylpyrazolyl, propylpyrazolyl, methylpyrimidinyl, methylpyrazinyl, methyl benzimidazolyl, methyl benzopyrazolyl, and the like. When an alkylheteroaryl group is a linking group, and an alkylheteroaryl is recited for the definition of the Markush group, then alkylheteroaryl means a linked alkylheteroarylene group. For example, when M is an alkylheteroaryl group as defined in the present invention, it means that M is a linked alkylheteroarylene group. The term "alkylheteroarylene" means a divalent alkylheteroaryl group formed by removing a hydrogen atom from the alkyl group of the alkylheteroaryl group and removing a hydrogen atom from the ring atom of the heteroaryl group. The alkylheteroaryl group may be independently and optionally substituted by one or more substituents disclosed herein.

The term "alkenylheteroaryl" refers to a heteroaryl group substituted by an alkenyl group. The alkenyl and heteroaryl are as defined herein. In some embodiments, "alkenylheteroaryl" means C$_{2-6}$ alkenyl-(5-10 membered heteroaryl), i.e., 5-10 membered heteroaryl substituted by C$_{2-6}$ alkenyl; in other embodiments, "alkenylheteroaryl" means C$_{2-4}$ alkenyl-(5-6 membered heteroaryl), i.e., 5-6 membered heteroaryl substituted by C$_{2-4}$ alkenyl. Examples of the alkenylheteroaryl group include, but are not limited to, CH$_2$═CH-pyridyl, CH$_3$CH═CH-pyridyl, CH$_3$CH═CH—CH$_2$-pyridyl, CH$_2$═CH-pyrazolyl, CH$_3$CH═CH-pyrazolyl, CH$_2$═CH-pyrimidinyl, CH$_2$═CH-pyrazinyl, CH$_2$═CH-benzimidazolyl, CH$_2$═CH-benzopyrazolyl, and the like. When an alkenylheteroaryl group is a linking group, and an alkenylheteroaryl is recited for the definition of the Markush group, then alkenylheteroaryl means a linked alkenylheteroarylene group. For example, when M is an alkenylheteroaryl group as defined in the present invention, it means that M is a linked alkenylheteroarylene group. Examples of the alkenylheteroarylene group include, but are not limited to, —CH═CH-pyridyl, —CH$_2$CH═CH-pyridyl, —CH$_2$CH═CH—CH$_2$-pyridyl, —CH═CH-pyrazolyl, —CH$_2$CH═CH-pyrazolyl, —CH═CH-pyrimidinyl, —CH═CH-pyrazinyl, —CH═CH-benzimidazolyl, —CH═CH-benzopyrazolyl, and the like. The alkenylheteroaryl group may be independently and optionally substituted by one or more substituents disclosed herein.

The term "alkynylheteroaryl" refers to a heteroaryl group substituted by an alkynyl group. The alkynyl and heteroaryl are as defined herein. In some embodiments, "alkynylheteroaryl" means C$_{2-6}$ alkynyl-(5-10 membered heteroaryl), i.e., 5-10 membered heteroaryl substituted by C$_{2-6}$ alkynyl; in other embodiments, "alkynylheteroaryl" means C$_{2-4}$ alkynyl-(5-6 membered heteroaryl), i.e., 5-6 membered heteroaryl substituted by C$_{2-4}$ alkynyl. Examples of the alkynylheteroaryl group include, but are not limited to, CH≡C-pyridyl, CH$_3$C≡C-pyridyl, CH$_3$C≡C—CH$_2$-pyridyl, CH≡C-pyrazolyl, CH$_3$C≡C-pyrazolyl, CH≡C-pyrimidinyl, CH≡C-pyrazinyl, CH≡C-benzimidazolyl, CH≡C-benzopyrazolyl, and the like. When an alkynylheteroaryl group is a linking group, and an alkynylheteroaryl is recited for the definition of the Markush group, then alkynylheteroaryl means a linked alkynylheteroarylene group. For example, when M is an alkynylheteroaryl group as defined in the present invention, it means that M is a linked alkynylheteroarylene group. Examples of the alkynylheteroarylene group include, but are not limited to, —C≡C-pyridyl, —CH2C≡C-pyridyl, —CH$_2$C≡C—CH$_2$-pyridyl, —C≡C-pyrazolyl, —CH$_2$C≡C-pyrazolyl, —C≡C-pyrimidinyl, —C≡C-pyrazinyl, —C≡C-benzimidazolyl, —C≡C-benzopyrazolyl, and the like. The alkynylheteroaryl group may be independently and optionally substituted by one or more substituents disclosed herein.

The term "aminoalkyl" refers to an alkyl group substituted by one or more amino groups. In some embodiments, the term "aminoalkyl" refers to an alkyl group substituted by one amino group. In other embodiments, the term "aminoalkyl" refers to amino C$_{1-6}$ alkyl. In still other embodiments, the term "aminoalkyl" refers to amino C$_{1-4}$ alkyl. In yet other embodiments, the term "aminoalkyl" refers to amino C$_{1-3}$ alkyl. Examples of the aminoalkyl group include, but are not limited to, aminomethyl, aminoethyl, amino-n-propyl, aminoisopropyl, aminoisobutyl, amino-tert-butyl, 1,2-diaminoethyl, and the like.

The term "alkylamino" refers to an amino group substituted by an alkyl group. In some embodiments, the term "alkylamino" refers to C$_{1-6}$ alkylamino. In other embodiments, the term "alkylamino" refers to C$_{1-4}$ alkylamino. In some embodiments, the term "alkylamino" refers to C$_{1-3}$ alkylamino. Examples of the alkylamino group include, but are not limited to, methylamino, ethylamino, n-propylamino, isopropylamino, isobutylamino, tert-butylamino, and the like.

The term "dialkylamino" refers to an amino group substituted by two alkyl groups. In some embodiments, the term "dialkylamino" refers to a di(C$_{1-6}$ alkyl)amino group, i.e., an amino group substituted by two C$_{1-6}$ alkyl groups. In other embodiments, the term "dialkylamino" refers to a di(C$_{1-4}$ alkyl)amino group, i.e., an amino group substituted by two C$_{1-4}$ alkyl groups. In still other embodiments, the term "dialkylamino" refers to a di(C$_{1-3}$ alkyl)amino group, i.e., an amino group substituted with two C$_{1-3}$ alkyl groups. Examples of the dialkylamino group include, but are not limited to, dimethylamino, diethylamino, di-n-propylamino, diisopropylamino, diisobutylamino, di-tert-butylamino, and the like.

The term "alkylaminoalkyl" refers to an alkyl group substituted with an alkylamino group, wherein the alkyl group and the alkylamino group have the definitions as described herein. In some embodiments, the term "alkylaminoalkyl" refers to $C_{1-6}$ alkylamino-$C_{1-6}$ alkyl, i.e., $C_{1-6}$ alkyl substituted with $C_{1-6}$ alkylamino; in other embodiments, the term "alkylaminoalkyl" refers to $C_{1-4}$ alkylamino-$C_{1-4}$ alkyl, i.e., $C_{1-4}$ alkyl substituted by $C_{1-4}$ alkylamino. Examples of the alkylaminoalkyl group include, but are not limited to, methylaminomethyl, ethylaminoethyl, methylaminoethyl, ethylaminomethyl, propylaminomethyl, methylaminopropyl, methylamino-n-butyl, propylaminoethyl, and the like.

The term "dialkylaminoalkyl" refers to an alkyl group substituted by a dialkylamino group, wherein the dialkylamino group and the alkyl group have the definitions as described herein. In some embodiments, the term "dialkylaminoalkyl" is di($C_{1-6}$ alkyl)amino-$C_{1-6}$ alkyl; in other embodiments, "dialkylaminoalkyl" is di($C_{1-4}$ alkyl)amino-$C_{1-4}$ alkyl.

The term "alkylsulfonyl" refers to alkyl-$S(=O)_2$—, i.e., alkyl is attached to the parent molecular moiety via —$S(=O)_2$—. In some embodiments, alkylsulfonyl is $C_{1-6}$ alkylsulfonyl; in other embodiments, alkylsulfonyl is phenyl $C_{1-4}$ alkylsulfonyl; in still some embodiments, alkylsulfonyl is $C_{1-4}$ alkylsulfonyl. Examples of the alkylsulfonyl group include, but are not limited to, methylmethanesulfonyl, ethylmethanesulfonyl, n-propylmethanesulfonyl, isopropylmethanesulfonyl, n-butylmethanesulfonyl, and the like.

The term "Cyc" refers to cycloalkyl, bridged carbocyclyl or spirocarbocyclyl wherein the cycloalkyl, bridged carbocyclyl and spirocarbocyclyl have the definitions as described herein. In some embodiments, Cyc represents 3-12 membered Cyc; in other embodiments, Cyc represents 3-10 membered Cyc.

The term "hetCyc" refers to heterocyclyl, bridged heterocyclyl or spiroheterocyclyl wherein the heterocyclyl, bridged heterocyclyl and spiroheterocyclyl have the definitions as described herein. In some embodiments, hetCyc represents 3-12 membered hetCyc; in other embodiments, hetCyc represents 3-10 membered hetCyc.

The term "$R^5O(C=O)NR^6$alkyl" means that the hydrogen atom on the alkyl group is substituted by $R^5O(C=O)NR^6$—, wherein the alkyl group and $R^5O(C=O)NR^6$— have the definitions as described herein. The term "$R^5(C=O)NR^6$alkyl" means that the hydrogen atom on the alkyl group is substituted by $R^5(C=O)NR^6$—, wherein the alkyl group and $R^5(C=O)NR^6$— have the definitions as described herein.

The term "$NR^5R^6(C=O)$alkyl" means that the hydrogen atom on the alkyl group is substituted by $NR^5R^6(C=O)$—, wherein the alkyl group and $NR^5R^6(C=O)$— have the definitions as described herein. The term "$R^5(C=O)$alkyl" means that the hydrogen atom on the alkyl group is substituted by $R^5(C=O)$—, wherein the alkyl group and $R^5(C=O)$— have the definitions as described herein. The term "$NR^6R^7$alkyl" means that the hydrogen atom on the alkyl group is substituted by $NR^6R^7$—, wherein the alkyl group and $NR^6R^7$— have the definitions as described herein. The term "$NR^6R^7$alkoxy" means that the hydrogen atom on the alkoxy group is substituted by $NR^6R^7$—, wherein the alkoxy group and $NR^6R^7$— have the definitions as described herein. The term "$NR^6R^7$ alkoxy alkyl" refers to an alkyl group substituted by $NR^6R^7$ alkoxy, wherein $NR^6R^7$ alkoxy and alkyl have the definitions as described herein. The term "$NR^5R^6(C=O)$alkoxy" refers to an alkoxy group substituted by $NR^5R^6(C=O)$—, wherein $NR^5R^6(C=O)$— and alkoxy have the definitions as described herein. The term "$NR^5R^6(C=O)$alkoxyalkyl" refers to an alkyl group substituted by $NR^5R^6(C=O)$alkoxy, wherein $NR^5R^6(C=O)$alkoxy and alkyl have the definitions as described herein. The term "$R^5O$alkyl" means that the hydrogen atom on the alkyl group is substituted by $R^5O$—, wherein the alkyl group and $R^5O$— have the definitions as described herein.

The term "Cyc-alkyl" means that the hydrogen atom on the alkyl group is substituted by Cyc. wherein the alkyl and Cyc are as defined herein. In some embodiments, Cyc-alkyl represents (3-12 membered Cyc)-$C_{1-6}$ alkyl; in other embodiments, Cyc-alkyl represents (3-10 membered Cyc)-$C_{1-4}$ alkyl; in still other embodiments, Cyc-alkyl represents (3-10 membered Cyc)-$C_{1-3}$ alkyl. Examples of the Cyc-alkyl group include, but are not limited to, cyclopropylmethyl, cyclobutylmethyl, cyclopentylmethyl, cyclopentylethyl, cyclopentyl-n-propyl, cyclopropylethyl, cyclopropyl-n-propyl, cyclobutylethyl, cyclobutylpropyl, cyclohexylethyl, cyclohexylmethyl, and the like.

The term "hetCyc-alkyl" refers to that the hydrogen atom on the alkyl group is substituted by hetCyc, wherein alkyl and hetCyc have the definitions as described herein. In some embodiments, "hetCyc-alkyl" represents (3-12 membered hetCyc)-$C_{1-6}$ alkyl; in other embodiments, hetCyc-alkyl represents (3-10 membered hetCyc)-$C_{1-4}$ alkyl; in still other embodiments, hetCyc-alkyl represents (3-10 membered hetCyc)-$C_{1-3}$ alkyl. Examples of the hetCyc-alkyl group include, but are not limited to, azetidinylmethyl, pyrrolidinylmethyl, morpholinylmethyl, morpholinylethyl, piperazinylmethyl, piperazinylethyl, 2-oxopyrrolidinomethyl, 2-oxopyrrolidinylethyl, oxetanylmethyl, tetrahydrofuranylmethyl, and the like.

The term "alkylhetCyc" refers to a hetCyc substituted by an alkyl group, wherein the alkyl group and the hetCyc group have the definitions as described herein. In some embodiments, "alkylhetCyc" means $C_{1-6}$ alkyl-(3-12 membered hetCyc); in other embodiments, "alkylhetCyc" means $C_{1-4}$ alkyl-(3-10 membered hetCyc); in still other embodiments, "alkyl hetCyc" means $C_{1-3}$ alkyl-(3-10 membered hetCyc). Examples of the alkylhetCyc group include, but are not limited to, isopropylazetidinyl, methylpiperidinyl, methyloxetanyl, methylpyrrolidinyl, methylmorpholinyl, methylimidazolidinyl, etc.

In the formula of the compound of the present invention, the left end of Q is connected to A, and the right end of Q is connected to M. For example, when Q is —$S(=O)_2NR^5$—, then

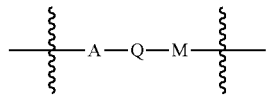

represents

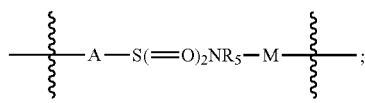

likewise, the left end of A is connected to E, and the right end of A is connected to Q. For example, when A is

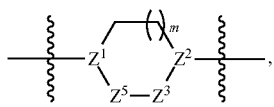

then

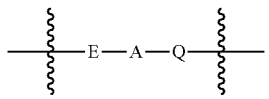

represents

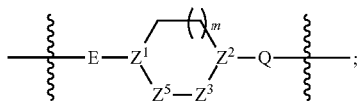

the left end of M is connected to Q, and the right end of M is connected to =—R$^3$. For example, when M is —CH$_2$-phenyl,

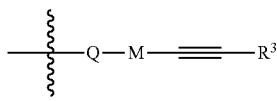

represents

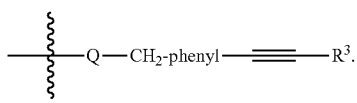

As described herein, unless otherwise specified, the ring substituent can attach to the rest of the molecule at any attachable position on the rings. For example, piperidinyl comprises piperidin-1-yl, piperidin-2-yl, piperidin-3-yl and piperidin-4-yl.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methyl, 2-(p-toluenesulfonyl) ethyl, 2-(p-nitrophenylsulfonyl)-ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991; and P. J. Kocienski, Protecting Groups, Thieme, Stuttgart, 2005.

The term "prodrug" refers to a compound that is transformed in vivo into a compound of Formula (I). Such transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C$_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds are derived from the phosphonation of a hydroxy group on the parent compound. A thorough discussion of prodrugs is provided in T. Higuchi and V. Stella, Pro-drugs as Novel Delivery Systems, Vol. 14 of the *A.C.S. Symposium Series*, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

A "metabolite" is a product produced through metabolism in the body of a specified compound or salt thereof. The metabolites of a compound may be identified using routine techniques known in the art and their activities may be determined using tests as those described herein. Such products may result for example from oxidation, reduction, hydrolysis, amidation, deamidation, esterification, deesterification, enzyme cleavage, etc., of the administered compound. Accordingly, the invention includes metabolites of a compound disclosed herein, including metabolites produced by contacting a compound disclosed herein with a mammal for a sufficient time period.

The "pharmaceutically acceptable salt" as used in the present invention means an organic salt and an inorganic salt of the compound of the present invention. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentylpropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and N$^+$(C$_{1-4}$ alkyl)$_4$ salts. This invention also envisions the quaternization of any basic nitrogen-containing groups of the compounds disclosed herein. Water soluble or oil soluble or dispersable products may be obtained by such quaternization. Representative alkali or alkaline earth metal salts include sodium, lithium, potassium, calcium, magnesium, and the like. Further pharmaceutically acceptable salts include appropriate and nontoxic ammonium, quaternary ammonium, and amine cations formed using counterions, such as halide, hydroxide, carboxylate, sulfate, phosphate, nitrate, $C_{1-8}$ sulfonate or aryl sulfonate.

The pharmaceutically acceptable salts of the present invention can be synthesized from the parent compound, basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid and ethanolamine. The term "hydrate" refers to the complex where the solvent molecule is water.

An "N-oxide" of the present invention refers to one or more than one nitrogen atoms oxidized to form an N-oxide, where a compound contains several amine functional groups. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, *Advanced Organic Chemistry*, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In still another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "RET-related cancer" as used herein refers to a cancer that is associated with the expression, activity or dysregulation of the RET gene, RET kinase (also referred to herein as RET kinase protein, RET kinase), or any one of them. Non-limiting examples of RET-related cancers are described herein, the expression or activity or dysregulation of the RET gene, RET kinase, or any one of them is one or more point mutations in the RET gene.

The phrase "expression, activity or dysregulation of RET gene, RET kinase, or any of them" refers to a mutation in a gene (e.g., a translocation of a RET gene resulting in expression of a fusion protein, a deletion in the RET gene resulting in expression of the RET protein comprising at least one amino acid deletion compared to the wild-type RET protein, or a mutation in the RET gene resulting in the expression of a RET protein with one or more point mutations, or alternatively spliced form of RET mRNA resulting in the deletion of at least one amino acid in the RET protein compared to the wild-type RET protein), or amplification of a RET gene, which results in overexpression of the RET protein or autocrine activity resulting from overexpression of the cellular RET gene and results in increased pathogenicity of the activity of the kinase domain of the RET protein in the cell (e.g., constitutive activation of the kinase domain of the RET protein). As another example, the expression or activity or dysregulation of the RET gene, RET kinase, or any one of them may be a mutation in the RET gene encoding a RET protein, wherein the RET protein has constitutive activity or increased activity compared to a protein encoded by the RET gene not comprising the mutation. For example, the expression or activity or dysregulation of the RET gene, RET kinase, or any one of them can be the result of a gene or chromosomal translocation which results in expression of a fusion protein, wherein the fusion protein comprises a first RET portion comprising a functional kinase domain and a second portion of a chaperone protein (i.e., not RET). In some examples, the RET gene, RET protein, or dysregulation of expression or activity can be the result of gene translation of one RET gene with another RET gene.

The expression or activity or dysregulation of RET kinase, the RET gene, or any (e.g., one or more) thereof may contribute to tumorigenesis. For example, the expression or activity or dysregulation of the RET gene, RET kinase, or any one of them can be a translocation, overexpression, activation, amplification or mutation of the RET kinase, RET gene or RET kinase domain. A translocation can include a translocation involving an RET kinase domain. A mutation can include a mutation involving a RET ligand binding site, and the amplification can be a RET gene. Other disorders may include RET mRNA splice variants and RET autocrine/paracrine signaling, which may also contribute to tumorigenesis.

In some embodiments, the expression or activity or dysregulation of the RET gene, RET kinase, or any one of them includes one or more deletions (e.g., deletions of the 4 amino acids), insertions, or point mutations in the RET kinase. In some embodiments, the expression or activity or dysregulation of the RET gene, RET kinase, or any one of them includes deletion of one or more residues of the RET kinase, resulting in constitutive activity of the RET kinase domain.

The term "Irritable Bowel Syndrome" includes diarrhea-predominant, constipation-predominant or alternating defecation patterns, functional bloating, functional constipation, functional diarrhea, non-specific functional bowel disease, functional abdominal pain syndrome, chronic idiopathic constipation, functional esophageal disease, functional gastroduodenal disease, functional anorectal pain, inflammatory bowel disease, etc.

Any formula given herein is also intended to represent isotopically unenriched forms as well as isotopically enriched forms of the compounds. Isotopically enriched compounds have the structure depicted by the general formula given herein, except that one or more atoms are replaced by the atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability. For example increased in vivo half-life or reduced dosage requirements or an improvement in therapeutic index. It is understood that deuterium in this context is regarded as a substituent of a compound of Formula (I), (I-1), (I-2), (I-3) or (I-4). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g., $D_2O$, acetone-$d_6$, DMSO-$d_6$.

Description of Compounds of the Invention

The present invention provides a novel compound exhibiting inhibition of Rearranged during transfection (RET) kinase, which has a good inhibitory effect on RET wild type and RET gene mutants, and has a good inhibition selectivity on RET wild type and RET gene mutants.

In one aspect, the present invention provides a compound having Formula (I) or a stereoisomer, a geometric isomer, a tautomer, an N-oxide, a solvate, a metabolite, a pharmaceutically acceptable salt or a prodrug thereof,

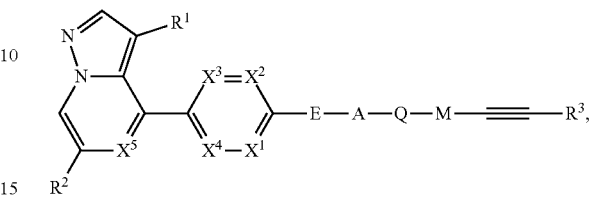

(I)

wherein each of $R^1$, $R^2$, $X^1$, $X^2$, $X^3$, $X^4$, $X^5$, E, A, Q, M and $R^3$ is as defined herein.

In some embodiments, each of $X^1$, $X^2$, $X^3$, $X^4$ and $X^5$ is independently $CR^4$ or N, wherein 0, 1, or 2 of $X^1$, $X^2$, $X^3$, $X^4$ are N.

In some embodiments, E is a bond, —$NR^6$— or —O—.

In some embodiments, A is Cyc or hetCyc, wherein each of Cyc and hetCyc is independently and optionally substituted by 1, 2, 3 or 4 substituents selected from F, Cl, Br, oxo, $NR^5R^6$, $R^5O$—, $R^5(C=O)NR^6$—, $NR^5R^6$ alkyl, $NR^5R^6$ (C=O) alkoxyalkyl, $NR^6R^7$ alkoxy, $NR^6R^7$ alkoxyalkyl, alkyl, haloalkyl, hydroxyalkyl, Cyc, hetCyc, hetCyc-alkyl, alkoxyalkyl, hetCyc-alkoxyalkyl, cycloalkylidene and heterocyclylidene.

In some embodiments, Q is —(C=O)—, —O—, —(C=O)$NR^5$—, —(C=S)$NR^5$—, —S(=O)$_2$—, —S(=O)$_2NR^5$—, —$NR^5$(C=O)—, —$NR^5$(C=O)O—, —$NR^5$(C=O)$NR^5$—, —$NR^5$—, —(C=O)O— or a bond.

In some embodiments, M is —(C=O)—, alkyl, alkenyl, alkynyl, alkylaryl, alkylheteroaryl, alkenylaryl, alkynylaryl, alkenylheteroaryl, alkynylheteroaryl, aryl, heteroaryl, Cyc, hetCyc, arylalkyl, heteroarylalkyl, Cyc-alkyl or hetCyc-alkyl, wherein each of alkyl, alkenyl, alkynyl, alkylaryl, alkylheteroaryl, alkenylaryl, alkynylaryl, alkenylheteroaryl, alkynylheteroaryl, aryl, heteroaryl, Cyc, hetCyc, arylalkyl, heteroarylalkyl, Cyc-alkyl and hetCyc-alkyl is independently and optionally substituted by 1, 2, 3 or 4 substituents selected from F, Cl, Br, OH, $CF_3$, $NR^5R^6$, oxo, alkoxy, cycloalkylidene, heterocyclidene, hydroxyalkyl, alkyl, cycloalkyl and heterocyclic group.

In some embodiments, $R^1$ is H, D, CN, F, Cl, Br, alkyl or cycloalkyl, wherein each of alkyl and cycloalkyl is independently and optionally substituted by 1, 2, 3 or 4 substituents selected from F, Cl, Br, CN, $NH_2$, OH and $NO_2$.

In some embodiments, $R^2$ is a 5-membered heteroaryl group, wherein the 5-membered heteroaryl group can be independently and optionally substituted by 1, 2, 3 or 4 substituents selected from F, Cl, Br, alkyl, Cyc, hetCyc, arylalkyl, heteroarylalkyl and alkyl hetCyc; wherein each of alkyl, Cyc, hetCyc, arylalkyl and alkyl hetCyc can be further independently and optionally substituted by 1, 2, 3 or 4 substituents selected from F, Cl, Br, CN, $R^5O$—, $R^5(C=O)$—, $R^5O(C=O)$—, $NR^5R^6$, $NR^5R^6(C=O)$—, $R^5S(=O)_2$—, alkyl, Cyc, hetCyc and alkoxy.

In some embodiments, $R^3$ is H, D, alkyl, alkynyl, Cyc, hetCyc, aryl, heteroaryl, Cyc-alkyl, hetCyc-alkyl, alkoxyalkyl, arylalkyl, heteroarylalkyl or aminoalkyl, wherein each of alkyl, alkynyl, Cyc, hetCyc, aryl, heteroaryl, Cyc-alkyl, hetCyc-alkyl, alkoxyalkyl, arylalkyl, heteroarylalkyl and aminoalkyl is independently and optionally substituted by 1, 2, 3 or 4 substituents selected from F, Cl, Br, $NR^5R^6$, $R^5O-$, $R^5O(C=O)-$, $R^5(C=O)-$, $NR^5R^6(C=O)NR^5-$, $R^5S(=O)_2-$, $NO_2$, $CN$, $CF_3$, alkyl and cycloalkyl.

In some embodiments, $R^4$ is H, D, alkyl, F, Cl, Br or alkoxy, wherein each of alkyl and alkoxy is independently and optionally substituted by 1, 2, 3 or 4 substituents selected from F, Cl, Br, CN, $NH_2$, OH and $NO_2$.

In some embodiments, $R^5$ is H, D, alkyl, Cyc, hetCyc, aryl, heteroaryl, arylalkyl, heteroarylalkyl, alkoxyalkyl, aryloxyalkyl, aminoalkyl, alkylaminoalkyl, dialkylaminoalkyl, Cyc-alkyl or hetCyc-alkyl, wherein each of alkyl, Cyc, hetCyc, aryl, heteroaryl, arylalkyl, heteroarylalkyl, alkoxyalkyl, aryloxyalkyl, aminoalkyl, alkylaminoalkyl, dialkylaminoalkyl, Cyc-alkyl and hetCyc-alkyl is independently and optionally substituted by 1, 2, 3 or 4 substituents selected from F, Cl, Br, OH, $NR^6R^7$, alkyl, alkylsulfonyl, alkoxy, aryl and heteroaryl.

In some embodiments, $R^6$ is H or alkyl.

In some embodiments, $R^7$ is alkyl, arylalkyl or heteroarylalkyl.

In some embodiments, each Cyc is independently cycloalkyl, bridged carbocyclyl or spirocarbocyclyl.

In some embodiments, each hetCyc is independently heterocyclyl, bridged heterocyclyl or spiroheterocyclyl.

In some embodiments, $R^2$ is one of the following sub-formulae:

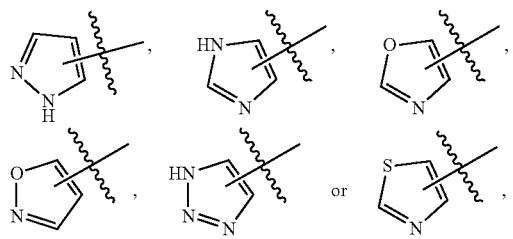

wherein each sub-formula of R can be independently and optionally substituted by F, Cl, Br, $C_{1-6}$ alkyl, 3-12 membered Cyc, 3-12 membered hetCyc, $C_{6-12}$ aryl $C_{1-6}$ alkyl, (5-10 membered heteroaryl)-$C_{1-6}$ alkyl and $C_{1-6}$ alkyl-(3-12 membered hetCyc); wherein each of $C_{1-6}$ alkyl, 3-12 membered Cyc, 3-12 membered hetCyc, $C_{6-12}$ aryl $C_{1-6}$ alkyl, (5-10 membered heteroaryl)-$C_{1-6}$ alkyl and $C_{1-6}$ alkyl-(3-12 membered hetCyc) can be further independently and optionally substituted by 1, 2, 3 or 4 substituents selected from F, Cl, Br, CN, $R^5O-$, $R^5(C=O)-$, $R^5O(C=O)-$, $NR^5R^6$, $NR^5R^6(C=O)-$, $R^5S(=O)_2-$, $C_{1-6}$ alkyl, 3-12 membered Cyc, 3-12 membered hetCyc and $C_{1-6}$ alkoxy.

In some embodiments, $R^2$ is one of the following sub-formulae:

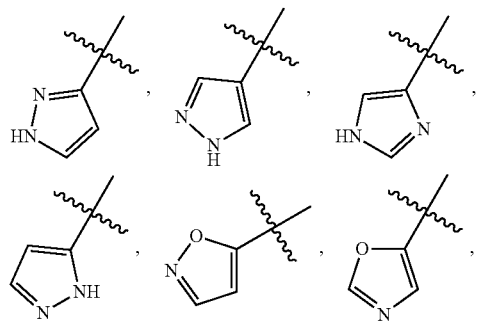

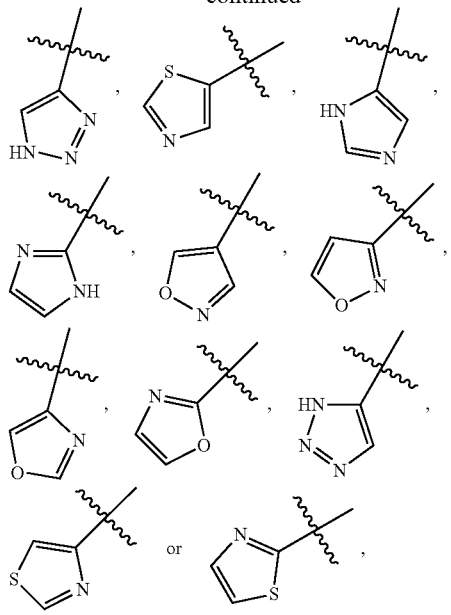

wherein each sub-formula of $R^2$ can be independently and optionally substituted by F, Cl, Br, $C_{1-4}$ alkyl, 3-10 membered Cyc, 3-10 membered hetCyc, phenyl $C_{1-4}$ alkyl, (5-10 membered heteroaryl)-$C_{1-4}$ alkyl and $C_{1-4}$ alkyl-(3-10 membered hetCyc); wherein each of $C_{1-4}$ alkyl, 3-10 membered Cyc, 3-10 membered hetCyc, phenyl $C_{1-4}$ alkyl, (5-10 membered heteroaryl)-$C_{1-4}$ alkyl and $C_{1-4}$ alkyl-(3-10 membered hetCyc) can be further independently and optionally substituted by 1, 2, 3 or 4 substituents selected from F, Cl, Br, CN, $R^5O-$, $R^5(C=O)-$, $R^5O(C=O)-$, $NR^5R^6$, $NR^5R^6(C=O)-$, $R^5S(=O)_2-$, $C_{1-4}$ alkyl, 3-10 membered Cyc, 3-10 membered hetCyc and $C_{1-4}$ alkoxy.

In some embodiments, R is one of the following sub-formula:

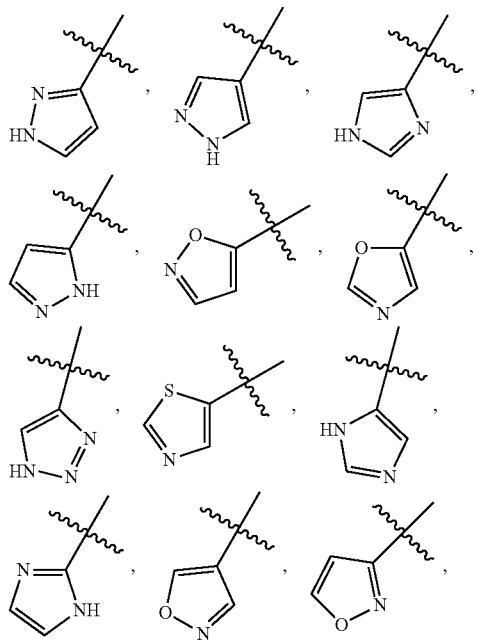

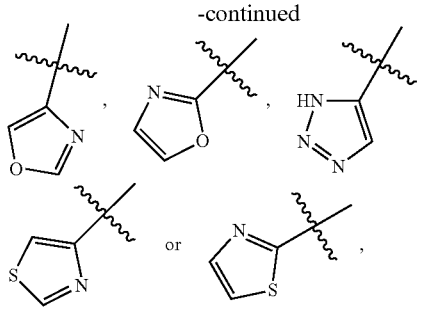

wherein each substructure of $R^2$ can be independently and optionally substituted by 1, 2, 3 or 4 substituents selected from F, Cl, Br, methyl, ethyl, n-propyl, isopropyl trifluoromethyl, difluoromethyl, 2-methylpropyl, 2-hydroxypropyl, benzyl, cyclopropyl, tert-butoxycarbonylazetidinyl, isopropylazetidinyl, 2-hydroxymethylpropyl, methoxymethyl, methoxyethyl, ethoxymethyl, piperidinyl, methoxybenzyl, isopropylsulfonylethyl, isopropylsulfonylmethyl, tetrahydropyranyl, aminocarbonylethyl, dimethylaminocarbonylethyl, 2-methoxypropyl, ethoxymethylpiperidinyl.

In some embodiments, A is 3-12 membered Cyc or 3-12 membered hetCyc, wherein each of 3-12 membered Cyc and 3-12 membered hetCyc is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$alkyl, $C_{1-6}$ haloalkyl, $C_{1-6}$ hydroxyalkyl, 3-12 membered Cyc, 3-12 membered hetCyc, 3-12 membered hetCyc-$C_{1-6}$ alkyl, $C_{1-6}$ alkoxy $C_{1-6}$ alkyl, 3-12 membered hetCyc-$C_{1-6}$ alkoxy $C_{1-6}$ alkyl, $C_{3-6}$ cycloalkylidene, 3-6 membered heterocyclylidene.

In some embodiments, A is one of the following sub-formulae:

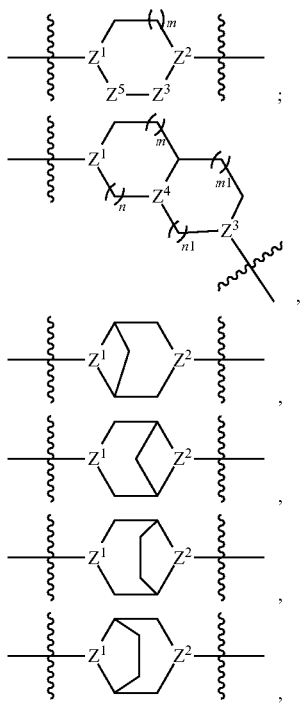

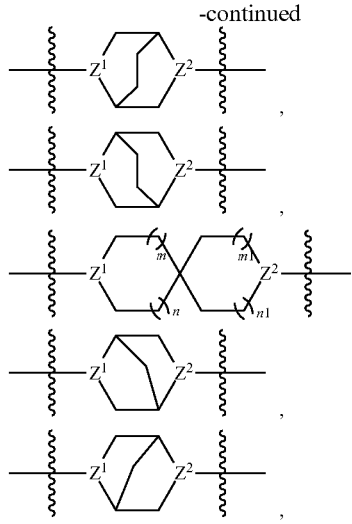

wherein each $Z^1$, $Z^2$ and $Z^4$ is independently CH or N;
each of $Z^3$, $Z^5$ is independently a bond, $CH_2$, O, S, NH, C=O, S=O or $S(=O)_2$;
each m is 0, 1, or 2;
each n, m1 and n1 is independently 0 or 1;
each sub-formula of A is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene, 3-6 membered heterocyclylidene.

In some embodiments, each substructure of A is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-4}$ alkyl, $NR^5R^6(C=O)C_{1-4}$ alkoxy $C_{1-4}$ alkyl, $NR^6R^7C_{1-4}$ alkoxy, $NR^6R^7C_{1-4}$ alkoxy $C_{1-4}$ alkyl, $C_{1-4}$ alkyl, $C_{1-4}$ haloalkyl, $C_{1-4}$ hydroxyalkyl, 3-10 membered Cyc, 3-10 membered hetCyc, 3-10 membered hetCyc-$C_{1-4}$ alkyl, $C_{1-4}$ alkoxy $C_{1-4}$ alkyl, 3-10 membered hetCyc-$C_{1-4}$ alkoxy $C_{1-4}$ alkyl, $C_{3-6}$ cycloalkylidene and 3-6 membered heterocyclylidene.

In some embodiments, A is one of the following sub-formulae:

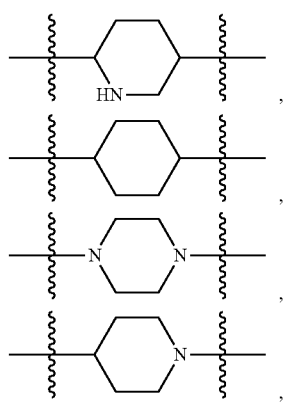

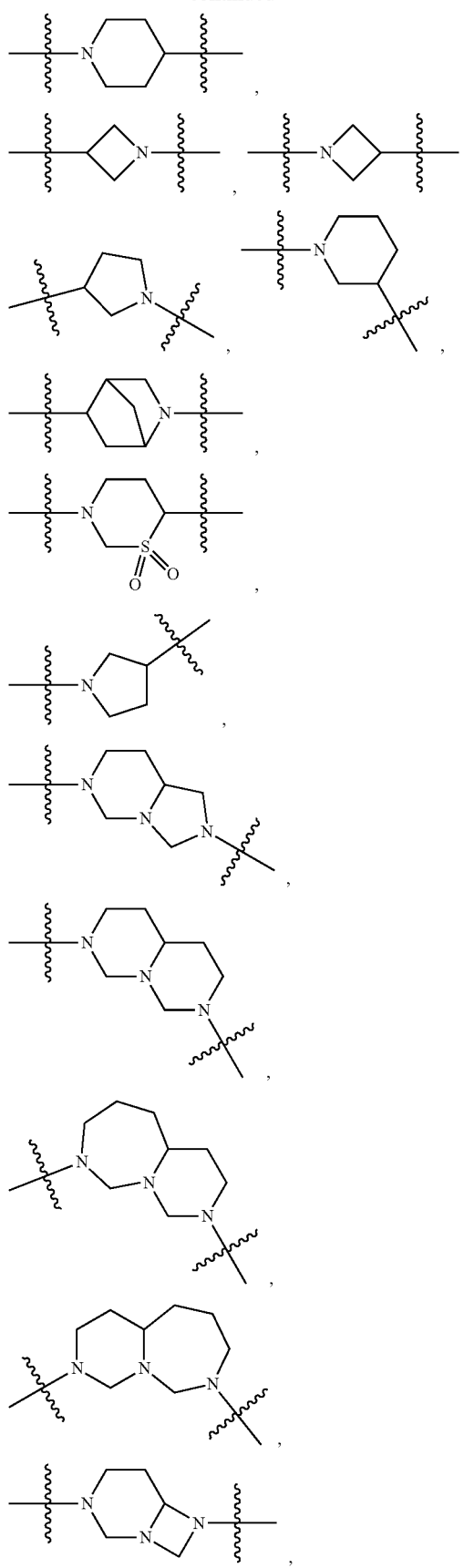
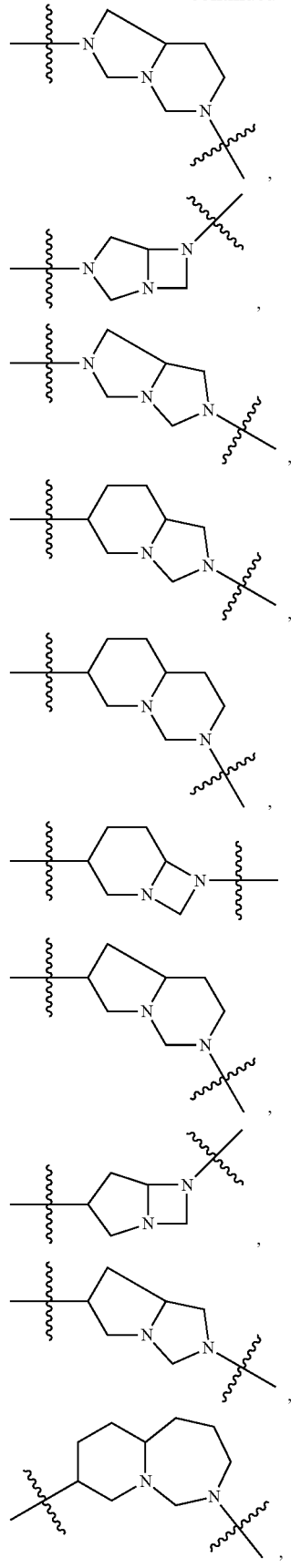

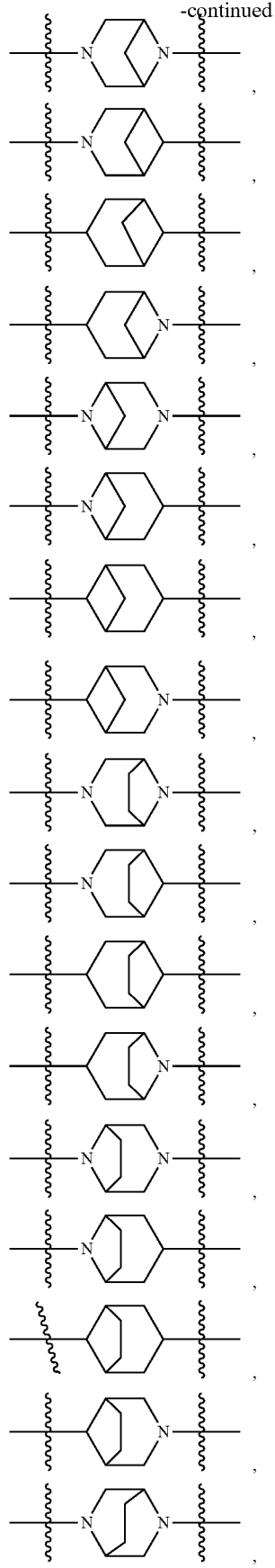
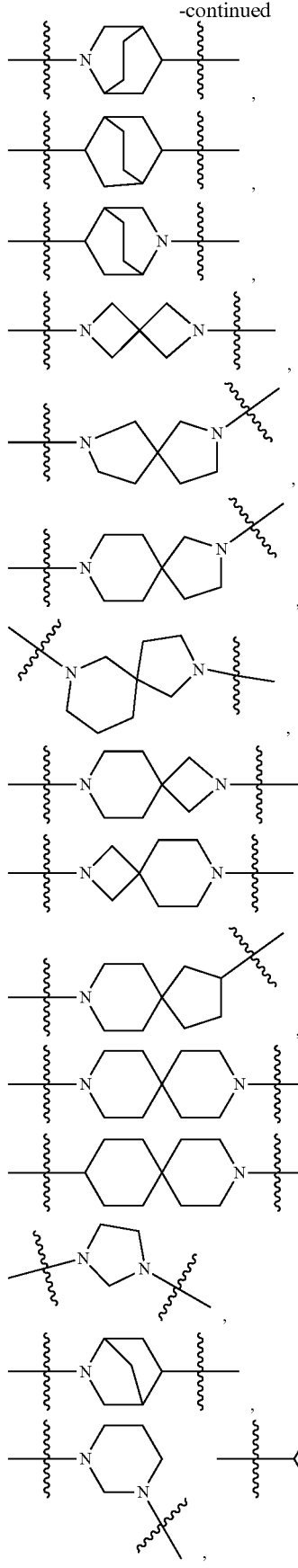

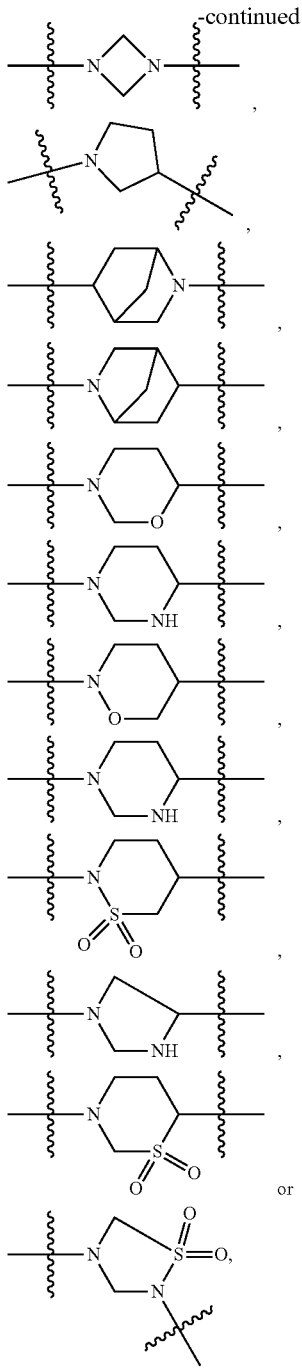

wherein each sub-formula of A is independently and optionally substituted by 1, 2, 3 or 4 substituents selected from F, Cl, Br, oxo, NR⁵R⁶, R⁵O—, R⁵(C=O)NR⁶—, NR⁵R⁶C₁₋₄ alkyl, NR⁶R⁷C₁₋₄ alkoxy, C₁₋₄ alkyl, C₁₋₄ haloalkyl, 3-10 membered Cyc, 3-10 membered hetCyc, 3-10 membered hetCyc-C₁₋₄ alkyl, 3-10 membered hetCyc-C₁₋₄ alkoxy C₁₋₄ alkyl, C₃₋₆ cycloalkylidene and 3-6 membered heterocyclylidene.

In some embodiments, each sub-formula of A is independently and optionally substituted by 1, 2, 3 or 4 substituents selected from F, Cl, Br, oxo, NH₂, NHCH₃, NH(CH₂)₃CH₃, N(CH₃)₂, benzyl OCH₂NH—, benzyl (C=O)NH—, pyridylmethyl (C=O)NH—, CH₃CH₂(C=O)NH—, methoxy, ethoxy, n-propoxy, isopropoxy, n-butoxy, isobutoxy, phenoxy-(CH₂)₂O—, NH₂(CH₂)₂O—, N(CH₃)₂(CH₂)₂ O—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, methoxymethyl, methoxyethyl, ethoxymethyl, cyclopropylidene, cyclobutylidene, cyclopentylidene, cyclohexylidene, azetidinylidene, oxetanylidene, pyrrolidinylidene and pyrazolidinylidene.

In some embodiments, M is —(C=O)—, C₁₋₆ alkyl, C₂₋₆ alkenyl, C₂₋₆ alkynyl, C₁₋₆ alkyl-C₆₋₁₀ aryl, C₁₋₆ alkyl-(5-10 membered heteroaryl), C₂₋₆ alkenyl-C₆₋₁₀ aryl, C₂₋₆ alkynyl-C₆₋₁₀ aryl, C₂₋₆ alkenyl-(5-10 membered heteroaryl), C₂₋₆ alkynyl-(5-10 membered heteroaryl), C₆₋₁₀ aryl, 5-10 membered heteroaryl, 3-12 membered hetCyc, 3-12 membered Cyc, C₆₋₁₀ aryl-C₁₋₆ alkyl, (5-10 membered heteroaryl)-C₁₋₆ alkyl, (3-12 membered hetCyc)-C₁₋₆ alkyl or (3-12 membered Cyc)-C₁₋₆ alkyl, wherein each of C₁₋₆ alkyl, C₂₋₆ alkenyl, C₂₋₆ alkynyl, C₁₋₆ alkyl-C₆₋₁₀ aryl, C₁₋₆ alkyl-(5-10 membered heteroaryl), C₂₋₆ alkenyl-C₆₋₁₀ aryl, C₂₋₆ alkynyl-C₆₋₁₀ aryl, C₂₋₆ alkenyl-(5-10 membered heteroaryl), C₂₋₆ alkynyl-(5-10 membered heteroaryl), C₆₋₁₀ aryl, 5-10 membered heteroaryl, 3-12 membered hetCyc, 3-12 membered Cyc, C₆₋₁₀ aryl-C₁₋₆ alkyl, (5-10 membered heteroaryl)-C₁₋₆ alkyl, (3-12 membered hetCyc)-C₁₋₆ alkyl and (3-12 membered Cyc)-C₁₋₆ alkyl is independently and optionally substituted by 1, 2, 3 or 4 substituents selected from F, Cl, Br, OH, NR⁵R⁶, oxo, C₁₋₆ alkoxy, C₃₋₆ cycloalkylidene, 3-6 membered heterocyclylidene, hydroxy C₁₋₆ alkyl, C₁₋₆ alkyl, C₃₋₆ cycloalkyl and 3-7 membered heterocyclic group.

In some embodiments, M is —(C=O)—, C₁₋₄ alkyl, C₂₋₄ alkenyl, C₂₋₄ alkynyl, C₁₋₄ alkylphenyl, C₁₋₄ alkyl-(5-10 membered heteroaryl), C₂₋₄ alkenylphenyl, C₂₋₄ alkynylphenyl, C₂₋₄ alkenyl-(5-10 membered heteroaryl), C₂₋₄ alkynyl-(5-10 membered heteroaryl), phenyl, 5-10 membered heteroaryl, 3-10 membered hetCyc, 3-10 membered Cyc, phenyl-C₁₋₄ alkyl, (5-10 membered heteroaryl)-C₁₋₄ alkyl, (3-10 membered hetCyc)-C₁₋₄-alkyl or (3-10 membered Cyc)-C₁₋₄ alkyl, wherein each of C₁₋₄ alkyl, C₂₋₄ alkenyl, C₂₋₄ alkynyl, C₁₋₄ alkylphenyl, C₁₋₄ alkyl-(5-10 membered heteroaryl), C₂₋₄ alkenylphenyl, C₂₋₄ alkynylphenyl, C₂₋₄ alkenyl-(5-10 membered heteroaryl), C₂₋₄ alkynyl-(5-10 membered heteroaryl), phenyl, 5-10 membered heteroaryl, 3-10 membered hetCyc, 3-10 membered Cyc, phenyl-C₁₋₄ alkyl, (5-10 membered heteroaryl)-C₁₋₄ alkyl, (3-10 membered hetCyc)-C₁₋₄-alkyl and (3-10 membered Cyc)-C₁₋₄ alkyl is independently optionally substituted by 1, 2, 3 or 4 substituents selected from F, Cl, Br, OH, CF₃, NR⁵R⁶, oxo, C₁₋₄ alkoxy, C₃₋₆ cycloalkylidene, 3-6 membered heterocyclylidene, hydroxy C₁₋₄ alkyl, C₁₋₄ alkyl, C₃₋₆ cycloalkyl and 3-6 membered heterocyclic group.

In some embodiments, M is —(C=O)—, —CH₂—, —(CH₂)₂—, —(CH₂)₃—, —(CH₂)₄—, —CH=CH₂—, —CH₂CH=CH—, —CH₂CH=CHCH₂—, —C≡C—, —CH₂CH≡CH—, —CH₂CH≡CHCH₂—, —CH=CH-phenyl, —CH₂CH=CH-phenyl, —CH₂CH=CH—CH₂-phenyl, —C≡C-phenyl, —CH₂C≡C-phenyl, —CH₂C≡C—CH₂-phenyl, —CH=CH-pyridyl, —CH₂CH=CH-pyridyl, —CH₂CH=CH—CH₂-pyridyl, —CH=CH-pyrazolyl, —CH₂CH=CH-pyrazolyl, —CH=CH-pyrimidinyl, —CH=CH-pyrazinyl, —CH=CH-benzimidazolyl, —CH=CH-benzopyrazolyl, —C≡C-pyridyl, —CH₂C≡C-pyridyl, —CH₂C≡C—CH₂-pyridyl, —C≡C-pyrazolyl, —CH₂C≡C-pyrazolyl, —C≡C-pyrimidinyl, —C≡C-pyrazinyl, —C≡C-benzimidazolyl, —C≡C-benzopyrazolyl, phenyl, pyridyl, pyrimidinyl, pyrazinyl, imidazolyl, pyrazolyl, —CH$_2$-pyridyl, —CH$_2$CH$_2$-pyridyl, —CH$_2$-phenyl, —CH$_2$CH$_2$-phenyl, —CH$_2$-pyrimidinyl, —CH$_2$-pyrazinyl, —CH$_2$-imidazolyl, —CH$_2$-pyrazolyl, phenyl-CH$_2$—, phenyl-CH$_2$CH$_2$—, pyridyl-CH$_2$—, pyridyl-CH$_2$CH$_2$—, pyrimidinyl-CH$_2$—, pyrazinyl-CH$_2$—, imidazolyl-CH$_2$— or pyrazolyl-CH$_2$—, wherein each of —CH$_2$—, —(CH$_2$)$_2$—, —(CH$_2$)$_3$—, —(CH$_2$)$_4$—, —CH═CH—, —CH$_2$CH═CH—, —CH$_2$CH═CHCH$_2$—, —C≡C—, —CH═CH-phenyl, —CH$_2$CH═CH-phenyl, —CH$_2$CH═CH—CH$_2$-phenyl, —C≡C-phenyl, —CH$_2$C≡C-phenyl, —CH$_2$C≡C—CH$_2$-phenyl, —CH═CH-pyridyl, —CH$_2$CH═CH-pyridyl, —CH$_2$CH═CH—CH$_2$-pyridyl, —CH═CH-pyrazolyl, —CH$_2$CH═CH-pyrazolyl, —CH═CH-pyrimidinyl, —CH═CH-pyrazinyl, —CH═CH-benzimidazolyl, —CH═CH-benzopyrazolyl, —C≡C-pyridyl, —CH$_2$C≡C-pyridyl, —CH$_2$C≡C—CH$_2$-pyridyl, —C≡C-pyrazolyl, —CH$_2$C≡C-pyrazolyl, —C≡C-pyrimidinyl, —C≡C-pyrazinyl, —C≡C-benzimidazolyl, —C≡C-benzopyrazolyl, phenyl, pyridyl, pyrimidinyl, pyrazinyl, imidazolyl, pyrazolyl, —CH$_2$-pyridyl, —CH$_2$CH$_2$-pyridyl, —CH$_2$-phenyl, —CH$_2$CH$_2$-phenyl, —CH$_2$-pyrimidinyl, —CH$_2$-pyrazinyl, —CH$_2$-imidazolyl, —CH$_2$-pyrazolyl, phenyl-CH$_2$—, phenyl-CH$_2$CH$_2$—, pyridyl-CH$_2$—, pyridyl-CH$_2$CH$_2$—, pyrimidinyl-CH$_2$—, pyrazinyl-CH$_2$—, imidazolyl-CH$_2$— and pyrazolyl-CH$_2$— is independently optionally substituted by 1, 2, 3 or 4 substituents selected from F, Cl, Br, OH, CF$_3$, NH$_2$, oxo, methoxy, ethoxy, n-propoxy, isopropoxy, cyclopropylidene, cyclobutylidene, cyclopentylidene, azetidinylidene, hydroxymethyl, hydroxyethyl, 2-hydroxy-2-propyl, methyl, ethyl, n-propyl, isopropyl, n-butyl, isobutyl, tert-butyl, cyclopropyl, cyclobutyl, cyclopentyl, pyrrolidinyl, morpholinyl.

In some embodiments, R$^3$ is H, D, C$_{1-6}$ alkyl, C$_{2-6}$ alkynyl, 3-12 membered Cyc, 3-12 membered hetCyc, C$_{6-10}$ aryl, 5-10 membered heteroaryl, (3-12 membered Cyc)-C$_{1-6}$ alkyl, (3-12 membered hetCyc)-C$_{1-6}$ alkyl, C$_{1-6}$ alkoxy C$_{1-6}$ alkyl, C$_{6-10}$ aryl C$_{1-6}$ alkyl, (5-10 membered heteroaryl) C$_{1-6}$ alkyl or amino C$_{1-6}$ alkyl, wherein each of C$_{1-6}$ alkyl, C$_{2-6}$ alkynyl, 3-12 membered Cyc, 3-12 membered hetCyc, C$_{6-10}$ aryl, 5-10 membered heteroaryl, (3-12 membered Cyc)-C$_{1-6}$ alkyl, (3-12 membered hetCyc)-C$_{1-6}$ alkyl, C$_{1-6}$ alkoxy C$_{1-6}$ alkyl, C$_{6-10}$ aryl C$_{1-6}$ alkyl, (5-10 membered heteroaryl) C$_{1-6}$ alkyl and amino C$_{1-6}$ alkyl is independently and optionally substituted by 1, 2, 3 or 4 substituents selected from F, Cl, Br, NR$^5$R$^6$, R$^5$O—, R$^5$O(C═O)—, R$^5$(C═O)—, NR$^5$R$^6$(C═O)NR$^5$—, R$^5$S(═O)$_2$—, NO$_2$, CN, CF$_3$, C$_{1-6}$ alkyl and C$_{3-6}$ cycloalkyl.

In some embodiments, R$^3$ is H, D, C$_{1-4}$ alkyl, C$_{2-4}$ alkynyl, 3-10 membered Cyc, 3-10 membered hetCyc, phenyl, 5-10 membered heteroaryl, (3-10 membered Cyc)-C$_{1-4}$ alkyl, (3-10 membered hetCyc)-C$_{1-4}$ alkyl, C$_{1-4}$ alkoxy C$_{1-4}$ alkyl, phenyl C$_{1-4}$ alkyl, (5-10 membered heteroaryl)-C$_{1-4}$ alkyl or amino C$_{1-4}$ alkyl, wherein each of C$_{1-4}$ alkyl, C$_{2-4}$ alkynyl, 3-10 membered Cyc, 3-10 membered hetCyc, phenyl, 5-10 membered heteroaryl, (3-10 membered Cyc)-C$_{1-4}$ alkyl, (3-10 membered hetCyc)-C$_{1-4}$ alkyl, C$_{1-4}$ alkoxy C$_{1-4}$ alkyl, phenyl C$_{1-4}$ alkyl, (5-10 membered heteroaryl)-C$_{1-4}$ alkyl or amino C$_{1-4}$ alkyl is independently and optionally substituted by 1, 2, 3 or 4 substituents selected from F, Cl, Br, NR$^5$R$^6$, R$^5$O—, R$^5$O(C═O)—, R$^5$(C═O)—, NR$^5$R$^6$(C═O)NR$^5$—, R$^5$S(═O)$_2$—, NO$_2$, CN, CF$_3$, C$_{1-4}$ alkyl and C$_{3-6}$ cycloalkyl.

In some embodiments, R$^3$ is H, D, methyl, ethyl, n-propyl, isopropyl, n-butyl, isobutyl, tert-butyl, ethynyl, trifluoromethyl, cyclopropyl, cyclobutyl, cyclopentyl, cyclohexyl, cyclopentylmethyl, cyclopropylmethyl, cyclobutylmethyl, cyclohexylmethyl, spiro[4.4]decylmethyl, bicyclo[3.3.0]octyl, pyrrolidinyl, azetidinyl, piperidinyl, morpholinyl, azetidinylmethyl, piperidinylmethyl, morpholinylmethyl, methoxymethyl, methoxyethyl, ethoxymethyl, ethoxyethyl, n-propoxymethyl, isopropoxymethyl, isopropoxyethyl, n-butoxymethyl, isobutoxymethyl, tert-butoxymethyl, tert-butoxy ethyl, phenyl, pyridyl, imidazolyl, pyrazolyl, pyrimidinyl, 3H-indolyl, indolyl, benzimidazolyl, 3,8a-dihydroindolizinyl, phenylmethyl, 3,8a-dihydroindolizinylmethyl, pyridylmethyl, imidazolylmethyl, pyrazolylmethyl, pyrimidinylmethyl, 3H-indolylmethyl, indolylmethyl, benzimidazolylmethyl, NH$_2$CH$_2$—, NH(CH$_3$)CH$_2$—, N(CH$_3$)$_2$CH$_2$—, NH$_2$(CH$_2$)$_2$—, NH(CH$_3$)CH$_2$—, NH(CH$_3$)(CH$_2$)$_2$— or N(CH$_3$)$_2$(CH$_2$)$_2$—, wherein each of methyl, ethyl, n-propyl, isopropyl, n-butyl, isobutyl, tert-butyl, ethynyl, trifluoromethyl, cyclopropyl, cyclobutyl, cyclopentyl, cyclohexyl, cyclopentylmethyl, cyclopropylmethyl, cyclobutylmethyl, cyclohexylmethyl, spiro[4.4]decylmethyl, bicyclo[3.3.0]octyl, pyrrolidinyl, azetidinyl, piperidinyl, morpholinyl, azetidinylmethyl, piperidinylmethyl, morpholinylmethyl, methoxymethyl, methoxyethyl, ethoxymethyl, ethoxyethyl, n-propoxymethyl, isopropoxymethyl, isopropoxyethyl, n-butoxymethyl, isobutoxymethyl, tert-butoxy methyl, tert-butoxy ethyl, phenyl, pyridyl, imidazolyl, pyrazolyl, pyrimidinyl, 3H-indolyl, indolyl, benzimidazolyl, 3,8a-dihydroindolizinyl, phenylmethyl, 3,8a-dihydroindolizinylmethyl, pyridylmethyl, imidazolylmethyl, pyrazolylmethyl, pyrimidinylmethyl, 3H-indolylmethyl, indolylmethyl, benzimidazolylmethyl, NH$_2$CH$_2$—, NH(CH$_3$)CH$_2$—, N(CH$_3$)$_2$CH$_2$—, NH$_2$(CH$_2$)$_2$—, NH(CH$_3$)CH$_2$—, NH(CH$_3$)(CH$_2$)$_2$— and N(CH$_3$)$_2$(CH$_2$)$_2$— is independently and optionally substituted by 1, 2, 3 or 4 substituents selected from F, Cl, Br, OH, NH$_2$, NO$_2$, CN, CF$_3$, C(CH$_3$)$_3$O(C═O)—, CH$_3$(C═O)—, NH$_2$(C═O)NH—, NHCH$_3$(C═O)NH—, CH$_3$S(═O)$_2$—, methyl, methoxy, ethoxy, n-propoxy, isopropoxy, phenoxy, pyridyloxy, cyclopropyl, cyclobutyl, cyclopentyl and cyclohexyl.

In some embodiments, R$^1$ is H, D, CN, F, Cl, Br, methyl, ethyl, n-propyl, isopropyl, n-butyl, isobutyl, tert-butyl, cyclopropyl, cyclobutyl, cyclopentyl or cyclohexyl, wherein each of methyl, ethyl, n-propyl, isopropyl, n-butyl, isobutyl, tert-butyl, cyclopropyl, cyclobutyl, cyclopentyl and cyclohexyl is independently and optionally substituted by 1, 2, 3 or 4 substituents selected from F, Cl, Br, CN, NH$_2$, OH and NO$_2$.

In some embodiments, R$^4$ is H, D, F, Cl, Br, CN, methyl, ethyl, n-propyl, isopropyl, n-butyl, isobutyl, tert-butyl-methoxy, ethoxy, n-propoxy, isopropoxy, n-butoxy, isobutoxy or tert-butoxy, wherein each of methyl, ethyl, n-propyl, isopropyl, n-butyl, isobutyl, tert-butylmethoxy, ethoxy, n-propoxy, isopropoxy, n-butoxy, isobutoxy and tert-butoxy is independently and optionally substituted by 1, 2, 3 or 4 substituents selected from F, Cl, Br, CN, NH$_2$, OH and NO$_2$.

In some embodiments, R$^5$ is H, D, C$_{1-6}$ alkyl, 3-12 membered Cyc, 3-12 membered hetCyc, C$_{6-10}$ aryl, 5-10 membered heteroaryl, C$_{6-10}$ aryl C$_{1-6}$ alkyl, (5-10 membered heteroaryl)-C$_{1-6}$ alkyl, C$_{1-6}$ alkoxy C$_{1-6}$ alkyl, C$_{6-10}$ aryloxy C$_{1-6}$ alkyl, amino C$_{1-6}$ alkyl, C$_{1-6}$ alkylamino C$_{1-6}$ alkyl, di(C$_{1-6}$ alkyl)amino C$_{1-6}$ alkyl, (3-12 membered Cyc)-C$_{1-6}$ alkyl or (3-12 membered hetCyc)-C$_{1-6}$ alkyl, wherein each of C$_{1-6}$ alkyl, 3-12 membered Cyc, 3-12 membered hetCyc, C$_{6-10}$ aryl, 5-10 membered heteroaryl, C$_{6-10}$ aryl C$_{1-6}$ alkyl, (5-10 membered heteroaryl)-C$_{1-6}$ alkyl, C$_{1-6}$ alkoxy C$_{1-6}$ alkyl, C$_{6-10}$ aryloxy C$_{1-6}$ alkyl, amino C$_{1-6}$ alkyl, C$_{1-6}$ alkylamino C$_{1-6}$ alkyl, di(C$_{1-6}$ alkyl)amino C$_{1-6}$ alkyl, (3-12 membered Cyc)-$C_{1-6}$ alkyl and (3-12 membered hetCyc)-$C_{1-6}$ alkyl is independently and optionally substituted by 1, 2, 3 or 4 substituents selected from F, Cl, Br, OH, $NR^6R^7$, $C_{1-6}$ alkyl, $C_{1-6}$ alkylsulfonyl, $C_{1-6}$ alkoxy, $C_{6-10}$ aryl and 5-10 membered heteroaryl.

In some embodiments, $R^6$ is H, D or $C_{1-6}$ alkyl.

In some embodiments, $R^7$ is H, D, $C_{1-6}$ alkyl, $C_{6-10}$ aryl $C_{1-6}$ alkyl or (5-10 membered heteroaryl) $C_{1-6}$ alkyl.

In some embodiments, $R^5$ is H, D, $C_{1-4}$ alkyl, 3-10 membered Cyc, 3-10 membered hetCyc, phenyl, 5-10 membered heteroaryl, phenyl $C_{1-4}$ alkyl, (5-10 membered heteroaryl)-$C_{1-4}$ alkyl, $C_{1-4}$ alkoxy $C_{1-4}$ alkyl, phenoxy $C_{1-4}$ alkyl, amino $C_{1-4}$ alkyl, $C_{1-4}$ alkylamino $C_{1-4}$ alkyl, di($C_{1-4}$ alkyl)amino $C_{1-4}$ alkyl, (3-10 membered Cyc)-$C_{1-4}$ alkyl or hetCyc-$C_{1-4}$ alkyl, wherein each of $C_{1-4}$ alkyl, 3-10 membered Cyc, 3-10 membered hetCyc, phenyl, 5-10 membered heteroaryl, phenyl $C_{1-4}$ alkyl, (5-10 membered heteroaryl)-$C_{1-4}$ alkyl, $C_{1-4}$ alkoxy $C_{1-4}$ alkyl, phenoxy $C_{1-4}$ alkyl, amino $C_{1-4}$ alkyl, $C_{1-4}$ alkylamino $C_{1-4}$ alkyl, di($C_{1-4}$ alkyl)amino $C_{1-4}$ alkyl, (3-10 membered Cyc)-$C_{1-4}$ alkyl and hetCyc-$C_{1-4}$ alkyl is independently and optionally substituted by 1, 2, 3 or 4 substituents selected from F, Cl, Br, OH, $NR^6R^7$, $C_{1-6}$ alkyl, $C_{1-4}$ alkylsulfonyl, $C_{1-4}$ alkoxy, phenyl and 5-10 membered heteroaryl.

In some embodiments, $R^6$ is H, D or $C_{1-4}$ alkyl.

In some embodiments, $R^7$ is H, D, $C_{1-4}$ alkyl, phenyl $C_{1-4}$ aryl or (5-10 membered heteroaryl) $C_{1-4}$ alkyl.

In some embodiments, $R^5$ is H, D, $NH_2CH_2-$, $NH_2(CH_2)_2-$, $NH(CH_3)CH_2-$, $NH(CH_3)(CH_2)_2-$, $N(CH_3)_2CH_2-$, $NH(CH_3)_2(CH_2)_2-$, methyl, ethyl, n-propyl, isopropyl, n-butyl, isobutyl, tert-butyl, cyclopropyl, cyclobutyl, cyclopentyl, cyclohexyl, cyclopropylmethyl, cyclopropylethyl, cyclobutylethyl, cyclobutylmethyl, cyclopentylmethyl, cyclopentylethyl, cyclohexylmethyl, cyclohexylethyl, methoxymethyl, methoxyethyl, ethoxyethyl, phenylmethyl, phenylethyl, phenyl-n-propyl, pyridylmethyl, pyridylethyl, pyridyl-n-propyl, phenoxymethyl, phenoxyethyl, phenoxy-/z-propyl, azetidinyl, oxetanyl or tetrahydropyranyl, wherein each of $NH_2CH_2-$, $NH_2(CH_2)_2-$, $NH(CH_3)CH_2-$, $NH(CH_3)(CH_2)_2-$, $N(CH_3)_2CH_2-$, $NH(CH_3)_2(CH_2)_2-$, methyl, ethyl, n-propyl, isopropyl, n-butyl, isobutyl, tert-butyl, cyclopropyl, cyclobutyl, cyclopentyl, cyclohexyl, cyclopropylmethyl, cyclopropylethyl, cyclobutylethyl, cyclobutylmethyl, cyclohexylmethyl, cyclopentylmethyl, cyclopentylethyl, cyclohexylmethyl, cyclohexylethyl, methoxymethyl, methoxyethyl, ethoxyethyl, phenylmethyl, phenylethyl, phenyl-/z-propyl, pyridylmethyl, pyridylethyl, pyridyl-n-propyl, phenoxymethyl, phenoxyethyl, phenoxy-/z-propyl, azetidinyl, oxetanyl and tetrahydropyranyl is independently and optionally substituted by 1, 2, 3 or 4 substituents selected from F, Cl, Br, OH, $NH_2$, $NH(CH_3)$, $CH_3S(=O)_2-$, $CH_3CH_2S(=O)_2-$, $CH(CH_3)_2S(=O)_2-$, $C(CH_3)_3S(=O)_2-$, methyl, ethyl, n-propyl, isopropyl, n-butyl, isobutyl, tert-butyl, methoxy, ethoxy, n-propoxy, phenyl, pyridyl, pyrazolyl and pyrimidinyl.

In some embodiments, $R^6$ is H, D, methyl, ethyl, n-propyl, isopropyl, n-butyl, isobutyl or tert-butyl.

In some embodiments, $R^7$ is H, D, methyl, ethyl, n-propyl, isopropyl, n-butyl, isobutyl, tert-butyl, phenylmethyl, phenylethyl, phenyl-n-propyl, imidazolylmethyl, pyrazolylmethyl, pyridylmethyl, pyridylethyl, pyrimidinylmethyl or pyrimidinylethyl.

In some embodiments, the present invention provides a compound having Formula (I-1), or a stereoisomer, a geometric isomer, a tautomer, an N-oxide, a solvate, a metabolite, a pharmaceutically acceptable salt or a prodrug thereof,

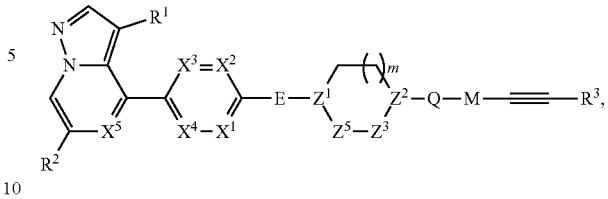

(I-1)

wherein each of $R^1$, $R^2$, $X^1$, $X^2$, $X^3$, $X^4$, $X^5$, E, Q, M and $R^3$ is as defined herein;
each of $Z^1$ and $Z^2$ is independently CH or N;
each of $Z^3$, $Z^5$ is independently a bond, $CH_2$, O, S, NH, C=O, S=O or $S(=O)_2$;
m is 0, 1 or 2;

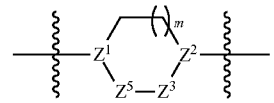

is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene and 3-6 membered heterocyclylidene.

In some embodiments,

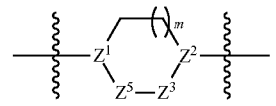

is one of the following sub-formulae:

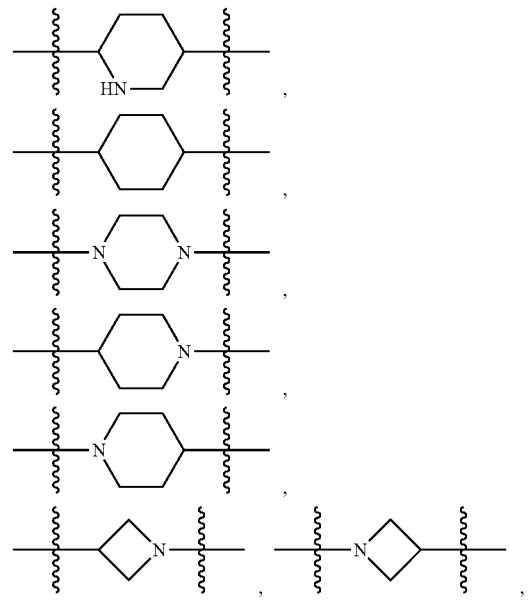

-continued

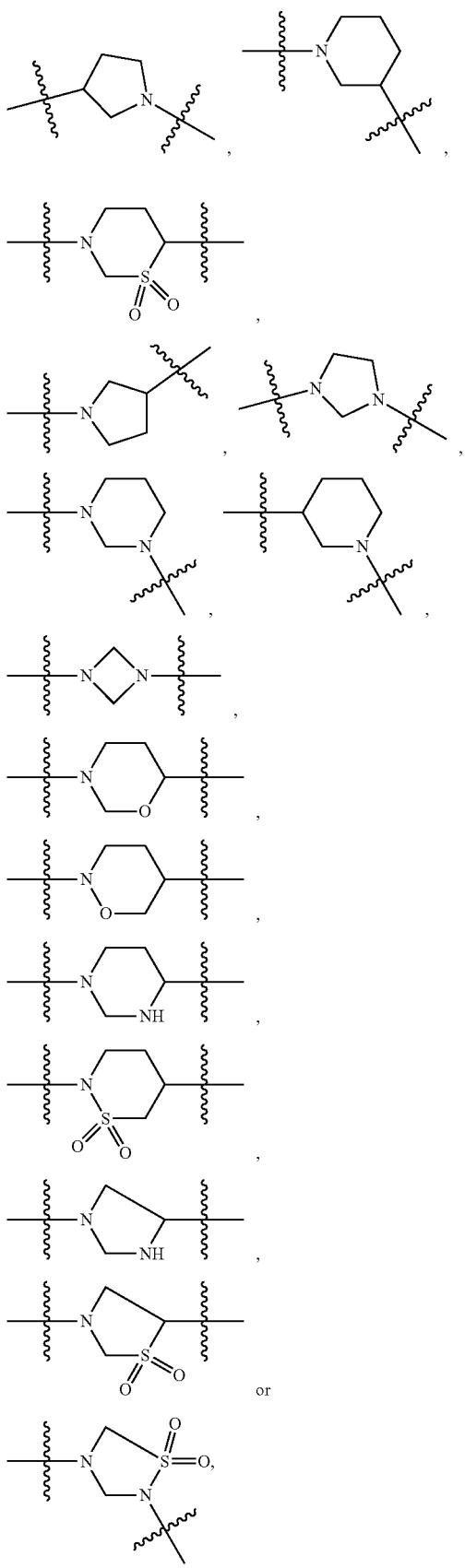

wherein each sub-formula of

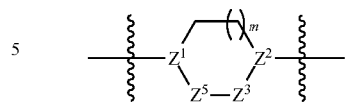

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH—$, benzyl $(C=O)NH—$, pyridylmethyl$(C=O)NH—$, $CH_3CH_2(C=O)NH—$, methoxy, ethoxy, n-propoxy, isopropoxy, n-butoxy, isobutoxy, phenoxy-$(CH_2)_2O—$, $NH_2(CH_2)_2O—$, $N(CH_3)_2(CH_2)_2O—$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxy methyl, methoxy ethyl, ethoxymethyl, cyclopropylidene, cyclobutylidene, cyclopentylidene, cyclohexylidene, azetidinylidene, oxetanylidene and pyrazolylidene.

In some embodiments, the present invention provides a compound having Formula (I-1a), or a stereoisomer, a geometric isomer, a tautomer, an TV-oxide, a solvate, a metabolite, a pharmaceutically acceptable salt or a prodrug thereof,

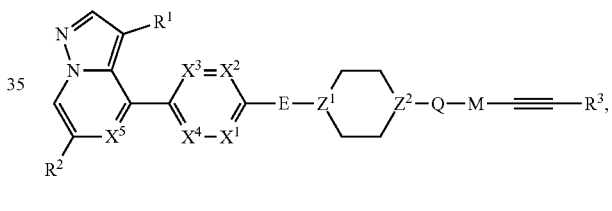

(I-1a)

wherein each of $R^1$, $R^2$, $X^1$, $X^2$, $X^3$, $X^4$, $X^5$, E, Q, M and $R^3$ is as defined herein;

each $Z^1$ and $Z^2$ is independently CH or N;

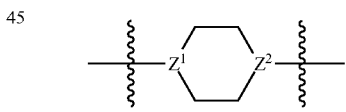

is optionally substituted by 1, 2, 3 or 4 substituents selected from F, Cl, Br, oxo, $NR^5R^6$, $R^5O—$, $R^5(C=O)NR^6—$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene, 3-6 membered heterocyclylidene.

In some embodiments,

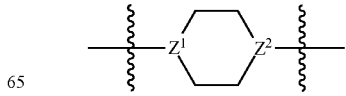

is one of the following sub-formulae:

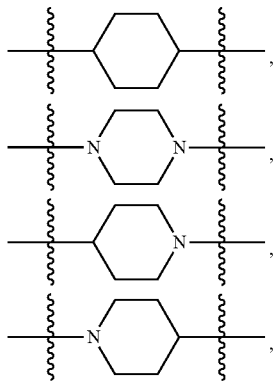

wherein each sub-formula of

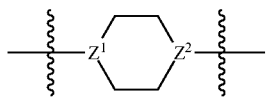

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH$—, benzyl (C=O)NH—, pyridylmethyl (C=O)NH—, $CH_3CH_2$(C=O)NH—, methoxy, ethoxy, n-propoxy, isopropoxy, n-butoxy, isobutoxy, phenoxy-$(CH_2)_2O$—, $NH_2(CH_2)_2O$—, $N(CH_3)_2(CH_2)_2O$—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene and pyrazolidinylidene.

In some embodiments, the present invention provides a compound having Formula (I-2), or a stereoisomer, a geometric isomer, a tautomer, an N-oxide, a solvate, a metabolite, a pharmaceutically acceptable salt or a prodrug thereof,

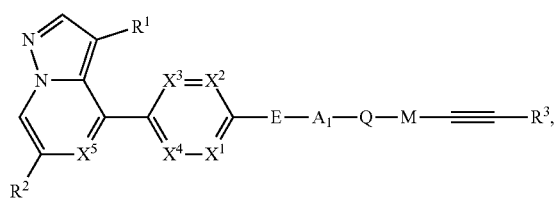

(I-2)

wherein each of $R^4$, $R^2$, $X^1$, $X^2$, $X^2$, $X^4$, $X^5$, E, Q, M and $R^3$ is as defined herein;

$A_1$ is the following substructure:

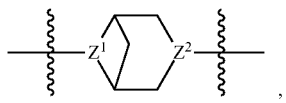

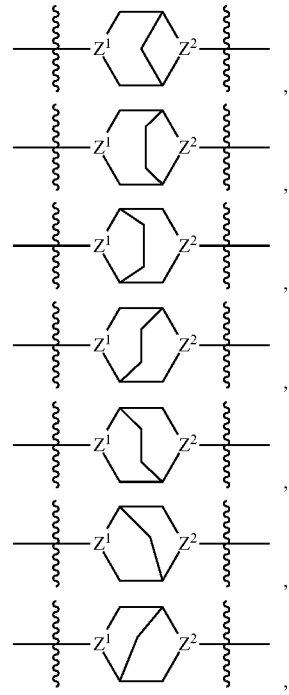

each $Z^1$ and $Z^2$ is independently CH or N;

each sub-formula of $A_1$ is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene and 3-6 membered heterocyclylidene.

In some embodiments, $A_1$ is one of the following sub-formulae:

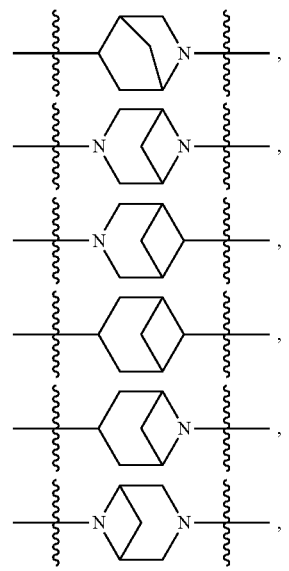

-continued

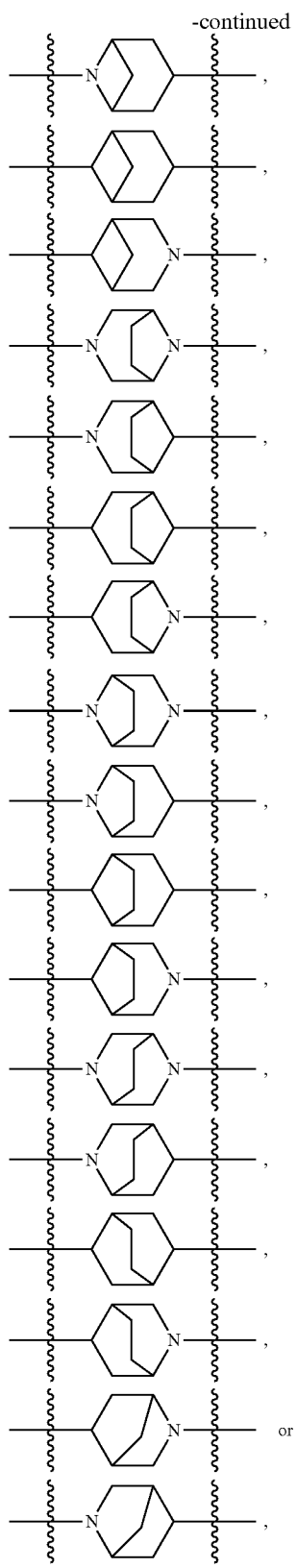

wherein each sub-formula of A₁ is independently and optionally substituted by 1, 2, 3 or 4 substituents selected from F, Cl, Br, oxo, NH₂, NHCH₃, NH(CH₂)₃CH₃, N(CH₃)₂, benzyl OCH₂NH—, benzyl (C=O) NH—, pyridylmethyl (C=O)NH—, CH₃CH₂(C=O)NH—, methoxy, ethoxy, n-propoxy, isopropoxy, n-butoxy, isobutoxy, phenoxy-(CH₂)₂O—, NH₂(CH₂)₂O—, N(CH₃)₂(CH₂)₂O—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, methoxymethyl, methoxyethyl, ethoxymethyl, cyclopropylidene, cyclobutylidene, cyclopentylidene, cyclohexylidene, azetidinylidene, oxetanylidene, pyrrolidinylidene and pyrazolidinylidene.

In some embodiments, the present invention provides a compound having Formula (I-3), or a stereoisomer, a geometric isomer, a tautomer, an N-oxide, a solvate, a metabolite, a pharmaceutically acceptable salt or a prodrug thereof,

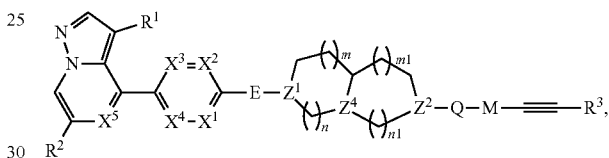

(I-3)

wherein each of R¹, R², X¹, X², X³, X⁴, X⁵, E, Q, M and R³ is as defined herein;

wherein each of Z¹, Z² and Z⁴ is independently CH or N;

m is 0, 1, or 2;

each of n, m1 and n1 is independently 0 or 1;

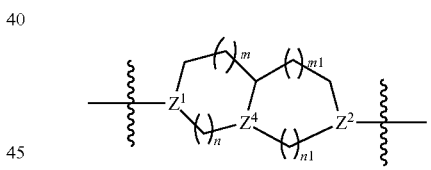

is optionally substituted by 1, 2, 3 or 4 substituents selected from F, Cl, Br, oxo, NR⁵R⁶, R⁵O—, R⁵(C=O)NR⁶—, NR⁵R⁶C₁₋₆ alkyl, NR⁵R⁶(C=O)C₁₋₆ alkoxy C₁₋₆ alkyl, NR⁶R⁷C₁₋₆ alkoxy, NR⁶R⁷C₁₋₆ alkoxy C₁₋₆ alkyl, C₁₋₆alkyl, C₁₋₆ haloalkyl, C₁₋₆ hydroxyalkyl, 3-10 membered Cyc, 3-10 membered hetCyc, 3-10 membered hetCyc-C₁₋₆ alkyl, C₁₋₆ alkoxy C₁₋₆ alkyl, 3-10 membered hetCyc-C₁₋₆ alkoxy C₁₋₆ alkyl, C₃₋₆ cycloalkylidene, 3-6 membered heterocyclylidene.

In some embodiments,

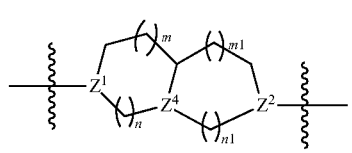

is one of the following sub-formulae:

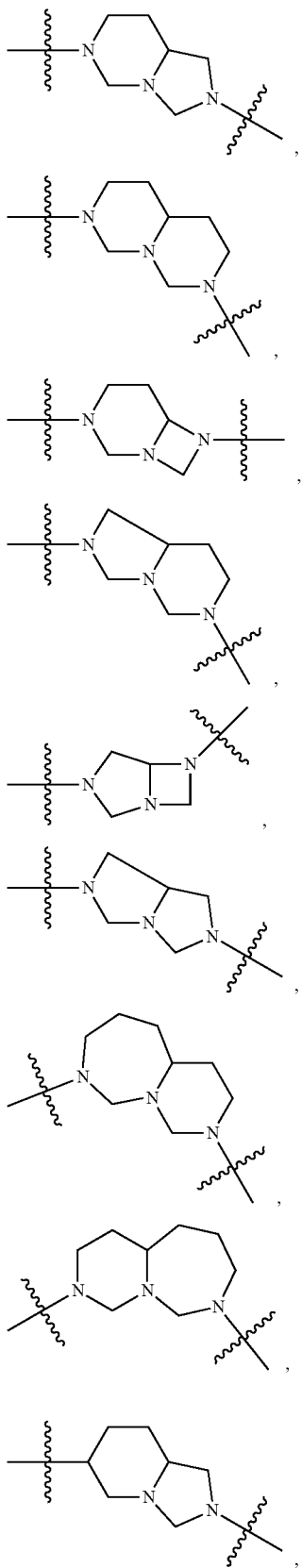

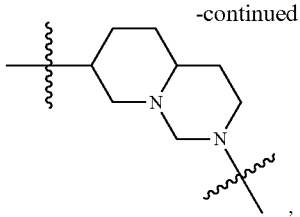

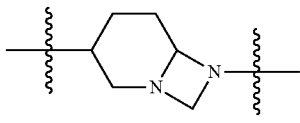

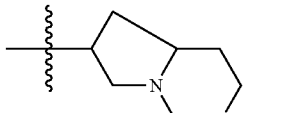

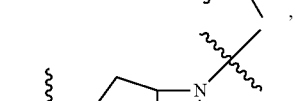

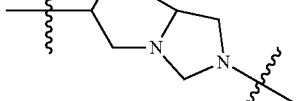

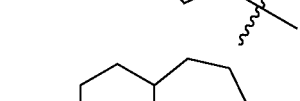

or

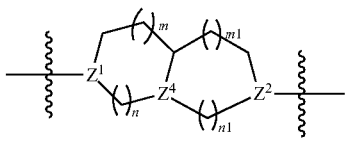

wherein each sub-formula of is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl (C=O)NH—, pyridylmethyl (C=O)NH—, $CH_3CH_2$(C=O)NH—, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene and pyrazolylidene.

In some embodiments, the present invention provides a compound having Formula (I-4), or a stereoisomer, a geometric isomer, a tautomer, an N-oxide, a solvate, a metabolite, a pharmaceutically acceptable salt or a prodrug thereof,

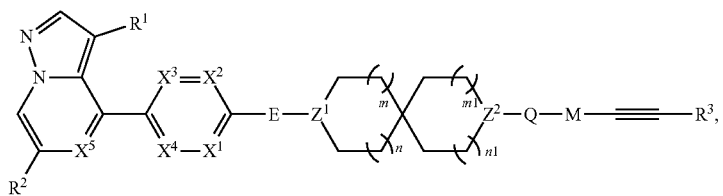
(I-4)

wherein each of R¹, R², X¹, X², X³, X⁴, X⁵, E, Q, M and R³ is as defined herein;

wherein each of Z¹ and Z² is independently CH or N;

m is independently 0, 1, or 2;

each of n, m1 and n1 is independently 0 or 1;

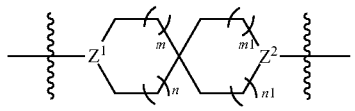

is optionally substituted by 1, 2, 3 or 4 substituents selected from F, Cl, Br, oxo, NR⁵R⁶, R⁵O—, R⁵(C=O)NR⁶—, NR⁵R⁶C$_{1-6}$ alkyl, NR⁵R⁶(C=O)C$_{1-6}$ alkoxy C$_{1-6}$ alkyl, NR⁶R⁷C$_{1-6}$ alkoxy, NR⁶R⁷C$_{1-6}$ alkoxy C$_{1-6}$ alkyl, C$_{1-6}$ alkyl, C$_{1-6}$ haloalkyl, C$_{1-6}$ hydroxyalkyl, 3-10 membered Cyc, 3-10 membered hetCyc, 3-10 membered hetCyc-C$_{1-6}$ alkyl, C$_{1-6}$ alkoxy C$_{1-6}$ alkyl, 3-10 membered hetCyc-C$_{1-6}$ alkoxy C$_{1-6}$ alkyl, C$_{3-6}$ cycloalkylidene, 3-6 membered heterocyclylidene.

In some embodiments,

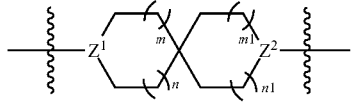

is one of the following sub-formulae:

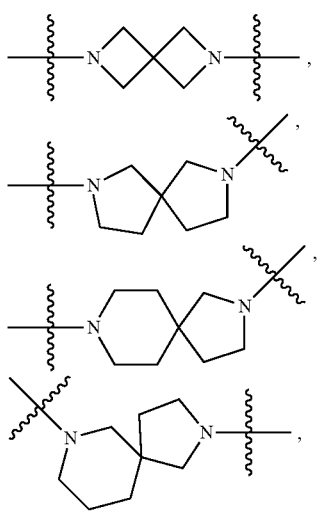

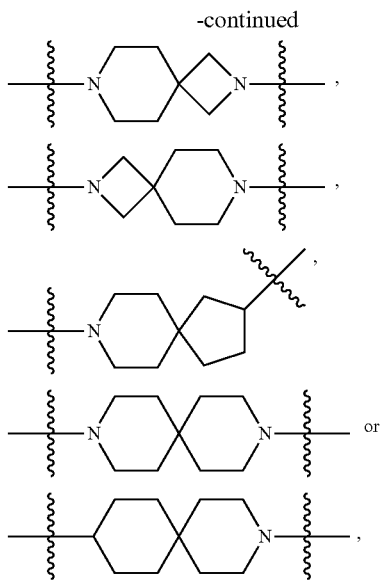

wherein each sub-formula of

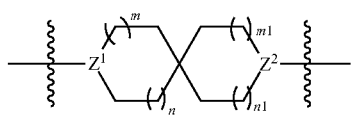

is independently and optionally substituted by 1, 2, 3 or 4 substituents selected from F, Cl, Br, oxo, NH₂, NHCH₃, NH(CH₂)₃CH₃, N(CH₃)₂, benzyl OCH₂NH—, benzyl (C=O)NH—, pyridylmethyl (C=O)NH—, CH₃CH₂ (C=O)NH—, methoxy, ethoxy, n-propoxy, isopropoxy, n-butoxy, isobutoxy, phenoxy-(CH₂)₂O—, NH₂(CH₂)₂O—, N(CH₃)₂(CH₂)₂O—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxy ethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene and pyrazolylidene.

In some embodiments, the compound described herein has one of the following structures, or a stereoisomer, a geometric isomer, a tautomer, an N-oxide, a solvate, a metabolite, a pharmaceutically acceptable salt or a prodrug thereof,

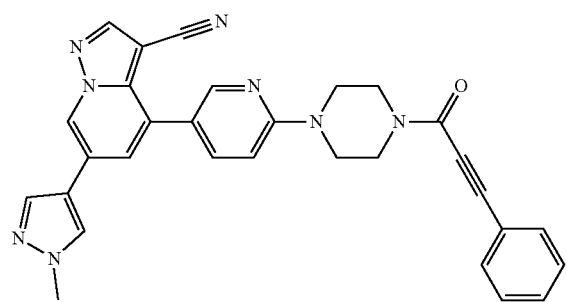
(1)
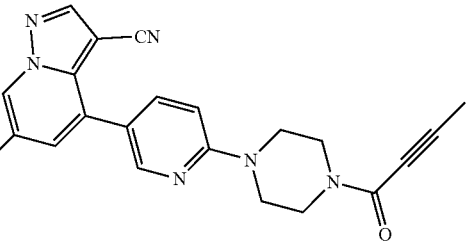
(6)
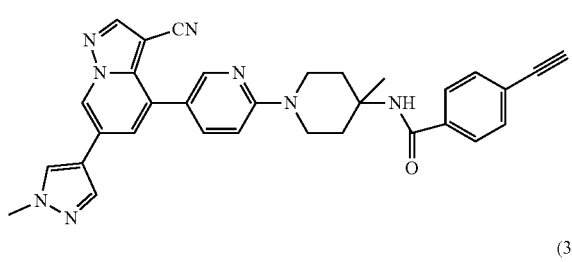
(2)
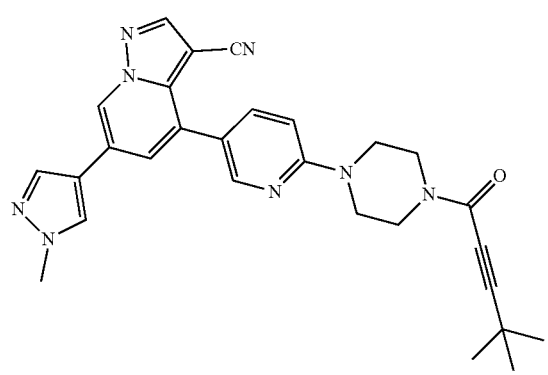
(7)
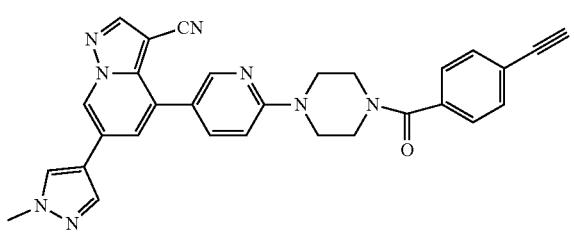
(3)
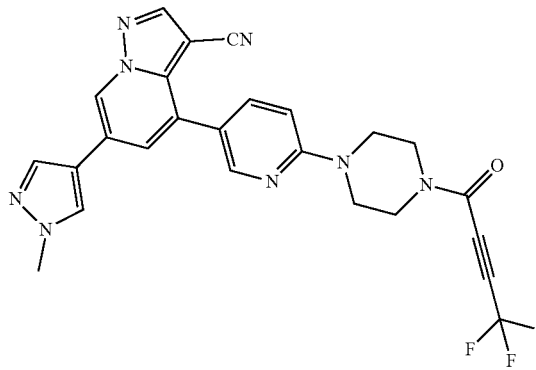
(8)
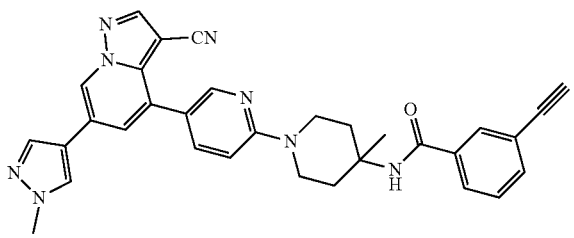
(4)
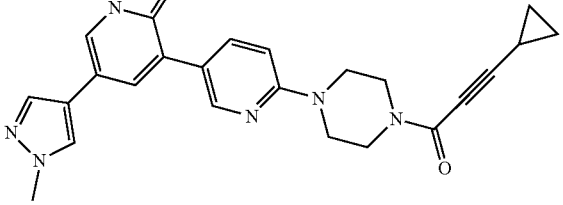
(9)
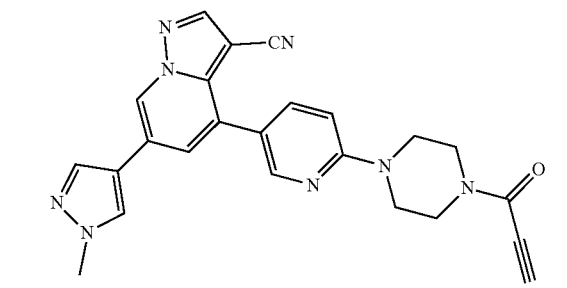
(5)
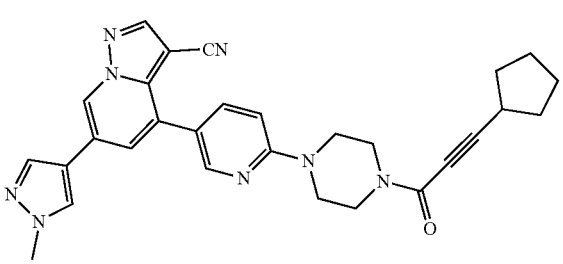
(10)

(11)
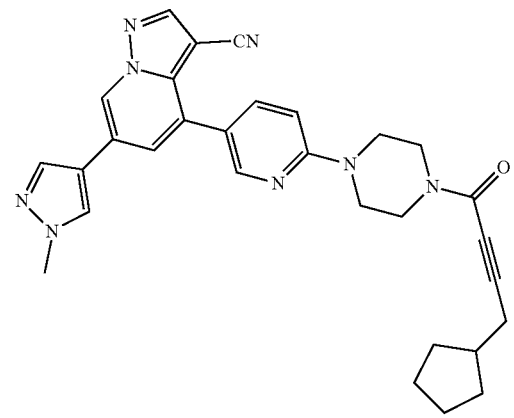
(12)
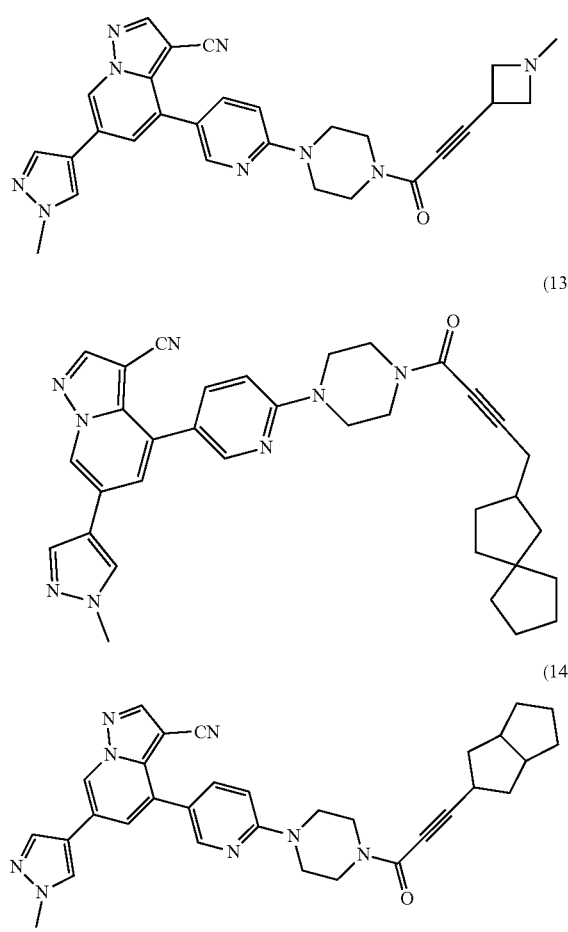
(13)
(14)
(15)
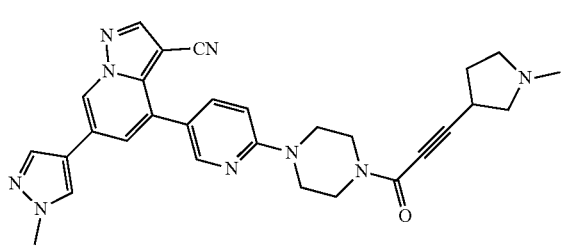
(16)
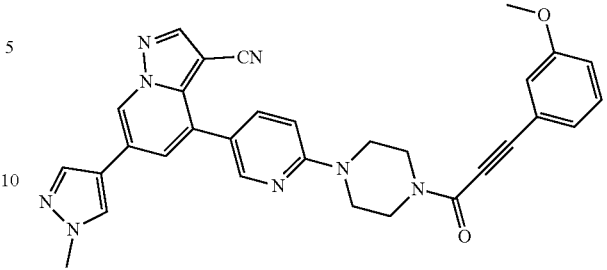
(17)
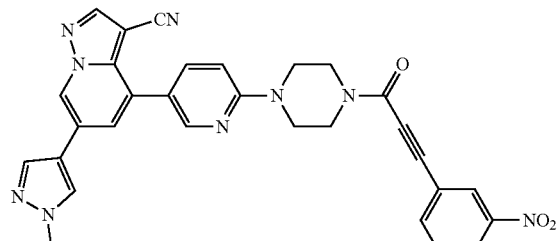
(18)
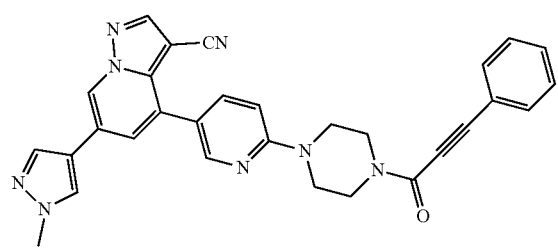
(19)
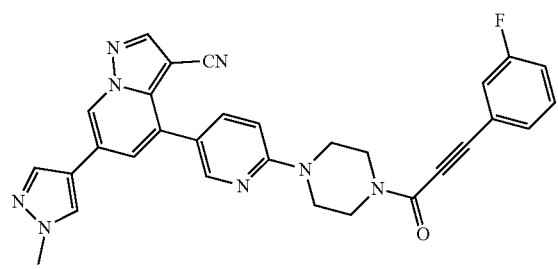
(20)
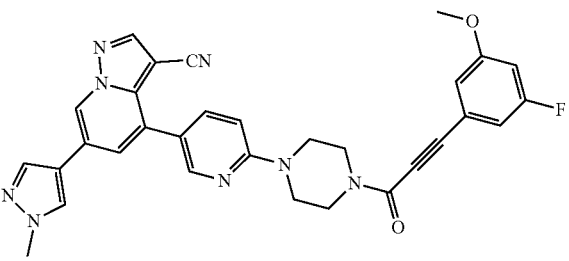

(21) 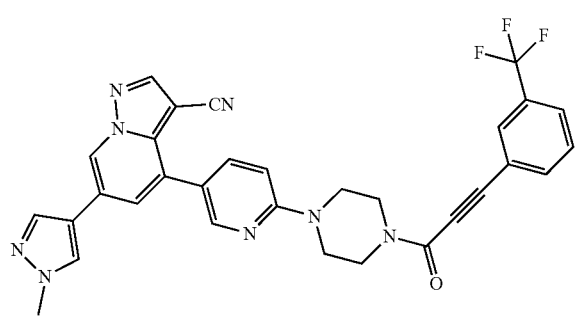
(22) 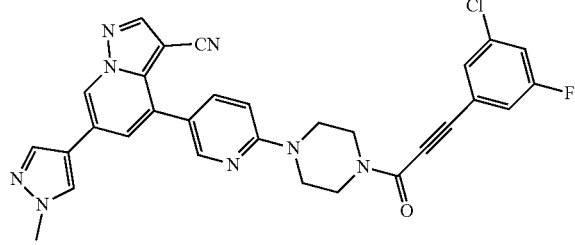
(23) 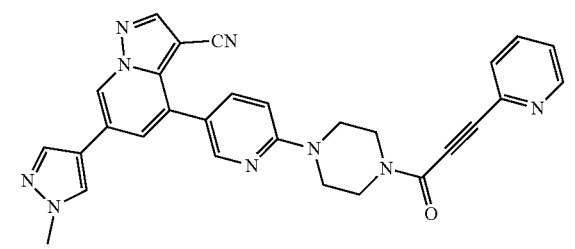
(24) 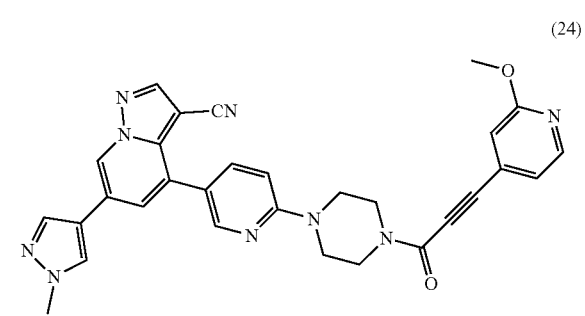
(25) 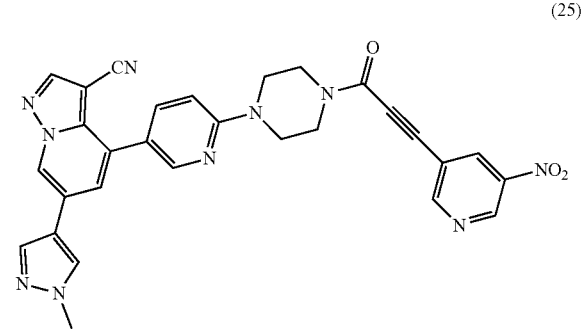
(26) 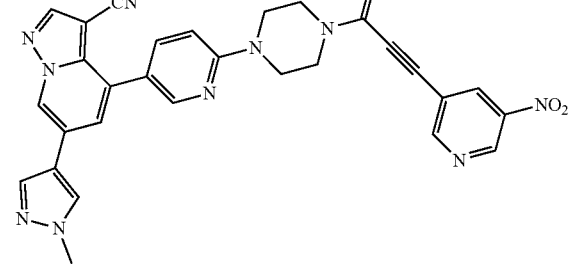
(27) 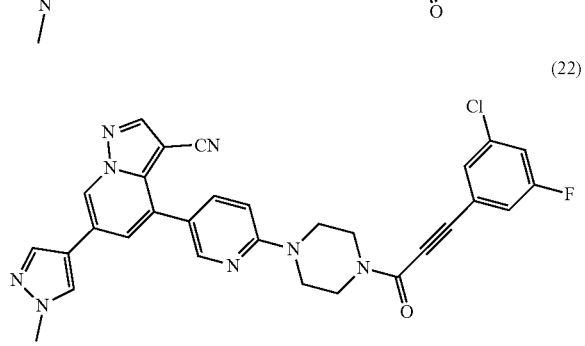
(28) 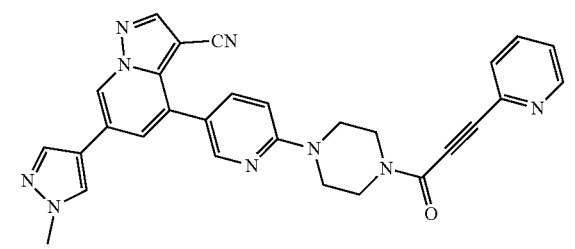
(29) 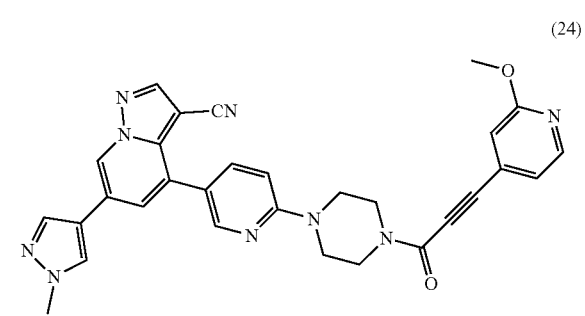
(30) 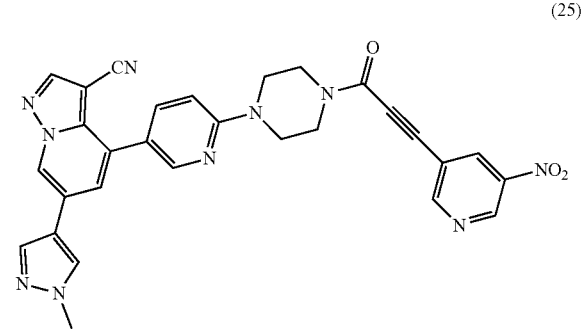

(31) 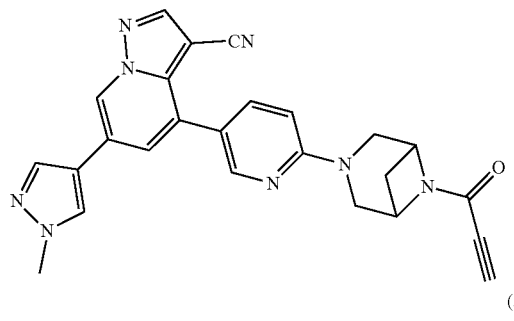
(32) 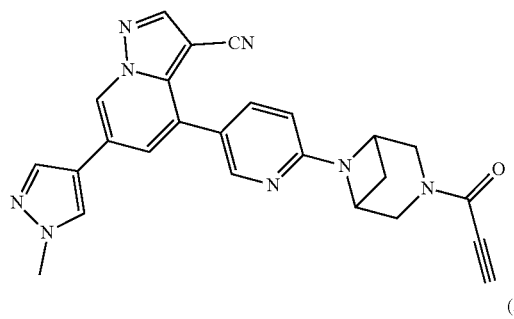
(33) 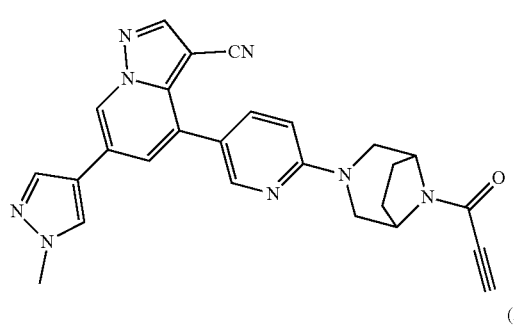
(34) 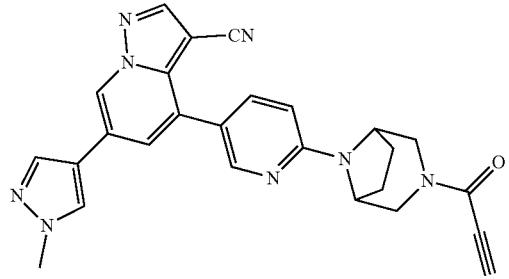
(35) 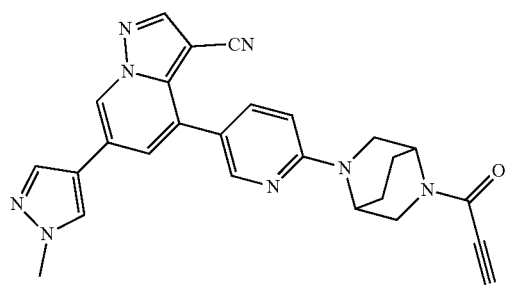
(36) 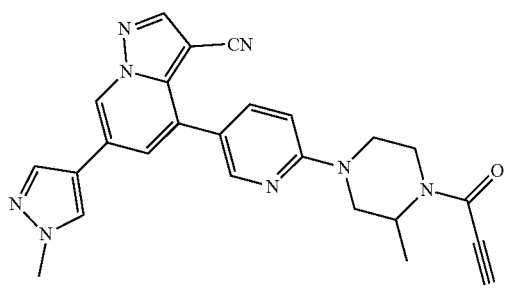
(37) 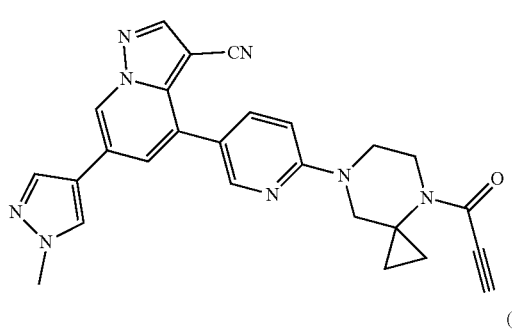
(38) 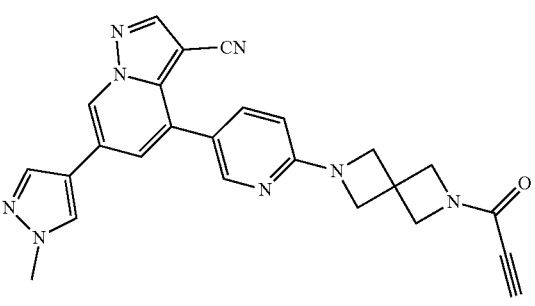
(39) 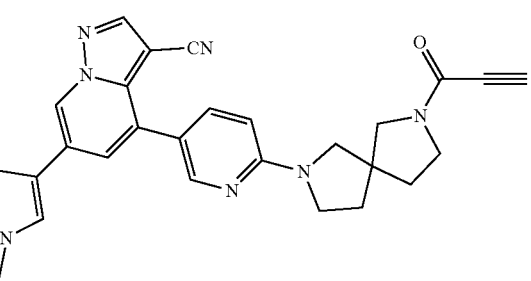
(40) 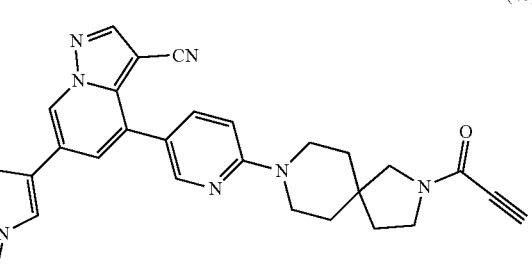

-continued
(41)
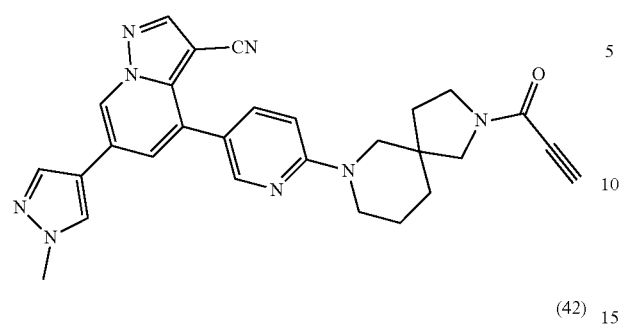
(42)
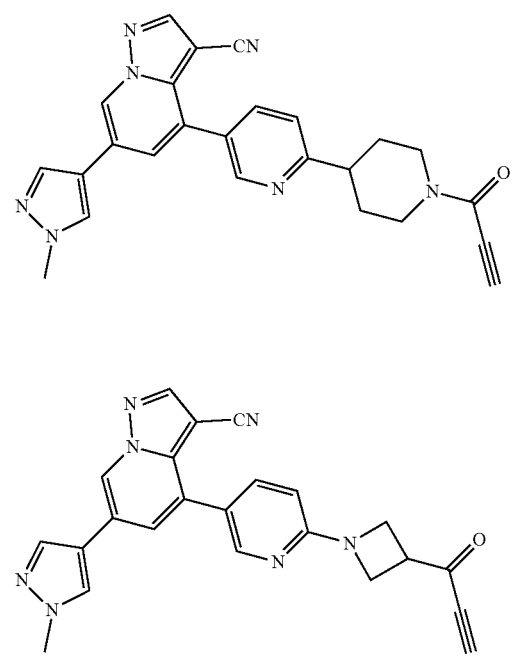
(43)
(44)
(45)
-continued
(46)
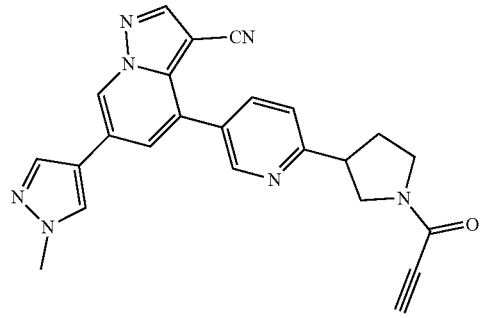
(47)
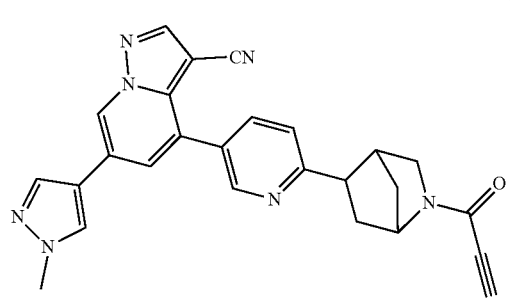
(48)
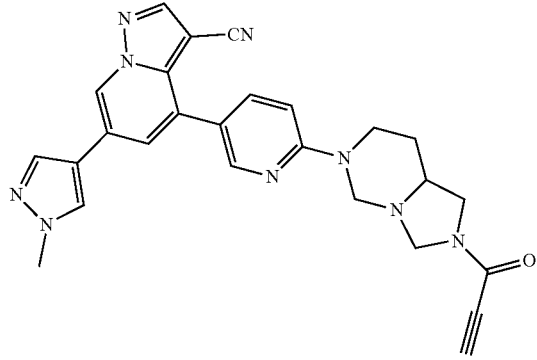
(49)
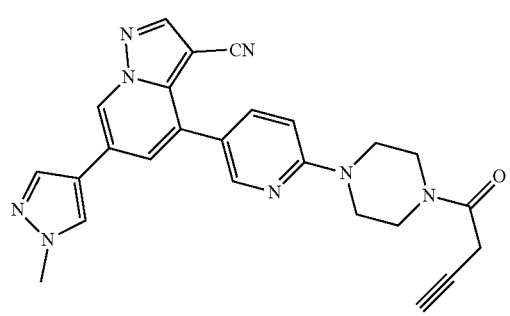

(50)
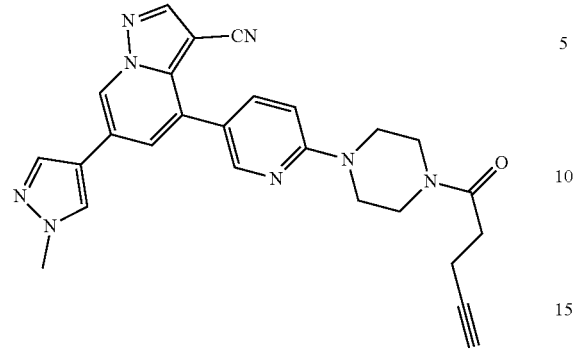
(51)
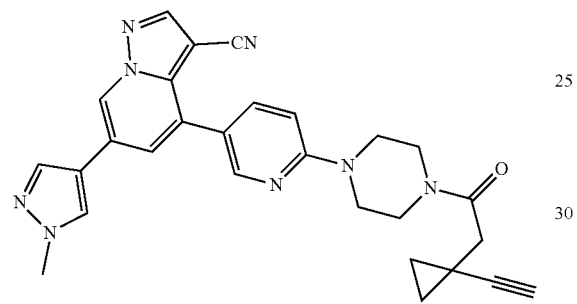
(52)
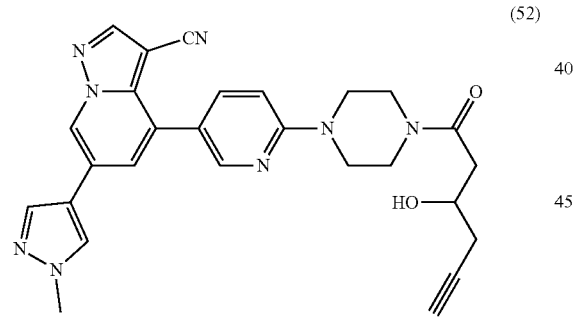
(53)
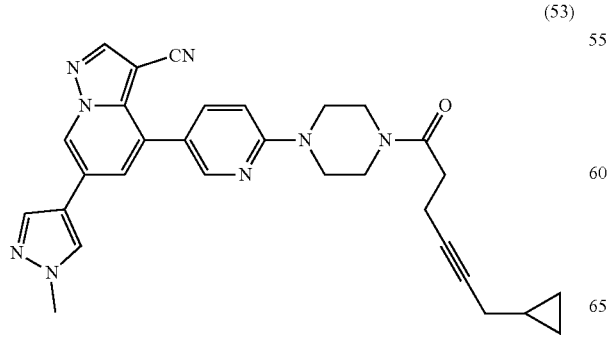
(54)
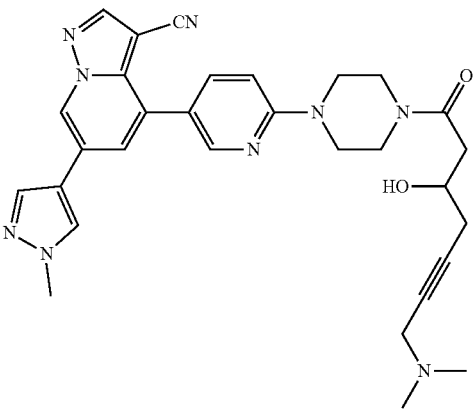
(55)
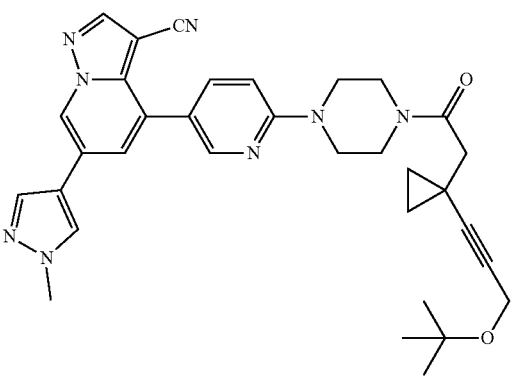
(56)
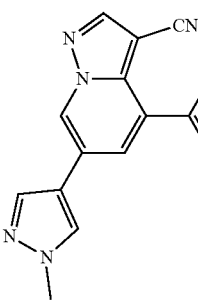

(57)
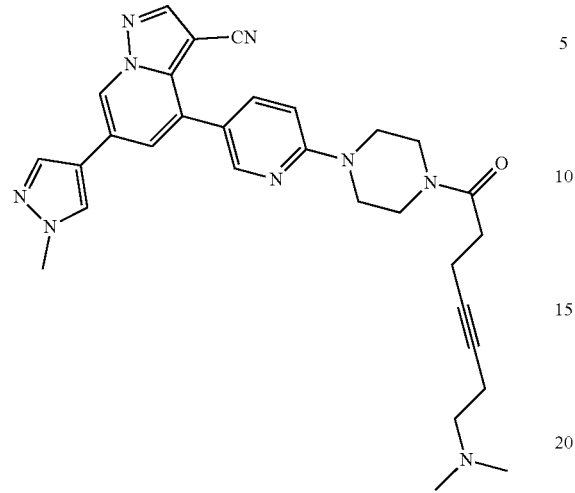
(58)
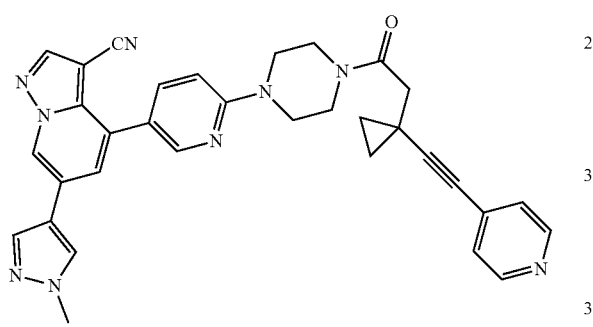
(59)
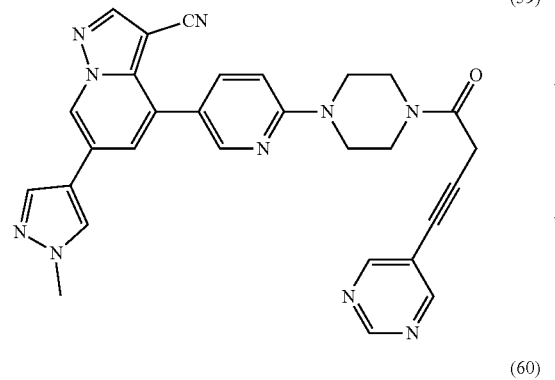
(60)
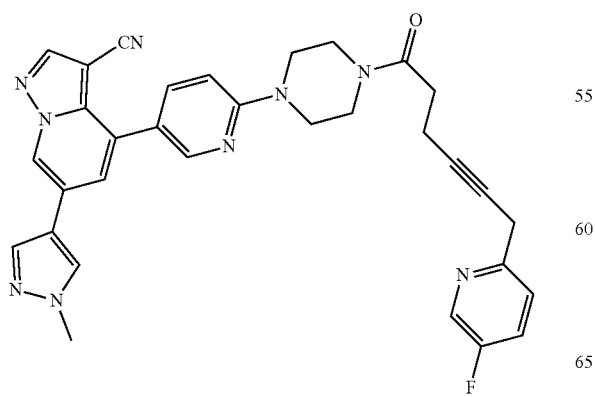
(61)
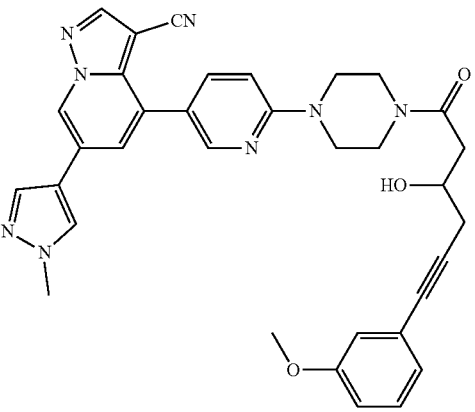
(62)
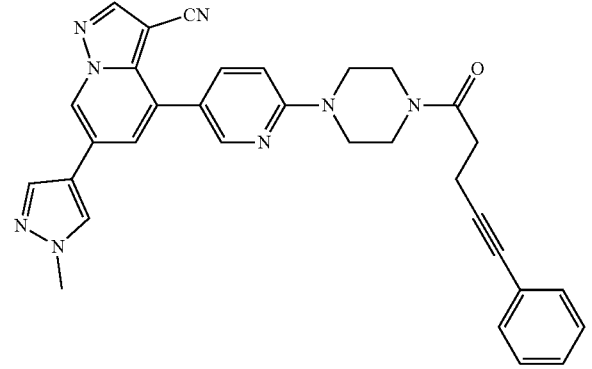
(63)
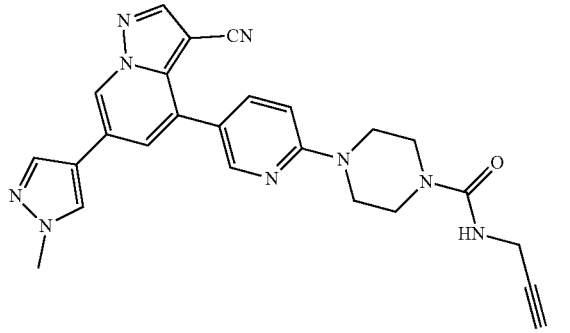
(64)
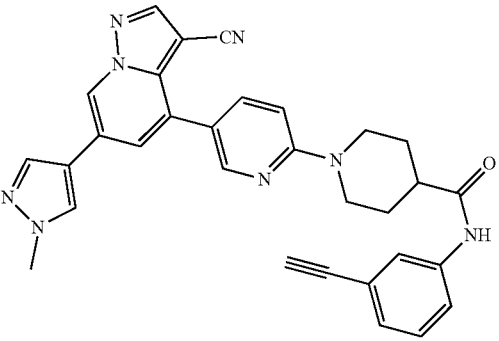

-continued
(65)
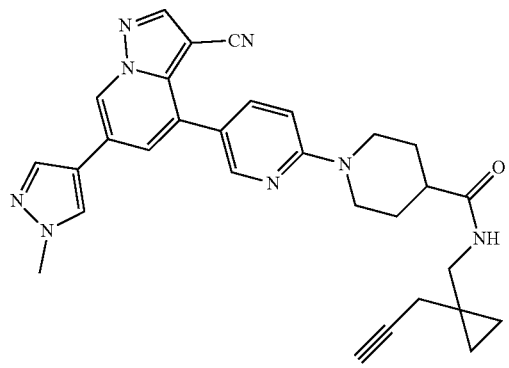
(66)
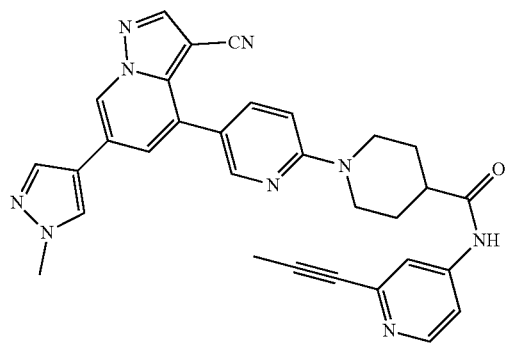
(67)
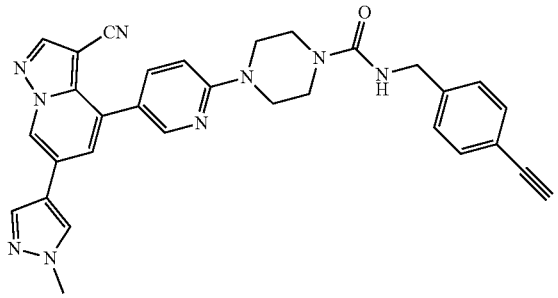
(68)
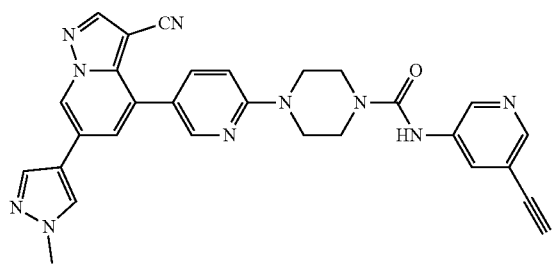
(69)
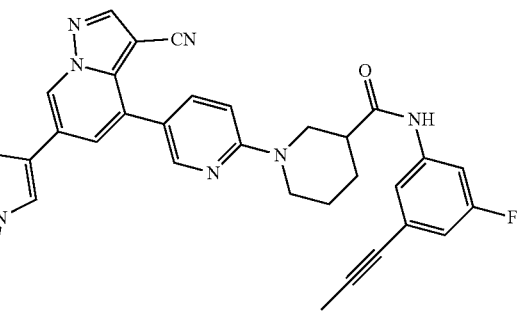
(70)
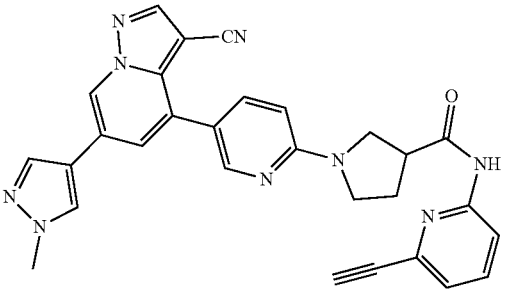
(71)
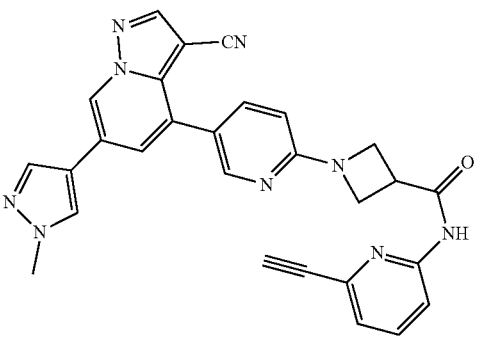
(72)
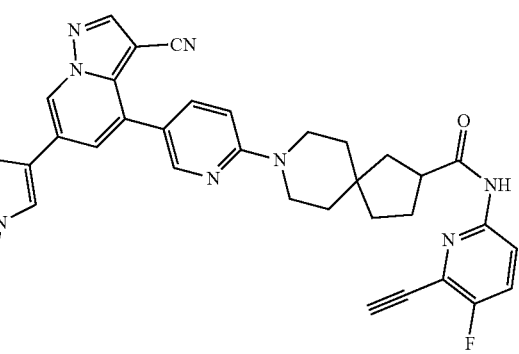

(73)
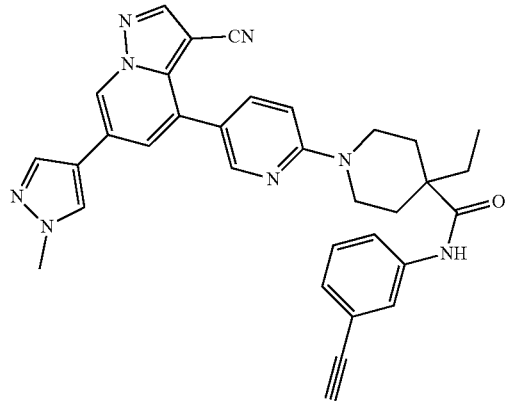
(78)
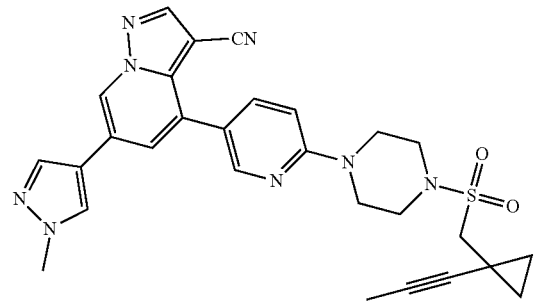
(74)
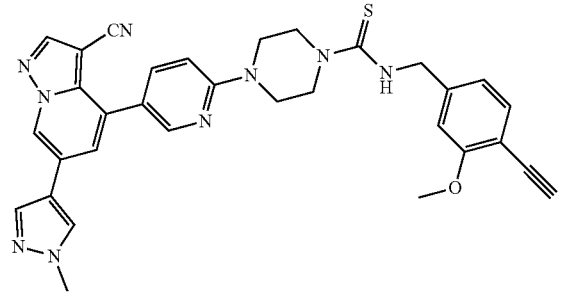
(79)
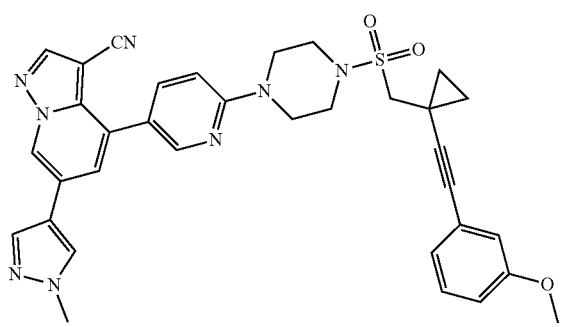
(75)
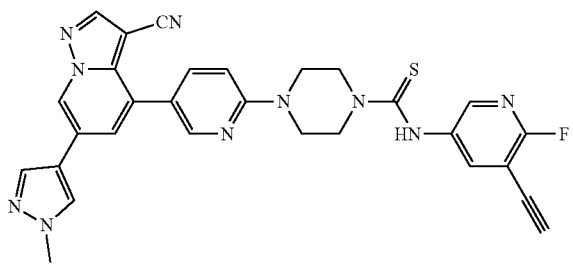
(80)
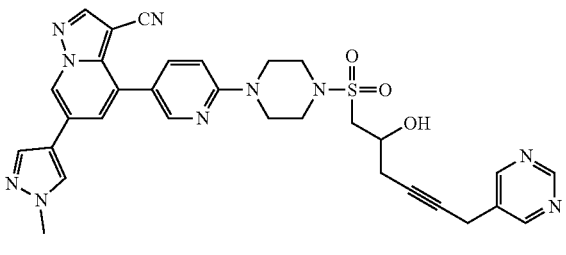
(76)
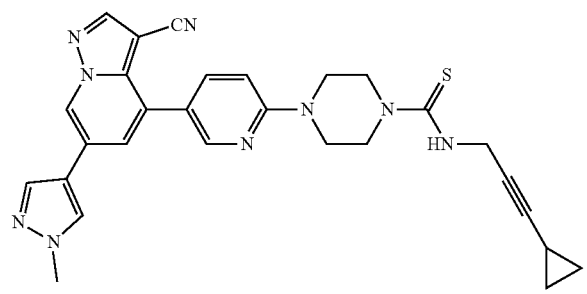
(81)
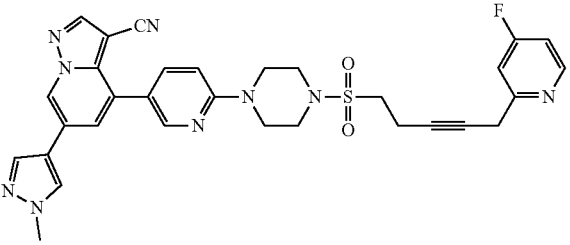
(77)
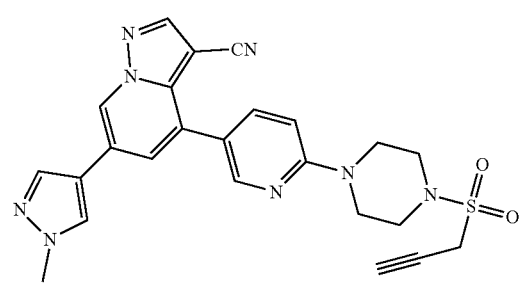
(82)
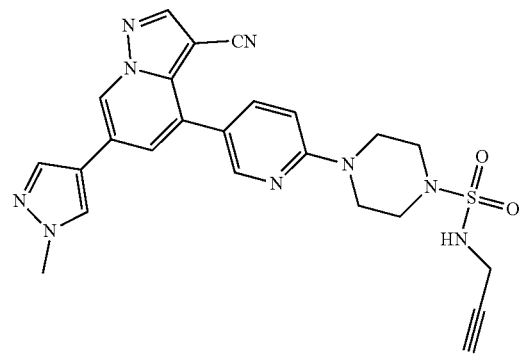

(83)
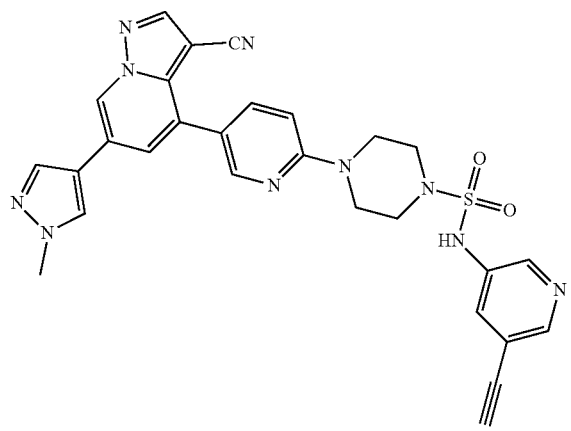
(84)
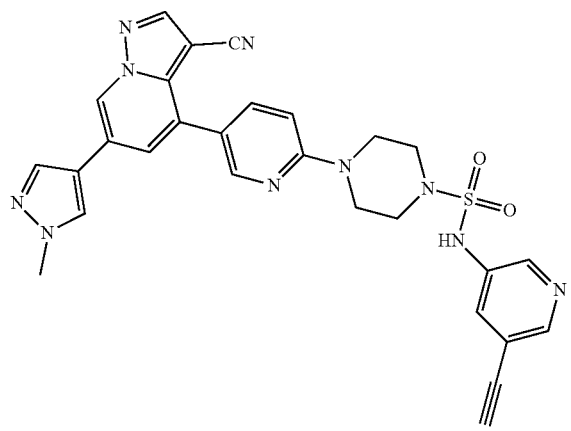
(85)
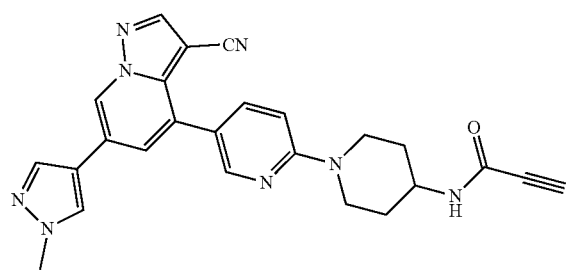
(86)
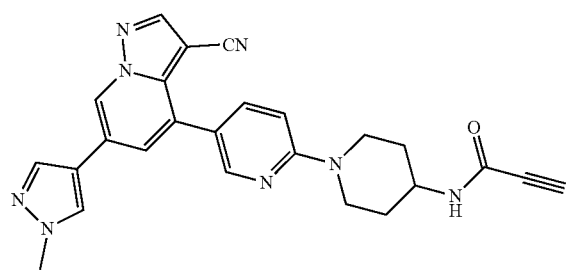
(87)
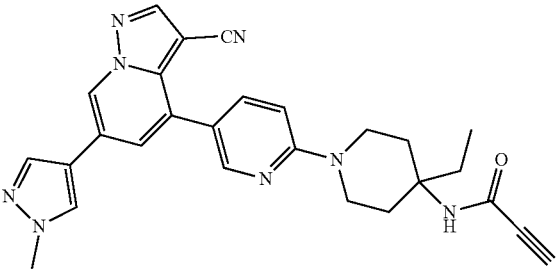
(88)
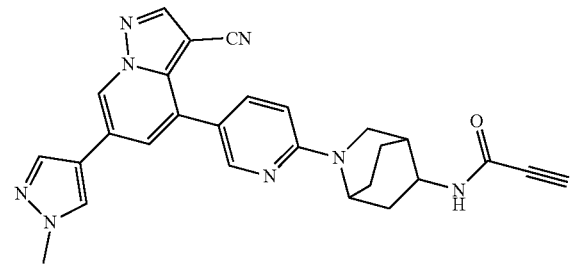
(89)
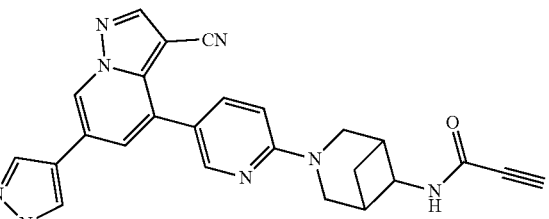
(90)
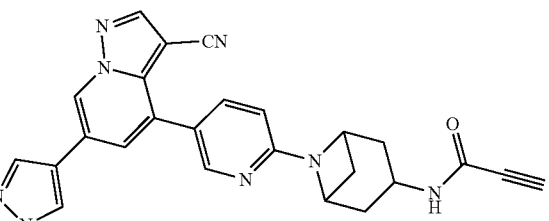
(91)
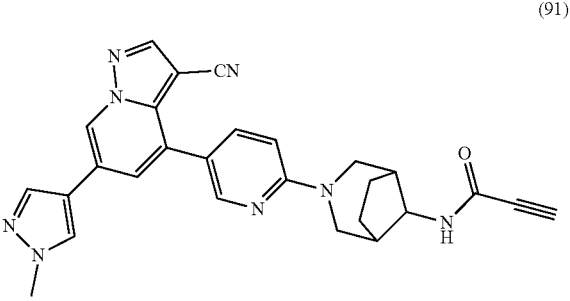

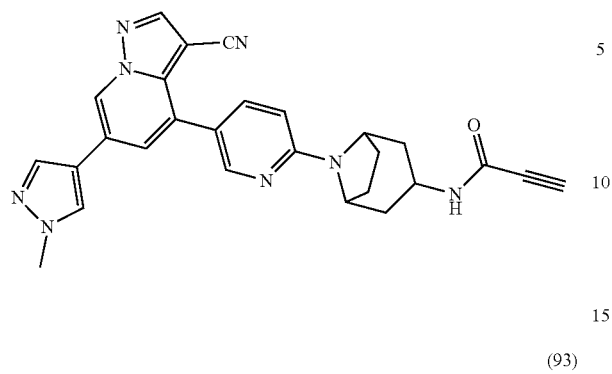
(92)
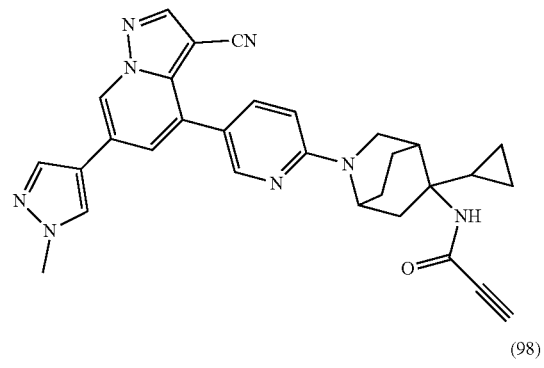
(97)
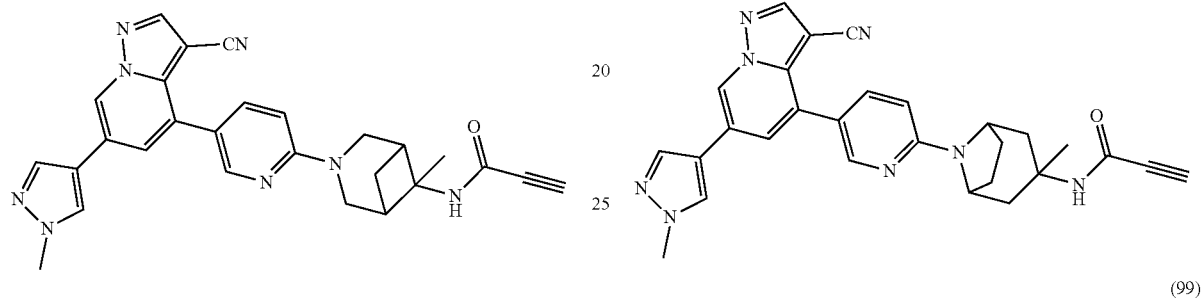
(93)
(98)
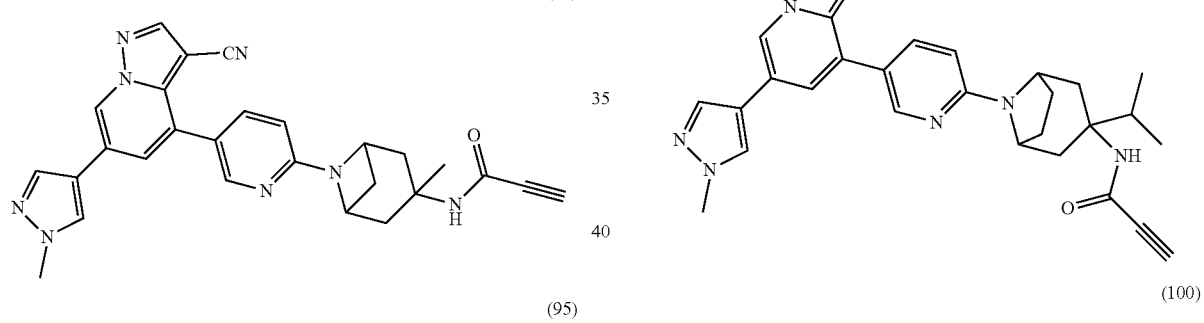
(94)
(99)
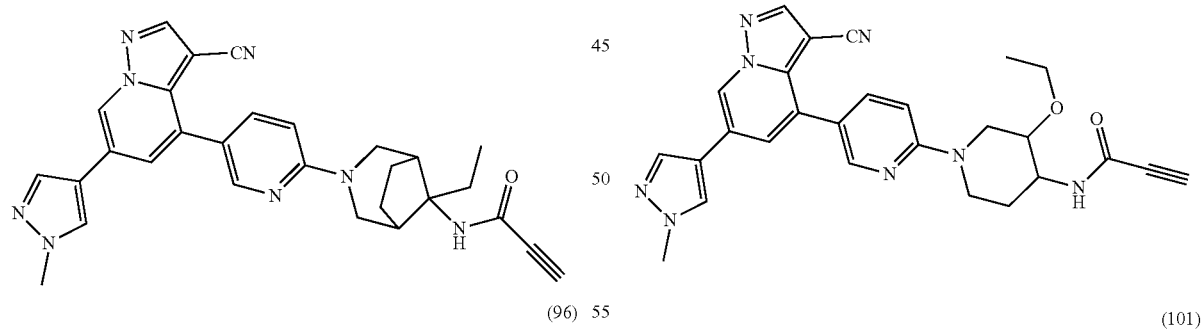
(95)
(100)
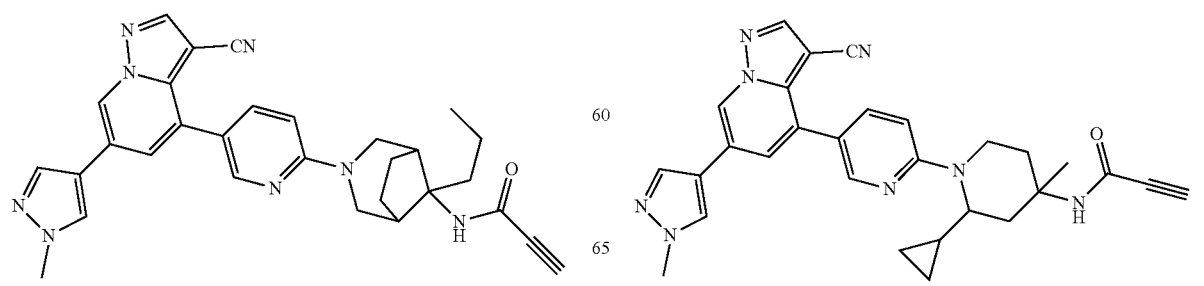
(96)
(101)

(102) 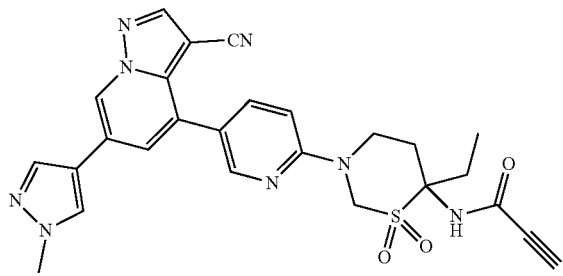
(103) 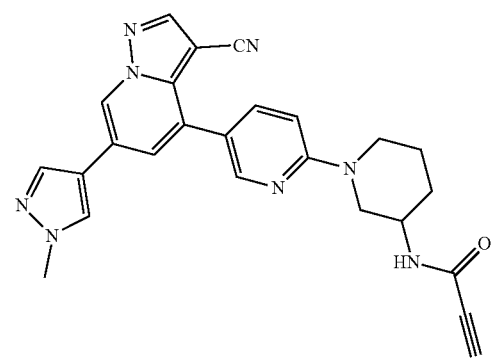
(104) 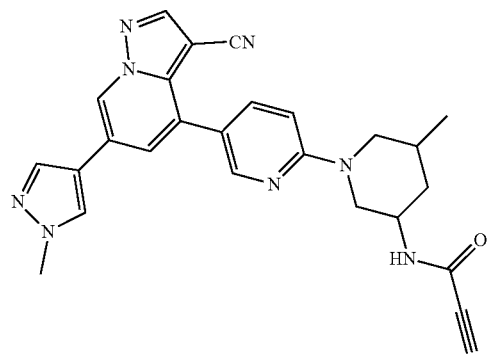
(105) 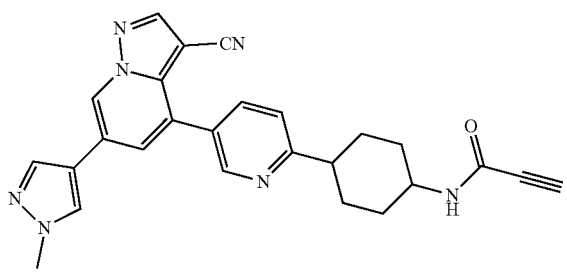
(106) 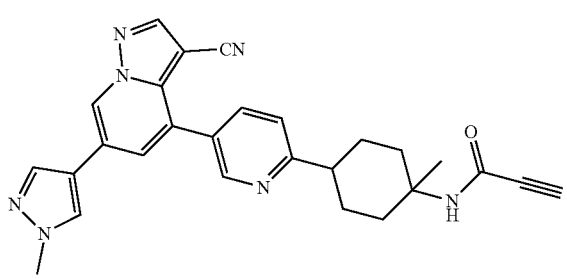
(107) 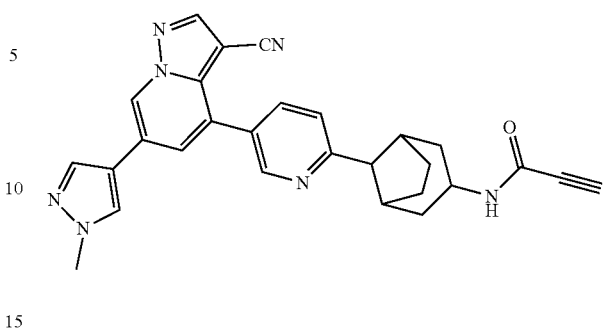
(108) 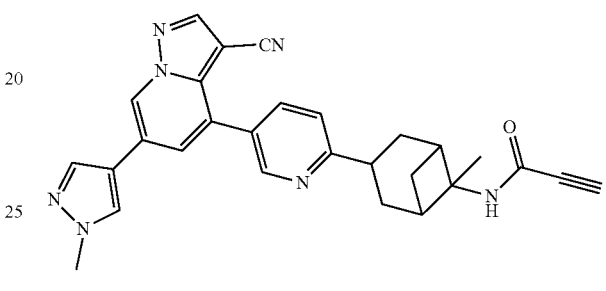
(109) 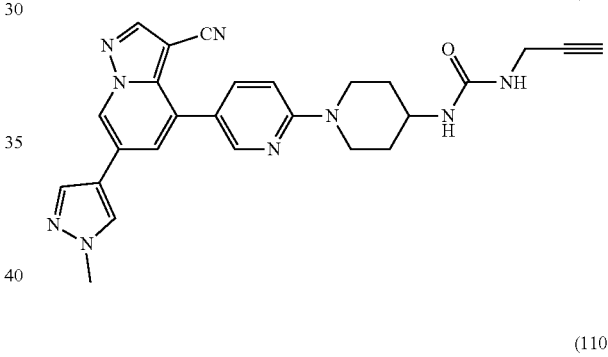
(110) 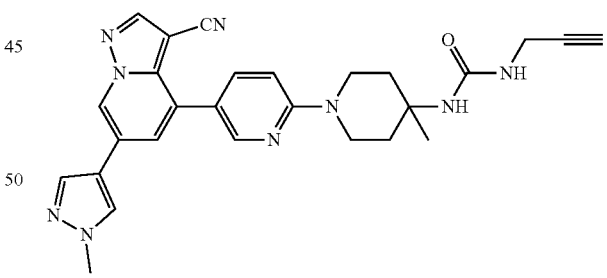
(111) 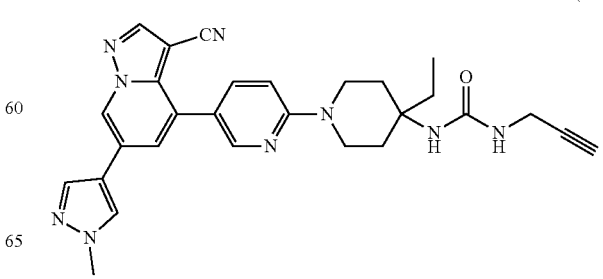

(112)
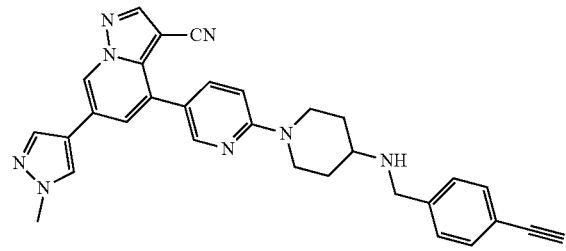
(113)
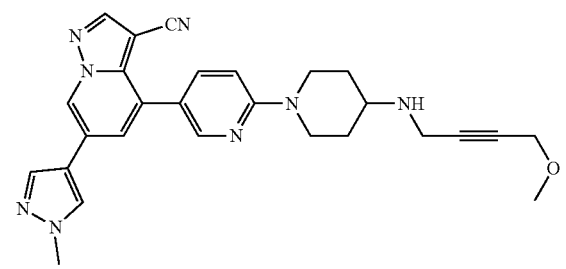
(114)
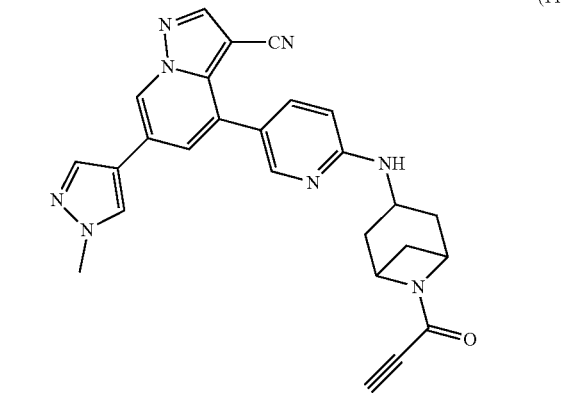
(115)
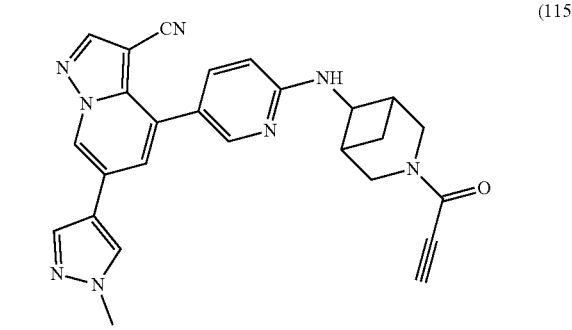
(116)
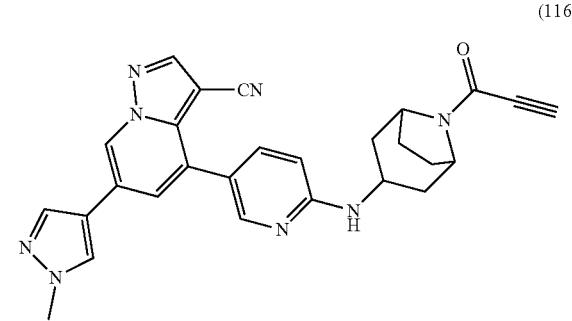
(117)
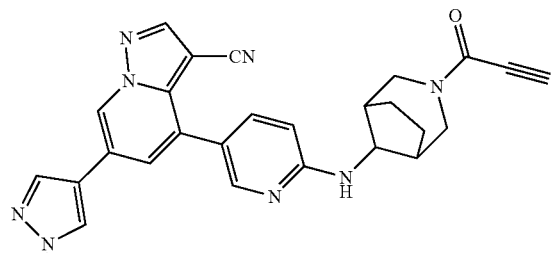
(118)
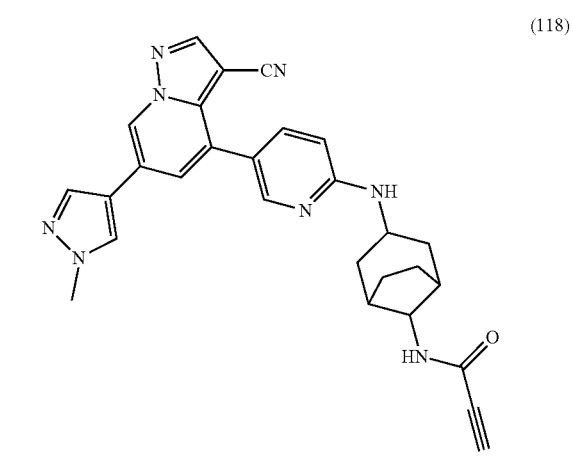
(119)
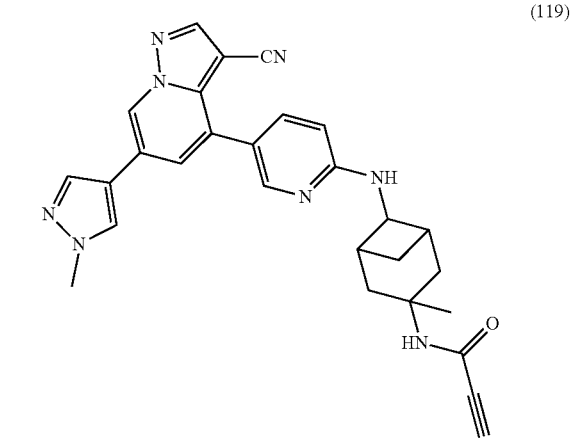
(120)
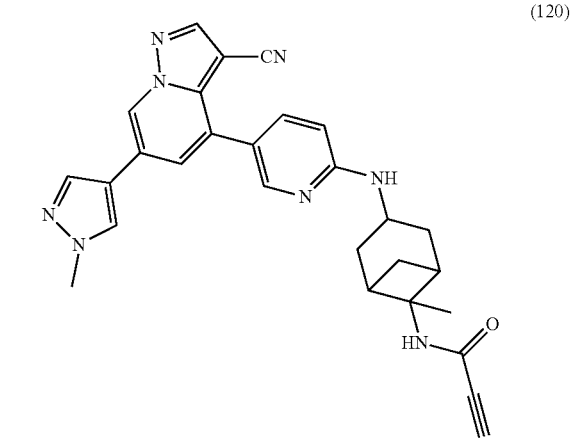

(121) 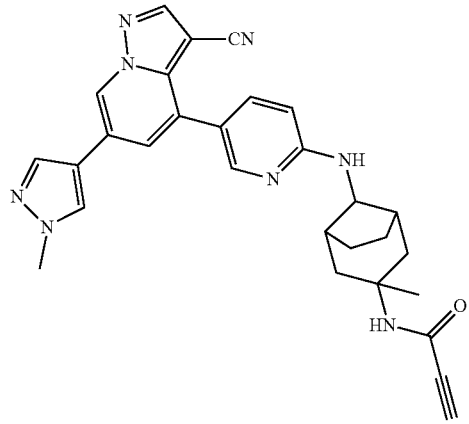
(122) 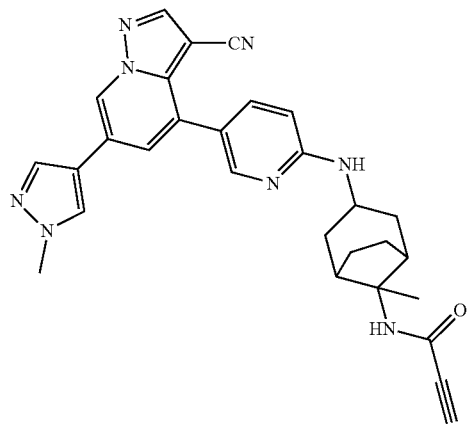
(123) 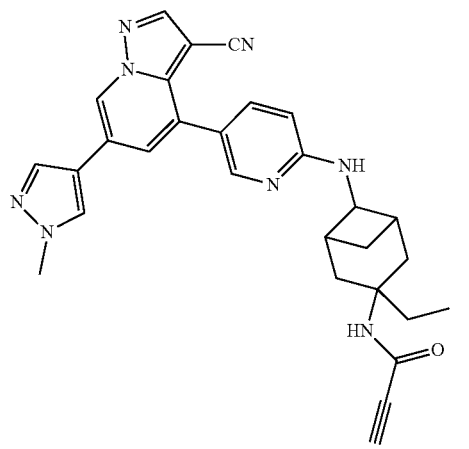
(124) 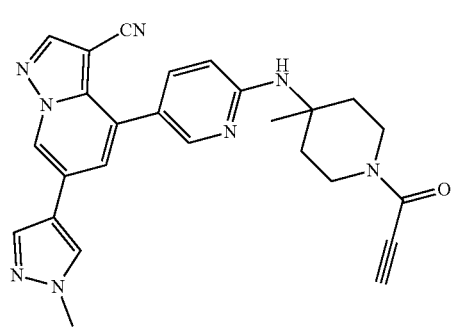
(125) 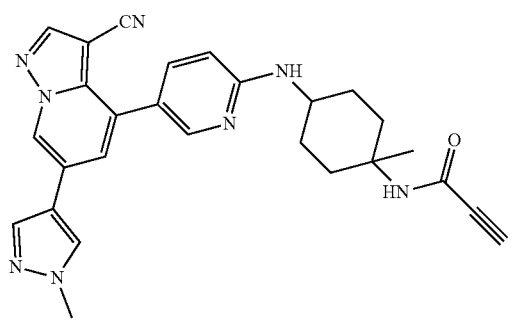
(126) 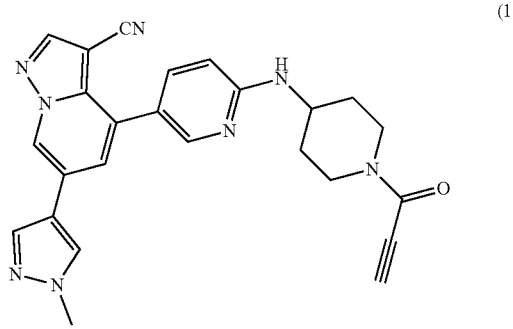
(127) 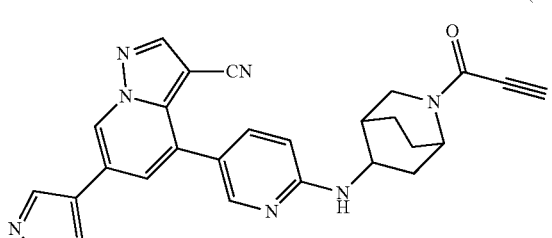
(128) 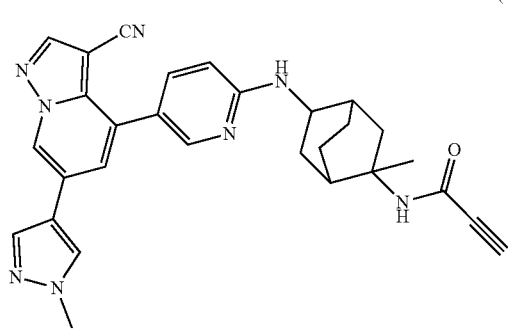
(129) 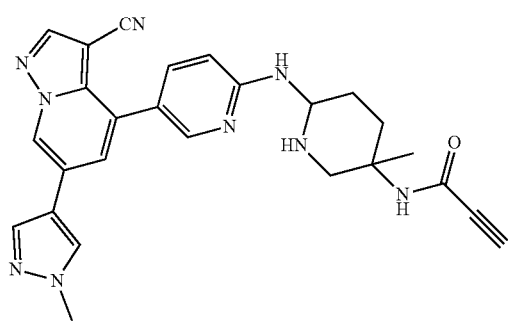

-continued
(130)
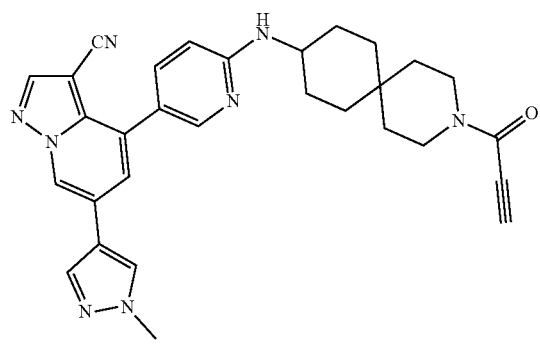
(131)
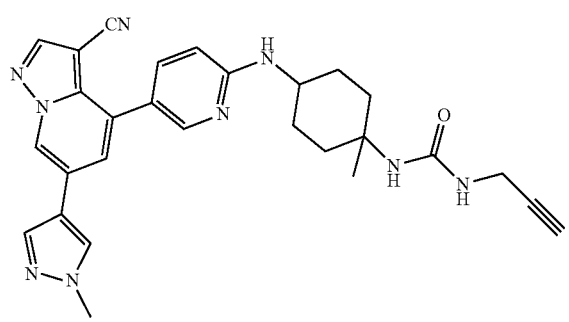
(132)
(133)
(134)
-continued
(135)
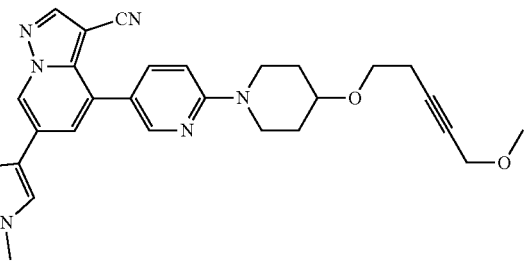
(136)
(137)
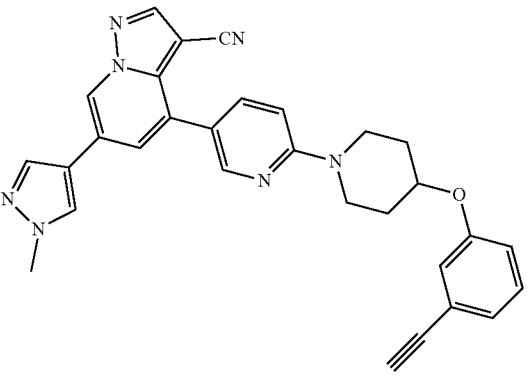
(138)
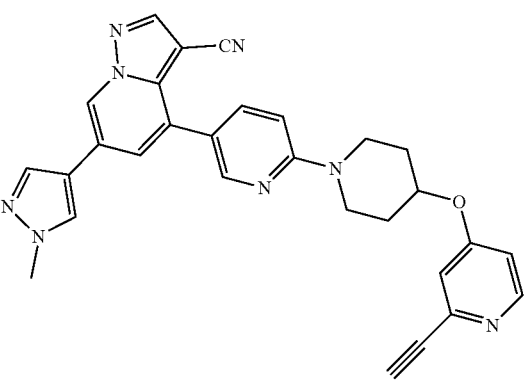

(139)
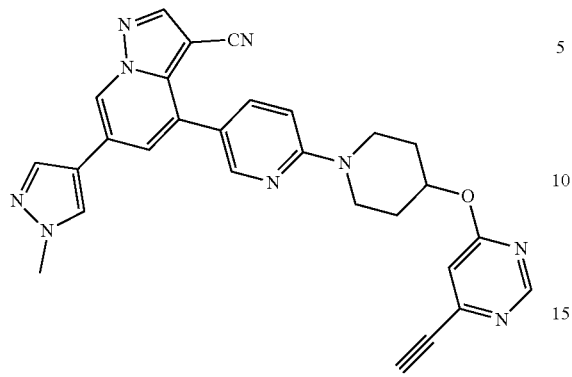
(140)
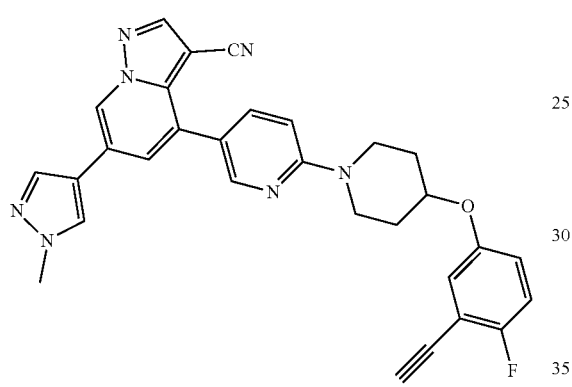
(141)
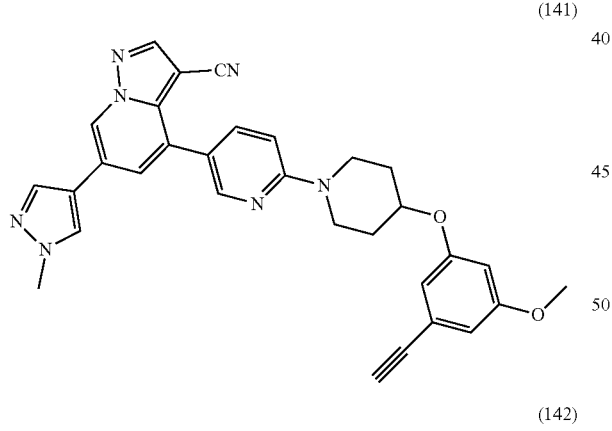
(142)
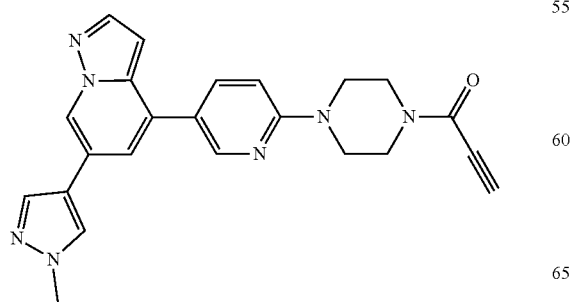
(143)
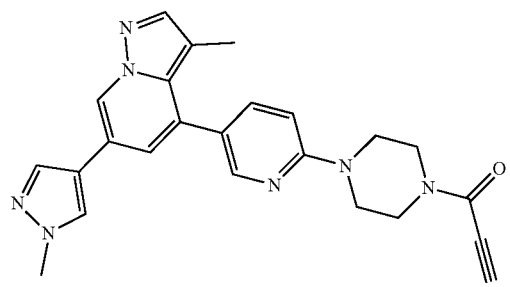
(144)
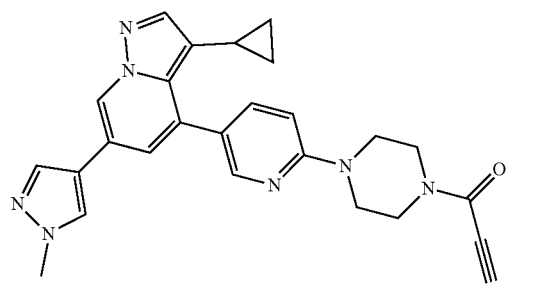
(145)
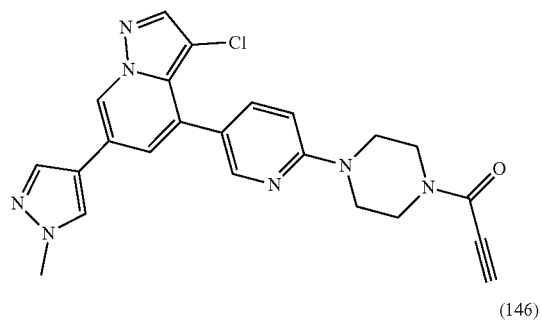
(146)
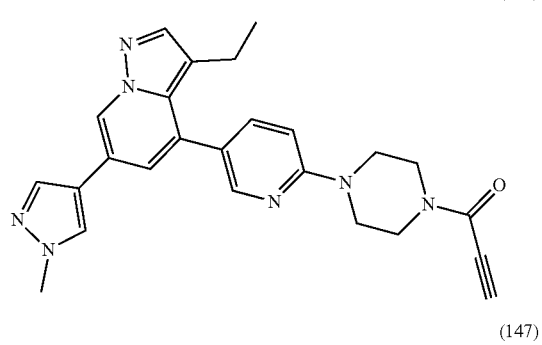
(147)
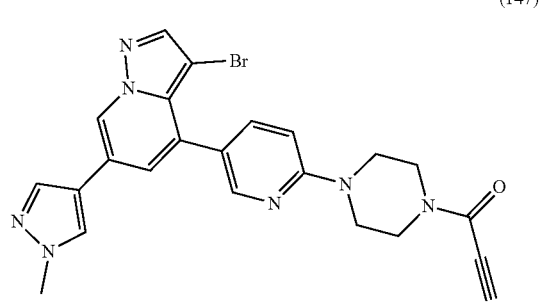

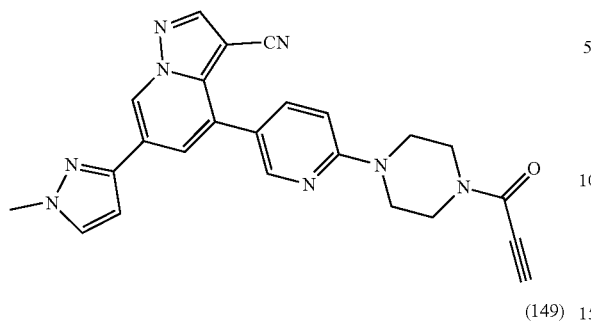
(148)
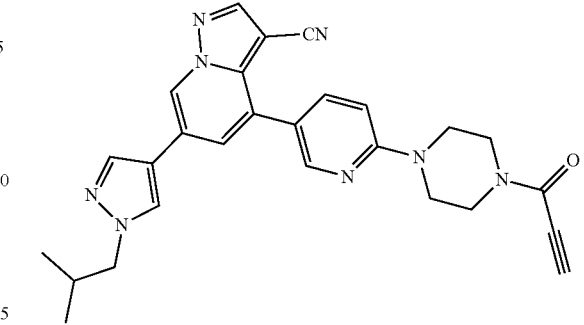
(153)
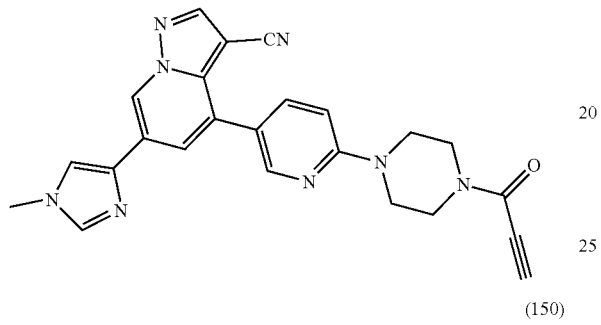
(149)
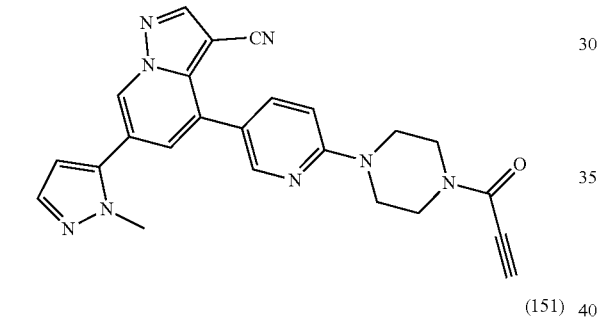
(150)
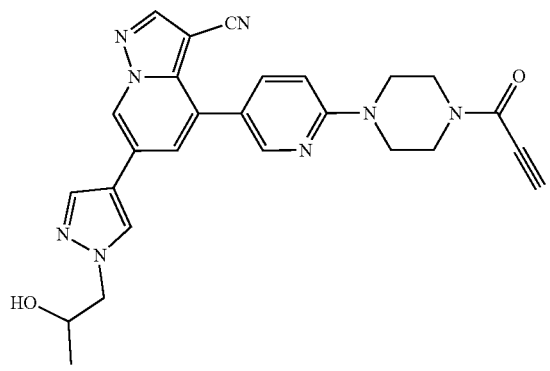
(154)
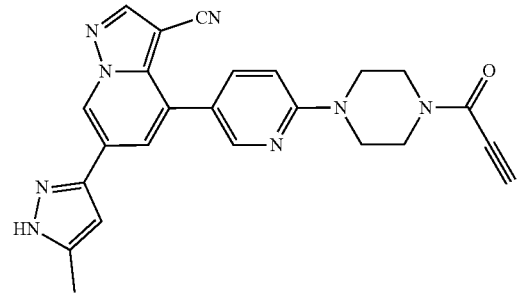
(155)
(151)
(152)
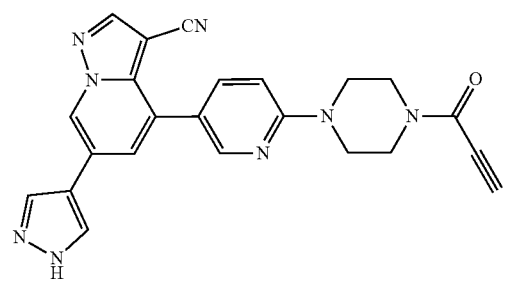
(156)

(157)
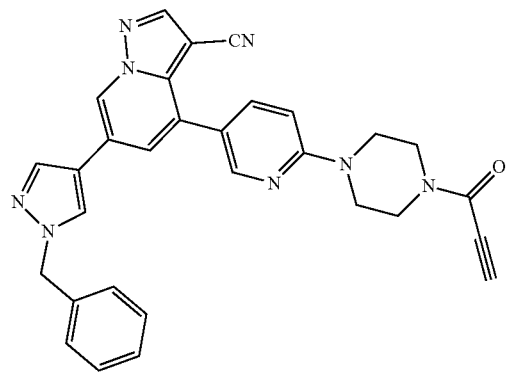
(158)
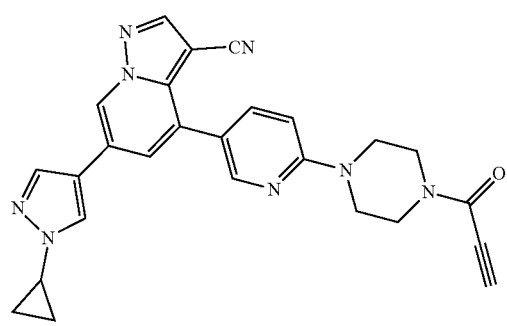
(159)
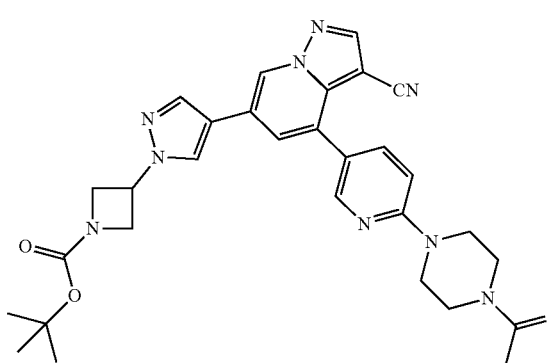
(160)
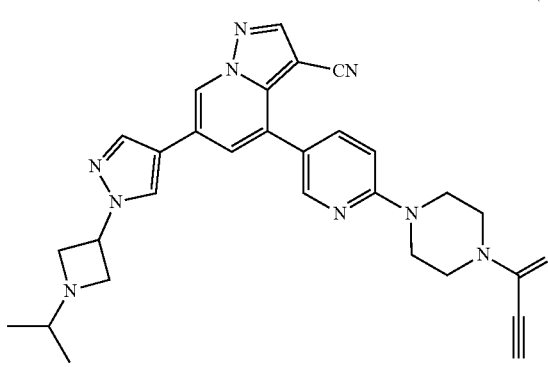
(161)
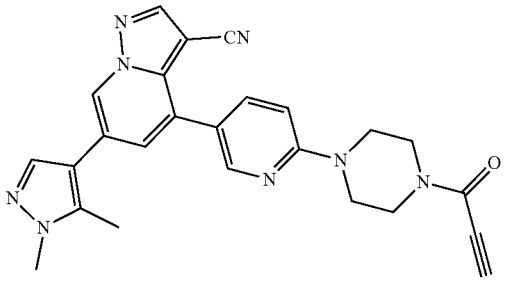
(162)
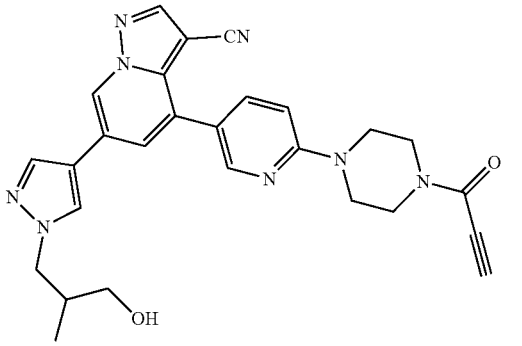
(163)
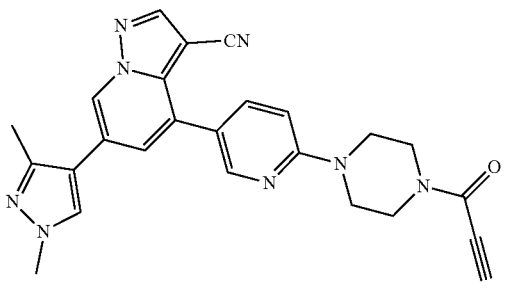
(164)
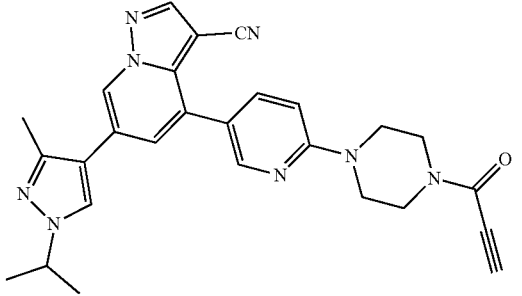
(165)
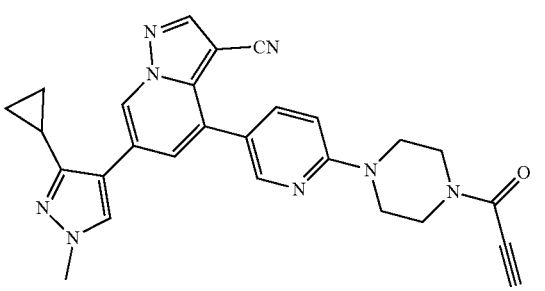

(166)
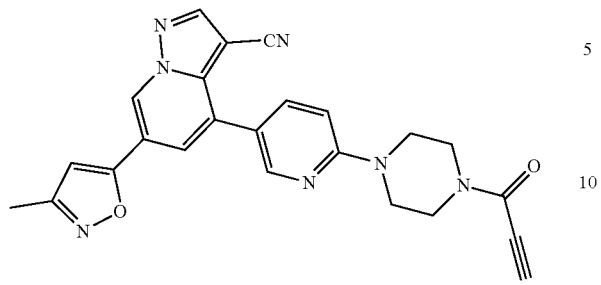
(167)
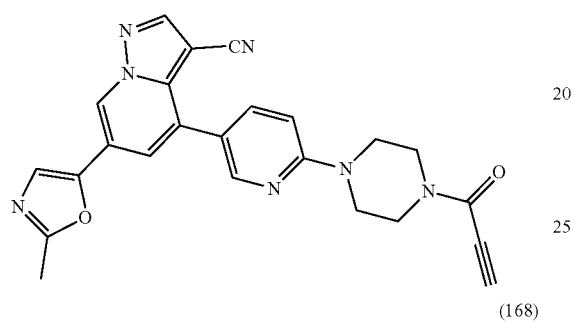
(168)
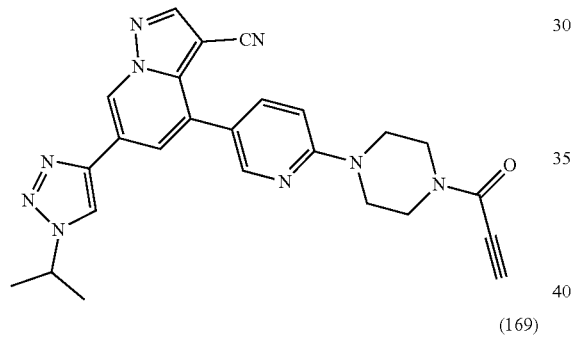
(169)
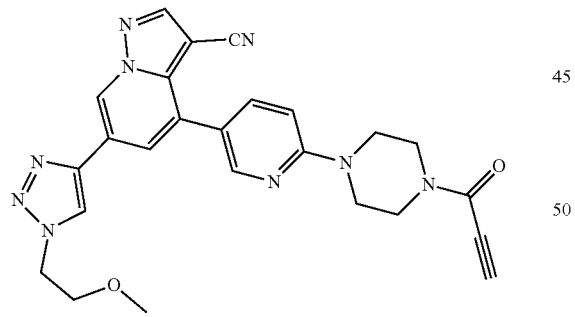
(170)
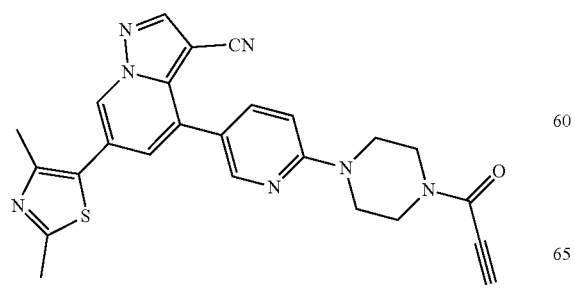
(171)
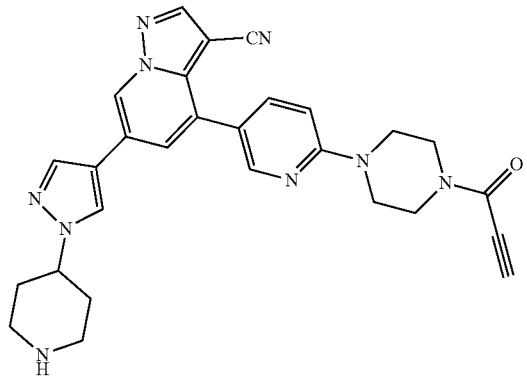
(172)
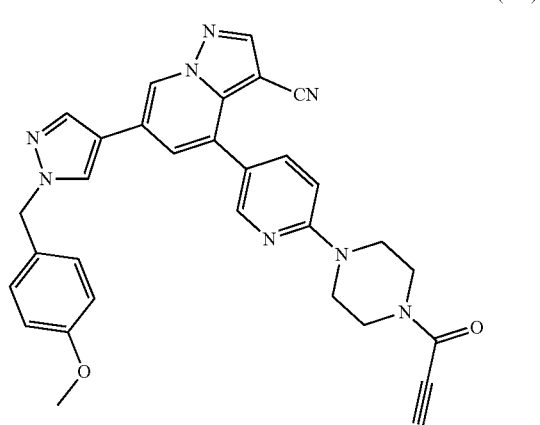
(173)
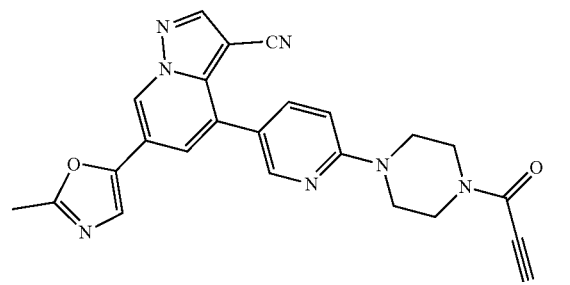
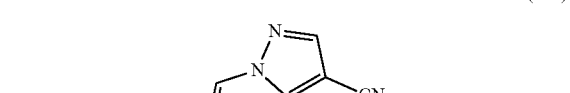
(174)
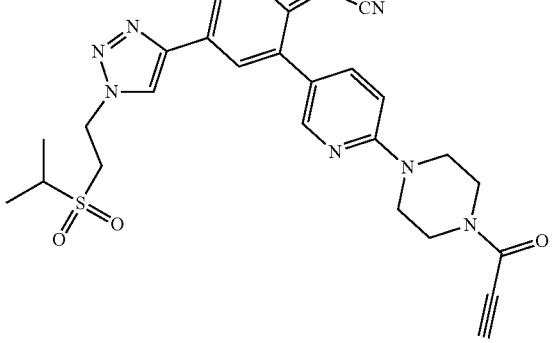

(175) 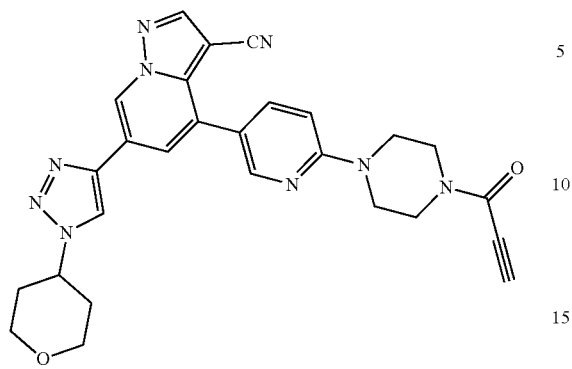
(176) 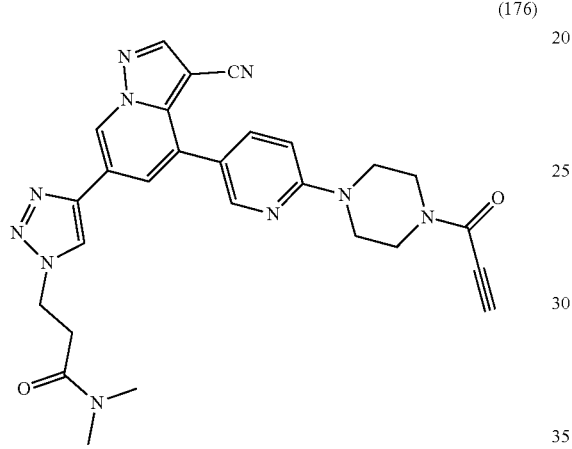
(177) 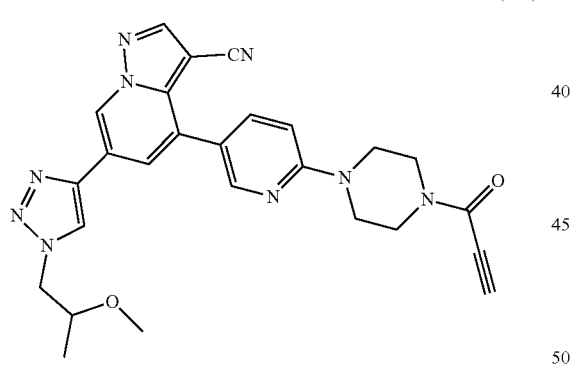
(178) 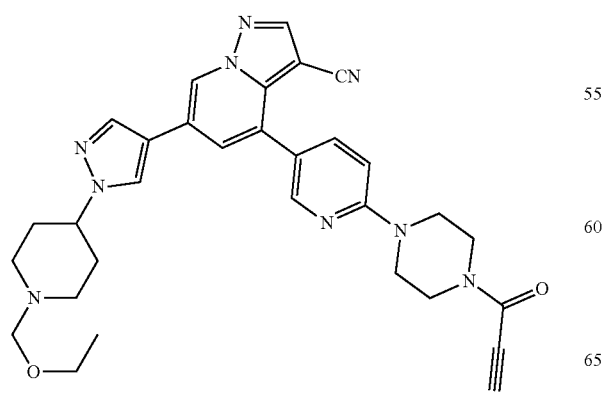
(179) 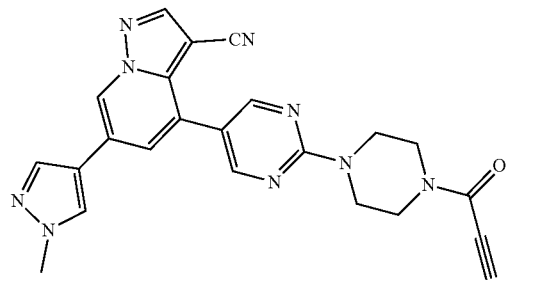
(180) 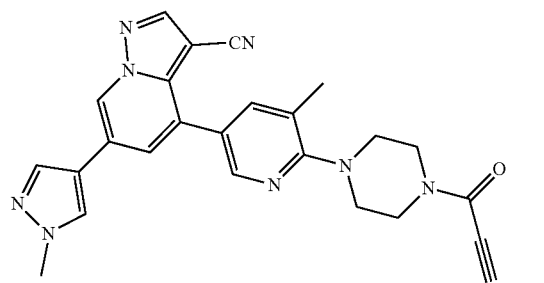
(181) 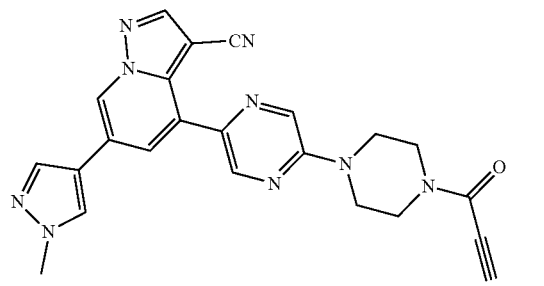
(182) 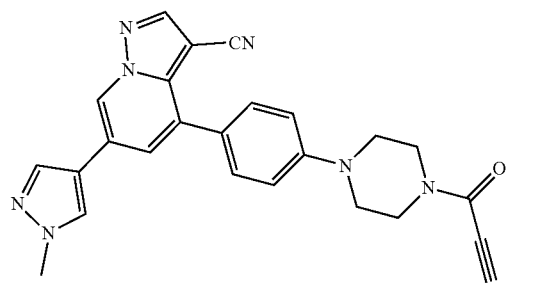
(183) 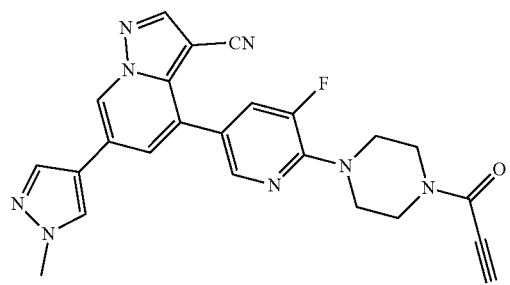

(184)
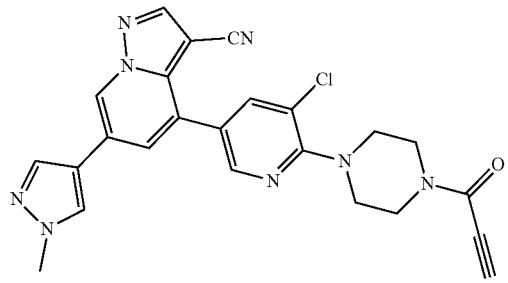
(185)
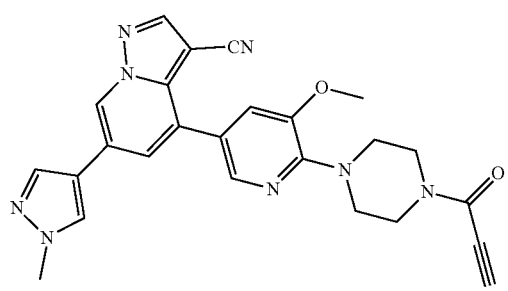
(186)
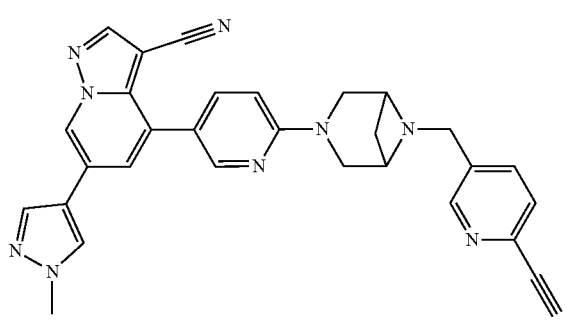
(187)
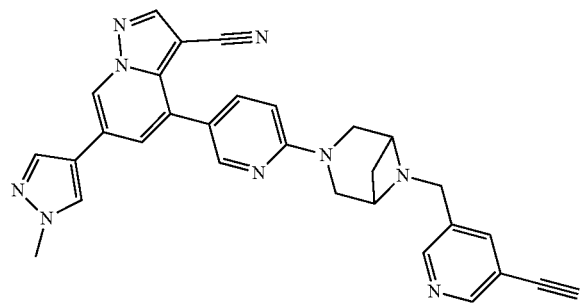
(188)
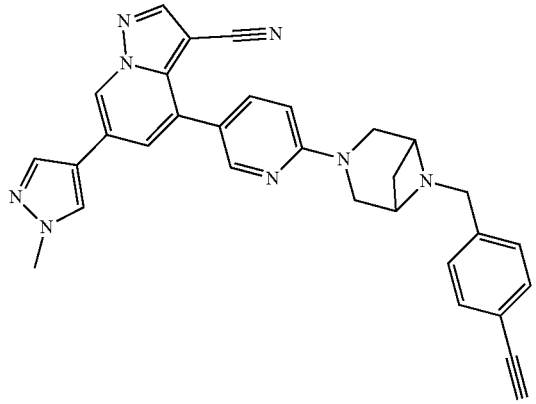
(189)
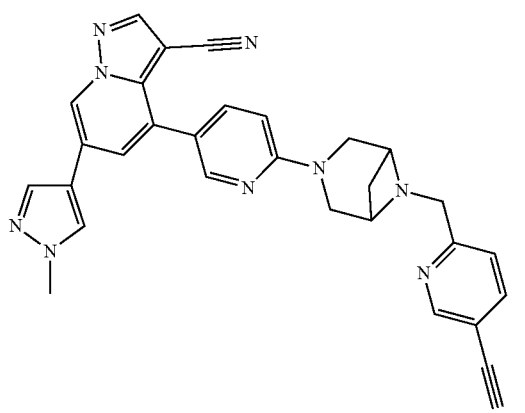
(190)
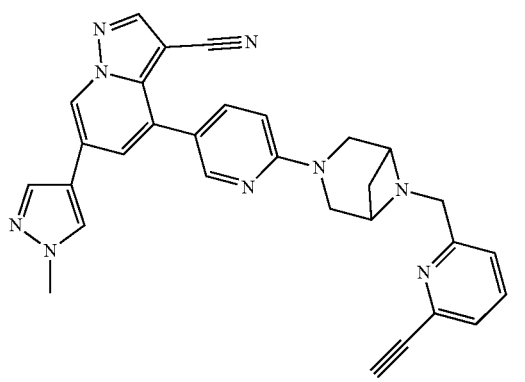
(191)
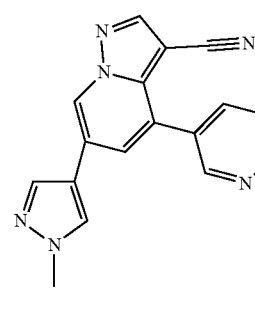

(192)
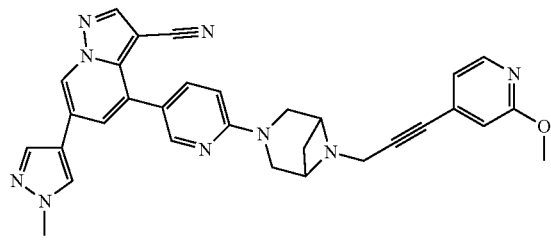
(193)
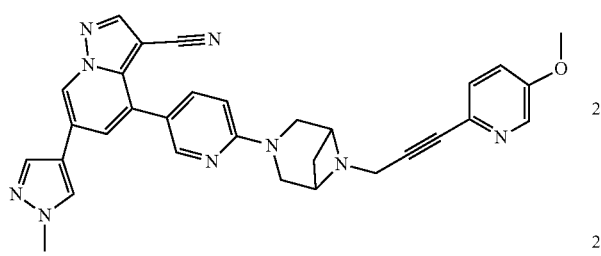
(194)
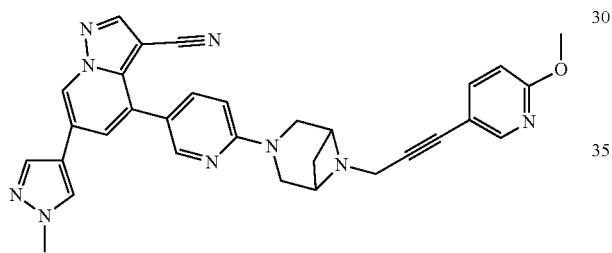
(195)
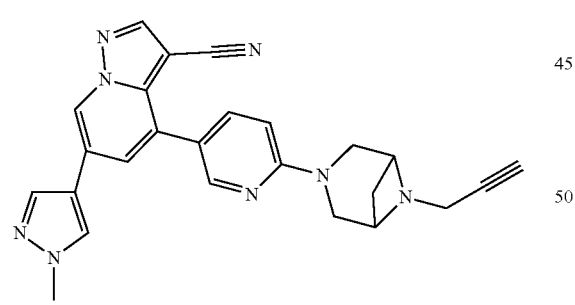
(196)
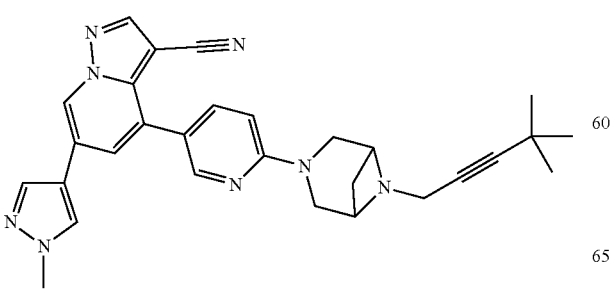
(197)
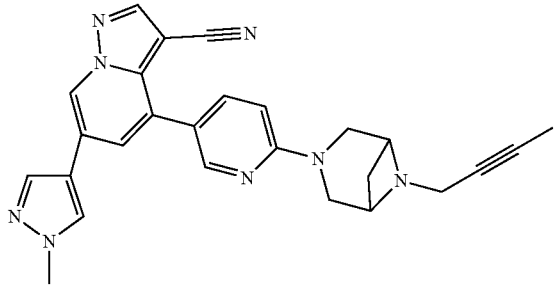
(198)
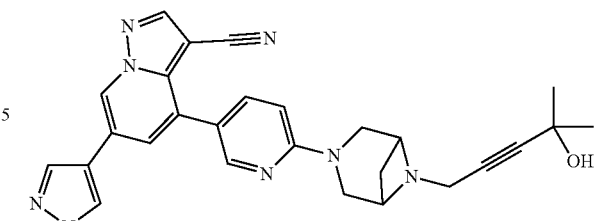
(199)
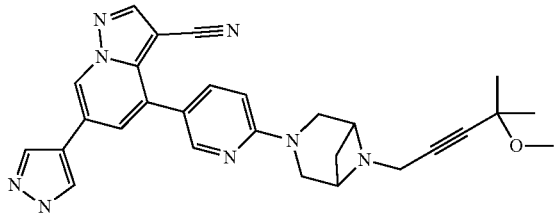
(200)
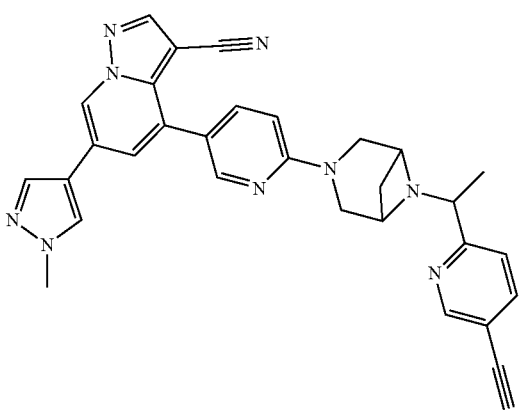

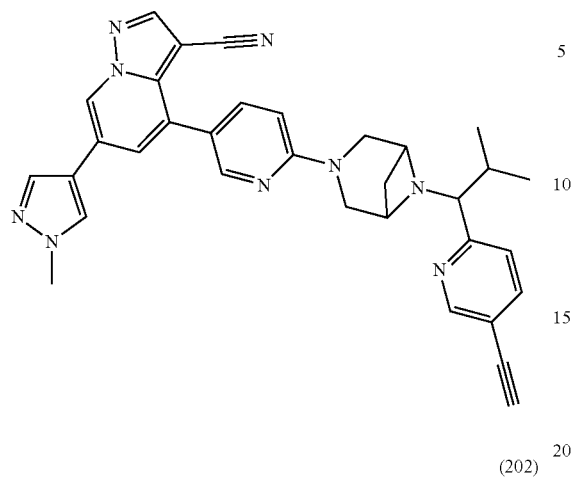
(201)
(202)
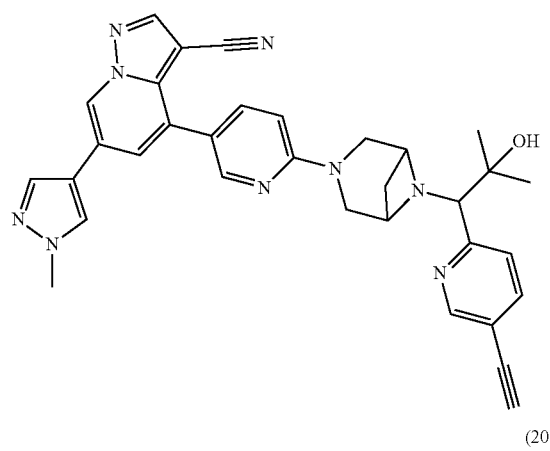
(203)
(204)
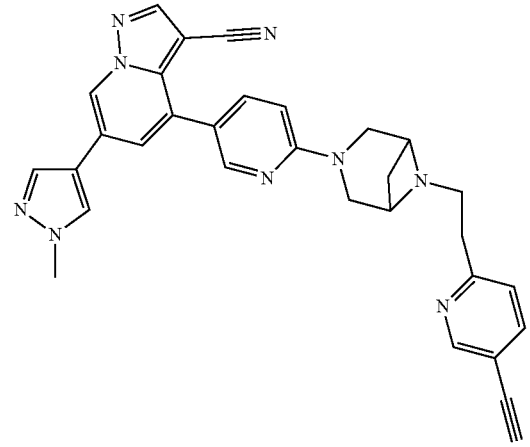
(205)
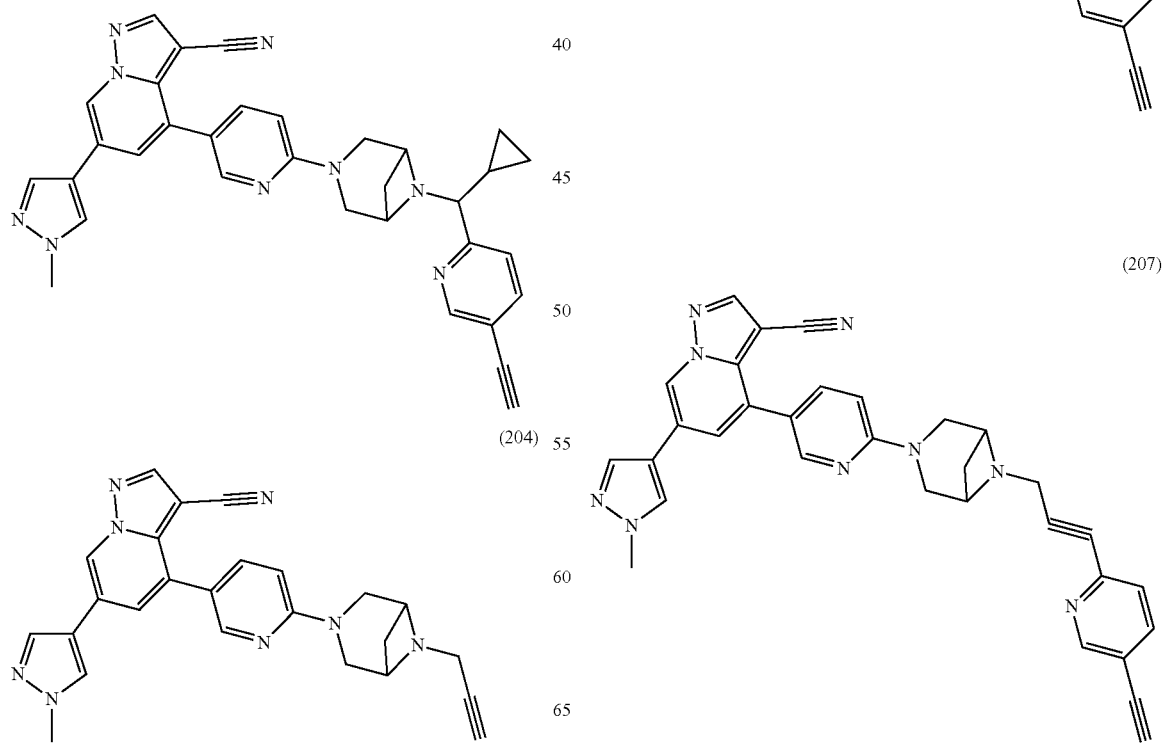
(206)
(207)

(208) 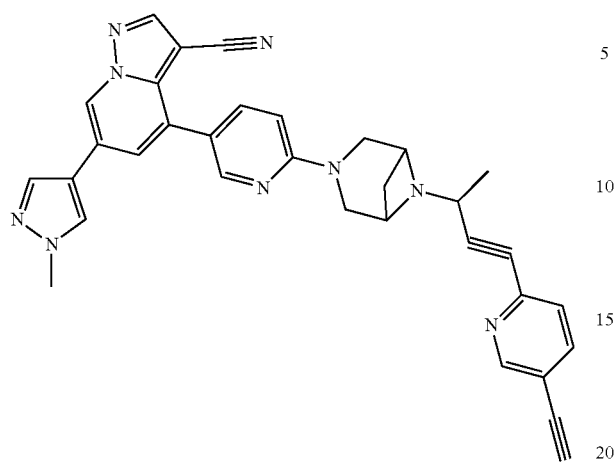
(210) 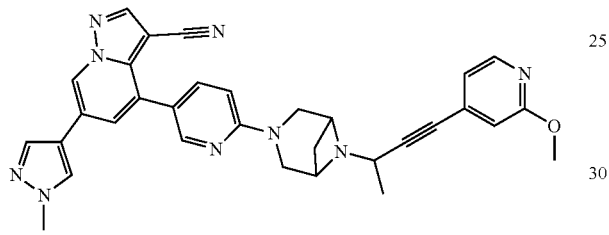
(211) 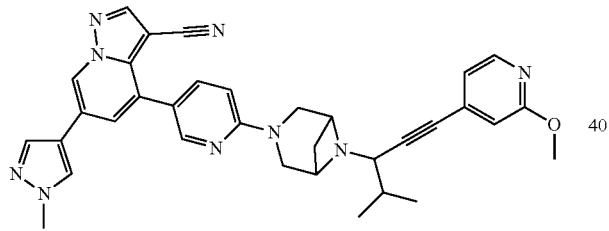
(212) 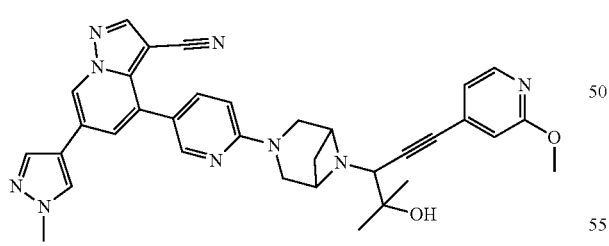
(213) 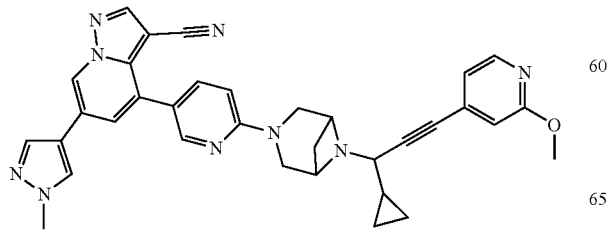
(214) 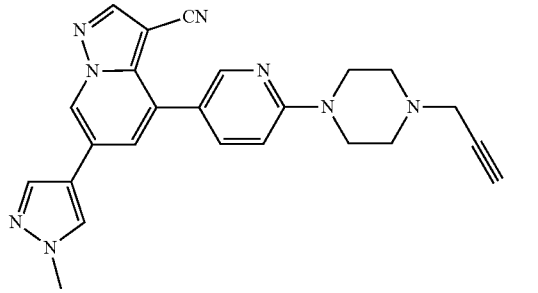
(215) 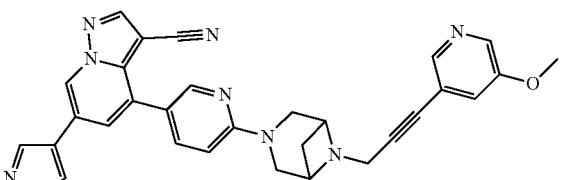
(216) 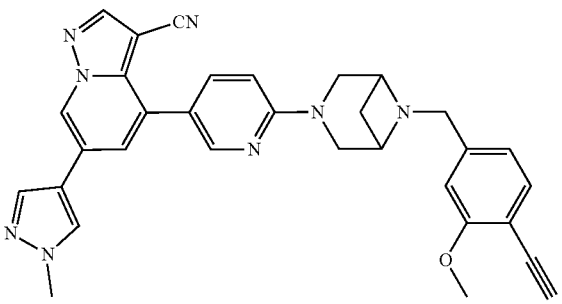
(217) 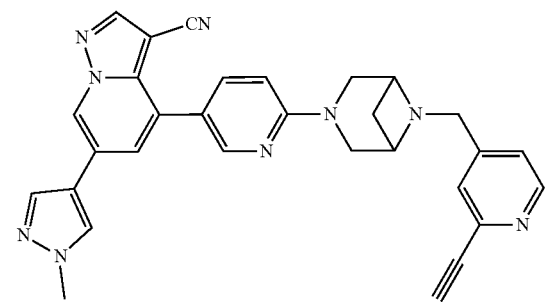
(218) 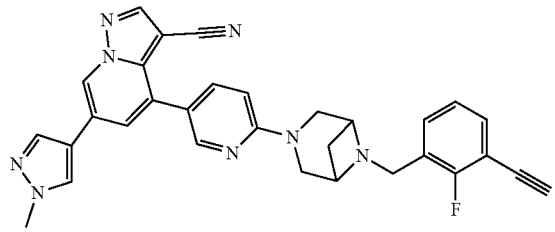

(219)
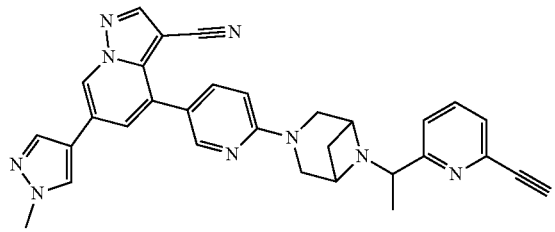
(220)
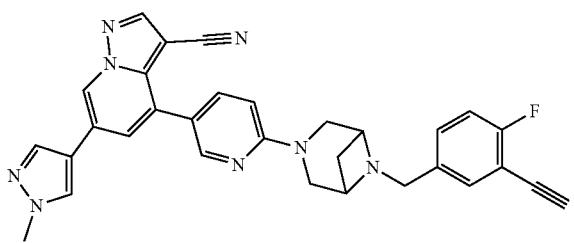
(221)
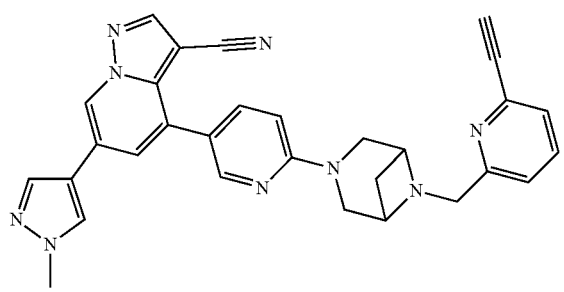
(222)
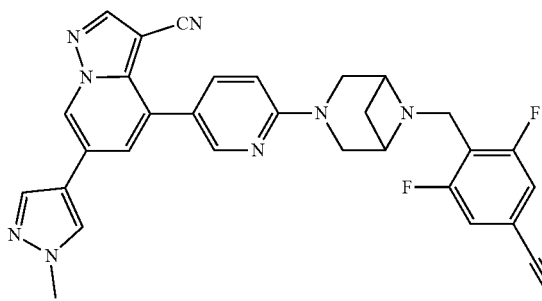
(223)
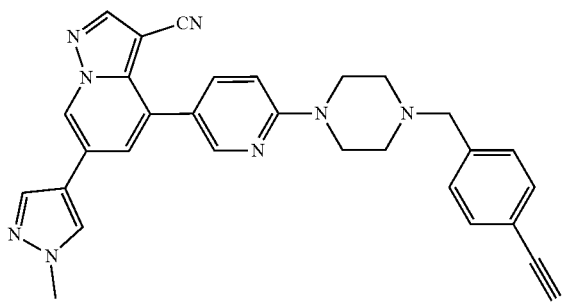
(224)
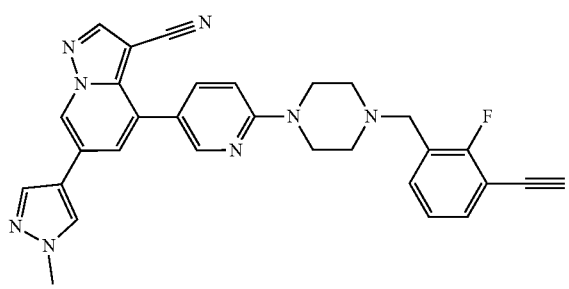
(225)
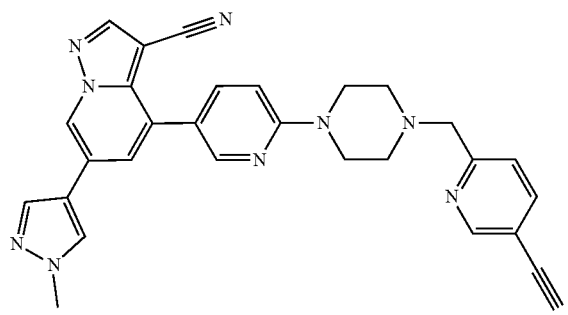
(226)
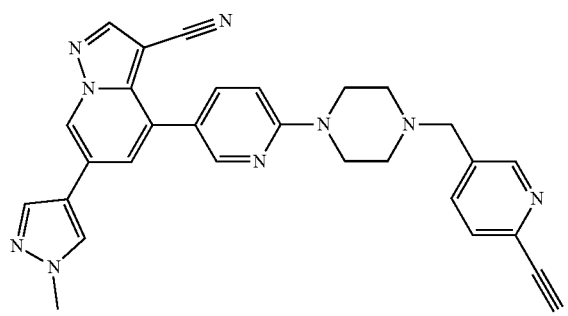
(227)
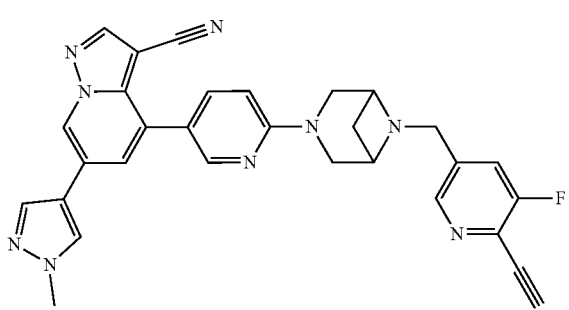
(228)
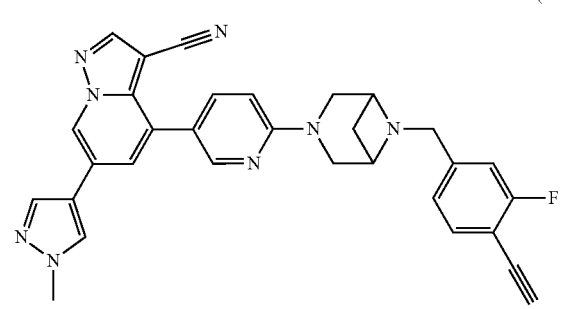

-continued
(229)
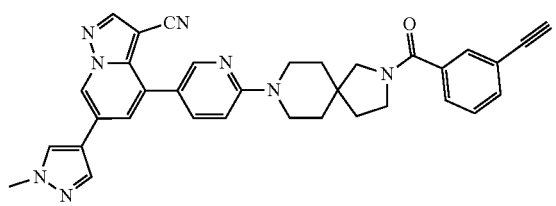
(230)
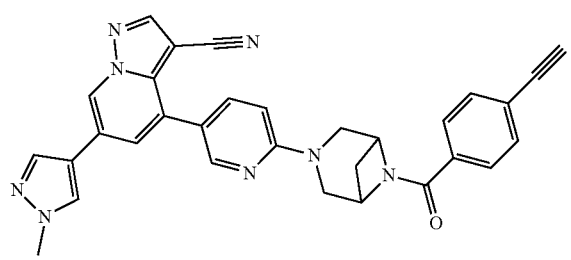
(231)
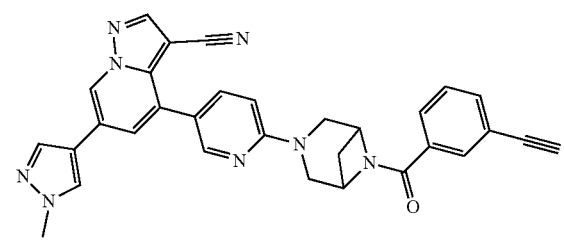
(232)
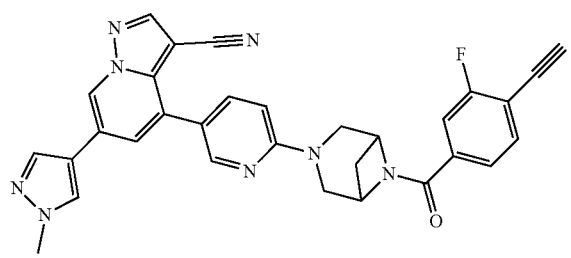
(233)
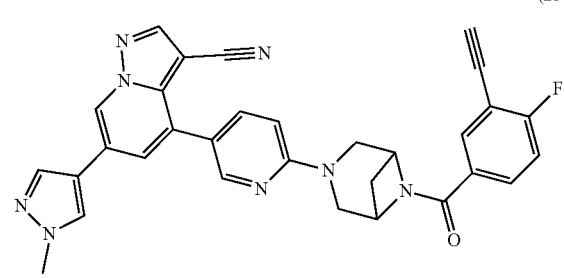
-continued
(234)
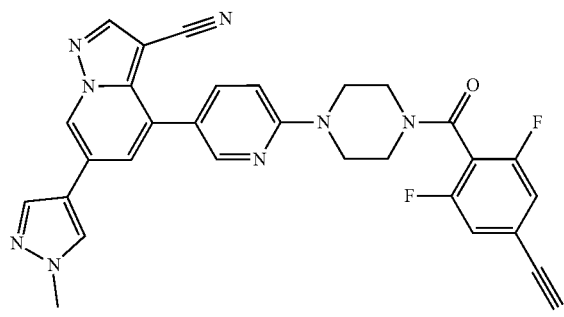
(235)
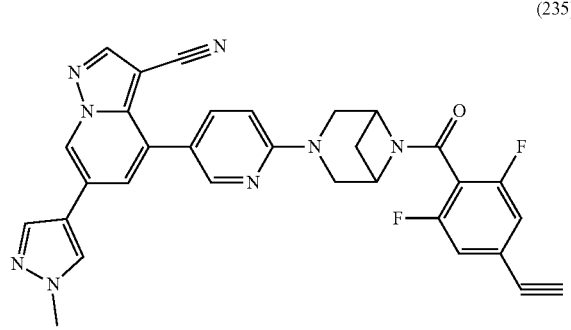
(236)
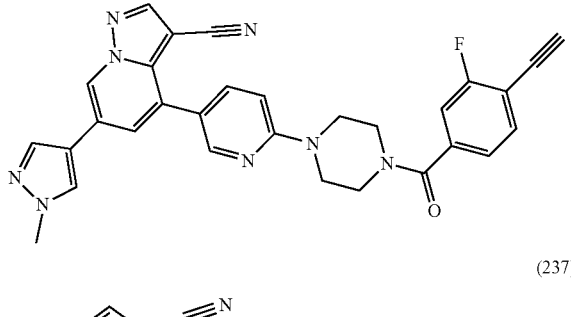
(237)
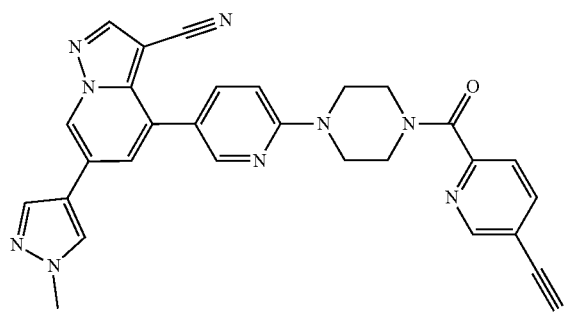
(238)
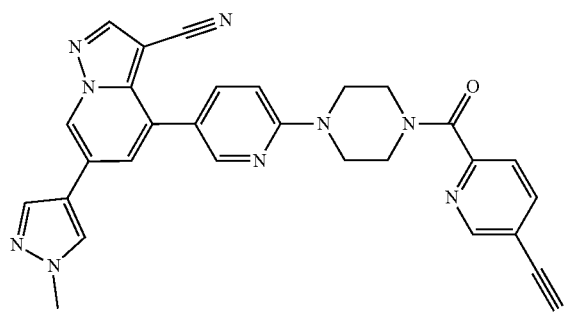

(239) 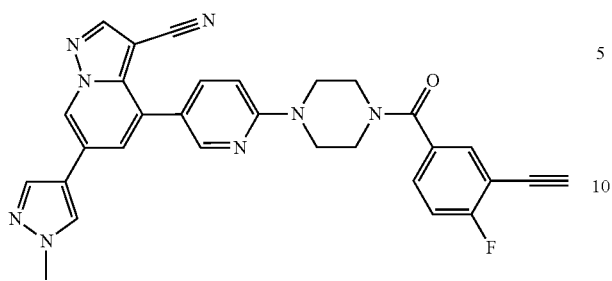
(240) 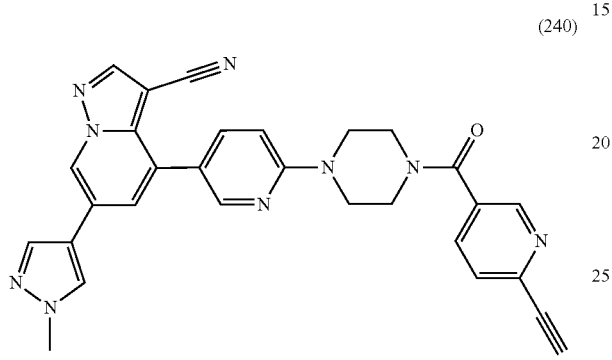
(241) 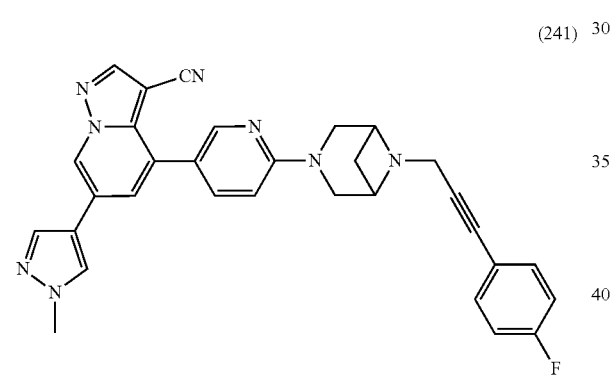
(242) 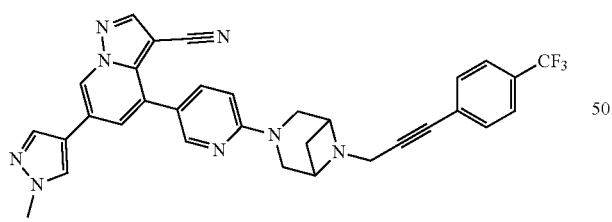
(243) 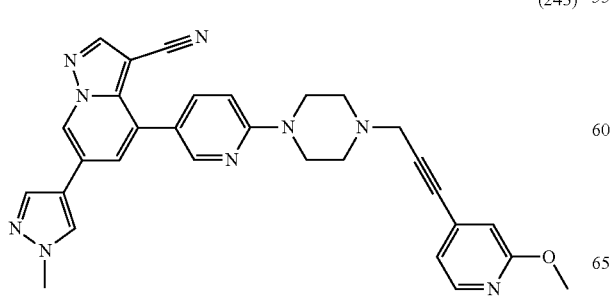
(244) 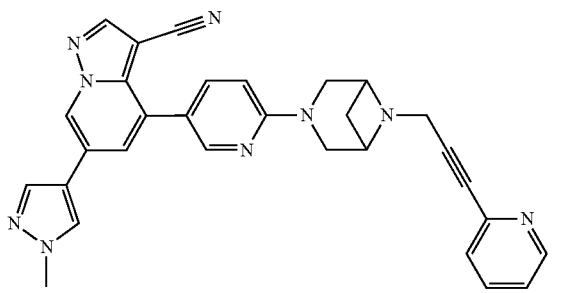
(245) 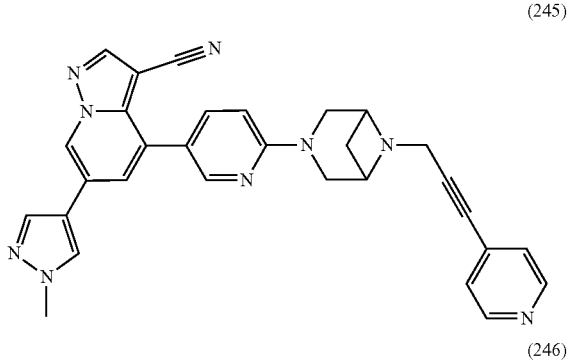
(246) 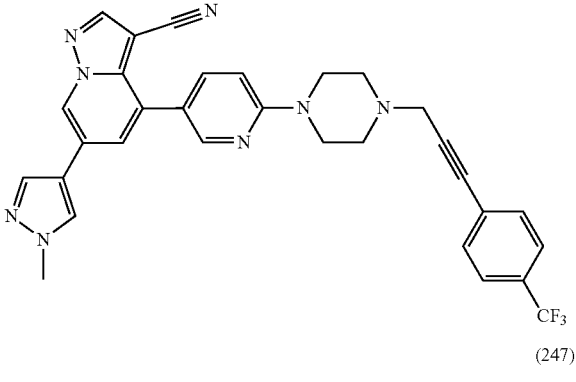
(247) 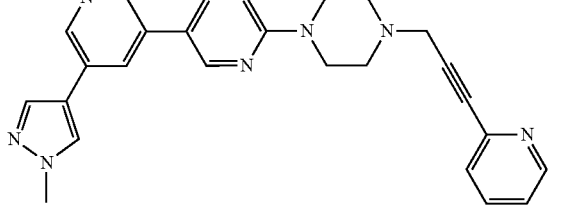
(248) 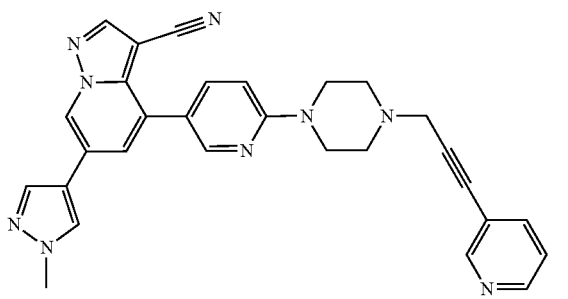

(249)
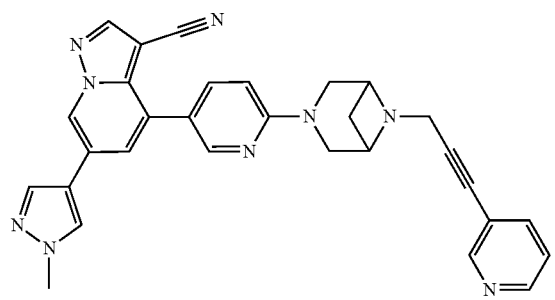
(250)
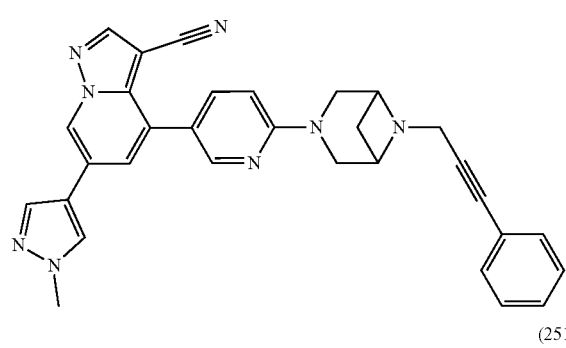
(251)
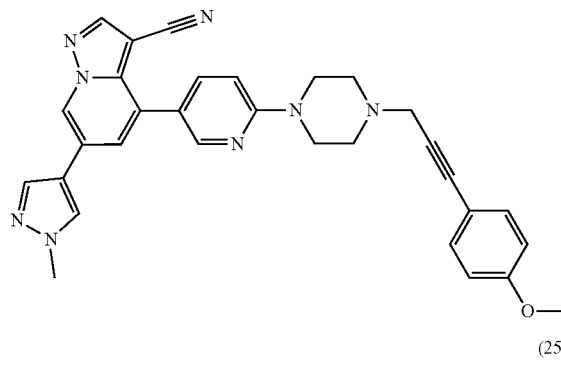
(252)
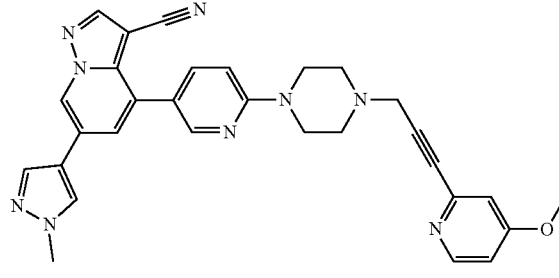
(253)
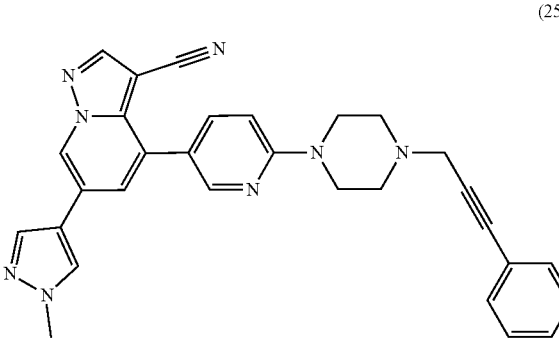
(254)
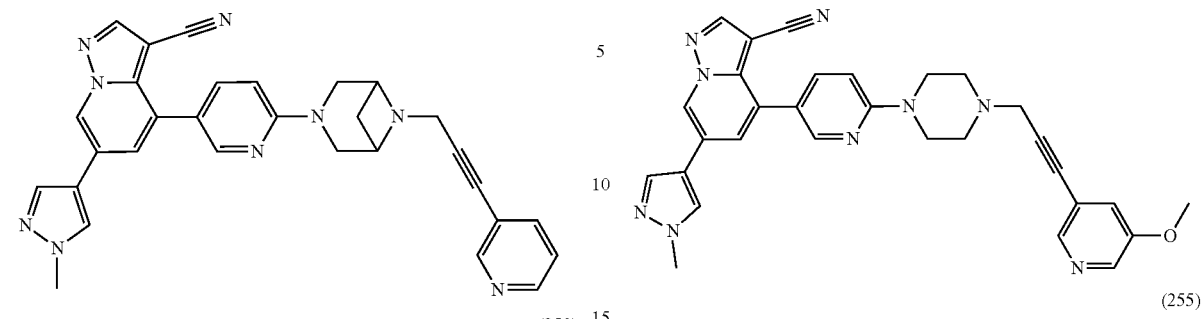
(255)
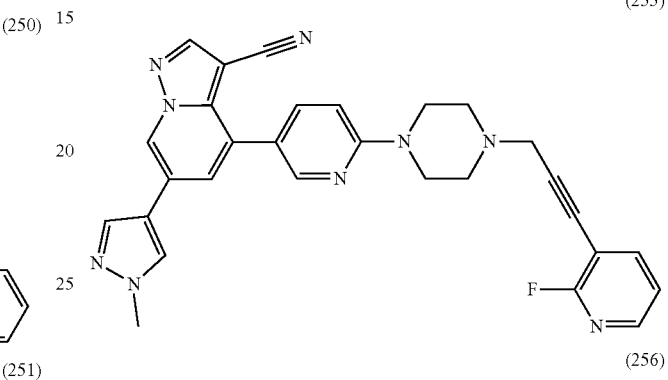
(256)
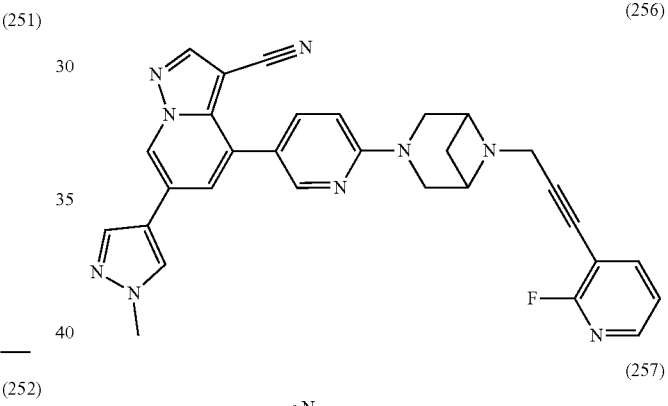
(257)
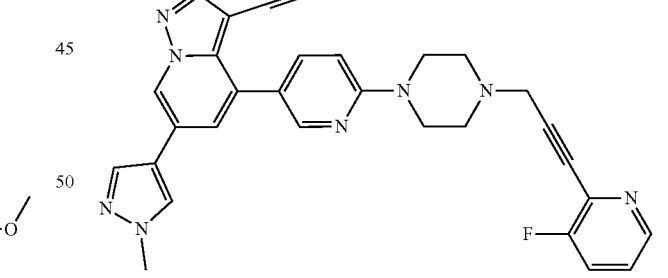
(258)
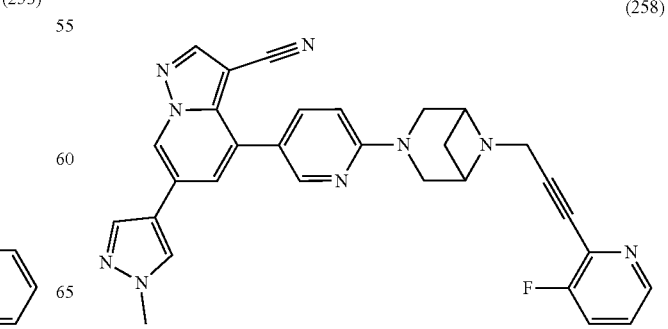

-continued
(259)
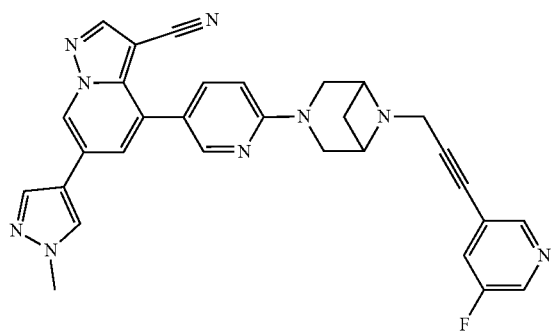
(260)
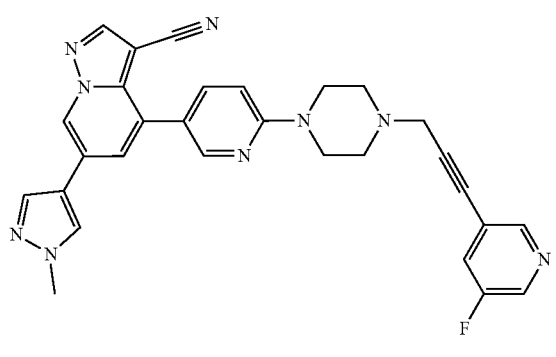
(261)
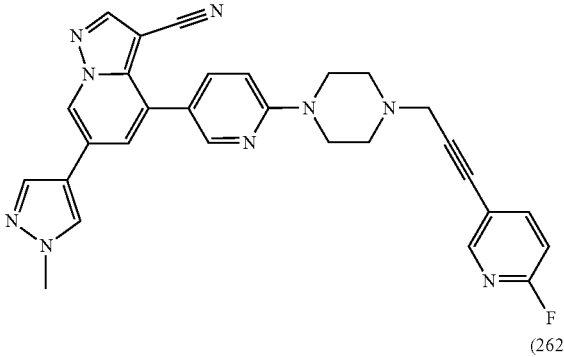
(262)
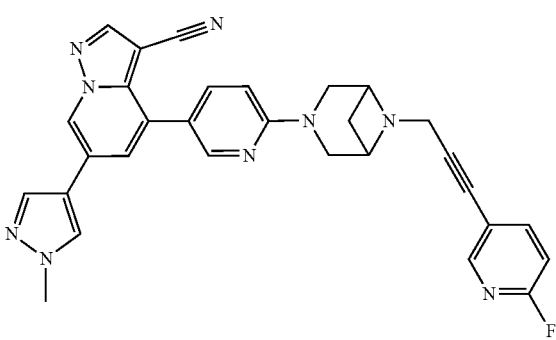
-continued
(263)
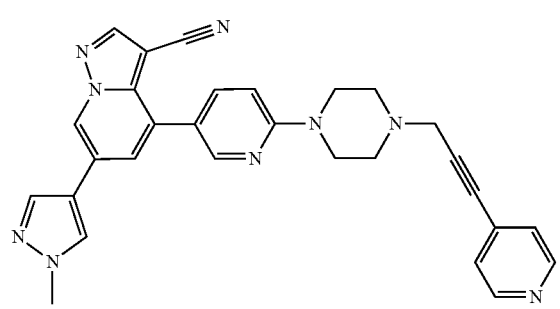
(264)
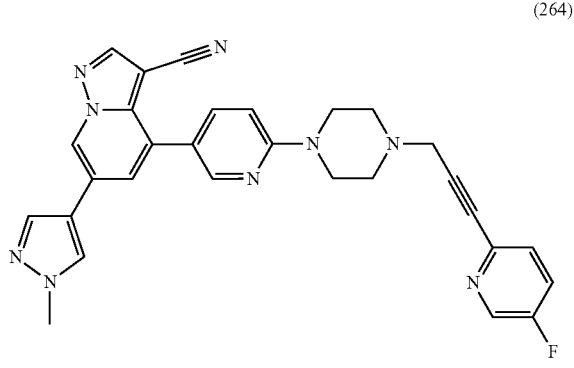
(265)
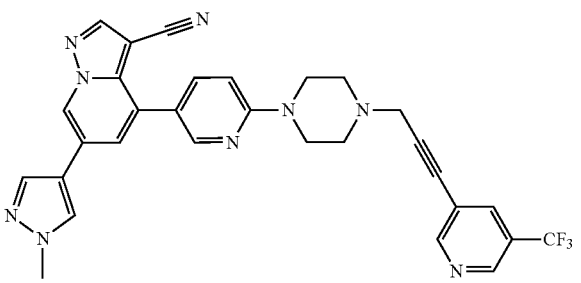
(266)
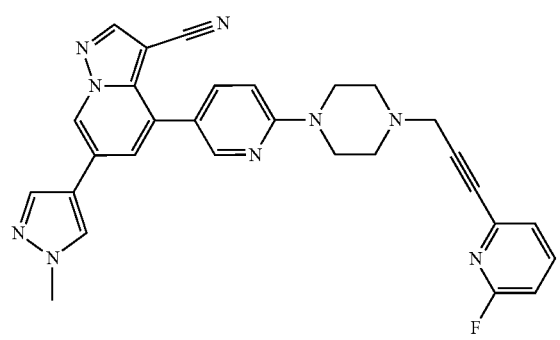

-continued
(267)
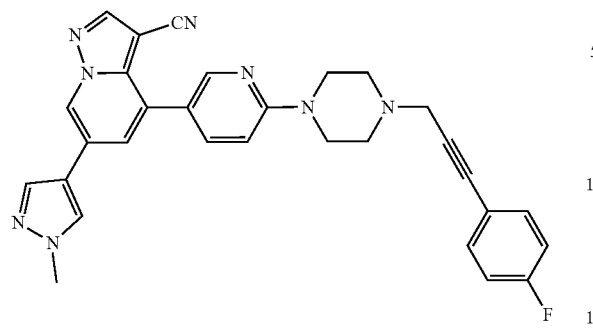
(268)
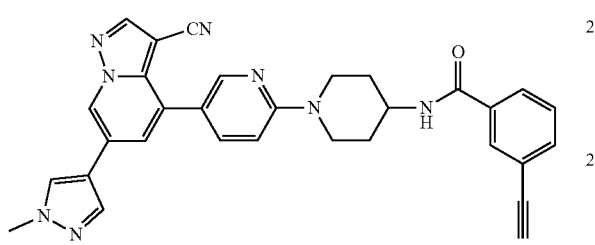
(269)
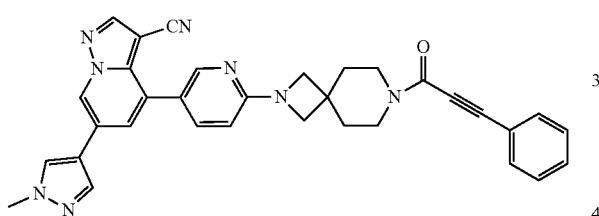
(270)
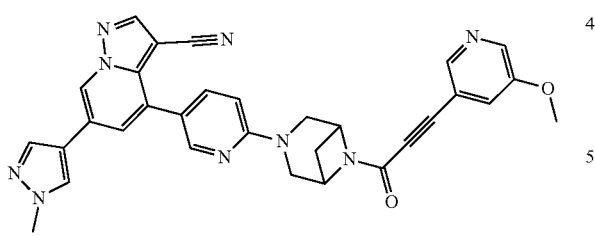
(271)
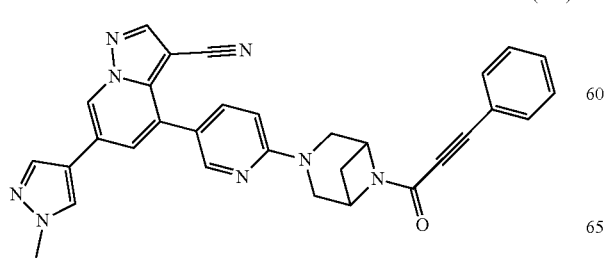
-continued
(272)
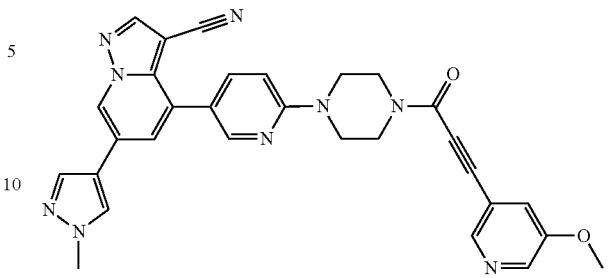
(273)
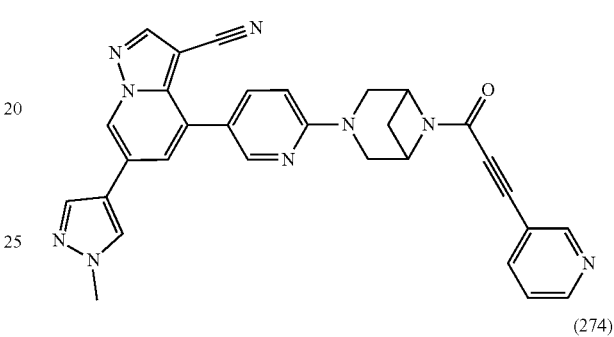
(274)
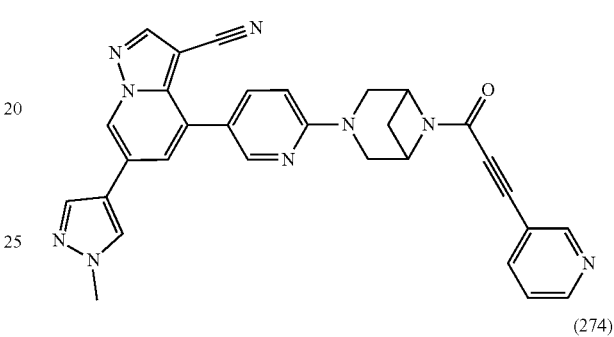
(275)
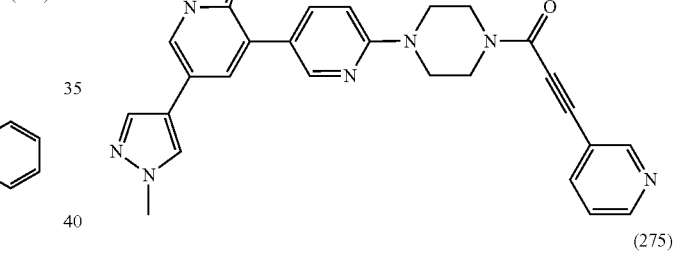
(276)
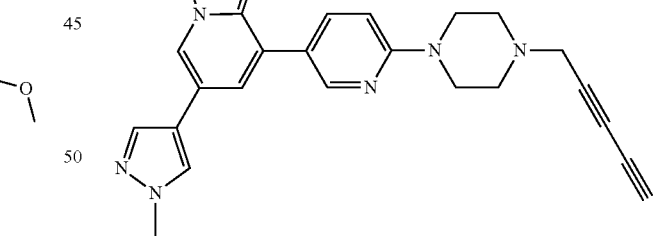

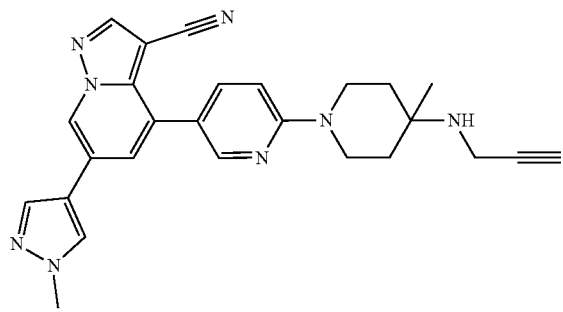
(277)
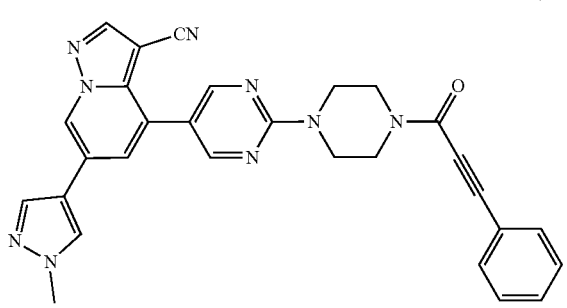
(278)
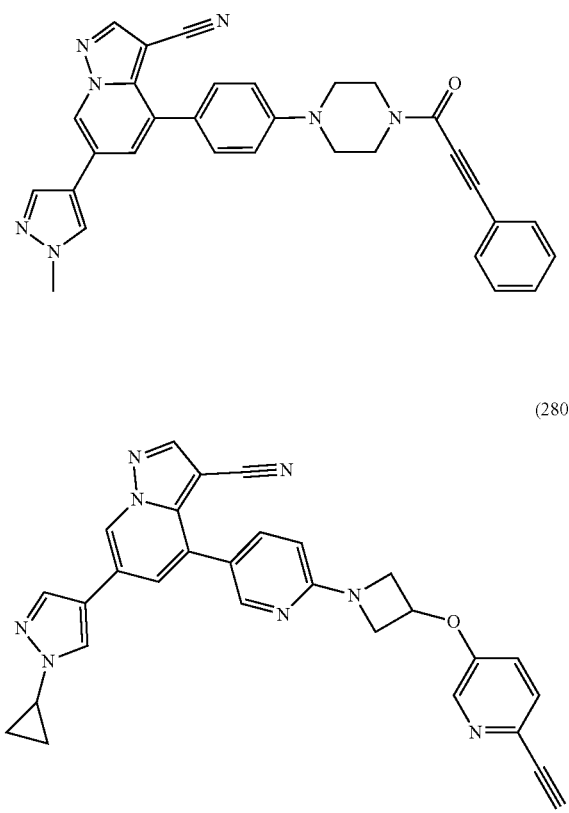
(279)
(280)
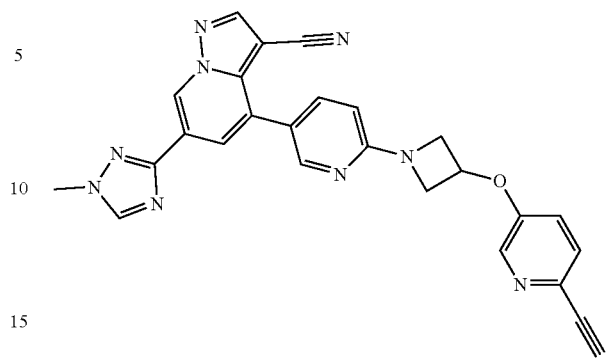
(281)
(282)
(283)
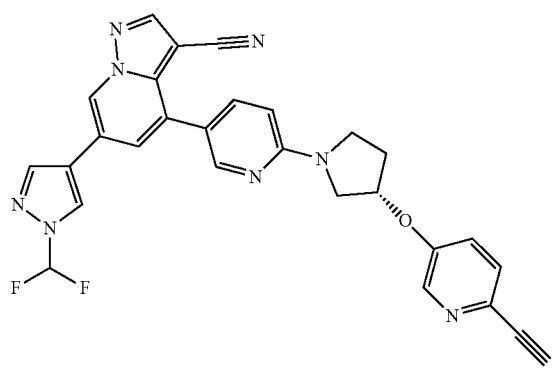
(284)

(285)
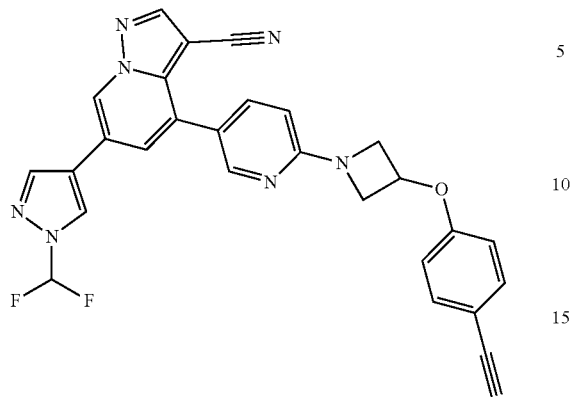
(289)
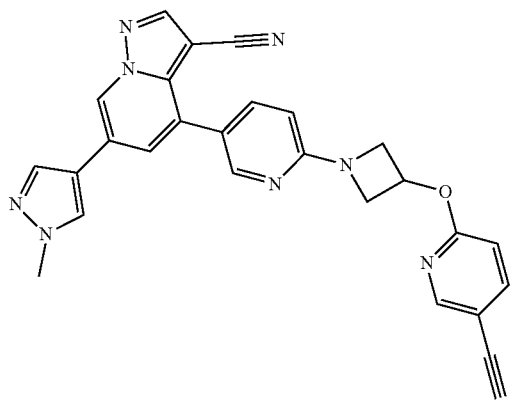
(286)
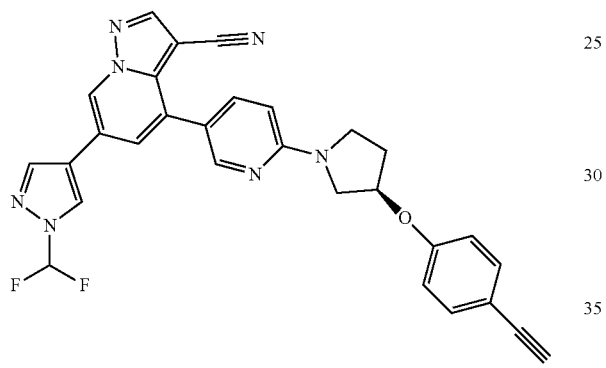
(290)
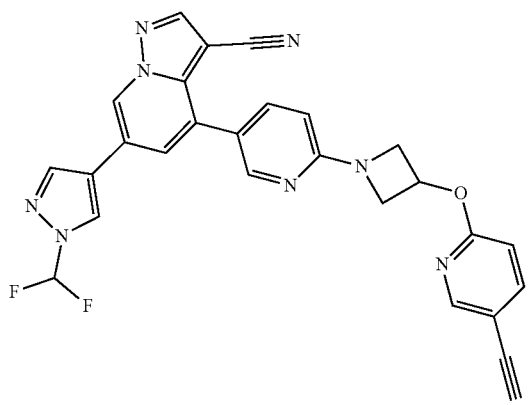
(287)
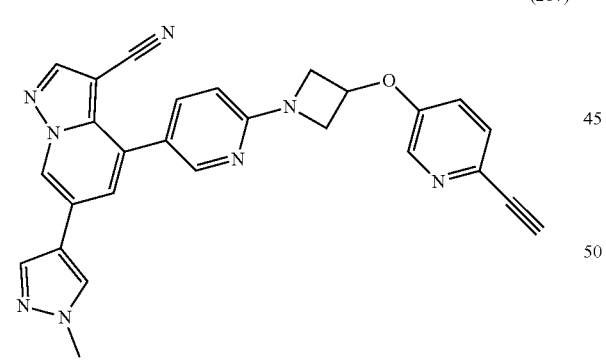
(288)
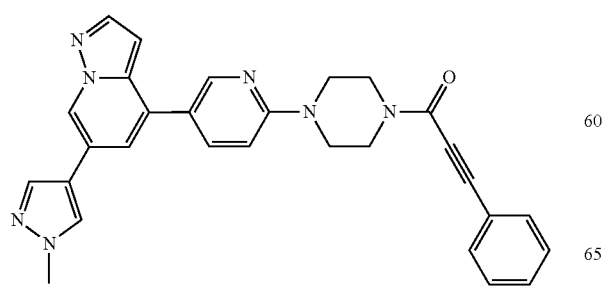
(291)
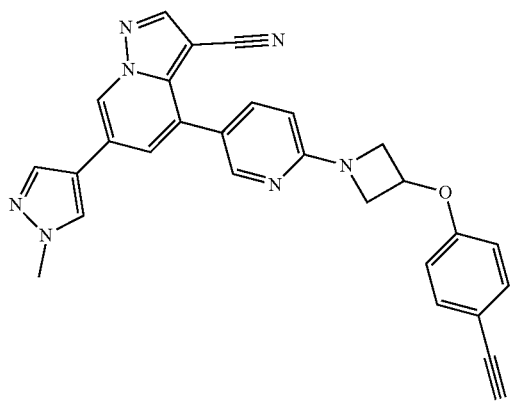

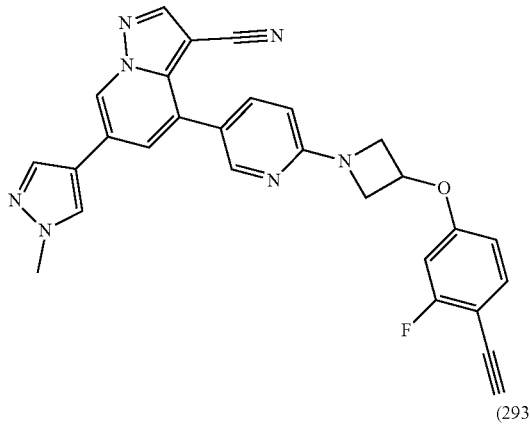
(292)

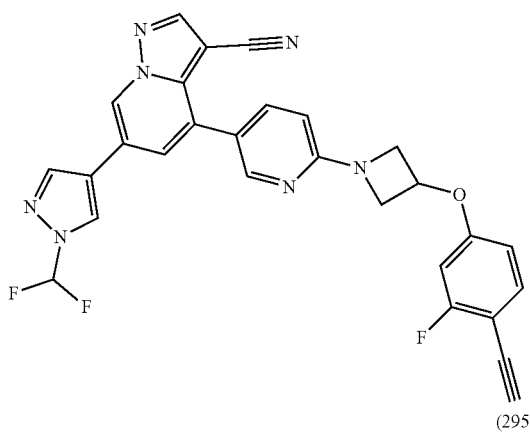
(293)

(294)

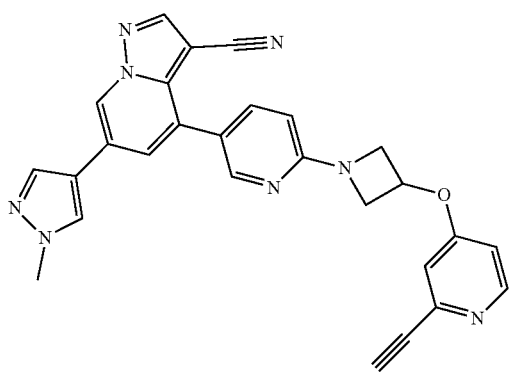
(295)

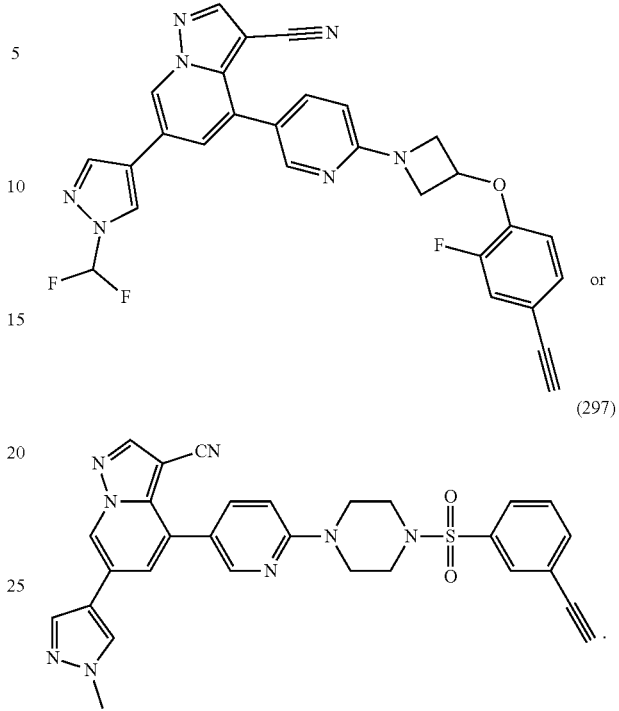
(296)

or (297)

In another aspect, the invention provides a pharmaceutical composition comprising a compound of the invention, and a pharmaceutically acceptable adjuvant.

In other aspect, provided herein is use of the compound or the pharmaceutical composition disclosed herein in the manufacture of a medicament for preventing or treating a RET-related disease.

In some embodiments, the RET-related diseases include cancer, irritable bowel syndrome, and/or pain associated with irritable bowel syndrome.

In other aspect, provided herein is use of the compound or the pharmaceutical composition disclosed herein for preventing or treating a RET-related disease.

In some embodiments, the RET-related diseases include cancer, irritable bowel syndrome, and/or pain associated with irritable bowel syndrome.

In another aspect, the invention provides a method of preventing or treating a RET-related disease, wherein the method comprises administering to a patient a therapeutically effective amount of a compound of the invention or a pharmaceutical composition thereof.

In some embodiments, the RET-related diseases include cancer, irritable bowel syndrome, and/or pain associated with irritable bowel syndrome.

In other aspect, the invention relates to the intermediate for the preparation of a compound of Formula (I), (I-1), (I-1a), (I-2), (I-3) or (I-4).

In another aspect, provided herein are methods for preparing, separating, and purifying the compound of formula (I), (I-1), (I-1a), (I-2), (I-3) or (I-4).

In another aspect, the invention provides a pharmaceutical composition comprising a compound of the invention, and a pharmaceutically acceptable adjuvant. In some embodiments, the adjuvants described herein include, but are not limited to, carriers, excipients, diluents, vehicles, or combinations thereof. In some embodiments, the pharmaceutical composition can be in the form of a liquid, solid, semi-solid, gel or spray.

The invention is also provided a method of inhibiting cell proliferation in vitro or in vivo, the method comprising contacting a cell with an effective amount of a compound of the invention or a pharmaceutical composition thereof.

The invention is also provided a method of treating irritable bowel syndrome (IBS) and/or pain associated with IBS in a patient in need of treatment, the method comprising administering to the patient a therapeutically effective amount of a compound of the invention or a pharmaceutical composition thereof.

Also provided herein is use of the compound or the pharmaceutical composition disclosed herein in the manufacture of a medicament for preventing or treating irritable bowel syndrome (IBS) and/or pain associated with IBS.

Also provided herein is use of the compound or the pharmaceutical composition disclosed herein for preventing or treating irritable bowel syndrome (IBS) and/or pain associated with IBS.

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention.

In particular, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

Salts of the compounds disclosed herein also include salts of the compounds which are not necessarily pharmaceutically acceptable salts, and which may be useful as intermediates for preparing and/or purifying compounds of Formula (I), (I-1a), (I-1), (I-2), (I-3) or (I-4) and/or for separating enantiomers of compounds of Formula (I), (I-1a), (I-1), (I-2), (I-3) or (I-4).

In the structures disclosed herein, when the stereochemistry of any particular chiral atom is not indicated, all stereoisomers of the structure are contemplated within the invention, and as disclosed herein are included in the present invention. When stereochemistry is indicated by a solid wedge or dashed line representing a particular configuration, the stereoisomer of the structure is defined.

N-oxides of the compound disclosed herein are also included in the invention. N-oxides of the compound of the invention can be prepared by oxidizing corresponding nitrogen-containing alkaline substances with common oxidants (e.g., hydrogen peroxide) under a rising temperature in the presence of an acid, such as acetic acid, or by reacting with peracid in a suitable solvent, e.g., by reacting with peracetic acid in dichloromethane, ethyl acetate or methyl acetate, or by reacting with 3-chloroperoxybenzoic acid in chloroform or dichloromethane.

If the compound disclosed herein is a base, the desired salt can be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, ethanesulfonic acid and the like.

If the compound disclosed herein is an acid, the desired salt may be prepared by any suitable method, for example, treatment of the free acid with an inorganic or organic base, such as an amine (primary, secondary or tertiary), an alkali metal hydroxide, ammonium or alkaline earth metal hydroxide, and the like. Some non-limiting examples of suitable salts include organic salts derived from amino acids, such as glycine and arginine; ammonia, such as primary, secondary and tertiary amine and cyclic amines, such as piperidine, morpholine and piperazine, and inorganic salts derived from sodium, calcium, potassium, magnesium, manganese, iron, copper, zinc, aluminum, lithium, and the like.

Compounds of the Invention and Pharmaceutical Compositions, Preparations, Administration The present invention provides a compound of the present invention or a pharmaceutical composition thereof which inhibits wild-type RET and RET mutants, for example, RET mutants which are resistant to current standard care treatments ("RET resistance mutant"). In addition, the compounds of the invention or pharmaceutical compositions thereof may be selective for wild-type RET relative to other kinases, resulting in reduced toxicity associated with inhibition of other kinases.

The pharmaceutical composition of the present invention comprises a compound having Formula (I), (I-1a), (I-1), (I-2), (I-3) or (I-4), a compound listed in the present invention, or a compound of the examples. The amount of the compound in the composition of the present invention is effective to treat or ameliorate a patient's RET-related disease or condition, including RET-related cancer, irritable bowel syndrome, and/or pain associated with irritable bowel syndrome.

As described above, the pharmaceutically acceptable compositions disclosed herein further comprise a pharmaceutically acceptable adjuvant, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As described in the following: In *Remington: The Science and Practice of Pharmacy*, 21st edition, 2005, ed. D. B. Troy, Lippincott Williams& Wilkins, Philadelphia, and *Encyclopedia of Pharmaceutical Technology*, eds. J. Swarbrick and J. C. Boylan, 1988-1999, Marcel Dekker, New York, both of which are herein incorporated by reference in their entireties, discloses various adjuvants used in formulating pharmaceutically acceptable compositions and known techniques for the preparation thereof. Except insofar as any conventional adjuvants incompatible with the compounds disclosed herein, such as by producing any undesirable biological effect or otherwise interacting in a deleterious manner with any other components of the pharmaceutically acceptable composition, its use is contemplated to be within the scope of this invention.

In preparing the compositions provided herein, the active ingredient is usually mixed with excipients, diluted by excipients or enclosed in such carriers, for example, in the form of capsules, sachets, paper or other containers. If the excipient is used as a diluent, it can be a solid, semi-solid or liquid material which acts as a vehicle, carrier or medium for the active ingredient. Suitable carriers include, but are not limited to, magnesium carbonate, magnesium stearate, talc, sugar, lactose, pectin, dextrin, starch, gelatin, tragacanth, methylcellulose, sodium carboxymethylcellulose, low melting point wax, cocoa butter, etc. Therefore, the composition may be in the form of a tablet, a pill, a powder, a troche, a sachet, a flat capsule, an elixirs, a suspension, an emulsion, a solution, a syrup, an aerosol (solid form or in a liquid medium), an ointment which for example contains up to 10% by weight of active compound, soft and hard gelatin capsules, a suppository, a sterile injectable solution, and a aseptically packaged powder. In one embodiment, the composition is formulated for oral administration. In one embodiment, the composition is formulated as a tablet or capsule.

When it is possible that, for use in therapy, therapeutically effective amounts of the compounds of the invention, especially the compound of formula (I), (I-1a), (I-1), (I-2), (I-3) or (I-4), as well as pharmaceutically acceptable salts thereof, may be administered as the raw chemical, it is possible to present the active ingredient as a pharmaceutical composition. Therefore, the invention further provides pharmaceutical compositions, which comprise therapeutically effective amounts of the compounds of the present invention, especially the compound of formula (I), (I-1a), (I-1), (I-2), (I-3) or (I-4) or pharmaceutically acceptable salts thereof, and one or more pharmaceutically acceptable adjuvants, including but not limited to carriers, diluents or excipients, and the like. The term "therapeutically effective amount," as used herein, refers to the total amount of each active component that is sufficient to show a meaningful patient benefit (such as a decrease in cancer cells). When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of the invention, especially the compound of formula (I), (I-1a), (1-1), (I-2), (I-3) or (I-4), and pharmaceutically acceptable salts thereof are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing the compounds of the invention, in particular the compound of formula (I), (I-1a), (I-1), (I-2), (I-3) or (I-4), or pharmaceutically acceptable salts thereof, with one or more pharmaceutically acceptable carriers, diluents, or excipients. The term "pharmaceutically acceptable" as used herein, refers to those compounds, materials, compositions, and/or dosage forms which are, within the scope of sound medical judgment, suitable for use in contacting with the tissues of patients without excessive toxicity, irritation, allergic response, or other problem or complication commensurate with a reasonable benefit/risk ratio, and are effective for their intended use.

The amount of active ingredient combined with one or more adjuvants to produce a single dosage form will necessarily vary depending upon the host treated and the particular route of administration. The amount of the active ingredient of the compound of formula (I), (I-1a), (I-1), (1-2), (I-3) or (I-4) mixed with the carrier material to prepare a single dosage form will vary depending upon the disease to be treated, the severity of the disease, the time of administration, the route of administration, the rate of excretion of the compound used, the time of treatment, and the age, sex, weight and condition of the patient. Preferred unit dosage forms are unit dosage forms containing a daily or divided dose of the active ingredient described herein, or a suitable fraction thereof. Treatment can be initiated with a small dose that is clearly below the optimal dose of the compound. Thereafter, the dose is increased in smaller increments until the best results are achieved in this case. In general, the level of concentration at which the compound is most desirably administered generally provides an effective result in anti-tumor without causing any harmful or toxic side effects.

Compositions comprising a compound of the invention may be formulated in unit dosage form, each containing from about 5 to about 1,000 mg (1 g), more typically from about 100 mg to about 500 mg of the active ingredient. The term "unit dosage form" refers to physically discrete units suitable for use as a single dose in a human subject or other patient, each unit containing a predetermined amount of active material (i.e., a compound of formula I as provided herein) and a suitable pharmaceutical excipient, wherein the predetermined amount is calculated to produce the desired therapeutic effect.

In some embodiments, the compositions provided herein contain from about 5 mg to about 50 mg of the active ingredient. Those of ordinary skill in the art will appreciate that this encompasses a compound or composition comprising from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg or from about 45 mg to about 50 mg of the active ingredient.

In some embodiments, the compositions provided herein contain from about 50 mg to about 500 mg of the active ingredient. Those of ordinary skill in the art will appreciate that this encompasses a compound or composition comprising from about 50 mg to about 100 mg, from about 100 mg to about 150 mg, from about 150 mg to about 200 mg, from about 200 mg to about 250 mg, from about 250 mg to about 300 mg, from about 350 mg to about 400 mg, from about 400 mg to about 450 mg or from about 450 mg to about 500 mg of the active ingredient.

In some embodiments, the compositions provided herein contain from about 500 mg to about 1000 mg of the active ingredient. Those of ordinary skill in the art will appreciate that this encompasses a compound or composition comprising from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg or from about 950 mg to about 1000 mg of the active ingredient.

The pharmaceutical compositions are suitable for administration by any suitable route, for example by oral administration (including buccal or sublingual), rectal, nasal, topical (including buccal, sublingual or transdermal), vaginal or parenteral (including subcutaneous, intradermal, intramuscular, intra-articular, intrasynovial, intrasternal, intrathecal, intralesional, intravenous or subdermal injection or infusion). Such formulations may be prepared by any method known in the art of pharmacy, for example by mixing the active ingredient with carriers or excipients. Oral administration or injection administration is preferred.

The invention also provides a method of treating an individual having a RET-related cancer, the method comprising administering a compound of the invention before, during or after administration of another anti-cancer drug (e.g., not a compound of the invention).

The invention provides a method for treating cancer in a patient in need thereof, the method comprising: (a) determining whether the cancer in the patient is a RET-related cancer (e.g., RET-related cancers including RET-related cancers with one or more RET inhibitor resistance mutations)(for example, using a regulatory agency-approved, e.g., FDA-approved, kit to identify RET genes, RET kinases, or any one of the expression or activity or levels of dysregulation in a patient's biopsy sample, or by performing any non-limiting examples of the invention described herein); (b) if the cancer is determined to be a RET-related cancer, a therapeutically effective amount of a compound of formula (I), (I-1a), (I-1), (I-2), (I-3), or (I-4) or a pharmaceutically acceptable salt or solvate thereof or a pharmaceutical composition thereof is administered to the patient. Some embodiments of these methods further comprise administering to the subject another anti-cancer agent (e.g., another RET inhibitor, e.g., a RET inhibitor that is not a compound of the invention). In some embodiments, the subject has been previously treated with a RET inhibitor that is not a compound of formula (I), (I-1a), (I-1), (I-2), (I-3) or (I-4) or a pharmaceutically acceptable salt or solvate thereof, or has been previously treated (e.g., after removal of a tumor or radiation therapy) with other anticancer agents.

In some embodiments of any of the methods described herein, the compound of formula (I), (I-1a), (I-1), (I-2), (I-3), or (I-4) (or a pharmaceutically acceptable salt or solvate thereof) is administered in combination with a therapeutically effective amount of at least one other therapeutic agent selected from one or more other therapies or therapeutic (e.g., chemotherapeutic) reagents.

Non-limiting examples of other therapeutic agents include: other RET targeted therapeutic agents (i.e., other RET kinase inhibitors: RET inhibitors that are not the compounds of the invention), receptor tyrosine kinase targeted therapeutic agents, signal transduction pathway inhibitors, checkpoint inhibitors, apoptotic pathway regulators (e.g., Obataclax); cytotoxic chemotherapeutic agents, angiogenesis targeted therapeutic agents, immunotargeting agents and radiation therapy.

In some embodiments, other RET targeted therapeutic agents are multi-kinase inhibitors that exhibit RET inhibitory activity.

Non-limiting examples of RET targeted therapeutic agents include alatinib, apatinib, cabozantinib (XL-184), vittinib, levabrinib, morsani, nidanib, punatinib, regrafenib, sitravatinib (MGCD516), sunitinib, sorafenib, vatalani, vandetanib, AUY-922 (5-(2,4-dihydroxy-5-isopropyl-phenyl)-N-ethyl-4-[4-(morpholinomethyl)phenyl]isoxazole-3-formamide), BLU6864, BLU-667, DCC-2157, NVP-AST487 (1-[4-[(4-ethylpiperazin-1-yl) methyl]-3-(trifluoromethyl) phenyl]-3-[4-[6-(methylamino)pyrimidine-4-yl]oxyphenyl] urea), PZ-1, RPI-1 (1,3-dihydro-5,6-dim ethoxy-3-[(4-hydroxyphenyl)methylene]-n-indole-2-one), RXDX-105 (1-(3-(6,7-dimethoxyquinazolin-4-yl)oxy)phenyl)-3-(5-(1,1,1-trifluoro-2-methylpropane)-2-yl)isoxazol-3-yl)urea), SPP86 (1-isopropyl-3-(phenylethynyl)-1H-pyrazolo[3,4-d]pyrimidin-4-amine) and TG101209 (N-(1,1-dimethylethyl))-3-[[5-methyl-2-[[4-(4-methyl-1-piperazinyl)phenyl]amino]-4-pyrimidinyl]amino]benzenesulfonamide).

Other therapeutic agents include RET inhibitors such as those described, for example, in U.S. Pat. Nos. 7,504,509; 8,299,057; 8,399,442; 8,067,434; 8,937,071; 9,006,256; and 9,035,063; U.S. Publication No. 2014/0121239; 20160176865; 2011/0053934; 2011/0301157; 2010/0324065; 2009/0227556; 2009/0130229; 2009/0099167; 2005/0209195; International Publication No. WO 2014/184069; WO 2014/072220; WO 2012/053606; WO 2009/017838; WO 2008/031551; WO 2007/136103; WO 2007/087245; WO2007/057399; WO 2005/051366; WO 2005/062795; and WO 2005/044835; and *J. Med. Chem.* 2012, 55(10), 4872-4876, all of which are incorporated herein by reference in its entirety.

Also provided herein is a method of treating cancer comprising administering to a patient in need thereof a pharmaceutical combination for treating cancer comprising (a) a compound of formula I or a pharmaceutically acceptable salt or solvate thereof, (b) other treatments, and (c) optionally at least one pharmaceutically acceptable carrier for simultaneous, separate or sequential use in the treatment of cancer, wherein the amount of the compound of formula I, or a pharmaceutically acceptable salt or solvate thereof, and the amount of other therapeutic agent are collectively effective in treating cancer.

The compounds and compositions described herein can be administered alone or in combination with other compounds (including other RET modulating compounds) or other therapeutic agents. In some embodiments, the compounds or compositions of the invention can be administered in combination with one or more compounds selected from the group consisting of: cabozantinib (COMETRIQ), vandetanib (CALPRESA), sorafenib (NEXAVAR), sunitinib (SUTENT), regrafenib (STAVARGA), punatinib (ICLUSIG), bevacizumab (Avastin), crizotinib (XALKORI) or gefitinib (IRESSA). The compounds or compositions of the invention may be administered simultaneously or sequentially with other therapeutic agents by the same or different routes of administration. The compounds of the invention may be included in a single formulation or in separate formulations with other therapeutic agents.

In some embodiments, the compounds of the invention are useful for treating irritable bowel syndrome (IBS) in combination with one or more other therapeutic agents or therapies which are effective in the treatment of irritable bowel syndrome by acting on the same or different mechanisms of action. According to standard pharmaceutical practice known to those skilled in the art, at least one additional therapeutic agent may be as part of the same or separate dosage form, administered via the same or different routes, and administered according to the same or different administration schedule with the compound of formula I, or a pharmaceutically acceptable salt or solvate thereof. Non-limiting examples of other therapeutic agents for treating irritable bowel syndrome (IBS) include probiotics, fiber supplements (e.g., psyllium, methylcellulose), antidiarrheals (e.g., loperamide), bile acid binders (e.g., cholestyramine, colestipol, colesevelam), anticholinergics and anticonvulsants (e.g., hyoscyamine, bicyclic amines), antidepressants (e.g., tricyclic antidepressants such as imipramine or nortriptyline, or selective serotonin reuptake inhibitors (SSRI) such as fluoxetine or paroxetine), antibiotics (such as rifaximin), alosetron and lubiprostone.

Use of the Compounds and Pharmaceutical Compositions

The present invention also provides the use of the compound or the pharmaceutical composition disclosed herein in the manufacture of a medicament for preventing or treating a RET-related disease or disorder, wherein the RET-related disease or disorder includes a RET-related cancer, irritable bowel syndrome and/or pain associated with irritable bowel syndrome.

The present invention provides a compound of the present invention or a pharmaceutical composition thereof which inhibits wild-type RET and RET mutants, for example, RET mutants which are resistant to current standard care treatments ("RET resistance mutant"). In addition, the compounds of the invention or pharmaceutical compositions thereof may be selective for wild-type RET relative to other kinases, resulting in reduced toxicity associated with inhibition of other kinases.

The present invention provides the use of a compound of the present invention or a pharmaceutical composition thereof for inhibiting wild-type RET and RET mutants of the present invention in the manufacture of a medicament for preventing or treating a wild-type RET and RET mutant-related disease or disorder.

In some embodiments of any of the methods or uses described herein, the cancer (e.g., RET-related cancer) is a hematological cancer. In some embodiments of any of the methods or uses described herein, the cancer (e.g., RET-related cancer) is a solid tumor. In some embodiments of any of the methods or uses described herein, the cancer (e.g., RET-related cancer) is a lung cancer (e.g., small cell lung cancer or non-small cell lung cancer), papillary thyroid cancer, medullary thyroid carcinoma, differentiated thyroid gland cancer, recurrent thyroid cancer, refractory differentiated thyroid cancer, lung adenocarcinoma, bronchiolar lung cancer, type 2A or 2B multiple endocrine tumors (MEN2A or MEN2B, respectively), pheochromocytoma, parathyroid hyperplasia, mammary gland cancer, colorectal cancer (e.g., metastatic colorectal cancer), papillary renal cell carcinoma, ganglion cell tumor of the gastrointestinal mucosa, inflammatory myofibroblastic tumor or cervical cancer. In some embodiments of any of the methods or uses described herein, the cancer (e.g., RET-related cancer) is selected from the group consisting of: acute lymphoblastic leukemia (ALL), acute myeloid leukemia (AML), juvenile cancer, adrenocortical carcinoma, anal cancer, appendix cancer, astrocytoma, atypical teratoma/rhabdoid tumor, basal cell carcinoma, cholangiocarcinoma, bladder cancer, bone cancer, brainstem glioma, brain tumor, breast cancer, bronchial neoplasm, Burkitt's lymphoma, carcinoid tumor, unknown primary cancer, cardiac tumor, cervical cancer, childhood cancer, chordoma, chronic lymphocytic leukemia (CLL), chronic myelogenous leukemia (CML), chronic myeloproliferative neoplasms, colon cancer, colorectal cancer, craniopharyngioma, cutaneous T-cell lymphoma, cholangiocarcinoma, ductal carcinoma in situ, embryonal tumor, endometrial cancer, ependymoma, esophageal cancer, sensory neuroblastoma, ewing sarcoma, extracranial germ cell tumor, extragonadal germ cell tumor, extrahepatic cholangiocarcinoma, eye cancer, fallopian tube cancer, bone fibrous histiocytoma, gallbladder cancer, gastric cancer, gastrointestinal carcinoid tumor, gastrointestinal stromal tumor (GIST), germ-cell tumor, gestational trophoblastic disease, glioma, hairy cell tumor, hairy cell leukemia, head and neck cancer, heart cancer, hepatocellular carcinoma, histiocytosis, Hodgkin's lymphoma, hypopharyngeal carcinoma, intraocular melanoma, islet cell tumor, pancreatic neuroendocrine tumor, Kaposi's sarcoma, kidney cancer, Langerhans cell histiocytosis, laryngeal cancer, leukemia, lip and oral cancer, liver cancer, lung cancer, lymphoma, macroglobulinemia, bone malignant fibrous histiocytoma, bone cancer, melanoma, Merkel cell carcinoma, mesothelioma, metastatic squamous neck carcinoma, midline cancer, oral cancer, multiple endocrine neoplasia syndrome, multiple myeloma, mycosis fungoides granuloma, myelodysplastic syndrome, myelodysplasia/myeloproliferative neoplasms, myeloid leukemia, myeloid leukemia, multiple myeloma, myeloproliferative neoplasms, nasal and sinus cancer, nasopharyngeal carcinoma, neurocytoma, non-Hodgkin's lymphoma, non-small cell lung cancer, oral cancer, mouth cancer, lip cancer, oropharyngeal cancer, osteosarcoma, ovarian cancer, pancreatic cancer, papillomatosis, paraganglioma, paranasal sinus and nasal cancer, parathyroid carcinoma, penile cancer, pharyngeal carcinoma, pheochromocytoma, pituitary cancer, plasmacytoma, pleural lung blastoma, pregnancy and breast cancer, primary central nervous system lymphoma, primary peritoneal cancer, prostate cancer, rectal cancer, renal cell carcinoma, retinoblastoma, rhabdomyosarcoma, salivary gland cancer, sarcoma, Sezari syndrome, skin cancer, small cell lung cancer, small intestine cancer, soft tissue sarcoma, squamous cell carcinoma, squamous neck cancer, gastric cancer, T-cell lymphoma, testicular cancer, throat cancer, thymoma and thymic cancer, thyroid cancer, transitional cell carcinoma of the renal pelvis and ureter, unknown primary cancer, urethral cancer, uterus cancer, uterine sarcoma, vaginal cancer, vulvar cancer and Wilm's tumor.

In some embodiments, the RET-related cancer of the present invention is selected from the group consisting of lung cancer, papillary thyroid cancer, medullary thyroid carcinoma, differentiated thyroid cancer, recurrent thyroid cancer, refractory differentiated thyroid cancer, type 2A or 2B multiple endocrine neoplasia (MEN2A or MEN2B, respectively), pheochromocytoma, parathyroid hyperplasia, breast cancer, colorectal cancer, papillary renal cell carcinoma, gastrointestinal mucosal ganglion cell tumor and cervical cancer. In some embodiments, the RET-related cancer is RET fusion lung cancer or medullary thyroid carcinoma.

In some embodiments, the compound of formula (I), (I-1a), (I-1), (I-2), (I-3), or (I-4), the pharmaceutically acceptable salt and solvate thereof can be used to treat patients with cancers with RET inhibitor resistance mutations (which result in increased resistance to the compound other than formula (I), (I-1a), (I-1), (I-2), (I-3), or (I-4), the pharmaceutically acceptable salt or solvate thereof, for example, a substitution at amino acid position 804, such as V804M, V804L or V804E), wherein the treatment is administered by combination or as a follow-up treatment of existing medical treatments (for example, other RET kinase inhibitor that is not a compound of formula (I), (I-1a), (I-1), (I-2), (I-3) or (I-4), a pharmaceutically acceptable salt or solvate thereof). Described herein are exemplary RET kinase inhibitors (e.g., other RET kinase inhibitor that is not a compound of formula (I), (I-1a), (I-1), (I-2), (I-3) or (I-4) or a pharmaceutically acceptable salt or solvate thereof). In some embodiments, the RET kinase inhibitor may be selected from the group consisting of cabozantinib, vandetanib, alatinib, sorafenib, levabrinib, punatinib, vittinib, sunitinib, foretinib, BLU667 and BLU6864.

In some embodiments of any of the methods or uses described herein, the irritable bowel syndrome (IBS) comprises diarrhea-predominant, constipation-dominant or alternating, functional bloating, functional constipation, functional diarrhea, non-specific functional bowel disorder, functional abdominal pain syndrome, chronic idiopathic constipation, functional esophageal disease, functional gastroduodenal disease, functional anorectal pain, and inflammatory bowel disease.

The compounds and compositions, according to the method disclosed herein, may be administered using any amount and any route of administration which is effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

General Synthetic Procedures of the Compounds of the Invention

Generally, the compounds disclosed herein may be prepared by methods described herein, wherein the substituents are as defined for formula (I), (I-1a), (I-1), (I-2), (I-3) or (I-4) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Unless otherwise stated, reagents are commercially available, for example, reagents were purchased from commercial suppliers such as Lingkai Pharmaceuticals, Aldrich Chemical Company, Inc., Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF was obtained by refluxing the solvent with sodium. Anhydrous $CH_2Cl_2$ and $CHCl_3$ were obtained by refluxing the solvent with $CaH_2$. Ethyl acetate, N,N-dimethylacetamide and petroleum ether were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were obtained by using $CDCl_3$ or $DMSO-d_6$ solutions (reported in ppm), with TMS (0 ppm) or chloroform (7.25 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants J, when given, were reported in Hertz (Hz).

Low-resolution mass spectral (MS) data were also determined on an Agilent 6320 series LC-MS spectrometer equipped with G1312A binary pumps and a G1316A TCC (Temperature Control of Column, maintained at 30° C.). A G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A binary pumps and a G1316A TCC (Temperature Control of Column, maintained at 30° C.). A G1329A autosampler and a G1315D DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B).

Purities of compounds were assessed by Agilent 1100 Series high performance liquid chromatography (HPLC) with UV detection at 210 nm and 254 nm (Zorbax SB-C18, 2.1×30 mm, 4 micron). The run time was 10 min, and the flow rate was 0.6 mL/min. The elution was performed with a gradient of 5 to 95% phase A (0.1% formic acid in $CH_3CN$) in phase B (0.1% formic acid in $H_2O$). Column was operated at 40° C.

The following abbreviations are used throughout the specification:

EDCI 1-(3-dimethylaminopropyl)-3-ethylcarbodiimide hydrochloride
DMAP 4-dimethylaminopyridine
TBu tert-butyl
Boc tert-butoxycarbonyl
Cbz benzyloxycarbonyl
Fmoc pentylmethoxycarbonyl
DCE 1,2-dichloroethane
$NaSO_4 \cdot 10H_2O$ sodium sulfate decahydrate
$Na_2CO_3$ sodium carbonate
$AlCl_3$ aluminum trichloride
$Pd(PPh_3)_4$ tetrakis(triphenylphosphine)palladium
$Tf_2O$ trifluoromethanesulfonic anhydride
THF tetrahydrofuran
MTBE methyl tert-butyl ether
TEA, $Et_3N$ triethylamine
DCC dicyclohexylcarbodiimide
DMSO dimethylsulfoxide
DIPEA N,N-diisopropylethylamine
DCM dichloromethane
TFA trifluoroacetic acid
PE petroleum ether
EA ethyl acetate
MeOH, $CH_3OH$ methanol
$Pd(PPh_3)_2Cl_2$, $PdCl_2(PPh_3)_2$ Bis(triphenylphosphine)palladium dichloride
$NaBH(OAc)_3$ sodium triacetoxyborohydride;
CuI cuprous iodide
$NaHCO_3$ sodium bicarbonate
$Na_2S_2O_3$ sodium thiosulfate
$K_2CO_3$ potassium carbonate
DCE 1,2-dichloroethane
$NH_4Cl$ ammonium chloride
NaH sodium hydride
$PBr_3$ phosphorus tribromide
$NaBH_4$ sodium borohydride
STAB sodium triacetoxyborohydride
DMF N,N-dimethylformamide
$SOCl_2$ dichlorosulfoxide
$NaH_2PO_4$ sodium dihydrogen phosphate
$PPh_3$ triphenylphosphine
$H_2O_2$ hydrogen peroxide
$NaClO_2$ sodium chlorite NiCl$_2$·6H$_2$O nickel dichloride hexahydrate
TMEDA tetramethylethylenediamine
t-BuOK potassium tert-butoxide
EtOH ethanol
rt room temperature
s seconds
mol/L, N mole per liter, mole/liter
mg milligram
g gram
mmol millimole
mL, ml milliliter
% percent sign
h hour, hours
d days, days
TLC thin layer chromatography
° C. Celsius The following synthetic schemes describe the steps for preparing the compounds disclosed herein. Unless otherwise stated, each R$^1$, R$^2$, R$^3$, R$^5$, R$^6$, X$^1$, X$^2$, X$^3$, X$^4$, X$^5$, A, Q and M is as defined herein.

Intermediate I-A Synthesis Scheme:

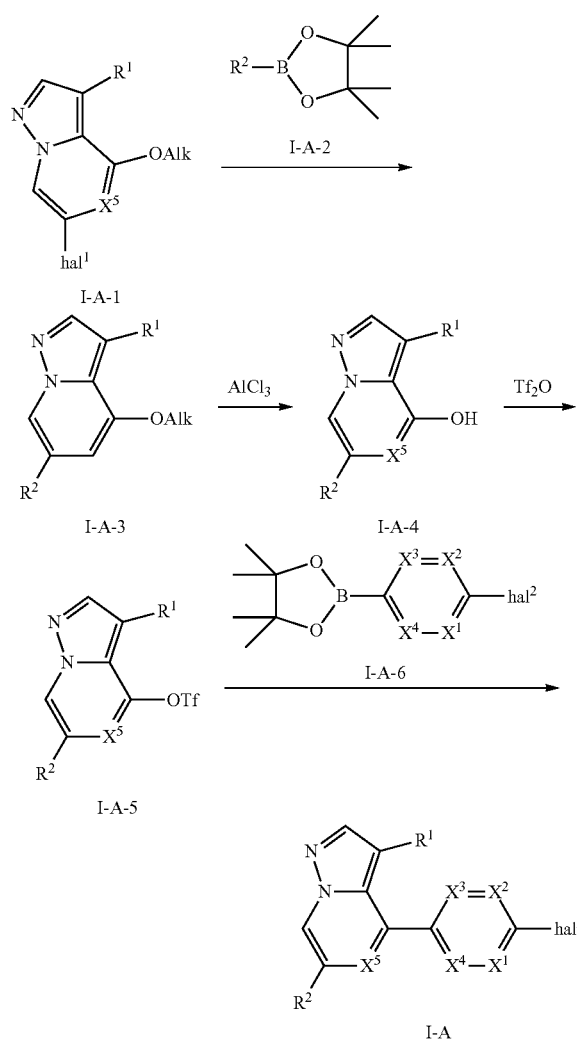

The synthesis of intermediate I-A can be obtained by referring to the synthetic procedure of the intermediate synthesis scheme above. Wherein hal$^1$ is F, Cl, Br, I, preferably Cl, Br; hal$^2$ is F, Cl, Br, I, preferably F, Cl, Br; Alk is C$_{1-6}$ alkyl, preferably C$_{1-4}$ alkyl, more preferably methyl, ethyl, isopropyl and tert-butyl. The compound of formula I-A-1 can be coupled with a compound of formula I-A-2 under suitable coupling agent conditions (e.g., palladium coupling agent, preferably Pd(PPh$_3$)$_4$) in a suitable solvent (e.g., dioxane) to give a compound of formula I-A-3; the compound of formula I-A-3 can react with anhydrous aluminum trichloride to give a compound of formula I-A-4, which can react with Tf$_2$O to give a compound of formula I-A-5; the compound of formula I-A-5 can be subjected to a coupling reaction with a compound of formula I-A-6 under suitable coupling agent conditions (e.g., palladium coupling agent, preferably Pd(PPh$_3$)$_4$) in a suitable solvent (e.g., dioxane) to give a compound of formula I-A.

Synthetic Scheme 1:

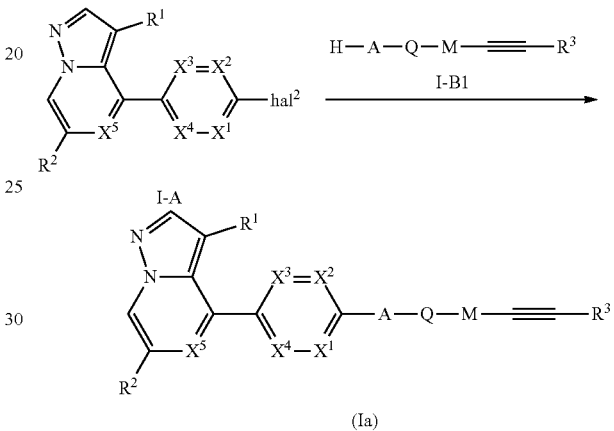

When E in the formula (I) of the present invention is a bond, the compound of the formula (I) of the present invention is the compound of the formula (Ia) in the synthesis scheme 1. The synthesis of the compound of the formula (Ia) of the present invention can be obtained by referring to the synthetic procedure of synthesis scheme 1. The compound of formula I-A can be subjected to a coupling reaction with a compound of formula I-B1 or a salt of compound of formula I-B1 (e.g., hydrochloride, trifluoroacetate, hydrobromide) under suitable reagent conditions (e.g., DIPEA) to give the compound of formula (Ia).

Synthetic Scheme 2:

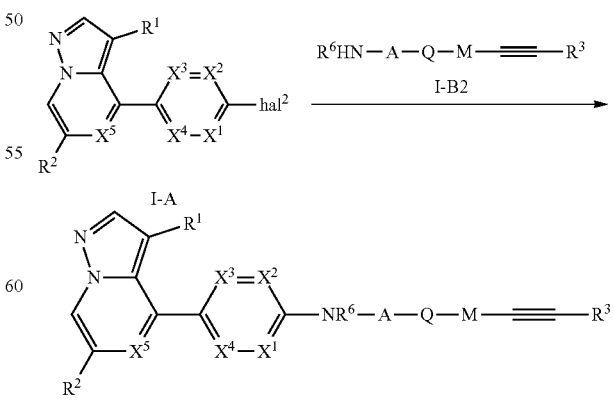

When E in the formula (I) of the present invention is —NR⁶—, the compound of the formula (I) of the present invention is the compound of the formula (Ib) in the synthesis scheme 2. The synthesis of the compound of the formula (Ib) of the present invention can be obtained by referring to the synthetic procedure of synthesis scheme 2. The compound of formula I-A can be subjected to a coupling reaction with a salt of compound of formula I-B2 (e.g., hydrochloride, trifluoroacetate, hydrobromide) under suitable reagent conditions (e.g., DIPEA) to give the compound of formula (Ib).

Synthetic Scheme 3:

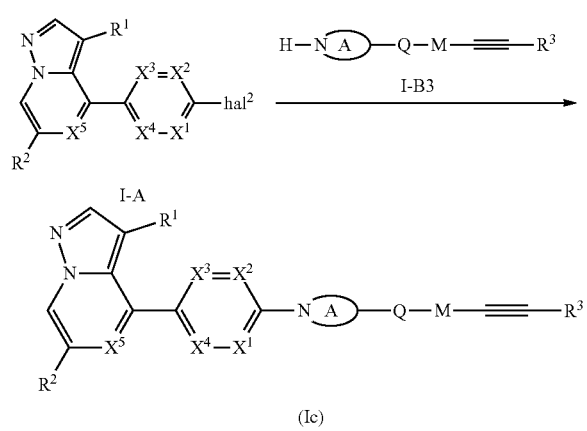

When E in the formula (I) of the present invention is a bond, and the left end of A is bonded to E through an N atom, the compound of the formula (I) of the present invention is the compound of the formula (Ic) in synthesis scheme 3. The synthesis of the compound of the formula (Ic) of the present invention can be obtained by referring to the synthetic procedure of synthesis scheme 3. The compound of formula I-A can be subjected to a coupling reaction with a salt of compound of formula I-B3 (e.g., hydrochloride, trifluoroacetate, hydrobromide) under suitable reagent conditions (e.g., DIPEA) to give the compound of formula (Ic).

Synthetic Scheme 4:

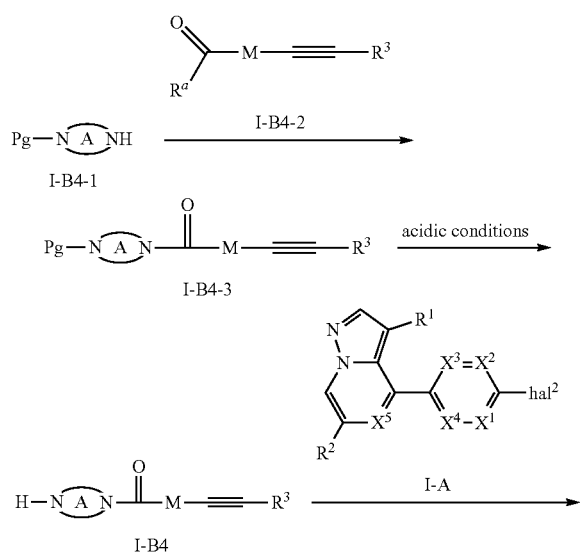

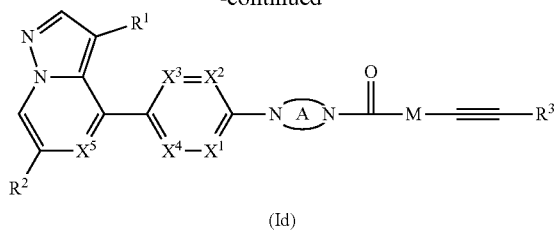

When E in the formula (I) of the present invention is a bond, Q is —(C=O)—, the left end of A is bonded to E through an N atom, and the right end of A is bonded to Q through an N atom, the compound of the formula (I) of the present invention is the compound of the formula (Id) in synthesis scheme 4. Wherein Pg is an amino protecting group, including but not limited to Boc, Cbz, Fmoc, etc., and $R^a$ is OH, Cl, Br. The compound of formula I-B4-1 can react with a compound of formula I-B4-2 under suitable basic conditions (e.g., DCC, DIPEA, TEA, DMAP) to give the compound of formula I-B4-3; the compound of formula I-B4-3 can be deaminated under acidic conditions (such as hydrochloric acid, trifluoroacetic acid, hydrobromic acid) to give a salt of the compound of formula I-B4 (such as hydrochloride, trifluoroacetate, hydrobromide); the salt of the compound of formula I-B4 can be coupled with a compound of formula I-A under suitable reagent conditions (e.g., DIPEA) to give a compound of formula (Id).

Synthetic Scheme 5:

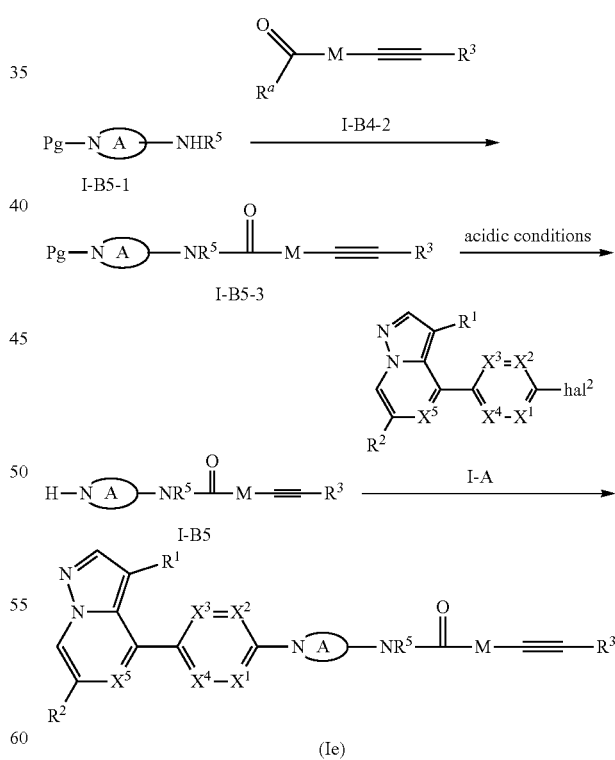

When E in the formula (I) of the present invention is a bond, Q is —NR⁵(C=O)—, the left end of A is bonded to E through an N atom, and the right end of A is bonded to an N atom in Q, the compound of the formula (I) of the present invention is the compound of the formula (Ie) in synthesis scheme 5. Wherein Pg is an amino protecting group, including but not limited to Boc, Cbz, Fmoc, etc., and $R^a$ is OH, Cl, Br. The compound of formula I-B5-1 can react with a compound of formula I-B4-2 under suitable basic conditions (e.g., DCC, DIPEA, TEA, DMAP) to give the compound of formula I-B5-3; the compound of formula I-B5-3 can be deaminated under acidic conditions (such as hydrochloric acid, trifluoroacetic acid, hydrobromic acid) to give a salt of the compound of formula I-B5 (such as hydrochloride, trifluoroacetate, hydrobromide); the salt of the compound of formula I-B5 can be coupled with a compound of formula I-A under suitable reagent conditions (e.g., DIPEA) to give a compound of formula (Ie).

Synthetic Scheme 6:

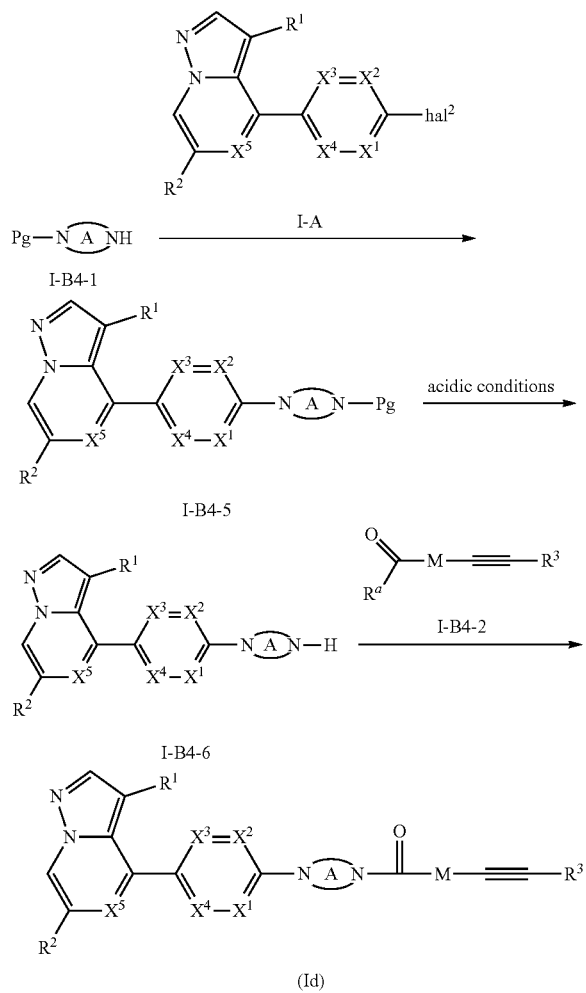

(Id)

When E in the formula (I) of the present invention is a bond, Q is —(C=O)—, the left end of A is bonded to E through an N atom, and the right end of A is bonded to Q through an N atom, the compound of the formula (I) of the present invention is the compound of the formula (Id) in synthesis scheme 6. Wherein Pg is an amino protecting group, including but not limited to Boc, Cbz, Fmoc, etc., and $R^a$ is OH, Cl, Br. The compound of formula I-B4-1 can react with a compound of formula I-A under suitable basic conditions (e.g., DCC, DIPEA, TEA, DMAP) to give the compound of formula I-B4-5; the compound of formula I-B4-5 can be deaminated under acidic conditions (such as hydrochloric acid, trifluoroacetic acid, hydrobromic acid) to give a salt of the compound of formula I-B4-6 (such as hydrochloride, trifluoroacetate, hydrobromide); the salt of the compound of formula I-B4-6 can be coupled with a compound of formula I-B4-2 under suitable reagent conditions (e.g., DCC, DIPEA, TEA, DMAP) to give a compound of formula (Id).

Synthetic Scheme 7:

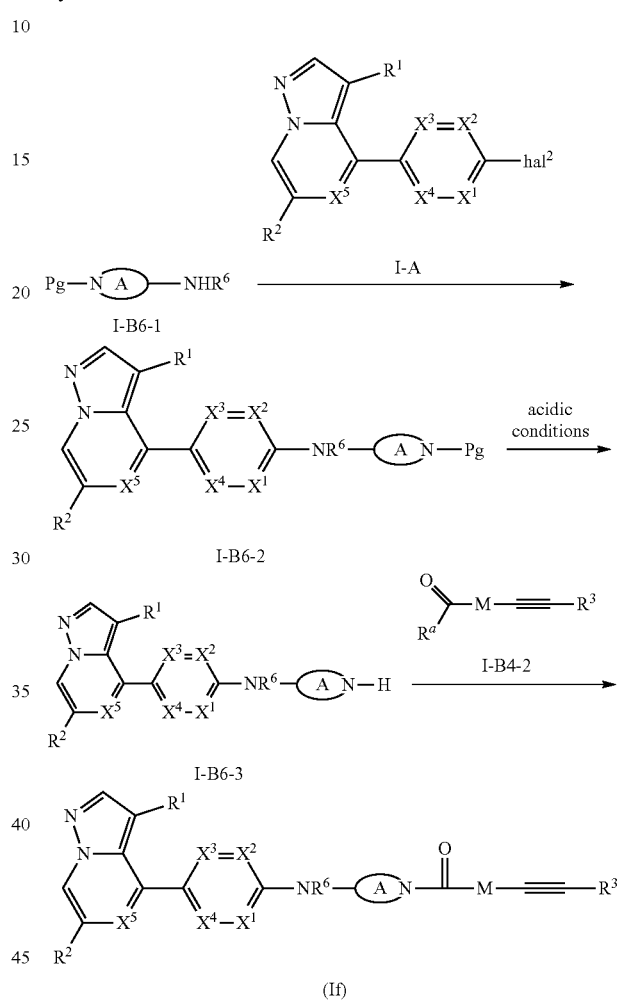

(If)

When E in the formula (I) of the present invention is —$NR^6$—, Q is —(C=O)—, and the right end of A is bonded to Q through an N atom, the compound of the formula (I) of the present invention is the compound of the formula (If) in synthesis scheme 7. Wherein Pg is an amino protecting group, including but not limited to Boc, Cbz, Fmoc, etc., and $R^a$ is OH, Cl, Br. The compound of formula I-B6-1 can react with a compound of formula I-A under suitable basic conditions (e.g., DCC, DIPEA, TEA, DMAP) to give the compound of formula I-B6-2; the compound of formula I-B6-2 can be deaminated under acidic conditions (such as hydrochloric acid, trifluoroacetic acid, hydrobromic acid) to give a salt of the compound of formula I-B6-3 (such as hydrochloride, trifluoroacetate, hydrobromide); the salt of the compound of formula I-B6-3 can be coupled with a compound of formula I-B4-2 under suitable reagent conditions (e.g., DCC, DIPEA, TEA, DMAP) to give a compound of formula (If).

Synthetic Scheme 8:

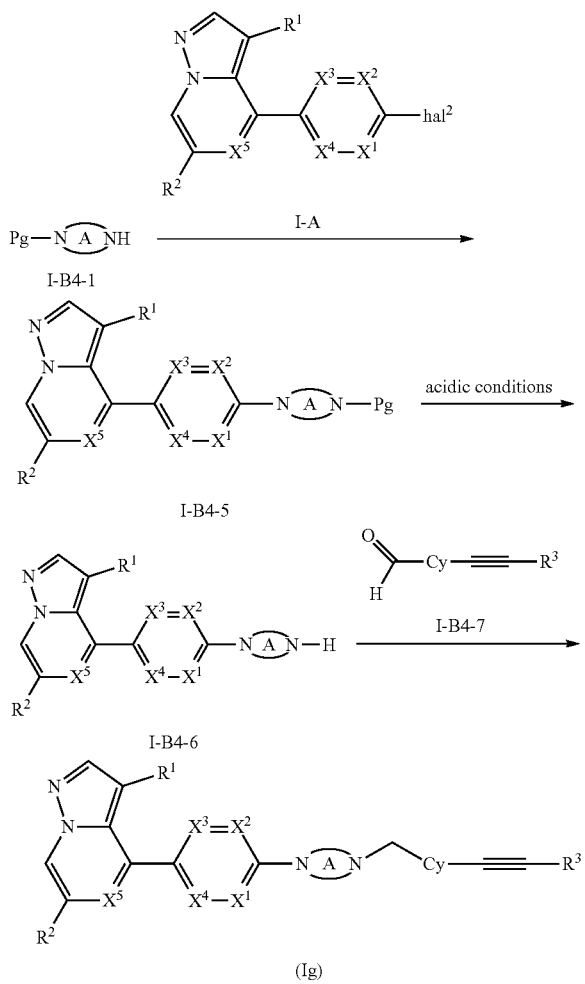

Synthetic Scheme 9:

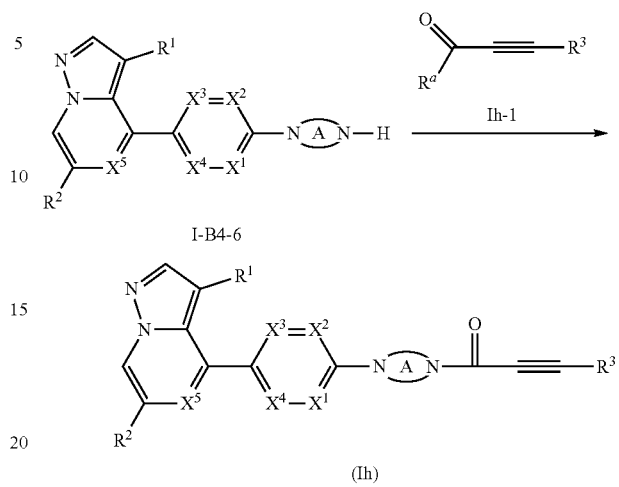

The compound of formula (Ih) can be obtained by the preparation method of synthesis scheme 9, wherein $R^a$ is OH, Cl, Br. The salt of the compound of formula I-B4-6 and the compound of formula Ih-1 can be subjected to a coupling reaction under appropriate reagent conditions (such as DCC, DIPEA, TEA, DMAP, etc.) to obtain a compound of formula (Ih).

Synthetic Scheme 10:

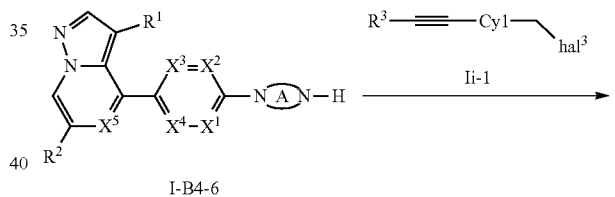

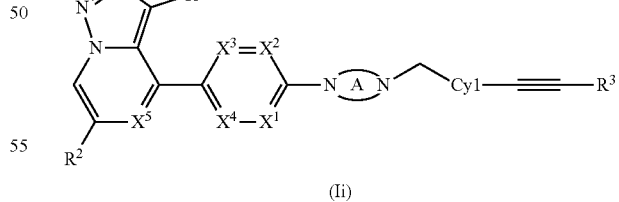

When E in the formula (I) of the present invention is a bond, Q is a bond, the left end of A is bonded to E through an N atom, the right end of A is bonded to Q through an N atom, and M is —CH$_2$—Cy-, the compound of the formula (I) of the present invention is the compound of the formula (Ig) in synthesis scheme 8. Wherein Pg is an amino protecting group, including but not limited to Boc, Cbz, Fmoc, etc.; Cy is a bond, aryl, heteroaryl, Cyc or hetCyc, wherein aryl, heteroaryl, Cyc, hetCyc have the definitions as described herein. The compound of formula I-B4-1 can react with a compound of formula I-A under suitable basic conditions (e.g., DCC, DIPEA, TEA, K$_2$CO$_3$, DMAP) to give the compound of formula I-B4-5; the compound of formula I-B4-5 can be deaminated under acidic conditions (such as hydrochloric acid, trifluoroacetic acid, hydrobromic acid) to give a salt of the compound of formula I-B4-6 (such as hydrochloride, trifluoroacetate, hydrobromide); the salt of the compound of formula I-B4-6 can react with a compound of formula I-B4-7 under suitable reagent conditions (e.g., DCE and NaBH(OAc)$_3$ conditions) to give a compound of formula (Id).

The compound of formula (Ii) can be obtained by the preparation method of synthesis scheme 10, wherein hal$^3$ is F, Cl, Br, preferably Cl, Br; Cyl is a bond, aryl or heteroaryl. The salt of the compound of formula I-B4-6 and the compound of formula Ii-1 can be subjected to a coupling reaction under basic conditions (e.g., potassium carbonate, triethylamine) in suitable solvents (e.g., N,N-dimethylformamide, acetonitrile, etc.) to obtain a compound of formula (Ii).

EXAMPLES

Intermediate 1: 3-cyano-4-(6-fluoro-pyridin-3-yl)-6 (1-methyl-1H-pyrazol-4-yl)pyrazolo[1,5-a]pyridine

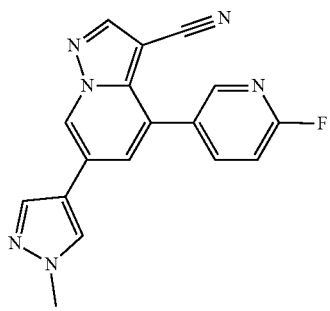 [SMILES: Cn1cc(-c2cc(-c3ccc(F)nc3)c3c(C#N)cnn3c2)cn1]

Step 1: 6-bromo-4-methoxypyrazolo[1,5-a]pyridin-3-carbonitrile (E)-6-Bromo-4-methoxypyrazolo[1,5-a]pyridin-3-formaldoxime (20.3 g, 75.2 mmol) was dissolved in acetic anhydride (508 mL) in a 1000 mL single-necked flask. The mixture was refluxed for reaction at 120° C. The solution gradually turned from light yellow to brown. The mixture was reacted for 2.5 h, then the completion of reaction was monitored by TLC. The resulting mixture was concentrated in vacuo to remove the solvent. To the residue was added water (200 mL), and the resulting mixture was stirred for 5 min, and then filtered by suction. The filter cake was washed with 20 mL of water, then dried in a vacuum oven at 50° C. for 24 h to obtain 16.1 g of a gray solid. The yield was 85.0%. Rf=0.3 (PE:EA=2:1).

Step 2: 3-cyano-4-methoxy-6-(1-methyl-1H-pyrazol-4-yl)pyrazolo[1,5-a]pyridine 6-Bromo-4-methoxypyrazolo[1,5-a]pyridin-3-carbonitrile (12 g, 47.606 mmol), sodium carbonate solution (71.4 mL, 142.8 mmol, 2 mol/L), tetrakis(triphenylphosphine palladium) (2.75 g, 2.38 mmol), 1-methyl-4-(4,4,5,5-tetramethyl-1,3,2-dioxaborolane-2-yl)pyrazole (11.89 g, 57.14 mmol) were dissolved in 1,4-dioxane (240 mL) under nitrogen, then the mixture was transferred to 80° C. and reacted with stirring overnight. The completion of reaction was monitored by TLC. The heating was stopped, and after stirring for 2 h, a large amount of gray solid precipitated. After suction filtration, the filter cake was washed with 50 mL of water and 50 mL of DCM, and drained to give an off-white solid 9.62 g. The yield was 79.8%. Rf=0.2 (PE:EA=1:1).

Step 3: 3-cyano-4-hydroxy-6-(1-methyl-1H-pyrazol-4-yl)pyrazolo[1,5-a]pyridine 3-Cyano-4-methoxy-6-(1-methyl-1H-pyrazol-4-yl)pyrazolo[1,5-a]pyridine (7.1 g, 28 mmol) was added into a 500 mL single-necked flask, and DCE (280 mL) was added to dissolve it. The solution was brown, and then aluminum trichloride (11 g, 82.496 mmol) was added in portions. The resulting mixture was transferred to 80° C. and refluxed with stirring overnight. On the next day, a large amount of black solid precipitated in the reaction system, most of which adhering to the wall of the flask. A drop of sample was taken, diluted with methanol, and then detected by TLC, which was showed that a point with a smaller polarity was formed and most of the raw material remained. Additional 3 g of aluminum trichloride was added to continue the reaction for 24 h. A drop of sample was taken, diluted with methanol, and then detected by TLC. The material point became lighter, the product point became thicker, and additional 3 g of aluminum trichloride was added to continue the reaction for 9 h. The completion of reaction was monitored by TLC. To the reaction solution was added 100 mL solution of $NaSO_4.10H_2O$ in THF, and the mixture was stirred at room temperature for 2 h to disperse the black solid adhering to the inner wall of the bottle into the solution, then 200 mL of water was added. The reaction solution was stirred for 2 h, and then filtered. The filter cake was washed with 200 mL of water and 200 mL of MTBE, and then dried in a vacuum oven at 50° C. for 24 h to obtain 7.2 g of a brown solid containing a portion of aluminum hydroxide, which was directly used in the next reaction according to the theoretical yield. Rf=0.1 (PE:EA=1:1).

Step 4: 3-cyano-6-(1-methyl-1H-pyrazol-4-yl)pyrazolo[1,5-a]pyridin-4-yl triflate 3-Cyano-4-hydroxy-6-(1-methyl-1H-pyrazol-4-yl)pyrazolo[1,5-a]pyridine (6.7 g, 28 mmol) and DCM (280 mL) were added to a 500 mL single-necked flask. After evenly dispersed, the mixture was transferred to 0° C., stirred for 10 min, then trifluoromethanesulfonic anhydride (5.7 mL, 34 mmol) was added. After 15 min of dropwise addition, the mixture was stirred for additional 10 min, then TEA (7.8 mL, 56 mmol) was added dropwise. After 15 min of dropwise addition, the mixture was stirred at this temperature for 22 h. TCL detected that it had the remaining material. The black solid was filtered off with suction, and the filtrate was washed with water (100 mL×3). The organic phase was dried over anhydrous sodium sulfate, concentrated in vacuo, and then purified by column chromatography (EA:PE(v/v)=1:4-1:1) to give a pale yellow solid 1.18 g. The yield was 11%. Rf=0.4 (PE:EA=1:1). $^{19}F$-NMR (376 MHz, $CDCl_3$) δ −71.96 (s). $^{1}H$-NMR (400 MHz, $CDCl_3$) δ 8.66 (s, 1H), 8.29 (s, 1H), 7.77 (s, 1H), 7.70 (s, 1H), 7.56 (s, 1H), 4.00 (s, 3H).

Step 5: 3-cyano-4-(6-fluoro-pyridin-3-yl)-6-(1-methyl-1H-pyrazol-4-yl)pyrazolo[1,5-a]pyridine 3-Cyano-6-(1-methyl-1H-pyrazol-4-yl)pyrazolo[1,5-a]pyridin-4-yl triflate (1.18 g, 3.18 mmol) and 2-fluoro-5-(4,4,5,5-tetramethyl-1,3,2-dioxaborolan-2-yl)pyridine (850 mg, 3.812 mmol) were dissolved in 1,4-dioxane (32 mL)) in a pressure tube. After tetrakis(triphenylphosphine palladium) (367 mg, 0.31758 mmol) and sodium carbonate solution (3.18 mL, 6.36 mmol, 2 mol/L) were added, the tube was sealed and heated in a 100° C. oil bath overnight. The reaction system became a viscous solid, and the completion of reaction was monitored by TLC. The reaction was quenched with 50 mL of saturated ammonium chloride solution, and the reaction solution was transferred to a separatory funnel, and 300 mL of EA and 50 mL of saturated brine were added. After shaking, the intermediate layer was flocculated with a gray solid, and the gray solid was separated. The organic phase was separated from the filtrate, and the aqueous phase was extracted twice with 250 mL of EA. The organic phases were combined, dried over anhydrous sodium sulfate, concentrated in vacuo, and then purified by column chromatography (EA:PE(v/v)=4:1-1:1) to give a pale yellow solid 890 mg. The yield was 88%. Rf=0.3 (PE:EA=1:1).

Intermediate 2: 6-(1-methyl-1H-pyrazol-4-yl)-4-(6-(piperazin-1-yl)pyridin-3-yl) pyrazolo[1,5-a]pyridin-3-carbonitrile dihydrochloride

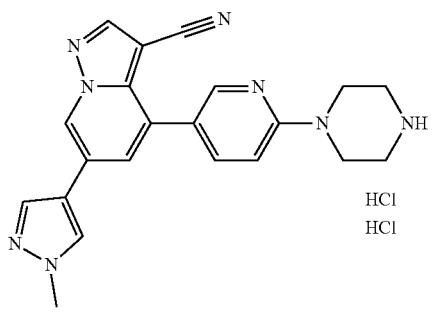 [SMILES: Cn1cc(-c2cc(-c3ccc(N4CCNCC4)nc3)c3c(C#N)cnn3c2)cn1 ; Cl ; Cl]

Step 1: tert-butyl 4-(5-(3-cyano-6-(1-methyl-1H-pyrazol-4-yl)pyrazolo[1,5-a]pyridin-4-yl) pyridin-2-yl)piperazin-1-carboxylate To a 30 mL microwave tube were added 4-(6-fluoropyridin-3-yl)-6-(1-methyl-1H-pyrazol-4-yl) pyrazolo[1,5-a]pyridin-3-carbonitrile (see synthesis of intermediate 1) (1.0 g, 3.142 mmol), tert-butylpiperazin-1-carboxylate (760 mg, 4.0805 mmol) and DIPEA (2.6 ml, 16 mmol) sequentially. The mixture was dissolved with dimethyl sulfoxide (10 ml) and reacted for 5 h at 140° C. under microwave. Then EA (100 mL) was added. The resulting mixture was washed with water (50 mL×2) and saturated saline solution (50 mL) in turn. The organic phases were combined, dried over anhydrous sodium sulfate and filtered. The filtrate was concentrated in vacuo and then purified by silica gel column chromatography (PE/EA=3:1-1:1) to give a white solid 1.3 g as the target product. The yield was 85%. Rf=0.20 (PE: EA=1:1.5). LC-MS: m/z=485.20[M+H]$^+$.

Step 2: 6-(1-methyl-1H-pyrazol-4-yl)-4-(6-(piperazin-1-yl)pyridin-3-yl)pyrazolo[1,5-a]pyridin-3-carbonitrile dihydrochloride To a 100 mL single-necked flask were added tert-butyl 4-(5-(3-cyano-6-(1-methyl-1H-pyrazol-4-yl)pyrazolo[1,5-a]pyridin-4-yl)pyridin-2-yl) piperazin-1-carboxylate (420 mg, 0.8667 mmol) and a solution of hydrochloric acid in methanol (4 mol/L, 20 ml) in turn. The mixture was stirred at room temperature overnight. The reaction solution was directly concentrated in vacuo to form a viscous oily substance, and placed in an oven at 60° C. for vacuum drying to obtain a white solid 0.3964 g as the target product. The yield was 100%. Rf=0 (DCM/MeOH=30:1). LC-MS: m/z=385.20[M−2HCl]$^+$.

Intermediate 3: 4-(6-(3,6-diazabicyclo[3.1.1]heptan-3-yl)pyridin-3-yl)-6-(1-methyl-1H-pyrazol-4-yl) pyrazole[1,5-a]pyridine-3-carbonitrile dihydrochloride

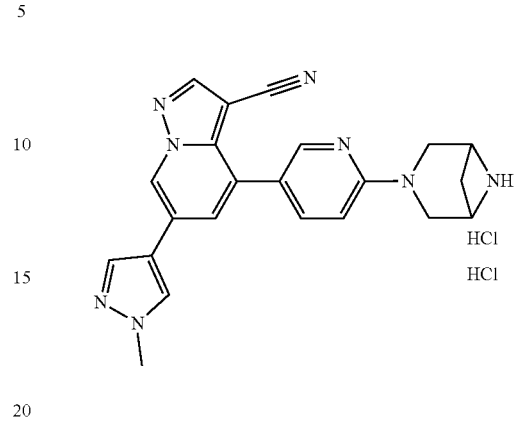

Step 1: tert-butyl 3-(5-(3-cyano-6-(1-methyl-1H-pyrazol-4-yl)pyrazolo[1,5-a]pyridin-4-yl) pyridin-2-yl)-3,6-diazabicyclo[3.1.1]heptane-6-carboxylate 4-(6-Fluoro-3-pyridyl)-6-(1-methylpyrazol-4-yl)pyrazolo[1,5-a]pyridine-3-carbonitrile (70 mg, 0.2199 mmol), tert-butyl 3,6-diazabicyclo[3.1.1]heptane-6-carboxylate (48 mg, 0.24211 mmol) and potassium carbonate (185 mg, 1.3194 mmol) were dissolved in DMSO (5 mL) under nitrogen, and then the solution was heated in a 100° C. oil bath and reacted for 6 d. The reaction mixture was poured into water (10 mL), extracted with EA (30 mL×2), and the organic phases were combined, washed with water (10 mL) and saturated saline (10 mL). The combined organic phases were dried over anhydrous sodium sulfate, filtered, concentrated in vacuo, and then purified by silica gel column chromatography (eluent EA:PE(v/v)=1:3-1:1) to give a white solid 92 mg as the desired product. The yield was 84.24%. LC-MS: m/z=497.30 [M+H]$^+$. $^1$H-NMR (400 MHz, CDCl$_3$) δ 8.63 (d, J=1.2 Hz, 1H), 8.40 (d, J=2.2 Hz, 1H), 8.26 (s, 1H), 7.80 (s, 1H), 7.77 (dd, J=8.8, 2.4 Hz, 1H), 7.69 (s, 1H), 7.40 (s, 1H), 6.67 (d, J=8.8 Hz, 1H), 4.32 (d, J=4.7 Hz, 2H), 4.20-4.13 (m, 2H), 3.99 (s, 3H), 3.61-3.51 (m, 2H), 2.99 (s, 1H), 2.09 (s, 1H), 1.39 (s, 9H).

Step 2: 4-(6-(3,6-diazabicyclo[3.1.1]heptan-3-yl) pyridin-3-yl)-6-(1-methyl-1H-pyrazol-4-yl) pyrazolo[1,5-a]pyridine-3-carbonitrile dihydrochloride tert-Butyl 3-(5-(3-cyano-6-(1-methyl-1H-pyrazol-4-yl) pyrazolo[1,5-a]pyridin-4-yl) pyridin-2-yl)-3,6-diazabicyclo[3.1.1]heptane-6-carboxylate (100 mg, 0.2014 mmol) and HCl/MeOH (5 mL, 20 mmol, 4 mol/L) were added in a 25 mL single-necked flask in one portion and the mixture was stirred and reacted overnight at room temperature. The reaction solution was directly concentrated in vacuo to obtain a pale red solid as the target product, which was used in the next step directly without further purification. The yield was calculated as 100%.

Intermediate 4: 4-(6-(4-amino-4-methylpiperidin-1-yl)pyridin-3-yl)-6-(1-methyl-1H-pyrazol-4-yl)pyrazolo[1,5-a]pyridin-3-carbonitrile hydrochloride

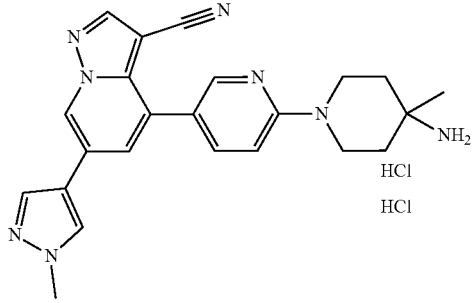 [SMILES: Cn1cc(-c2cc(-c3ccc(N4CCC(C)(N)CC4)nc3)c3c(C#N)cnn3c2)cn1 ; Cl ; Cl]

Step 1: tert-butyl 1-(5-(3-cyano-6-(1-methyl-1H-pyrazol-4-yl)pyrazolo[1,5-a]pyridin-4-yl) pyridin-2-yl)-4-methylpiperidin-4-yl)carbamate To a 10 mL microwave tube were added 4-(6-fluoropyridin-3-yl)-6-(1-methyl-1H-pyrazol-4-yl)pyrazolo[1,5-a]pyridin-3-carbonitrile (see synthesis of intermediate 1, 500 mg, 1.571 mmol), tert-butyl N-(4-methyl-4-piperidinyl)carbamate (440 mg, 2.053 mmol) and DIPEA (1.3 mL, 7.9 mmol) sequentially. The mixture was dissolved with dimethyl sulfoxide (5 ml) and reacted for 4 h at 135° C. under microwave. Then EA (50 mL) was added. The resulting mixture was washed with water (30 mL×2) and saturated saline (50 mL) separately. The organic phases were combined, dried over anhydrous sodium sulfate and filtered. The filtrate was concentrated in vacuo and then purified by silica gel column chromatography (PE/EA=3:1-1:1) to give a yellow solid 0.73 g as the target product. The yield was 91%. Rf=0.20 (PE:EA=1:1.5). LC-MS: m/z=513.20[M+H]$^+$.

Step 2: 4-(6-(4-amino-4-methylpiperidin-1-yl)pyridin-3-yl)-6-(1-methyl-1H-pyrazol-4-yl) pyrazolo[1,5-a]pyridin-3-carbonitrile hydrochloride To a 100 mL single-necked flask were added tert-butyl 1-(5-(3-cyano-6-(1-methyl-1H-pyrazol-4-yl)pyrazolo[1,5-a]pyridin-4-yl)pyridin-2-yl)-4-methyl piperidin-4-yl)carbamate (730 mg, 1.424 mmol) and a solution of hydrochloric acid in methanol (4 mol/L, 10 ml) in turn. The mixture was stirred at room temperature overnight. The reaction solution was directly concentrated in vacuo to form a viscous oily substance, and placed in an oven at 60° C. for vacuum drying to obtain a yellow solid 0.6931 g as the target product. The yield was 100%. Rf=0 (DCM/MeOH=30:1). LC-MS: m/z=413.20[M−2HCl]$^+$.

Intermediate 5: 6-bromo-4-(6-fluoropyridin-3-yl)pyrazolo[1,5-a]pyridin-3-carbonitrile

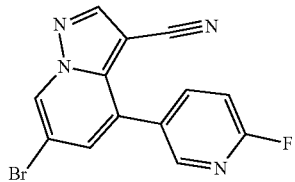 [SMILES: N#Cc1cnn2cc(Br)cc(-c3ccc(F)nc3)c12]

Step 1: 6-bromo-4-hydroxypyrazolo[1,5-a]pyridin-3-carbonitrile

To a 1 L single-necked flask were added 6-bromo-4-methoxypyrazolo[1,5-a]pyridine-3-carbonitrile (50 g, 198.36 mmol), water (16.5 mL, 916 mmol), sodium hydroxide (16.03 g, 396.8 mmol) and DMAE (500 mL) in turn at room temperature. The mixture was stirred at room temperature for 5 min, then transferred to 0° C. and slowly added with dodecyl mercaptan (97 mL, 397 mmol). After the addition, the resulting mixture was transferred to 45° C. and reacted overnight. The reaction solution was poured into 3 L of ice water. The mixture was slowly added with saturated aqueous citric acid solution to adjust pH=5. The resulting mixture was stirred for half an hour, then stood still, and filtered. The filter cake was washed with water and petroleum ether several times, and dried at 60° C. to give a yellow solid 44.1 g as the target product (the yield was 93.4%). Rf=0.35 (PE:EA=3:1). LC-MS: m/z=239.05[M+H]$^+$.

Step 2: 3-bromo-3-cyanopyrazolo[1,5-a]pyridin-4-yl trifluoromethanesulfonate To a 1 L single-necked flask were added 6-bromo-4-hydroxypyrazolo[1,5-a]pyridin-3-carbonitrile (44.1 g, 185 mmol), pyridine (45 mL, 559 mmol) and DCM (800 mL). The mixture was cooled to below −10° C., then trifluoromethanesulfonic anhydride (50 mL, 297.2 mmol) was slowly added. The mixture was stirred for 1 h, then naturally warmed to room temperature and reacted overnight. The mixture was concentrated in vacuo to remove DCM, then diluted with water (250 mL) and extracted with EA (500 mL×3). The organic phases were collected, washed with saturated brine (250 mL), dried over anhydrous sodium sulfate, filtered. The filtrate was concentrated in vacuo, and then purified by silica gel column chromatography (eluent PE/EA=50:1-25:1) to give a yellowish solid 61.5 g as the target product. The yield was 89.7%. Rf=0.45 (PE:EA=5:1).

Step 3: 6-bromo-4-(6-fluoropyridin-3-yl)pyrazolo[1,5-a]pyridine-3-carbonitrile To a 1 L three-necked flask were added 3-bromo-3-cyanopyrazolo[1,5-a]pyridin-4-yl trifluoromethanesulfonate (61.5 g, 166 mmol), 2-fluoropyridin-5-borate (44.5 g, 200 mmol), [1,1'-bis(diphenylphosphino)ferrocene]palladium dichloride dichloromethane complex (6.8 g, 8.3 mmol) and 1,4-dioxane (850 mL). The mixture was cooled to −10° C., then potassium acetate solution (115 mL, 345 mmol, 3 mol/L) was slowly added. The mixture was stirred at this temperature for 1 hour, and then naturally warmed to room temperature to continue for reaction tot overnight. The mixture was filtered, and the filter cake was washed with EA (500 mL×3). The filtrate was separated, washed with water (500 mL) and saturated brine (250 mL), dried over anhydrous sodium sulfate, and filtered. The filtrate was concentrated in vacuo, and then purified by silica gel column chromatography (eluent PE/DCM=2:1-0:1) to give a white solid 49 g as the target product. The yield was 93.0%. Rf=0.50 (PE:EA=1:1). LC-MS: m/z=318.10[M+H]$^+$. $^1$H NMR (400 MHz, DMSO-d$_6$) δ 9.49 (d, J=1.2 Hz, 1H), 8.73 (s, 1H), 8.51 (d, J=1.9 Hz, 1H), 8.27 (td, J=8.2, 2.5 Hz, 1H), 7.86 (d, J=1.2 Hz, 1H), 7.40 (dd, J=8.4, 2.5 Hz, 1H).

159

Intermediate 6: 6-(1-(difluoromethyl)-1H-pyrazol-4-yl)-4-(6-fluoropyridin-3-yl)pyrazolo[1,5-a]pyridine-3-carbonitrile

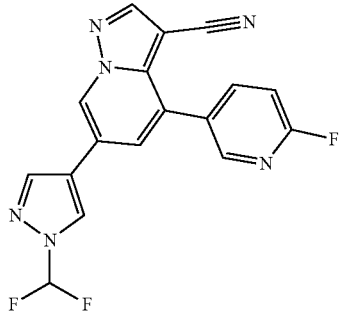 [SMILES: N#Cc1cnn2cc(-c3cnn(C(F)F)c3)cc(-c3ccc(F)nc3)c12]

Step 1: 1-(difluoromethyl)-4-(4,4,5,5-tetramethyl-1,3,2-dioxaborolan-2-yl)-1H-pyrazole To a 250 mL single-necked flask were sequentially added 4-pyrazoleboronic acid pinacol ester (5.0 g, 26 mmol), 18-crown-6 (1.4 g, 5.2 mmol) and acetonitrile (130 ml). The mixture was stirred to dissolve at room temperature, then sodium difluorochloroacetate (4.7 g, 31 mmol) was added. After the end of the addition, the reaction was transferred to reflux at 90° C. overnight. The reaction mixture was filtered through a celite pad to remove the precipitated solid. The filter cake was washed with EA (100 mL×3), and the filtrate was concentrated in vacuo to give light yellow oil, which was purified by silica gel column chromatography (eluent PE/EA=1/0-8/1) to give a white solid 4.85 g as the target product (the yield was 77%). Rf=0.45 (PE/EA=5:1). LC-MS: m/z=245.20[M+H]$^+$. $^1$H NMR (400 MHz, CDCl$_3$) δ 8.13 (s, 1H), 7.89 (s, 1H), 7.38 (s, 0.25H), 7.23 (s, 0.5H), 7.08 (s, 0.25H), 1.32 (s, 12H).

Step 2: 6-(1-(difluoromethyl)-1H-pyrazol-4-yl)-4-(6-fluoropyridin-3-yl)pyrazolo[1,5-a]pyridine-3-carbonitrile To a 50 mL single-necked flask under nitrogen were added 6-bromo-4-(6-fluoropyridin-3-yl)pyrazolo[1,5-a]pyridine-3-carbonitrile (0.6 g, 2 mmol), 1-(difluoromethyl)-4-(4,4,5,5-tetramethyl-1,3,2-dioxaborolan-2-yl)-1H-pyrazole (0.5 g, 2 mmol), sodium carbonate aqueous solution (3 mL, 6 mmol, 2 mol/L) and 1,4-dioxane (10 mL). After bubbling for 5 min under nitrogen, tetrakistriphenylphosphine palladium (0.1 g, 0.09 mmol) was added. Then after bubbling for 5 min under nitrogen, the mixture was heated to 80° C. and reacted overnight. The mixture was diluted with water (50 mL) and extracted with EA (100 mL×3). The organic phases were combined, washed with saturated brine (250 mL), dried over anhydrous sodium sulfate and filtered. The filtrate was concentrated in vacuo and then purified by silica gel column chromatography (eluent PE/EA=10:1-3:1) to give a pale yellow solid 0.68 g as the target product. The yield was 97.2%. Rf=0.40 (PE/EA=1:1). LC-MS: m/z=355.20[M+H]$^+$. $^1$H NMR (400 MHz, DMSO-d$_6$) δ 9.54 (d, J=1.2 Hz, 1H), 9.01 (s, 1H), 8.73 (s, 1H), 8.61-8.52 (m, 2H), 8.33 (td, J=8.2, 2.5 Hz, 1H), 8.09 (d, J=1.3 Hz, 1H), 8.04 (s, 0.25H), 7.90 (s, 0.5H), 7.75 (s, 0.25H), 7.43 (dd, J=8.4, 2.5 Hz, 1H).

160

Example 1: 3-cyano-6-(1-methyl-1H-pyrazol-4-yl)-4-(6-(4-(3-phenylpropioloyl)piperazin-1-yl) pyridine-3-yl)pyrazolo[1,5-a]pyridine

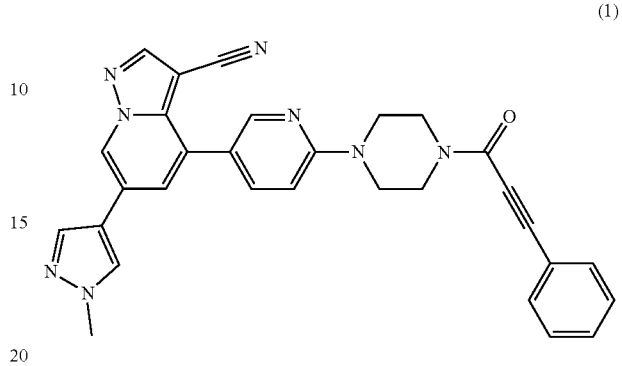

(1)

Step 1: tert-butyl 4-(3-phenylpropioloyl)piperazine-1-carboxylate tert-Butyl piperazine-1-carboxylate (500 mg, 2.6846 mmol) was dissolved in DCM (10 mL) in a single-necked flask. 3-Phenylprop-2-ynoic acid (0.47 g, 3.2 mmol and DCC (0.83 g, 4.0 mmol) were added with stirring at room temperature. The mixture was reacted overnight. 20 mL of DCM and 15 mL of water were added, and the aqueous phase was separated and extracted with 20 mL of DCM. The organic phases were combined, washed with 15 mL of saturated brine, dried over anhydrous sodium sulfate, concentrated in vacuo, and then purified by silica gel column chromatography (PE:EA(v/v)=10:1-4:1) to give a pale yellow solid 0.57 g. The yield was 68%.

Step 2: 3-phenyl-1-(piperazin-1-yl)prop-2-yn-1-one trifluoroacetate tert-Butyl 4-(3-phenylpropioloyl)piperazin-1-carboxylate (0.57 g, 1.8 mmol) was dissolved in DCM (6 mL) in a single-necked flask, then TFA (2.0 mL) was added. The mixture was stirred and reacted at room temperature. The completion of reaction was monitored by TLC after 3 h. The reaction solution was directly concentrated in vacuo to give a colorless, transparent oily liquid product, which was directly used in the next reaction according to the theoretical yield. Rf=0.01 (PE:EA=1:1).

Step 3: 3-cyano-6-(1-methyl-1H-pyrazol-4-yl)-4-(6-(4-(3-phenylpropioloyl)piperazin-1-yl) pyridine-3-yl)pyrazolo[1,5-a]pyridine 3-Cyano-4-(6-fluoro-pyridin-3-yl)-6-(1-methyl-1H-pyrazol-4-yl)pyrazolo[1,5-a]pyridine (100 mg, 0.3142 mmol, see the synthetic part of the intermediate) and 3-phenyl-1-(piperazin-1-yl) prop-2-yn-1-one trifluoroacetate (258 mg, 0.7859 mmol) were added in a microwave tube, then DMSO (1.58 mL) was added. After the mixture was dissolved, DIPEA (0.26 mL, 1.6 mmol) was added, and the mixture was reacted under microwave at 150° C. for 5 h. The reaction was quenched with 10 mL of water, then 30 mL of EA was added. The organic phase was separated, and the aqueous phase was extracted with EA (30 mL×2). The organic phases were combined, dried over anhydrous sodium sulfate, concentrated in vacuo, and then purified by column chromatography (EA:PE(v/v)=1:3-2:1) to give a pale yellow solid 30 mg. Rf=0.2 (PE:EA=1:1). LC-MS: 513.3[M+H]+, 1H-NMR (400 MHz, CDCl3) δ 8.65 (s, 1H), 8.40 (s, 1H), 8.27 (s, 1H), 7.80 (d, J=5.3 Hz, 2H), 7.69 (s, 1H), 7.58 (d, J=7.1 Hz, 2H), 7.42 (dd, J=15.2, 7.2 Hz, 4H), 6.83 (d, J=8.9 Hz, 1H), 3.99 (m, 5H), 3.87-3.81 (m, 4H), 3.73 (d, J=5.5 Hz, 2H).

Example 2: N-(1-(5-(3-cyano-6-(1-methyl-1H-pyrazol-4-yl)pyrazolo[1,5-a]pyridin-4-yl) pyridin-2-yl)-4-methyl-piperidin-4-yl)-4-ethynylbenzamide (2)

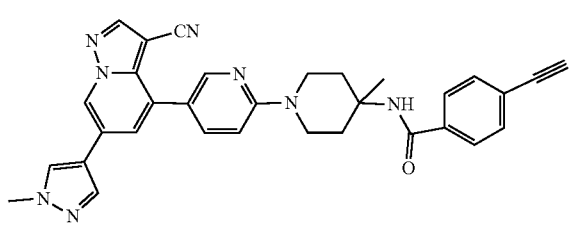

Step 1: tert-butyl 4-(4-ethynylbenzoylamino)-4-methylpiperidin-1-carboxylate tert-Butyl 4-amino-4-methyl-piperidin-1-carboxylate (600 mg, 2.7998 mmol), DCM (12 mL), 4-ethynylbenzoic acid (0.50 g, 3.4 mmol), EDCI (0.8 g, 4 mmol) and DMAP (0.034 g, 0.28 mmol) were added in a 25 mL single-necked flask. The mixture was stirred and reacted at room temperature overnight. 20 mL of DCM and 15 mL of water were added, and the aqueous phase was separated and extracted with 20 mL of DCM. The organic phases were combined, washed with 15 mL of saturated brine, dried over anhydrous sodium sulfate, concentrated in vacuo, and then purified by silica gel column chromatography (PE:EA(v/v)=20:1-4:1) to give a white foam solid 423 mg. The yield was 30%. LC-MS: m/z=287.1[M-t-Bu+2H]+, 1H NMR (400 MHz, CDCl3) δ 7.67 (d, J=8.4 Hz, 2H), 7.54 (d, J=8.3 Hz, 2H), 5.78 (s, 1H), 3.71 (s, 2H), 3.26-3.16 (m, 3H), 2.16 (s, 2H), 1.68 (ddd, J=14.1, 10.3, 4.2 Hz, 2H), 1.52 (s, 3H), 1.46 (s, 9H).

Step 2: 4-ethynyl-N-(4-methylpiperidin-4-yl)benzamide trifluoroacetate tert-Butyl 4-(4-ethynylbenzoylamino)-4-methylpiperidin-1-carboxylate (0.42 g, 1.2 mmol) was added in a 50 mL single-necked flask, then DCM (5 mL) and TFA (1.5 mL) were added. The mixture was stirred and reacted at room temperature. The completion of reaction was monitored by TLC after 3.5 h. The reaction solution was directly concentrated in vacuo to give a colorless, transparent oily liquid product, which was directly used in the next reaction according to the theoretical yield. LC-MS: m/z=243.1[M-CF3COO-]+.

Step 3: N-(1-(5-(3-cyano-6-(1-methyl-1H-pyrazol-4-yl)pyrazolo[1,5-a]pyridin-4-yl)pyridin-2-yl)-4-methyl-piperidin-4-yl)-4-ethynylbenzamide 3-Cyano-4-(6-fluoro-pyridin-3-yl)-6-(1-methyl-17T-pyrazol-4-yl)pyrazolo[1,5-a]pyridine (25 mg, 0.07854 mmol, see the synthetic part of the intermediate), 4-ethynyl-N-(4-methylpiperidin-4-yl)benzamide trifluoroacetate (77 mg, 0.2161 mmol), DMSO (2 mL) and N,N-diisopropyl ethylamine (0.05 mL, 0.3 mmol) were added in a microwave tube, and the mixture was reacted under microwave at 150° C. for 4 h. To the reaction solution were added 30 mL of ethyl acetate and 15 mL of water. The aqueous phase was extracted with EA (30 mL×2). The organic phases were combined and washed with saturated brine (15 mL). The organic phases were dried over anhydrous sodium sulfate, filtered, concentrated in vacuo, and then purified by column chromatography (PE:EA(v/v)=8:1-1:1) to give a pale yellow solid 30 mg. The yield was 55.6%. Rf=0.1 (PE:EA=1:1). LC-MS: 541.1[M+H]+, 1H NMR (400 MHz, CDCl3) δ 8.63 (s, 1H), 8.37 (d, J=2.1 Hz, 1H), 8.25 (s, 1H), 7.78 (s, 1H), 7.76-7.67 (m, 4H), 7.55 (d, J=8.2 Hz, 2H), 7.39 (s, 1H), 6.82 (d, J=8.9 Hz, 1H), 5.91 (s, 1H), 4.00 (m, 5H), 3.43 (t, J=10.5 Hz, 2H), 3.19 (s, 1H), 2.33 (d, J=13.7 Hz, 2H), 1.85 (dd, J=16.8, 7.0 Hz, 2H), 1.59 (s, 3H).

Example 3: 3-cyano-4-(6-(4-(4-ethynylbenzoyl)piperazin-1-yl)pyridin-3-yl)-6-(1-methyl-1H-pyrazol-4-yl)pyrazolo[1,5-a]pyridine (3)

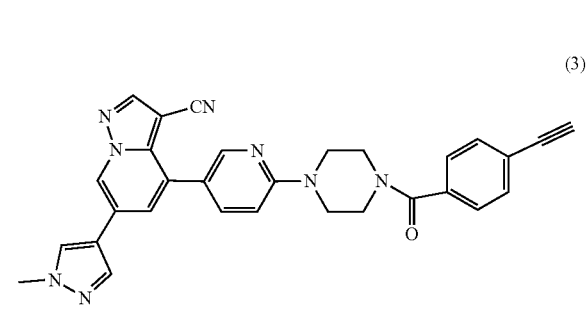 [SMILES: C#Cc1ccc(C(=O)N2CCN(c3ccc(-c4cc(-c5cnn(C)c5)cn5ncc(C#N)c45)cn3)CC2)cc1]

Step 1: tert-butyl 4-(4-ethynylbenzoyl)piperazine-1-carboxylate tert-Butyl piperazine-1-carboxylate (600 mg, 3.2215 mmol), DCM (12 mL), 4-ethynylbenzoic acid (0.57 g, 3.9 mmol), EDCI (0.93 g, 4.9 mmol) and DMAP (0.04 g, 0.3 mmol) were added in a 25 mL single-necked flask. The mixture was stirred and reacted at room temperature overnight. 20 mL of DCM and 15 mL of water were added into the mixture, and the aqueous phase was separated and extracted with 20 mL of DCM. The organic phases were combined, washed with 15 mL of saturated brine, dried over anhydrous sodium sulfate, concentrated in vacuo, and then purified by silica gel column chromatography (PE:EA(v/v)=15:1-4:1) to give a pale yellow foam solid 423 mg. The yield was 41.8%. LC-MS: m/z=259.1[M-t-Bu+2H]+, 1H NMR (400 MHz, CDCl3) δ 7.53 (d, J=8.1 Hz, 2H), 7.36 (d, J=8.1 Hz, 2H), 3.82-3.61 (m, 2H), 3.55-3.32 (m, 6H), 3.15 (s, 1H), 1.47 (s, 9H).

Step 2: (4-ethynylphenyl)(piperazin-1-yl)methanone trifluoroacetate tert-Butyl 4-(4-ethynylbenzoyl)piperazine-1-carboxylate (500 mg, 1.590 mmol) was added in a 50 mL single-necked flask, then DCM (5 mL) and TFA (2 mL) were added. The mixture was reacted with stirring at room temperature. The completion of reaction was monitored by TLC after 2.5 h. The reaction solution was directly concentrated in vacuo to give a colorless, transparent oily liquid product, which was directly used in the next reaction according to the theoretical yield. Rf=0.01 (PE:EA=1:1). LC-MS: 215.1[M-CF$_3$COO$^-$]$^+$. $^1$H NMR (400 MHz, CDCl$_3$) δ 8.80 (s, 2H), 7.57 (d, J=7.9 Hz, 2H), 7.35 (d, J=7.9 Hz, 2H), 4.11-3.62 (m, 4H), 3.25 (d, J=39.9 Hz, 5H).

Step 3: 4-(6-(4-(4-ethynylbenzoyl)piperazin-1-yl) pyridin-3-yl)-6-(1-methyl-1H-pyrazol-4-yl) pyrazolo [1,5-a]pyridin-3-carbonitrile 3-Cyano-4-(6-fluoro-pyridin-3-yl)-6-(1-methyl-17T-pyrazol-4-yl)pyrazolo[1,5-a]pyridine (25 mg, 0.07854 mmol, see the synthetic part of the intermediate), (4-ethynylphenyl)(piperazin-1-yl)methanone trifluoroacetate (77 mg, 0.2345 mmol), N,N-isopropyl ethylamine (0.05 mL, 0.3 mmol) and DMSO (2 mL) were added in a microwave tube, and the mixture was reacted under microwave at 150° C. for 5 h. To the mixture were added 30 mL of EA and 15 mL of water. The mixture was partitioned. Then the aqueous phase was extracted with EA (25 mL×2). The organic phases were combined and washed with saturated brine (15 mL). The organic phases were dried over anhydrous sodium sulfate, filtered, concentrated in vacuo, and then purified by silica gel column chromatography (PE:EA(v/v)=5:1-1:1.5) to give a pale yellow solid 26 mg. Rf=0.1 (PE:EA=1:1). LC-MS: 513.3[M+H]$^+$, $^1$H NMR (400 MHz, CDCl$_3$) δ 8.64 (s, 1H), 8.38 (s, 1H), 8.26 (s, 1H), 7.78 (d, J=7.3 Hz, 2H), 7.68 (s, 1H), 7.57 (d, J=7.9 Hz, 2H), 7.45-7.38 (m, 3H), 6.81 (d, J=8.9 Hz, 1H), 3.99 (s, 3H), 3.64 (d, J=55.3 Hz, 8H), 3.17 (s, 1H).

Example 4: N-(1-(5-(3-cyano-6-(1-methyl-1H-pyrazol-4-yl)pyrazolo[1,5-a]pyridin-4-yl) pyridin-2-yl)-4-methylpiperidin-4-yl)-3-ethynylbenzamide (4)

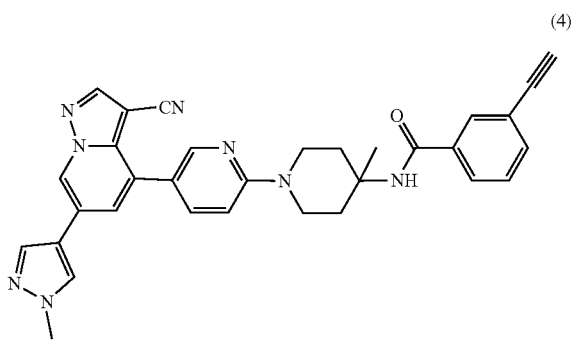 [SMILES: C#Cc1cccc(C(=O)NC2(C)CCN(c3ccc(-c4cc(-c5cnn(C)c5)cn5ncc(C#N)c45)cn3)CC2)c1]

Step 1: tert-butyl 4-(3-ethynylbenzoylamino)-4-methylpiperidin-1-carboxylate tert-Butyl 4-amino-4-methyl-piperidin-1-carboxylate (500 mg, 2.33 mmol), 3-ethynylbenzoic acid (409 mg, 2.80 mmol), DCC (729 mg, 3.50 mmol) and DMAP (28 mg, 0.23 mmol) were added in a 50 mL reaction flask. The reaction mixture was degassed and refilled with nitrogen, and then stirred and reacted at room temperature overnight. After the completion of reaction was monitored by TLC, the white insoluble solid of the reaction mixture was filtered by sand core funnel, and the filter cake was washed twice with methylene chloride. The filtrate was concentrated in vacuo and purified by silica gel column chromatography (PE:EA=6:1-4:1) to give a white solid 795 mg as the desired product (yield: 99.5%). LC-MS: m/z=365.20 [M+Na]$^+$, 287.20 [M-tBu+2H]$^+$. $^1$H-NMR (400 MHz, CDCl$_3$) δ 7.79 (s, 1H), 7.72 (d, J=7.8 Hz, 1H), 7.60 (d, J=7.7 Hz, 1H), 7.41 (t, J=7.8 Hz, 1H), 5.79 (s, 1H), 3.70 (br s, 2H), 3.21 (ddd, J=13.6, 10.3, 3.2 Hz, 2H), 3.13 (s, 1H), 2.18 (br s, 2H), 1.72-1.64 (m, 2H), 1.52 (s, 3H), 1.46 (s, 9H).

Step 2: 4-(3-ethynylbenzoylamino)-4-methylpiperidin-1-ium 2,2,2-trifluoroacetate tert-Butyl 4-(3-ethynylbenzoylamino)-4-methylpiperidine-1-carboxylate (790 mg, 2.31 mmol) was dissolved in DCM (23 mL). The mixture was stirred and trifluoroacetic acid (1.7 mL, 23 mmol) was added. The mixture was reacted overnight. The completion of reaction was monitored by TLC. The resulting mixture was concentrated in vacuo to give the crude product, which was used in the next step without further purification. The reaction was carried out in 100% yield. LC-MS: m/z=243.1 [M-CF$_3$COO$^-$]$^+$; $^1$H NMR (400 MHz, CDCl$_3$) δ 8.46 (br s, 1H), 8.23 (br s, 1H), 7.78 (s, 1H), 7.66 (dd, J=18.3, 7.8 Hz, 2H), 7.42 (t, J=7.8 Hz, 1H), 6.18 (s, 1H), 3.33 (br s, 4H), 3.15 (s, 1H), 2.64 (d, J=15.0 Hz, 2H), 2.02-1.90 (m, 2H), 1.58 (s, 3H).

Step 3: N-(1-(5-(3-cyano-6-(1-methyl-1H-pyrazol-4-yl)pyrazolo[1,5-a]pyridin-4-yl)pyridin-2-yl)-4-methylpiperidin-4-yl)-3-ethynylbenzamide 3-Cyano-4-(6-fluoro-pyridin-3-yl)-6-(1-methyl-1H-pyrazol-4-yl)pyrazolo[1,5-a]pyridine (35 mg, 0.11 mmol, see the synthetic part of the intermediate) was added in a 10 mL reaction flask, then DMSO (1 mL) and 4-(3-ethynylbenzoylamino)-4-methylpiperidin-1-onium2 2,2-trifluoroacetate (78 mg, 0.22 mmol) were added. The mixture was reacted under microwave for 6.5 h (150° C., 10 bar). The reaction solution was dispersed in two phases of EA (50 mL) and water (20 mL), and the aqueous phase was extracted with EA (30 mL×2). The organic phases were combined, and then washed with water (20 mL×2) and saturated brine (30 mL) in turn. The combined organic phases were dried over anhydrous sodium sulfate, filtered, concentrated in vacuo. The residue was purified by silica gel column chromatography (PE:EA=1.5:1-1:1.5 (1% triethylamine was added)) to afford a white solid 47.8 mg (yield: 80.4%) as the desired product. LC-MS: m/z=541.1 [M+H]$^+$; $^1$H-NMR (400 MHz, CDCl$_3$) δ 8.62 (s, 1H), 8.37 (d, J=2.1 Hz, 1H), 8.25 (s, 1H), 7.83 (s, 1H), 7.78 (s, 1H), 7.76-7.70 (m, 2H), 7.68 (s, 1H), 7.60 (d, J=7.6 Hz, 1H), 7.45-7.36 (m, 2H), 6.82 (d, J=8.8 Hz, 1H), 5.93 (s, 1H), 4.05-3.93 (m, 5H), 3.43 (t, J=10.5 Hz, 2H), 3.13 (s, 1H), 2.33 (d, J=13.9 Hz, 2H), 1.90-1.79 (m, 2H), 1.59 (s, 3H).

Example 5: 6-(1-methyl-1H-pyrazol-4-yl)-4-(6-(4-propionylpiperazin-1-yl)pyridin-3-yl) pyrazolo[1,5-a]pyridin-3-carbonitrile (5)

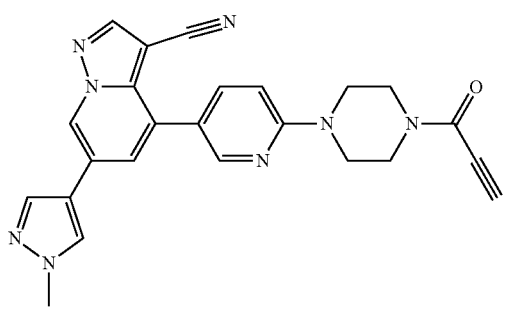

To a 5 mL reaction flask were sequentially added 6-(1-methyl pyrazol-4-yl)-4-(6-piperazin-1-yl-3-pyridyl)pyrazolo[1,5-a]pyridin-3-carbonitrile dihydrochloride (see synthesis of intermediate 2) (20 mg, 0.044 mmol) and DCM (2 mL), then prop-2-ynyl acid (0.009 mL, 0.1 mmol), N,N'-dicyclohexyl carbon (13 mg, 0.0624 mmol) and DIPEA (0.014 mL, 0.084 mmol) were added under ice bath conditions. The mixture was stirred at room temperature overnight. To the reaction mixture were added DCM (30 mL) and water (10 mL). The aqueous phase was extracted with DCM (20 mL×2). The combined organic layers were washed with saturated brine (10 mL), dried over anhydrous sodium sulfate and filtered. The mother liquid was concentrated in vacuo, and the residue was purified by silica gel column chromatography (DCM:MeOH=0-100:3) to give a white solid 7.0 mg as the target product (the yield was 36.68%). (Rf=0.5, DCM/MeOH=30:1). LC-MS, m/z=437.2 [M+H]⁺. HPLC: 98.65%.

Example 31: 6-(1-methyl-1H-pyrazol-4-yl)-4-(6-(6-propioloyl-3,6-diazabicyclo[3.1.1]heptan-3-yl)pyridin-3-yl)pyrazolo[1,5-a]pyridine-3-carbonitrile (31)

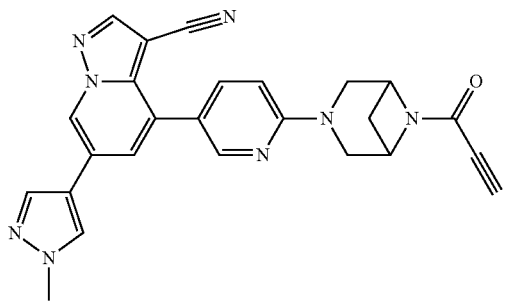

4-(6-(3,6-diazabicyclo[3.1.1]heptan-3-yl)pyridin-3-yl)-6-(1-methyl-1H-pyrazol-4-yl)pyrazole[1,5-a]pyridin-3-cyano dihydrochloride (see synthesis of intermediate 3) (25 mg, 0.05 mmol) was dissolved in DCM (5 mL)) in ice water bath, and propynoic acid (8 mg, 0.11 mmol) was added. Then DCC (17 mg, 0.08 mmol) and DIPEA (137 mg, 1.06 mmol) were added slowly. The mixture was naturally warmed to room temperature and continued for reaction with stirring for 4 h. The mixture was quenched with water (10 mL) and extracted with DCM (10 mL×3). The combined organic layers were washed with water (10 mL), dried over anhydrous sodium sulfate, and filtered. The mother liquor was concentrated in vacuo, and then purified by silica gel column chromatography (eluent DCM/CH₃OH=50/1-30/1) to give a brownish yellow solid 12 mg as the target product (the yield was 50.24%). Rf=0.26 (DCM/CH₃OH=30/1). LC-MS: m/z=449.1[M+H]⁺. ¹H NMR (400 MHz, CDCl₃) δ 8.67 (s, 1H), 8.43 (d, J=2.1 Hz, 1H), 8.29 (s, 1H), 7.82 (d, J=3.6 Hz, 1H), 7.71 (s, 1H), 7.42 (s, 1H), 6.69 (d, J=8.8 Hz, 1H), 5.56-5.21 (m, 1H), 4.74 (d, J=6.0 Hz, 2H), 4.13 (d, J=11.4 Hz, 2H), 4.02 (s, 3H), 3.95 (d, J=11.9 Hz, 1H), 3.77 (d, J=11.3 Hz, 1H), 3.01 (s, 1H), 2.91-2.84 (m, 1H), 2.07-2.00 (m, 1H). HPLC: 94.96%.

Example 186: 4-[6-[6-[(6-ethynyl-3-pyridyl)methyl]-3,6-diazabicyclo[3.1.1]heptan-3-yl]-3-pyridinyl]-6-(1-methylpyridin-4-yl)pyrazolo[1,5-a]pyridine-3-carbonitrile (186)

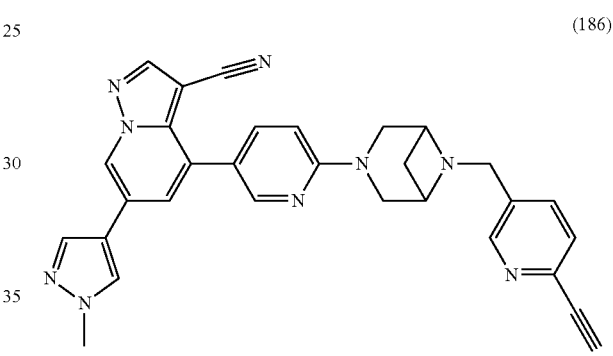

Step 1:
6-(2-trimethylsilylethynyl)pyridin-3-carbaldehyde

To a 25 mL two-necked flask were sequentially added 6-bromopyridine-3-carbaldehyde (1000 mg, 5.376 mmol), PdCl₂(PPh₃)₂ (151 mg, 0.215 mmol) and CuI (52 mg, 0.273 mmol) at room temperature. The reaction mixture was degassed and refilled with nitrogen. Triethylamine (8.1 mL, 58 mmol) and ethynyl (trimethyl)silane (1.52 mL, 10.8 mmol) were added to the mixture and a black turbid liquid was obtained. The resulting mixture was continued for reaction overnight. TLC showed the reaction was completed. The mixture was concentrated in vacuo, and then purified by silica gel column chromatography (eluent PE:EA=10:1-8:1) to give a yellow-white product 0.66 g (the yield was 60%), which was the target product. LC-MS (ES-API): m/z=204.2[M+H]⁺.

Step 2: 6-ethynylpyridine-3-carbaldehyde

To a 25 mL single-necked flask were sequentially added 6-(2-trimethylsilylethynyl)pyridine-3-carbaldehyde (660 mg, 3.246 mmol), K₂CO₃ (897 mg, 6.490 mmol) and MeOH (8.12 mL). The mixture was stirred to react at room temperature. TLC showed the reaction was completed. The reaction was quenched by dropwise addition of saturated ammonium chloride (10 mL). Most of the methanol was removed under reduced pressure. The resulting turbid liquid was extracted with EA (20 mL×2). The organic phase was washed with saturated brine (10 mL×2), dried over anhydrous sodium sulfate, filtered, and concentrated in vacuo. The mixture was purified by silica gel column chromatography (eluent PE:EA=10:1-4:1) to give a yellow-white product 0.240 g (the yield was 56.4%), which was the target product. LC-MS (ES-API): m/z=132.1 [M+H]$^+$.

Step 3: (6-ethynyl-3-pyridyl)methanol

To a 10 mL two-necked flask were added 6-ethynylpyridine-3-carbaldehyde (50 mg, 0.381 mmol) and sodium borohydride (22.1 mg, 0.572 mmol). The reaction mixture was degassed and refilled with nitrogen. Then anhydrous THF (5 mL) was added. The mixture was reacted at 0° C. with stirring for 15 min in a cryogenic tank, and then placed at room temperature for reaction. TLC showed the reaction was completed. The mixture was quenched with water (4 mL) and extracted with EA (10 mL×2). The organic phase was washed with water (10 mL), dried over anhydrous sodium sulfate, filtered, and concentrated in vacuo. The mixture was purified by silica gel column chromatography (eluent PE:EA=2:1-1:2) to give a yellow-white solid 0.037 g (the yield was 73%), which was the target product. LC-MS (ES-API): m/z=132.1 [M+H]$^+$.

Step 4: 5-(bromomethyl)-2-ethynyl-pyridine

To a 10 mL single-necked flask was added a solution of (6-ethynyl-3-pyridyl)methanol (18 mg, 0.135 mmol) in DCM (2 mL) at 0° C. in the cryogenic tank, then PBr$_3$ (0.03 mL, 0.3 mmol) was added slowly. After 30 minutes of reaction, TLC showed that the reaction was completed. The mixture was slowly added with water (1 mL) to quench the reaction. Saturated potassium carbonate solution (4 mL) was added dropwise to adjust the pH to alkaline. The resulting mixture was extracted with DCM (10 mL×2), concentrated in vacuo to remove part of DCM, and then directly used for the next step. The yield was calculated by 100%. LC-MS (ES-API): m/z=196.0 [M+H]$^+$.

Step 5: 4-[6-[6-[(6-ethynyl-3-pyridyl)methyl]-3,6-diazabicyclo[3.1.1]heptan-3-yl]-3-pyridinyl]-6-(1-methylpyridin-4-yl)pyrazolo[1,5-a]pyridine-3-carbonitrile To a 10 mL single-necked flask was added 4-[6-(3,6-diazabicyclo[3.1.1]heptan-3-yl)-3-pyridyl]-6-(1-methylpyrazol-4-yl)pyrazolo[1,5-a]pyridine-3-carbonitrile dihydrochloride (see synthesis of intermediate 3, 20 mg, 0.043 mmol), K$_2$CO$_3$ (24 mg, 0.172 mmol), N,N-dimethylformamide (3 mL) and 5-(bromomethyl)-2-ethynyl-pyridine (26.5 mg, 0.135 mmol). The mixture was slowly warmed to 40° C. for reaction. TLC showed that the reaction was completed. The mixture was quenched with water (10 mL) and extracted with EA (10 mL×2). The combined organic phases were washed with saturated saline (10 mL×2), dried over anhydrous sodium sulfate, filtered, and concentrated in vacuo. The mixture was purified by silica gel column chromatography (eluent: DCM-DCM:MeOH (v:v=100:3) to give a pale yellow solid 0.008 g (the yield was 40%), which was the target product. LC-MS (ES-API): m/z=512.30 [M+H]$^+$. $^1$H NMR (400 MHz, CDCl$_3$) δ 8.65 (d, J=1.2 Hz, 1H), 8.58 (s, 1H), 8.44 (d, J=2.2 Hz, 1H), 8.28 (s, 1H), 7.82 (dd, J=8.8, 2.4 Hz, 1H), 7.80 (s, 1H), 7.74 (s, 1H), 7.69 (s, 1H), 7.45 (d, J=8.0 Hz, 1H), 7.42 (d, J=1.3 Hz, 1H), 6.71 (d, J=8.7 Hz, 1H), 4.00 (s, 3H), 3.82 (s, 4H), 3.73-3.68 (m, 2H), 3.64 (s, 2H), 3.13 (s, 1H), 2.76 (s, 1H), 2.08-1.97 (m, 1H). HPLC: 89.65%.

Example 187: 4-(6-(6-((5-ethynylpyridin-3-yl)methyl)-3,6-diazabicyclo[3.1.1]heptan-3-yl) pyridin-3-yl)-6-(1-methyl-1H-pyrazol-4-yl)pyrazolo[1,5-a] pyridine-3-carbonitrile

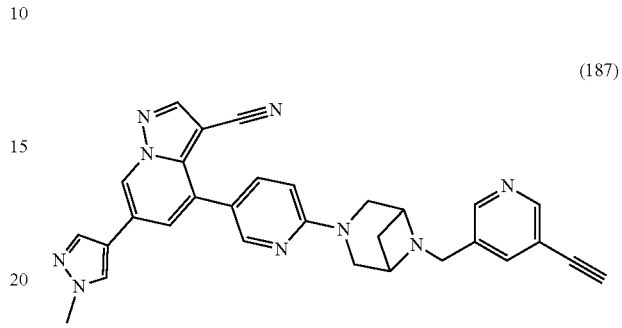

(187)

Step 1: 5-((trimethylsilyl)ethynyl)pyridine

To a mixture of 5-bromonicotinaldehyde (600 mg, 3.23 mmol), Pd(PPh$_3$)$_2$Cl$_2$ (90 mg, 0.13 mmol) and CuI (30 mg, 0.16 mmol) were sequentially added Et$_3$N (4.8 mL, 34 mmol) and trimethylsilylacetylene (0.91 mL, 6.4 mmol) at room temperature under nitrogen. A black suspension was obtained. The mixture was reacted at room temperature overnight. The mixture was concentrated in vacuo to remove the solvent, and the residue was purified by silica gel column chromatography (PE:EA=10:1) to give a pale yellow solid 591 mg as the target product (the yield was 90.1%). Rf=0.45 (PE:EA=10:1).

Step 2: 5-ethynyl nicotinic aldehyde

To a solution of 5-((trimethylsilyl)ethynyl)pyridine (591 mg, 2.90 mmol) in MeOH (7.3 mL) was added K$_2$CO$_3$ (40 mg, 0.29 mmol) at room temperature, and the mixture was reacted at room temperature for 1 h. The reaction was quenched with saturated NH$_4$Cl solution (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=10:1-8:1) to afford a white solid 350 mg as the target product (the yield was 91.8%). Rf=0.15 (PE:EA=10:1). LC-MS: m/z=132.10 [M+H]$^+$. $^1$H NMR (400 MHz, CDCl$_3$) 510.10 (s, 1H), 9.02 (s, 1H), 8.92 (s, 1H), 8.22 (s, 1H), 3.32 (s, 1H).

Step 3: 4-(6-(6-((5-ethynylpyridin-3-yl)methyl)-3,6-diazabicyclo[3.1.1]heptan-3-yl)pyridin-3-yl)-6-(1-methyl-1H-pyrazol-4-yl)pyrazolo[1,5-a]pyridin-3-carbonitrile To a 10 mL single-necked flask were added 4-(6-(3,6-diazabicyclo[3.1.1]heptane-3-yl) pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and 5-ethynyl nicotinic aldehyde (10 mg, 0.076 mmol). The mixture was dissolved with 1,2-dichloroethane (2 mL), then sodium triacetoxyborohydride (22 mg, 0.1038 mmol) was added. The mixture was reacted at 35° C. for 4 h. The mixture was concentrated in vacuo, and the residue was purified by silica gel column chromatography (eluent MeOH:DCM=1:50-1:30) to give a pale yellow solid 12 mg as the target product (the yield was 73.4%). Rf=0.5 (MeOH:DCM=1:20). LC-MS: 512.10[M+H]$^+$. $^1$H NMR (400 MHz, CDCl$_3$) δ 8.72-8.50 (m, 3H), 8.44 (d, J=2.1 Hz, 1H), 8.28 (s, 1H), 7.86 (s, 1H), 7.83 (dd, J=8.8, 2.4 Hz, 1H), 7.80 (s, 1H), 7.69 (s, 1H), 7.42 (s, 1H), 6.72 (d, J=8.8 Hz, 1H), 4.00 (s, 3H), 3.86-3.79 (m, 4H), 3.69-3.60 (m, 4H), 3.21 (s, 1H), 2.78-2.71 (m, 1H), 2.09 (s, 1H). HPLC: 96.84%.

Example 194: 4-(6-(6-(3-(6-methoxypyridin-3-yl)prop-2-yn-1-yl)-3,6-diazabicyclo[3.1.1]heptane-3-yl)pyridin-3-yl)-6-(1-methyl-1H-pyrazol-4-yl)pyrazolo[1,5-a]pyridin-3-carbonitrile

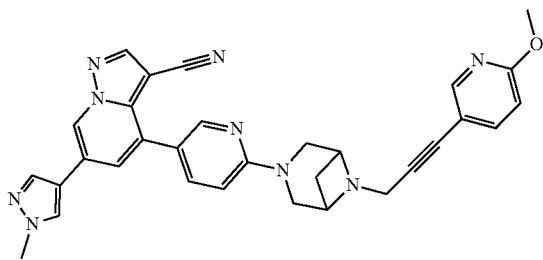 [SMILES: COc1ccc(C#CCN2C3CC2CN(c2ccc(-c4cc(-c5cnn(C)c5)cn5ncc(C#N)c45)cn2)C3)cn1]

Step 1: 3-(6-methoxypyridin-3-yl)prop-2-yn-1-ol

To a mixture of 5-bromo-2-methoxypyridine (500 mg, 2.66 mmol), Pd(PPh$_3$)$_2$C$_{1-2}$ (93 mg, 0.13 mmol), CuI (25 mg, 0.13 mmol) were added Et$_3$N (4.0 mL, 29 mmol) and 2-propyn-1-ol (0.76 mL, 13 mmol) in turn at room temperature under nitrogen. A black suspension was obtained, then heated to 80° C., reacted overnight, and concentrated in vacuo to remove the solvent. The residue was purified by silica gel column chromatography (PE:EA(v/v)=3:1) to give a pale yellow solid 80 mg (yield: 18.4%). LC-MS: 164.20 [M+H]$^+$; $^1$H NMR (400 MHz, CDCl$_3$) δ 8.26 (d, J=1.7 Hz, 1H), 7.59 (dd, J=8.6, 2.2 Hz, 1H), 6.69 (d, J=8.6 Hz, 1H), 4.49 (s, 2H), 3.94 (s, 3H).

Step 2: 3-(6-methoxypyridin-3-yl)propynal

To a solution of 3-(6-methoxypyridin-3-yl)prop-2-yn-1-ol (80 mg, 0.49 mmol) in DCM (4.9 mL) were added NaHCO$_3$ (207 mg, 2.45) and Dess-Martin oxidant (420 mg, 0.98 mmol) in turn, and the mixture was reacted for 1 h at room temperature. The reaction was quenched with saturated Na$_2$S$_2$O$_2$ (5 mL). After the layering was clear, the mixture was extracted with DCM (20 mL×2). The organic phases were combined and dried over anhydrous sodium sulfate, and concentrated in vacuo. The residue was purified by silica gel column chromatography (PE:EA=4:1) to give a pale yellow solid 56 mg (yield: 70.9%). LC-MS: 162.10 [M+H]$^+$; $^1$H NMR (600 MHz, CDCl$_3$) δ 9.43 (s, 1H), 8.48 (d, J=2.3 Hz, 1H), 7.76 (dd, 7=8.6, 2.3 Hz, 1H), 6.80 (d, J=8.6 Hz, 1H), 4.01 (s, 3H).

Step 3: 4-(6-(6-(3-(6-methoxypyridin-3-yl)prop-2-yn-1-yl)-3,6-diazabicyclo[3.1.1]heptane-3-yl) pyridin-3-yl)-6-(1-methyl-1H-pyrazol-4-yl)pyrazolo[1,5-a]pyridin-3-carbonitrile 4-(6-(3,6-Diazabicyclo[3.1.1]heptane-3-yl)pyridin-3-yl)-6-(1-methyl-1H-pyrazole-4-yl)pyrazolo[1,5-a]pyridine-3-carbonitrile dihydrochloride (see synthesis of intermediate 3, 15 mg, 0.038 mmol), 3-(6-methoxypyridine-3-yl)propynal (13 mg, 0.081 mmol), sodium triacetoxyborohydride (25 mg, 0.12 mmol) and DCM (2 mL) were added sequentially to a 10 mL single-neck flask. The mixture was reacted at 35° C. overnight. After the completion of reaction was monitored by TLC, the reaction solution was concentrated in vacuo, and then purified by silica gel column chromatography (DCM:MeOH (v/v)=100/0-100/6) to give a white solid 6.5 mg (yield: 29%). LC-MS: 542.2 [M+H]$^+$; $^1$H NMR (400 MHz, CDCl$_3$) 58.64 (s, 1H), 8.43 (s, 1H), 8.28 (s, 1H), 8.23 (s, 1H), 7.84-7.77 (m, 2H), 7.68 (s, 1H), 7.58 (d, 1H), 7.40 (s, 1H), 6.72 (d, 1H), 6.66 (d, 1H), 3.99 (s, 3H), 3.95-3.91 (m, 5H), 3.89-3.83 (m, 2H), 3.69-3.61 (m, 2H), 3.49 (s, 2H), 2.80-2.70 (m, 1H), 2.08-1.91 (m, 1H).

Example 195: 6-(1-methyl-1H-pyrazol-4-yl)-4-(6-(6-(prop-2-yn-1-yl)-3,6-diazabicyclo[3.1.1]heptan-3-yl)pyridin-3-yl)pyrazolo[1,5-a]pyridine-3-carbonitrile (195)

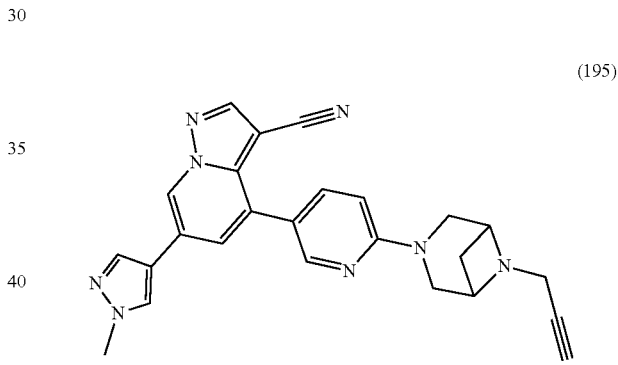

To a 10 mL single-necked flask were sequentially added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.03196 mmol), potassium carbonate (22.08 mg, 0.1598 mmol) and acetonitrile (1.0 mL). Then bromopropyne (4.5 mg, 0.038 mmol) was added slowly. The resulting mixture was stirred at room temperature overnight. The reaction solution was filtered, and the filtrate was concentrated in vacuo, purified by silica gel column chromatography (eluent DCM/MeOH=50:1-30:1) to give a white solid 7.1 mg as the target product (the yield was 51.0%). Rf=0.15 (DCM/MeOH=30/1). LC-MS (ES-API): m/z=435.40 [M+H]$^+$. $^1$H NMR (400 MHz, CDCl$_3$) δ 8.66 (d, J=1.0 Hz, 1H), 8.44 (d, J=2.2 Hz, 1H), 8.30 (s, 1H), 7.84 (d, J=2.4 Hz, 1H), 7.82 (s, 1H), 7.71 (s, 1H), 7.43 (d, J=1.1 Hz, 1H), 6.72 (d, J=8.8 Hz, 1H), 4.02 (s, 3H), 3.91 (d, J=5.7 Hz, 2H), 3.83 (d, J=12.1 Hz, 2H), 3.64 (d, J=10.7 Hz, 2H), 3.29 (d, J=2.2 Hz, 2H), 2.74 (dd, J=13.9, 6.4 Hz, 1H), 2.27-2.20 (m, 2H), 2.03 (dd, J=12.2, 6.6 Hz, 2H). HPLC: 96.65%.

Example 214: 6-(1-methyl-1H-pyrazol-4-yl)-4-(6-(4-propargylpiperazin-1-yl)pyridin-3-yl) pyrazolo[1,5-a]pyridine-3-carbonitrile

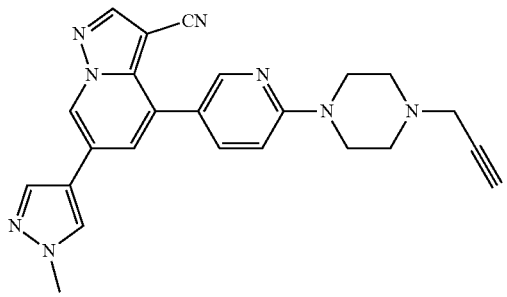 [SMILES: C#CCN1CCN(c2ccc(-c3cc(-c4cnn(C)c4)cn4ncc(C#N)c34)cn2)CC1]

Step 1: tert-butyl 4-propargylpiperazin-1-carboxylate

To a solution of 1-Boc-piperazine (1.00 g, 5.37 mmol) in acetonitrile (27 mL) were added potassium carbonate (1.11 g, 8.03 mmol) and 3-bromopropyne (0.5 mL, 6 mmol) sequentially. The mixture was stirred at room temperature overnight. The reaction solution was filtered, the filtrate was concentrated in vacuo, and then purified by silica gel column chromatography (DCM:MeOH (v/v)=30:1) to give a yellow oil 1.03 g (yield: 85.5%) as the desired product. LC-MS: 225.15[M+H]$^+$; $^1$H NMR (400 MHz, CDCl$_3$) δ 3.46 (t, J=4.9 Hz, 4H), 3.30 (d, J=2.3 Hz, 2H), 2.50 (t, J=4.8 Hz, 4H), 2.25 (t, J=2.3 Hz, 1H), 1.45 (s, 9H).

Step 2: 1-propargylpiperazine tert-Butyl 4-propargylpiperazin-1-carboxylate (1.03 g, 4.59 mmol) was dissolved in DCM (46 mL) at 0° C., and then trifluoroacetic acid (3.4 mL, 46.0 mmol) was added with stirring. After the addition, the mixture was removed from the cold bath and naturally warmed to room temperature. The mixture was reacted overnight. After the completion of reaction was monitored by TLC, the mixture was adjusted with saturated sodium carbonate solution to pH 11. The aqueous phase was extracted with DCM (30 mL×5), and the organic phases were combined, dried over anhydrous sodium sulfate, filtered, and concentrated in vacuo to give light yellow oil 350 mg (yield: 61.4%) as a crude product which became a yellow solid after standing overnight. LC-MS: 125.20[M+H]$^+$; $^1$H NMR (400 MHz, CDCl$_3$) δ 3.28 (d, J=2.2 Hz, 2H), 3.02-2.85 (m, 4H), 2.53 (br s, 4H), 2.24 (t, J=2.2 Hz, 1H).

Step 3: 6-(1-methyl-1H-pyrazol-4-yl)-4-(6-(4-propargylpiperazin-1-yl)pyridin-3-yl)pyrazolo[1,5-a]pyridine-3-carbonitrile 1-Propargylpiperazine (58 mg, 0.47 mmol) and 3-cyano-4-(6-fluoro-pyridin-3-yl)-6-(1-methyl-1H-pyrazol-4-yl) pyrazolo[1,5-a]pyridine (28.3 mg, 0.089 mmol) were dissolved in DMSO (1 mL), then DIPEA (0.10 mL, 0.60 mmol) was added, and the mixture was stirred for 3.5 h under microwave (150° C., 10 bar, pre-mixed for 30 s). After the completion of the reaction, the reaction mixture was cooled to room temperature, then diluted with EA (100 mL), and the organic phases were washed with water (20 mL) and saturated brine (20 mL) in turn, dried over anhydrous sodium, filtered, and concentrated in vacuo. The residue was purified by silica gel column chromatography (PE:EA=1:1.5-1:2) to give a pale yellow solid 20 mg (yield: 53.2%) as the desired product. LC-MS: 423.20 [M+H]$^+$; $^1$H NMR (400 MHz, CDCl$_3$) δ 8.63 (s, 1H), 8.36 (d, J=2.2 Hz, 1H), 8.25 (s, 1H), 7.78 (s, 1H), 7.75 (dd, J=8.8, 2.5 Hz, 1H), 7.68 (s, 1H), 7.38 (s, 1H), 6.79 (d, J=8.9 Hz, 1H), 3.99 (s, 3H), 3.73-3.69 (m, 4H), 3.39-3.37 (m, 2H), 2.73-2.68 (m, 4H), 2.28-2.26 (m, 1H).

Example 215: 4-(6-(6-(3-(5-methoxypyridin-3-yl)prop-2-yn-1-yl)-3,6-diazabicyclo[3.1.1]heptane-3-yl)pyridin-3-yl)-6-(1-methyl-1H-pyrazol-4-yl)pyrazolo[1,5-a]pyridine-3-carbonitrile

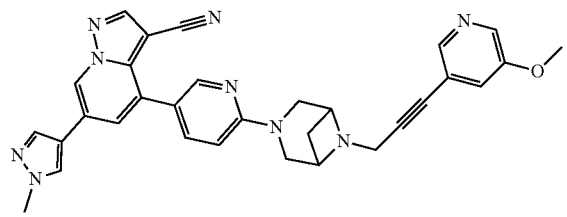

(215)

Step 1: 3-(5-methoxypyridin-3-yl)prop-2-yn-1-ol

To a mixture of 3-bromo-5-methoxypyridine (500 mg, 2.66 mmol), Pd(PPh$_3$)$_2$C$_{1-2}$ (93 mg, 0.13 mmol) and CuI (25 mg, 0.13 mmol) were added Et$_3$N (4.0 mL, 29 mmol) and 2-propyn-1-ol (0.76 mL, 13 mmol) at room temperature under nitrogen. A black suspension was obtained, heated to 80° C. and reacted overnight. The reaction mixture was diluted with EA (40 mL), and the organic phase was poured out, then the residual black viscous solid was washed with EA (30 mL×3). The organic phases were combined, concentrated in vacuo, and then purified by silica gel column chromatography (PE:EA(v/v)=4:1-2:1) to give a pale yellow solid 280 mg (yield: 68%). LC-MS: 164.15 [M+H]$^+$; $^1$H NMR (400 MHz, CDCl$_3$) δ 8.31 (s, 1H), 8.25 (s, 1H), 7.23 (s, 1H), 4.51 (s, 2H), 3.85 (s, 3H).

Step 2: 3-(5-methoxypyridin-3-yl)propynal

To a solution of 3-(5-methoxypyridin-3-yl)prop-2-yn-1-ol (280 mg, 1.72 mmol) in DCM (17.2 mL) were added NaHCO$_3$ (724 mg, 8.58 mmol) and Dess-Martin oxidant (1.10 g, 2.57 mmol) in turn, and the mixture was reacted for 0.75 h at room temperature. The reaction was quenched with saturated Na$_2$S$_2$O$_2$ (20 mL). After the layering was clear, the mixture was extracted with DCM (50 mL×2). The organic phases were combined and dried over anhydrous sodium sulfate, and concentrated in vacuo. The residue was purified by silica gel column chromatography (PE:EA=3:1) to give a white solid 202 mg (yield: 73.0%). LC-MS: 162.10 [M+1]$^+$; $^1$H NMR (400 MHz, CDCl$_3$) δ 9.42 (s, 1H), 8.42 (s, 1H), 8.38 (d, J=2.5 Hz, 1H), 7.34 (s, 1H), 3.87 (s, 3H).

Step 3: 4-(6-(6-(3-(5-methoxypyridin-3-yl)prop-2-yn-1-yl)-3,6-diazabicyclo[3.1.1]heptane-3-yl) pyridin-3-yl)-6-(1-methyl-1H-pyrazol-4-yl)pyrazolo[1,5-a]pyridin-3-carbonitrile 4-(6-(3,6-Diazabicyclo[3.1.1]heptane-3-yl)pyridin-3-yl)-6-(1-methyl-1H-pyrazole-4-yl)pyrazolo[1,5-a]pyridine-3- carbonitrile dihydrochloride (see synthesis of intermediate 3, 15 mg, 0.038 mmol), 3-(5-methoxypyridine-3-yl) propynal (13 mg, 0.081 mmol), sodium triacetoxyborohydride (25 mg, 0.12 mmol) and DCM (2 mL) were added sequentially to a 10 mL single-necked flask. The mixture was reacted at 35° C. overnight. After the completion of reaction was monitored by TLC, the reaction solution was directly concentrated in vacuo, and then purified by silica gel column chromatography (DCM:MeOH (v/v)=100/0-100/6) to give a white solid 15.5 mg (yield: 73.5%). LC-MS: 542.2 [M+H]$^+$; $^1$H NMR (400 MHz, CDCl$_3$) δ 8.65 (s, 1H), 8.43 (d, 1H), 8.29-8.21 (m, 3H), 7.85-7.77 (m, 2H), 7.69 (s, 1H), 7.41 (s, 1H), 7.22 (s, 1H), 6.71 (d, 1H), 4.02-3.96 (m, 5H), 3.89 (d, 2H), 3.84 (s, 3H), 3.69 (d, 2H), 3.54 (s, 2H), 2.85-2.74 (m, 1H), 2.09-1.89 (m, 1H).

Example 216: 4-(6-(6-(4-ethynyl-3-methoxybenzyl)-3,6-diazabicyclo[3.1.1]heptan-3-yl) pyridin-3-yl)-6-(1-methyl-1H-pyrazol-4-yl)pyrazolo[1,5-a]pyridin-3-carbonitrile (216)

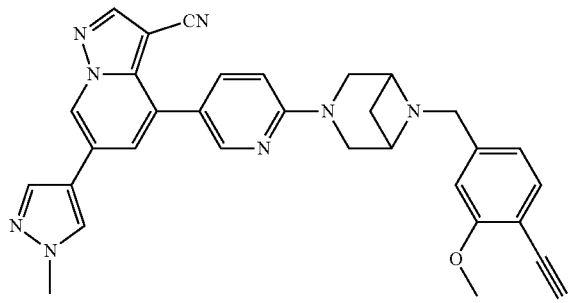

Step 1: 4-iodo-3-methoxybenzaldehyde

3-Hydroxy-4-iodo-benzaldehyde (400 mg, 1.6128 mmol) and K$_2$CO$_3$ (340 mg, 2.4248 mmol) were dissolved in acetone (16 mL) in a two-necked flask under nitrogen. The mixture was stirred at room temperature for 10 min, and then methyl iodide (0.3 mL, 5 mmol) was added dropwise. After the addition, the mixture was transferred 60° C. and refluxed for reaction. The completion of reaction was monitored by TLC after 3 h. The reaction solution was concentrated in vacuo, and the residue was added with 10 mL of water and extracted with 30 mL of EA twice. The organic phases were combined, dried over anhydrous sodium sulfate, concentrated in vacuo, and then purified by column chromatography (EA:PE(v/v)=1:20-1:10) to give a white solid 370 mg. The yield was 87.5%. LC-MS: 262.80 [M+H]$^+$; $^1$H NMR (400 MHz, CDCl$_3$) δ 9.95 (s, 1H), 7.99 (d, J=7.8 Hz, 1H), 7.29 (s, 1H), 7.19 (dd, J=7.8, 1.5 Hz, 1H), 3.96 (s, 3H).

Step 2: 3-methoxy-4-((trimethylsilyl)ethynyl)benzaldehyde

To a two-necked flask were added 4-iodo-3-methoxybenzaldehyde (370 mg, 1.4120 mmol), CuI (11 mg, 0.057758 mmol) and PdCl$_2$(PPh$_3$)$_2$ (26 mg, 0.03704 mmol) under nitrogen. Then THF (8 mL) was added to dissolve the mixture. After the dissolution, TEA (0.4 mL, 3 mmol) and trimethylsilylacetylene (217 mg, 2.209 mmol) were added. The reaction mixture became black, and the mixture was stirred for reaction at room temperature for 5 h. The reaction solution was poured into 10 mL of saturated ammonium chloride solution, and the resulting mixture was extracted with 30 mL of EA twice. The organic phases were combined, dried over anhydrous sodium sulfate, concentrated in vacuo, and then purified by column chromatography (EA:PE(v/v)=1:80-1:50) to give pale yellow oil 270 mg. The yield was 82.2%. LC-MS: 232.90 [M+H]$^+$; $^1$H NMR (400 MHz, CDCl$_3$) δ 9.96 (s, 1H), 7.59 (d, J=7.7 Hz, 1H), 7.39 (d, J=7.7 Hz, 1H), 7.36 (s, 1H), 3.94 (s, 3H), 0.28 (s, 9H).

Step 3: 4-ethynyl-3-methoxybenzaldehyde 3-methoxy-4-((trimethylsilyl)ethynyl)benzaldehyde (270 mg, 1.162 mmol) was dissolved in methanol (5 mL) in a single-necked flask, and then potassium carbonate (326 mg, 2.3249 mmol) was added with stirring. The reaction solution was reacted at room temperature. The completion of reaction was monitored by TLC after 2 h. The reaction solution was concentrated in vacuo to remove methanol, and the residue was added with 30 mL of EA to dissolve and washed with 10 mL of water twice. The organic phases were dried over anhydrous sodium sulfate, concentrated in vacuo, and then purified by column chromatography (EA:PE(v/v)=1:70-1:40) to give a white solid 35 mg. The yield was 18.8%. LC-MS: 161.20 [M+H]$^+$; $^1$H NMR (400 MHz, CDCl$_3$) δ 9.98 (s, 1H), 7.63 (d, J=7.6 Hz, 1H), 7.42 (dd, J=9.5, 1.7 Hz, 2H), 3.98 (s, 3H), 3.50 (s, 1H).

Step 4: 4-(6-(6-(4-ethynyl-3-methoxybenzyl)-3,6-diazabicyclo[3.1.1]heptan-3-yl)pyridin-3-yl)-6-(1-methyl-1H-pyrazol-4-yl)pyrazolo[1,5-a]pyridin-3-carbonitrile 4-(6-(3,6-Diazabicyclo[3.1.1]heptane-3-yl)pyridin-3-yl)-6-(1-methyl-1H-pyrazole-4-yl)pyrazolo[1,5-a]pyridine-3-carbonitrile dihydrochloride (see synthesis of intermediate 3, 15 mg, 0.038 mmol) and 4-ethynyl-3-methoxybenzaldehyde (12 mg, 0.074920 mmol) were dissolved in DCM (2 mL) in a 10 mL single-necked flask, then sodium triacetoxyborohydride (22 mg, 0.10380 mmol) was added. The mixture was reacted at 35° C. overnight. The reaction solution was diluted with 20 mL of EA, washed twice with 10 mL of water, and once with 10 mL of saturated brine, dried over anhydrous sodium sulfate, concentrated in vacuo, and then purified by column chromatography (DCM:MeOH (v/v)=1:50-1:30) to give a pale yellow solid 3.5 g. The yield was 19%. LC-MS: 541.10 [M+H]$^+$; $^1$H-NMR (400 MHz, CDCl$_3$) δ 8.67 (s, 1H), 8.46 (d, J=2.0 Hz, 1H), 8.30 (s, 1H), 7.86-7.81 (m, 2H), 7.71 (s, 1H), 7.44 (s, 1H), 7.42 (d, J=7.8 Hz, 1H), 7.37 (d, J=2.2 Hz, 1H), 6.94 (d, J=7.7 Hz, 1H), 6.73 (d, J=8.8 Hz, 1H), 4.02 (s, 3H), 3.94 (s, 3H), 3.91-3.81 (m, 4H), 3.75-3.64 (m, 4H), 3.31 (s, 1H), 2.82-2.76 (m, 1H), 1.60-1.59 (m, 1H).

Example 217: 4-(6-(6-((2-ethynylpyridin-4-yl)methyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile

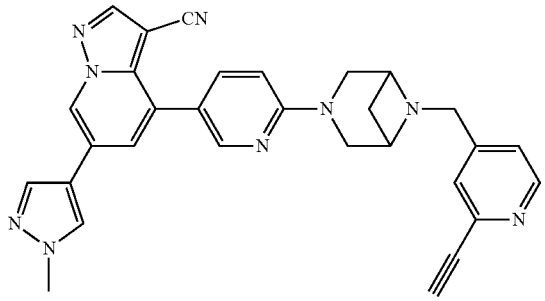

(217)

Step 1: 2-((trimethylsilyl)ethynyl)-4-formylpyridine

To a mixture of 2-bromo-4-formylpyridine (1,600 mg, 3.23 mmol), Pd(PPh$_3$)$_2$Cl$_2$ (90 mg, 0.13 mmol) and CuI (30 mg, 0.16 mmol) were added Et$_3$N (4.8 mL, 34 mmol) and trimethylsilylacetylene (0.91 mL, 6.4 mmol) in turn at room temperature under nitrogen. The mixture was stirred at room temperature overnight, concentrated in vacuo to remove the solvent. The residue was purified by silica gel column chromatography (PE:EA(v/v)=6:1) to give a pale yellow solid 537 mg (yield: 81.9%).

Step 2: 2-ethynyl-4-formylpyridine

To a solution of 2-((trimethylsilyl)ethynyl)-4-formylpyridine (2.537 mg, 2.64 mmol) in MeOH (6.6 mL) was added K$_2$CO$_3$ (36 mg, 0.26 mmol) at room temperature, and the mixture was reacted at room temperature for 2 h. The reaction was quenched with saturated NH$_4$Cl (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=4:1-2:1) to afford a white solid 297 mg (yield: 85.8%) LC-MS: 132.10 [M+H]$^+$; $^1$H NMR (400 MHz, CDCl$_3$) δ 10.05 (s, 1H), 8.84 (d, J=4.8 Hz, 1H), 7.86 (s, 1H), 7.67 (d, J=4.7 Hz, 1H), 3.27 (s, 1H).

Step 3: tert-butyl 3-(5-(3-cyano-6-(1-methyl-1H-pyrazol-4-yl)pyrazolo[1,5-a]pyridin-4-yl) pyridin-2-yl)-3,6-diazabicyclo[3.1.1]heptane-6-carboxylate 3-Cyano-4-(6-fluoro-pyridin-3-yl)-6-(1-methyl-1H-pyrazol-4-yl)pyrazolo[1,5-a]pyridine (70 mg, 0.22 mmol), tert-butyl 3,6-diazabicyclo[3.1.1]heptane-6-carboxylate (48 mg, 0.24 mmol) and potassium carbonate (185 mg, 1.32 mmol) were dissolved in DMSO (5 mL) under nitrogen, and then the solution was heated in a 100° C. oil bath and reacted for 3 d. After the completion of reaction was monitored by TLC, the reaction solution was poured into 10 mL of water, extracted twice with 30 mL. The organic phases were combined, washed with 10 mL of water, then washed with 10 mL of saturated brine. The combined organic phases were dried over anhydrous sodium sulfate, concentrated in vacuo, and then purified by silica gel column chromatography (EA:PE(v/v)=1:3-1:1) to give a white solid 92 mg. The yield was 84.24%. LC-MS: 497.30[M+H]$^+$; $^1$H NMR (400 MHz, CDCl$_3$) δ 8.63 (d, J=1.2 Hz, 1H), 8.40 (d, J=2.2 Hz, 1H), 8.26 (s, 1H), 7.80 (s, 1H), 7.77 (dd, J=8.8, 2.4 Hz, 1H), 7.69 (s, 1H), 7.40 (s, 1H), 6.67 (d, J=8.8 Hz, 1H), 4.32 (d, J=4.7 Hz, 2H), 4.20-4.13 (m, 2H), 3.99 (s, 3H), 3.61-3.51 (m, 2H), 2.99 (s, 1H), 2.09 (s, 1H), 1.39 (s, 9H).

Step 4: 4-(6-(3,6-diazabicyclo[3.1.1]heptan-3-yl) pyridin-3-yl)-6-(1-methyl-1H-pyrazole-4-yl) pyrazolo[1,5-a]pyridine-3-carbonitrile dihydrochloride tert-Butyl 3-(5-(3-cyano-6-(1-methyl-1H-pyrazol-4-yl)pyrazolo[1,5-a]pyridin-4-yl) pyridin-2-yl)-3,6-diazabicyclo[3.1.1]heptane-6-carboxylate (100 mg, 0.2014 mmol) and 4 mol/L methanolic hydrochloric acid (5 mL, 20 mmol) were added in a 25 mL single-necked flask in one portion and the mixture was stirred and reacted overnight at room temperature. After the completion of reaction was monitored by TLC, the reaction solution was concentrated in vacuo directly to obtain a pale red solid, which was used in the next step directly without further purification. The yield was calculated as 100%.

Step 5: 4-(6-(6-((2-ethynylpyridin-4-yl)methyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile 4-(6-(3,6-Diazabicyclo[3.1.1]heptane-3-yl)pyridin-3-yl)-6-(1-methyl-1H-pyrazole-4-yl)pyrazolo[1,5-a]pyridine-3-carbonitrile dihydrochloride (15 mg, 0.035 mmol) and 2-ethynyl-4-formylpyridine (14 mg, 0.11 mmol) were dissolved in DCM (2 mL) in a 10 mL single-necked flask, then sodium triacetoxyborohydride (22 mg, 0.10 mmol) was added. The mixture was reacted at 35° C. for 9 h. The reaction solution was diluted with 20 mL of EA, washed twice with 10 mL of water, and once with 10 mL of saturated brine, dried over anhydrous sodium sulfate, concentrated in vacuo, and then purified by column chromatography (EA:PE(v/v)=1:5-1:3) to give a pale yellow solid 10 mg. The yield was 56.4%. LC-MS: 512.05 [M+H]$^+$; $^1$H NMR (400 MHz, CDCl$_3$) δ 8.64 (s, 1H), 8.50 (d, J=5.1 Hz, 1H), 8.43 (d, J=2.1 Hz, 1H), 8.28 (s, 1H), 7.84-7.79 (m, 2H), 7.69 (s, 1H), 7.54 (s, 1H), 7.41 (s, 1H), 7.30 (d, J=4.9 Hz, 1H), 6.71 (d, J=8.8 Hz, 1H), 3.99 (s, 3H), 3.84-3.76 (m, 4H), 3.67-3.58 (m, 4H), 3.13 (s, 1H), 2.78-2.72 (m, 1H), 1.68 (d, J=8.7 Hz, 1H).

Example 218: 4-(6-(6-(3-ethynyl-2-fluorobenzyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile

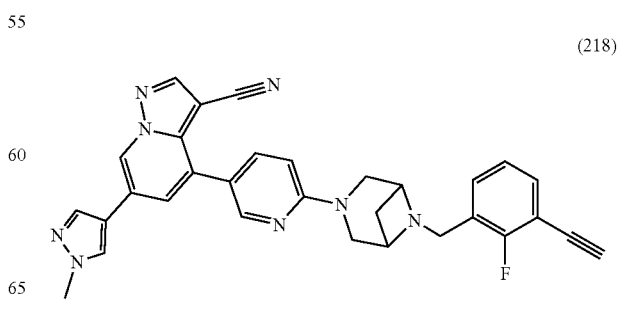

(218)

Step 1: 2-fluoro-3-((trimethylsilyl)ethynyl)benzaldehyde

To a mixture of 3-bromo-2-fluorobenzaldehyde (600 mg, 2.955 mmol), Pd(PPh$_3$)$_2$Cl$_2$ (82 mg, 0.1168 mmol) and CuI (28 mg, 0.147 mmol) were sequentially added Et$_3$N (4.4 mL, 32 mmol) and trimethylsilylacetylene (0.84 mL, 5.9 mmol) at room temperature under nitrogen. A black suspension was obtained. The mixture was reacted with stirring at room temperature overnight. The solvent was evaporated under reduced pressure, and the residue was purified by silica gel column chromatography (eluent PE) to give light yellow oil 600 mg (the yield was 92.1%) as the target product. $^1$H NMR (400 MHz, CDCl$_3$) δ 10.36 (s, 1H), 7.84-7.77 (m, 1H), 7.69 (td, J=7.6, 1.6 Hz, 1H), 7.21 (t, J=7.7 Hz, 1H), 0.28 (s, 9H).

Step 2: 3-ethynyl-2-fluorobenzaldehyde

To a solution of 2-fluoro-3-((trimethylsilyl)ethynyl)benzaldehyde (600 mg, 2.723 mmol) in methanol (6.8 mL) was added K$_2$CO$_3$ (37 mg, 0.267 mmol) at room temperature, and the mixture was reacted at room temperature for 2 h. The reaction was quenched with saturated NH$_4$Cl (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=20:1) to afford a light yellow solid 345 mg (the yield was 85.5%) as the target product. LC-MS: m/z=149.10 [M+H]$^+$. $^1$H NMR (400 MHz, CDCl$_3$) δ 10.38 (s, 1H), 7.86 (t, J=7.0 Hz, 1H), 7.74 (t, J=6.6 Hz, 1H), 7.26 (d, J=7.5 Hz, 1H), 3.39 (s, 1H).

Step 3: 4-(6-(6-(3-ethynyl-2-fluorobenzyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile To a 10 mL single-necked flask were sequentially added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 15.2 mg, 0.032 mmol), 3-ethynyl-2-fluoro-benzaldehyde (11.1 mg, 0.075 mmol), sodium triacetoxyborohydride (23 mg, 0.108 mmol) and DCE (2 mL). The mixture was stirred at room temperature overnight. The resulting mixture was filtered, and the filtrate was concentrated in vacuo, purified by silica gel column chromatography (eluent DCM/MeOH=100:0-25:1) to give a white solid 5.1 mg as the target product (the yield was 30.0%). Rf=0.6 (DCM/MeOH=20/1). LC-MS (ES-API): m/z=529.05 [M+H]$^+$. $^1$H NMR (400 MHz, CDCl$_3$) δ 8.68 (s, 1H), 8.47 (d, J=1.9 Hz, 1H), 8.31 (s, 1H), 7.86 (d, J=2.2 Hz, 1H), 7.83 (s, 1H), 7.73 (s, 1H), 7.51 (t, J=7.0 Hz, 1H), 7.46 (s, 1H), 7.43-7.36 (m, 1H), 7.12 (t, J=7.7 Hz, 1H), 6.76 (d, J=8.8 Hz, 1H), 4.03 (s, 3H), 3.92 (d, J=11.8 Hz, 2H), 3.87 (d, J=5.5 Hz, 2H), 3.76 (s, 2H), 3.70 (s, 2H), 3.31 (s, 1H), 2.77 (dd, J=13.8, 7.1 Hz, 1H), 2.40-2.19 (m, 1H). HPLC: 92.19%.

Example 219: 4-(6-(6-(1-(6-ethynylpyridin-2-yl)ethyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile

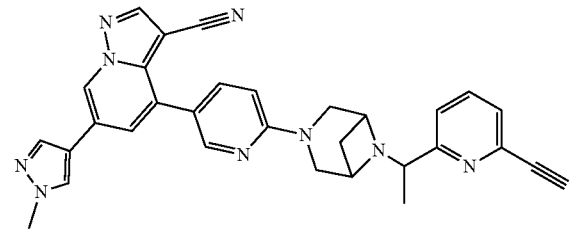

(219)

Step 1: 1-(6-((trimethylsilyl)ethynyl)pyridin-2-yl)ethanone

To a mixture of 1-(6-bromopyridin-2-yl)ethanone (600 mg, 3.00 mmol), Pd(PPh$_3$)$_2$Cl$_2$ (84 mg, 0.12 mmol) and CuI (28 mg, 0.15 mmol) were sequentially added triethylamine (4.5 mL, 32 mmol) and trimethylsilylacetylene (0.85 mL, 6.0 mmol) at room temperature under nitrogen. A black suspension was obtained. The mixture was reacted at room temperature overnight. The mixture was concentrated in vacuo to remove the solvent, and the residue was purified by silica gel column chromatography (PE:EA=20:1) to give a pale yellow solid 640 mg as the target product (the yield was 98.17%). Rf=0.85 (PE:EA=10:1).

Step 2: 1-(6-ethynylpyridin-2-yl)ethanone

To a solution of 1-(6-((trimethylsilyl)ethynyl)pyridin-2-yl)ethanone (640 mg, 2.90 mmol) in MeOH (7.3 mL) was added K$_2$CO$_3$ (40 mg, 0.29 mmol) at room temperature, and the mixture was reacted at room temperature for 0.75 h. The reaction was quenched with saturated NH$_4$Cl solution (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=15:1) to afford a white solid 416 mg as the target product (the yield was 97.32%). Rf=0.6 (PE:EA=10:1). LC-MS: m/z=146.20 [M+H]$^+$. $^1$H NMR (400 MHz, CDCl$_3$) δ 7.99 (d, J=7.8 Hz, 1H), 7.80 (t, J=7.8 Hz, 1H), 7.63 (d, J=7.7 Hz, 1H), 3.21 (s, 1H), 2.72 (s, 3H).

Step 3: 4-(6-(6-(1-(6-ethynylpyridin-2-yl)ethyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile To a 10 mL single-necked flask were added 4-(6-(3,6-diazabicyclo[3.1.1]heptane-3-yl)pyridin-3-yl)-6-(1-methyl-1H-pyrazole-4-yl)pyrazolo[1,5-a]pyridine-3-carbonitrile dihydrochloride (see synthesis of intermediate 3, 15 mg, 0.032 mmol) and 1-(6-ethynylpyridin-2-yl)ethanone (10 mg, 0.069 mmol). The mixture was dissolved with 1,2-dichloroethane (2 mL), then sodium triacetoxyborohydride (22 mg, 0.1038 mmol) was added. The mixture was reacted at 35° C. overnight. Then additional 1-(6-ethynylpyridin-2-yl)ethanone (10 mg, 0.069 mmol) and sodium triacetoxyborohydride (22 mg, 0.1038 mmol) were added and the reaction was continued for 24 h. The mixture was concentrated in vacuo, and the residue was purified by silica gel column chromatography (eluent MeOH:DCM=1:50-1:30) to give a pale yellow solid 5 mg as the target product (the yield was 29.77%). Rf=0.5 (MeOH:DCM=1:30). LC-MS: m/z=526.10[M+H]$^+$. $^1$H NMR (400 MHz, CDCl$_3$) δ 8.64 (s, 1H), 8.40 (s, 1H), 8.26 (s, 1H), 7.82 (s, 1H), 7.80-7.78 (m, 1H), 7.71 (s, 1H), 7.56-7.54 (m, 1H), 7.42 (s, 1H), 7.36-7.35 (m, 1H), 6.83 (d, J=7.2 Hz, 1H), 6.65 (d, J=8.8 Hz, 1H), 4.00 (s, 3H), 3.74-3.58 (m, 7H), 3.11 (s, 1H), 2.71-2.68 (m, 1H), 2.23-2.21 (m, 1H), 1.33 (s, 3H). HPLC: 91.83%.

Example 220: 4-(6-(3-(3-ethynyl-4-fluorobenzyl)-3,6-diazabicyclo[3.1.1]hept-3-yl)pyridin-3-yl)-6-(1-methyl-1H-pyrazol-4-yl)pyrazolo[1,5-a]pyridine-3-carbonitrile

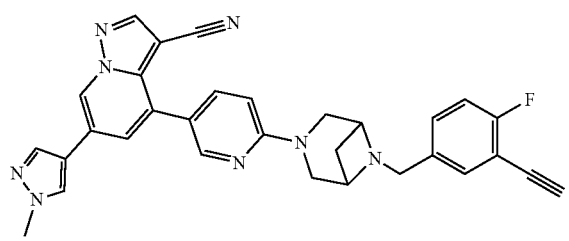

(220)

Step 1:
4-fluoro-3-((trimethylsilyl)ethynyl)benzaldehyde

To a mixture of 3-bromo-4-fluoro-benzaldehyde (600 mg, 2.9555 mmol), bis(triphenylphosphine)palladium dichloride (82 mg, 0.116825 mmol) and cuprous iodide (28 mg, 0.14702 mmol) were sequentially added triethylamine (4.4 mL, 32 mmol) and trimethylsilylacetylene (0.84 mL, 5.9 mmol) at room temperature under nitrogen. The mixture was reacted at room temperature overnight. The mixture was concentrated in vacuo to remove the solvent, and the residue was purified by silica gel column chromatography (PE:EA=20:1) to give a yellow solid 367 mg (yield: 56.4%) as the target product.

Step 2: 3-ethynyl-4-fluorobenzaldehyde

To a solution of 4-fluoro-3-((trimethylsilyl)ethynyl)benzaldehyde (367 mg, 1.6658 mmol) in methanol (4.2 mL) was added K$_2$CO$_3$ (23 mg, 0.16641 mmol) at room temperature, and the mixture was reacted at room temperature for 2 h. The reaction was quenched with saturated NH$_4$Cl (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=20:1) to afford a white solid 184 mg (yield: 74.6%) as the target product. $^1$H NMR (400 MHz, CDCl$_3$) δ 9.94 (s, 1H), 8.02 (dd, J=6.7, 2.0 Hz, 1H), 7.89 (ddd, J=8.2, 5.0, 2.0 Hz, 1H), 7.25 (t, J=8.6 Hz, 1H), 3.40 (s, 1H).

Step 3: 4-(6-(3-(3-ethynyl-4-fluorobenzyl)-3,6-diazabicyclo[3.1.1]hept-3-yl)pyridin-3-yl)-6-(1-methyl-1H-pyrazol-4-yl)pyrazolo[1,5-a]pyridine-3-carbonitrile To a 10 mL single-necked flask were added 4-(6-(3,6-diazabicyclo[3.1.1]heptane-3-yl)pyridin-3-yl)-6-(1-methyl-1H-pyrazole-4-yl)pyrazolo[1,5-a]pyridine-3-carbonitrile dihydrochloride (see synthesis of intermediate 3, 15 mg, 0.032 mmol) and 3-ethynyl-4-fluorobenzaldehyde (10 mg, 0.064 mmol). The mixture was dissolved with 1,2-dichloroethane (2 mL), then sodium triacetoxyborohydride (21 mg, 0.096 mmol) was added. The mixture was reacted at 35° C. overnight. The mixture was concentrated in vacuo, and the residue was purified by silica gel column chromatography (eluent MeOH:DCM=1:50-1:30) to give a pale yellow solid 12 mg as the target product (the yield was 70.04%). Rf=0.5 (MeOH:DCM=1:20). LC-MS: m/z=529.60[M+H]$^+$. $^1$H NMR (400 MHz, CDCl$_3$) δ 8.64 (s, 1H), 8.44 (d, J=2.1 Hz, 1H), 8.28 (s, 1H), 7.82 (dd, J=8.8, 2.4 Hz, 1H), 7.80 (s, 1H), 7.69 (s, 1H), 7.51 (d, J=8.6 Hz, 1H), 7.42 (s, 1H), 7.34 (s, 1H), 7.03 (t, J=8.8 Hz, 1H), 6.71 (d, J=8.9 Hz, 1H), 4.00 (s, 3H), 3.85-3.77 (m, 4H), 3.64-3.55 (m, 4H), 3.29 (s, 1H), 2.76-2.67 (m, 1H), 2.04-1.99 (m, 1H). HPLC: 93.81%.

Example 221: 4-(6-(6-((6-ethynylpyridin-2-yl)methyl)-3,6-diazabicyclo[3.1.1]hept-3-yl) pyridin-3-yl)-6-(1-methyl-1H-pyrazol-4-yl)pyrazolo[1,5-a]pyridine-3-carbonitrile

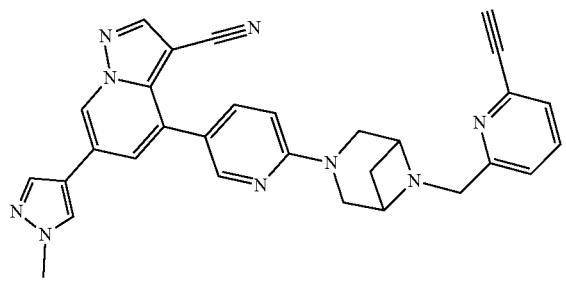

(221)

Step 1:
6-(2-trimethylsilylethynyl)pyridin-2-carbaldehyde

To a mixture of 6-bromopyridine-2-carbaldehyde (600 mg, 3.226 mmol), bis(triphenylphosphine)palladium dichloride (90 mg, 0.128 mmol) and cuprous iodide (30 mg, 0.157 mmol) were sequentially added triethylamine (4.8 mL, 34 mmol) and trimethylsilylacetylene (0.91 mL, 6.4 mmol) at room temperature under nitrogen. The mixture was reacted at room temperature overnight. The mixture was concentrated in vacuo to remove the solvent, and the residue was purified by silica gel column chromatography (PE:EA=10:1) to give a yellow solid 398 mg (yield: 60.7%) as the target product.

Step 2: 6-ethynylpyridinecarboxaldehyde

To a solution of 6-(2-trimethylsilylethynyl)pyridine-2-carbaldehyde (398 mg, 1.957 mmol) in methanol (4.9 mL) was added K$_2$CO$_3$ (27 mg, 0.195 mmol) at room temperature. The mixture was reacted at room temperature for 1 h.

The reaction was quenched with saturated NH₄Cl (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=10:1) to afford a white solid 214 mg (yield: 83.4%) as the target product. LC-MS(ESI): m/z=132.1 5[M+H]⁺; ¹H NMR (400 MHz, CDCl₃) δ 10.04 (s, 1H), 7.92 (dd, J=7.7, 0.9 Hz, 1H), 7.86 (t, J=7.7 Hz, 1H), 7.68 (dd, J=7.6, 1.0 Hz, 1H), 3.26 (s, 1H).

Step 3: 4-(6-(6-(((6-ethynylpyridin-2-yl)methyl)-3,6-diazabicyclo[3.1.1]hept-3-yl)pyridin-3-yl)-6-(1-methyl-1H-pyrazol-4-yl)pyrazolo[1,5-a]pyridin-3-carbonitrile To a 10 mL single-necked flask were added 4-(6-(3,6-diazabicyclo[3.1.1]heptane-3-yl) pyridin-3-yl)-6-(1-methyl-1H-pyrazole-4-yl)pyrazolo[1,5-a]pyridine-3-carbonitrile dihydrochloride (see synthesis of intermediate 3.15 mg, 0.035 mmol) and 6-ethynylpyridinecarboxaldehyde (9 mg, 0.069 mmol). The mixture was dissolved with 1,2-dichloroethane (2 mL), then sodium triacetoxyborohydride (20 mg, 0.094 mmol) was added. The mixture was reacted at 35° C. overnight. Then additional 6-ethynylpyridinecarboxaldehyde (5 mg, 0.035 mmol) and sodium triacetoxyborohydride (11 mg, 0.035 mmol) were added and the reaction was continued for 8 h. The mixture was concentrated in vacuo, and the residue was purified by silica gel column chromatography (eluent MeOH:DCM=1:50-1:30) to give a pale yellow solid 8 mg as the target product (the yield was 48.93%). Rf=0.5 (MeOH:DCM=1:20). LC-MS: m/z=512.10 [M+H]⁺. ¹H NMR (400 MHz, CDCl₃) δ 8.64 (s, 1H), 8.41 (d, J=2.2 Hz, 1H), 8.27 (s, 1H), 7.81 (s, 1H), 7.79 (s, 1H), 7.71 (s, 1H), 7.65 (d, J=7.9 Hz, 1H), 7.50 (d, J=7.6 Hz, 1H), 7.42 (s, 1H), 7.36 (d, J=7.6 Hz, 1H), 6.70 (d, J=8.8 Hz, 1H), 4.00 (s, 3H), 3.93-3.88 (m, 4H), 3.83 (s, 2H), 3.69-3.63 (m, 2H), 3.11 (s, 1H), 2.84-2.74 (m, 1H), 2.03-1.98 (m, 1H). HPLC: 97.42%.

Example 222: 4-(6-(6-(4-ethynyl-2,6-difluorobenzyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile (222)

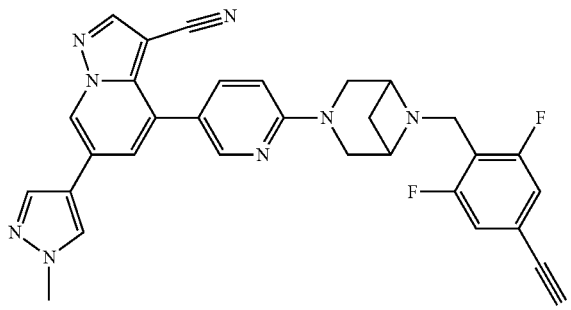

Step 1: 3-(5-methoxypyridin-3-yl)prop-2-yn-1-ol

To a 100 mL two-necked flask were sequentially added 4-bromo-2,6-difluoro-benzoic acid (1 g, 4.2194 mmol) and THF (40 mL) under nitrogen, then a mixture of borane-dimethyl sulfide (4.3 mL, 45 mmol) in 100 ml of THF was slowly added. After the completion of the dropwise addition, the mixture was reacted for 6 h at room temperature. To the reaction mixture was added methanol until no air bubbles were generated, and the mixture was transferred to a 500 mL single-necked flask to concentrate in vacuo. The residue was added with ethyl acetate (200 mL) and water (80 mL). The organic phase was separated, and washed with water (80 mL) and saturated saline (80 mL), dried over anhydrous sodium sulfate, filtered, concentrated in vacuo, and then purified by silica gel column chromatography (PE/EA=100:1-100:5) to give a white solid 880 mg as the target product (the yield was 93.5%). ¹H NMR (400 MHz, CDCl₃) δ 7.13 (d, J=6.7 Hz, 2H), 4.76 (d, J=6.3 Hz, 2H), 1.90 (t, J=6.5 Hz, 1H).

Step 2: (2,6-difluoro-4-((trimethylsilyl)ethynyl)phenyl)methanol

To a three-neck flask were added 3-(5-methoxypyridin-3-yl)prop-2-yn-1-ol (500 mg, 2.2420 mmol,), CuI (51 mg, 0.268 mmol), PdCl₂(PPh₃)₂ (47 mg, 0.067 mmol), TEA (5 mL) and ethynyl (trimethyl) silane (0.4 mL, 3 mmol) under nitrogen. The mixture was reacted overnight at 70° C. The reaction mixture was added with EA (30 mL). Then the mixture was filtered by suction with celite, and washed with appropriate amount of EA. The filtrate was concentrated in vacuo, and then purified by silica gel column chromatography (EA:PE=0:100-3:100) to give pale yellow liquid 158 mg as the desired product 1.18 g (the yield was 29.3%). ¹H NMR (400 MHz, CDCl₃) δ 7.03-6.95 (m, 2H), 4.75 (s, 2H), 1.93 (s, 1H), 0.25 (s, 9H).

Step 3: (4-ethynyl-2,6-difluorophenyl)methanol

To a 10 mL single-necked flask were added 2,6-difluoro-4-((trimethylsilyl) ethynyl)phenyl)methanol (150 mg, 0.624 mmol) and methanol (5 mL). After the solid was dissolved, K₂CO₃ (170 mg, 1.23 mmol) was added, and the mixture was stirred at room temperature for 3 h. The reaction solution was added with EA (15 mL) and water (10 mL), then partitioned. The aqueous phase was extracted with EA (10 mL×3), dried over anhydrous sodium sulfate, filtered, concentrated in vacuo, and then purified by silica gel column chromatography (PE/EA=100/0-100/3) to give a white solid 88 mg as the target product (the yield was 83.85%). ¹H NMR (400 MHz, CDCl₃) δ 7.03 (d, J=7.5 Hz, 2H), 4.77 (d, J=6.2 Hz, 2H), 3.16 (s, 1H), 1.90 (t, J=6.5 Hz, 1H).

Step 4: 2-(bromomethyl)-5-ethynyl-1,3-difluorobenzene

To a 10 mL single-necked flask were added 4-ethynyl-2,6-difluorophenyl)methanol (85 mg, 0.50553 mmol) and DCM (2.5 mL). After the solid was dissolved, PBr₃ (0.1 mL, 1 mmol) was slowly added in the ice salt bath. The mixture was reacted with stirring for 5 h in an ice bath. After the reaction was stopped, DCM (15 mL) and saturated sodium bicarbonate solution (5 mL) were added. The mixture was partitioned, and the aqueous phase was extracted with DCM (10 mL). The combined organic phases were washed with saturated saline (10 mL), dried over anhydrous sodium sulfate, concentrated in vacuo, and then used for the next step without further purification.

Step 5: 4-(6-(6-(4-ethynyl-2,6-difluorobenzyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile To a 10 mL single-necked flask were sequentially added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 20 mg, 0.043 mmol), 2-(bromomethyl)-5-ethynyl-1,3-difluorobenzene (14 mg, 0.061 mmol), DMF (2 mL) and potassium carbonate (23 mg, 0.170 mmol). The resulting mixture was reacted with stirring at room temperature overnight. The reaction mixture was added with water (8 mL) and EA (20 mL). The separated aqueous phase was extracted with EA (20 mL). The combined organic phases were washed with water (10 mL×2) and saturated saline (10 mL), dried over anhydrous sodium sulfate, filtered, concentrated in vacuo, and then purified by silica gel column chromatography (DCM/MeOH=100/0-100/3) to give a white solid 11.8 mg as the target product (the yield was 50.7%). LC-MS (ESI): m/z=547.2[M+H]$^+$. $^1$H NMR (400 MHz, CDCl$_3$) δ 8.64 (s, 1H), 8.44 (d, J=2.2 Hz, 1H), 8.27 (s, 1H), 7.82 (dd, J=8.8, 2.4 Hz, 1H), 7.79 (s, 1H), 7.68 (s, 1H), 7.42 (s, 1H), 7.01 (d, J=7.3 Hz, 2H), 6.75 (d, J=8.8 Hz, 1H), 4.07-3.97 (m, 5H), 3.90-3.82 (m, 2H), 3.70-3.60 (m, 4H), 3.13 (s, 1H), 2.78-2.66 (m, 1H), 2.05-1.97 (m, 1H). HPLC: 94.71%.

Example 223: 4-(6-(4-(4-ethynylbenzyl)piperazin-1-yl)pyridin-3-yl)-6-(1-methyl-1H-pyrazol-4-yl)pyrazolo[1,5-a]pyridine-3-carbonitrile

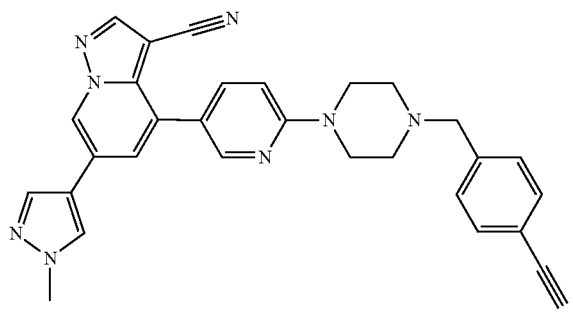

(223)

Step 1: 4-((trimethylsilyl)ethynyl)benzaldehyde

To a mixture of 4-bromobenzaldehyde (600 mg, 3.2429 mmol), bis(triphenylphosphine)palladium dichloride (91 mg, 0.13 mmol) and cuprous iodide (30 mg, 0.15752 mmol) were sequentially added triethylamine (4.9 mL, 35 mmol) and trimethylsilylacetylene (0.92 mL, 6.5 mmol) at room temperature under nitrogen. The mixture was reacted at room temperature overnight. The mixture was concentrated in vacuo to remove the solvent, and the residue was purified by silica gel column chromatography (PE:EA=20:1) to give a yellow solid 631 mg (yield: 96.2%) as the target product.

Step 2: 4-ethynylbenzaldehyde

To a solution of 4-((trimethylsilyl)ethynyl)benzaldehyde (631 mg, 3.1188 mmol) in methanol (7.8 mL) was added K$_2$CO$_3$ (43 mg, 0.31 mmol) at room temperature. The mixture was reacted at room temperature for 4 h. The reaction was quenched with saturated NH$_4$Cl (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=15:1) to afford a white solid 378 mg (yield: 93.1%) as the target product. LC-MS (ESI): m/z=131.10 [M+H]$^+$; $^1$H NMR (400 MHz, CDCl$_3$) δ 9.99 (s, 1H), 7.82 (d, J=8.2 Hz, 2H), 7.61 (d, J=8.1 Hz, 2H), 3.29 (s, 1H).

Step 3: 4-(6-(4-(4-ethynylbenzyl)piperazin-1-yl)pyridin-3-yl)-6-(1-methyl-1H-pyrazol-4-yl) pyrazolo[1,5-a]pyridine-3-carbonitrile To a single-necked flask were added 6-(1-methylpyrazol-4-yl)-4-(6-piperazin-1-yl-3-pyridyl)pyrazolo[1,5-a]pyridine-3-carbonitrile dihydrochloride (see synthesis of intermediate 2.20 mg, 0.044 mmol) and 4-ethynylbenzaldehyde (12 mg, 0.092 mmol). The mixture was dissolved with DCE (2 mL), then sodium triacetoxyborohydride (28 mg, 0.128 mmol) was added. The mixture was stirred at 40° C. overnight. The reaction solution was directly concentrated in vacuo, and the residue was purified by silica gel column chromatography (eluent DCM:MeOH=0-100:3.5) to give a pale yellow solid 13 mg as the target product (the yield was 59.63%). Rf=0.5 (DCM/MeOH=20/1). LC-MS: m/z=499.2 [M+H]$^+$. $^1$H NMR (400 MHz, CDCl$_3$) δ 8.65 (d, J=1.0 Hz, 1H), 8.38 (d, J=2.4 Hz, 1H), 8.28 (s, 1H), 7.81 (s, 1H), 7.76 (dd, J=8.8, 2.5 Hz, 1H), 7.70 (s, 1H), 7.50 (d, J=8.0 Hz, 2H), 7.41 (s, 1H), 7.37 (d, J=4.8 Hz, 2H), 6.79 (d, J=8.8 Hz, 1H), 4.01 (s, 3H), 3.70 (s, 4H), 3.61 (s, 2H), 3.10 (s, 1H), 2.61 (s, 4H). HPLC: 97.55%.

Example 224: 4-(6-(4-(3-ethynyl-2-fluorobenzyl)piperazin-1-yl)pyridin-3-yl)-6-(1-methyl-1H-pyrazol-4-yl)pyrazolo[1,5-a]pyridine-3-carbonitrile

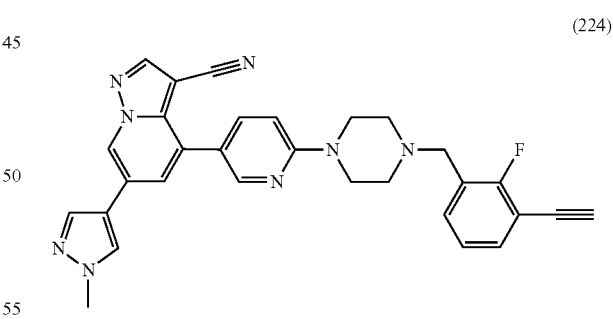

(224)

Step 1: 2-fluoro-3-((trimethylsilyl)ethynyl)benzaldehyde

To a mixture of 3-bromo-2-fluorobenzaldehyde (600 mg, 2.955 mmol), Pd(PPh$_3$)$_2$Cl$_2$ (82 mg, 0.1168 mmol) and CuI (28 mg, 0.147 mmol) were sequentially added Et$_3$N (4.4 mL, 32 mmol) and trimethylsilylacetylene (0.84 mL, 5.9 mmol) at room temperature under nitrogen. A black suspension was obtained. The mixture was reacted with stirring at room temperature overnight. The solvent was evaporated under reduced pressure, and the residue was purified by silica gel column chromatography (eluent PE) to give light yellow oil 600 mg (the yield was 92.1%) as the target product. $^1$H NMR (400 MHz, CDCl$_3$) δ 10.36 (s, 1H), 7.84-7.77 (m, 1H), 7.69 (td, J=7.6, 1.6 Hz, 1H), 7.21 (t, J=7.7 Hz, 1H), 0.28 (s, 9H).

Step 2: 3-ethynyl-2-fluorobenzaldehyde

To a solution of 2-fluoro-3-((trimethylsilyl)ethynyl)benzaldehyde (600 mg, 2.723 mmol) in methanol (6.8 mL) was added K$_2$CO$_3$ (37 mg, 0.267 mmol) at room temperature, and the mixture was reacted at room temperature for 2 h. The reaction was quenched with saturated NH$_4$Cl (10 mL). The organic solvent was evaporated under reduced pressure, and the residue was extracted with EA (40 mL×2). The organic phases were combined, and then washed with saturated brine (30 mL), dried over anhydrous sodium sulfate, filtered, concentrated in vacuo. The residue was purified by silica gel column chromatography (PE:EA=20:1) to afford a light yellow solid 345 mg (the yield was 85.5%) as the target product. LC-MS: m/z=149.10 [M+H]$^+$. $^1$H NMR (400 MHz, CDCl$_3$) δ 10.38 (s, 1H), 7.86 (t, J=7.0 Hz, 1H), 7.74 (t, J=6.6 Hz, 1H), 7.26 (d, J=7.5 Hz, 1H), 3.39 (s, 1H).

Step 3: 4-(6-(4-(3-ethynyl-2-fluorobenzyl)piperazin-1-yl)pyridin-3-yl)-6-(1-methyl-1H-pyrazol-4-yl)pyrazolo[1,5-a]pyridine-3-carbonitrile To a single-necked flask were added 6-(1-methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 20 mg, 0.044 mmol) and 3-ethynyl-2-fluoro-benzaldehyde (12 mg, 0.081 mmol). The mixture was dissolved with DCE (2 mL), then sodium triacetoxyborohydride (28 mg, 0.128 mmol) was added. The mixture was reacted at 40° C. overnight. Then the mixture was directly concentrated in vacuo, and the residue was purified by silica gel column chromatography (DCM/MeOH=0-100:3.5) to give a yellow solid 5.0 mg as the target product (the yield was 22.14%). Rf=0.5 (DCM/MeOH=10/1). LC-MS: m/z=517.2[M+H]$^+$. $^1$H NMR (400 MHz, CDCl$_3$) δ 8.65 (d, J=1.3 Hz, 1H), 8.38 (d, J=2.4 Hz, 1H), 8.28 (s, 1H), 7.81 (s, 1H), 7.76 (dd, J=8.9, 2.5 Hz, 1H), 7.70 (s, 1H), 7.51-7.43 (m, 2H), 7.41 (d, J=1.3 Hz, 1H), 7.15 (s, 1H), 6.79 (d, J=8.8 Hz, 1H), 4.01 (s, 3H), 3.75 (s, 2H), 3.74-3.72 (m, 4H), 3.33 (s, 1H), 2.67 (s, 4H). HPLC: 93.88%.

Example 225: 4-(6-(4-((5-ethynylpyridin-2-yl)methyl)pyrazol-1-yl)pyridin-3-yl)-6-(1-methyl-1H-pyrazoline-4-yl)pyrazoline[1,5-a]pyridine-3-carbonitrile (225)

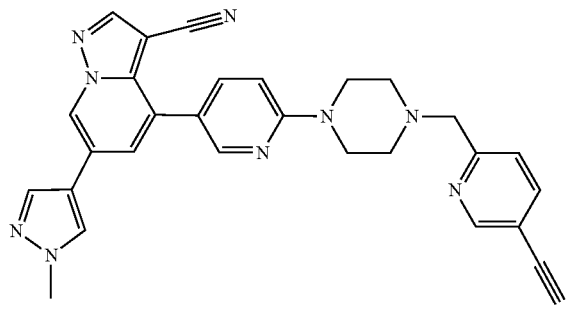

Step 1: 5-((trimethylsilyl)ethynyl)pyridine aldehyde

5-Bromopyridine-2-acetaldehyde (1.00 g, 5.38 mmol), PdCl$_2$(PPh$_3$)$_2$ (0.38 g, 0.54 mmol), CuI (102 mg, 0.54 mmol) and PPh$_3$ (141 mg, 0.54 mmol) were dissolved in THF (15 mL) Under N$_2$ protection, then trimethylsilylacetylene (0.79 g, 8.0 mmol) and Et$_3$N (1.09 g, 10.8 mmol) were added. The mixture was reacted with stirring at room temperature for 2 h. The reaction was stopped, and quenched with saturated NH$_4$Cl. The resulting mixture was extracted with DCM (10 mL×3), washed with water (10 mL), dried over anhydrous sodium sulfate, and filtered. The mother liquor was concentrated in vacuo. The residue was purified by silica gel column chromatography (eluent PE/EA=10/1-3/1) to give a brownish yellow solid 0.69 g as the target product (the yield was 63%). LC-MS: m/z=204.1[M+H]$^+$.

Step 2: 5-ethynylpyridine aldehyde 5-((Trimethylsilyl)ethynyl)pyridine aldehyde (120 mg, 0.59 mmol) was dissolved in methanol (5 mL), then K$_2$CO$_3$ (163 mg, 1.18 mmol) was added, and the mixture was stirred at room temperature for 2 h. The reaction solution was concentrated in vacuo, and the residue was purified by silica gel column chromatography (eluent PE) to give a brownish yellow solid 54 mg as the target product (the yield was 89%). LC-MS: m/z=132.1[M+H]$^+$. $^1$H NMR (400 MHz, CDCl$_3$) δ 10.10 (s, 1H), 8.88 (s, 1H), 8.02-7.90 (m, 2H), 3.45 (s, 1H).

Step 3: (5-ethynylpyridin-2-yl)methanol

At 0° C., 5-ethynylpyridine aldehyde (150 mg, 0.74 mmol) was dissolved in methanol (5 mL), then NaBH$_4$ (84 mg, 2.2 mmol) was slowly added and the mixture was reacted at low temperature for 0.5 h. The reaction was stopped, and quenched with saturated NH$_4$Cl. The resulting mixture was concentrated in vacuo, extracted with DCM (10 mL×3), washed with water (10 mL), dried over anhydrous sodium sulfate, and filtered. The mother liquor was concentrated in vacuo to give a brownish yellow solid 142 mg as the target product (the yield was 93.7%). LC-MS: m/z=134.1 [M+H]$^+$. $^1$H NMR (400 MHz, CDCl$_3$) δ 8.68 (s, 1H), 7.86-7.75 (m, 1H), 7.26 (s, 1H), 4.78 (s, 2H), 3.45 (s, 1H).

Step 4: 2-(bromomethyl)-5-ethynylpyridine (5-Ethynylpyridin-2-yl)methanol (40 mg, 0.30 mmol) was dissolved in DCM (5 mL) at 0° C., and PBr$_3$ (0.16 g, 0.59 mmol) was slowly added. The mixture was reacted with stirring at low temperature for 2 h. The reaction was stopped, and quenched with water. The resulting mixture was extracted with DCM (10 mL×3), washed with water (10 mL), dried over anhydrous sodium sulfate, and filtered. The mother liquor was concentrated in vacuo to give brown viscous liquid (53 mg) which was directly used for the next reaction without further purification. LC-MS: m/z=196.1 [M+H]$^+$.

Step 5: 4-(6-(4-((5-ethynylpyridin-2-yl)methyl)pyrazol-1-yl)pyridin-3-yl)-6-(1-methyl-1H-pyrazoline-4-yl)pyrazoline[1,5-a]pyridine-3-carbonitrile 6-(1-Methyl-1H-pyrazol-4-yl)-4-(6-(piperazin-1-yl)pyridine-3-pyridine)pyrazole[1,5-a]pyridine-3-cyano dihydrochloride (see synthesis of intermediate 2, 16 mg, 0.03 mmol)

was dissolved in DMF (5 mL)), and K$_2$CO$_3$ (24 mg, 0.17 mmol) was added. 2-(Bromomethyl)-5-ethynylpyridine (21 mg, 0.11 mmol) was added slowly, and the mixture was stirred for reaction at room temperature for 3 h. The reaction was stopped. The mixture was added with ice water (10 mL), extracted with EA (10 mL×3), washed with water (10 mL), dried over anhydrous sodium sulfate, filtered, and then concentrated in vacuo. The residue was purified by silica gel column chromatography (eluent DCM/CH$_3$OH=50/1-20/1) to give a light yellow solid 10 mg as the target product (the yield was 57.22%). LC-MS: m/z=500.1[M+H]$^+$. Rf=0.31 (DCM/CH$_3$OH=30/1). $^1$H NMR (400 MHz, CDCl$_3$) δ 8.72 (s, 1H), 8.65 (d, J=1.3 Hz, 1H), 8.38 (d, J=2.3 Hz, 1H), 8.28 (s, 1H), 7.81 (d, J=5.8 Hz, 2H), 7.77 (dd, J=8.8, 2.5 Hz, 1H), 7.70 (s, 1H), 7.54 (s, 1H), 7.41 (d, J=1.3 Hz, 1H), 6.80 (d, J=8.9 Hz, 1H), 4.01 (s, 3H), 3.81 (s, 2H), 3.77 (s, 4H), 3.24 (s, 1H), 2.72 (s, 4H). HPLC: 95.97%.

Example 226: 4-[6-[4-[(6-ethynyl-3-pyridyl)methyl] piperazin-1-yl]-3-pyridyl]-6-(1-methylpyrazol-4-yl) pyrazolo[1,5-a]pyridine-3-carbonitrile

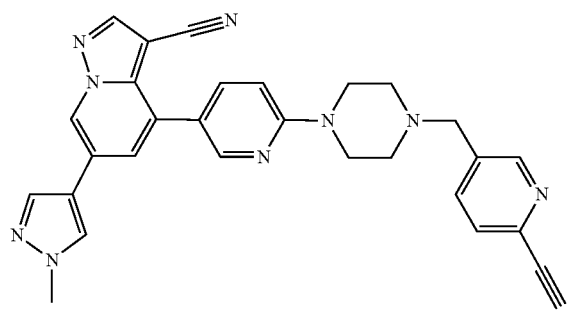

(226)

Step 1: 6-(2-trimethylsilylethynyl)pyridin-3-carbaldehyde

To a 25 mL two-necked flask were sequentially added 6-bromopyridine-3-carbaldehyde (1000 mg, 5.376 mmol), PdCl$_2$(PPh$_3$)$_2$ (151 mg, 0.215 mmol) and CuI (52 mg, 0.273 mmol) at room temperature. The reaction mixture was degassed and refilled with nitrogen. Triethylamine (8.1 mL, 58 mmol) and ethynyl (trimethyl)silane (1.52 mL, 10.8 mmol) were added to the mixture and a black turbid liquid was obtained. The resulting mixture was reacted overnight. TLC showed the reaction was completed. The mixture was concentrated in vacuo, and then purified by silica gel column chromatography (eluent PE:EA=10:1-8:1) to give a yellow-white product 0.66 g (the yield was 60%), which was the target product. LC-MS (ES-API): m/z=204.2[M+H]$^+$.

Step 2: 6-ethynylpyridine-3-carbaldehyde

To a 25 mL single-necked flask were sequentially added 6-(2-trimethylsilylethynyl)pyridine-3-carbaldehyde (660 mg, 3.246 mmol), K$_2$CO$_3$ (897 mg, 6.490 mmol) and MeOH (8.12 mL). The mixture was stirred to react at room temperature. TLC showed the reaction was completed. The mixture was quenched with saturated ammonium chloride (10 mL). Most of the methanol was removed under reduced pressure. The resulting turbid liquid was extracted with EA (20 mL×2). The organic phase was washed with saturated brine (10 mL×2), dried over anhydrous sodium sulfate, filtered, and concentrated in vacuo. The mixture was purified by silica gel column chromatography (eluent PE:EA=10:1-4:1) to give a yellow-white product 0.240 g (the yield was 56.4%), which was the target product. LC-MS (ES-API): m/z=132.1 [M+H]$^+$.

Step 3: 4-[6-[4-[(6-ethynyl-3-pyridyl)methyl]piperazin-1-yl]-3-pyridyl]-6-(1-methylpyrazol-4-yl) pyrazolo[1,5-a]pyridine-3-carbonitrile To a 5 mL single-necked flask were added 6-(1-methyl pyrazol-4-yl)-4-(6-piperazin-1-yl-3-pyridyl)pyrazolo[1,5-a] pyridine-3-carbonitrile dihydrochloride (see synthesis of intermediate 2, 15 mg, 0.033 mmol), 6-ethynylpyridine-3-carbaldehyde (10 mg, 0.076 mmol), STAB (34 mg, 0.156 mmol) and DCE (2 mL). The mixture was stirred to react at room temperature overnight. TLC showed the reaction was completed. The reaction solution was directly concentrated in vacuo, and then purified by silica gel column chromatography (eluent DCM-DCM:MeOH=20:1) to give a pale yellow solid 0.005 g (the yield was 30%), which was the target product. LC-MS (ES-API): m/z=500.2[M+H]$^+$. $^1$H NMR (400 MHz, CDCl$_3$) δ 8.63 (d, J=1.3 Hz, 1H), 8.57 (s, 1H), 8.36 (d, J=2.4 Hz, 1H), 8.26 (s, 1H), 7.78 (s, 1H), 7.73 (td, J=9.1, 2.1 Hz, 2H), 7.68 (s, 1H), 7.48 (d, J=8.0 Hz, 1H), 7.39 (d, J=1.3 Hz, 1H), 6.77 (d, J=8.8 Hz, 1H), 3.99 (s, 3H), 3.69-3.64 (m, 4H), 3.59 (s, 2H), 3.15 (s, 1H), 2.61-2.54 (m, 4H). HPLC: 92.94%.

Example 227: 4-(6-(6-((6-ethynyl-5-fluoropyridin-3-yl)methyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile

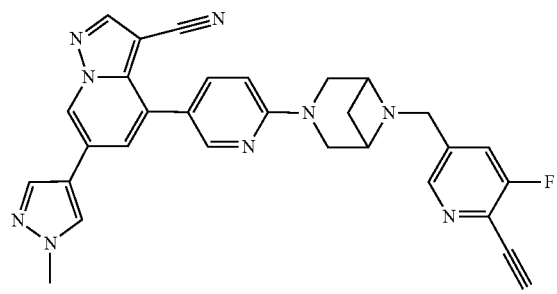

(227)

Step 1: 6-bromo-5-fluoropyridin-3-yl)methanol

To a 25 mL single-necked flask was added 2-bromo-5-(bromomethyl)-3-fluoropyridine (300 mg, 1.1 mmol), which was dissolved by adding 1,4-dioxane (3.1 mL), and a sodium hydroxide solution (3.1 mL, 5.6 mmol, 1.8 mol/L) was added. The mixture was refluxed at 100° C. The completion of reaction was monitored by TLC. The reaction solution was cooled to room temperature, and was added with 1 N hydrochloric acid with stirring to adjust pH to 5. The resulting mixture was extracted with EA (20 mL×2), and the organic phases were combined, washed with water (10 mL×2) and saturated saline (10 mL). Then the organic phases were dried over anhydrous sodium sulfate and filtered. The filtrate was concentrated in vacuo, and then purified by silica gel column chromatography (eluent EA:PE=1:8-1:5) to give a light yellow solid 90 mg as the desired product.

Step 2: (5-fluoro-6-((trimethylsilyl)ethynyl)pyridin-3-yl)methanol

To a two-necked flask were added (6-bromo-5-fluoropyridin-3-yl)methanol (40 mg, 0.19 mmol), CuI (8 mg, 0.042 mmol), PdCl$_2$(PPh$_3$)$_2$ (14 mg, 0.020 mmol), 2 mL of THF and 2 mL of TEA under nitrogen, and ethynyl (trimethyl) silane (29 mg, 0.29 mmol) was added with stirring. The reaction mixture was transferred to 70° C. to stir for reaction. After the completion of reaction was monitored by TLC, the reaction mixture was filtered by suction through a celite pad. The filter cake was washed with a small amount of EA, and the filtrate was dried over anhydrous sodium sulfate and filtered. The mother liquor was concentrated in vacuo, and then purified by silica gel column chromatography (eluent EA:PE=1:5-1:2) to give a brown solid 36 mg as the desired product.

Step 3: 5-(bromomethyl)-3-fluoro-2-((trimethylsilyl)ethynyl)pyridine

To a single-necked flask was added (5-fluoro-6-((trimethylsilyl)ethynyl)pyridin-3-yl)methanol (30 mg, 0.13 mmol), which was dissolved by adding 2 mL of DCM. Then PBr$_3$ (0.02 mL, 0.2 mmol) was added dropwise with stirring. After the end of addition, the mixture was continued stirring at this temperature. After the completion of reaction was monitored by TLC, the reaction mixture was added with saturated sodium bicarbonate with stirring to adjust the pH of the aqueous phase to 8. The resulting mixture was diluted with DCM (10 mL), and the organic phase was separated, washed with water (5 mL), dried over anhydrous sodium sulfate, concentrated in vacuo to remove most of the DCM, then was directly used for the next reaction, which was calculated according to the theoretical yield.

Step 4: 4-(6-(6-((6-ethynyl-5-fluoropyridin-3-yl)methyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile At room temperature, to a single-necked flask were added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and potassium carbonate (23 mg, 0.16 mmol), which were dissolved by adding 2 mL of DMF. 5-(Bromomethyl)-3-fluoro-2-((trimethylsilyl)ethynyl)pyridine (14 mg, 0.049 mmol) dissolved in DCM was added with stirring. After the end of addition, the mixture was reacted continuously at this temperature. After the reaction was completed, the reaction mixture was poured into ice water (10 mL) and extracted with EA (30 mL×2). The organic phases were washed with water (20 mL×3) and saturated saline (20 mL), dried over anhydrous sodium sulfate and filtered. The mother liquor was concentrated in vacuo, and then purified by silica gel column chromatography (eluent DCM:MeOH=80:1-20:1) to give a pale yellow solid 6 mg. The pale yellow solid was dissolved in methanol (5 mL), and 20 mg of potassium carbonate was added with stirring. The mixture was stirred at room temperature for 2 h. The reaction mixture was directly concentrated in vacuo, and then purified by silica gel column chromatography (eluent DCM:MeOH=80:1-20:1) to give a pale yellow solid 4 mg, which was the target product. LC-MS: m/z=526.00 [M+H]$^+$. $^1$H NMR (400 MHz, CDCl$_3$) δ 8.65 (s, 1H), 8.44 (s, 1H), 8.39 (s, 1H), 8.28 (s, 1H), 7.82 (d, J=9.6 Hz, 1H), 7.80 (s, 1H), 7.69 (s, 1H), 7.57 (d, J=9.4 Hz, 1H), 7.42 (s, 1H), 6.71 (d, J=8.6 Hz, 1H), 4.00 (s, 3H), 3.82-3.78 (m, 4H), 3.69 (s, 2H), 3.66-3.61 (m, 2H), 3.41 (s, 1H), 2.76-2.71 (m, 1H), 1.71-1.67 (m, 1H). HPLC: 94.03%.

Example 228: 4-[6-[6-[(4-ethynyl-3-fluoro-phenyl)methyl]-3,6-diazabicyclo[3.1.1]heptan-3-yl]-3-pyridinyl]-6-(1-methylpyrazol-4-yl)pyrazolo[1,5-a]pyridine-3-carbonitrile

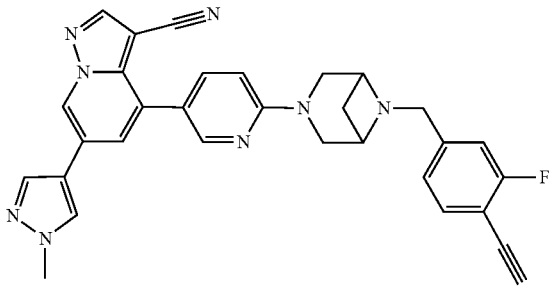

(228)

Step 1: (3-fluoro-4-iodo-phenyl)methanol

To a 25 mL two-necked flask was added LiAlH$_4$ (295 mg, 7.539 mmol). The flask was degassed and refilled with nitrogen. Anhydrous THF (10 mL) was added to dissolve the solid at 0° C. 3-Fluoro-4-iodo-benzoic acid (1000 mg, 3.759 mmol) was added in portions with continuously filling with nitrogen. After the end of addition, the mixture was kept reacting for 30 minutes at 0° C., and then was reacted with stirring at room temperature. TLC showed the reaction was completed. To the resulting mixture was added 15 mL of water to quench the reaction in an ice bath, then the mixture was extracted with EA (40 mL×3). The organic phases were combined, washed with saturated saline (40 mL), dried over anhydrous sodium sulfate, filtered, and concentrated in vacuo, then purified by silica gel column chromatography (eluent PE/EA=30:1-8:1) to give yellow oil 0.54 g (yield: 57%) as the target product. $^1$H NMR (400 MHz, CDCl$_3$) δ 7.69 (dd, J=8.0, 6.5 Hz, 1H), 7.07 (dd, J=5.6, 4.8 Hz, 1H), 6.88 (d, J=8.1 Hz, 1H), 4.63 (s, 2H), 2.25 (s, 1H).

Step 2: 3-fluoro-4-iodo-benzaldehyde

To a 25 mL single-necked flask were added (3-fluoro-4-iodo-phenyl)methanol (540 mg, 2.143 mmol), NaHCO$_3$ (0.9 g, 10 mmol) and Dess Martin oxidant (1.2 g, 2.8 mmol), which were dissolved by adding DCM (15 mL). The mixture was stirred for reaction at room temperature. TLC showed the reaction was completed. To the resulting mixture was added 10 mL of saturated sodium thiosulfate solution to quench the reaction. After the mixture was partitioned, the organic phase was separated and the aqueous phase was extracted with DCM (20 mL×2). The organic phases were combined, washed with saturated saline (15 mL), dried over anhydrous sodium sulfate, filtered, and concentrated in vacuo, then purified by silica gel column chromatography (eluent PE/EA=10:1-2:1) to give a yellow-white solid 0.45 g (yield: 84%) as the target product. ¹H NMR (400 MHz, CDCl₃) δ 9.95 (d, J=1.6 Hz, 1H), 7.97 (dd, J=8.0, 6.0 Hz, 1H), 7.52 (dd, J=7.6, 1.6 Hz, 1H), 7.41 (dd, J=8.0, 1.7 Hz, 1H).

Step 3: 3-fluoro-4-(2-trimethylsiloxy)benzaldehyde

To a 25 mL two-necked flask were added 3-fluoro-4-iodobenzaldehyde (450 mg, 1.80 mmol), CuI (35 mg, 0.184 mmol) and PdCl₂(PPh₃)₂ (64 mg, 0.091 mmol). The reaction mixture was degassed and refilled with nitrogen. Then anhydrous THF (4.5 mL) and triethylamine (4.5 mL, 32 mmol) were added. After the dissolution, ethynyl (trimethyl) silane (0.51 mL, 3.6 mmol) was added. The mixture was stirred for reaction at room temperature. TLC showed the reaction was completed. The resulting mixture was filtered by suction. The filter cake was washed with 120 mL of EA several times, and the filtrate with washed with 30 mL of saturated saline, dried over anhydrous sodium sulfate, filtered, and concentrated in vacuo, then purified by silica gel column chromatography (eluent PE/EA=100:1-30:1) to give brownish yellow oil 0.195 g (yield: 49.2%) as the target product. ¹H NMR (400 MHz, CDCl₃) δ 9.95 (d, J=1.7 Hz, 1H), 7.61-7.59 (m, 2H), 7.55 (d, J=9.1 Hz, 1H), 0.27 (s, 9H).

Step 4: 4-ethynyl-3-fluoro-benzaldehyde

To a 10 mL single-necked flask were sequentially added 3-fluoro-4-(2-trimethylsiloxy)benzaldehyde (195 mg, 0.885 mmol), K₂CO₃ (245 mg, 1.773 mmol) and MeOH (2.5 mL). The mixture was stirred to react at room temperature. TLC showed the reaction was completed. To the mixture was added water (2 mL), then the mixture extracted with EA (10 mL×3), washed with saturated saline (8 mL), dried over anhydrous sodium sulfate, filtered, and concentrated in vacuo. The mixture was purified by silica gel column chromatography (eluent: pure PE-PE:EA (50:1)) to give a white solid 0.071 g (the yield was 54%), which was the target product. ¹H NMR (400 MHz, CDCl₃) δ 9.98 (d, 7=1.7 Hz, 1H), 7.68-7.62 (m, 2H), 7.59 (d, J=9.2 Hz, 1H), 3.51 (s, 1H).

Step 5: 4-[6-[6-[(4-ethynyl-3-fluoro-phenyl)methyl]-3,6-diazabicyclo[3.1.1]heptan-3-yl]-3-pyridinyl]-6-(1-methyl pyrazol-4-yl)pyrazolo[1,5-a]pyridine-3-carbonitrile To a 5 mL single-necked flask were sequentially added 4-[6-(3,6-diazabicyclo[3.1.1]heptan-3-yl)-3-pyridyl]-6-(1-methylpyrazol-4-yl)pyrazolo[1,5-a]pyridine-3-carbonitrile dihydrochloride (see synthesis of intermediate 3, 20 mg, 0.043 mmol) and 4-ethynyl-3-fluoro-benzaldehyde (25 mg, 0.169 mmol), which were dissolved by adding DCE (2 mL). Then a drop of glacial acetic acid was added. The mixture was stirred for reaction at room temperature for 30 min, then sodium triacetoxyborohydride (37 mg, 0.169 mmol) was added and the mixture was stirred for reaction at room temperature. TLC showed the reaction was completed. The reaction solution was directly concentrated in vacuo, and then purified by silica gel column chromatography (eluent DCM/MeOH=20/0-20/1) to give a white solid 0.008 g (the yield was 40%), which was the target product. LC-MS (ES-API): m/z=529.2 [M+H]⁺. ¹H NMR (400 MHz, CDCl₃) δ 8.68 (s, 1H), 8.48 (s, 1H), 8.28 (s, 1H), 7.81 (s, 1H), 7.71 (s, 1H), 7.54 (dd, J=11.9, 5.6 Hz, 2H), 7.44 (s, 1H), 7.35 (s, 1H), 7.08 (d, J=8.3 Hz, 1H), 6.76 (d, J=8.5 Hz, 1H), 4.58 (s, 1H), 4.11 (s, 6H), 4.00 (s, 3H), 3.65 (s, 1H), 3.36 (s, 1H), 2.28 (dt, J=49.7, 7.5 Hz, 1H), 2.03 (s, 1H). HPLC: 94.64%.

Example 229: 4-(6-(2-(3-ethynyl)-2,8-diazaspiro[4.5]dec-8-yl)pyridin-3-yl)-6-(1-methyl-1H-pyrazol-4-yl)pyrazolo[1,5-a]pyridine-3-carbonitrile

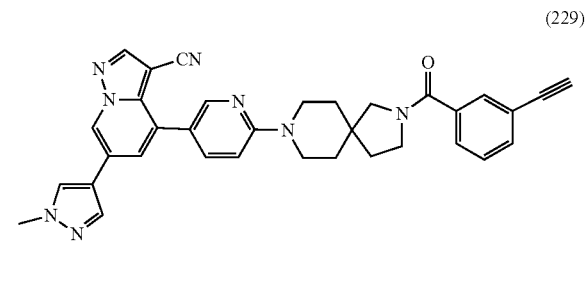 [SMILES: C#Cc1cccc(C(=O)N2CCC3(CCN(c4ccc(-c5cc(-c6cnn(C)c6)cn6ncc(C#N)c56)cn4)CC3)C2)c1]

(229)

Step 1: Step 1: tert-butyl 2-(3-ethynylbenzoyl)-2,8-diazaspiro[4.5]decane-8-carboxylate To a 25 mL single-necked flask were added tert-butyl 2,8-diazaspiro[4.5]decane-8-carboxylate (500 mg, 2.081 mmol), DCM (10 mL), 3-ethynylbenzoic acid (0.365 g, 2.50 mmol), EDCI (0.6 g, 3 mmol) and DMAP (0.025 g, 0.20 mmol). The mixture was stirred and reacted at room temperature overnight. Dichloromethane (30 mL) and water (20 mL) were added, and the aqueous phase was separated and extracted with DCM (30 mL). The organic phases were combined, washed with 15 mL of saturated brine, dried over anhydrous sodium sulfate, concentrated in vacuo, and then purified by silica gel column chromatography (eluent PE/EA=80/1-2/1) to give a white foam solid 295 mg as the target product (yield: 38.47%). ¹H NMR (400 MHz, CDCl₃) δ 7.61 (s, 1H), 7.50 (dd, J=16.7, 7.1 Hz, 2H), 7.36 (s, 1H), 3.78-3.12 (m, 8H), 3.09 (s, 1H), 1.86 (d, J=4.0 Hz, 2H), 1.57 (d, J=16.4 Hz, 4H), 1.44 (d, J=8.4 Hz, 5H), 1.39 (s, 4H). ¹H NMR showed two sets of peaks, which were chiral compounds.

Step 2: (3-ethynylphenyl) (2,8-diazaspiro[4.5]dec-2-yl)methanone 2,2,2-trifluoroacetate To a 50 mL single-necked flask was added tert-butyl 2-(3-ethynylbenzoyl)-2,8-diazaspiro[4.5]decane-8-carboxylate (1.22 g, 3.31 mmol), then DCM (13 mL) and TFA (4 mL) were added. The mixture was stirred at room temperature overnight. The reaction solution was directly concentrated in vacuo to give colorless transparent oily liquid as the target compound (yield: 100%), which was directly used for the next reaction without further purification.

Step 3: 4-(6-(2-(3-ethynyl)-2,8-diazaspiro[4.5]dec-8-yl)pyridin-3-yl)-6-(1-methyl-1H-pyrazol-4-yl) pyrazolo[1,5-a]pyridine-3-carbonitrile To a 2-5 mL microwave tube were added (3-ethynylphenyl) (2,8-diazaspiro[4.5]dec-2-yl)methanone 2,2,2-trifluoroacetate (90 mg, 0.2354 mmol), 4-(6-fluoropyridin-3-yl)-6-(1-methyl-1H-pyrazol-4-yl)pyrazolo[1,5-a]pyridine-3-carbonitrile (see synthesis of intermediate 1, 30 mg, 0.094 mmol), DMSO (1.5 mL), and N,N-diisopropylethylamine (0.06 mL, 0.4 mmol). The mixture was reacted under microwave at 135° C. for 7 h. The reaction solution was added with EA (30 mL) and water (15 mL), and the aqueous phase was extracted with EA (25 mL×2). The organic phases were combined, washed with 15 mL of saturated brine. The organic phases were separated, dried over anhydrous sodium sulfate, filtered, and then purified by silica gel column chromatography (eluent PE/EA=5/1-1/1.5) to give a yellow solid 22 mg as the target product (yield 41.19%). LC-MS (ESI): m/z=567.4 [M+H]⁺; ¹H NMR (400 MHz, CDCl₃) δ 8.66-8.61 (m, 1H), 8.33-8.28 (m, 1H), 8.27-8.22 (m, 1H), 7.82-7.78 (m, 1H), 7.72-7.66 (m, 2H), 7.56-7.51 (m, 1H), 7.43-7.35 (m, 3H), 7.32-7.28 (m, 1H), 6.84-6.67 (m, 1H), 3.99 (d, J=5.9 Hz, 3H), 3.76-3.58 (m, 5H), 3.57-3.37 (m, 4H), 1.80-1.65 (m, 6H). ¹H NMR showed two sets of peaks, which were chiral compounds. HPLC: 94.11%.

Example 230: 4-(6-(6-(4-ethynyl)-3,6-diazabicyclo [3.1.1]heptan-3-yl)pyridin-3-yl)-6-(1-methyl-1H-pyrazol-4-yl)pyrazolo[1,5-a]pyridine-3-carbonitrile

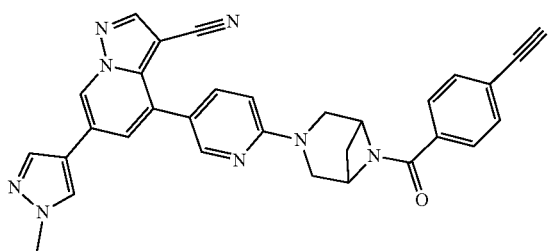

(230)

Under nitrogen, to a 10 mL double-necked flask were added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 20 mg, 0.0426 mmol) and 4-ethynylbenzoic acid (10 mg, 0.0684 mmol), which were dissolved by adding DCM (2 mL). Then DMAP (2 mg, 0.0163 mmol) and EDCI (16 mg, 0.0834 mmol) were added. The mixture was stirred at room temperature overnight. The reaction mixture was added with DCM (30 mL) and water (10 mL). The organic phase was separated, washed with water (10 mL), dried over anhydrous sodium sulfate, filtered, and the filtrated was concentrated in vacuo, and then the residue was purified by silica gel column chromatography (DCM/MeOH=100/0-50/1) to give a white solid 5.3 mg as the desired product. LC-MS (ESI): m/z=525.0[M+1]⁺. ¹H NMR (400 MHz, CDCl₃) δ 8.64 (s, 1H), 8.36 (d, J=2.1 Hz, 1H), 8.26 (s, 1H), 7.79 (s, 1H), 7.68 (s, 1H), 7.61 (d, J=8.2 Hz, 2H), 7.53 (d, J=8.2 Hz, 2H), 7.39 (d, J=1.0 Hz, 1H), 7.35 (d, J=2.2 Hz, 1H), 6.65 (d, J=8.6 Hz, 1H), 4.82-4.69 (m, 2H), 4.39-4.25 (m, 2H), 3.99 (s, 3H), 3.70-3.61 (m, 2H), 3.19 (s, 1H), 2.96-2.89 (m, 1H), 2.24-2.19 (m, 1H). HPLC: 95.96%.

Example 231: 4-(6-(6-(3-ethynyl)-3,6-diazabicyclo [3.1.1]heptan-3-yl)pyridin-3-yl)-6-(1-methyl-1H-pyrazol-4-yl)pyrazolo[1,5-a]pyridine-3-carbonitrile

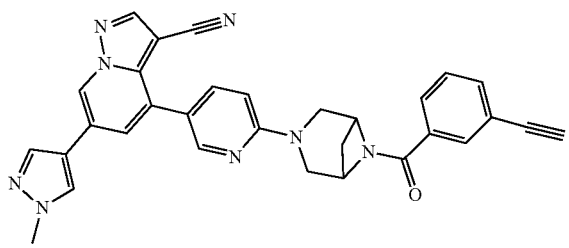

(231)

Under nitrogen, to a 5 mL double-necked flask were added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 20 mg, 0.0426 mmol) and 3-ethynylbenzoic acid (10 mg, 0.0684 mmol), which were dissolved by adding DCM (2 mL). Then DMAP (2 mg, 0.0163 mmol) and EDCI (16 mg, 0.0834 mmol) were added. The mixture was stirred at room temperature overnight. To the reaction mixture were added DCM (30 mL) and water (10 mL). The organic phase was separated, washed with water (10 mL), dried over anhydrous sodium sulfate, filtered, and the filtrate was concentrated in vacuo, and then the residue was purified by silica gel column chromatography (DCM/MeOH=100/0-50/1) to give a white solid 5.5 mg as the desired product (yield: 25%). LC-MS (ESI): m/z=525.0[M+1]⁺. ¹H NMR (400 MHz, CDCl₃) 8.64 (s, 1H), 8.37 (d, 7=1.8 Hz, 1H), 8.26 (s, 1H), 7.82-7.74 (m, 3H), 7.68 (s, 1H), 7.66-7.58 (m, 2H), 7.43-7.37 (m, 2H), 6.66 (d, J=8.6 Hz, 1H), 4.79-4.69 (m, 2H), 4.39-4.26 (m, 2H), 3.99 (s, 3H), 3.72-3.63 (m, 2H), 3.11 (s, 1H), 2.96-2.90 (m, 1H), 2.25-2.20 (m, 1H). HPLC: 95.96%.

Example 232: 4-(6-(6-(4-ethynyl-3-fluorobenzoyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile

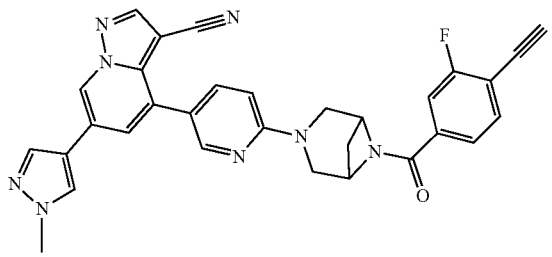

(232)

Step 1: methyl 3-fluoro-4-((trimethylsilyl)ethynyl)benzoate

To a three-neck flask were added methyl 3-fluoro-4-iodobenzoate (500 mg, 1.7855 mmol), CuI (40 mg, 0.21 mmol), PdCl₂(PPh₃)₂ (37 mg, 0.0527 mmol), TEA (5 mL)

and ethynyl (trimethyl) silane (210 mg, 2.138 mmol) under nitrogen. The mixture was reacted overnight at room temperature. The reaction mixture was filtered by suction with celite, and the filter cake was washed with EA (20 mL). The mother liquid was concentrated in vacuo, and then the residue was purified by silica gel column chromatography (eluent EA:PE=0:500-1:100) to give pale yellow transparent liquid 442 mg as the desired product (the yield was 98.9%). $^1$H NMR (400 MHz, CDCl$_3$) δ 7.79-7.66 (m, 2H), 7.51 (t, J=7.4 Hz, 1H), 3.92 (s, 3H), 0.27 (s, 9H).

Step 2: 4-ethynyl-3-fluorobenzoic acid

Methyl 3-fluoro-4-((trimethylsilyl)ethynyl)benzoate (440 mg, 1.758 mmol) was dissolved in methanol (9 mL) and water (0.45 mL) in a double-necked flask, and then potassium carbonate (500 mg, 3.6177 mmol) was added in one portion. The mixture was reacted with stirring at room temperature overnight. The reaction mixture was added with water (30 mL) and EA (20 mL). The aqueous phase was separated and adjusted with IN diluted hydrochloric acid to pH=1, then extracted with EA (50 mL×3). The organic phases were combined and washed with saturated brine (30 mL). The combined organic phases were dried over anhydrous sodium sulfate and concentrated in vacuo to give a pale pink solid 194 mg as the target product (yield: 67.25%). $^1$H NMR (400 MHz, DMSO-d$_6$) δ 13.49 (s, 1H), 7.75 (dd, J=12.2, 9.0 Hz, 2H), 7.69 (t, J=7.5 Hz, 1H), 4.75 (s, 1H).

Step 3: 4-(6-(6-(4-ethynyl-3-fluorobenzoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile Under nitrogen, to a 25 mL double-necked flask were added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and 4-ethynyl-3-fluorobenzoic acid (8 mg, 0.049 mmol), which were dissolved by adding DCM (5 mL). Then DMAP (2 mg, 0.0164 mmol) and EDCI (13 mg, 0.0678 mmol) were added. The mixture was reacted at room temperature for 5 h. The reaction mixture was added with DCM (30 mL) and water (10 mL). The organic phase was separated, washed with water (30 mL), dried over anhydrous sodium sulfate and filtered. The mother liquid was concentrated in vacuo, and then purified by silica gel column chromatography (eluent MeOH:DCM=1:50-1:20) to give a pale yellow solid 6 mg as the desired product (yield 34.60%). Rf=0.3 (MeOH:DCM=1:30). LC-MS: m/z=543.15[M+H]$^+$. $^1$H NMR (400 MHz, CDCl$_3$) δ 8.64 (s, 1H), 8.37 (d, J=2.1 Hz, 1H), 8.26 (s, 1H), 7.80-7.76 (m, 2H), 7.68 (s, 1H), 7.55-7.51 (m, 1H), 7.39 (t, J=6.3 Hz, 3H), 6.66 (d, J=8.7 Hz, 1H), 4.74 (d, J=19.9 Hz, 2H), 4.31 (s, 1H), 3.99 (s, 3H), 3.81-3.69 (m, 3H), 3.41 (s, 1H), 2.94 (dd, J=14.4, 6.4 Hz, 1H), 1.79 (d, J=8.7 Hz, 1H). HPLC: 98.65%.

Example 233: 4-(6-(6-(3-ethynyl-4-fluorobenzoyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile

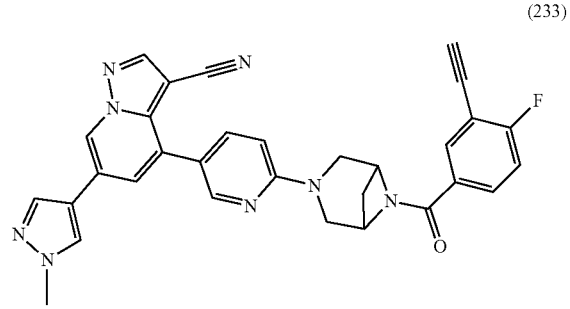 [SMILES: C#Cc1cc(C(=O)N2C3CC2CN(c2ccc(-c4cc(-c5cnn(C)c5)cn5ncc(C#N)c45)cn2)C3)ccc1F]

(233)

Step 1: methyl 4-fluoro-3-((trimethylsilyl)ethynyl)benzoate

To a three-necked flask were added methyl 3-bromo-4-fluorobenzoate (500 mg, 2.1456 mmol), CuI (49 mg, 0.25729 mmol), PdCl$_2$(PPh$_3$)$_2$ (45 mg, 0.06411 mmol), TEA (5 mL) and ethynyl (trimethyl) silane (260 mg, 2.647 mmol) under nitrogen. The mixture was reacted overnight at 80° C. The reaction solution was quenched by the addition of water (20 mL), then EA (50 mL) was added. The resulting mixture was filtered by suction through a celite pad. The organic phase was separated from the filtrate. The aqueous phase was extracted with EA (50 mL×2). The organic phases were combined, washed with 30 mL of saturated brine, dried over anhydrous sodium sulfate, concentrated in vacuo, and then purified by silica gel column chromatography (eluent EA:PE=1:500-1:50) to give pale yellow liquid 352 mg as the target product (yield: 65.5%). $^1$H NMR (400 MHz, CDCl$_3$) δ 8.05 (d, J=1.3 Hz, 1H), 7.85 (dd, J=8.1, 1.6 Hz, 1H), 7.55 (d, J=8.1 Hz, 1H), 3.92 (s, 3H), 0.28 (s, 9H).

Step 2: 3-ethynyl-4-fluorobenzoic acid

Methyl 4-fluoro-3-((trimethylsilyl)ethynyl)benzoate (350 mg, 1.9645 mmol) was dissolved in methanol (7 mL) and water (0.35 mL) in a double-necked flask, and then potassium carbonate (400 mg, 2.8941 mmol) was added with stirring in one portion. The mixture was stirred to react at room temperature overnight. The reaction mixture was added with water (30 mL) and EA (20 mL). The aqueous phase was separated and adjusted with IN diluted hydrochloric acid to pH=1, then extracted with EA (50 mL×3). The organic phases were combined and washed with saturated brine (30 mL). The combined organic phases were dried over anhydrous sodium sulfate and concentrated in vacuo to give a white solid 219 mg as the target product (yield: 67.9%). $^1$H NMR (400 MHz, CDCl$_3$) δ 8.26 (dd, J=6.7, 2.0 Hz, 1H), 8.13-8.06 (m, 1H), 7.18 (t, J=8.7 Hz, 1H), 3.36 (s, 1H).

Step 3: 4-(6-(6-(3-ethynyl-4-fluorobenzoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile Under nitrogen, to a 25 mL double-necked flask were added 4-(6-(3,6-diazabicyclo[3.1.1]heptane-3-yl)pyridin-3- yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and 3-ethynyl-4-fluorobenzoic acid (8 mg, 0.049 mmol), which were dissolved by adding DCM (5 mL). Then DMAP (2 mg, 0.0164 mmol) and EDCI (13 mg, 0.0678 mmol) were added. The mixture was stirred at room temperature for 5 h. The reaction mixture was added with DCM (30 mL) and water (10 mL). The organic phase was separated, washed with water (10 mL), dried over anhydrous sodium sulfate and filtered. The filtrate was concentrated in vacuo, and then purified by silica gel column chromatography (eluent MeOH:DCM=1:50-1:20) to give an off-white solid 5 mg as the desired product (yield: 28.84%). Rf=0.3 (MeOH:DCM=1:30. LC-MS: m/z=543.15[M+H]$^+$. $^1$H NMR (400 MHz, CDCl$_3$) δ 8.66 (s, 1H), 8.42 (d, J=1.8 Hz, 1H), 8.27 (s, 1H), 7.85-7.79 (m, 3H), 7.70-7.64 (m, 2H), 7.41 (s, 1H), 7.15 (t, J=8.7 Hz, 1H), 6.72 (d, J=8.8 Hz, 1H), 4.76 (d, J=3.7 Hz, 2H), 4.43-4.28 (m, 1H), 3.99 (s, 3H), 3.86-3.72 (m, 3H), 3.35 (s, 1H), 2.98-2.93 (m, 1H), 2.06-2.01 (m, 1H). HPLC: 92.39%.

Example 234: 4-(6-(4-(4-ethynyl-2,6-difluorobenzoyl)piperazin-1-yl)pyridin-3-yl)-6-(1-methyl-1H-pyrazol-4-yl)pyrazolo[1,5-a]pyridine-3-carbonitrile

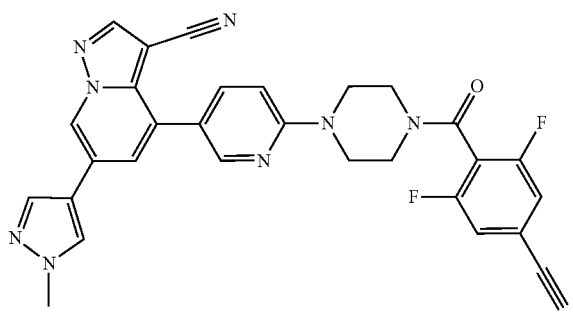

(234)

Step 1: methyl 2,6-difluoro-4-((trimethylsilyl)ethynyl)benzoate

To a three-necked flask were added methyl 4-bromo-2,6-difluorobenzoate (590 mg, 2.3504 mmol), CuI (53 mg, 0.27829 mmol) and PdCl$_2$(PPh$_3$)$_2$ (50 mg, 0.07124 mmol) under nitrogen, then TEA (6 mL) and ethynyl (trimethyl) silane (0.4 mL, 3 mmol) were added. The mixture was reacted overnight at 70° C. The reaction mixture was added with EA (30 mL), then the mixture was filtered by suction through a celite pad. The filtrate was concentrated in vacuo, and then purified by silica gel column chromatography (eluent EA:PE=1:500-1:50) to give pale yellow liquid 489 mg as the desired product (the yield was 77.54%). $^1$H NMR (400 MHz, CDCl$_3$) δ 7.02 (d, J=8.4 Hz, 2H), 3.94 (s, 3H), 0.25 (s, 9H).

Step 2: 4-ethynyl-2,6-difluorobenzoic acid

Methyl 2,6-difluoro-4-((trimethylsilyl)ethynyl)benzoate (480 mg, 1.789 mmol) was dissolved in methanol (10 mL) and water (0.5 mL) in a double-necked flask, and then NaOH (145 mg, 3.625 mmol) was added with stirring in one portion. The mixture was stirred to react at room temperature overnight. The reaction mixture was added with water (30 mL) and EA (20 mL). The aqueous phase was separated and adjusted with IN diluted hydrochloric acid to pH=1, then extracted with EA (50 mL×3). The organic phases were combined and washed with saturated brine (30 mL). The combined organic phases were dried over anhydrous sodium sulfate and concentrated in vacuo to give a light yellow solid 304 mg as the target product (yield: 93.3%).

Step 3: 4-(6-(4-(4-ethynyl-2,6-difluorobenzoyl)piperazin-1-yl)pyridin-3-yl)-6-(1-methyl-1H-pyrazol-4-yl)pyrazolo[1, 5-a]pyridine-3-carbonitrile To a 5 mL reaction flask were sequentially added 6-(1-methyl pyrazol-4-yl)-4-(6-piperazin-1-yl-3-pyridyl)pyrazolo[1,5-a]pyridine-3-carbonitrile dihydrochloride (see synthesis of intermediate 2, 20 mg, 0.043 mmol), 4-ethynyl-2, 6-difluoro-benzoic acid (10 mg, 0.055 mmol), DMAP (2 mg, 0.016 mmol), 1-(3-dimethylaminopropyl)-3-ethyldithioamide hydrochloride (16 mg, 0.083 mmol) and DCM (2 mL). The mixture was stirred at room temperature overnight. The reaction mixture was added with DCM (30 mL) and water (10 mL). The aqueous phase was extracted with DCM (20 mL×2). The combined organic layers were washed with saturated brine (10 mL), dried over anhydrous sodium sulfate and filtered. The filtrate was concentrated in vacuo, and the residue was purified by silica gel column chromatography (DCM:MeOH=0-60:1) to give a white solid 7 mg as the target product (the yield was 29.19%). Rf=0.5 (DCM/MeOH=10/1). LC-MS: m/z=549.2 [M+H]$^+$. $^1$H NMR (400 MHz, CDCl$_3$) 58.65 (s, 1H), 8.39 (d, J=2.3 Hz, 1H), 8.26 (s, 1H), 7.82-7.76 (m, 2H), 7.69 (s, 1H), 7.40 (s, 1H), 7.11 (d, J=7.4 Hz, 2H), 6.81 (d, J=8.8 Hz, 1H), 3.99 (s, 3H), 3.99-3.94 (m, 2H), 3.77 (m, 2H), 3.73-3.69 (m, 2H), 3.49-3.45 (m, 2H), 3.24 (s, 1H). HPLC: 94.68%.

Example 235: 4-(6-(6-(4-ethynyl-2,6-difluoro-benzoyl)-3,6-diazabicyclo[3.1.1]heptan-3-yl)-3-pyridin-6-(1-methyl-1H-pyrazol-4-yl)pyrazolo[1,5-a]pyridine-3-carbonitrile

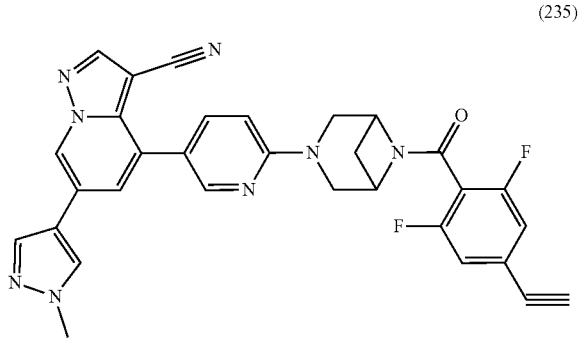 [SMILES: C#Cc1cc(F)c(C(=O)N2C3CC2CN(c2ccc(-c4cc(-c5cnn(C)c5)cn5ncc(C#N)c45)cn2)C3)c(F)c1]

(235)

Step 1: methyl 2,6-difluoro-4-((trimethylsilyl)ethynyl)benzoate

To a three-necked flask were added methyl 4-bromo-2,6-difluorobenzoate (590 mg, 2.3504 mmol), CuI (53 mg, 0.27829 mmol) and PdCl$_2$(PPh$_3$)$_2$ (50 mg, 0.07124 mmol) under nitrogen, then TEA (6 mL) and ethynyl (trimethyl) silane (0.4 mL, 3 mmol) were added. The mixture was reacted overnight at 70° C. TLC showed the reaction was completed. To the reaction mixture was added EA (30 mL), then the mixture was filtered by suction through a celite pad. The filtrate was concentrated in vacuo, and then purified by silica gel column chromatography (eluent EA:PE=1:500-1:50) to give pale yellow liquid 489 mg as the desired product (the yield was 77.54%). ¹H NMR (400 MHz, CDCl₃) δ 7.02 (d, J=8.4 Hz, 2H), 3.94 (s, 3H), 0.25 (s, 9H).

Step 2: 4-ethynyl-2,6-difluorobenzoic acid

Methyl 2,6-difluoro-4-((trimethylsilyl)ethynyl)benzoate (480 mg, 1.789 mmol) was dissolved in methanol (10 mL) and water (0.5 mL) in a double-necked flask, and then NaOH (145 mg, 3.625 mmol) was added with stirring in one portion. The mixture was stirred to react at room temperature overnight. The reaction mixture was added with water (30 mL) and EA (20 mL). The aqueous phase was separated and adjusted with IN diluted hydrochloric acid to pH=1, then extracted with EA (50 mL×3). The organic phases were combined and washed with saturated brine (30 mL). The combined organic phases were dried over anhydrous sodium sulfate and concentrated in vacuo to give a light yellow solid 304 mg as the target product (yield: 93.3%).

Step 3: 4-(6-(6-(4-ethynyl-2,6-difluoro-benzoyl)-3,6-diazabicyclo[3.1.1]heptan-3-yl]-3-pyridin-6-(1-methyl-1H-pyrazol-4-yl)pyrazolo[1,5-a]pyridine-3-carbonitrile To a 10 mL single-necked flask were sequentially added 4-[6-(3,6-diazabicyclo[3.1.1]heptan-3-yl)-3-pyridyl]-6-(1-methylpyrazol-4-yl)pyrazolo[1,5-a]pyridine-3-carbonitrile dihydrochloride (see synthesis of intermediate 3, 25 mg, 0.053 mmol), 4-ethynyl-2,6-difluorobenzoic acid (30 mg, 0.165 mmol), EDCI (51 mg, 0.266 mmol) and DMAP (1.3 mg, 0.011 mmol). Then DCM (3 mL) was added. The resulting mixture was reacted with stirring at room temperature overnight. TLC showed the reaction was completed. The reaction solution was added with DCM (30 mL) and water (15 mL), and the aqueous phase was separated and extracted with DCM (25 mL×2). The organic phases were combined, washed with 15 mL of saturated brine. The organic phases were separated, dried over anhydrous sodium sulfate, filtered, concentrated in vacuo, and then purified by silica gel column chromatography (eluent: pure DCM-DCM:MeOH (v:v=25:1) to give a pale yellow solid 11 mg as the target product (yield: 37%). LC-MS(ESI): m/z=561.2 [M+H]⁺. ¹H NMR (400 MHz, CDCl₃) δ 8.66 (s, 1H), 8.41 (d, J=2.1 Hz, 1H), 8.28 (s, 1H), 7.86-7.78 (m, 2H), 7.72 (s, 1H), 7.44 (s, 1H), 7.09 (d, J=7.5 Hz, 2H), 6.68 (d, J=8.7 Hz, 1H), 4.45-4.21 (m, 2H), 4.02 (s, 3H), 3.88-3.71 (m, 4H), 3.26 (s, 1H), 2.35 (d, J=8.0 Hz, 1H), 2.28-2.19 (m, 1H). HPLC: 91.46%.

Example 236: 4-(6-(4-(4-ethynyl-3-fluorobenzoyl)piperazin-1-yl)pyridin-3-yl)-6-(1-methyl-1H-pyrazol-4-yl)pyrazolo[1,5-a]pyridine-3-carbonitrile

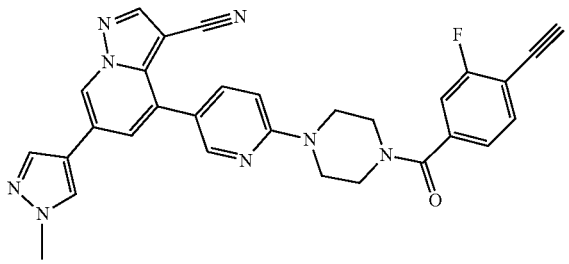

(236)

Step 1: methyl 3-fluoro-4-((trimethylsilyl)ethynyl)benzoate

To a three-necked flask were added methyl 3-fluoro-4-iodobenzoate (500 mg, 1.785 mmol), CuI (40 mg, 0.210 mmol) and PdCl₂(PPh₃)₂ (37 mg, 0.053 mmol) under nitrogen. Then TEA (5 mL) and ethynyl (trimethyl) silane (0.4 mL, 2.138 mmol) were added. The mixture was reacted at room temperature overnight. The reaction mixture was filtered through a celite pad, and the filter cake was washed with a proper amount of EA. The mother liquor was concentrated in vacuo, and then purified by silica gel column chromatography (eluent EA:PE=0:500-1:100) to give pale yellow transparent liquid 442 mg as the desired product (the yield was 98.9%). ¹H NMR (400 MHz, CDCl₃) δ 7.79-7.66 (m, 2H), 7.51 (t, J=7.4 Hz, 1H), 3.92 (s, 3H), 0.27 (s, 9H).

Step 2: 4-ethynyl-3-fluorobenzoic acid

Methyl 3-fluoro-4-((trimethylsilyl)ethynyl)benzoate (440 mg, 1.758 mmol) was dissolved in methanol (9 mL) and water (0.45 mL) in a double-necked flask, and then potassium carbonate (500 mg, 3.618 mmol) was added in one portion with stirring. The mixture was stirred to react at room temperature overnight. The reaction mixture was added with water (30 mL) and EA (20 mL). The aqueous phase was separated and adjusted with IN diluted hydrochloric acid to pH=1, then extracted with EA (50 mL×3). The organic phases were combined and washed with saturated brine (30 mL). The combined organic phases were dried over anhydrous sodium sulfate, filtered and concentrated in vacuo to give a pale pink solid 194 mg as the target product (yield: 67.25%). ¹H NMR (400 MHz, DMSO-d₆) δ 13.49 (s, 1H), 7.75 (dd, J=12.2, 9.0 Hz, 2H), 7.69 (t, J=7.5 Hz, 1H), 4.75 (s, 1H).

Step 3: 4-(6-(4-(4-ethynyl-3-fluorobenzoyl)piperazin-1-yl)pyridin-3-yl)-6-(1-methyl-1H-pyrazol-4-yl)pyrazolo[1,5-a]pyridine-3-carbonitrile Under nitrogen, to a 25 mL double-necked flask were added 6-(1-methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 20 mg, 0.044 mmol) and 4-ethynyl-3-fluorobenzoic acid (11 mg, 0.066 mmol), which were dissolved by adding DCM (3 mL). Then DMAP (3 mg, 0.025 mmol) and EDCI (17 mg, 0.088 mmol)

were added. The mixture was stirred at room temperature overnight. The resulting mixture was directly concentrated in vacuo, and then purified by silica gel column chromatography (eluent DCM/MeOH=100/1-100/3) to give a light yellow solid 8 mg, which was the target product (the yield was 34.48%). LC-MS: m/z=531.2 [M+H]$^+$; $^1$H NMR (400 MHz, CDCl$_3$) δ 8.65 (d, 1H), 8.38 (d, J=2.1 Hz, 1H), 8.26 (s, 1H), 7.81-7.75 (m, 2H), 7.69 (s, 1H), 7.56 (t, J=7.4 Hz, 1H), 7.40 (s, 1H), 7.22 (s, 1H), 7.20 (s, 1H), 6.81 (d, J=8.8 Hz, 1H), 3.99 (s, 3H), 3.94-3.53 (m, 8H), 3.39 (s, 1H). HPLC: 95.13%.

Example 237: 4-(6-(4-(5-ethynylpicolinoyl)piperazin-1-yl)pyridin-3-yl)-6-(1-methyl-1H-pyrazol-4-yl)pyrazolo[1,5-a]pyridine-3-carbonitrile

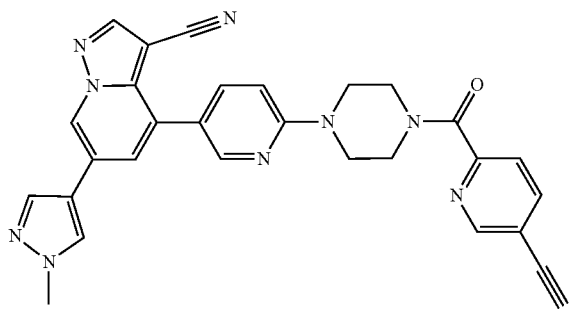

(237)

Step 1: methyl 5-((trimethylsilyl)ethynyl)picolinate

To a three-necked flask were added methyl 5-bromopyridinecarboxylate (500 mg, 2.3145 mmol), CuI (53 mg, 0.27829 mmol) and PdCl$_2$(PPh$_3$)$_2$ (49 mg, 0.06981 mmol) under nitrogen. After the solids were dissolved by adding anhydrous THF (3 mL), ethynyl (trimethyl) silane (273 mg, 2.779 mmol) was added dropwise. The solution was orange and then TEA (1.5 mL) was added dropwise with stirring at room temperature. The solution turned to black. The completion of reaction was monitored by TLC after reaction for 4 h. The reaction solution was quenched by the addition of water (20 mL), then EA (50 mL) was added. A large amount of brown solid precipitated. The resulting mixture was filtered by suction through a celite pad. The organic phase was separated from the filtrate. The aqueous phase was extracted with EA (50 mL×2). The organic phases were combined, washed once with 30 mL of saturated brine. The combined organic phases were dried over anhydrous sodium sulfate, concentrated in vacuo, and then purified by silica gel column chromatography (eluent EA:PE=1:10-1:5) to give a yellow solid 450 mg. The yield was 83.32%. Rf=0.5 (PE:EA=5:1). LC-MS: m/z=234.20[M+H]$^+$. $^1$H NMR (400 MHz, CDCl$_3$) δ 8.76 (s, 1H), 8.07 (d, J=8.1 Hz, 1H), 7.87 (dd, J=8.1, 1.8 Hz, 1H), 4.00 (s, 3H), 0.27 (s, 9H).

Step 2: 5-ethynyl picolinic acid

Methyl 5-((trimethylsilyl)ethynyl)picolinate (450 mg, 1.9285 mmol) was dissolved in anhydrous methanol (9 mL) under nitrogen in a double-necked flask, and then potassium carbonate (533 mg, 3.8565 mmol) was added with stirring in one portion at room temperature. The mixture was stirred overnight. The reaction mixture was added with water (20 mL) and adjusted with 1N diluted hydrochloric acid to pH=1, then extracted with EA (50 mL×3). The organic phases were combined and washed once with saturated brine (30 mL). The combined organic phases were dried over anhydrous sodium sulfate and concentrated in vacuo to give a yellow solid 280 mg. The yield was 98.68%. Rf=0.01 (PE:EA=5:1). LC-MS: m/z=148.10[M+H]$^+$. $^1$H NMR (400 MHz, d$_6$-DMSO) δ 8.78 (s, 1H), 8.08 (d, J=8.1 Hz, 1H), 8.03 (d, J=8.1 Hz, 1H), 4.67 (s, 1H).

Step 3: 5-ethynylpicolinic acid chloride

5-Ethynylpicolinic acid (20 mg, 0.134 mmol) was dissolved in DCM (5 mL) in a two-necked flask under nitrogen, and DMF (0.01 mL) was added with stirring. After 5 min, SOCl$_2$ (20 mg, 0.168 mmol) was added dropwise. After addition, the solution precipitated with a large amount of yellow solid. The mixture was continuously stirred at this temperature. The solid gradually dissolved over time and the solution gradually turned orange, clear and transparent. The mixture was reacted for 0.5 h and then the mixture was directly concentrated in vacuo, which was directly used for the next step without further purification. The yield was calculated as 100%.

Step 4: 4-(6-(4-(5-ethynylpicolinoyl)piperazin-1-yl)pyridin-3-yl)-6-(1-methyl-1H-pyrazol-4-yl) pyrazolo[1,5-a]pyridine-3-carbonitrile To a single-necked flask were added 6-(1-methyl pyrazol-4-yl)-4-(6-piperazin-1-yl-3-pyridyl)pyrazolo[1,5-a]pyridine-3-carbonitrile dihydrochloride (see synthesis of intermediate 2, 15 mg, 0.033 mmol) and 2 mL of DCM at room temperature. After the solids were dissolved, TEA (17 mg, 0.17 mmol) was added with stirring. After 5 min, a solution of 5-ethynyl-2-chloroacylpyridine (8 mg, 0.048 mmol) in 1 mL of DCM was added. After the end of addition, the mixture was reacted continuously at this temperature. After the completion of reaction was monitored by TLC, the reaction mixture was poured into water (5 mL) and extracted with DCM (10 mL×2). The organic phases were washed with water (5 mL), dried over anhydrous sodium sulfate and filtered. The mother liquor was concentrated in vacuo, and then purified by silica gel column chromatography (eluent MeOH:DCM=1:50-1:30) to give an off-white solid 11 mg as the target product. LC-MS: m/z=514.20[M+H]$^+$. $^1$H NMR (400 MHz, CDCl$_3$) δ 8.70 (s, 1H), 8.64 (d, J=1.4 Hz, 1H), 8.38 (d, 7=2.1 Hz, 1H), 8.26 (s, 1H), 7.91 (dd, 7=8.1, 2.0 Hz, 1H), 7.80-7.76 (m, 2H), 7.72 (d, J=7.9 Hz, 1H), 7.68 (s, 1H), 7.40 (d, J=1.3 Hz, 1H), 6.81 (d, J=8.8 Hz, 1H), 3.99 (s, 3H), 3.98-3.93 (m, 2H), 3.83-3.79 (m, 4H), 3.74 (d, J=4.7 Hz, 2H), 3.31 (s, 1H). HPLC: 93.07%.

Example 238: 4-(6-(6-(5-ethynylpicolinoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile

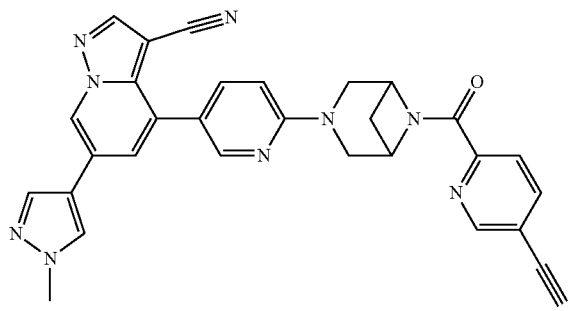

(238)

Step 1: methyl 5-((trimethylsilyl)ethynyl)picolinate

To a three-necked flask were added methyl 5-bromopyridinecarboxylate (500 mg, 2.3145 mmol), CuI (53 mg, 0.278 mmol) and PdCl$_2$(PPh$_3$)$_2$ (49 mg, 0.070 mmol) under nitrogen. After the solids were dissolved by adding anhydrous THF (3 mL), ethynyl (trimethyl) silane (273 mg, 2.779 mmol) was added dropwise. The solution was orange and then TEA (1.5 mL) was added dropwise with stirring at room temperature. The solution turned to black. The completion of reaction was monitored by TLC after reaction for 4 h. The reaction solution was quenched by the addition of water (20 mL), then EA (50 mL) was added. A large amount of brown solid precipitated. The resulting mixture was filtered by suction through a celite pad. The organic phase was separated from the filtrate. The aqueous phase was extracted with EA (50 mL×2). The organic phases were combined, washed once with 30 mL of saturated brine. The combined organic phases were dried over anhydrous sodium sulfate, concentrated in vacuo, and then purified by silica gel column chromatography (eluent EA:PE=1:10-1:5) to give a yellow solid 450 mg. The yield was 83.32%. Rf=0.5 (PE:EA=5:1). LC-MS: m/z=234.20[M+H]$^+$. $^1$H-NMR (400 MHz, CDCl$_3$) δ 8.76 (s, 1H), 8.07 (d, J=8.1 Hz, 1H), 7.87 (dd, J=8.1, 1.8 Hz, 1H), 4.00 (s, 3H), 0.27 (s, 9H).

Step 2: 5-ethynyl picolinic acid

Methyl 5-((trimethylsilyl)ethynyl)picolinate (450 mg, 1.9285 mmol) was dissolved in anhydrous methanol (9 mL) under nitrogen in a double-necked flask, and then potassium carbonate (533 mg, 3.8565 mmol) was added with stirring in one portion at room temperature. The mixture was stirred overnight. The reaction mixture was added with water (20 mL) and adjusted with 1N diluted hydrochloric acid to pH=1, then extracted with EA (50 mL×3). The organic phases were combined and washed once with saturated brine (30 mL). The combined organic phases were dried over anhydrous sodium sulfate and concentrated in vacuo to give a yellow solid 280 mg. The yield was 98.68%. Rf=0.01 (PE:EA=5:1). LC-MS: m/z=148.10[M+H]$^+$. $^1$H NMR (400 MHz, d$_6$-DMSO) δ 8.78 (s, 1H), 8.08 (d, J=8.1 Hz, 1H), 8.03 (d, J=8.1 Hz, 1H), 4.67 (s, 1H).

Step 3: 5-ethynylpicolinic acid chloride

5-Ethynylpicolinic acid (20 mg, 0.13593 mmol) was dissolved in DCM (5 mL) in a two-necked flask under nitrogen, and DMF (0.01 mL) was added with stirring. After 5 min, SOCl$_2$ (20 mg, 0.168 mmol) was added dropwise. After addition, the solution precipitated with a large amount of yellow solid. The mixture was continuously stirred at this temperature. The solid gradually dissolved over time and the solution gradually turned orange, clear and transparent. The mixture was reacted for 0.5 h and then directly concentrated in vacuo, which was directly used for the next step without further purification. The yield was calculated as 100%.

Step 4: 4-(6-(6-(5-ethynylpicolinoyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile At room temperature, to a single-necked flask were added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and 5-ethynyl picolinic acid (10 mg, 0.068 mmol), which were dissolved by adding 2 mL of DMF. Then DCC (10 mg, 0.048 mmol) was added with stirring. After addition, the mixture was reacted continuously at this temperature. The completion of reaction (Rf=0.4 (DCM:MeOH=30:1)) was monitored by TLC. Then the reaction mixture was concentrated in vacuo, and the residue was purified by silica gel column chromatography (eluent MeOH:DCM=1:80-1:30) to give a pale yellow solid 3 mg as the target product. LC-MS: m/z=526.00[M+H]$^+$. $^1$H NMR (400 MHz, CDCl$_3$) δ 8.67 (d, J=1.4 Hz, 1H), 8.62 (d, J=1.3 Hz, 1H), 8.36 (d, J=2.2 Hz, 1H), 8.25 (s, 1H), 8.08 (d, J=8.1 Hz, 1H), 7.87 (dd, J=8.2, 2.0 Hz, 1H), 7.77 (s, 1H), 7.77-7.73 (m, 1H), 7.66 (s, 1H), 7.35 (d, J=1.4 Hz, 1H), 6.65 (d, J=8.9 Hz, 1H), 5.51-5.47 (m, 1H), 4.87-4.83 (m, 1H), 4.23 (d, J=10.7 Hz, 1H), 4.06 (d, J=10.2 Hz, 1H), 3.98 (s, 3H), 3.91 (d, J=12.6 Hz, 1H), 3.79 (d, J=12.4 Hz, 1H), 3.32 (s, 1H), 2.93 (dd, J=14.9, 6.4 Hz, 1H), 1.81 (d, J=8.6 Hz, 1H). HPLC: 96.08%.

Example 239: 4-(6-(4-(3-ethynyl-4-fluorobenzoyl)piperazin-1-yl)pyridin-3-yl)-6-(1-methyl-1H-pyrazol-4-yl)pyrazolo[1,5-a]pyridine-3-carbonitrile

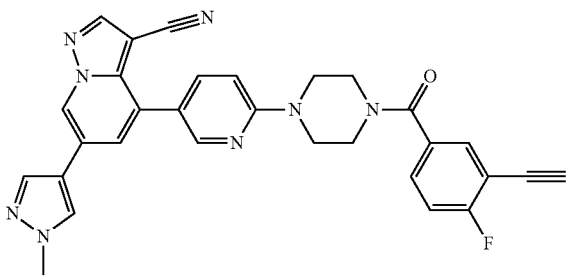

(239)

Step 1: 3-ethynyl-4-fluorobenzoic acid

Methyl 3-ethynyl-4-fluoro-benzoate (350 mg, 1.9645 mmol) was dissolved in methanol (7 mL) and water (0.35 mL) in a double-necked flask, and then potassium carbonate (400 mg, 2.8941 mmol) was added in one portion with stirring. The mixture was stirred to react at room temperature overnight. To the reaction mixture were added water (30 mL) and EA (20 mL). The aqueous phase was separated and adjusted with 1N diluted hydrochloric acid to pH=1, then extracted with EA (50 mL×3). The organic phases were combined, washed with saturated brine (30 mL), dried over anhydrous sodium sulfate and filtered, and then the filtrate was concentrated in vacuo to give a pale yellow solid 219 mg (yield: 84.7%) as the target product. $^1$H NMR (400 MHz, CDCl$_3$) δ 8.26 (dd, J=6.7, 2.0 Hz, 1H), 8.13-8.06 (m, 1H), 7.18 (t, J=8.7 Hz, 1H), 3.36 (s, 1H).

Step 2: 4-(6-(4-(3-ethynyl-4-fluorobenzoyl)piperazin-1-yl)pyridin-3-yl)-6-(1-methyl-1H-pyrazol-4-yl)pyrazolo[1,5-a]pyridine-3-carbonitrile To a solution of 6-(1-methyl-1T-pyrazol-4-yl)-4-(6-(piperazin-1-yl)pyridin-3-yl) pyrazolo[1,5-a]pyridine-3-carbonitrile dihydrochloride (see synthesis of intermediate 2, 20 mg, 0.0437 mmol) and 3-ethynyl-4-fluorobenzoic acid (11 mg, 0.0670 mmol) in DCM (3 mL) were added DMAP (3 mg, 0.0245 mmol) and EDCI (17 mg, 0.088 mmol) under nitrogen at room temperature. The mixture was stirred at room temperature overnight. After the reaction was completed, the reaction solution was directly concentrated in vacuo, and then purified by silica gel column chromatography (DCM:MeOH=100/1-100/3) to give a pale yellow solid 7 mg (the yield was 30.17%), which was the target product. LC-MS(ESI): m/z=531.25 [M+H]$^+$; $^1$H NMR (400 MHz, CDCl$_3$) δ 8.67 (d, 1H), 8.41 (d, J=2.3 Hz, 1H), 8.29 (s, 1H), 7.82 (s, 1H), 7.71 (s, 1H), 7.63 (dd, J=6.5, 2.1 Hz, 1H), 7.56 (d, J=3.3 Hz, 1H), 7.43 (d, 1H), 7.37 (d, J=2.5 Hz, 1H), 7.20 (t, J=8.7 Hz, 1H), 6.84 (d, J=8.8 Hz, 1H), 4.02 (s, 3H), 3.83-3.63 (m, 8H), 3.39 (s, 1H); HPLC: 98.09%.

Example 240: 4-(6-(4-(3-(4-methoxypyridin-2-yl)propan-2-yn-1-yl)piperazin-1-yl)pyridin-3-yl)-6-(1-methyl-1H-pyrazol-4-yl)pyrazole[1,5-a]pyridine-3-carbonitrile

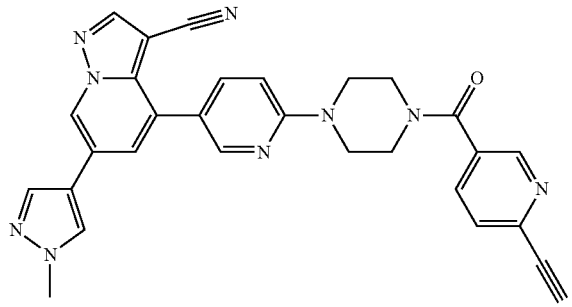

(240)

Step 1: 6-((trimethylsilyl)ethynyl)nicotinaldehyde

2-Bromo-5-aldehydepyridine (2.00 g, 10.8 mmol), PdCl$_2$(PPh$_3$)$_2$ (0.76 g, 1.1 mmol) and CuI (0.21 g, 1.1 mmol) were dissolved in THF (15 mL) under N$_2$, then trimethylsilylacetylene (1.58 g, 16.1 mmol) and Et$_3$N (2.17 g, 21.5 mmol) were added. The mixture was reacted with stirring at room temperature for 4 h. The reaction was stopped. The resulting mixture was filtered by suction, and the filter cake was washed with EA. The filtrate was concentrated in vacuo, and the residue was purified by silica gel column chromatography (eluent PE/EA=30/1-10/1) to give a yellow-brown solid 1.43 g as the target product (the yield was 68%). LC-MS: m/z=204.1[M+H]$^+$. $^1$H NMR (600 MHz, CDCl$_3$) δ 10.09 (s, 1H), 9.01 (d, J=1.7 Hz, 1H), 8.15-8.08 (m, 1H), 7.59 (d, J=8.1 Hz, 1H), 0.28 (s, 9H).

Step 2: 6-((trimethylsilyl)ethynyl)nicotinic acid 6-((Trimethylsilyl)ethynyl)nicotinaldehyde (0.20 g, 0.98 mmol) was dissolved in CH$_3$CN (2 mL) at −5° C., then NaH$_2$PO$_4$ (0.24 g, 2.0 mmol) and H$_2$O$_2$ solution (0.5 mL) were added. The mixture was stirred for 5 min. NaClO$_2$ (0.21 g, 2.0 mmol) (dissolved in 2 mL of H$_2$O) was added slowly at low temperature. The mixture was reacted with stirring. The completion of reaction (DCM/CH$_3$OH=20/1, Rf=0.06) was monitored by TLC. The reaction was stopped. To the resulting mixture was added H$_2$O (3 mL) and the resulting mixture was extracted with EA (10 mL×3). The organic phase was separated, dried over anhydrous sodium sulfate and filtered, and the filtrate was concentrated in vacuo to give a yellow-brown solid 149 mg as the target product. LC-MS: m/z=220.1 [M+H]$^+$. $^1$H NMR (600 MHz, CDCl$_3$) δ 10.09 (s, 1H), 9.01 (d, J=1.7 Hz, 1H), 8.15-8.08 (m, 1H), 7.59 (d, J=8.1 Hz, 1H), 0.28 (s, 9H).

Step 3: 4-(6-(4-(3-(4-methoxypyridin-2-yl)propan-2-yn-1-yl)piperazin-1-yl)pyridin-3-yl)-6-(1-methyl-1T-pyrazol-4-yl)pyrazole[1,5-a]pyridine-3-carbonitrile 6-(1-Methyl-1H-pyrazol-4-yl)-4-(6-(piperazin-1-yl)pyridin-3-yl)pyrazolo[1,5-a]pyridine-3-carbonitrile hydrochloride (see synthesis of intermediate 2, 22 mg, 0.05 mmol) and 6-((trimethylsilyl)ethynyl)nicotinic acid (16 mg, 0.07 mmol) were dissolved in DCM (4 mL), then DCC (23 mg, 0.11 mmol) and DIPEA (25 mg, 0.19 mmol) were added slowly. The mixture was reacted with stirring at room temperature for 12 h. The completion of reaction (DCM/CH$_3$OH=30/1, Rf=0.16) was monitored by TLC. The reaction solution was concentrated in vacuo, and then CH$_3$OH (3 mL) and K$_2$CO$_3$ (0.3 g) were added. The mixture was stirred at room temperature for 0.5 h. The resulting mixture was filtered by suction. The filtrate was concentrated in vacuo, and the residue was purified by silica gel column chromatography (eluent DCM/CH$_3$OH=50/1-30/1) to give a yellow-white solid 2 mg as the target product. $^1$H NMR (400 MHz, CDCl$_3$) δ 8.72 (s, 1H), 8.67 (s, 1H), 8.41 (d, J=2.2 Hz, 1H), 8.29 (s, 1H), 7.81 (dd, J=9.9, 5.1 Hz, 3H), 7.71 (s, 1H), 7.60 (d, J=7.9 Hz, 1H), 7.43 (s, 1H), 6.84 (d, J=8.8 Hz, 1H), 5.37 (s, 2H), 4.02 (s, 3H), 3.77 (s, 4H), 3.29 (s, 1H), 2.04 (s, 2H). HPLC: 95.39%.

Example 241: 4-(6-(6-(3-(4-fluorophenyl)prop-2-yn-1-yl)-3,6-diazabicyclo[3.1.1]heptyl-3-yl) pyridine-3-yl)-6-(1-methyl-1H-pyrazol-4-yl)pyrazolo[1,5-a]pyridine-3-carbonitrile

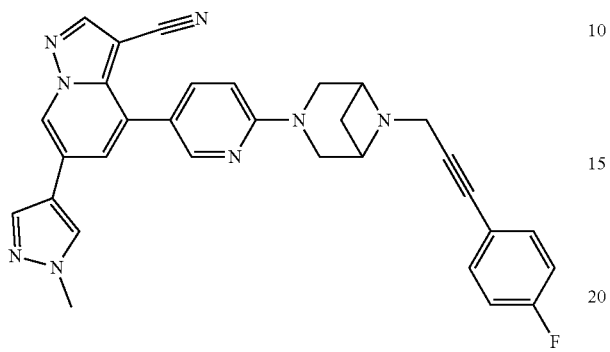

(241)

Step 1: 3-(4-fluorophenyl)prop-2-yn-1-ol

To a 50 mL two-necked flask were sequentially added PdCl$_2$(PPh$_3$)$_2$ (159 mg, 0.23 mmol), CuI (95 mg, 0.50 mmol), 1-fluoro-4-iodobenzene (0.52 mg, 4.50 mmol) and TEA (10 mL). Propargyl alcohol (0.34 mL, 5.8 mmol) was added under N$_2$. The mixture was stirred at room temperature for 4-5 h. 25 mL of EA was added, and the resulting mixture was filtered. The filtrate was concentrated in vacuo, and then purified by column chromatography (eluent PE/EA=4:1) to give oily liquid 500 mg. The yield was 74%. $^1$H NMR (400 MHz, CDCl$_3$) δ 7.40 (m, 2H), 7.01 (m, 2H), 4.48 (s, 2H).

Step 2: 1-(3-bromoprop-1-yn-1-yl)-4-fluorobenzene

To a 25 mL single-necked flask were sequentially added 3-(4-fluorophenyl)prop-2-yn-1-ol (91 mg, 0.61 mmol) and DCM (5 mL) at −10° C., then PBr$_3$ (0.12 mL, 1.3 mmol) was added slowly. After 10 min of addition, the mixture was continuously stirring for 2 h. To the reaction solution was slowly added 20 mL of 5% K$_2$CO$_3$ solution, and the organic phase was collected. The aqueous phase was extracted with DCM once. The organic phases were combined, dried over sodium sulfate, filtered, and the filtrate was concentrated in vacuo, which was directly used for the next reaction in equivalent amounts.

Step 3: 4-(6-(6-(3-(4-fluorophenyl)prop-2-yn-1-yl)-3,6-diazabicyclo[3.1.1]heptan-3-yl) pyridine-3-yl)-6-(1-methyl-1H-pyrazol-4-yl)pyrazolo[1,5-a]pyridine-3-carbonitrile To a 10 mL single-necked flask was sequentially added 4-[6-(3,6-diazabicyclo[3.1.1]heptan-3-yl)-3-pyridyl]-6-(1-methylpyrazol-4-yl)pyrazoline [1,5-a]pyridine-3-carbonitrile dihydrochloride (see synthesis of intermediate 3, 25 mg, 0.058 mmol), DMF (1 mL), K$_2$CO$_3$ (29 mg, 0.21 mmol) and 1-(3-bromoprop-1-yn-1-yl)-4-fluorobenzene (60 mg, 0.28 mmol). The mixture was stirred for reaction at rt overnight. To the reaction solution was added EA 20 mL, and the resulting mixture was washed with water (8 mL×3), and the combined aqueous phases were extracted with EA 15 mL. The organic phases were combined, dried over anhydrous sodium sulfate, filtered, and the filtrate was concentrated in vacuo, and then purified by silica gel column chromatography (eluent DCM/MeOH=20:1) to give a pale yellow solid 6 mg (yield: 18%). LC-MS(ESI): m/z=529.1 [M+H]$^+$. $^1$H NMR (400 MHz, CDCl$_3$) δ 8.64 (d, J=1.2 Hz, 1H), 8.43 (d, J=2.3 Hz, 1H), 8.27 (s, 1H), 7.85-7.77 (m, 2H), 7.68 (s, 1H), 7.40 (m, 3H), 6.98 (m, 2H), 6.72 (d, J=8.8 Hz, 1H), 3.99 (s, 3H), 3.98 (m, 2H), 3.88 (d, J=12.0 Hz, 2H), 3.67 (d, J=11.9 Hz, 2H), 3.51 (s, 2H), 2.78 (d, J=7.4 Hz, 1H), 2.04 (m, 1H). HPLC: 96.55%.

Example 242: 6-(1-methyl-1H-pyrazol-4-yl)-4-(6-(6-(3-(4-(trifluoromethyl)phenyl)prop-2-yn-1-yl)-3,6-diazabicyclo[3.1.1]heptan-3-yl)pyridin-3-yl)pyrazolo[1,5-a]pyridine-3-carbonitrile

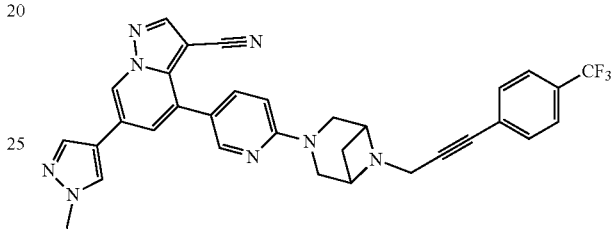

(242)

Step 1: 3-(4-(trifluoromethyl)phenyl)prop-2-yn-1-ol

To a mixture of 1-iodo-4-(trifluoromethyl)benzene (700 mg, 2.57 mmol), Pd(PPh$_3$)$_2$Cl$_2$ (90 mg, 0.13 mmol) and CuI (24 mg, 0.13 mmol) were sequentially added triethylamine (4.5 mL, 32 mmol) and propargyl alcohol (0.30 mL, 5.1 mmol) at room temperature under nitrogen. A black suspension was obtained. The mixture was reacted at room temperature overnight. The mixture was concentrated in vacuo to remove the solvent, and the residue was purified by silica gel column chromatography (PE:EA=4:1) to give pale yellow oil 500 mg as the target product (the yield was 97.07%). Rf=0.25 (PE:EA=4:1).

Step 2: 3-(4-(trifluoromethyl)phenyl)propynal

To a solution of 3-(4-(trifluoromethyl)phenyl)prop-2-yn-1-ol (500 mg, 2.50 mmol) in DCM (25.0 mL) were added sodium bicarbonate (1.05 g, 12.4 mmol) and Dess Martin reagent (1.39 g, 3.24 mmol) at room temperature. The mixture was reacted for 2 h at room temperature. The reaction was quenched with saturated sodium thiosulfate solution (20 mL). After layering, the mixture was extracted with DCM (50 mL×2). The organic phases were combined, dried over anhydrous sodium sulfate, filtered and concentrated in vacuo. The residue was purified by silica gel column chromatography (PE:EA=10:1) to give a white solid 434 mg as the target product (yield: 87.68%). Rf=0.8 (PE:EA=4:1). $^1$H NMR (400 MHz, CDCl$_3$) δ 9.44 (s, 1H), 7.70 (t, J=8.2 Hz, 2H), 7.66 (d, J=8.3 Hz, 2H).

Step 3: 6-(1-methyl-1H-pyrazol-4-yl)-4-(6-(6-(3-(4-(trifluoromethyl)phenyl)prop-2-yn-1-yl)-3,6-diazabicyclo[3.1.1]heptan-3-yl)pyridin-3-yl)pyrazolo[1,5-a]pyridine-3-carbonitrile To a 10 mL single-necked flask were added 4-(6-(3,6-diazabicyclo[3.1.1]heptane-3-yl)pyridin-3-yl)-6-(1-methyl- 1H-pyrazole-4-yl)pyrazolo[1,5-a]pyridine-3-carbonitrile dihydrochloride (see synthesis of intermediate 3, 15 mg, 0.035 mmol) and 3-(4-(trifluoromethyl)phenyl)propynal (14 mg, 0.071 mmol). The mixture was dissolved with 1,2-dichloroethane (2 mL), then sodium triacetoxyborohydride (22 mg, 0.1038 mmol) was added. The mixture was reacted at 35° C. for 5 h. The completion of reaction was monitored by TLC. The reaction mixture was concentrated in vacuo, and then purified by silica gel column chromatography (eluent MeOH:DCM=1:50-1:30) to give a white solid 13 mg as the target product (the yield was 64.84%). Rf=0.5 (MeOH:DCM=1:30). LC-MS: m/z=579.00[M+H]⁺. ¹H NMR (400 MHz, CDCl₃) δ 8.64 (s, 1H), 8.43 (d, J=2.2 Hz, 1H), 8.27 (s, 1H), 7.82 (dd, J=8.8, 2.4 Hz, 1H), 7.79 (s, 1H), 7.68 (s, 1H), 7.53 (d, J=4.9 Hz, 4H), 7.40 (d, J=1.1 Hz, 1H), 6.72 (d, J=8.8 Hz, 1H), 3.99 (s, 3H), 3.95 (d, J=5.5 Hz, 2H), 3.72 (d, J=7.0 Hz, 2H), 3.66-3.63 (m, 2H), 3.52 (s, 2H), 2.79-2.73 (m, 1H), 2.08-1.97 (m, 1H). HPLC: 95.11%.

Example 243: 4-(6-(4-(3-(2-methoxypyridin-4-yl)prop-2-yn-1-yl)piperazin-1-yl)pyridin-3-yl)-6-(1-methyl-1H-pyrazol-4-yl)pyrazolo[1,5-a]pyridine-3-carbonitrile

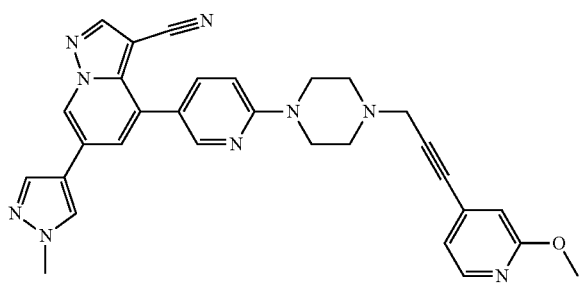

(243)

Step 1: 3-(2-methoxypyridin-4-yl)prop-2-yn-1-ol

To a 50 mL two-necked flask were sequentially added 4-bromo-2-methoxy-pyridine (500 mg, 2.6593 mmol), Pd(PPh₃)₂Cl₂ (9.4 mg, 0.013 mmol) and CuI (20 mg, 0.105 mmol). The reaction mixture was degassed and refilled with nitrogen, and then propargyl alcohol (0.31 mL, 5.3 mmol), THF (5 mL) and Et₃N (2.5 mL, 18 mmol) were added. The resulting mixture was reacted at 80° C. overnight. The reaction mixture was filtered, then washed with EA (100 mL). The filtrate was concentrated in vacuo, and then purified by silica gel column chromatography (PE:EA=50:1-20:1) to give a pale yellow solid 245 mg as the target product. ¹H NMR (400 MHz, CDCl₃) δ 8.13 (d, J=5.2 Hz, 1H), 6.89 (d, J=5.2 Hz, 1H), 6.79 (s, 1H), 4.52 (d, J=4.3 Hz, 2H), 3.95 (s, 3H), 1.86 (s, 1H).

Step 2: 3-(2-methoxypyridin-4-yl)propynal

To a solution of 3-(2-methoxypyridin-4-yl)prop-2-yn-1-ol (240 mg, 1.4709 mmol) in DCE (22 mL) were sequentially added sodium bicarbonate (618 mg, 7.35 mmol) and Dess Martin reagent (945 mg, 2.20577 mmol) at room temperature. The reaction was reacted for 1.5 h at room temperature. The reaction was quenched with saturated Na₂S₂O₃ and the resulting mixture was extracted with DCM (30 mL×2). The organic phases were combined, dried over anhydrous sodium sulfate and filtered. The mother liquid was concentrated in vacuo and purified by silica gel column chromatography (PE:EA=50:1-20:1) to give a white fluffy solid 210 mg as the target product (yield: 88.591%). LC-MS(ESI): m/z=162.0[M+H]⁺. ¹H NMR (400 MHz, CDCl₃) δ 9.45 (s, 1H), 8.24 (d, J=5.2 Hz, 1H), 7.01 (d, J=5.2 Hz, 1H), 6.93 (s, 1H), 3.97 (s, 3H).

Step 3: 4-(6-(4-(3-(2-methoxypyridin-4-yl)prop-2-yn-1-yl)piperazin-1-yl)pyridin-3-yl)-6-(1-methyl-1H-pyrazol-4-yl)pyrazolo[1,5-a]pyridine-3-carbonitrile To a single-necked flask were sequentially added 6-(1-methylpyrazol-4-yl)-4-(6-piperazin-1-yl-3-pyridyl)pyrazolo[1,5-a]pyridine-3-carbonitrile dihydrochloride (see synthesis of intermediate 2, 15 mg, 0.033 mmol), 3-(2-methoxy-4-pyridyl)prop-2-ynaldehyde (10 mg, 0.062 mmol) and DCE (2 mL). After stirring for 10 min, sodium triacetoxyborohydride (21 mg, 0.096 mmol) was added. The mixture was stirred at room temperature overnight. The reaction mixture was directly concentrated in vacuo, and the residue was purified by silica gel column chromatography (eluent DCM/MeOH=0-100:1) to give a yellow solid 8.5 mg as the target product (yield: 49%). Rf=0.5 (DCM/MeOH=30/1). LC-MS: m/z=530.3[M+H]⁺. ¹H NMR (400 MHz, CDCl₃) δ 8.66 (s, 1H), 8.40 (s, 1H), 8.28 (s, 1H), 8.12 (d, J=5.3 Hz, 1H), 7.79 (dd, J=12.1, 3.1 Hz, 2H), 7.70 (s, 1H), 7.41 (s, 1H), 6.91 (d, J=5.3 Hz, 1H), 6.87-6.76 (m, 2H), 4.01 (s, 3H), 3.94 (s, 3H), 3.76 (m, 4H), 3.64 (s, 2H), 2.85-2.72 (m, 4H). HPLC: 94.11%.

Example 244: 6-(1-methyl-1H-pyrazol-4-yl)-4-(6-(6-(3-(pyridin-2-yl)(prop-2-yn-1-yl)-3,6-diazabicyclo[3.1.1]heptan-3-yl)pyridin-3-yl)pyrazolo[1,5-a]pyridine-3-carbonitrile

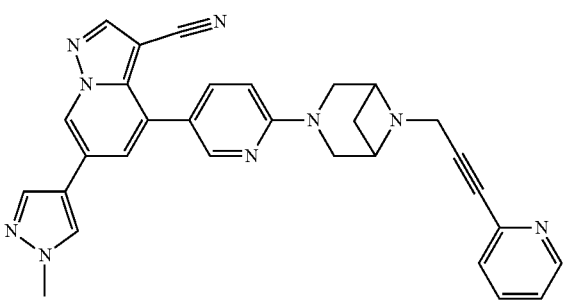

(244)

Step 1: 3-(2-pyridin)prop-2-yn-1-ol

To a 25 mL two-necked flask were added CuI (60 mg, 0.315 mmol) and PdCl₂(PPh₃)₂ (222 mg, 0.316 mmol) at room temperature. The reaction mixture was degassed and refilled with nitrogen. Then triethylamine (9.5 mL, 68 mmol), propynyl alcohol (0.744 mL, 12.7 mmol) and 2-bromopyridine (0.6 mL, 6 mmol) were added. The mixture was reacted at 50° C. overnight. TLC showed the reaction was completed. The reaction solution was concentrated in vacuo, washed with 15 mL of saturated ammonium chloride, extracted with EA (40 mL×2), and filtered by suction. The solid was washed with EA (10 mL×3). The combined organic phases were washed with saturated saline (15 mL×2), dried over anhydrous sodium sulfate, filtered, and concentrated in vacuo. The mixture was purified by silica gel column chromatography (eluent PE:EA=3:1-1:1) to give a yellow-white product 0.664 g (the yield was 80%), which was the target product. LC-MS (ES-API): m/z=134.25 [M+H]+. 1H NMR (400 MHz, CDCl3) δ 8.56 (d, J=4.3 Hz, 1H), 7.66 (td, J=7.8, 1.7 Hz, 1H), 7.43 (d, J=7.8 Hz, 1H), 7.24 (dd, J=4.6, 3.0 Hz, 1H), 4.53 (s, 2H), 2.63 (s, 1H).

Step 2: 2-(3-bromoprop-1-ynyl)pyridine 3-(2-Pyridyl)prop-2-yn-1-ol (30 mg, 0.225 mmol) was dissolved in DCM (3 mL) in a 5 mL single-necked flask at 0° C., then PBr3 (0.042 mL, 0.45 mmmol) was slowly added. The mixture was continuously reacted at this temperature. TLC showed the reaction was completed. The reaction was quenched by the addition of water (1.5 mL) slowly. Saturated potassium carbonate solution (6 mL) was added dropwise to adjust the pH of the mixture to alkaline. The mixture was extracted with DCM (15 mL×2) and saturated brine (10 mL), then dried over anhydrous sodium sulfate. The resulting mixture was filtered and concentrated in vacuo, which was directly used for the next step. The yield was calculated as 100%.

Step 3: 6-(1-methyl-1H-pyrazol-4-yl)-4-(6-(6-(3-(pyridin-2-yl)(prop-2-yn-1-yl)-3,6-diazabicyclo[3,1,1]heptan-3-yl)pyridin-3-yl)pyrazolo[1,5-a]pyridine-3-carbonitrile To a 10 mL single-necked flask was added 4-[6-(3,6-diazabicyclo[3.1.1]heptan-3-yl)-3-pyridyl]-6-(1-methylpyrazol-4-yl)pyrazolo[1,5-a]pyridine-3-carbonitrile dihydrochloride (see synthesis of intermediate 3, 25 mg, 0.053 mmol), K2CO3 (30 mg, 0.215 mmol), DMF (3 mL), and 2-(3-bromoprop-1-ynyl)pyridine (44 mg, 0.224 mmol). The mixture was stirred for reaction at room temperature overnight. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent pure DCM-DCM:MeOH (v:v=20:1)) to give a pale yellow solid 8 mg (the yield was 30%), which was the target product. LC-MS (ES-API): m/z=512.30 [M+H]+. 1H NMR (400 MHz, CDCl3) δ 8.64 (d, 7=1.3 Hz, 1H), 8.55 (s, 1H), 8.42 (d, J=2.2 Hz, 1H), 8.27 (s, 1H), 7.80 (s, 1H), 7.69 (s, 1H), 7.62 (dd, J=7.8, 1.6 Hz, 1H), 7.41 (d, J=1.3 Hz, 1H), 7.24 (s, 1H), 6.92 (t, J=7.4 Hz, 1H), 6.83 (d, J=7.7 Hz, 1H), 6.71 (d, J=8.8 Hz, 1H), 4.00 (s, 3H), 3.99-3.95 (m, 2H), 3.88 (d, J=12.9 Hz, 2H), 3.73-3.64 (m, 2H), 3.53 (s, 2H), 2.81-2.72 (m, 1H), 2.05-1.98 (m, 1H). HPLC: 92.64%.

Example 245: 6-(1-methyl-1H-pyrazol-4-yl)-4-(6-(6-(3-(pyridin-4-yl)propan-2-yn-1-yl)-3,6-diazabicyclo[3.1.1]heptan-3-yl)pyridin-3-yl)pyrazole[1,5-a]pyridine-3-carbonitrile (245)

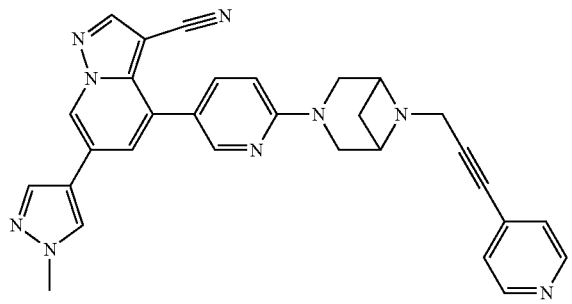

Step 1: 3-(pyridin-4-yl)propane-2-yn-1-ol

4-Iodopyridine (1.00 g, 4.88 mmol), PdCl2(PPh3)2 (0.34 g, 0.48 mmol), CuI (93 mg, 0.49 mmol) and PPh3 (128 mg, 0.49 mmol) were dissolved in THF (15 mL) Under N2, then propane-2-yn-1-ol (0.55 g, 9.8 mmol) and Et3N (0.99 g, 9.8 mmol) were added. The mixture was reacted with stirring at room temperature for 4 h. The reaction was quenched with saturated NH4Cl. The resulting mixture was extracted with EA (10 mL×3), washed with water (10 mL), dried over anhydrous sodium sulfate, and filtered. The mother liquor was concentrated in vacuo and the residue was purified by silica gel column chromatography (eluent PE/EA=10/1-3/1) to give a yellow-brown solid 0.52 g as the target product (the yield was 72%). Rf=0.09 (PE/EA=5/l). LC-MS: m/z=134.1 [M+H]+. 1H NMR (400 MHz, CDCl3) δ 8.59 (s, 2H), 7.34-7.27 (m, 2H), 4.53 (s, 2H).

Step 2: 4-(3-bromopropan-1-yn-1-yl)pyridine 3-(Pyridin-4-yl)propane-2-yn-1-ol (125 mg, 0.94 mmol) was dissolved in DCM (5 mL) at 0° C., and PBr3 (0.51 g, 1.9 mmol) was slowly added. The mixture was reacted with stirring at low temperature for 1 h. The reaction was stopped, and quenched with water (5 mL). The resulting mixture was extracted with DCM (10 mL×3), washed with water (10 mL), dried over anhydrous sodium sulfate, and filtered. The mother liquid was concentrated in vacuo to give brown viscous liquid 136 mg as the target product (yield: 86%), which was directly used for the next reaction without further purification. Rf=0.41 (PE/EA=5/l). LC-MS: m/z=196.1[M+H]+.

Step 3: 6-(1-methyl-1H-pyrazol-4-yl)-4-(6-(6-(3-(pyridin-4-yl)propan-2-yn-1-yl)-3,6-diazabicyclo[3.1.1]heptan-3-yl)pyridin-3-yl)pyrazole[1,5-a]pyridine-3-carbonitrile 4-(6-(3,6-diazabicyclo[3.1.1]heptan-3-yl)pyridin-3-yl)-6-(1-methyl-17T-pyrazol-4-yl)pyrazole[1,5-a]pyridin-3-cyano dihydrochloride (see synthesis of intermediate 3.13 mg, 0.07 mmol) was dissolved in DMF (5 mL)), and K2CO3 (24 mg, 0.17 mmol) was added. The mixture was warmed to 40° C. slowly and stirred for reaction for 3 h. The mixture was cooled to room temperature, and the reaction was stopped.

The reaction mixture was concentrated in vacuo, and the residue was purified by silica gel column chromatography (eluent DCM/CH₃OH=50/1-30/1) to give a yellowish white solid 10 mg as the target product (the yield was 46%). Rf=0.31 (DCM/CH₃OH=30/1). LC-MS: m/z=512.1[M+H]⁺. ¹H NMR (400 MHz, CDCl₃) δ 8.67 (s, 1H), 8.59 (s, 1H), 8.45 (d, J=2.0 Hz, 1H), 8.30 (s, 1H), 7.87-7.82 (m, 1H), 7.82 (s, 1H), 7.71 (s, 1H), 7.43 (s, 1H), 7.31 (brs, 3H), 6.74 (d, J=8.8 Hz, 1H), 4.02 (s, 3H), 3.99 (s, 2H), 3.89 (d, J=12.6 Hz, 2H), 3.69 (d, J=13.3 Hz, 2H), 3.53 (d, J=17.2 Hz, 2H), 2.87-2.73 (m, 1H), 2.07-2.00 (m, 1H). HPLC: 91.70%.

Example 246: 6-(1-methyl-1H-pyrazol-4-yl)-4-(6-(4-(3-(4-(trifluoromethyl)phenyl)prop-2-yn-1-yl) piperazine-1-yl)pyridin-3-yl)pyrazolo[1,5-a]pyridine-3-carbonitrile

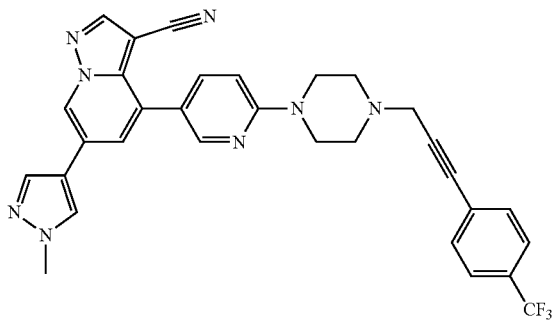

(246)

Step 1: 3-(4-(trifluoromethyl)phenyl)prop-2-yn-1-ol

To a mixture of 1-iodo-4-(trifluoromethyl)benzene (700 mg, 2.57 mmol), Pd(PPh₃)₂Cl₂ (90 mg, 0.13 mmol) and CuI (24 mg, 0.13 mmol) were sequentially added triethylamine (4.5 mL, 32 mmol) and propargyl alcohol (0.30 mL, 5.1 mmol) at room temperature under nitrogen. A black suspension was obtained. The mixture was reacted at room temperature overnight. The mixture was concentrated in vacuo to remove the solvent, and the residue was purified by silica gel column chromatography (PE:EA=4:1) to give pale yellow oil 500 mg as the target product (the yield was 97.07%). Rf=0.25 (PE:EA=4:1).

Step 2: 3-(4-(trifluoromethyl)phenyl)propynal

To a solution of 3-(4-(trifluoromethyl)phenyl)prop-2-yn-1-ol (500 mg, 2.50 mmol) in DCM (25.0 mL) were added sodium bicarbonate (1.05 g, 12.4 mmol) and Dess Martin reagent (1.39 g, 3.24 mmol) at room temperature. The mixture was reacted for 2 h at room temperature. The reaction was quenched with saturated sodium thiosulfate solution (20 mL). After layering, the mixture was extracted with DCM (50 mL×2). The organic phases were combined, dried over anhydrous sodium sulfate, filtered and concentrated in vacuo. The residue was purified by silica gel column chromatography (PE:EA=10:1) to give a white solid 434 mg as the target product (yield: 87.68%). Rf=0.8 (PE:EA=4:1). ¹H NMR (400 MHz, CDCl₃) δ 9.44 (s, 1H), 7.70 (t, J=8.2 Hz, 2H), 7.66 (d, J=8.3 Hz, 2H).

Step 3: 6-(1-methyl-1H-pyrazol-4-yl)-4-(6-(4-(3-(4-(trifluoromethyl)phenyl)prop-2-yn-1-yl) piperazine-1-yl)pyridin-3-yl)pyrazolo[1,5-a]pyridine-3-carbonitrile To a single-necked flask were sequentially added 6-(1-methyl pyrazol-4-yl)-4-(6-piperazin-1-yl-3-pyridyl)pyrazolo[1,5-a]pyridine-3-carbonitrile dihydrochloride (see synthesis of intermediate 2, 15 mg, 0.033 mmol), 3-[4-(trifluoromethyl)phenyl]prop-2-ynaldehyde (13 mg, 0.065 mmol) and DCE (2 mL). After stirring for 10 min, sodium triacetoxyborohydride (21 mg, 0.096 mmol) was added. The mixture was stirred at room temperature overnight. Then the mixture was directly concentrated in vacuo, and then purified by silica gel column chromatography (DCM:MeOH=0-100:3.5) to give a pale yellow solid 15 mg as the target product (the yield was 80.73%). Rf=0.5 (DCM/MeOH=20/1). LC-MS: m/z=567.2 [M+H]⁺. ¹H NMR (400 MHz, CDCl₃) δ 8.66 (d, J=1.3 Hz, 1H), 8.40 (d, J=2.3 Hz, 1H), 8.28 (s, 1H), 7.81 (s, 1H), 7.78 (dd, J=8.8, 2.5 Hz, 1H), 7.70 (s, 1H), 7.63-7.51 (m, 4H), 7.41 (d, J=1.3 Hz, 1H), 6.83 (d, J=8.8 Hz, 1H), 4.01 (s, 3H), 3.84-3.71 (m, 4H), 3.66 (s, 2H), 2.88-2.73 (m, 4H). ¹⁹F NMR (376 MHz, CDCl₃) δ −62.82. HPLC: 87.54%.

Example 247: 6-(1-methylpyrazol-4-yl)-4-[6-[4-[3-(2-pyridyl)prop-2-ynyl]piperazin-1-yl]-3-pyridyl]pyrazolo[1,5-a]pyridine-3-carbonitrile

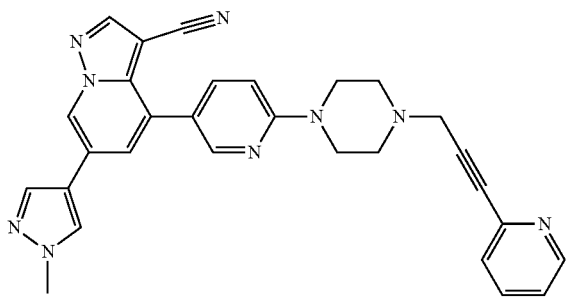

(247)

Step 1: 3-(2-pyridyl)prop-2-yn-1-ol

To a 25 mL two-necked flask were added CuI (60 mg, 0.315 mmol) and PdCl₂(PPh₃)₂ (222 mg, 0.316 mmol) at room temperature. The reaction mixture was degassed and refilled with nitrogen. Then triethylamine (9.5 mL, 68 mmol), propynyl alcohol (0.744 mL, 12.7 mmol) and 2-bromopyridine (0.6 mL, 6 mmol) were added. The mixture was reacted at 50° C. overnight. TLC showed the reaction was completed. The reaction solution was concentrated in vacuo, washed with 15 mL of saturated ammonium chloride, extracted with EA (40 mL×2), and filtered by suction. The solid was washed with EA (10 mL×3). The combined organic phases were washed with saturated saline (15 mL×2), dried over anhydrous sodium sulfate, filtered, and concentrated in vacuo. The mixture was purified by silica gel column chromatography (eluent PE:EA=3:1-1:1) to give a yellow-white product 0.664 g (the yield was 80%), which was the target product. LC-MS (ES-API): m/z=134.25 [M+H]⁺. ¹H NMR (400 MHz, CDCl₃) δ 8.56 (d, J=4.3 Hz, 1H), 7.66 (td, J=7.8, 1.7 Hz, 1H), 7.43 (d, J=7.8 Hz, 1H), 7.24 (dd, J=4.6, 3.0 Hz, 1H), 4.53 (s, 2H), 2.63 (s, 1H).

Step 2: 2-(3-bromoprop-1-ynyl)pyridine 3-(2-Pyridyl)prop-2-yn-1-ol (100 mg, 0.225 mmol) was dissolved in DCM (10 mL) in a 25 mL single-necked flask at 0° C., then PBr₃ (0.141 mL, 0.45 mmol) was slowly added. The mixture was continuously reacted at this temperature. TLC showed the reaction was completed. The reaction was quenched by the addition of water (5 mL) slowly, and saturated potassium carbonate solution (15 mL) was added dropwise to adjust the pH of the reaction mixture to alkaline. The mixture was extracted with DCM (30 mL×2) and saturated brine (20 mL), dried over anhydrous sodium sulfate, filtered, and concentrated in vacuo, which was directly used in the next step. The yield was calculated as 100%.

Step 3: 6-(1-methylpyrazol-4-yl)-4-[6-[4-[3-(2-pyridyl)prop-2-ynyl]piperazin-1-yl]-3-pyridyl]pyrazolo[1,5-a]pyridine-3-carbonitrile To a 5 mL single-necked flask were added 6-(1-methyl pyrazol-4-yl)-4-(6-piperazin-1-yl-3-pyridyl)pyrazolo[1,5-a] pyridine-3-carbonitrile dihydrochloride (see synthesis of intermediate 2, 15 mg, 0.033 mmol), K₂CO₃ (18.3 mg, 0.131 mmol), DMF (2 mL) and 2-(3-bromoprop-1-ynyl)pyridine (25 mg, 0.128 mmol). The mixture was stirred for reaction at room temperature. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent pure DCM-DCM:MeOH (v:v=20:1)) to give a pale yellow solid 0.012 g (the yield was 73%), which was the target product. LC-MS (ES-API): m/z=500.2[M+H]⁺. ¹H NMR (400 MHz, CDCl₃) δ 8.63 (d, J=1.1 Hz, 1H), 8.57 (d, J=4.8 Hz, 1H), 8.36 (d, J=2.4 Hz, 1H), 8.26 (s, 1H), 7.78 (d, J=6.1 Hz, 1H), 7.75 (dd, J=8.8, 2.5 Hz, 1H), 7.67 (d, 7=5.1 Hz, 1H), 7.66-7.60 (m, 1H), 7.45 (d, J=7.8 Hz, 1H), 7.39 (s, 1H), 7.25-7.20 (m, 1H), 6.80 (d, J=8.9 Hz, 1H), 3.99 (s, 3H), 3.78-3.70 (m, 4H), 3.65 (s, 2H), 2.83-2.75 (m, 4H). HPLC: 91.10%.

Example 248: 6-(1-methylpyrazol-4-yl)-4-[6-[4-[3-(3-pyridyl)prop-2-ynyl]piperazin-1-yl]-3-pyridyl]pyrazolo[1,5-a]pyridine-3-carbonitrile (248)

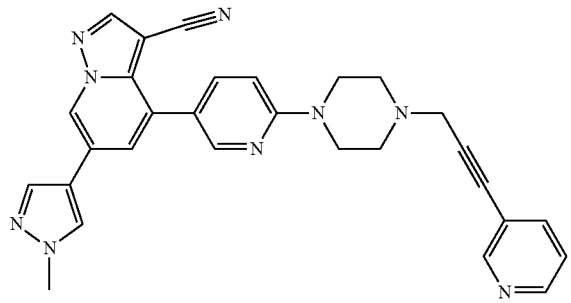

Step 1: 3-(3-pyridyl)prop-2-yn-1-ol

To a 25 mL two-necked flask were added CuI (72 mg, 0.378 mmol) and PdCl₂(PPh₃)₂ (270 mg, 0.385 mmol) at room temperature. The reaction mixture was degassed and refilled with nitrogen. Then triethylamine (11 mL, 78.9 mmol), propynyl alcohol (0.89 mL, 15 mmol) and 3-bromopyridine (0.73 mL, 7.6 mmol) were added. The mixture was reacted at 50° C. overnight. TLC showed the reaction was completed. The mixture was quenched with saturated ammonium chloride (20 mL) and filtered by suction. The filter cake was washed with 40 mL of EA. The organic phase was separated, and then the aqueous phase was extracted with EA (40 mL×2). The organic phases were combined, washed with saturated brine (30 mL), dried over anhydrous sodium sulfate, filtered and concentrated in vacuo. The mixture was purified by silica gel column chromatography (eluent PE:EA=3:1-1:1) to give a brownish yellow solid 0.705 g (the yield was 70%), which was the target product. LC-MS (ES-API): m/z=134.20 [M+H]⁺. ¹H NMR (400 MHz, CDCl₃) δ 8.76 (d, J=1.3 Hz, 1H), 8.51 (dd, J=4.9, 1.5 Hz, 1H), 7.73 (dt, J=7.9, 1.8 Hz, 1H), 7.31-7.26 (m, 1H), 4.50 (s, 2H), 3.72 (s, 1H).

Step 2: 3-(3-bromoprop-1-ynyl)pyridine 3-(3-Pyridyl)prop-2-yn-1-ol (200 mg, 1.502 mmol) was dissolved in DCM (15 mL) in a 25 mL single-necked flask at 0° C., then PBr₃ (0.282 mL, 3.00 mmmol) was slowly added. The mixture was reacted at this temperature. TLC showed the reaction was completed. The reaction was quenched by the addition of water (5 mL) slowly, and saturated potassium carbonate solution was added dropwise to adjust the pH to alkaline. The mixture was extracted with DCM (20 mL×2) and saturated brine (15 mL), dried over anhydrous sodium sulfate, filtered, and concentrated in vacuo, which was directly used in the next step. The yield was calculated as 100%.

Step 3: 6-(1-methylpyrazol-4-yl)-4-[6-[4-[3-(3-pyridyl)prop-2-ynyl]piperazin-1-yl]-3-pyridyl]pyrazolo[1,5-a]pyridine-3-carbonitrile To a 5 mL single-necked flask were added 6-(1-methyl pyrazol-4-yl)-4-(6-piperazin-1-yl-3-pyridyl)pyrazolo[1,5-a] pyridine-3-carbonitrile dihydrochloride (see synthesis of intermediate 2, 15 mg, 0.033 mmol), K₂CO₃ (18.3 mg, 0.131 mmol) and 3-(3-bromoprop-1-ynyl)pyridine (25 mg, 0.128 mmol, 100 mass %), which was dissolved by adding DMF (1.5 mL). The mixture was stirred for reaction at room temperature overnight. TLC showed that the reaction was completed. The mixture was quenched with water (9 mL) and extracted with EA (15 mL×2). The organic phases were washed with saturated saline (10 mL), dried over anhydrous sodium sulfate, filtered, and concentrated in vacuo. The mixture was purified by silica gel column chromatography (eluent pure DCM-DCM:MeOH (v:v=25:1)) to give a pale yellow solid 0.008 g (the yield was 50%), which was the target product. LC-MS (ES-API): m/z=500.2 [M+H]⁺. ¹H NMR (600 MHz, CDCl₃) δ 8.68 (s, 1H), 8.63 (s, 1H), 8.52 (d, J=4.5 Hz, 1H), 8.37 (d, J=2.3 Hz, 1H), 8.26 (s, 1H), 7.78 (s, 1H), 7.77-7.72 (m, 2H), 7.68 (s, 1H), 7.39 (s, 1H), 7.25-7.22 (m, 1H), 6.81 (d, J=8.8 Hz, 1H), 3.99 (s, 3H), 3.75 (s, 4H), 3.64 (s, 2H), 2.84-2.73 (m, 4H). HPLC: 94.92%.

Example 249: 6-(1-methylpyrazol-4-yl)-4-[6-[6-[3-(3-pyridyl)prop-2-ynyl]-3,6-diazabicyclo[3.1.1]heptan-3-yl]-3-pyridyl]pyrazolo[1,5-a]pyridine-3-carbonitrile

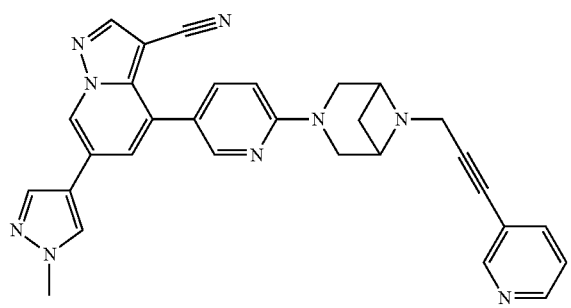

(249)

Step 1: 3-(3-pyridyl)prop-2-yn-1-ol

To a 25 mL two-necked flask were added CuI (72 mg, 0.378 mmol) and PdCl$_2$(PPh$_3$)$_2$ (270 mg, 0.385 mmol) at room temperature. The reaction mixture was degassed and refilled with nitrogen. Then triethylamine (11 mL, 78.9 mmol), propynyl alcohol (0.89 mL, 15 mmol) and 3-bromopyridine (0.73 mL, 7.6 mmol) were added. The mixture was reacted at 50° C. overnight. TLC showed the reaction was completed. The mixture was quenched with saturated ammonium chloride (20 mL) and filtered by suction. The filter cake was washed with 40 mL of EA. The organic phase was separated, and then the aqueous phase was extracted with EA (40 mL×2). The organic phases were combined, washed with saturated brine (30 mL), dried over anhydrous sodium sulfate, filtered and concentrated in vacuo. The mixture was purified by silica gel column chromatography (eluent PE:EA=3:1-1:1) to give a brownish yellow solid 0.705 g (the yield was 70%), which was the target product. LC-MS (ES-API): m/z=134.20 [M+H]$^+$. $^1$H NMR (400 MHz, CDCl$_3$) δ 8.76 (d, J=1.3 Hz, 1H), 8.51 (dd, J=4.9, 1.5 Hz, 1H), 7.73 (dt, J=1.9, 1.8 Hz, 1H), 7.31-7.26 (m, 1H), 4.50 (s, 2H), 3.72 (s, 1H).

Step 2: 3-(3-bromoprop-1-ynyl)pyridine 3-(3-Pyridyl)prop-2-yn-1-ol (200 mg, 1.502 mmol) was dissolved in DCM (15 mL) in a 25 mL single-necked flask at 0° C., then PBr$_3$ (0.282 mL, 3.00 mmmol) was slowly added. The mixture was reacted at this temperature. TLC showed the reaction was completed. The reaction was quenched by the addition of water (5 mL) slowly, and saturated potassium carbonate solution was added dropwise to adjust the pH of reaction mixture to alkaline. The mixture was extracted with DCM (20 mL×2) and saturated brine (15 mL), dried over anhydrous sodium sulfate, filtered, and concentrated in vacuo, which was directly used in the next step. The yield was calculated as 100%.

Step 3: 6-(1-methylpyrazol-4-yl)-4-[6-[6-[3-(3-pyridyl)prop-2-ynyl]-3,6-diazabicyclo[3.1.1]heptan-3-yl]-3-pyridyl]pyrazolo[1,5-a]pyridine-3-carbonitrile To a 5 mL single-necked flask were added 4-(6-(3,6-diazabicyclo[3.1.1]heptan-3-yl)pyridin-3-yl)-6-(1-methyl-1H-pyrazol-4-yl)pyrazole[1,5-a]pyridine-3-carbonitrile dihydrochloride (see synthesis of intermediate 3, 15 mg, 0.032 mmol), K$_2$CO$_3$ (18.3 mg, 0.131 mmol) and 3-(3-bromoprop-1-ynyl)pyridine (25 mg, 0.128 mmol), which were dissolved by adding DMF (1.5 mL). The mixture was stirred for reaction at room temperature overnight. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent pure DCM-DCM:MeOH (v:v=25:1)) to give a pale yellow solid 0.0065 g (the yield was 40%), which was the target product. LC-MS (ES-API): m/z=512.2 [M+H]$^+$. $^1$H NMR (400 MHz, CDCl$_3$) δ 8.68 (s, 2H), 8.55 (d, 1H), 8.46 (d, J=2.2 Hz, 1H), 8.31 (s, 1H), 7.88-7.79 (m, 2H), 7.78-7.69 (m, 2H), 7.44 (s, 1H), 7.25 (s, 1H), 6.76 (d, J=8.9 Hz, 1H), 4.03 (s, 4H), 3.92 (d, J=12.3 Hz, 2H), 3.78-3.63 (m, 2H), 3.58 (s, 2H), 2.31 (dt, J=49.8, 7.6 Hz, 1H), 2.09-1.96 (m, 2H). HPLC: 94.79%.

Example 250: 6-(1-methyl-1H-pyrazol-4-yl)-4-(6-(6-(3-phenylprop-2-yn-1-yl)-3,6-diazabicyclo[3.1.1]heptanpyridin-3-yl)pyridin-3-yl)pyrazolo[1,5-a]pyridine-3-carbonitrile

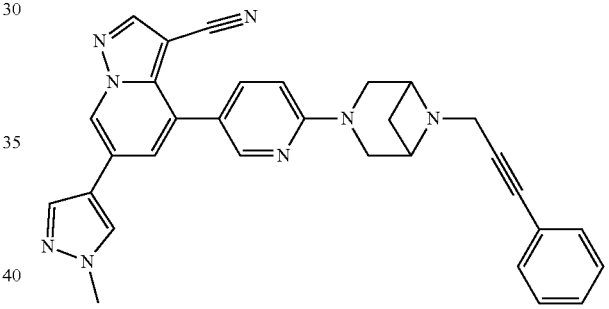

(250)

Step 1: 3-phenylpropan-2-yn-1-ol

To a 50 mL two-necked bottle were sequentially added with Pd(PPh$_3$)$_2$Cl$_2$ (209 mg, 0.295 mmol), CuI (112 mg, 0.588 mmol), triethylamine (20 mL), iodobenzene (1.64 mL, 14.7 mmol) and prop-2-yn-1-ol (1.71 mL, 29.4 mmol) under nitrogen. The mixture was stirred at room temperature for 12 h. The reaction mixture was filtered, then washed with EA (100 mL). The filtrate was concentrated in vacuo, and the residue was purified by silica gel column chromatography (PE:EA=50:1-20:1) to give pale yellow oil 1.94 g as the target product (yield: 99.8%). $^1$H NMR (600 MHz, CDCl$_3$) δ 7.47-7.41 (m, 2H), 7.35-7.28 (m, 3H), 4.50 (d, J=3.8 Hz, 2H), 1.96 (s, 1H).

Step 2: 3-phenylpropiolaldehyde

To a solution of 3-phenylprop-2-yn-1-ol (1.00 g, 7.57 mmol) in DCE (20 mL) were sequentially added sodium bicarbonate (3.18 g, 37.8 mmol) and Dess Martin reagent (4.86 g, 11.3 mmol) at room temperature. The mixture was reacted for 5.5 h at room temperature. The reaction was quenched with saturated Na$_2$S$_2$O$_3$ and the resulting mixture was extracted with DCM (100 mL×2). The organic phases were combined, dried over anhydrous sodium sulfate and filtered. The mother liquor was concentrated in vacuo and purified by silica gel column chromatography (PE:EA=50:1-20:1) to give yellow oil 832 mg as the target product (yield: 84.5%). $^1$H NMR (400 MHz, CDCl$_3$) δ 9.43 (s, 1H), 7.61 (d, J=7.1 Hz, 2H), 7.50 (t, J=7.5 Hz, 1H), 7.41 (t, J=7.5 Hz, 2H).

Step 3: 6-(1-methyl-1H-pyrazol-4-yl)-4-(6-(6-(3-phenylprop-2-yn-1-yl)-3,6-diazabicyclo[3.1.1]heptanpyridin-3-yl)pyridin-3-yl)pyrazolo[1,5-a]pyridine-3-carbonitrile In a single-necked flask, 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and 3-phenylprop-2-ynaldehyde (18 mg, 0.138 mmol) were dissolved in DCE (1 mL), then sodium triacetoxyborohydride (19 mg, 0.087 mmol) was added. The mixture was stirred at room temperature overnight. The reaction mixture was directly concentrated in vacuo, and the residue was purified by silica gel column chromatography (DCM/MeOH=0-100:3.5) to give a pale yellow solid 9.6 mg as the target product (the yield is 59%). LC-MS: m/z=511.2 [M+H]$^+$. $^1$H NMR (400 MHz, CDCl$_3$) δ 8.64 (d, 7=1.1 Hz, 1H), 8.43 (d, 7=2.3 Hz, 1H), 8.27 (s, 1H), 7.83-7.79 (m, 2H), 7.68 (s, 1H), 7.43-7.41 (m, 3H), 7.31-7.27 (m, 3H), 6.72 (d, J=8.8 Hz, 1H), 3.99 (s, 3H), 3.97 (d, J=6.1 Hz, 2H), 3.88 (d, J=12.3 Hz, 2H), 3.67 (d, J=11.3 Hz, 2H), 3.52 (s, 2H), 2.41-2.28 (m, 1H), 2.27-2.15 (m, 1H). HPLC: 90.48%.

Example 251: 4-(6-(4-(3-(4-methoxyphenyl)prop-2-yn-1-yl)piperazin-1-yl)pyridin-3-yl)-6-(1-methyl-1H-pyrazolpyridin-4-yl)pyrazolo[1,5-a]pyridine-3-carbonitrile (251)

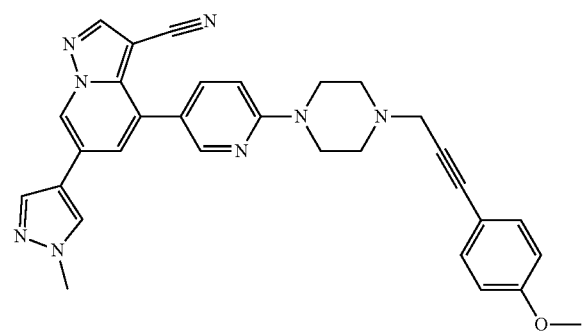

Step 1: 3-(4-methoxyphenyl)prop-2-yn-1-ol

To a 25 mL three-necked flask under nitrogen were sequentially added 4-iodoanisole (2.5 g, 11 mmol), cuprous iodide (0.24 g, 1.3 mmol) and bistriphenylphosphine palladium dichloride (0.22 g, 0.31 mmol), which were dissolved by adding triethylamine (25 mL). Then propargyl alcohol (0.93 mL, 16 mmol) was added dropwise at 0° C. After the dropwise addition, the mixture was reacted at this temperature. The completion of reaction was monitored by TLC. The mixture was filtered through a celite pad. The filter cake was washed with EA (50 mL), filtered, concentrated in vacuo, and then purified by silica gel column chromatography (eluent: PE:EA=20:1-10:1) to give a yellow solid 1.56 g as the target product (yield: 90.0%, Rf=0.1 (PE/EA=20/1)). $^1$H NMR (400 MHz, CDCl$_3$) δ 7.38 (d, J=8.8 Hz, 2H), 6.84 (d, J=8.8 Hz, 2H), 4.48 (s, 2H), 3.81 (s, 3H).

Step 2: 3-(4-methoxyphenyl)propiolaldehyde

To a 50 mL single-necked flask were sequentially added 3-(4-methoxyphenyl)prop-2-yn-1-ol (600 mg, 3.6996 mmol,), Dess Martin reagent (2.1 g, 5.0 mmol), sodium bicarbonate (1.6 g, 19 mmol) and dichloromethane solution (30 mL). The mixture was stirred at room temperature overnight. The reaction mixture was quenched with saturated sodium thiosulfate solution (50 mL). After static stratification, the organic phase was separated, and the aqueous phase was extracted with DCM (100 ml×2). The organic phases were combined, dried over anhydrous sodium sulfate, filtered, concentrated in vacuo, and then purified by silica gel column chromatography (PE/EA=15:1) to give yellow liquid 510 mg, which was the target product (yield: 86.067%, Rf=0.7 (PE/EA=8/1)). $^1$H NMR (400 MHz, CDCl$_3$) δ 9.39 (s, 1H), 7.62-7.52 (m, 2H), 6.92 (d, J=8.9 Hz, 2H), 3.85 (s, 3H).

Step 3: 4-(6-(4-(3-(4-methoxyphenyl)prop-2-yn-1-yl)piperazin-1-yl)pyridin-3-yl)-6-(1-methyl-1H-pyrazolpyridin-4-yl)pyrazolo[1,5-a]pyridine-3-carbonitrile To a 5 mL single-necked flask were sequentially added 6-(1-methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 15 mg, 0.033 mmol), STAB (23 mg, 0.1085 mmol), DCE (2 mL) and 3-(4-methoxyphenyl)propiolaldehyde (25 mg, 0.156 mmol). The mixture was stirred at room temperature overnight. The reaction mixture was filtered, and the mother liquor was concentrated in vacuo. The residue was purified by silica gel column chromatography (DCM/MeOH=50:1-30:1) to give a yellow solid 6.2 mg as the target product. Rf=0.15 (DCM/MeOH=30/1). LC-MS (ES-API): m/z=529.20 [M+H]$^+$. $^1$H NMR (400 MHz, CDCl$_3$) δ 8.63 (d, J=1.1 Hz, 1H), 8.37 (d, J=2.4 Hz, 1H), 8.26 (s, 1H), 7.78 (s, 1H), 7.76 (dd, J=8.7, 2.5 Hz, 1H), 7.67 (s, 1H), 7.41-7.38 (m, 2H), 7.37 (s, 1H), 6.83 (d, J=8.8 Hz, 3H), 3.99 (s, 3H), 3.80 (s, 3H), 3.76-3.72 (m, 4H), 3.59 (s, 2H), 2.81-2.75 (m, 4H). HPLC: 89.27%.

Example 252: 4-(6-(4-(3-(4-methoxypyridin-2-yl)propan-2-ynyl-1-yl)piperazin-1-yl)pyridin-3-yl)-6-(1-methyl-1H-pyrazolin-4-yl)pyrazole[1,5-a]pyridine-3-carbonitrile (252)

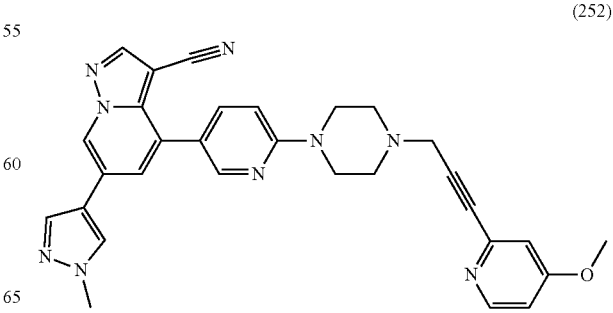

Step 1: 3-(4-methoxypyridin-2-yl)propane-2-yn-1-ol

To a reaction flask were added 2-bromo-4-methoxy-pyridine (1.00 g, 5.32 mmol), CuI (0.10 g, 0.53 mmol), PdCl$_2$(PPh$_3$)$_2$ (0.37 g, 0.53 mmol), PPh$_3$ (0.14 g, 0.53 mmol) and Et$_3$N (10 mL) in turn under N$_2$. Then propane-2-yn-1-ol (0.60 g, 11 mmol) was slowly added. The mixture was reacted with stirring at room temperature for 18 h. The reaction was stopped, and quenched with saturated NH$_4$Cl. The resulting mixture was extracted with EA (10 mL×3), washed with water (10 mL), dried over anhydrous sodium sulfate, and filtered. The filtrate was concentrated in vacuo. The mixture was purified by silica gel column chromatography (eluent PE/EA=10/1-3/1) to give a brownish yellow solid 0.42 g as the target product (the yield was 48%). LC-MS: m/z=164.1[M+H]$^+$.

Step 2: 2-(3-bromopropan-1-yn-1-yl)-4-methoxypyridine 3-(4-Methoxypyridin-2-yl)propane-2-yn-1-ol (120 mg, 0.74 mmol) was dissolved in DCM (5 mL) at 0° C., and PBr$_3$ (0.40 g, 1.5 mmol) was slowly added. The mixture was reacted with stirring at low temperature for 1 h. The reaction was stopped, and quenched with water (5 mL). The resulting mixture was extracted with DCM (10 mL×3), washed with water (10 mL), dried over anhydrous sodium sulfate, and filtered. The filtrate was concentrated in vacuo to give brown viscous liquid 151 mg as the target product (yield: 90%).

Step 3: 4-(6-(4-(3-(4-methoxypyridin-2-yl)propan-2-ynyl-1-yl)piperazin-1-yl)pyridin-3-yl)-6-(1-methyl-1H-pyrazolin-4-yl)pyrazole[1,5-a]pyridine-3-carbonitrile 6-(1-Methyl-1H-pyrazol-4-yl)-4-(6-(piperazin-1-yl)pyridine-3-pyridine)pyrazole[1,5-a]pyridine-3-carbonitrile dihydrochloride (see synthesis of intermediate 2, 18 mg, 0.04 mmol) was dissolved in DMF (2 mL)), and K$_2$CO$_3$ (22 mg, 0.16 mmol) was added. 2-(3-Bromopropan-1-yn-1-yl)-4-methoxypyridine (27 mg, 0.12 mmol) was added slowly, and the mixture was stirred for reaction at room temperature for 16 h. The reaction mixture was poured into ice water (10 mL), then the resulting mixture was extracted with EA (10 mL×3), washed with water (10 mL), dried over anhydrous sodium sulfate, filtered, and then concentrated in vacuo. The mixture was purified by silica gel column chromatography (eluent DCM/CH$_3$OH=50/1-20/1) to give a brown solid 10 mg as the target product (the yield was 29%). LC-MS: m/z=530.1[M+H]$^+$. HPLC purity: 92.21%. $^1$H NMR (400 MHz, CDCl$_3$) δ 8.65 (s, 1H), 8.39 (d, J=5.6 Hz, 2H), 8.28 (s, 1H), 7.81 (s, 1H), 7.77 (dd, J=8.8, 2.4 Hz, 1H), 7.70 (s, 1H), 7.41 (s, 1H), 7.00 (d, J=2.4 Hz, 1H), 6.82 (d, J=8.9 Hz, 1H), 6.79 (dd, J=5.8, 2.4 Hz, 1H), 4.01 (s, 3H), 3.87 (s, 3H), 3.80-3.72 (m, 4H), 3.66 (s, 2H), 2.86-2.75 (m, 4H). HPLC: 92.21%.

Example 253: 6-(1-methyl-1H-pyrazol-4-yl)-4-(6-(4-(3-phenylprop-2-yn-1-yl)piperazin-1-yl) pyridine-3-yl)pyrazolo[1,5-a]pyridine-3-carbonitrile

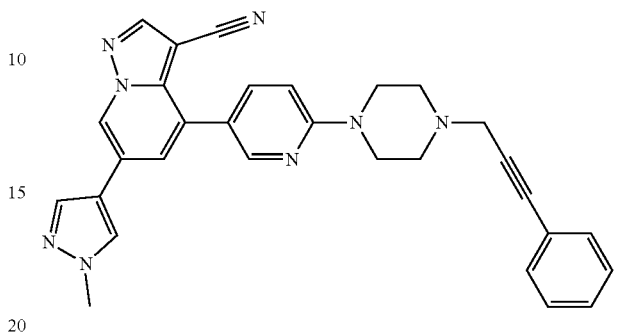

(253)

Step 1: 3-phenylpropan-2-yn-1-ol

To a 50 mL two-necked bottle were sequentially added with Pd(PPh$_3$)$_2$Cl$_2$ (209 mg, 0.295 mmol), CuI (112 mg, 0.588 mmol), triethylamine (20 mL), iodobenzene (1.64 mL, 14.7 mmol) and prop-2-yn-1-ol (1.71 mL, 29.4 mmol) under nitrogen. The mixture was stirred at room temperature for 12 h. The reaction mixture was filtered, then washed with EA (100 mL). The filtrate was concentrated in vacuo, and the residue was purified by silica gel column chromatography (PE:EA=50:1-20:1) to give pale yellow oil 1.94 g as the target product (yield: 99.8%). $^1$H NMR (600 MHz, CDCl$_3$) δ 7.47-7.41 (m, 2H), 7.35-7.28 (m, 3H), 4.50 (d, J=3.8 Hz, 2H), 1.96 (s, 1H).

Step 2: 3-phenylpropiolaldehyde

To a solution of 3-phenylprop-2-yn-1-ol (1.00 g, 7.57 mmol) in DCE (20 mL) were sequentially added sodium bicarbonate (3.18 g, 37.8 mmol) and Dess Martin reagent (4.86 g, 11.3 mmol) at room temperature. The mixture was reacted for 5.5 h at room temperature. The reaction was quenched with saturated Na$_2$S$_2$O$_3$ and the resulting mixture was extracted with DCM (100 mL×2). The organic phases were combined, dried over anhydrous sodium sulfate and filtered. The mother liquor was concentrated in vacuo and purified by silica gel column chromatography (PE:EA=50:1-20:1) to give yellow oil 832 mg as the target product (yield: 84.5%). $^1$H NMR (400 MHz, CDCl$_3$) δ 9.43 (s, 1H), 7.61 (d, J=7.1 Hz, 2H), 7.50 (t, J=7.5 Hz, 1H), 7.41 (t, J=7.5 Hz, 2H).

Step 3: 6-(1-methyl-1H-pyrazol-4-yl)-4-(6-(4-(3-phenylprop-2-yn-1-yl)piperazin-1-yl)pyridine-3-yl) pyrazolo[1,5-a]pyridine-3-carbonitrile 6-(1-Methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 15 mg, 0.033 mmol) and 3-phenylpropan-2-ynaldehyde (18 mg, 0.138 mmol) were dissolved with DCE (2 mL) in a single-necked flask, then sodium triacetoxyborohydride (19 mg, 0.087 mmol) was added. The mixture was stirred at room temperature overnight. The reaction mixture was concentrated in vacuo, and then purified by silica gel column chromatography (DCM/MeOH=0-100/3.5) to give a pale yellow solid 7 mg as the target product (the yield was 42.81%). LC-MS: m/z=499.2[M+H]+. 1H NMR (400 MHz, CDCl3) δ 8.66 (d, J=1.2 Hz, 1H), 8.40 (d, J=2.3 Hz, 1H), 8.28 (s, 1H), 7.85-7.75 (m, 2H), 7.70 (s, 1H), 7.47 (dd, J=6.5, 3.0 Hz, 2H), 7.41 (d, J=1.3 Hz, 1H), 7.38-7.30 (m, 3H), 6.83 (d, J=8.9 Hz, 1H), 4.01 (s, 3H), 3.79 (s, 4H), 3.66 (s, 2H), 2.85 (s, 4H). HPLC: 97.82%.

Example 254: 4-(6-(4-(3-(5-methoxypyridin-3-yl) prop-2-yn-1-yl)piperazin-1-yl)pyridin-3-yl)-6-(1-methyl-1H-pyrazol-4-yl)pyrazolo[1,5-a]pyridine-3-carbonitrile

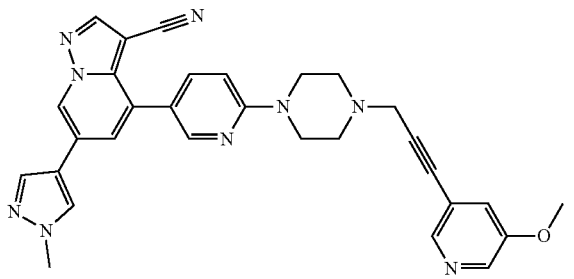

(254)

Step 1: 3-(5-methoxypyridin-3-yl)prop-2-yn-1-ol

To a two-necked flask under nitrogen were added 3-bromo-5-methoxy-pyridine (600 mg, 3.2 mmol), PdCl2(PPh3)2 (224 mg, 0.32 mmol) and copper iodide (122 mg, 0.64 mmol), which were dissolved by adding 5 mL of TEA. Then prop-2-yn-1-ol (0.23 mL, 4.0 mmol) was added with stirring, and the mixture was reacted in an oil bath at 70° C. for heating. After the reaction was completed, the reaction mixture was filtered by suction through a celite pad. The filter cake was washed with a small amount of EA, and the filtrate was concentrated in vacuo, and then purified by silica gel column chromatography (eluent EA:PE=1:5-1:2) to give a white solid 233 mg as the desired product. 1H NMR (400 MHz, CDCl3) δ 8.34 (d, J=1.0 Hz, 1H), 8.23 (d, J=2.7 Hz, 1H), 7.23 (s, 1H), 4.50 (s, 2H), 3.84 (s, 3H), 3.08 (s, 1H).

Step 2: 3-(3-bromoprop-1-yn-1-yl)-5-methoxypyridine 3-(5-Methoxypyridin-3-yl)prop-2-yn-1-ol (60 mg, 0.37 mmol) was dissolved in 2 mL of DCM in a single-necked flask at 0° C., and PBr3 (10 mg, 0.037 mmol) was added dropwise with stirring. After the addition, the mixture was continuously stirred at this temperature. After the raw materials were consumed completely monitored by TLC, the reaction mixture was added with saturated sodium bicarbonate with stirring to adjust the pH of the aqueous phase to 8. The resulting mixture was diluted with DCM (10 mL), and the organic phase was separated, washed with water (5 mL) once, dried over anhydrous sodium sulfate, concentrated in vacuo to remove part of DCM to obtain a thick material, which was directly used for the next reaction and was calculated according to the theoretical yield.

Step 3: 4-(6-(4-(3-(5-methoxypyridin-3-yl)prop-2-yn-1-yl)piperazin-1-yl)pyridin-3-yl)-6-(1-methyl-1H-pyrazol-4-yl)pyrazolo[1,5-a]pyridine-3-carbonitrile To a 10 mL single-necked flask were added 6-(1-methyl pyrazol-4-yl)-4-(6-piperazin-1-yl-3-pyridyl)pyrazolo[1,5-a] pyri di ne-3-carbonitrile dihydrochloride (see synthesis of intermediate 2, 15 mg, 0.033 mmol), K2CO3 (14 mg, 0.10 mmol) and DMF (2 mL). 3-(3-bromoprop-1-ynyl)-5-methoxy-pyridine (11 mg, 0.049 mmol) was added with stirring at 0° C. After the addition, the mixture was continuously reacted at room temperature. After the completion of reaction was monitored by TLC, the reaction mixture was added with water (10 mL) and extracted with EA (30 mL×2). The organic phases were washed with water (10 mL×2) and saturated saline (10 mL), dried over anhydrous sodium sulfate and filtered. The mother liquor was concentrated in vacuo, and then purified by silica gel column chromatography (eluent MeOH:DCM=1:50-1:30) to give a light yellow solid 2 mg as the target product. Rf=0.3 (DCM/MeOH=20: 1). LC-MS: m/z=530.20[M+H]+. 1H NMR (400 MHz, CDCl3) δ 8.63 (s, 1H), 8.38 (d, J=2.4 Hz, 1H), 8.26 (s, 1H), 7.79 (s, 1H), 7.76 (dd, J=8.8, 2.4 Hz, 1H), 7.68 (s, 1H), 7.39 (s, 1H), 7.35 (d, J=2.3 Hz, 2H), 7.08 (dd, J=8.3, 2.4 Hz, 1H), 6.81 (d, J=8.9 Hz, 1H), 3.99 (s, 3H), 3.85 (s, 3H), 3.77-3.73 (m, 4H), 3.63 (s, 2H), 2.81-2.77 (m, 4H). HPLC: 93.46%.

Example 255: 4-[6-[4-[3-(2-fluoro-3-pyridyl)prop-2-ynyl]piperazin-1-yl]-3-pyridyl]-6-(1-methylpyrazol-4-yl)pyrazolo[1,5-a]pyridine-3-carbonitrile

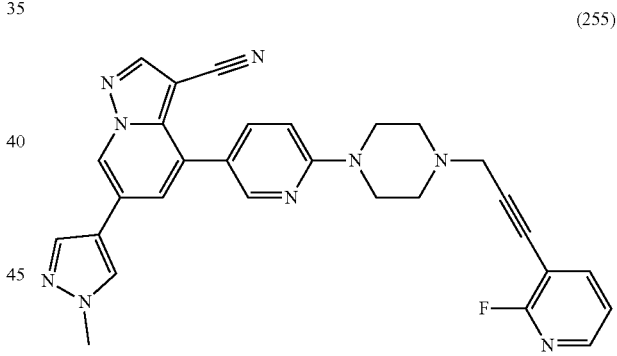

(255)

Step 1: 3-(2-fluoro-3-pyridyl)prop-2-yn-1-ol

To a 25 mL two-necked flask were added 2-fluoro-3-iodo-pyridine (800 mg, 3.587 mmol), CuI (68.3 mg, 0.359 mmol) and PdCl2(PPh3)2 (126 mg, 0.179 mmol) at room temperature. The reaction mixture was degassed and refilled with nitrogen. Then TEA (5.4 mL, 39 mmol) and prop-2-yn-1-ol (0.42 mL, 7.2 mmol) were added. The mixture was reacted at 50° C. overnight. TLC showed the reaction was completed. The mixture was quenched with saturated ammonium chloride (20 mL) and filtered by suction. The filter cake was washed with 40 mL of EA. The organic phase was separated, and then the aqueous phase was extracted with EA (40 mL×2). The organic phases were combined, washed with saturated brine (30 mL), dried over anhydrous sodium sulfate, filtered and concentrated in vacuo. The mixture was purified by silica gel column chromatography (eluent PE:EA=3:1-1:1) to give a brownish yellow solid 0.485 g (the yield was 89.4%), which was the target product. ¹H NMR (400 MHz, CDCl₃) δ 8.13 (d, J=4.8 Hz, 1H), 7.86-7.78 (m, 1H), 7.14 (ddd, J=6.8, 4.9, 1.6 Hz, 1H), 4.49 (d, J=5.2 Hz, 2H), 3.27 (t, J=5.7 Hz, 1H).

Step 2: 3-(3-bromoprop-1-ynyl)-2-fluoro-pyridine 3-(2-Fluoro-3-pyridyl)prop-2-yn-1-ol (70 mg, 0.463 mmol) was dissolved in DCM (5 mL) in a 10 mL single-necked flask at 0° C., then PBr₃ (0.09 mL, 1 mmol) was slowly added. The mixture was reacted with stirring at this temperature. TLC showed the reaction was completed. The reaction was quenched by the addition of water (2 mL) slowly, and saturated potassium carbonate solution was added dropwise to adjust the pH to alkaline. The mixture was extracted with DCM (10 mL×2) and then concentrated in vacuo to remove DCM, which was directly used in the next step. The yield was calculated as 100%.

Step 3: 4-[6-[4-[3-(2-fluoro-3-pyridyl)prop-2-ynyl]piperazin-1-yl]-3-pyridyl]-6-(1-methylpyrazol-4-yl)pyrazolo[1,5-a]pyridine-3-carbonitrile To a 5 mL single-necked flask were added 6-(1-methyl-1H-pyrazol-4-yl)-4-(6-piperazin-1-yl)pyridin-3-yl)pyrazolo[1,5-a]pyridine-3-carbonitrile dihydrochloride (15 mg, 0.032 mmol) and 3-(3-bromoprop-1-ynyl)-2-fluoro-pyridine (25 mg, 0.117 mmol), then K₂CO₃ (18.3 mg, 0.131 mmol) and DMF (1.5 mL) were added. The mixture was stirred for reaction at room temperature overnight. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent: pure DCM-DCM:MeOH (v:v)=20:1)) to give a pale yellow solid 0.007 g (the yield was 40%), which was the target product. LC-MS (ES-API): m/z=518.0 [M+H]⁺. ¹H NMR (400 MHz, CDCl₃) δ 8.63 (d, 7=1.3 Hz, 1H), 8.37 (d, J=2.4 Hz, 1H), 8.26 (s, 1H), 8.14 (d, J=4.0 Hz, 1H), 7.89-7.80 (m, 1H), 7.79 (s, 1H), 7.75 (dd, J=8.8, 2.5 Hz, 1H), 7.68 (s, 1H), 7.39 (d, J=1.3 Hz, 1H), 7.18-7.13 (m, 1H), 6.81 (d, J=8.8 Hz, 1H), 3.99 (s, 3H), 3.78-3.71 (m, 4H), 3.66 (s, 2H), 2.84-2.74 (m, 4H). HPLC: 95.01%.

Example 256: 4-[6-[6-[3-(2-fluoro-3-pyridyl)prop-2-ynyl]-3,6-diazabicyclo[3.1.1]heptan-3-yl]3-pyridyl]-6-(1-methylpyrazol-4-yl)pyrazolo[1,5-a]pyridine-3-carbonitrile (256)

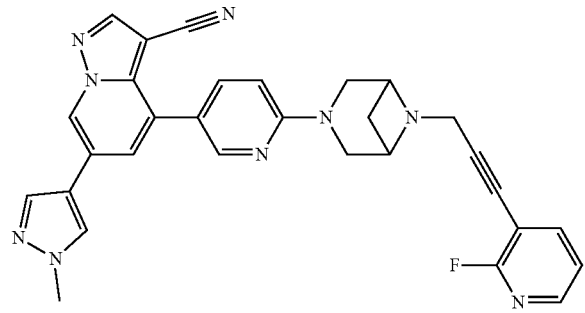

Step 1: 3-(2-fluoro-3-pyridyl)prop-2-yn-1-ol

To a 25 mL two-necked flask were added 2-fluoro-3-iodo-pyridine (800 mg, 3.587 mmol), CuI (68.3 mg, 0.359 mmol) and PdCl₂(PPh₃)₂ (126 mg, 0.179 mmol) at room temperature. The reaction mixture was degassed and refilled with nitrogen. Then TEA (5.4 mL, 39 mmol) and prop-2-yn-1-ol (0.42 mL, 7.2 mmol) were added. The mixture was reacted at 50° C. overnight. TLC showed the reaction was completed. The mixture was quenched with saturated ammonium chloride (20 mL) and filtered by suction. The filter cake was washed with 40 mL of EA. The organic phase was separated, and then the aqueous phase was extracted with EA (40 mL×2). The organic phases were combined, washed with saturated brine (30 mL), dried over anhydrous sodium sulfate, filtered and concentrated in vacuo. The mixture was purified by silica gel column chromatography (eluent PE:EA=3:1-1:1) to give a brownish yellow solid 0.485 g (the yield was 89.4%), which was the target product. ¹H NMR (400 MHz, CDCl₃) δ 8.13 (d, J=4.8 Hz, 1H), 7.86-7.78 (m, 1H), 7.14 (ddd, J=6.8, 4.9, 1.6 Hz, 1H), 4.49 (d, J=5.2 Hz, 2H), 3.27 (t, J=5.7 Hz, 1H).

Step 2: 3-(3-bromoprop-1-ynyl)-2-fluoro-pyridine 3-(2-Fluoro-3-pyridyl)prop-2-yn-1-ol (70 mg, 0.463 mmol) was dissolved in DCM (5 mL) in a 10 mL single-necked flask at 0° C., then PBr₃ (0.09 mL, 1 mmmol) was slowly added. The mixture was reacted with stirring at this temperature. TLC showed the reaction was completed. The reaction was quenched by the addition of water (2 mL) slowly, and saturated potassium carbonate solution was added dropwise to adjust the pH to alkaline. The mixture was extracted with DCM (10 mL×2) and then concentrated in vacuo to remove DCM, which was directly used in the next step. The yield was calculated as 100%.

Step 3: 4-[6-[6-[3-(2-fluoro-3-pyridyl)prop-2-ynyl]-3,6-diazabicyclo[3.1.1]heptan-3-yl]3-pyridyl]-6-(1-methyl pyrazol-4-yl)pyrazolo[1,5-a]pyridine-3-carbonitrile To a 5 mL single-necked flask were added 4-[6-(3,6-diazabicyclo[3.1.1]heptan-3-yl)-3-pyridyl]-6-(1-methylpyrazol-4-yl)pyrazolo[1,5-a]pyridine-3-carbonitrile dihydrochloride (see synthesis of intermediate 3, 15 mg, 0.032 mmol) and 3-(3-bromoprop-1-ynyl)-2-fluoro-pyridine (25 mg, 0.117 mmol). Then K₂CO₃ (18.3 mg, 0.032 mmol) and DMF (1.5 mL) were added. The mixture was stirred for reaction at room temperature overnight. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent: pure DCM-DCM:MeOH (v:v)=20:1)) to give a pale yellow solid 0.007 g (the yield was 40%), which was the target product. LC-MS (ES-API): m/z=530.2 [M+H]⁺. ¹H NMR (400 MHz, CDCl₃) δ 8.65 (d, J=1.1 Hz, 1H), 8.43 (d, J=2.3 Hz, 1H), 8.27 (s, 1H), 8.14 (d, J=3.9 Hz, 1H), 7.82 (dd, J=8.8, 2.1 Hz, 2H), 7.79 (s, 1H), 7.69 (s, 1H), 7.41 (d, J=1.2 Hz, 1H), 7.17-7.13 (m, 1H), 6.73 (d, J=8.8 Hz, 1H), 4.00 (s, 3H), 3.90 (d, J=12.6 Hz, 2H), 3.75-3.69 (m, 2H), 3.59 (s, 2H), 2.83 (s, 1H), 2.22 (t, J=7.7 Hz, 1H), 2.06-1.95 (m, 2H). HPLC: 88.8%.

Example 257: 4-(6-(6-(3-(3-fluoropyridin-2-yl)prop-2-yn-1-yl)piperazin-3-yl)pyridin-3-yl)-6-(1-methyl-1H-pyrazol-4-yl)pyrazoline[1,5-a]pyridine-3-carbonitrile Step 1: 3-(3-fluoropyridin-2-yl)prop-2-yn-1-ol

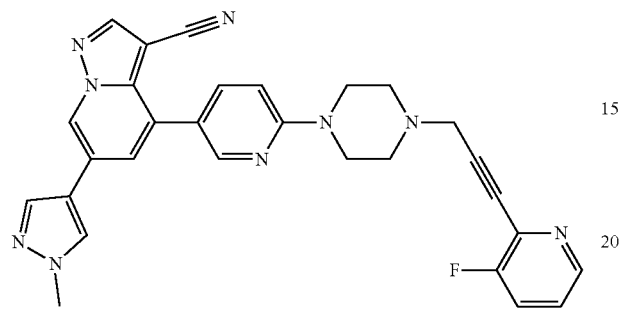

(257)

To a 50 mL two-necked flask under N$_2$ were sequentially added PdCl$_2$(PPh$_3$)$_2$ (180 mg, 0.26 mmol), CuI (136 mg, 0.71 mmol), 2-bromo-3-fluoro-pyridine (830 mg, 4.72 mmol), TEA (12 mL), propargyl alcohol (0.35 mL, 6.0 mmol). The mixture was stirred and heated for reaction for 6 h in a 60° C. oil bath. After the reaction mixture was cooled, water (25 mL) was added, and the resulting mixture was extracted with EA (25 mL×2). The organic phases were combined, dried over anhydrous sodium sulfate and filtered. The mother liquid was concentrated in vacuo, and then purified by silica gel column chromatography (eluent PE/EA=1/1) to give a yellow-white solid 600 mg as the target product (yield 84%). LC-MS(ESI-MS): m/z=152.1 [M+H]$^+$. $^1$H NMR (400 MHz, CDCl$_3$) δ 8.39 (m, 1H), 7.43 (td, J=8.5, 1.0 Hz, 1H), 7.29 (m, 1H), 4.57 (d, 7=5.1 Hz, 2H), 2.82 (t, 7=5.6 Hz, 1H).

Step 2: 2-(3-bromopropan-1-yn-1-yl)-3-fluoropyridine

To a 25 mL single-necked flask were sequentially added 3-(3-fluoropyridin-2-yl)prop-2-yn-1-ol (91 mg, 0.60 mmol) and DCM (6 mL), then PBr$_3$ (0.11 mL, 1.2 mmol) was added slowly at −10° C. After 20 min of addition, the mixture was continuously stirring for 1.5 h. To the reaction solution was slowly added 20 mL of 5% K$_2$CO$_3$ aqueous solution. The aqueous phase was extracted with DCM (30 mL×3). The organic phase was combined, dried over sodium sulfate, filtered, and concentrated in vacuo, which was directly used for the next reaction in equivalent amounts. LC-MS(ESI): m/z=214.0, 216.0 [M+H]$^+$.

Step 3: 4-(6-(6-(3-(3-fluoropyridin-2-yl)prop-2-yn-1-yl)piperazin-3-yl)pyridin-3-yl)-6-(1-methyl-1H-pyrazol-4-yl)pyrazoline[1,5-a]pyridine-3-carbonitrile To a 10 mL single-necked flask were sequentially added 6-(1-methyl-1H-pyrazol-4-yl)-4-(6-(piperazin-1-yl)pyridin-3-yl)pyrazole[1,5-a]pyridine-3-carbonitrile hydrochloride (see synthesis of intermediate 2, 22.5 mg, 0.054 mmol), DMF (2 mL), K$_2$CO$_3$ (29 mg, 0.21 mmol) and 2-(3-bromopropan-1-yn-1-yl)-3-fluoropyridine (60 mg, 0.28 mmol). The mixture was stirred for reaction at rt overnight. The reaction solution was added with EA (20 mL) and washed with water (5 mL×4). The aqueous phases were combined and extracted with EA (30 mL). The combined organic layers were dried over anhydrous sodium sulfate, filtered and concentrated in vacuo. The resulting mixture was purified by silica gel column chromatography (eluent DCM/MeOH=35/1) to give a light yellow solid 16 mg, which was the target product (the yield was 58%). LC-MS(ESI): m/z=518.3 [M+H]$^+$. $^1$H NMR (400 MHz, CDCl$_3$) δ 8.63 (d, J=1.3 Hz, 1H), 8.38 (m, 2H), 8.25 (s, 1H), 7.81-7.72 (m, 2H), 7.68 (s, 1H), 7.43-7.39 (m, 2H), 7.28 (m, 1H), 6.80 (d, J=8.9 Hz, 1H), 3.99 (s, 3H), 3.76-3.72 (m, 5H), 2.87-2.78 (m, 5H). HPLC: 91.09%.

Example 258: 4-(6-(6-(3-(3-fluoropyridin-2-yl)prop-2-yn-1-yl)-3,6-diazabicyclo[3.1.1]heptane-3-yl)pyridin-3-yl)-6-(1-methyl-1H-pyrazol-4-yl)pyrazoline[1,5-a]pyridin-3-carbonitrile

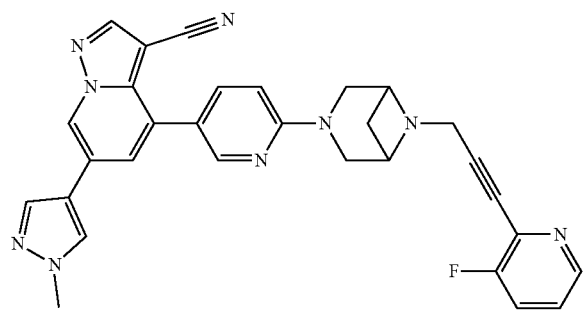

(258)

Step 1: 3-(3-fluoropyridin-2-yl)prop-2-yn-1-ol

To a 50 mL two-necked flask under N$_2$ were sequentially added PdCl$_2$(PPh$_3$)$_2$ (180 mg, 0.26 mmol), CuI (136 mg, 0.71 mmol), 2-bromo-3-fluoro-pyridine (830 mg, 4.72 mmol), TEA (12 mL) and propargyl alcohol (0.35 mL, 6.0 mmol). The mixture was stirred and heated for reaction for 6 h in a 60° C. oil bath. After the reaction mixture was cooled, water (25 mL) was added, and the resulting mixture was extracted with EA (25 mL×2). The organic phases were combined, dried over anhydrous sodium sulfate and filtered. The mother liquid was concentrated in vacuo, and then purified by silica gel column chromatography (eluent PE/EA=1/1) to give a yellow-white solid 600 mg as the target product (yield 84%). LC-MS(ESI): m/z=152.1 [M+H]$^+$. $^1$H NMR (400 MHz, CDCl$_3$) δ 8.39 (m, 1H), 7.43 (td, J=8.5, 1.0 Hz, 1H), 7.29 (m, 1H), 4.57 (d, 7=5.1 Hz, 2H), 2.82 (t, 7=5.6 Hz, 1H).

Step 2: 2-(3-bromopropan-1-yn-1-yl)-3-fluoropyridine

To a 25 mL single-necked flask were sequentially added 3-(3-fluoropyridin-2-yl)prop-2-yn-1-ol (91 mg, 0.60 mmol) and DCM (6 mL), then PBr$_3$ (0.11 mL, 1.2 mmol) was added slowly at −10° C. After 20 min of addition, the mixture was continuously stirring for 1.5 h. To the reaction solution was slowly added 20 mL of 5% K$_2$CO$_3$ aqueous solution. The aqueous phase was extracted with DCM (30 mL×3). The organic phases were combined, dried over sodium sulfate, filtered, and concentrated in vacuo, which was directly used for the next reaction in equivalent amounts. LC-MS(ESI): m/z=214.0, 216.0 [M+H]+.

Step 3: 4-(6-(6-(3-(3-fluoropyridin-2-yl)prop-2-yn-1-yl)-3,6-diazabicyclo[3.1.1]heptane-3-yl) pyridin-3-yl)-6-(1-methyl-1H-pyrazol-4-yl)pyrazoline[1,5-a]pyridin-3-carbonitrile To a 10 mL single-necked flask were sequentially added 4-[6-(3,6-diazabicyclo[3.1.1]heptan-3-yl)-3-pyridyl]-6-(1-methylpyrazol-4-yl)pyrazoline[1,5-a]pyri dine-3-carbonitrile dihydrochloride (see synthesis of intermediate 3, 25 mg, 0.058 mmol), DMF (2 mL), $K_2CO_3$ (27 mg, 0.20 mmol) and 2-(3-bromopropan-1-yn-1-yl)-3-fluoropyridine (60 mg, 0.28 mmol). The mixture was stirred for reaction at rt overnight. The reaction mixture was concentrated in vacuo, and the residue was purified by silica gel column chromatography (eluent DCM/MeOH=30/l) to give a light yellow solid 12 mg, which was the target product (the yield was 39%). LC-MS(ESI): m/z=530.3 [M+H]+. $^1$H NMR (400 MHz, $CDCl_3$) δ 8.64 (d, J=1.2 Hz, 1H), 8.42 (d, J=2.3 Hz, 1H), 8.37 (d, J=4.6 Hz, 1H), 8.27 (s, 1H), 7.83-7.77 (m, 2H), 7.69 (s, 1H), 7.43-7.38 (m, 2H), 7.24 (m, 1H), 6.72 (d, J=8.8 Hz, 1H), 3.95-4.05 (m, 5H), 3.89 (d, 7=12.1 Hz, 2H), 3.67 (d, J=12.0 Hz, 2H), 3.59 (s, 2H), 2.77 (m, 1H), 2.61 (s, 1H). HPLC: 88.87%.

Example 259: 4-(6-(6-(3-(5-fluoropyridin-3-yl)prop-2-yn-1-yl)-3,6-diazabicyclo[3.1.1]heptane-3-yl)pyridin-3-yl)-6-(1-methyl-1H-pyrazol-4-yl)pyrazolo[1,5-a]pyridin-3-carbonitrile

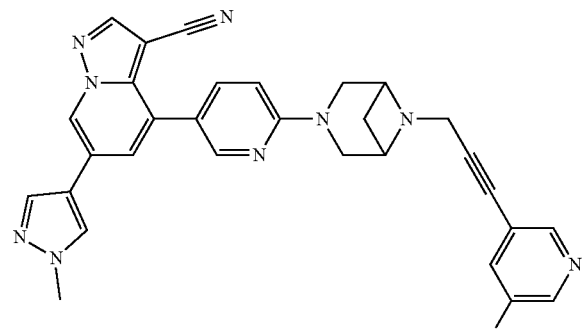

(259)

Step 1: 3-(5-fluoropyridin-3-yl)prop-2-yn-1-ol

To a 25 mL two-necked flask were added 3-bromo-5-fluoropyridine (300 mg, 1.7046 mmol), cuprous iodide (35 mg, 0.18 mmol), $PdCl_2(PPh_3)_2$ (60 mg, 0.085 mmol) at room temperature. The reaction mixture was degassed and refilled with nitrogen. Then triethylamine (3 mL, 21.5 mmol) and prop-2-yn-1-ol (0.2 mL, 3 mmol) were added. The mixture was reacted at 60° C. overnight. To the reaction solution were added EA (40 mL) and saturated ammonium chloride solution (20 mL), and then filtered by suction. The filter cake was washed with EA (20 mL). The organic phases were combined, washed with 20 mL of saturated brine, dried over anhydrous sodium sulfate, filtered, concentrated in vacuo, and then purified by silica gel column chromatography (PE/EA=3/1-1/1) to give a pale yellow solid 89 mg (yield: 34.54%) as the target product. $^1$H NMR (400 MHz, $CDCl_3$) δ 8.51 (s, 1H), 8.41 (d, J=2.6 Hz, 1H), 7.44 (d, J=8.2 Hz, 1H), 4.51 (s, 2H), 2.47 (s, 1H).

Step 2: 3-(3-bromoprop-1-yn-1-yl)-5-fluoropyridine 3-(5-Fluoropyridin-3-yl)prop-2-yn-1-ol (80 mg, 0.529 mmol) was dissolved in DCM (2 mL) at 0° C., and $PBr_3$ (0.1 mL, 1 mmol) was slowly added. The mixture was reacted with stirring at low temperature for 2 h. The reaction was stopped and quenched with water (10 mL). Saturated $NaHCO_3$ solution was added to adjust the pH to alkaline. The mixture was extracted with DCM (20 mL×3), washed with water, dried over anhydrous sodium sulfate, concentrated in vacuo at 30° C. to give a pale yellow concentrate, which was used in the next step directly without further purification.

Step 3: 4-(6-(6-(3-(5-fluoropyridin-3-yl)prop-2-yn-1-yl)-3,6-diazabicyclo[3.1.1]heptane-3-yl) pyridin-3-yl)-6-(1-methyl-1H-pyrazol-4-yl)pyrazolo[1,5-a]pyridin-3-carbonitrile To a 10 mL single-necked flask were sequentially added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile hydrochloride (see synthesis of intermediate 3, 25 mg, 0.05326 mmol), 3-(3-bromoprop-1-yn-1-yl)-5-fluoropyridine (23 mg, 0.10746 mmol), DMF (2 mL) and potassium carbonate (0.03 g, 0.2 mmol). The resulting mixture was reacted at room temperature overnight. After the reaction was completed, EA (20 mL) and water (20 mL) were added. The aqueous phase was separated and extracted with EA (20 mL). The combined organic phases were washed with saturated brine (20 mL), dried over anhydrous sodium sulfate, filtered, concentrated in vacuo, and then purified by silica gel column chromatography (DCM/MeOH=100/0-100/3) to give an off-white solid (yield: 28.36%) as the desired product. LC-MS: m/z=530.1 [M+H]+; $^1$H NMR (400 MHz, $CDCl_3$) δ 8.64 (d, 7=1.3 Hz, 1H), 8.46 (s, 1H), 8.43 (d, J=2.0 Hz, 1H), 8.39 (d, J=2.4 Hz, 1H), 8.27 (s, 1H), 7.82 (dd, J=8.8, 2.4 Hz, 1H), 7.79 (s, 1H), 7.68 (s, 1H), 7.45-7.39 (m, 2H), 6.72 (d, J=8.8 Hz, 1H), 4.02-3.95 (m, 5H), 3.91-3.83 (m, 2H), 3.73-3.63 (m, 2H), 3.55 (s, 2H), 2.83-2.74 (m, 1H), 1.73-1.70 (m, 1H). HPLC: 93.90%.

Example 260: 4-(6-(4-(3-(5-fluoropyridin-3-yl)prop-2-yn-1-yl)piperazin-1-yl)pyridin-3-yl)-6-(1-methyl-1H-pyrazol-4-yl)pyrazolo[1,5-a]pyridine-3-carbonitrile

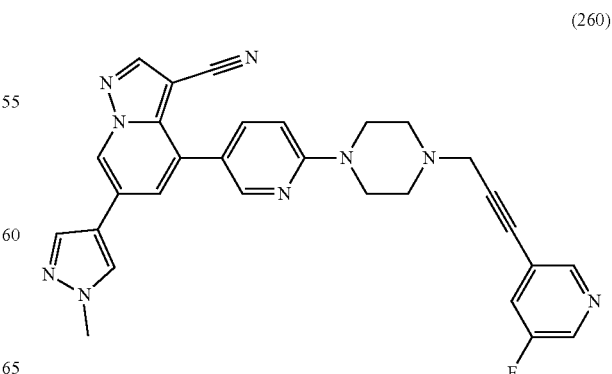

(260)

Step 1: 3-(5-fluoropyridin-3-yl)prop-2-yn-1-ol

To a 25 mL two-necked flask were added 3-bromo-5-fluoropyridine (300 mg, 1.704 mmol), cuprous iodide (35 mg, 0.18 mmol), PdCl$_2$(PPh$_3$)$_2$ (60 mg, 0.085 mmol) at room temperature. The reaction mixture was degassed and refilled with nitrogen. Then triethylamine (3 mL, 21.5 mmol) and prop-2-yn-1-ol (0.2 mL, 3 mmol) were added. The mixture was reacted at 60° C. overnight. To the reaction mixture were added EA (40 mL) and saturated ammonium chloride solution (20 mL), and then the resulting mixture was filtered by suction. The filter cake was washed with EA (20 mL). The combined organic phases were washed with saturated brine (20 mL), dried over anhydrous sodium sulfate, filtered, and the filtrate was concentrated in vacuo, and then purified by silica gel column chromatography (PE:EA=3:1-1:1) to give a pale yellow solid 89 mg (yield: 34.54%) as the desired product. $^1$H NMR (400 MHz, CDCl$_3$) δ 8.51 (s, 1H), 8.41 (d, J=2.6 Hz, 1H), 7.44 (d, J=8.2 Hz, 1H), 4.51 (s, 2H), 2.47 (s, 1H).

Step 2: 3-(3-bromoprop-1-yn-1-yl)-5-fluoropyridine 3-(5-Fluoropyridin-3-yl)prop-2-yn-1-ol (80 mg, 0.53 mmol) was dissolved in DCM (2 mL) at 0° C., and then PBr$_3$ (0.1 mL, 1 mmol) was added slowly. The mixture was stirred for reaction at low temperature for 2 h. The reaction was stopped and quenched with water (10 mL). Saturated NaHCO$_3$ solution was added to adjust the pH of the reaction mixture to alkaline. The mixture was extracted with DCM (20 mL×3), and the combined organic layers were washed with water, dried over anhydrous sodium sulfate, concentrated in vacuo at 30° C. to give a pale yellow concentrate, which was used in the next step directly without further purification.

Step 3: 4-(6-(4-(3-(5-fluoropyridin-3-yl)prop-2-yn-1-yl)piperazin-1-yl)pyridin-3-yl)-6-(1-methyl-1H-pyrazol-4-yl)pyrazolo[1,5-a]pyridine-3-carbonitrile To a 10 mL single-necked flask were sequentially added 6-(1-methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 20 mg, 0.044 mmol), 3-(3-bromoprop-1-yn-1-yl)-5-fluoropyridine (19 mg, 0.089 mmol), DMF (2 mL) and potassium carbonate (0.024 g, 0.17 mmol). The mixture was reacted overnight at room temperature. To the reaction mixture were added EA (20 mL) and water (20 mL). The aqueous layer was separated and extracted with EA (20 mL). The combined organic phases were washed with saturated brine (20 mL), dried over anhydrous sodium sulfate, filtered, concentrated in vacuo, and then purified by silica gel column chromatography (DCM/MeOH=100/0-100/3) to give a white solid 5 mg (yield: 22.09%) as the desired product. LC-MS: m/z=518.3 [M+H]$^+$; $^1$H NMR (400 MHz, CDCl$_3$) δ 8.66 (d, 1H), 8.52 (s, 1H), 8.43 (s, 1H), 8.40 (d, J=2.2 Hz, 1H), 8.28 (s, 1H), 7.81 (s, 1H), 7.79 (dd, J=8.9, 2.5 Hz, 1H), 7.70 (s, 1H), 7.42 (d, J=1.3 Hz, 1H), 7.37 (d, J=2.4 Hz, 1H), 6.83 (d, J=8.8 Hz, 1H), 4.01 (s, 3H), 3.82-3.76 (m, 4H), 3.68 (s, 2H), 2.86-2.79 (m, 4H). HPLC: 95.06%.

Example 261: 4-[6-[4-[3-(6-fluoro-3-pyridyl)prop-2-ynyl]piperazin-1-yl]-3-pyridyl]-6-(1-methylpyrazol-4-yl)pyrazolo[1,5-a]pyridine-3-carbonitrile

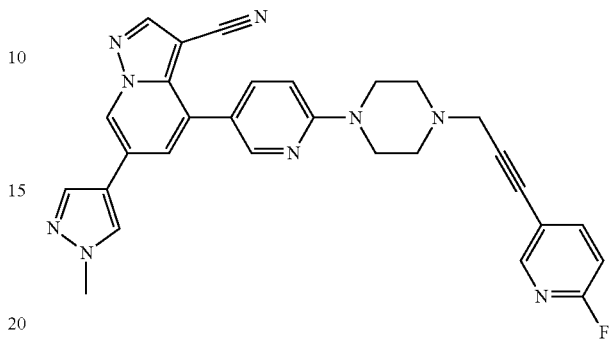

(261)

Step 1: 3-(6-fluoro-3-pyridyl)prop-2-yn-1-ol

To a 25 ml two-necked flask were added CuI (43.3 mg, 0.227 mmol) and PdCl$_2$(PPh$_3$)$_2$ (80 mg, 0.114 mmol) at room temperature. The mixture was degassed and refilled with nitrogen. Then triethylamine (3.5 mL, 25 mmol), 5-bromo-2-fluoro-pyridine (0.234 mL, 2.27 mmol) and prop-2-yn-1-ol (0.265 mL, 4.55 mmol) were added. The mixture was reacted at 50° C. overnight. TLC showed the reaction was completed. The reaction was quenched by the addition of 10 mL of saturated ammonium chloride. The mixture was filtered and the filter cake was washed with 20 mL of EA. The organic phase was separated and the aqueous phase was extracted with EA (20 mL×2). The organic phases were combined, washed with 20 mL of saturated brine, dried over anhydrous sodium sulfate, filtered, and the filtrate was concentrated in vacuo, and then purified by silica gel column chromatography (eluent PE:EA=10: 1-2:1) to give a brown-yellow solid 0.08 g (yield: 20%) as the desired product. $^1$H NMR (400 MHz, CDCl$_3$) δ 8.31 (s, 1H), 7.82 (td, J=8.3, 2.3 Hz, 1H), 6.91 (dd, J=8.4, 2.8 Hz, 1H), 4.50 (s, 2H), 2.04 (s, 1H).

Step 2: 5-(3-bromoprop-1-ynyl)-2-fluoro-pyridine 3-(6-Fluoro-3-pyridyl)prop-2-yn-1-ol (70 mg, 0.463 mmol) was dissolved in DCM (5 mL) in a 10 ml single-necked flask at 0° C., then PBr$_3$ (0.09 mL, 1 mmol) was added slowly. The mixture was stirred for reaction at low temperature. TLC showed that the reaction was completed. The reaction was quenched by the addition of water (2 mL) slowly, and saturated potassium carbonate solution was added dropwise to adjust the pH to alkaline. The mixture was extracted with DCM (15 mL×2), washed with saturated brine (10 mL), dried over anhydrous sodium sulfate, filtered, and concentrated in vacuo, which was directly used in the next step. The yield was calculated as 100%.

Step 3: 4-[6-[4-[3-(6-fluoro-3-pyridyl)prop-2-ynyl]piperazin-1-yl]-3-pyridyl]-6-(1-methylpyrazol-4-yl)pyrazolo[1,5-a]pyridine-3-carbonitrile To a 5 mL single-necked flask were added 6-(1-methyl pyrazol-4-yl)-4-(6-piperazin-1-yl-3-pyridyl)pyrazolo[1,5-a]

pyridine-3-carbonitrile dihydrochloride (see synthesis of intermediate 2, 15 mg, 0.033 mmol) and 5-(3-bromoprop-1-ynyl)-2-fluoro-pyridine (33.4 mg, 0.156 mmol), then $K_2CO_3$ (22 mg, 0.158 mmol, 99 mass %) and DMF (1.5 mL) were added. The mixture was stirred for reaction at room temperature. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent: pure DCM-DCM:MeOH (v:v=20:1)) to give a white powdery solid 0.009 g (the yield was 50%), which was the target product. LC-MS (ES-API): m/z=518.2 [M+H]$^+$. $^1$H NMR (400 MHz, d$_6$-DMSO) δ 9.25 (s, 1H), 8.65 (s, 1H), 8.52-8.43 (m, 2H), 8.39 (s, 1H), 8.19 (t, J=7.2 Hz, 1H), 8.12 (s, 1H), 7.93 (dd, J=8.7, 2.1 Hz, 1H), 7.79 (s, 1H), 7.30 (dd, J=8.6, 2.4 Hz, 1H), 7.11 (d, J=9.0 Hz, 1H), 4.38 (s, 2H), 3.88 (s, 3H), 3.49 (d, J=7.3 Hz, 2H), 3.42 (t, J=4.7 Hz, 4H), 3.27 (d, J=21.0 Hz, 2H). HPLC: 97.06%.

Example 262: 4-[6-[6-[3-(6-fluoro-3-pyridyl)prop-2-ynyl]-3,6-diazabicyclo[3.1.1]heptan-3-yl]3-pyridyl]-6-(1-methylpyrazol-4-yl)pyrazolo[1,5-a]pyridine-3-carbonitrile

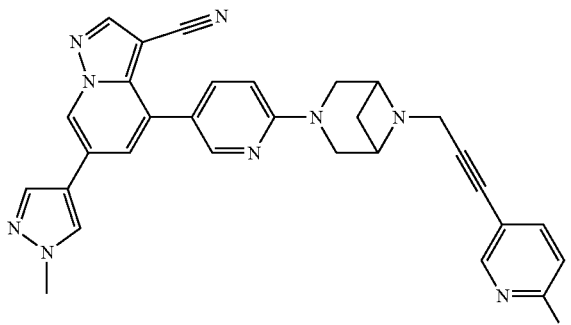

(262)

Step 1: 3-(6-fluoro-3-pyridyl)prop-2-yn-1-ol

To a 25 ml two-neck flask were added CuI (43.3 mg, 0.227 mmol) and PdCl$_2$(PPh$_3$)$_2$ (80 mg, 0.114 mmol) at room temperature. The mixture was degassed and refilled with nitrogen. Then triethylamine (3.5 mL, 25 mmol), 5-bromo-2-fluoro-pyridine (0.234 mL, 2.27 mmol) and prop-2-yn-1-ol (0.265 mL, 4.55 mmol) were added. The mixture was reacted at 50° C. overnight. TLC showed the reaction was completed. The reaction was quenched by the addition of 10 mL of saturated ammonium chloride. The mixture was filtered by suction and the filter cake was washed with 20 mL of EA. The organic phase was separated and the aqueous phase was extracted with EA (20 mL×2). The organic phases were combined, washed with 20 mL of saturated brine, dried over anhydrous sodium sulfate, filtered, concentrated in vacuo, and then purified by silica gel column chromatography (eluent PE:EA=10: 1-2:1) to give a brown-yellow solid 0.08 g (yield: 20%) as the desired product. $^1$H NMR (400 MHz, CDCl$_3$) δ 8.31 (s, 1H), 7.82 (td, J=8.3, 2.3 Hz, 1H), 6.91 (dd, J=8.4, 2.8 Hz, 1H), 4.50 (s, 2H), 2.04 (s, 1H).

Step 2: 5-(3-bromoprop-1-ynyl)-2-fluoro-pyridine 3-(6-Fluoro-3-pyridyl)prop-2-yn-1-ol (70 mg, 0.463 mmol) was dissolved in DCM (5 mL) in a 10 mL single-necked flask at 0° C., then PBr$_3$ (0.09 mL, 1 mmmol) was slowly added. The mixture was reacted with stirring at this temperature. TLC showed the reaction was completed. The reaction was quenched by the addition of water (2 mL) slowly, and saturated potassium carbonate solution was added dropwise to adjust the pH of the reaction mixture to alkaline. The mixture was extracted with DCM (15 mL×2), washed with saturated brine (10 mL), dried over anhydrous sodium sulfate, filtered, and concentrated in vacuo, which was directly used in the next step. The yield was calculated as 100%.

Step 3: 4-[6-[6-[3-(6-fluoro-3-pyridyl)prop-2-ynyl]-3,6-diazabicyclo[3.1.1]heptan-3-yl]3-pyridyl]-6-(1-methylpyrazol-4-yl)pyrazolo[1,5-a]pyridine-3-carbonitrile To a 5 mL single-necked flask were added 4-(6-(3,6-diazabicyclo[3.1.1]heptan-3-yl)pyridin-3-yl)-6-(1-methyl-1H-pyrazol-4-yl)pyrazole[1,5-a]pyridine-3-carbonitrile dihydrochloride (see synthesis of intermediate 3, 15 mg, 0.032 mmol) and 5-(3-bromoprop-1-ynyl)-2-fluoro-pyridine (32.4 mg, 0.151 mmol). Then $K_2CO_3$ (21 mg, 0.032 mmol) and DMF (1.5 mL) were added. The mixture was stirred for reaction at room temperature overnight. TLC showed the reaction was completed. The mixture was quenched with water (9 mL) and extracted with EA (20 mL×2). The organic phases were washed with saturated saline (10 mL), dried over anhydrous sodium sulfate, filtered, and concentrated in vacuo. The mixture was purified by silica gel column chromatography (eluent: pure DCM-DCM:MeOH (v:v=20: 1)) to give a white powdery solid 0.009 g (the yield was 50%), which was the target product. LC-MS (ES-API): m/z=530.2 [M+H]$^+$. $^1$H NMR (400 MHz, CDCl$_3$) δ 8.64 (s, 1H), 8.43 (d, 7=1.9 Hz, 1H), 8.27 (s, 2H), 7.82 (s, 1H), 7.79 (s, 2H), 7.69 (s, 1H), 7.41 (s, 1H), 6.91-6.86 (m, 1H), 6.72 (d, J=8.8 Hz, 1H), 4.00 (s, 3H), 3.94 (d, J=5.9 Hz, 2H), 3.86 (d, J=12.2 Hz, 2H), 3.67 (d, J=17.3 Hz, 2H), 3.51 (s, 2H), 2.75 (dd, J=13.6, 6.8 Hz, 1H), 2.00 (dd, J=16.2, 10.9 Hz, 1H). HPLC: 91.25%.

Example 263: 6-(1-methyl-1H-pyrazol-4-yl)-4-(6-(4-(3-(pyridin-4-yl)prop-2-yn-1-yl) piperazin-1-yl)pyridine-3-yl)pyrazolo[1,5-a]pyridine-3-carbonitrile

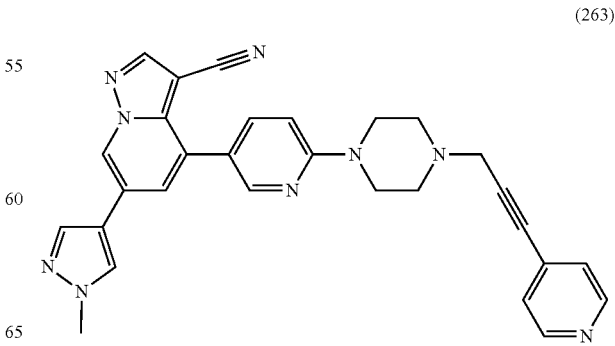

(263)

Step 1: 3-(pyridin-4-yl)propane-2-yn-1-ol

4-Iodopyridine (1.00 g, 4.88 mmol), PdCl$_2$ (PPh$_3$) 2 (0.34 g, 0.48 mmol), CuI (93 mg, 0.49 mmol) and PPh$_3$ (128 mg, 0.49 mmol) were dissolved in THF (15 mL) Under N$_2$, then propane-2-yn-1-ol (0.55 g, 9.8 mmol) and Et$_3$N (0.99 g, 9.8 mmol) were added. The mixture was reacted with stirring at room temperature for 4 h. The reaction was quenched with saturated NH$_4$Cl. The resulting mixture was extracted with EA (10 mL×3), washed with water (10 mL), dried over anhydrous sodium sulfate, and filtered. The mother liquor was concentrated in vacuo and the residue was purified by silica gel column chromatography (eluent PE/EA=10/1-3/1) to give a yellow-brown solid 0.52 g as the target product (the yield was 72%)(Rf=0.09 (PE/EA=5/1). LC-MS: m/z=134.1 [M+H]$^+$. $^1$H NMR (400 MHz, CDCl$_3$) δ 8.59 (s, 2H), 7.34-7.27 (m, 2H), 4.53 (s, 2H).

Step 2: 4-(3-bromopropan-1-yn-1-yl)pyridine 3-(Pyridin-4-yl)propane-2-yn-1-ol (125 mg, 0.94 mmol) was dissolved in DCM (5 mL) at 0° C., and PBr$_3$ (0.51 g, 1.9 mmol) was slowly added. The mixture was reacted with stirring at low temperature for 1 h. The reaction was stopped, and quenched with water (5 mL). The resulting mixture was extracted with DCM (10 mL×3), washed with water (10 mL), dried over anhydrous sodium sulfate, and filtered. The mother liquor was concentrated in vacuo to give brown viscous liquid 136 mg as the target product (yield: 86%), which was directly used for the next reaction without further purification. Rf=0.41 (PE/EA=5/1). LC-MS: m/z=196.1 [M+H]$^+$.

Step 3: 6-(1-methyl-1H-pyrazol-4-yl)-4-(6-(4-(3-(pyridin-4-yl)prop-2-yn-1-yl)piperazin-1-yl) pyridine-3-yl)pyrazolo[1,5-a]pyridine-3-carbonitrile 6-(1-Methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 15 mg, 0.033 mmol) was dissolved in DMF (0.5 mL) in a single-necked flask. Potassium carbonate (17 mg, 0.123 mmol) was added, then a solution of 4-(3-bromoprop-1-ynyl)pyridine (0.18 mg, 0.0009 mmol) in dichloromethane was added. The mixture was stirred for reaction at rt overnight. The reaction mixture was extracted with ethyl acetate (50 mL) and washed with water (5 mL×3). The organic phases were concentrated in vacuo, and the residue was purified by silica gel column chromatography (DCM/MeOH=0-100:3.5) to give a pale yellow solid 4.0 mg as the target product (the yield was 24.41%). LC-MS: m/z=500.2 [M+H]$^+$. $^1$H NMR (400 MHz, CDCl$_3$) δ 8.66 (d, J=1.3 Hz, 1H), 8.58 (d, J=5.7 Hz, 2H), 8.40 (d, J=2.3 Hz, 1H), 8.29 (s, 1H), 7.87-7.76 (m, 2H), 7.70 (s, 1H), 7.41 (d, 7=1.4 Hz, 1H), 7.40-7.32 (m, 2H), 6.83 (d, J=9.0 Hz, 1H), 4.01 (s, 3H), 3.77 (d, J=4.7 Hz, 4H), 3.67 (s, 2H), 2.87-2.76 (m, 4H). HPLC: 92.08%.

Example 264: 4-(6-(6-(3-(5-fluoropyridin-2-yl)prop-2-yn-1-yl)-3,6-diazabicyclo[3.1.1]heptane-3-yl)pyridin-3-yl)-6-(1-methyl-1H-pyrazol-4-yl)pyrazolo[1,5-a]pyridine-3-carbonitrile (264)

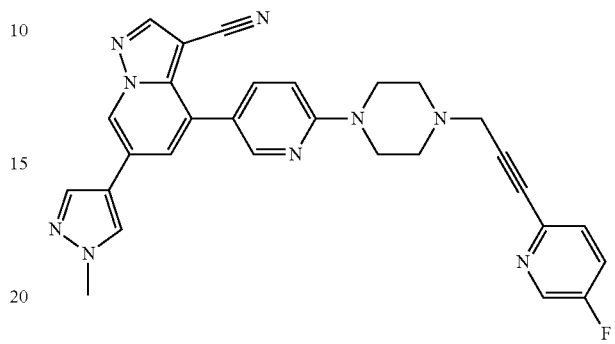

Step 1: 3-(5-fluoropyridin-2-yl)prop-2-yn-1-ol

To a 50 mL two-necked flask were sequentially added 2-bromo-5-fluoro-pyridine (570 mg, 3.24 mmol), Pd(PPh$_3$)$_2$Cl$_2$ (114 mg, 0.16 mmol) and CuI (24 mg, 0.13 mmol) under nitrogen, and then prop-2-yn-1-ol (0.33 mL, 5.7 mmol) and triethylamine (3 mL) were added. The resulting mixture was reacted at room temperature overnight. The reaction mixture was filtered, then washed with EA (100 mL). The filtrate was concentrated in vacuo, and the residue was purified by silica gel column chromatography (PE:EA=50:1-20:1) to give a pale yellow solid 435 mg as the target product (yield: 88.86%). LC-MS: m/z=152.1 [M+H]$^+$. $^1$H NMR (400 MHz, CDCl$_3$) δ 8.43 (d, J=2.7 Hz, 1H), 7.46 (dd, J=8.6, 4.5 Hz, 1H), 7.39 (td, J=8.2, 2.8 Hz, 1H), 4.52 (s, 2H), 2.76 (s, 1H).

Step 2: 2-(3-bromoprop-1-yn-1-yl)-5-fluoropyridine 3-(5-Fluoro-2-pyridinyl)prop-2-yn-1-ol (120 mg, 0.79397 mmol) was dissolved in dichloromethane (6 mL) at 0° C., and phosphorus tribromide (0.15 mL, 1.6 mmol) was slowly added. The mixture was reacted at low temperature for 1 h. The reaction was quenched by the addition of water slowly. The mixture was added with saturated potassium carbonate to adjust pH of the reaction mixture to alkaline, and then extracted with DCM (50 mL). The organic phases were separated, dried over anhydrous sodium sulfate and filtered. The mother liquid was concentrated in vacuo which was directly used for the next step. The yield was calculated as 100%.

Step 3: 4-(6-(6-(3-(5-fluoropyridin-2-yl)prop-2-yn-1-yl)-3,6-diazabicyclo[3.1.1]heptane-3-yl) pyridin-3-yl)-6-(1-methyl-1H-pyrazol-4-yl)pyrazolo[1,5-a] pyridine-3-carbonitrile 6-(1-Methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 15 mg, 0.033 mmol) was dissolved in DMF (0.5 mL) in a single-necked flask. Potassium carbonate (17 mg, 0.122 mmol) was added, then a solution of 2-(3-bromoprop-1-ynyl)-5-fluoropyridine (0.18 mg, 0.0008 mmol) in DCM was added. The mixture was reacted at rt overnight. The reaction mixture was added with water (5 mL) and extracted with EA (20 mL). The combined organic layers were washed with water (5 mL×3), dried over anhydrous sodium sulfate and filtered. The mother liquid was concentrated in vacuo, and then purified by silica gel column chromatography (DCM:MeOH=0-100: 3.5) to give a light yellow solid 4 mg as the target product (the yield was 23.57%). LC-MS: m/z=518.2 [M+H]$^+$. $^1$H NMR (400 MHz, CDCl$_3$) δ 8.66 (d, 7=1.1 Hz, 1H), 8.42 (dd, J=21.8, 2.5 Hz, 2H), 8.28 (s, 1H), 7.81 (s, 1H), 7.78 (dd, J=8.8, 2.4 Hz, 1H), 7.70 (s, 1H), 7.49 (dd, J=8.4, 4.4 Hz, 1H), 7.41 (s, 1H), 7.40-7.35 (m, 1H), 6.82 (d, J=8.9 Hz, 1H), 4.01 (s, 3H), 3.82-3.71 (m, 4H), 3.68 (s, 2H), 2.90-2.77 (m, 4H). HPLC: 97.60%.

Example 265: 6-(1-methyl-1H-pyrazol-4-yl)-4-(6-(4-(3-(5-(trifluoromethyl)(pyridin-3-yl)prop-2-yn-1-yl)piperazin-1-yl)pyridine-3-yl)pyrazolo[1,5-a]pyridine-3-carbonitrile

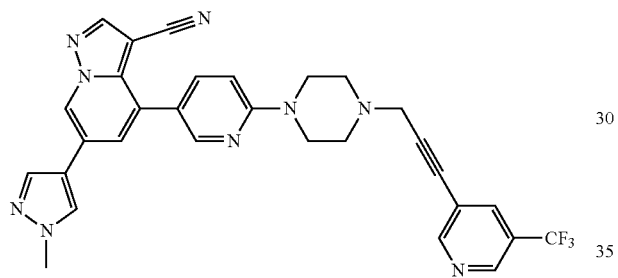

(265)

Step 1: 3-(5-(trifluoromethyl)pyridin-3-yl)prop-2-yn-1-ol

To a 50 mL two-necked flask were sequentially added 3-bromo-5-(trifluoromethyl)-pyridine (500 mg, 2.2125 mmol), Pd(PPh$_3$)$_2$Cl$_2$ (78 mg, 0.110 mmol) and CuI (16 mg, 0.084 mmol) under nitrogen, and then prop-2-yn-1-ol (0.26 mL, 4.5 mmol) and triethylamine (4 mL) were added. The resulting mixture was stirred at room temperature overnight. The reaction mixture was filtered, then washed with EA (100 mL). The filtrate was concentrated in vacuo, and the residue was purified by silica gel column chromatography (PE: EA=50:1-20:1) to give pale yellow oil 190 mg as the target product (yield: 42.70%). LC-MS: m/z=202.1 [M+H]$^+$. $^1$H NMR (400 MHz, CDCl$_3$) δ 8.85 (d, J=16.3 Hz, 2H), 7.99 (s, 1H), 4.56 (d, J=4.3 Hz, 2H), 2.20 (s, 1H).

Step 2: 3-(3-bromoprop-1-ynyl)-5-(trifluoromethyl)pyridine

3-[5-(Trifluoromethyl)-3-pyridyl]prop-2-yn-1-ol (190 mg, 0.94462 mmol) was dissolved in DCM (6 mL) at 0° C., and phosphorus tribromide (0.18 mL, 1.9 mmol) was slowly added. The mixture was reacted at 0° C. for 2 h. The reaction was quenched by the addition of water slowly. The mixture was added with saturated potassium carbonate to adjust pH to alkaline, extracted with DCM (50 mL×2) and concentrated in vacuo, which was directly used for the next step. The yield was calculated as 100%.

Step 3: 6-(1-methyl-1H-pyrazol-4-yl)-4-(6-(4-(3-(5-(trifluoromethyl)(pyridin-3-yl)prop-2-yn-1-yl) piperazin-1-yl)pyridine-3-yl)pyrazolo[1,5-a]pyridine-3-carbonitrile 6-(1-Methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 15 mg, 0.03279 mmol) was dissolved in DMF (0.5 mL) in a single-necked flask. Potassium carbonate (17 mg, 0.122 mmol) was added, then a solution of 3-(3-bromoprop-1-ynyl)-5-(trifluoromethyl)pyridine (0.18 mg, 0.00068 mmol) in DCM was added. The mixture was reacted at rt overnight. The reaction mixture was added with water (10 mL), extracted with ethyl acetate (30 mL×3) and then washed with water (5 mL×3). The organic phases were concentrated in vacuo, and the residue was purified by silica gel column chromatography (DCM/MeOH=0-100:3.5) to give a white solid 13 mg as the target product (the yield was 69.84%). LC-MS: m/z=568.2 [M+H]$^+$. $^1$H NMR (400 MHz, CDCl$_3$) δ 8.83 (d, J=20.9 Hz, 2H), 8.66 (d, J=1.3 Hz, 1H), 8.40 (d, J=2.3 Hz, 1H), 8.28 (s, 1H), 7.99 (s, 1H), 7.81 (s, 1H), 7.78 (dd, J=8.8, 2.5 Hz, 1H), 7.70 (s, 1H), 7.41 (d, J=1.3 Hz, 1H), 6.83 (d, J=8.9 Hz, 1H), 4.01 (s, 3H), 3.82-3.74 (m, 4H), 3.67 (s, 2H), 2.84-2.76 (m, 4H). HPLC: 95.09%.

Example 266: 4-(6-(4-(3-(6-fluoropyridin-2-yl)prop-2-yn-1-yl)piperazin-1-yl)pyridin-3-yl)-6-(1-methyl-1H-pyrazol-4-yl)pyrazolo[1,5-a]pyridine-3-carbonitrile

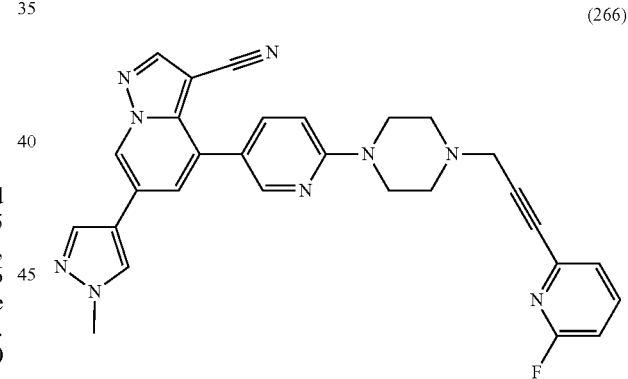

(266)

Step 1: 3-(6-fluoropyridin-2-yl)prop-2-yn-1-ol

To a 50 mL two-necked flask were sequentially added 2-bromo-6-fluoropyridine (500 mg, 2.84 mmol), Pd(PPh$_3$)$_2$Cl$_2$ (100 mg, 0.14 mmol) and CuI (21 mg, 0.11 mmol) under nitrogen, and then prop-2-yn-1-ol (0.331 mL, 5.69 mmol) and triethylamine (4 mL, 28.6 mmol) were added. The resulting mixture was stirred at room temperature overnight. The reaction mixture was filtered, then washed with EA (100 mL). The filtrate was concentrated in vacuo, and the residue was purified by silica gel column chromatography (PE:EA=50:1-20:1) to give a pale yellow solid 368 mg as the target product (yield: 85.70%). Rf=0.3 (PE/EA=3/1). LC-MS: m/z=152.2 [M+H]$^+$. $^1$H NMR (400 MHz, CDCl$_3$) δ 7.79-7.75 (m, 1H), 7.34 (dd, 7=7.4, 2.0 Hz, 1H), 6.93 (dd, 7=8.3, 2.6 Hz, 1H), 4.53 (s, 2H), 2.18 (s, 1H).

Step 2: 2-(3-bromopropan-1-yn-1-yl)-6-fluoropyridine 3-(6-Fluoropyridin-2-yl)prop-2-yn-1-ol (150 mg, 0.99 mmol) was dissolved in DCM (6 mL) at 0° C., and phosphorus tribromide (0.19 mL, 2.0 mmol) was slowly added. The mixture was reacted at low temperature for 2 h. The reaction was quenched by the addition of water slowly. The mixture was added with saturated potassium carbonate to adjust pH of the reaction mixture to alkaline (bubbles began to generate), and then extracted with DCM (50 mL). The organic phases were dried over anhydrous sodium sulfate and filtered. The mother liquid was concentrated in vacuo, and the residue was directly used for the next step. The yield was calculated as 100%.

Step 3: 4-(6-(4-(3-(6-fluoropyridin-2-yl)prop-2-yn-1-yl)piperazin-1-yl)pyridin-3-yl)-6-(1-methyl-1H-pyrazol-4-yl)pyrazolo[1,5-a]pyridine-3-carbonitrile 6-(1-Methylpyrazol-4-yl)-4-(6-piperazin-1-yl-3-pyridyl)pyrazolo[1,5-a]pyridine-3-carbonitrile dihydrochloride (see synthesis of intermediate 2, 15 mg, 0.03279 mmol) was dissolved in DMF (0.5 mL) in a single-necked flask. Potassium carbonate (17 mg, 0.121777 mmol) was added, then a solution of 2-(3-bromoprop-1-ynyl)-6-fluoro-pyridine (0.18 mg, 0.00084 mmol) in DCM was added. The mixture was reacted at rt overnight. To the reaction mixture was added water (5 mL), and the resulting mixture was extracted with EA (30 mL×2). The organic phases were washed with water (5 mL×3), dried over anhydrous sodium sulfate and filtered. The mother liquid was concentrated in vacuo, and then purified by silica gel column chromatography (DCM: MeOH=100:0-100:3.5) to give a white solid 8 mg as the target product (the yield was 47.13%). LC-MS: m/z=518.0 [M+H]$^+$. $^1$H NMR (600 MHz, CDCl$_3$) δ 8.66 (d, J=1.4 Hz, 1H), 8.39 (d, J=2.3 Hz, 1H), 8.28 (s, 1H), 7.81 (s, 1H), 7.80-7.73 (m, 2H), 7.70 (s, 1H), 7.42 (d, J=1.4 Hz, 1H), 7.36 (dd, J=7.5, 1.7 Hz, 1H), 6.92 (dd, J=8.2, 2.4 Hz, 1H), 6.82 (d, J=8.8 Hz, 1H), 4.01 (s, 3H), 3.80-3.73 (m, 4H), 3.67 (s, 2H), 2.85-2.76 (m, 4H). HPLC: 90.61%.

Example 267: 4-(6-(4-(3-(4-(fluorophenyl))prop-2-yn-1-yl)piperazin-1-yl)pyridin-3-yl)-6-(1-methyl-1H-pyrazol-4-yl)pyrazolo[1,5-a]pyridine-3-carbonitrile (267)

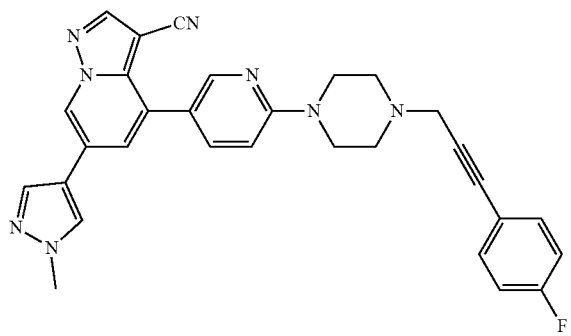

Step 1: 3-(4-fluorophenyl)prop-2-yn-1-ol

To a 50 mL two-necked flask were sequentially added PdCl$_2$(PPh$_3$)$_2$ (159 mg, 0.23 mmol), CuI (95 mg, 0.50 mmol), 1-fluoro-4-iodobenzene (0.52 mg, 4.50 mmol) and TEA (10 mL). Propargyl alcohol (0.34 mL, 5.8 mmol) was added under N$_2$. The mixture was stirred at room temperature for 4-5 h. 25 mL of EA was added, and the resulting mixture was filtered. The filtrate was concentrated in vacuo, and then purified by column chromatography (eluent PE/EA=4:1) to give oily liquid 500 mg. The yield was 74%. $^1$H NMR (400 MHz, CDCl$_3$) δ 7.40 (m, 2H), 7.01 (m, 2H), 4.48 (s, 2H).

Step 2: 1-(3-bromoprop-1-yn-1-yl)-4-fluorobenzene

To a 25 mL single-necked flask were sequentially added 3-(4-fluorophenyl)prop-2-yn-1-ol (91 mg, 0.61 mmol) and DCM (5 mL) at −10° C., then PBr$_3$ (0.12 mL, 1.3 mmol) was added slowly. After 10 min of addition, the mixture was continuously stirring for 2 h. To the reaction solution was slowly added 20 mL of 5% K$_2$CO$_3$ solution, and the organic phase was collected. The aqueous phase was extracted with DCM once. The organic phases were combined, dried over sodium sulfate, filtered, and concentrated in vacuo, which was directly used for the next reaction in equivalent amounts.

Step 3: 4-(6-(4-(3-(4-(fluorophenyl))prop-2-yn-1-yl)piperazin-1-yl)pyridin-3-yl)-6-(1-methyl-1H-pyrazol-4-yl)pyrazolo[1,5-a]pyridine-3-carbonitrile To a 10 mL single-necked flask were sequentially added 6-(1-methyl-1H-pyrazol-4-yl)-4-(6-(piperazin-1-yl)pyridin-3-yl)pyrazolo[1,5-a]pyridine-3-carbonitrile hydrochloride (see synthesis of intermediate 2, 23 mg, 0.055 mmol), DMF (1 mL), K$_2$CO$_3$ (30 mg, 0.22 mmol) and 1-(3-bromoprop-1-yn-1-yl)-4-fluorobenzene (60 mg, 0.28 mmol). The mixture was stirred for reaction at rt overnight. To the reaction solution was added EA (20 mL), and the resulting mixture was washed with water (8 mL×3). The combined aqueous phases were extracted with EA (15 mL). The organic phases were combined, dried over anhydrous sodium sulfate and filtered. The filtrate was concentrated in vacuo, and the residue was purified by silica gel column chromatography (eluent DCM/MeOH=25:1) to give a pale yellow solid 9 mg (yield: 33%). LC-MS(ESI): m/z=517.1 [M+H]$^+$. $^1$H NMR (400 MHz, CDCl$_3$) δ 8.63 (d, J=1.2 Hz, 1H), 8.37 (d, J=2.3 Hz, 1H), 8.26 (s, 1H), 7.82-7.73 (m, 2H), 7.68 (s, 1H), 7.47-7.37 (m, 3H), 6.99 (m, 2H), 6.80 (d, J=8.8 Hz, 1H), 3.99 (s, 3H), 3.81-3.68 (m, 4H), 3.60 (s, 2H), 2.92-2.64 (m, 4H). HPLC: 87.59%.

Example 268: N-(1-(5-(3-cyano-6-(1-methyl-1H-pyrazol-4-yl)pyrazolo[1,5-a]pyridin-4-yl) pyridine-2-yl)piperidinylpyridin-4-yl)-3-ethylbenzamide (268)

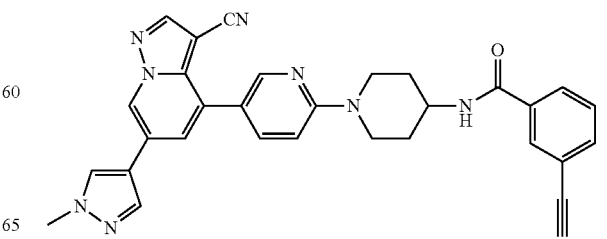

Step 1: tert-butyl 4-(3-ethynylbenzoylamino)piperidine-1-carboxylate

To a 25 mL single-necked flask were added tert-butyl 4-aminopiperidine-1-carboxylate (800 mg, 3.9944 mmol), DCM (16 mL), 3-ethynylbenzoic acid (0.70 g, 4.8 mmol), EDCI (1.15 g, 6.00 mmol) and DMAP (0.048 g, 0.39 mmol). The mixture was stirred and reacted at room temperature overnight. Dichloromethane (30 mL) and water (20 mL) were added, and the aqueous phase was separated and extracted with DCM (30 mL). The organic phases were combined, washed with 15 mL of saturated brine, dried over anhydrous sodium sulfate, concentrated in vacuo, and then purified by silica gel column chromatography (eluent PE/EA=20/1-4/1) to give a white foam solid 1.220 g as the target product (yield: 93%). LC-MS(ESI): m/z=287.1 [M-n-Bu+H]$^+$. $^1$H NMR (400 MHz, CDCl$_3$) δ 7.83 (s, 1H), 7.75 (d, J=7.8 Hz, 1H), 7.60 (d, J=7.7 Hz, 1H), 7.40 (t, J=7.8 Hz, 1H), 6.03 (d, J=7.6 Hz, 1H), 4.22-4.00 (m, 3H), 3.13 (s, 1H), 2.90 (t, J=12.2 Hz, 2H), 2.01 (d, J=11.6 Hz, 2H), 1.46 (s, 9H), 1.44-1.37 (m, 2H).

Step 2: 3-ethynyl-N-(piperidin-4-yl)benzamide 2,2,2-trifluoroacetate

To a 50 mL single-necked flask was added tert-butyl 4-(3-ethynylbenzoylamino)piperidine-1-carboxylate (1.22 g, 3.71 mmol), then DCM (13 mL) and TFA (4 mL) were added. The mixture was stirred and reacted at room temperature overnight. The reaction solution was directly concentrated in vacuo to give colorless transparent oily liquid as the target compound (yield 100%), which was directly used for the next reaction without further purification.

Step 3: N-(1-(5-(3-cyano-6-(1-methyl-1H-pyrazol-4-yl)pyrazolo[1,5-a]pyridin-4-yl)pyridin-2-yl)piperidinylpyridin-4-yl)-3-ethylbenzamide To a 2-5 ml microwave tube were added 4-(6-fluoropyridin-3-yl)-6-(1-methyl-1H-pyrazol-4-yl)pyrazolo[1,5-a]pyridine-3-carbonitrile (see synthesis of intermediate 1, 30 mg, 0.09425 mmol), 3-ethynyl-N-(piperidin-4-yl)benzamide 2,2,2-trifluoroacetate (96 mg, 0.2805 mmol) and DMSO (2 mL). The mixture was reacted under microwave at 150° C. for 5 h. To the reaction solution were added EA (30 mL) and water (15 mL), and the aqueous phase was extracted with EA (25 mL×2). The organic phases were combined, washed with 15 mL of saturated brine. The organic phases were separated, dried over anhydrous sodium sulfate, filtered, and then the filtrate was purified by silica gel column chromatography (eluent PE/EA=5/1-1/1.5) to give a yellow solid 10 mg as the target product (yield: 20.15%). LC-MS(ESI): m/z=527.3 [M+H]$^+$; $^1$H NMR (400 MHz, CDCl$_3$) δ 8.66 (s, 1H), 8.40 (s, 1H), 8.28 (s, 1H), 7.89 (s, 1H), 7.82 (s, 1H), 7.76-7.74 (m, 1H), 7.71 (s, 1H), 7.55 (s, 1H), 7.42 (s, 3H), 7.32-7.31 (m, 1H), 6.86 (d, J=8.0 Hz, 1H), 4.02 (d, 3H), 3.97-3.95 (m, 1H), 3.75 (s, 1H), 3.60-3.54 (m, 4H), 2.13-2.08 (m, 4H). HPLC: 91.52%.

Example 269: 6-(1-methyl-1H-pyrazol-4-yl)-4-(6-(7-(3-phenylpropioloyl)-2,7-diazaspiro[3.5]nonan-2-yl)pyridin-3-yl)pyrazolo[1,5-a]pyridine-3-carbonitrile

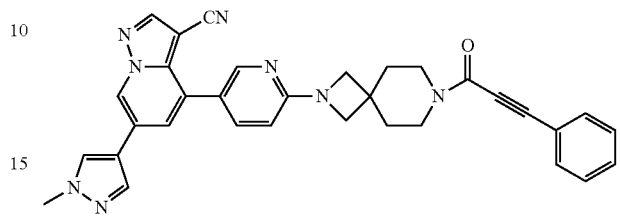

(269)

Step 1: tert-butyl 7-(3-phenylpropioloyl)-2,7-diazaspiro[3.5]nonane-2-carboxylate To a 25 mL single-necked flask were added 3-phenylpropynoic acid (0.093 g, 0.646 mmol), DCM (5 mL), tert-butyl 2,7-diazaspiro[3.5]nonane-2-carboxylate (0.12 g, 0.53 mmol), EDCI (0.15 g, 0.78 mmol) and DMAP (0.010 g, 0.082 mmol). The mixture was stirred and reacted at room temperature overnight. Dichloromethane (30 mL) and water (20 mL) were added, and the aqueous phase was separated and extracted with DCM (30 mL). The organic phases were combined, washed with 15 mL of saturated brine, dried over anhydrous sodium sulfate, filtered, and then purified by silica gel column chromatography (eluent PE/EA=10/1-3/1) to give a white foam solid 52 mg as the target product (yield 27.67%). $^1$H NMR (400 MHz, CDCl$_3$) δ 7.54 (d, J=6.9 Hz, 2H), 7.43 (t, J=7.3 Hz, 1H), 7.37 (t, J=7.3 Hz, 2H), 3.79-3.73 (m, 2H), 3.73-3.66 (m, 4H), 3.65-3.58 (m, 2H), 1.90-1.71 (m, 4H), 1.45 (s, 9H).

Step 2: 3-phenyl-1-(2,7-diazaspiro[3.5]non-7-yl)prop-2-yn-1-one 2,2,2-trifluoroacetate To a 50 mL single-necked flask was added tert-butyl 7-(3-phenylmalonyl)-2,7-diazaspiro[3.5]nonane-2-carboxylate (1.31 g, 3.70 mmol), then DCM (13 mL) and TFA (4 mL) were added. The mixture was stirred at room temperature overnight. The reaction solution was directly concentrated in vacuo to give colorless transparent oily liquid as the target compound (yield: 100%), which was directly used for the next reaction without further purification.

Step 3: 6-(1-methyl-1H-pyrazol-4-yl)-4-(6-(7-(3-phenylpropioloyl)-2,7-diazaspiro[3.5]nonan-2-yl)pyridin-3-yl)pyrazolo[1,5-a]pyridine-3-carbonitrile To a 2-5 mL microwave tube were added 4-(6-fluoropyridin-3-yl)-6-(1-methyl-1H-pyrazol-4-yl)pyrazolo[1,5-a]pyridine-3-carbonitrile (see synthesis of intermediate 1, 15 mg, 0.04713 mmol), 3-phenyl-1-(2,7-diazaspiro[3.5]non-7-yl)prop-2-yn-1-one 2,2,2-trifluoroacetate (26 mg, 0.07058 mmol) and DMSO (1 mL). The mixture was reacted under microwave at 150° C. for 5 h. To the reaction solution were added EA (30 mL) and water (15 mL), and the aqueous phase was extracted with EA (25 mL×2). The organic phases were combined, washed with 15 mL of saturated brine. The organic phases were separated, dried over anhydrous sodium sulfate, filtered, and then the filtrate was purified by silica gel column chromatography (eluent PE/EA=5/1-1/1.5) to give a yellow solid 8.6 mg as the target product (yield 33.0%). LC-MS (ESI): m/z=553.2 [M+H]+; 1H NMR (400 MHz, DMSO-d6) δ 9.23 (d, 1H), 8.64 (s, 1H), 8.39 (s, 1H), 8.34 (d, J=2.2 Hz, 1H), 8.12 (s, 1H), 7.81 (d, J=8.5 Hz, 1H), 7.76 (s, 1H), 7.64 (d, J=6.9 Hz, 2H), 7.54-7.45 (m, 3H), 6.52 (d, J=8.6 Hz, 1H), 3.88 (s, 3H), 3.83 (s, 4H), 3.82-3.78 (m, 2H), 3.58 (t, 2H), 1.90 (t, 2H), 1.79 (t, 2H). HPLC: 93.57%.

Example 270: 4-(6-(6-(3-(5-methoxypyridin-3-yl)propioloyl)-3,6-diazabicyclo[3.1.1]heptan-3-yl)pyridin-3-yl)-6-(1-methyl-1H-pyrazol-4-yl)pyrazolo[1,5-a]pyridine-3-carbonitrile (270)

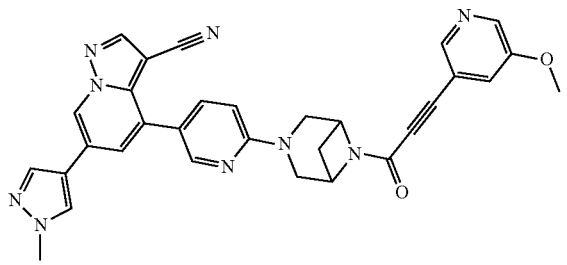

Step 1: 3-(5-methoxypyridin-3-yl)prop-2-yn-1-ol

To a mixture of 3-bromo-5-methoxy-pyridine (500 mg, 2.6593 mmol), bis(triphenylphosphine)palladium dichloride (93 mg, 0.132496 mmol) and CuI (25 mg, 0.13127 mmol) were sequentially added triethylamine (4.0 mL, 29 mmol) and prop-2-yn-1-ol (0.76 mL, 13 mmol) at room temperature under nitrogen. The resulting mixture was heated to 80° C. and reacted for 5 h. The reaction mixture was diluted with EA (40 mL), and the organic phase was poured out, then the residual black viscous solid was washed with EA (30 mL×3). The organic phases were combined, concentrated in vacuo, and then purified by silica gel column chromatography (PE:EA=4:1-2:1) to give a pale yellow solid 280 mg as the target product (the yield was 64.54%). LC-MS: m/z=164.15 [M+H]+. 1H NMR (400 MHz, CDCl3) δ 8.31 (s, 1H), 8.25 (s, 1H), 7.23 (s, 1H), 4.51 (s, 2H), 3.85 (s, 3H).

Step 2: 3-(5-methoxypyridin-3-yl)propynal

To a solution of 3-(5-methoxy-3-pyridyl)prop-2-yn-1-ol (280 mg, 1.7160 mmol) in dichloromethane (17.2 mL) were sequentially added sodium bicarbonate (724 mg, 8.58 mmol) and Dess Martin reagent (1.102 g, 2.572 mmol) at room temperature. The mixture was reacted for 1 h at room temperature. The reaction mixture was added with 20 mL of saturated sodium thiosulfate solution to quench the reaction. The aqueous phase was extracted with DCM (50 mL×2). The organic phases were combined, dried over anhydrous sodium sulfate, filtered, and concentrated in vacuo, then purified by silica gel column chromatography (PE/EA=3:1) to give a white solid 202 mg (yield: 73.0%) as the target product. LC-MS: m/z=162.10 [M+H]+. 1H NMR (600 MHz, CDCl3) δ 9.42 (s, 1H), 8.42 (s, 1H), 8.38 (d, J=2.5 Hz, 1H), 7.34 (s, 1H), 3.87 (s, 3H).

Step 3: 3-(5-methoxypyridin-3-yl)propynoic acid

To a solution of 3-(5-methoxypyridin-3-yl)propynal (150 mg, 0.93075 mmol) in acetonitrile (0.76 mL) were added aqueous sodium dihydrogen phosphate solution (0.31 mL, 0.28 mmol, 0.91 mol/L, concentrated hydrochloric acid adjusted to pH=2), hydrogen peroxide (0.11 mL, 1.1 mmol, 30 mass %) in a 10 mL single-necked flask. An aqueous solution of sodium chlorite (1.1 mL, 1.1 mmol, 1 mol/L) was slowly added to the above solution under ice bath conditions. The temperature was kept below 10° C. and the mixture was reacted for 2 h. The reaction was stopped. The aqueous phase was separated and extracted with EA (20 mL×3). The combined organic phases were back-extracted with saturated sodium bicarbonate solution (20 mL×3). The combined aqueous phases were adjusted to pH=1 with concentrated hydrochloric acid and extracted with EA (20 mL×3). The combined organic phases were washed with saturated brine (20 mL), dried over anhydrous sodium sulfate and concentrated in vacuo to give a white solid 0.84 mg as the target product (yield: 51%). LC-MS: m/z=178.2 [M+H]+. 1H NMR (400 MHz, MeOD) δ 8.37-8.31 (m, 2H), 7.63 (s, 1H), 3.91 (s, 3H).

Step 4: 4-(6-(6-(3-(5-methoxypyridin-3-yl)propioloyl)-3,6-diazabicyclo[3.1.1]heptan-3-yl) pyridin-3-yl)-6-(1-methyl-1H-pyrazol-4-yl)pyrazolo[1,5-a]pyridine-3-carbonitrile To a 5 mL single-necked flask were sequentially added 4-(6-(3,6-diazabicyclo[3.1.1]heptan-3-yl)pyridin-3-yl)-6-(1-methyl-1H-pyrazol-4-yl)pyrazolo[1,5-a]pyridine-3-carbonitrile dihydrochloride (see synthesis of intermediate 3, 25 mg, 0.0533 mmol), 3-(5-methoxypyridin-3-yl)propynoic acid (15 mg, 0.0847 mmol), DMAP (1 mg, 0.0082 mmol), EDCI (30 mg, 0.1565 mmol), DCM (1 mL), N,N-diisopropylethylamine (0.05 mL, 0.3 mmol). The mixture was reacted with stirring at room temperature overnight. To the reaction solution were added DCM (30 mL) and water (15 mL), and the aqueous phase was separated and extracted with DCM (25 mL×2). The organic phases were combined and washed with 15 mL of saturated brine. The organic phases were separated, dried over anhydrous sodium sulfate, filtered, and the filtrate was concentrated in vacuo, and then purified by silica gel column chromatography (eluent DCM/MeOH=100/0-100/3) to give a white solid 8.6 mg as the target product (yield: 29.0%). LC-MS (ESI): m/z=556.5[M+1]+. 1H NMR (400 MHz, CDCl3) δ 8.65 (s, 1H), 8.40 (d, 1H), 8.36 (s, 2H), 8.27 (s, 1H), 7.79 (s, 1H), 7.69 (s, 1H), 7.39 (d, 1H), 7.35 (s, 1H), 7.32 (s, 1H), 6.69 (d, 1H), 4.84-4.71 (m, 2H), 4.22-4.11 (m, 2H), 3.99 (s, 3H), 3.87 (s, 3H), 3.80-3.71 (m, 1H), 3.65 (s, 1H), 2.93-2.85 (m, 1H), 2.25-2.18 (m, 1H). HPLC: 90.90%.

Example 271: 6-(1-methyl-1H-pyrazol-4-yl)-4-(6-(6-(3-phenylpropioloyl)-3,6-diazabicyclo[3.1.1]heptane-3-yl)pyridin-3-yl)pyrazolo[1,5-a]pyridine-3-carbonitrile (271)

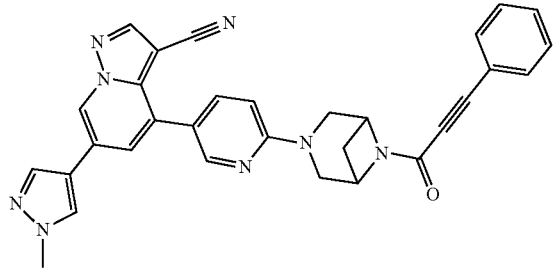

Under nitrogen, to a 10 mL double-necked flask were added 4-(6-(3,6-diazabicyclo[3.1.1]heptane-3-yl)pyridin-3-yl)-6-(1-methyl-1H-pyrazol-4-yl)pyrazolo[1,5-a]pyridine-3-carbonitrile dihydrochloride (see synthesis of intermediate 3, 15 mg, 0.032 mmol) and phenylpropynoic acid (7 mg, 0.048 mmol), which were dissolved by adding DCM (5 mL). Then DMAP (2 mg, 0.0164 mmol) and EDCI (12 mg, 0.0626 mmol) were added. The mixture was stirred at room temperature for 6 h. To the reaction mixture were added DCM (30 mL) and water (10 mL). The organic phase was separated, washed with water (10 mL) once, dried over anhydrous sodium sulfate and filtered. The mother liquor was concentrated in vacuo, and then purified by silica gel column chromatography (eluent MeOH:DCM=1:50-1:20) to give a white solid 3 mg as the desired product (yield: 17.90%). Rf=0.3 (MeOH:DCM=1:30). LC-MS: m/z=525.00[M+H]$^+$. $^1$H NMR (400 MHz, CDCl$_3$) δ 8.64 (d, J=1.1 Hz, 1H), 8.40 (d, J=2.1 Hz, 1H), 8.26 (s, 1H), 7.80-7.77 (m, 2H), 7.68 (s, 1H), 7.54 (d, J=7.0 Hz, 2H), 7.39-7.35 (m, 4H), 6.68 (d, J=8.8 Hz, 1H), 4.79-4.73 (m, 2H), 4.17 (d, J=10.3 Hz, 2H), 3.99 (s, 3H), 3.77-3.66 (m, 2H), 2.92-2.82 (m, 1H), 2.02-2.00 (m, 1H). HPLC: 96.81%.

Example 272: 4-(6-(4-(3-(5-methoxypyridin-3-yl)propioloyl)piperazin-1-yl)pyridin-3-yl)-6-(1-methyl-1H-pyrazol-4-yl)pyrazolo[1,5-a]pyridine-3-carbonitrile

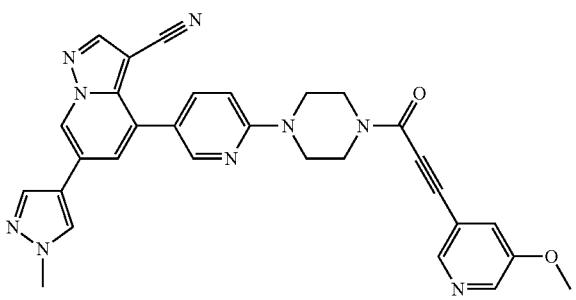

(272)

Step 1: 3-(5-methoxypyridin-3-yl)prop-2-yn-1-ol

To a mixture of 3-bromo-5-methoxy-pyridine (500 mg, 2.6593 mmol), bis(triphenylphosphine)palladium dichloride (93 mg, 0.132496 mmol) and CuI (25 mg, 0.13127 mmol) were sequentially added triethylamine (4.0 mL, 29 mmol) and prop-2-yn-1-ol (0.76 mL, 13 mmol) at room temperature under nitrogen. The resulting mixture was heated to 80° C. and reacted for 5 h. The reaction mixture was diluted with EA (40 mL), and the organic phase was poured out, then the residual black viscous solid was washed with EA (30 mL×3). The organic phases were combined, concentrated in vacuo, and then purified by silica gel column chromatography (PE:EA=4:1-2:1) to give a pale yellow solid 280 mg as the target product (the yield was 64.54%). LC-MS: m/z=164.15 [M+H]$^+$. $^1$H NMR (400 MHz, CDCl$_3$) δ 8.31 (s, 1H), 8.25 (s, 1H), 7.23 (s, 1H), 4.51 (s, 2H), 3.85 (s, 3H).

Step 2: 3-(5-methoxypyridin-3-yl)propynal

To a solution of 3-(5-methoxy-3-pyridyl)prop-2-yn-1-ol (280 mg, 1.7160 mmol) in dichloromethane (17.2 mL) were sequentially added sodium bicarbonate (724 mg, 8.58 mmol) and Dess Martin reagent (1.102 g, 2.572 mmol) at room temperature. The mixture was reacted for 1 h at room temperature. The reaction mixture was added with 20 mL of saturated sodium thiosulfate solution to quench the reaction. The aqueous phase was extracted with DCM (50 mL×2). The organic phases were combined, dried over anhydrous sodium sulfate, filtered, and concentrated in vacuo, then purified by silica gel column chromatography (PE/EA=3:1) to give a white solid 202 mg (yield: 73.0%) as the target product. LC-MS: m/z=162.10 [M+H]$^+$. $^1$H NMR (600 MHz, CDCl$_3$) δ 9.42 (s, 1H), 8.42 (s, 1H), 8.38 (d, J=2.5 Hz, 1H), 7.34 (s, 1H), 3.87 (s, 3H).

Step 3: 3-(5-methoxypyridin-3-yl)propynoic acid

To a solution of 3-(5-methoxypyridin-3-yl)propynal (150 mg, 0.93075 mmol) in acetonitrile (0.76 mL) were added sodium dihydrogen phosphate aqueous solution (0.31 mL, 0.28 mmol, 0.91 mol/L, using concentrated hydrochloric acid to adjust pH to 2), hydrogen peroxide (0.11 mL, 1.1 mmol, 30 mass %) in a 10 mL single-necked flask. An aqueous solution of sodium chlorite (1.1 mL, 1.1 mmol, 1 mol/L) was slowly added to the above solution under ice bath conditions. The temperature was kept below 10° C. and the mixture was reacted for 2 h. The reaction was stopped. The aqueous phase was separated and extracted with EA (20 mL×3). The combined organic phases were back-extracted with saturated sodium bicarbonate solution (20 mL×3). The combined aqueous phases were adjusted to pH=1 with concentrated hydrochloric acid and extracted with EA (20 mL×3). The combined organic phases were washed with saturated brine (20 mL), dried over anhydrous sodium sulfate and concentrated in vacuo to give a white solid 0.84 mg as the target product (yield: 51%). LC-MS: m/z=178.2 [M+H]$^+$. $^1$H NMR (400 MHz, MeOD) δ 8.37-8.31 (m, 2H), 7.63 (s, 1H), 3.91 (s, 3H).

Step 4: 4-(6-(4-(3-(5-methoxypyridin-3-yl)propioloyl)piperazin-1-yl)pyridin-3-yl)-6-(1-methyl-1H-pyrazol-4-yl)pyrazolo[1,5-a]pyridine-3-carbonitrile To a solution of 6-(1-methyl-17T-pyrazol-4-yl)-4-(6-(piperazin-1-yl)pyridin-3-yl) pyrazolo[1,5-a]pyridine-3-carbonitrile dihydrochloride (see synthesis of intermediate 2, 15 mg, 0.033 mmol) and 3-(5-methoxypyridin-3-yl)propanoic acid (9 mg, 0.051 mmol) in DCM (2 mL) were added DMAP (2 mg, 0.016 mmol) and EDCI (13 mg, 0.068 mmol) under nitrogen. The mixture was stirred and reacted at room temperature overnight. The reaction mixture was added with DCM (30 mL) and water (10 mL). The organic phase was separated, washed with water (10 mL), dried over anhydrous sodium sulfate and filtered. The mother liquid was concentrated in vacuo, and then purified by silica gel column chromatography (eluent MeOH:DCM=1:50-1:30) to give a white solid 4.5 mg as the desired product (yield: 25.00%). Rf=0.3 (MeOH:DCM=1:30). LC-MS: m/z=544.20[M+H]$^+$. $^1$H NMR (400 MHz, CDCl$_3$) δ 8.65 (s, 1H), 8.40 (s, 2H), 8.36 (s, 1H), 8.27 (s, 1H), 7.81-7.78 (m, 2H), 7.69 (s, 1H), 7.41 (s, 1H), 7.36 (s, 1H), 6.83 (d, J=8.9 Hz, 1H), 3.99 (s, 3H), 3.97 (d, J=6.6 Hz, 2H), 3.89 (s, 3H), 3.86-3.81 (m, 4H), 3.74-3.71 (m, 2H). HPLC: 96.22%.

Example 273: 6-(1-methyl-1H-pyrazol-4-yl)-4-(6-(6-(3-(pyridin-3-yl)propioloyl]-3,6-diazabicyclo[3.1.1]heptan-3-yl]-3-pyridin]pyrazolo[1,5-a]pyridine-3-carbonitrile

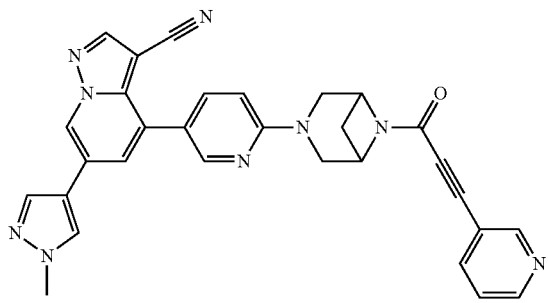

(273)

Step 1: 3-(3-pyridyl)prop-2-yn-1-ol

To a 25 mL two-necked flask were added CuI (72 mg, 0.378 mmol) and PdCl$_2$(PPh$_3$)$_2$ (270 mg, 0.385 mmol) at room temperature. The reaction mixture was degassed and refilled with nitrogen. Then triethylamine (11 mL, 78.9 mmol), propynyl alcohol (0.89 mL, 15 mmol) and 3-bromopyridine (0.73 mL, 7.6 mmol) were added. The mixture was reacted at 50° C. overnight. TLC showed the reaction was completed. The mixture was quenched with saturated ammonium chloride (20 mL) and filtered by suction. The filter cake was washed with 40 mL of EA. The organic phase was separated, and then the aqueous phase was extracted with EA (40 mL×2). The organic phases were combined, washed with saturated brine (30 mL), dried over anhydrous sodium sulfate, filtered and concentrated in vacuo. The mixture was purified by silica gel column chromatography (eluent PE:EA=3:1-1:1) to give a brownish yellow solid 0.705 g (the yield was 70%), which was the target product. LC-MS (ES-API): m/z=134.20 [M+H]$^+$. $^1$H NMR (400 MHz, CDCl$_3$) δ 8.76 (d, J=1.3 Hz, 1H), 8.51 (dd, J=4.9, 1.5 Hz, 1H), 7.73 (dt, J=1.9, 1.8 Hz, 1H), 7.31-7.26 (m, 1H), 4.50 (s, 2H), 3.72 (s, 1H).

Step 2: 3-(3-pyridyl)prop-2-ynaldehyde

To a 100 mL single-necked flask were added 3-(3-pyridyl)prop-2-yn-1-ol (200 mg, 1.502 mmol), NaHCO$_3$ (0.634 g, 7.51 mmol) and Dess Martin oxidant (0.83 g, 2.0 mmol), which were dissolved by adding DCM (15 mL). The mixture was stirred and reacted at room temperature for 3 h. TLC showed the reaction was completed. To the resulting mixture was added 10 mL of saturated sodium thiosulfate solution to quench the reaction. The organic phase was separated and the aqueous phase was extracted with DCM (20 mL×2). The organic phases were combined, dried over anhydrous sodium sulfate, filtered, and concentrated in vacuo. The residue was purified by silica gel column chromatography (eluent PE/EA=6:1-3:1) to give a brownish yellow solid 136 mg (yield: 69.0%) as the target product. $^1$H NMR (400 MHz, CDCl$_3$) δ 9.43 (s, 1H), 8.83 (d, 7=1.1 Hz, 1H), 8.69 (dd, J=4.8, 1.2 Hz, 1H), 7.89 (dd, J=7.9, 1.6 Hz, 1H), 7.37 (dd, J=7.9, 5.0 Hz, 1H).

Step 3: 3-(3-pyridyl)prop-2-ynoic acid

A concentrated hydrochloric acid solution was added to adjust the pH of a solution of NaH$_2$PO$_4$ (0.32 mL, 0.32 mmol) and H$_2$O$_2$ (0.12 mL, 1.2 mmol) to 3 in a 10 ml single-necked flask at 0° C., then a solution of 3-(3-pyridyl)prop-2-ynaldehyde (60 mg, 0.45756 mmol) in acetonitrile (1.5 mL) was added. NaClO$_2$ (136 mg, 1.037 mmol) was added slowly in three portions. The mixture was reacted at 0° C. for 20 min, and then transferred to room temperature for reaction. TLC showed the reaction was completed. The resulting mixture was added with 1 mL of water to quench the reaction, then extracted with EA (5 mL×3). The organic phases were combined, washed with saturated saline (5 mL), dried over anhydrous sodium sulfate, filtered, and concentrated in vacuo to give a yellow solid 0.07 g (yield: 50%.) as the target product. LC-MS (ES-API): m/z=148.10 [M+H]$^+$.

Step 4: 6-(1-methyl-1H-pyrazol-4-yl)-4-(6-(6-(3-(pyridin-3-yl)propioloyl]-3,6-diazabicyclo[3.1.1]heptan-3-yl]-3-pyridin]pyrazolo[1,5-a]pyridine-3-carbonitrile To a 5 mL single-necked flask were sequentially added 4-(6-(3,6-diazabicyclo[3.1.1]heptan-3-yl)pyridin-3-yl)-6-(1-methyl-1H-pyrazol-4-yl)pyrazole[1,5-a]pyridine-3-carbonitrile dihydrochloride (15 mg, 0.032 mmol), 3-(3-pyridyl)prop-2-ynoic acid (15 mg, 0.102 mmol), EDCI (36 mg, 0.162 mmol) and DMAP (1.0 mg, 0.0082 mmol), which were dissolved by adding DCM (2 mL). The mixture was reacted with stirring at room temperature overnight. TLC showed the reaction was completed. The reaction solution was directly concentrated in vacuo, and then purified by silica gel column chromatography (eluent: pure DCM-DCM:MeOH (v:v)=25:1)) to give a white solid 0.006 g (the yield was 40%), which was the target product. LC-MS (ES-API): m/z=526.2 [M+H]$^+$. $^1$H NMR (400 MHz, CDCl$_3$) δ 8.64 (s, 1H), 8.40 (s, 1H), 8.26 (s, 1H), 7.84 (d, J=7.5 Hz, 1H), 7.79 (s, 2H), 7.68 (s, 1H), 7.39 (s, 1H), 7.35 (s, 1H), 7.23 (d, J=7.1 Hz, 1H), 6.84 (d, J=ID Hz, 1H), 6.68 (d, J=8.7 Hz, 1H), 4.78 (d, J=16.1 Hz, 2H), 4.17 (d, J=11.4 Hz, 2H), 3.99 (s, 3H), 3.76 (d, J=9.9 Hz, 1H), 2.90 (d, J=7.3 Hz, 1H), 2.01 (d, J=6.4 Hz, 1H), 1.83 (d, J=9.0 Hz, 1H). HPLC: 91.90%.

Example 274: 6-(1-methyl-1H-pyrazol-4-yl)-4-(6-(4-(3-(pyridin-3-yl)propioloyl)piperazin-1-yl) pyridin-3-yl)pyrazolo[1,5-a]pyridine-3-carbonitrile

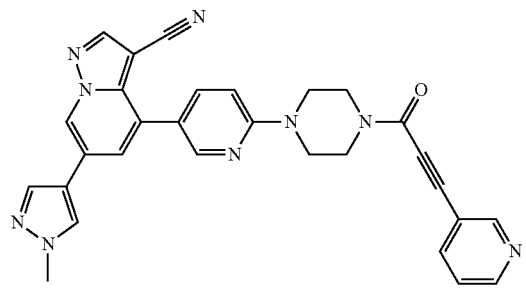

(274)

Step 1: 3-(3-pyridyl)prop-2-yn-1-ol

To a 25 mL two-necked flask were added CuI (72 mg, 0.378 mmol) and PdCl$_2$(PPh$_3$)$_2$ (270 mg, 0.385 mmol) at room temperature. The reaction mixture was degassed and refilled with nitrogen. Then triethylamine (11 mL, 78.9 mmol), propynyl alcohol (0.89 mL, 15 mmol) and 3-bromopyridine (0.73 mL, 7.6 mmol) were added. The mixture was reacted at 50° C. overnight. TLC showed the reaction was completed. The mixture was quenched with saturated ammonium chloride (20 mL) and filtered by suction. The filter cake was washed with 40 mL of EA. The organic phase was separated, and then the aqueous phase was extracted with EA (40 mL×2). The organic phases were combined, washed with saturated brine (30 mL), dried over anhydrous sodium sulfate, filtered and concentrated in vacuo. The residue was purified by silica gel column chromatography (eluent PE:EA=3:1-1:1) to give a brownish yellow solid 0.705 g (the yield was 70%), which was the target product. LC-MS (ES-API): m/z=134.20 [M+H]$^+$. $^1$H NMR (400 MHz, CDCl$_3$) δ 8.76 (d, J=1.3 Hz, 1H), 8.51 (dd, J=4.9, 1.5 Hz, 1H), 7.73 (dt, J=1.9, 1.8 Hz, 1H), 7.31-7.26 (m, 1H), 4.50 (s, 2H), 3.72 (s, 1H).

Step 2: 3-(3-pyridyl)prop-2-ynaldehyde

To a 100 mL single-necked flask were added 3-(3-pyridyl)prop-2-yn-1-ol (200 mg, 1.502 mmol), NaHCO$_3$ (0.634 g, 7.51 mmol) and Dess Martin oxidant (0.83 g, 2.0 mmol), which were dissolved by adding DCM (15 mL). The mixture was stirred and reacted at room temperature for 3 h. TLC showed the reaction was completed. To the resulting mixture was added 10 mL of saturated sodium thiosulfate solution to quench the reaction. The organic phase was separated and the aqueous phase was extracted with DCM (20 mL×2). The organic phases were combined, dried over anhydrous sodium sulfate, filtered, and concentrated in vacuo. The residue was purified by silica gel column chromatography (eluent PE/EA=6:1-3:1) to give a brownish yellow solid 136 mg (yield: 69.0%) as the target product. $^1$H NMR (400 MHz, CDCl$_3$) δ 9.43 (s, 1H), 8.83 (d, 7=1.1 Hz, 1H), 8.69 (dd, J=4.8, 1.2 Hz, 1H), 7.89 (dd, J=7.9, 1.6 Hz, 1H), 7.37 (dd, J=7.9, 5.0 Hz, 1H).

Step 3: 3-(3-pyridyl)prop-2-ynoic acid

A concentrated hydrochloric acid solution was added to adjust the pH of a solution of NaH$_2$PO$_4$ (0.32 mL, 0.32 mmol) and H$_2$O$_2$ (0.12 mL, 1.2 mmol) to 3 in a 10 ml single-necked flask at 0° C., then a solution of 3-(3-pyridyl)prop-2-ynaldehyde (60 mg, 0.458 mmol) in acetonitrile (1.5 mL) was added. NaClO$_2$ (136 mg, 1.037 mmol) was added slowly in three portions. The mixture was reacted at 0° C. for 20 min, and then transferred to room temperature for reaction. TLC showed the reaction was completed. The resulting mixture was added with 1 mL of water to quench the reaction, then extracted with EA (5 mL×3). The organic phases were combined, washed with saturated saline (5 mL), dried over anhydrous sodium sulfate, filtered, and concentrated in vacuo to give a yellow solid 0.07 g (yield: 50%.) as the target product. LC-MS (ES-API): m/z=148.10 [M+H]$^+$.

Step 4: 6-(1-methyl-1H-pyrazol-4-yl)-4-(6-(4-(3-(pyridin-3-yl)propioloyl)piperazin-1-yl)pyridin-3-yl)pyrazolo[1,5-a]pyridine-3-carbonitrile To a 5 mL single-necked flask were sequentially added 6-(1-methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 20 mg, 0.044 mmol), 3-(3-pyridyl)prop-2-ynoic acid (19 mg, 0.129 mmol), EDCI (42 mg, 0.219 mmol) and DMAP (1.0 mg, 0.0082 mmol), which were dissolved by adding DCM (2 mL). The mixture was reacted with stirring at room temperature overnight. TLC showed the reaction was completed. The reaction solution was directly concentrated in vacuo, and then purified by silica gel column chromatography (eluent pure DCM-DCM:MeOH=25:1) to give a pale yellow solid 0.006 g (the yield was 30%), which was the target product. LC-MS (ES-API): m/z=514.2 [M+H]$^+$. $^1$H NMR (400 MHz, CDCl$_3$) δ 8.81 (s, 1H), 8.65 (s, 1H), 8.40 (s, 1H), 8.27 (s, 1H), 7.89 (d, J=7.5 Hz, 1H), 7.79 (s, 2H), 7.69 (s, 1H), 7.41 (s, 1H), 7.08 (d, J=8.5 Hz, 2H), 6.83 (d, J=8.8 Hz, 1H), 3.99 (s, 3H), 3.88-3.82 (m, 4H), 3.77-3.68 (m, 4H). HPLC: 93.56%.

Example 275: 6-(1-methyl-1H-pyrazol-4-yl)-4-(6-(4-(penta-2,4-diyn-1-yl)piperazin-1-yl) pyridine-3-yl)pyrazolo[1,5-a]pyridine-3-carbonitrile (275)

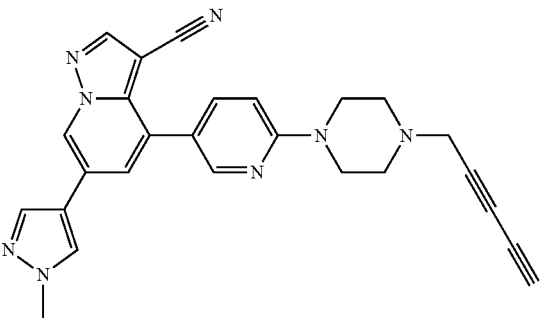

Step 1: 5-(trimethyl silyl)penta-2,4-diyn-1-ol

To a mixture of THF (150 mL) and TMEDA (2.67 mL, 17.8 mmol) were added CuI (849 mg, 4.4579 mmol) and NiCl$_2$ 6H$_2$O (1.123 g, 4.461 mmol) at room temperature. The mixture was stirred at room temperature for 5 min, then ethynyl (trimethyl) silane (25.2 mL, 178 mmol) and prop-2-yn-1-ol (5.19 mL, 89.2 mmol) were added sequentially. The resulting mixture was stirred at room temperature for 12 h and concentrated in vacuo. The residue was purified by silica gel column chromatography (Rf=0.5, PE:EA=10:1) to give colorless liquid 4.36 g, which was the target product (yield 32.1%). $^1$H NMR (400 MHz, CDCl$_3$) δ 4.35 (s, 2H), 0.22 (s, 9H).

Step 2: pent-2,4-diyn-1-ol

To a single-necked flask were sequentially added 5-(trimethylsilyl)penta-2,4-diyn-1-ol (4.36 g, 28.6 mmol), methanol (50 mL) and K$_2$CO$_3$ (12.0 g, 86.0 mmol). The mixture was stirred at room temperature 3.5 h. The reaction was quenched with saturated ammonium chloride solution and the resulting mixture was extracted with EA (100 mL×2). The organic phases were combined, dried over anhydrous sodium sulfate and filtered. The mother liquor was concentrated in vacuo and the residue was purified by silica gel column chromatography (Rf=0.5, PE:EA=5:1) to give brown liquid 2.29 g as the target product (yield: 100%). $^1$H NMR (400 MHz, CDCl$_3$) δ 4.35 (d, J=5.7 Hz, 2H), 2.22 (s, 1H), 1.74 (t, J=6.4 Hz, 1H).

Step 3: 5-bromo-1,3-diyne

Pent-2,4-diyn-1-ol (77 mg, 0.9615 mmol) was dissolved in DCM (10 mL) at 0° C., and PBr$_3$ (0.2 mL, 2 mmol) was slowly added. The mixture was reacted at 0° C. for 1 h. The reaction was quenched by the addition of water (5 mL). The mixture was added with saturated potassium carbonate to adjust pH to alkaline, and then extracted with DCM (20 mL×2). The organic phases were combined, dried over anhydrous sodium sulfate and filtered. The mother liquid was concentrated in vacuo to 4 mL (easy to deteriorate) which was directly used for the next step. The yield was calculated as 100%.

Step 4: 6-(1-methyl-1H-pyrazol-4-yl)-4-(6-(4-(pent-2,4-diyn-1-yl)piperazin-1-yl)pyridine-3-yl)pyrazole[1,5-a]pyridine-3-carbonitrile 6-(1-Methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 20 mg, 0.04373 mmol) was dissolved in DMF (1 mL) in a single-necked flask. 5-Bromo-1,3-diyne (12 mg, 0.083928 mmol) and K$_2$CO$_3$ (18 mg, 0.128940 mmol, 99 mass %) were added. The mixture was reacted at rt overnight. The reaction was quenched by the addition of water (5 mL). The mixture was extracted with EA (30 mL). The organic layers were washed with water (5 mL×3), dried over anhydrous sodium sulfate and filtered. The mother liquid was concentrated in vacuo, and then purified by silica gel column chromatography (Rf=0.5, DCM:MeOH=10:1) to give a white solid 8.0 mg as the target product (the yield was 40.98%). LC-MS: m/z=447.2[M+H]$^+$. $^1$H NMR (400 MHz, CDCl$_3$) δ 8.66 (s, 1H), 8.39 (d, J=2.4 Hz, 1H), 8.28 (s, 1H), 7.81 (s, 1H), 7.78 (dd, J=8.8, 2.5 Hz, 1H), 7.70 (s, 1H), 7.42 (s, 1H), 6.82 (d, J=8.8 Hz, 1H), 4.01 (s, 3H), 3.74 (s, 4H), 3.67 (s, 1H), 3.50 (s, 2H), 2.75 (s, 4H). HPLC: 88.46%.

Example 276: 6-(1-methyl-1H-pyrazol-4-yl)-4-(6-(6-(pent-2,4-diyn-1-yl)-3,6-diazabicyclo[3.1.1]heptanepyridin-3-yl)pyridin-3-yl)pyrazolo[1,5-a]pyridine-3-carbonitrile

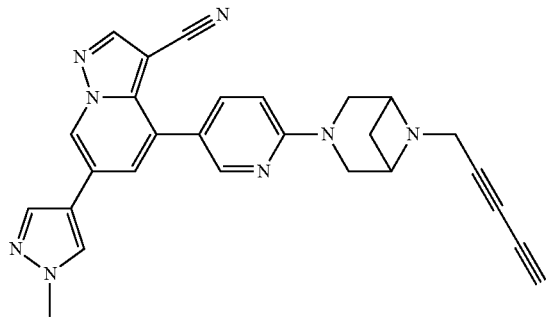

(276)

Step 1: 5-(trimethyl silyl)penta-2,4-diyn-1-ol

To a mixture of THF (150 mL) and TMEDA (2.67 mL, 17.8 mmol) were added CuI (849 mg, 4.4579 mmol) and NiCl$_2$ 6H$_2$O (1.123 g, 4.461 mmol) at room temperature. The mixture was stirred at room temperature for 5 min, then ethynyl (trimethyl) silane (25.2 mL, 178 mmol) and prop-2-yn-1-ol (5.19 mL, 89.2 mmol) were added sequentially. The resulting mixture was stirred at room temperature for 12 h and concentrated in vacuo. The residue was purified by silica gel column chromatography (Rf=0.5, PE:EA=10:1) to give colorless liquid 4.36 g, which was the target product (yield 32.1%). $^1$H NMR (400 MHz, CDCl$_3$) δ 4.35 (s, 2H), 0.22 (s, 9H).

Step 2: pent-2,4-diyn-1-ol

To a single-necked flask were sequentially added 5-(trimethylsilyl)penta-2,4-diyn-1-ol (4.36 g, 28.6 mmol), methanol (50 mL) and K$_2$CO$_3$ (12.0 g, 86.0 mmol). The mixture was stirred at room temperature 3.5 h. The reaction was quenched with saturated ammonium chloride solution and the resulting mixture was extracted with EA (100 mL×2). The organic phases were combined, dried over anhydrous sodium sulfate and filtered. The mother liquid was concentrated in vacuo and the residue was purified by silica gel column chromatography (Rf=0.5, PE:EA=5:1) to give brown liquid 2.29 g as the target product (yield: 100%). $^1$H NMR (400 MHz, CDCl$_3$) δ 4.35 (d, J=5.7 Hz, 2H), 2.22 (s, 1H), 1.74 (t, J=6.4 Hz, 1H).

Step 3: 5-bromo-1,3-diyne

Pent-2,4-diyn-1-ol (77 mg, 0.9615 mmol) was dissolved in DCM (10 mL) at 0° C., and PBr$_3$ (0.2 mL, 2 mmol) was slowly added. The mixture was reacted at 0° C. for 1 h. The reaction was quenched by the addition of water (5 mL). The mixture was added with saturated potassium carbonate to adjust pH to alkaline, and then extracted with DCM (20 mL×2). The organic phases were combined, dried over anhydrous sodium sulfate and filtered. The mother liquid was concentrated in vacuo to 4 mL (easy to deteriorate) which was directly used for the next step. The yield was calculated as 100%.

Step 4: 6-(1-methyl-1H-pyrazol-4-yl)-4-(6-(6-(pent-2,4-diyn-1-yl)-3,6-diazabicyclo[3.1.1]heptanepyridin-3-yl)pyridin-3-yl)pyrazolo[1,5-a]pyridine-3-carbonitrile 4-(6-(3,6-Diazabicyclo[3.1.1]heptan-3-yl)pyridin-3-yl)-6-(1-methyl-1H-pyrazol-4-yl)pyrazole[1,5-a]pyridine-3-carbonitrile dihydrochloride (see synthesis of intermediate 3, 25 mg, 0.053 mmol) was dissolved in DMF (1 mL) in a single-necked flask. 5-Bromo-1,3-diyne (12 mg, 0.084 mmol) and K$_2$CO$_3$ (17 mg, 0.122 mmol, 99 mass %) were added. The mixture was reacted at rt overnight. Water (5 mL) and DCM (50 mL) were added. The organic phases were separated, washed with water (5 mL×2), dried over anhydrous sodium sulfate and filtered. The mother liquid was concentrated in vacuo, and then purified by silica gel column chromatography (Rf=0.5, DCM:MeOH=30:1) to give a pale yellow solid 4 mg as the target product (the yield was 16.38%). LC-MS: m/z=460.2[M+H]$^+$. $^1$H NMR (400 MHz, CDCl$_3$) δ 8.66 (s, 1H), 8.44 (d, J=2.2 Hz, 1H), 8.29 (s, 1H), 7.82 (s, 1H), 7.71 (s, 1H), 7.43 (d, J=0.9 Hz, 1H), 7.37 (d, J=2.1 Hz, 1H), 6.72 (d, J=8.8 Hz, 1H), 4.02 (s, 3H), 3.92 (d, J=5.6 Hz, 2H), 3.81 (d, J=12.4 Hz, 2H), 3.67 (s, 2H), 3.64 (s, 1H), 3.36 (s, 2H), 2.40-2.33 (m, 1H), 2.27-2.20 (m, 1H). HPLC: 98.74%.

Example 277: 6-(1-methyl-1H-pyrazol-4-yl)-4-(6-(4-methyl-4-(prop-2-yn-1-ylamino) piperidin-1-yl) pyridin-3-yl)pyrazolo[1,5-a]pyridine-3-carbonitrile (277)

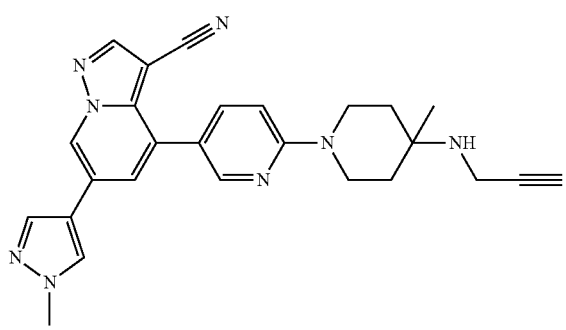

To a 10 mL single-necked flask were sequentially added 4-(6-(4-amino-4-methylpiperidin-1-yl)pyridin-3-yl)-6-(1-methyl-1H-pyrazol-4-yl)pyrazolo[1,5-a]pyridine-3-carbonitrile dihydrochloride (see synthesis of intermediate 4, 15 mg, 0.031 mmol), potassium carbonate (25 mg, 0.181 mmol) and acetonitrile (1.0 mL). Then bromopropyne (0.05 ml, 0.06 mmol) was added slowly. The resulting mixture was stirred at room temperature overnight. The resulting mixture was filtered, and the filtrate was concentrated in vacuo, purified by silica gel column chromatography (eluent DCM/MeOH=50:1-30:1) to give a white solid 12.7 mg as the target product (the yield was 91.2%)(Rf=0.15, DCM/MeOH=30/1). LC-MS (ES-API): m/z=451.20 [M+H]$^+$. $^1$H NMR (400 MHz, CDCl$_3$) δ 8.62 (d, J=1.2 Hz, 1H), 8.35 (d, J=2.4 Hz, 1H), 8.25 (s, 1H), 7.79 (s, 1H), 7.72 (dd, J=8.8, 2.5 Hz, 1H), 7.68 (s, 1H), 7.39 (d, J=1.2 Hz, 1H), 7.08 (dd, J=8.4, 2.3 Hz, 1H), 3.99 (s, 3H), 3.76-3.65 (m, 4H), 3.45 (s, 2H), 2.34 (t, J=7.5 Hz, 1H), 2.21 (d, J=12 Hz, 1H), 2.01 (dd, J=6.8, 4.0 Hz, 4H), 1.42 (s, 3H). HPLC: 96.93%.

Example 278: 6-(1-methyl-1H-pyrazol-4-yl)-4-(2-(4-(3-phenylpropoxy)piperazin-1-yl) pyrimidin-5-yl)pyrazolo[1,5-a]pyridine-5-carbonitrile (278)

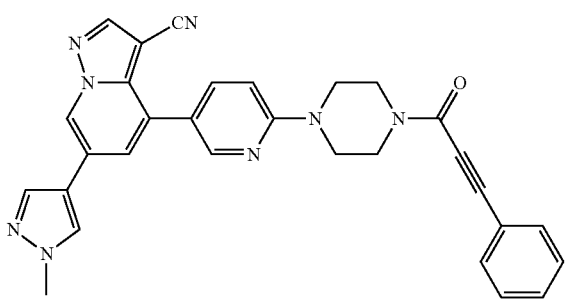

Step 1: tert-butyl 4-(3-phenylprop-2-ynyl)piperazine-1-carboxylate

To a 25 mL single-necked flask was added 3-phenylprop-2-ynoic acid (500 mg, 3.422 mmol), which was dissolved by adding DMF (5 mL). The mixture was placed in a low temperature bath at 0° C. Then tert-butyl piperazine-1-carboxylate (637 mg, 3.420 mmol) was added. N,N-dicyclohexylcarbodiimide (706 mg, 3.422 mmol) was added in portions. The resulting mixture was reacted for 4 h at 0° C. TLC showed the reaction was completed. To the reaction mixture was added water (25 mL), then the resulting mixture was extracted with EA (10 mL×2) and washed with saturated saline (40 mL). The organic phases were separated, dried over anhydrous sodium sulfate, filtered, and concentrated in vacuo. The mixture was purified by silica gel column chromatography (eluent PE:EA=8:1-2:1) to give a yellow-white solid 0.985 g (the yield was 91.6%), which was the target product. LC-MS (ES-API): m/z=315.3[M+H]$^+$. $^1$H NMR (400 MHz, CDCl$_3$) δ 7.57-7.52 (m, 2H), 7.39 (ddd, J=15.9, 7.2, 1.9 Hz, 3H), 3.84-3.78 (m, 2H), 3.70-3.63 (m, 2H), 3.5-3.50 (m, 2H), 3.48-3.42 (m, 2H), 1.48 (s, 9H).

Step 2: 3-phenyl-1-piperazin-1-yl-prop-2-yn-1-one hydrochloride

To a 100 mL single-necked flask were added tert-butyl 4-(3-phenylprop-2-ynyl)piperazine-1-carboxylate (0.985 g, 3.13 mmol) and a solution of hydrogen chloride in ethyl acetate (9.85 mL, 39.4 mmol). The mixture was stirred at room temperature, and the solid was dissolved, then a white solid was precipitated. The solution was changed to a white suspension, and the reaction was continued for 3 h. TLC showed the reaction was completed. The reaction solution was directly concentrated in vacuo to give yellow oil, which was dried in an oven at 60° C. to obtain a theoretical amount of yellow white solid 0.785 g as the target product. LC-MS (ES-API): m/z=215.3 [M+H]$^+$.

Step 3: 4-(2-chloropyrimidin-5-yl)-6-(1-methyl-1H-pyrazol-4-yl)pyrazolo[1,5-a]pyridine-3-carbonitrile To a 10 mL two-necked flask were added 3-cyano-6-(1-methyl-1H-pyrazol-4-yl)pyrazolo[1,5-a]pyridin-4-yl trifluoromethanesulfonate (see step 4 of the synthesis of intermediate 1, 110 mg, 0.296 mmol), (2-chloropyrimidin-5-yl) boronic acid (70 mg, 0.442 mmol) and [1,1'-bis(diphenylphosphino)ferrocene]palladium dichloride dichloromethane complex (25 mg, 0.030 mmol). The reaction mixture was degassed and refilled with nitrogen. The mixture was dissolved with 1,4-dioxane (2 mL), and then added with potassium acetate aqueous solution (0.6 mL, 0.6 mmol, 1 mmol/mL). The resulting mixture was placed in an oil bath at 80° C. and reacted for 48 h. The reaction mixture was added with water (5 mL) and extracted with EA (15 mL×3). The combined organic phases were washed with saline (10 mL), dried over anhydrous sodium sulfate and filtered. The mother liquor was concentrated in vacuo, and the residue was purified by silica gel column chromatography (DCM/MeOH=100/1-50/1) to give a white solid 35 mg (the yield was 35%). LC-MS (ES-API): m/z=336.0[M+H]$^+$. $^1$H NMR (600 MHz, CDCl$_3$) δ 8.88 (s, 2H), 8.76 (s, 1H), 8.31 (s, 1H), 7.81 (s, 1H), 7.72 (s, 1H), 7.47 (s, 1H), 4.01 (s, 3H).

Step 4: 6-(1-methyl-1H-pyrazol-4-yl)-4-(2-(4-(3-phenylpropoxy)piperazin-1-yl)pyrimidin-5-yl)pyrazolo[1,5-a]pyridine-5-carbonitrile To a 25 mL single-necked flask were added 4-(2-chloropyrimidin-5-yl)-6-(1-methyl-1H-pyrazol-4-yl)pyrazolo[1,5-a]pyridine-3-carbonitrile (35 mg, 0.104 mmol) and 3-phenyl-1-piperazin-1-yl-prop-2-yn-1-one hydrochloride (36 mg, 0.143 mmol), which were dissolved by adding 1,4-dioxane (3 mL). Then potassium carbonate (56 mg, 0.405 mmol) was added. The mixture was heated in a 60° C. oil bath and reacted for 12 h. The reaction mixture was poured into 15 mL of saturated saline solution. The resulting mixture was extracted with EA (30 mL×3). The combined organic phases were dried over anhydrous sodium sulfate and filtered. The mother liquid was concentrated in vacuo, and the residue was purified by silica gel column chromatography (eluent DCM/MeOH=100/1-30/1) to give a white solid 15.8 mg (the yield was 29.5%). LC-MS (ES-API): m/z=514.15[M+H]$^+$. $^1$H NMR (400 MHz, CDCl$_3$) δ 8.65 (s, 1H), 8.40 (s, 1H), 8.27 (s, 1H), 7.80 (d, J=5.3 Hz, 2H), 7.69 (s, 1H), 7.58 (s, 1H), 7.42 (dd, J=15.2, 7.2 Hz, 4H), 6.83 (d, J=8.9 Hz, 1H), 3.99 (m, 5H), 3.87-3.81 (m, 4H), 3.73 (d, J=5.5 Hz, 2H). HPLC: 98.53%.

Example 279: 6-(1-methylpyrazol-4-yl)-4-[4-[4-(3-phenylprop-2-ynyl)piperazin-1-yl]phenyl]pyrazolo[1,5-a]pyridine-3-carbonitrile

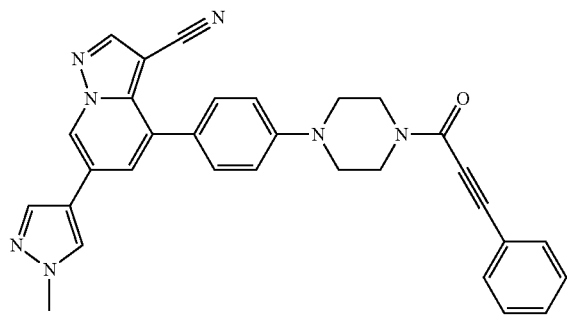

(279)

Step 1: 4-hydroxy-6-(1-methylpyrazol-4-yl)pyrazolo[1,5-a]pyridine-3-carbonitrile To a 50 mL two-necked flask were added 6-bromo-4-hydroxy-pyrazolo[1,5-a]pyridine-3-carbonitrile (1.0 g, 4.2 mmol), l-methyl-4-(4,4,5,5-tetramethyl-1,3,2-dioxaborolan-2-yl)pyrazole (1.3 g, 6.2 mmol) and Pd(PPh$_3$)$_4$ (490 mg, 0.420 mmol). The mixture was degassed and refilled with nitrogen. 1,4-dioxane (20 mL) was added by injection to dissolve the solid, and then potassium acetate aqueous solution (6.3 mL, 13 mmol, 2 mmol/mL) was added. The solution turned from red to grayish brown, and a solid precipitated. The mixture was heated to 80° C. and reacted with stirring. After the completion of reaction was monitored by TLC, to the mixture was added 15 mL of water and the resulting mixture was extracted with EA (40 mL×2). The organic phases were washed with saturated saline (20 mL), dried over anhydrous sodium sulfate, filtered, and the filtrate was concentrated in vacuo, and then purified by silica gel column chromatography (eluent: pure DCM-DCM:MeOH (v:v=10:1)) to give a gray solid 0.945 g (yield: 94%) as the target product. LC-MS (ES-API): m/z=240.10[M+H]$^+$.

Step 2: [3-cyano-6-(1-methyl pyrazol-4-yl)pyrazolo[1,5-a]pyridin-4-yl]triflate

To a 50 mL two-necked flask was added 4-hydroxy-6-(1-methyl pyrazol-4-yl)pyrazolo[1,5-a]pyridine-3-carbonitrile (400 mg, 1.672 mmol). The mixture was degassed and refilled with nitrogen. DCM (12 mL) was added by injection to dissolve the solid, and then pyridine (0.33 mL, 4.1 mmol) was added. Trifluoromethanesulfonic anhydride (0.42 mL, 2.0 mmol) was slowly added dropwise at 0° C., and the reaction was continued at this temperature. After the completion of reaction was monitored by TLC, to the reaction mixture was added water (30 mL), then the resulting mixture was extracted with DCM (80 mL×2). The organic phases were washed with saturated saline (30 mL), dried over anhydrous sodium sulfate, filtered, and concentrated in vacuo. The mixture was purified by silica gel column chromatography (eluent: pure DCM-DCM:MeOH (v:v=50:1)) to give a brownish yellow solid 0.1 g (the yield was 20%), which was the target product. $^1$H NMR (400 MHz, CDCl$_3$) δ 8.66 (s, 1H), 8.29 (s, 1H), 7.78 (s, 1H), 7.70 (s, 1H), 7.55 (s, 1H), 4.01 (s, 3H).

Step 3: tert-butyl 4-(4-bromophenyl)piperazine-1-carboxylate

To a 50 mL two-necked flask were sequentially added 1-bromo-4-iodobenzene (1.276 g, 4.510 mmol), tert-butyl piperazine-1-carboxylate (800 mg, 4.295 mmol), Pd$_2$(dba)$_3$ (393 mg, 0.430 mmol), 4,5-bis(diphenylphosphino)-9,9-dimethylxanthine (131 mg, 0.215 mmol) and sodium tert-butoxide (1.65 g, 17.2 mmol). The reaction mixture was degassed and refilled with nitrogen. The mixture was dissolved by adding toluene (12 mL) and placed in a 60° C. oil bath to heat the reaction. After the completion of reaction was monitored by TLC, to the resulting mixture was added 15 mL of water to quench the reaction, and the resulting mixture was extracted with EA (40 mL×2). The organic phases were washed with saturated saline (20 mL), dried over anhydrous sodium sulfate, filtered, concentrated in vacuo, and then purified by silica gel column chromatography (eluent pure PE-PE:EA=10:1) to give a yellow-white solid 1.1145 g (yield: 76.05%) as the target product. LC-MS (ES-API): m/z=341.10[M+H]$^+$. $^1$H NMR (600 MHz, CDCl$_3$) δ 7.35 (d, J=8.9 Hz, 2H), 6.79 (d, J=8.9 Hz, 2H), 3.59-3.54 (m, 4H), 3.12-3.06 (m, 4H), 1.48 (s, 9H).

Step 4: tert-butyl 4-[4-(4,4,5,5-tetramethyl-1,3,2-dioxaborolan-2-yl)phenyl]piperazine-1-carboxylate To a 50 mL two-necked flask were added tert-butyl 4-(4-bromophenyl)piperazine-1-carboxylate (500 mg, 1.465 mmol), potassium acetate (432 mg, 4.402 mmol), 4,4,5,5-tetramethyl-2-(4,4,5,5-tetramethyl-1,3,2-dioxaborolan-2-yl)-1,3,2-dioxaborolane (595 mg, 2.343 mmol) and PdCl$_2$(dppf)CH$_2$Cl$_2$ (121 mg, 0.147 mmol). The reaction mixture was degassed and refilled with nitrogen. 1,4-Dioxane (10 mL) was added, and the mixture was heated under reflux at 100° C. After the completion of reaction was monitored by TLC, the resulting mixture was filtered by suction and washed with EA (80 mL). The organic phases were washed with saturated saline (20 mL), dried over anhydrous sodium sulfate, concentrated in vacuo, and then purified by silica gel column chromatography (eluent: pure PE-PE:EA(v:v=9:1)) to give a white solid 0.4598 g (yield: 80.81%) as the target product. LC-MS (ES-API): m/z=389.20[M+H]$^+$. $^1$H NMR (400 MHz, CDCl$_3$) δ 7.71 (d, J=8.6 Hz, 2H), 6.88 (d, J=8.6 Hz, 2H), 3.59-3.54 (m, 4H), 3.27-3.18 (m, 4H), 1.48 (s, 9H), 1.32 (s, 12H).

Step 5: tert-butyl 4-[4-[3-cyano-6-(1-methyl pyrazol-4-yl)pyrazolo[1,5-a]pyridin-4-yl]phenyl]piperazine-1-carboxylate To a 10 mL two-necked flask were added [3-cyano-6-(1-methylpyrazol-4-yl)pyrazolo[1,5-a]pyridin-4-yl]trifluoromethanesulfonate (40 mg, 0.108 mmol), tert-butyl 4-[4-(4,4,5,5-tetramethyl-1,3,2-dioxaborolan-2-yl)phenyl]piperazine-1-carboxylate (50 mg, 0.129 mmol), PdCl$_2$(dppf)CH$_2$Cl$_2$ (9 mg, 0.011 mmol) and potassium acetate (32 mg, 0.326 mmol). The reaction mixture was degassed and refilled with nitrogen for several times. 1,4-Dioxane (3 mL) was added. The mixture was heated to 90° C. and reacted with stirring. After the completion of reaction was monitored by TLC, to the resulting mixture was added 6 mL of water, and the resulting mixture was extracted with EA (15 mL×2). The organic phases were washed with saturated saline (10 mL), dried over anhydrous sodium sulfate, concentrated in vacuo, and then purified by silica gel column chromatography (eluent PE:EA=4:1-1:4) to give a brownish yellow solid 0.02 g (yield: 40%) as the target product. LC-MS (ES-API): m/z=484.20[M+H]$^+$. $^1$H NMR (400 MHz, CDCl$_3$) δ 8.62 (d, J=1.3 Hz, 1H), 8.54 (d, J=1.0 Hz, 1H), 8.25 (s, 1H), 8.19 (s, 1H), 7.79 (s, 1H), 7.76 (s, 1H), 7.41 (d, J=1.3 Hz, 1H), 7.05 (d, J=8.7 Hz, 2H), 3.99 (s, 3H), 3.63-3.58 (m, 4H), 3.29-3.23 (m, 4H), 1.50 (s, 9H).

Step 6: 6-(1-methylpyrazol-4-yl)-4-(4-piperazin-1-ylphenyl)pyrazolo[1,5-a]pyridine-3-carbonitrile dihydrochloride To a 10 mL single-necked flask were added tert-butyl 4-[4-[3-cyano-6-(1-methylpyrazol-4-yl)pyrazolo[1,5-a]pyridin-4-yl]phenyl]piperazine-1-carboxylat e (20 mg, 0.042 mmol) and a solution of hydrogen chloride in ethyl acetate (2 mL, 8 mmol). The mixture was stirred and reacted at room temperature, and the solid was dissolved, then a yellow-white solid was precipitated. The completion of reaction was monitored by TLC. The reaction solution was directly concentrated in vacuo to obtain a theoretical amount of yellow-white solid 0.019 g as the target product. LC-MS (ES-API): m/z=384.30[M+H]$^+$.

Step 7: 6-(1-methylpyrazol-4-yl)-4-[4-[4-(3-phenyl-prop-2-ynyl)piperazin-1-yl]phenyl]pyrazolo[1,5-a]pyridine-3-carbonitrile To a 5 mL single-necked flask were sequentially added 6-(1-methyl pyrazol-4-yl)-4-(4-piperazin-1-yl phenyl)pyrazolo[1,5-a]pyridine-3-carbonitrile dihydrochloride (19 mg, 0.042 mmol), EDCI (40 mg, 0.209 mmol) and DMAP (1 mg, 0.008 mmol). Then DCM (2 mL) was added. The mixture was slightly dissolved, and 3-phenylprop-2-ynoic acid (18.3 mg, 0.125 mmol) was added. The mixture was stirred to react at room temperature overnight. The completion of reaction was monitored by TLC. The reaction solution was directly concentrated in vacuo, and the residue was purified by silica gel column chromatography (eluent: pure DCM-DCM:MeOH (v:v=20:1)) to give a white solid 6.5 mg (the yield was 31%), which was the target product. LC-MS (ES-API): m/z=512.20[M+H]$^+$. $^1$H NMR (400 MHz, CDCl$_3$) δ 8.63 (d, J=1.2 Hz, 1H), 8.26 (s, 1H), 7.79 (s, 1H), 7.68 (s, 1H), 7.58 (d, J=7.1 Hz, 2H), 7.53 (d, J=8.3 Hz, 2H), 7.42 (dd, J=14.1, 8.7 Hz, 4H), 7.13 (d, J=8.4 Hz, 2H), 4.08-4.03 (m, 2H), 3.99 (s, 3H), 3.94-3.89 (m, 2H), 3.43-3.39 (m, 2H), 3.38-3.33 (m, 2H). HPLC: 93.47%.

Example 280: 6-(1-cyclopropyl-1H-pyrazol-4-yl)-4-(6-(3-((6-ethynylpyridin-3-yl)oxy) azetidin-1-yl)pyridin-3-yl)pyrazolo[1,5-a]pyridine-3-carbonitrile

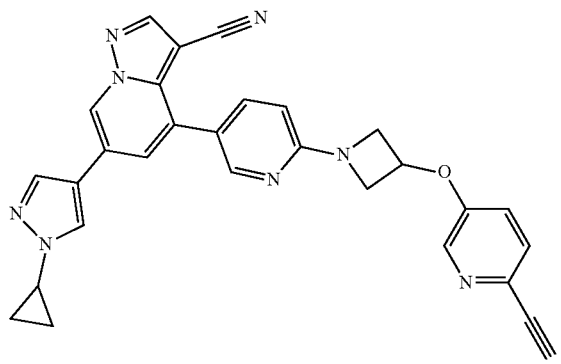

(280)

Step 1: tert-butyl 3-hydroxyazetidin-1-carboxylate

To a single-necked flask were added tert-butyl 3-oxoazetidine-1-carboxylate (5.0 g, 29 mmol) and EtOH (50 mL) at room temperature, then NaBH$_4$ (1.1 g, 29 mmol) was added portionwise with stirring. After the completion of reaction was monitored by TLC, a saturated ammonium chloride solution was added to the reaction solution until no bubbles were generated, and a large amount of white solid was precipitated. The mixture was filtered with suction. The filter cake was washed with ethanol (10 mL), and the filtrate was concentrated in vacuo to remove most of the ethanol. To the residue was added with 30 mL of water and the mixture was extracted with EA (100 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 5.0 g as the target product. LC-MS: m/z=118.10[M-t-Bu+H]$^+$, $^1$H NMR (400 MHz, CDCl$_3$) δ 4.53 (s, 1H), 4.13-4.09 (m, 2H), 3.78 (dd, J=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask were added tert-butyl 3-hydroxyazetidine-1-carboxylate (500 mg, 2.89 mmol), DCM (15 mL) and NaH (0.14 g, 5.8 mmol) under nitrogen. The mixture was transferred to 0° C. and MsCl (0.25 mL, 3.2 mmol) was added dropwise with stirring. After the addition, the mixture was reacted continuously at this temperature. After the completion of reaction was monitored by TLC, water (20 mL) and DCM (50 mL) were added to the reaction mixture. The organic phase was separated, and the aqueous phase was extracted with EA (50 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 566 mg as the target product. LC-MS: m/z=196.10[M-t-Bu+H]$^+$, m/z=152.10[M-Boc+H]$^+$, $^1$H NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-((6-bromopyridin-3-yl)oxy)azetidin-1-carboxylate

6-Bromopyridin-3-ol (200 mg, 1.15 mmol) was dissolved in DMSO (4 mL) at room temperature, and t-BuOK (168 mg, 1.5 mmol) was added to the solution with stirring. After stirring for 20 min, the temperature was raised to 80° C. tert-Butyl 3-((methylsulfonyl)oxy)azetidin-1-carboxylate (347 mg, 1.4 mmol) dissolved in DMSO (2 mL) was added dropwise slowly. After the addition, the mixture was kept at this temperature with stirring. After the completion of reaction was monitored by TLC, the reaction mixture was poured into water (20 mL). The resulting mixture was extracted with EA (50 mL×2). The combined organic phases were washed with water (20 mL×2) and saturated saline (20 mL), dried over anhydrous sodium sulfate and filtered. The mother liquid was concentrated in vacuo, and then purified by silica gel column chromatography (eluent EA:PE=1:20-1:10) to give a light yellow solid 320 mg as the target product. LC-MS: m/z=329.05[M+H]$^+$.

Step 4: tert-butyl 3-((6-((trimethylsilyl)ethynyl)pyridin-3-yl)oxy)azetidin-1-carboxylate To a two-necked flask were added tert-butyl 3-((6-bromopyridin-3-yl)oxy)azetidin-1-carboxylate (320 mg, 0.97 mmol), CuI (37 mg, 0.19 mmol), PdCl$_2$(PPh$_3$)$_2$ (68 mg, 0.097 mmol), THF (3 mL) and TEA (3 mL) under nitrogen. The mixture was transferred to 50° C. and ethynyl (trimethyl) silane (191 mg, 1.95 mmol) was added dropwise with stirring. After the addition, the mixture was kept at this temperature and reacted. After the completion of reaction was monitored by TLC, the reaction mixture was filtered by suction through a celite pad. The filter cake was washed with a small amount of EA, and the filtrate was concentrated in vacuo, and then purified by silica gel column chromatography (eluent EA:PE=1:20-1:10) to give a brown solid 240 mg as the desired product. LC-MS: m/z=347.25[M+H]$^+$. $^1$H NMR (400 MHz, CDCl$_3$) δ 8.12 (s, 1H), 7.39 (d, J=8.6 Hz, 1H), 6.97 (dd, J=8.6, 2.9 Hz, 1H), 4.92 (ddd, J=10.4, 6.3, 4.0 Hz, 1H), 4.31 (dd, J=9.6, 6.8 Hz, 2H), 4.00 (dd, 7=9.8, 3.4 Hz, 2H), 1.45 (s, 9H), 0.26 (s, 9H).

Step 5: tert-butyl 3-((6-ethynylpyridin-3-yl)oxy)azetidin-1-carboxylate tert-Butyl 3-((6-((trimethylsilyl)ethynyl)pyridin-3-yl)oxy)azetidin-1-carboxylate (240 mg, 0.69 mmol) was dissolved in methanol (2 mL) at room temperature, and then potassium carbonate (194 mg, 1.38 mmol) was added with stirring. The reaction solution was reacted at room temperature. After the completion of reaction was monitored by TLC, the reaction mixture was concentrated in vacuo. To the residue was added water (10 mL), and the mixture was extracted with EA (30 mL×3). The combined organic phases were washed with saturated saline (30 mL), dried over anhydrous sodium sulfate and filtered. The mother liquid was concentrated in vacuo, and then purified by silica gel column chromatography (eluent EA:PE=1:20-1:10) to give a light yellow solid 180 mg as the target product. LC-MS: m/z=275.20[M+H]$^+$. $^1$H NMR (400 MHz, CDCl$_3$) δ 8.14 (d, J=2.8 Hz, 1H), 7.43 (d, J=8.6 Hz, 1H), 6.99 (dd, J=8.6, 2.9 Hz, 1H), 4.92 (tt, J=6.4, 4.1 Hz, 1H), 4.32 (ddd, J=9.7, 6.3, 0.6 Hz, 2H), 4.01 (dd, J=9.9, 3.9 Hz, 2H), 3.09 (s, 1H), 1.45 (s, 9H).

Step 6: 5-(azetidin-3-yloxy)-2-ethynylpyridine hydrochloride tert-Butyl 3-((6-ethynylpyridin-3-yl)oxy)azetidin-1-carboxylate (180 mg, 0.66 mmol) was dissolved in HCl/dioxane (3 mL, 12 mmol, 4 mol/L) with stirring at room temperature. After the completion of reaction was monitored by TLC, the reaction mixture was concentrated in vacuo to give a light yellow solid 158 mg as the target product.

Step 7: 6-(1-cyclopropyl-1H-pyrazol-4-yl)-4-(6-fluoropyridin-3-yl)pyrazolo[1,5-a]pyridine-3-carbonitrile 6-Bromo-4-(6-fluoropyridin-3-yl)pyrazolo[1,5-a]pyridine-3-carbonitrile (see Synthesis of Intermediate 5, 150 mg, 0.47 mmol), sodium carbonate solution (0.7 mL, 1 mmol, 2 mol/L), tetrakis(triphenylphosphine) palladium (0.03 g, 0.03 mmol), 1-cyclopropylpyrazole-4-boronic acid sterol ester (0.13 g, 0.56 mmol) were dissolved in 1,4-dioxane (3 mL) under nitrogen, then the mixture was transferred to 80° C. and reacted with stirring overnight. The completion of reaction was monitored by TLC. The heating was stopped. To the mixture was added 10 mL of water and the resulting mixture was extracted with DCM (20 mL×3). The organic phases were combined, dried over anhydrous sodium sulfate and filtered. The filtrate was concentrated in vacuo, and then purified by silica gel column chromatography (eluent PE/EA=1/1) to give a pale yellow solid 0.154 g as the target product (yield: 95%). Rf=0.4 (PE:EA=1:1). $^1$H NMR (400 MHz, CDCl$_3$) δ 8.74 (d, J=1.3 Hz, 1H), 8.45 (d, J=2.2 Hz, 1H), 8.31 (s, 1H), 8.07 (ddd, J=8.5, 7.6, 2.7 Hz, 1H), 7.82 (d, J=5.3 Hz, 2H), 7.48 (d, J=1.2 Hz, 1H), 7.17 (dd, J=8.6, 2.9 Hz, 1H), 3.73-3.68 (m, 1H), 1.25-1.20 (m, 2H), 1.13 (dt, J=12.9, 6.4 Hz, 2H).

Step 8: 6-(1-cyclopropyl-1H-pyrazol-4-yl)-4-(6-(3-((6-ethynylpyridin-3-yl)oxy)azetidin-1-yl) pyridin-3-yl)pyrazolo[1,5-a]pyridine-3-carbonitrile To a microwave tube were added 6-(1-cyclopropyl-1H-pyrazol-4-yl)-4-(6-fluoropyridin-3-yl)pyrazolo[1,5-a]pyridine-3-carbonitrile (30 mg, 0.087 mmol) and 5-(azetidin-3-yloxy)-2-ethynyl-pyridine hydrochloride (27.5 mg, 0.131 mmol), which were dissolved by adding 1 mL DMSO. Then DIPEA (0.05 mL, 0.3 mmol) was added. The mixture was reacted at 100° C. for 6 h under microwave. After the reaction was completed, to the reaction mixture was added water (2 mL), and the resulting mixture was extracted with EA (10 mL×3). The combined organic phases were washed with water (10 mL) and saturated sodium chloride (10 mL), dried over anhydrous sodium sulfate and filtered. The mother liquor was concentrated in vacuo, and then purified by silica gel column chromatography (eluent PE:EA=1:1-3:1) to give a brown solid 15 mg as the target product. Rf=0.15 (PE:EA=1:1). LC-MS: m/z=499.20[M+H]$^+$. $^1$H NMR (400 MHz, CDCl$_3$) δ 8.63 (d, J=1.0 Hz, 1H), 8.35 (d, J=1.8 Hz, 1H), 8.25 (s, 1H), 8.22 (d, J=2.6 Hz, 1H), 7.77 (d, J=1.1 Hz, 2H), 7.75 (dd, J=8.6, 2.3 Hz, 1H), 7.46 (d, J=8.5 Hz, 1H), 7.38 (d, J=1.1 Hz, 1H), 7.08 (dd, 7=8.6, 2.9 Hz, 1H), 6.49 (d, J=8.6 Hz, 1H), 5.21-5.15 (m, 1H), 4.56 (dd, J=9.0, 6.5 Hz, 2H), 4.21 (dd, J=9.4, 3.7 Hz, 2H), 3.66 (td, 7=6.8, 3.3 Hz, 1H), 3.10 (s, 1H), 1.19 (dd, 7=9.5, 6.8 Hz, 2H), 1.09 (dd, 7=13.3, 6.8 Hz, 2H).

Example 281: 6-(1-cyclopropyl-1H-pyrazol-4-yl)-4-(6-(3-((6-ethynylpyridin-3-yl)oxy) azetidin-1-yl) pyridin-3-yl)pyrazolo[1,5-a]pyridine-3-carbonitrile (281)

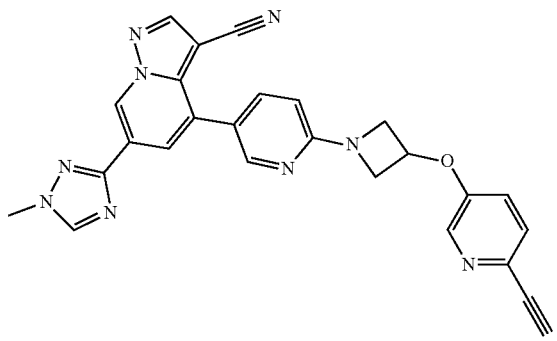

Step 1: tert-butyl 3-hydroxyazetidin-1-carboxylate

To a single-necked flask were added tert-butyl 3-oxoazetidine-1-carboxylate (5.0 g, 29 mmol) and EtOH (50 mL) at room temperature, then NaBH$_4$ (1.1 g, 29 mmol) was added portionwise with stirring. After the completion of reaction was monitored by TLC, a saturated ammonium chloride solution was added to the reaction solution until no bubbles were generated, and a large amount of white solid was precipitated. The mixture was filtered with suction. The filter cake was washed with ethanol (10 mL), and the filtrate was concentrated in vacuo to remove most of the ethanol. To the residue was added with 30 mL of water and the mixture was extracted with EA (100 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 5.0 g as the target product. LC-MS: m/z=118.10[M-t-Bu+H]$^+$, $^1$H NMR (400 MHz, CDCl$_3$) δ 4.53 (s, 1H), 4.13-4.09 (m, 2H), 3.78 (dd, 7=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask were added tert-butyl 3-hydroxyazetidine-1-carboxylate (500 mg, 2.89 mmol), DCM (15 mL) and NaH (0.14 g, 5.8 mmol) under nitrogen. The mixture was transferred to 0° C. and MsCl (0.25 mL, 3.2 mmol) was added dropwise with stirring. After the addition, the mixture was reacted continuously at this temperature. After the completion of reaction was monitored by TLC, water (20 mL) and DCM (50 mL) were added to the reaction mixture. The organic phase was separated, and the aqueous phase was extracted with EA (50 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 566 mg as the target product. LC-MS: m/z=196.10[M-t-Bu+H]$^+$, m/z=152.10[M-Boc+H]$^+$, $^1$H NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-((6-bromopyridin-3-yl)oxy)azetidin-1-carboxylate

6-Bromopyridin-3-ol (200 mg, 1.15 mmol) was dissolved in DMSO (4 mL) at room temperature, and t-BuOK (168 mg, 1.5 mmol) was added to the solution with stirring. After stirring for 20 min, the temperature was raised to 80° C. tert-Butyl 3-((methylsulfonyl)oxy)azetidin-1-carboxylate (347 mg, 1.4 mmol) dissolved in DMSO (2 mL) was added dropwise slowly. After the addition, the mixture was kept at this temperature with stirring. After the completion of reaction was monitored by TLC, the reaction mixture was poured into water (20 mL). The resulting mixture was extracted with EA (50 mL×2). The combined organic phases were washed with water (20 mL×2) and saturated saline (20 mL), dried over anhydrous sodium sulfate and filtered. The mother liquid was concentrated in vacuo, and then purified by silica gel column chromatography (eluent EA:PE=1:20-1:10) to give a light yellow solid 320 mg as the target product. LC-MS: m/z=329.05[M+H]$^+$.

Step 4: tert-butyl 3-((6-((trimethylsilyl)ethynyl)pyridin-3-yl)oxy)azetidin-1-carboxylate To a two-necked flask were added tert-butyl 3-((6-bromopyridin-3-yl)oxy)azetidin-1-carboxylate (320 mg, 0.97 mmol), CuI (37 mg, 0.19 mmol), PdCl$_2$(PPh$_3$)$_2$ (68 mg, 0.097 mmol), THF (3 mL) and TEA (3 mL) under nitrogen. The mixture was transferred to 50° C. and ethynyl (trimethyl) silane (191 mg, 1.95 mmol) was added dropwise with stirring. After the addition, the mixture was kept at this temperature and reacted. After the completion of reaction was monitored by TLC, the reaction mixture was filtered by suction through a celite pad. The filter cake was washed with a small amount of EA, and the filtrate was concentrated in vacuo, and then purified by silica gel column chromatography (eluent EA:PE=1:20-1:10) to give a brown solid 240 mg as the desired product. LC-MS: m/z=347.25[M+H]$^+$. $^1$H NMR (400 MHz, CDCl$_3$) δ 8.12 (s, 1H), 7.39 (d, J=8.6 Hz, 1H), 6.97 (dd, J=8.6, 2.9 Hz, 1H), 4.92 (ddd, J=10.4, 6.3, 4.0 Hz, 1H), 4.31 (dd, J=9.6, 6.8 Hz, 2H), 4.00 (dd, 7=9.8, 3.4 Hz, 2H), 1.45 (s, 9H), 0.26 (s, 9H).

Step 5: tert-butyl 3-((6-ethynylpyridin-3-yl)oxy) azetidin-1-carboxylate tert-Butyl 3-((6-((trimethylsilyl)ethynyl)pyridin-3-yl) oxy)azetidin-1-carboxylate (240 mg, 0.69 mmol) was dissolved in methanol (2 mL) at room temperature, and then potassium carbonate (194 mg, 1.38 mmol) was added with stirring. The reaction solution was reacted at room temperature. After the completion of reaction was monitored by TLC, the reaction mixture was concentrated in vacuo. To the residue was added water (10 mL), and the mixture was extracted with EA (30 mL×3). The combined organic phases were washed with saturated saline (30 mL), dried over anhydrous sodium sulfate and filtered. The mother liquid was concentrated in vacuo, and then purified by silica gel column chromatography (eluent EA:PE=1:20-1:10) to give a light yellow solid 180 mg as the target product. LC-MS: m/z=275.20[M+H]$^+$. $^1$H NMR (400 MHz, CDCl$_3$) δ 8.14 (d, J=2.8 Hz, 1H), 7.43 (d, J=8.6 Hz, 1H), 6.99 (dd, J=8.6, 2.9

Hz, 1H), 4.92 (tt, J=6.4, 4.1 Hz, 1H), 4.32 (ddd, J=9.7, 6.3, 0.6 Hz, 2H), 4.01 (dd, J=9.9, 3.9 Hz, 2H), 3.09 (s, 1H), 1.45 (s, 9H).

Step 6: 5-(azetidin-3-yloxy)-2-ethynylpyridine hydrochloride tert-Butyl 3-((6-ethynylpyridin-3-yl)oxy)azetidin-1-carboxylate (180 mg, 0.66 mmol) was dissolved in HCl/dioxane (3 mL, 12 mmol, 4 mol/L) with stirring at room temperature. After the completion of reaction was monitored by TLC, the reaction mixture was concentrated in vacuo to give a light yellow solid 158 mg as the target product.

Step 7: 4-(6-fluoropyridin-3-yl)-6-(4,4,5,5-tetramethyl-1,3,2-dioxaborolan-2-yl)pyrazolo[1,5-a]pyridine-3-carbonitrile To a 250 mL single-necked flask were sequentially added 6-bromo-4-(6-fluoropyridin-3-yl)pyrazolo[1,5-a]pyridine-3-carbonitrile (see synthesis of intermediate 5, 8 g, 25.23 mmol), bis(pinacolato)diboron (10 g, 39.39 mmol), potassium acetate (10 g, 101.9 mmol) and re-distilled toluene (150 mL) under nitrogen. After bubbling for 10 min under nitrogen, [1,1'-bis(diphenylphosphino)ferrocene]palladium dichloride dichloromethane complex (2.1 g, 2.6 mmol) was added. After bubbling for 10 min under nitrogen, the mixture was heated at 120° C. and reacted overnight. javascript:showMsgDetail('ProductSynonyms.aspx?CBNumber=CB4306719&postData3=CN&SYMBOL_Type=D'); javascript.showMsgDetail('ProductSynonyms.aspx?CBNumber=CB1347621&postData3=CN&SYMBOL_Type=D'); The mixture was filtered through a celite pad, and the filter cake was washed with EA (50 mL×3). The organic phases were washed with water (250 mL) and saturated brine (250 mL), dried over anhydrous sodium sulfate, and filtered. The filtrate was concentrated in vacuo, and the residue was purified by silica gel column chromatography (eluent PE/DCM=2:1-0:1) to give an orange solid 8.5 g as the target product (yield: 93.0%). Rf=0.15 (DCM). $^1$H NMR (400 MHz, CDCl$_3$) δ 8.99 (s, 1H), 8.43 (d, 7=2.1 Hz, 1H), 8.34 (s, 1H), 8.02 (td, J=8.0, 2.5 Hz, 1H), 7.66 (s, 1H), 7.13 (dd, J=8.5, 2.8 Hz, 1H), 1.40 (s, 12H).

Step 8: 4-(6-fluoropyridin-3-yl)-6-(1-methyl-1H-1,2,3-triazol-4-yl)pyrazolo[1,5-a]pyridine-3-carbonitrile 4-(6-Fluoropyridin-3-yl)-6-(4,4,5,5-tetramethyl-1,3,2-dioxaborolan-2-yl)pyrazolo[1,5-a]pyridine-3-carbonitrile (100 mg, 0.3 mmol), sodium carbonate solution (0.4 mL, 0.8 mmol, 2 mol/L), tetrakis(triphenylphosphine palladium) (0.02 g, 0.02 mmol) and 3-bromo-1-methyl-1,2,4-thiazole (0.05 g, 0.3 mmol) were dissolved in 1,4-dioxane (2 mL) under nitrogen, then the mixture was transferred to 80° C. and reacted with stirring overnight. The completion of reaction was monitored by TLC. The heating was stopped. To the mixture was added 10 mL of water and then the resulting mixture was extracted with DCM (20 mL×3). The organic phases were combined, dried over anhydrous sodium sulfate, concentrated in vacuo, and then purified by silica gel column chromatography (eluent PE/EA=1/1-1/3) to give a pale yellow solid 0.0345 g as the target product. The yield was 40%. Rf=0.1 (PE:EA=1:1). $^1$H NMR (400 MHz, CDCl$_3$) δ 9.38 (d, J=1.0 Hz, 1H), 8.50 (d, J=1.8 Hz, 1H), 8.36 (s, 1H), 8.15 (s, 1H), 8.12 (d, J=1.1 Hz, 1H), 8.08 (dd, J=8.0, 1.9 Hz, 1H), 7.17 (dd, J=8.5, 2.7 Hz, 1H), 4.04 (s, 3H).

Step 9: 6-(1-cyclopropyl-1H-pyrazol-4-yl)-4-(6-(3-((6-ethynylpyridin-3-yl)oxy)azetidin-1-yl) pyridin-3-yl)pyrazolo[1,5-a]pyridine-3-carbonitrile To a microwave tube were added 4-(6-fluoropyridin-3-yl)-6-(1-methyl-1H-1,2,3-triazol-4-yl)pyrazolo[1,5-a]pyridine-3-carbonitrile (25 mg, 0.078 mmol) and 5-(azetidin-3-yloxy)-2-ethynyl-pyridine hydrochloride (24 mg, 0.114 mmol), which were dissolved by adding 0.5 mL DMSO. Then DIPEA (0.05 mL, 0.3 mmol) was added. The mixture was reacted at 100° C. for 5 h under microwave. After the reaction was completed, to the reaction mixture was added water (2 mL), and the resulting mixture was extracted with EA (10 mL×3). The combined organic phases were washed with water (10 mL) and saturated sodium chloride (10 mL), dried over anhydrous sodium sulfate and filtered. The mother liquor was concentrated in vacuo, and then purified by silica gel column chromatography (eluent PE:EA=1:1-0:1) to give a white solid 15.2 mg as the target product. Rf=0.15 (PE:EA=1:1). LC-MS: m/z=474.10[M+H]$^+$. $^1$H NMR (400 MHz, CDCl$_3$) δ 9.28 (s, 1H), 8.40 (d, J=1.8 Hz, 1H), 8.31 (s, 1H), 8.23 (d, J=2.0 Hz, 1H), 8.11 (s, 1H), 7.76 (d, 7=8.1 Hz, 1H), 7.46 (d, J=8.5 Hz, 1H), 7.35 (s, 1H), 7.13 (dd, J=8.6, 2.3 Hz, 1H), 6.49 (d, J=8.4 Hz, 1H), 5.18 (s, 1H), 4.56 (dd, J=8.8, 7.0 Hz, 2H), 4.21 (dd, J=9.3, 3.5 Hz, 2H), 4.01 (s, 3H), 3.10 (s, 1H).

Example 282: 6-(3,5-dimethylisoxazol-4-yl)-4-(6-(3-((6-ethynylpyridin-3-yl)oxy)azetidin-1-yl) pyridin-3-yl)pyrazolo[1,5-a]pyridine-3-carbonitrile

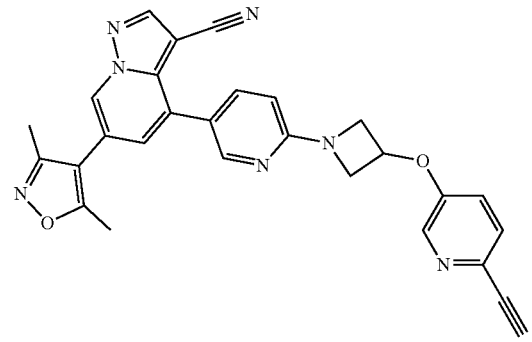

(282)

Step 1: tert-butyl 3-hydroxyazetidin-1-carboxylate '

'

To a single-necked flask were added tert-butyl 3-oxoazetidine-1-carboxylate (5.0 g, 29 mmol) and EtOH (50 mL) at room temperature, then NaBH$_4$ (1.1 g, 29 mmol) was added portionwise with stirring. After the completion of reaction was monitored by TLC, a saturated ammonium chloride solution was added to the reaction solution until no bubbles were generated, and a large amount of white solid was precipitated. The mixture was filtered with suction. The filter cake was washed with ethanol (10 mL), and the filtrate was concentrated in vacuo to remove most of the ethanol. To the residue was added with 30 mL of water and the mixture was extracted with EA (100 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 5.0 g as the target product. LC-MS: m/z=118.10[M-t-Bu+H]$^+$, $^1$H NMR (400 MHz, CDCl$_3$) δ 4.53 (s, 1H), 4.13-4.09 (m, 2H), 3.78 (dd, J=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask were added tert-butyl 3-hydroxyazetidine-1-carboxylate (500 mg, 2.89 mmol), DCM (15 mL) and NaH (0.14 g, 5.8 mmol) under nitrogen. The mixture was transferred to 0° C. and MsCl (0.25 mL, 3.2 mmol) was added dropwise with stirring. After the addition, the mixture was reacted continuously at this temperature. After the completion of reaction was monitored by TLC, water (20 mL) and DCM (50 mL) were added to the reaction mixture. The organic phase was separated, and the aqueous phase was extracted with EA (50 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 566 mg as the target product. LC-MS: m/z=196.10[M-t-Bu+H]$^+$, m/z=152.10[M-Boc+H]$^+$, $^1$H NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-((6-bromopyridin-3-yl)oxy)azetidin-1-carboxylate

6-Bromopyridin-3-ol (200 mg, 1.15 mmol) was dissolved in DMSO (4 mL) at room temperature, and t-BuOK (168 mg, 1.5 mmol) was added to the solution with stirring. After stirring for 20 min, the temperature was raised to 80° C. tert-Butyl 3-((methylsulfonyl)oxy) azetidin-1-carboxylate (347 mg, 1.4 mmol) dissolved in DMSO (2 mL) was added dropwise slowly. After the addition, the mixture was kept at this temperature with stirring. After the completion of reaction was monitored by TLC, the reaction mixture was poured into water (20 mL). The resulting mixture was extracted with EA (50 mL×2). The combined organic phases were washed with water (20 mL×2) and saturated saline (20 mL), dried over anhydrous sodium sulfate and filtered. The mother liquid was concentrated in vacuo, and then purified by silica gel column chromatography (eluent EA:PE=1:20-1:10) to give a light yellow solid 320 mg as the target product. LC-MS: m/z=329.05 [M+H]$^+$.

Step 4: tert-butyl 3-((6-((trimethylsilyl)ethynyl)pyridin-3-yl)oxy)azetidin-1-carboxylate To a two-necked flask were added tert-butyl 3-((6-bromopyridin-3-yl)oxy)azetidin-1-carboxylate (320 mg, 0.97 mmol), CuI (37 mg, 0.19 mmol), PdCl$_2$(PPh$_3$)$_2$ (68 mg, 0.097 mmol), THF (3 mL) and TEA (3 mL) under nitrogen. The mixture was transferred to 50° C. and ethynyl (trimethyl) silane (191 mg, 1.95 mmol) was added dropwise with stirring. After the addition, the mixture was kept at this temperature and reacted. After the completion of reaction was monitored by TLC, the reaction mixture was filtered by suction through a celite pad. The filter cake was washed with a small amount of EA, and the filtrate was concentrated in vacuo, and then purified by silica gel column chromatography (eluent EA:PE=1:20-1:10) to give a brown solid 240 mg as the desired product. LC-MS: m/z=347.25[M+H]$^+$. $^1$H NMR (400 MHz, CDCl$_3$) δ 8.12 (s, 1H), 7.39 (d, J=8.6 Hz, 1H), 6.97 (dd, J=8.6, 2.9 Hz, 1H), 4.92 (ddd, J=10.4, 6.3, 4.0 Hz, 1H), 4.31 (dd, J=9.6, 6.8 Hz, 2H), 4.00 (dd, 7=9.8, 3.4 Hz, 2H), 1.45 (s, 9H), 0.26 (s, 9H).

Step 5: tert-butyl 3-((6-ethynylpyridin-3-yl)oxy) azetidine-1-carboxylate tert-Butyl 3-((6-((trimethylsilyl)ethynyl)pyridin-3-yl)oxy)azetidin-1-carboxylate (240 mg, 0.69 mmol) was dissolved in methanol (2 mL) at room temperature, and then potassium carbonate (194 mg, 1.38 mmol) was added with stirring. The reaction solution was reacted at room temperature. After the completion of reaction was monitored by TLC, the reaction mixture was concentrated in vacuo. To the residue was added water (10 mL), and the mixture was extracted with EA (30 mL×3). The combined organic phases were washed with saturated saline (30 mL), dried over anhydrous sodium sulfate and filtered. The mother liquor was concentrated in vacuo, and then purified by silica gel column chromatography (eluent EA:PE=1:20-1:10) to give a light yellow solid 180 mg as the target product. LC-MS: m/z=275.20[M+H]$^+$. $^1$H NMR (400 MHz, CDCl$_3$) δ 8.14 (d, J=2.8 Hz, 1H), 7.43 (d, J=8.6 Hz, 1H), 6.99 (dd, J=8.6, 2.9 Hz, 1H), 4.92 (tt, J=6.4, 4.1 Hz, 1H), 4.32 (ddd, J=9.7, 6.3, 0.6 Hz, 2H), 4.01 (dd, J=9.9, 3.9 Hz, 2H), 3.09 (s, 1H), 1.45 (s, 9H).

Step 6: 5-(azetidin-3-yloxy)-2-ethynylpyridine hydrochloride tert-Butyl 3-((6-ethynylpyridin-3-yl)oxy)azetidin-1-carboxylate (180 mg, 0.66 mmol) was dissolved in HCl/dioxane (3 mL, 12 mmol, 4 mol/L) with stirring at room temperature. After the completion of reaction was monitored by TLC, the reaction mixture was concentrated in vacuo to give a light yellow solid 158 mg as the target product.

Step 7: 6-(3,5-dimethylisoxazol-4-yl)-4-(6-fluoropyridin-3-yl)pyrazolo[1,5-a]pyridine-3-carbonitrile To a 25 mL two-necked flask were added 6-bromo-4-(6-fluoro-3-pyridyl)pyrazolo[1,5-a]pyridine-3-carbonitrile (see synthesis of intermediate 5, 100 mg, 0.32 mmol), (3,5-dimethylisoxazole-4-yl)boronic acid (67 mg, 0.48 mmol), 1,4-dioxane (3 mL) and sodium carbonate (0.5 mL, 1 mmol, 2 mol/L). The reaction mixture was degassed and refilled with nitrogen. Then tetrakistriphenylphosphine palladium (36 mg, 0.029) was added and the reaction was carried out in an oil bath at 80° C. After the completion of reaction was monitored by TLC, the reaction solution was cooled to room temperature, added with water (10 mL) and extracted with EA (30 mL×2). The organic phases were washed with water (10 mL×2) and saturated saline (10 mL), dried over anhydrous sodium sulfate and filtered. The filtrate was concentrated in vacuo, and then purified by silica gel column chromatography (eluent PE:EA=2:1) to give a white solid 48 mg as the target product. $^1$H NMR (400 MHz, CDCl$_3$) δ 8.55 (s, 1H), 8.42 (s, 1H), 8.36 (s, 1H), 8.10-8.02 (m, 1H), 7.26 (s, 1H), 7.17 (dd, J=8.4, 2.8 Hz, 1H), 2.50 (s, 3H), 2.34 (s, 3H).

Step 8: 6-(3,5-dimethylisoxazol-4-yl)-4-(6-(3-((6-ethynylpyridin-3-yl)oxy)azetidin-1-yl) pyridin-3-yl) pyrazolo[1,5-a]pyridine-3-carbonitrile To a 10 mL microwave tube were added 6-(3,5-dimethylisoxazol-4-yl)-4-(6-fluoro-3-pyridyl)pyrazolo[1,5-a]pyridine-3-carbonitrile (30 mg, 0.09 mmol), 5-(azetidin-3-yloxy)-2-ethynyl-pyridine hydrochloride (28 mg, 0.13), N,N-diisopropylethylamine (0.05 mL, 0.3 mmol) and dimethyl sulfoxide (0.8 mL). The mixture was reacted for 5 h under microwave at 100° C., then reacted at 100° C. in an oil bath. After the completion of reaction was monitored by TLC, to the reaction solution was added water (5 mL), and the resulting mixture was extracted with EA (20 mL×2). The organic phases were washed with water (5 mL×5) and saturated saline (5 mL), dried over anhydrous sodium sulfate and filtered. The filtrate was concentrated in vacuo, and then purified by silica gel column chromatography (eluent PE:EA=2:1-1:1) to give a white solid 7 mg as the target product. LC-MS: m/z=488.20[M+H]$^+$. $^1$H NMR (400 MHz, CDCl$_3$) δ 8.46 (d, J=1.3 Hz, 1H), 8.35 (d, J=1.9 Hz, 1H), 8.33 (s, 1H), 8.22 (d, J=2.7 Hz, 1H), 7.76 (dd, J=8.6, 2.3 Hz, 1H), 7.47 (d, J=8.5 Hz, 2H), 7.08 (dd, J=8.5, 2.9 Hz, 1H), 6.50 (d, J=8.6 Hz, 1H), 5.19 (s, 1H), 4.57 (dd, J=8.9, 6.5 Hz, 2H), 4.21 (dd, 7=9.5, 3.9 Hz, 2H), 3.11 (s, 1H), 2.49 (s, 3H), 2.33 (s, 3H). HPLC: 96.05%.

Example 283: 6-(1-(difluoromethyl)-1H-pyrazol-4-yl)-4-(6-(3-((6-ethynylpyridin-3-yl)oxy) azetidin-1-yl)pyridin-3-yl)pyrazolo[1,5-a]pyridine-3-carbonitrile (283)

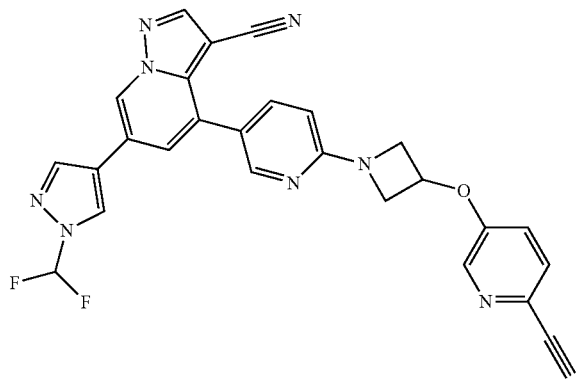

Step 1: tert-butyl 3-hydroxyazetidin-1-carboxylate

To a single-necked flask was added tert-butyl 3-oxoazetidine-1-carboxylate (5.0 g, 29 mmol) at room temperature, which was dissolved by adding EtOH (50 mL). Then NaBH$_4$ (1.1 g, 29 mmol) was added portionwise with stirring. After the reaction was completed, a saturated ammonium chloride solution was added to the reaction solution until no bubbles were generated, and a large amount of white solid was precipitated. The mixture was filtered with suction. The filter cake was washed with ethanol (10 mL), and the filtrate was concentrated in vacuo to remove most of the ethanol. A large amount of white solid was precipitated. 30 mL of water was added and the white solid was dissolved. The mixture was extracted with EA (100 mL×2). The combined organic phases were washed with water (20 mL×2) and saturated sodium chloride (20 mL). The organic phases were dried over anhydrous sodium sulfate, concentrated in vacuo, and then purified by silica gel column chromatography (eluent EA:PE=1:5) to give colorless oil 5.0 g. LC-MS: m/z=118.10 [M-t-Bu+2H]$^+$, $^1$H NMR (400 MHz, CDCl$_3$) δ 4.53 (s, 1H), 4.13-4.09 (m, 2H), 3.78 (dd, J=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask was added tert-butyl 3-hydroxyazetidine-1-carboxylate (500 mg, 2.89 mmol) under nitrogen, which was dissolved in DCM (15 mL). Then NaH (0.14 g, 5.8 mmol) was added. The mixture was transferred to 0° C. and MsCl (0.25 mL, 3.2 mmol) was added dropwise with stirring. After the addition, the mixture was reacted continuously at this temperature. After the reaction was completed, water (20 mL) and DCM (50 mL) were added to the reaction mixture. The organic phase was separated, and the aqueous phase was extracted with EA (50 mL) once. The combined organic phases were washed with water (20 mL×2) and saturated sodium chloride (20 mL). The organic phases were dried over anhydrous sodium sulfate, concentrated in vacuo, and then purified by silica gel column chromatography (eluent EA:PE=1:5) to give colorless oil 566 mg. LC-MS: m/z=196.10[M-t-Bu+2H]$^+$, m/z=152.10[M-Boc+H]$^+$, $^1$H NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-((6-bromopyridin-3-yl)oxy)azetidin-1-carboxylate

6-Bromopyridin-3-ol (200 mg, 1.15 mmol) was dissolved in DMSO (4 mL) at room temperature, and t-BuOK (168 mg, 1.5 mmol) was added to the solution with stirring. After stirring for 20 min, the temperature was raised to 80° C. tert-Butyl 3-((methylsulfonyl)oxy)azetidin-1-carboxylate (347 mg, 1.4 mmol) dissolved in DMSO (2 mL) was added dropwise slowly. After the addition, the mixture was kept at this temperature with stirring. After the reaction was completed, the reaction mixture was poured into water (20 mL). The resulting mixture was extracted with EA (50 mL×2). The combined organic phases were washed with water (20 mL×2) and saturated saline (20 mL). The organic phases were dried over anhydrous sodium sulfate, concentrated in vacuo, and then purified by silica gel column chromatography (eluent EA:PE=1:20-1:10) to give a light yellow solid 320 mg as the target product. LC-MS: m/z=329.05 [M+H]$^+$.

Step 4: tert-butyl 3-((6-((trimethylsilyl)ethynyl)pyridin-3-yl)oxy)azetidin-1-carboxylate To a two-necked flask were added tert-butyl 3-((6-bromopyridin-3-yl)oxy)azetidin-1-carboxylate (320 mg, 0.97 mmol), CuI (37 mg, 0.19 mmol) and PdCl$_2$ (PPh$_3$)$_2$ (68 mg, 0.097 mmol) under nitrogen, which were dissolved in THF (3 mL) and TEA (3 mL). The mixture was transferred to 50° C. and ethynyl (trimethyl) silane (191 mg, 1.95 mmol) was added dropwise with stirring. After the addition, the mixture was kept at this temperature and reacted. After the reaction was completed, the reaction mixture was filtered by suction through a celite pad. The filter cake was washed with a small amount of EA, and the filtrate was concentrated in vacuo, and then purified by silica gel column chromatography (eluent EA:PE=1:20-1:10) to give a brown solid 240 mg. LC-MS: m/z=347.25[M+H]$^+$, $^1$H NMR (400 MHz, CDCl$_3$) δ 8.12 (s, 1H), 7.39 (d, J=8.6 Hz, 1H), 6.97 (dd, J=8.6, 2.9

Hz, 1H), 4.92 (ddd, J=10.4, 6.3, 4.0 Hz, 1H), 4.31 (dd, J=9.6, 6.8 Hz, 2H), 4.00 (dd, J=9.8, 3.4 Hz, 2H), 1.45 (s, 9H), 0.26 (s, 9H).

Step 5: tert-butyl 3-((6-ethynylpyridin-3-yl)oxy) azetidin-1-carboxylate tert-Butyl 3-((6-((trimethylsilyl)ethynyl)pyridin-3-yl)oxy)azetidin-1-carboxylate (240 mg, 0.69 mmol) was dissolved in methanol (2 mL) at room temperature, and then potassium carbonate (194 mg, 1.38 mmol) was added with stirring. After the reaction was completed, the reaction mixture was concentrated in vacuo. To the residue was added water (10 mL), and the mixture was extracted with EA (30 mL×3). The combined organic phases were washed with saturated saline (30 mL) once, dried over anhydrous sodium sulfate, concentrated in vacuo, and then purified by silica gel column chromatography (eluent EA:PE=1:20-1:10) to give a light yellow solid 180 mg. LC-MS: m/z=275.20 [M+H]+, 1H NMR (400 MHz, CDCl3) δ 8.14 (d, J=2.8 Hz, 1H), 7.43 (d, J=8.6 Hz, 1H), 6.99 (dd, 7=8.6, 2.9 Hz, 1H), 4.92 (tt, J=6.4, 4.1 Hz, 1H), 4.32 (ddd, J=9.7, 6.3, 0.6 Hz, 2H), 4.01 (dd, J=9.9, 3.9 Hz, 2H), 3.09 (s, 1H), 1.45 (s, 9H).

Step 6: 5-(azetidin-3-yloxy)-2-ethynylpyridine hydrochloride tert-Butyl 3-((6-ethynylpyridin-3-yl)oxy)azetidin-1-carboxylate (180 mg, 0.66 mmol) was dissolved in HCl/dioxane (3 mL, 12 mmol, 4 mol/L) with stirring at room temperature. A sample was taken and then detected by TLC. A point with a larger polarity was formed and there was no remaining material. The reaction mixture was concentrated in vacuo to give a light yellow solid 158 mg.

Step 7: 6-(1-(difluoromethyl)-1H-pyrazol-4-yl)-4-(6-fluoropyridin-3-yl)pyrazolo[1,5-a]pyridine-3-carbonitrile To a 10 mL single-necked flask were sequentially added 6-bromo-4-(6-fluoro-3-pyridyl)pyrazolo[1,5-a]pyridine-3-carbonitrile (see Synthesis of Intermediate 5, 100 mg, 0.3154 mmol), 1-(difluoromethyl)-4-(4,4,5,5-tetramethyl-1,3,2-dioxaborolan-2-yl)pyrazole (92 mg, 0.3770 mmol), sodium carbonate aqueous solution (0.5 mL, 1 mmol, 2 mol/L) and 1,4-dioxane (2 mL). The reaction mixture was degassed and refilled with nitrogen. Pd(PPh3)4 (15 mg, 0.0123 mmol) was added. The mixture was reacted at 80° C. overnight. To the reaction mixture was added water (20 mL), and the resulting mixture was extracted with EA (50 mL). The organic layers were washed with saturated brine (15 mL), dried over anhydrous sodium sulfate and filtered. The filtrate was concentrated in vacuo, and the residue was purified by silica gel column chromatography (DCM:MeOH=0-100:2) to give a light yellow solid 105 mg as the target product (the yield was 93.98%). (Rf=0.4, PE/EA=2/1). LC-MS, m/z: 355.1[M+H]+. 19F NMR (376 MHz, CDCl3) δ −65.69, −93.74.

Step 8: 6-(1-(difluoromethyl)-1H-pyrazol-4-yl)-4-(6-(3-((6-ethynylpyridin-3-yl)oxy)azetidin-1-yl)pyridin-3-yl)pyrazolo[1,5-a]pyridine-3-carbonitrile To a solution of 6-[1-(difluoromethyl)pyrazol-4-yl]-4-(6-fluoro-3-pyridyl)pyrazolo[1,5-a]pyridine-3-carbonitrile (25 mg, 0.071 mmol) in DMSO (1.5 mL) were added 5-(azetidin-3-yloxy)-2-ethynyl-pyridine hydrochloride (19.32 mg, 0.091 mmol) and DIPEA (0.05 mL, 0.3 mmol). The mixture was reacted for 5 h under microwave (130° C., 10 bar, preheating for 30 s). After the reaction was completed, the reaction mixture was cooled to the room temperature. To the reaction mixture was added water (10 mL), and the resulting mixture was extracted with ethyl acetate (50 mL). The organic phases were washed with water (5×3 mL), concentrated in vacuo, and the residue was purified by silica gel column chromatography (DCM/MeOH=0-100:4) to give a light yellow solid 3 mg as the target product (the yield was 8.361%). LC-MS: m/z=509.1 [M+H]+. 1H NMR (400 MHz, CDCl3) δ 8.72 (s, 1H), 8.36 (s, 1H), 8.30 (s, 1H), 8.22 (s, 1H), 8.15 (s, 1H), 7.97 (s, 1H), 7.47 (d, J=8.5 Hz, 1H), 7.41 (s, 1H), 7.35 (s, 1H), 7.12-7.06 (m, 2H), 6.50 (d, J=8.7 Hz, 1H), 5.22-5.16 (m, 1H), 4.61-4.52 (m, 2H), 4.22 (dd, J=9.2, 3.3 Hz, 2H), 3.11 (s, 1H). HPLC: 96.22%.

Example 284: (S)-6-(1-(difluoromethyl)-1H-pyrazol-4-yl)-4-(6-(3-((6-ethynylpyridin-3-yl)oxy) pyrrolidin-1-yl)pyridin-3-yl) pyrazolo[1,5-a]pyridine-3-carbonitrile

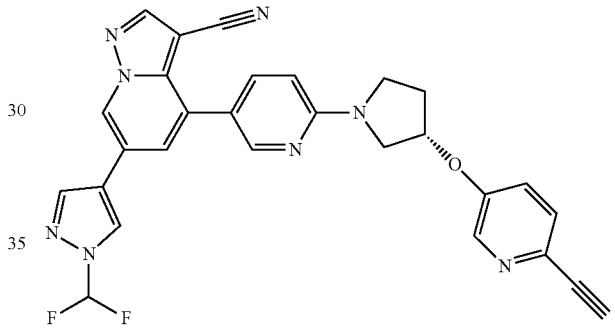

(284)

Step 1: tert-butyl (R)-3-((methylsulfonyl)oxy)pyrrolidine-1-carboxylate tert-Butyl (3R)-3-hydroxypyrrolidine-1-carboxylate (2.00 g, 10.7 mmol) was dissolved in THF (50 mL) in a double-neck flask. The reaction mixture was degassed and refilled with nitrogen, then NaH (0.856 g, 21.4 mmol) was added (a large amount of bubbles were generated). Methanesulfonyl chloride (0.911 mL, 11.8 mmol) was added under ice bath conditions, and the mixture was reacted at room temperature for 5.5 h (the reaction liquid was a white solid suspension). To the reaction mixture were added water (10 mL) and EA (100 mL). The aqueous phase was extracted with EA (50 mL×2). The combined organic phases were washed with saturated brine (10 mL), dried over anhydrous sodium sulfate and filtered. The filtrate was concentrated in vacuo to give colorless transparent liquid 2.84 g as the target product (the yield was 100%). (Rf=0.5, PE/EA=4/1). LC-MS: m/z=210.1[M-t-Bu+H]+.

Step 2: tert-butyl (S)-3-((6-bromopyridin-3-yl)oxy) pyrrolidine-1-carboxylate 6-Bromopyridin-3-ol (590 mg, 3.3908 mmol) was dissolved in DMSO (6 mL) at room temperature, and potassium tert-butoxide (580 mg, 4.39 mmol) was added with stirring. After stirring for 20 min, the temperature was raised to 100°

C. tert-Butyl (S)-3-((methylsulfonyl)oxy)pyrrolidine-1-carboxylate (1.00 g, 3.77 mmol) dissolved in DMSO (30 mL) was added dropwise slowly. After the addition, the mixture was reacted at 100° C. for 12 h. To the reaction mixture were added water (10 mL) and EA (100 mL). The organic layers were washed with saturated brine (10 mL×4), concentrated in vacuo, and the residue was purified by silica gel column chromatography (PE:EA=0-100:10) to give a white solid 0.72 g as the target product (the yield was 62%). (Rf=0.5, PE/EA=4/1). LC-MS: m/z=289.0 [M-t-Bu+2H]$^+$.

Step 3: tert-butyl (S)-3-((6-((trimethylsilyl)ethynyl)pyridin-3-yl)oxy)pyrrolidine-1-carboxylate To a 50 mL two-necked flask were sequentially added tert-butyl (3A)-3-(((6-bromo-3-pyridyl)oxy)pyrrolidine-1-carboxylate (0.72 g, 2.1 mmol), Pd(PPh$_3$)$_2$Cl$_2$ (30 mg, 0.0423 mmol), triethylamine (5 mL) and THF (5 mL). The reaction mixture was degassed and refilled with nitrogen. After stirring for 15 min, CuI (20 mg, 0.10502 mmol) and ethynyl (trimethyl)silane (0.59 mL, 4.2 mmol) were added and the mixture was stirred overnight. The reaction mixture was directly concentrated in vacuo, and the residue was purified by silica gel column chromatography (PE:EA=0-5:1) to give brown liquid 341 mg as the target product (the yield was 45%). (Rf=0.5, PE/EA=4/1). LC-MS: m/z=361.1 [M+H]$^+$.

Step 4: tert-butyl (S)-3-((6-ethynylpyridin-3-yl)oxy)pyrrolidine-1-carboxylate

To a single-necked flask were sequentially added tert-butyl (3S)-3-((6-(2-trimethylsilylacetylene)-3-pyridyl)oxy)pyrrolidine-1-carboxylate (340 mg, 0.9431 mmol), potassium carbonate (261 mg, 1.8884 mmol) and methanol (3 mL). The mixture was stirred at room temperature for 0.5 h. The reaction mixture was directly concentrated in vacuo and purified by silica gel column chromatography (PE:EA=0-3:1) to give pale yellow liquid 272 mg as the target product (the yield was 100%). (Rf=0.3, PE/EA=3/1). LC-MS: m/z=289.5 [M+H]$^+$.

Step 5: (S)-2-ethynyl-5-(pyrrolidin-3-yloxy)pyridine hydrochloride

To a single-necked flask were sequentially added tert-butyl (S)-3-((6-ethynylpyridin-3-yl)oxy)pyrrolidine-1-carboxylate (272 mg, 0.9435 mmol) and a solution of 4N hydrochloric acid in EA (4 mL, 16 mmol, 4 mol/L). The mixture was stirred at room temperature for 0.5 h. The reaction mixture was directly concentrated in vacuo to give a khaki solid 212 mg as the target product (the yield was 100%). LC-MS: m/z=189.2 [M+H]$^+$.

Step 6: (S)-6-(1-(difluoromethyl)-1H-pyrazol-4-yl)-4-(6-(3-((6-ethynylpyridin-3-yl)oxy)pyrrolidin-1-yl)pyridine-3-yl)pyrazolo[1,5-a]pyridine-3-carbonitrile To a solution of 6-[1-(difluoromethyl)pyrazol-4-yl]-4-(6-fluoro-3-pyridyl)pyrazolo[1,5-a]pyridine-3-carbonitrile (see synthesis of intermediate 6, 25 mg, 0.070 mmol) in DMSO (1.5 mL) were added (S)-2-ethynyl-5-(pyrrolidin-3-yloxy)pyridine hydrochloride (21 mg, 0.093 mmol) and DIPEA (0.05 mL, 0.3 mmol) at room temperature. The mixture was reacted for 8 h under microwave (100° C., 10 bar). To the reaction mixture was added EA (50 mL) and the resulting mixture was washed with water (10 mL×3). The organic phases were concentrated in vacuo, dried over anhydrous sodium sulfate and filtered. The filtrate was concentrated in vacuo, and then purified by silica gel column chromatography (DCM:MeOH=0-100:4) to give a white solid 12 mg as the target product (the yield was 32.55%). Rf=0.5, (DCM:MeOH=20:1). LC-MS: m/z=523.1[M+H]$^+$. $^1$H NMR (400 MHz, CDCl$_3$) δ 8.71 (d, J=1.0 Hz, 1H), 8.37 (d, J=1.7 Hz, 1H), 8.30 (s, 1H), 8.14 (s, 1H), 7.97 (s, 1H), 7.78 (dd, J=8.9, 1.8 Hz, 1H), 7.46 (d, J=8.5 Hz, 1H), 7.41 (d, J=1.0 Hz, 1H), 7.35 (d, J=2.3 Hz, 1H), 7.26-7.23 (m, 1H), 7.22-7.17 (m, 1H), 6.59 (d, J=8.5 Hz, 1H), 5.19-5.11 (m, 1H), 3.92 (s, 2H), 3.84-3.70 (m, 2H), 3.09 (s, 1H), 2.42-2.32 (m, 2H). HPLC: 94.48%.

Example 285: 6-(1-(difluoromethyl)-1H-pyrazol-4-yl)-4-(6-(3-(4-ethynylphenoxy)azetidin-1-yl)pyridin-3-yl)pyrazolo[1,5-a]pyridine-3-carbonitrile (285)

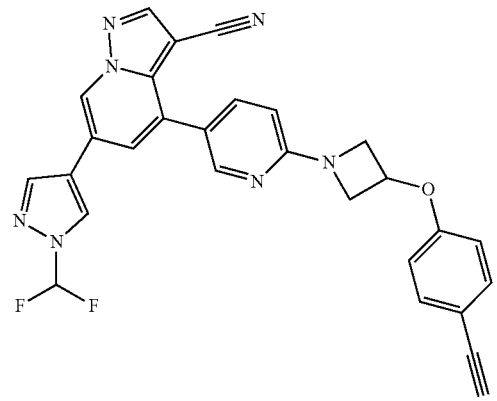

Step 1: tert-butyl 3-hydroxyazetidin-1-carboxylate

To a 100 mL single-necked flask were added tert-butyl 3-oxoazetidine-1-carboxylate (2.0 g, 12 mmol) and EtOH (20 mL) at room temperature, then NaBH$_4$ (0.88 g, 23 mmol) was added portionwise with stirring. The mixture was stirred at room temperature for reaction. After the completion of reaction was monitored by TLC, a saturated ammonium chloride solution was added to the reaction solution until no bubbles were generated. The mixture was filtered with suction, and a large amount of white solid precipitated. The filter cake was washed with ethanol (10 mL), and the filtrate was concentrated in vacuo to remove most of the ethanol. To the mixture was added 30 mL of water and the resulting mixture was extracted with EA (100 mL×3). The combined organic phases were washed with water (20 mL×2) and saturated sodium chloride (20 mL). The organic phases were dried over anhydrous sodium sulfate and filtered. The filtrate was concentrated in vacuo, and purified by silica gel column chromatography (eluent EA:PE=1:5) to give colorless oil 2.0 g as the target product. LC-MS: m/z=118.10[M-t-Bu+H]$^+$, $^1$H NMR (400 MHz, CDCl$_3$) δ 4.53 (s, 1H), 4.13-4.09 (m, 2H), 3.78 (dd, J=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask were added tert-butyl 3-hydroxyazetidine-1-carboxylate (500 mg, 2.89 mmol), DCM (15 mL) and NaH (0.14 g, 5.8 mmol) under nitrogen. The mixture was transferred to 0° C. and MsCl (0.25 mL, 3.2 mmol) was added dropwise with stirring. After the addition, the mixture was reacted continuously at this temperature. After the completion of reaction was monitored by TLC, water (20 mL) and DCM (50 mL) were added to the reaction mixture. The organic phase was separated, and the aqueous phase was extracted with DCM (50 mL). The combined organic phases were washed with water (20 mL×2) and saturated sodium chloride (20 mL). The organic phases were dried over anhydrous sodium sulfate and filtered. The filtrate was concentrated in vacuo and purified by silica gel column chromatography (eluent EA:PE=1:5) to give colorless oil 680 mg as the target product. LC-MS: m/z=196.10[M-t-Bu+H]$^+$, m/z=152.10[M-Boc+H]$^+$; $^1$H-NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-(4-iodophenoxy)azetidin-1-carboxylate

P-iodophenol (550 mg, 2.5 mmol) was dissolved in DMF (4 mL) at room temperature, and t-BuOK (320 mg, 2.85 mmol) was added to the solution with stirring. After stirring for 20 min, the temperature was raised to 80° C. tert-Butyl 3-((methylsulfonyl)oxy)azetidin-1-carboxylate (680 mg, 2.75 mmol) dissolved in DMF (1.5 mL) was added dropwise slowly. After the addition, the mixture was kept at this temperature for reaction. After the completion of reaction was monitored by TLC, the reaction mixture was poured into water (20 mL). The resulting mixture was extracted with EA (50 mL×2). The combined organic phases were washed with water (20 mL×2) and saturated saline (20 mL). The organic phases were dried over anhydrous sodium sulfate and filtered. The filtrate was concentrated in vacuo, and then purified by silica gel column chromatography (eluent EA:PE=1:20-1:10) to give a white solid 615 mg as the target product. LC-MS: m/z=319.9[M-t-Bu+H]$^+$. $^1$H NMR (400 MHz, CDCl$_3$) δ 7.56 (d, J=8.8 Hz, 2H), 6.52 (d, J=8.8 Hz, 2H), 4.83 (ddd, J=10.4, 6.3, 4.1 Hz, 1H), 4.28 (dd, J=9.6, 6.5 Hz, 2H), 3.98 (dd, J=9.7, 4.0 Hz, 2H), 1.44 (s, 9H).

Step 4: 3-(4-iodophenoxy)azetidine hydrochloride tert-Butyl 3-(4-iodophenoxy)azetidin-1-carboxylate (615 mg, 1.64 mmol) was dissolved in HCl/EA (3 mL, 12 mmol, 4 mol/L) with stirring at room temperature. After the completion of reaction was monitored by TLC, the reaction mixture was concentrated in vacuo to give a white solid 510 mg as the target product. $^1$H NMR (400 MHz, DMSO-d$_6$) δ 11.96 (s, 1H), 7.64 (d, J=8.9 Hz, 2H), 6.73 (d, J=8.9 Hz, 2H), 5.11-5.02 (m, 1H), 4.41 (dd, J=12.3, 6.6 Hz, 2H), 3.96 (dd, J=12.3, 4.7 Hz, 2H), 1.91 (s, 1H).

Step 5: 6-(1-(difluoromethyl)-1H-pyrazol-4-yl)-4-(6-(3-(4-iodophenoxy)azetidin-1-yl) pyridin-3-yl) pyrazolo[1,5-a]pyridine-3-carbonitrile To a solution of 6-(1-(difluoromethyl)-1H-pyrazol-4-yl)-4-(6-fluoropyridin-3-yl) pyrazolo[1,5-a]pyridine-3-carbonitrile (see synthesis of intermediate 6, 25 mg, 0.07 mmol) in DMSO (1.5 mL) were added 3-(4-iodophenoxy)azetidine hydrochloride (21 mg, 0.064 mmol) and DIPEA (0.05 mL, 0.3 mmol) at room temperature. The mixture was reacted for 8 h under microwave (100° C., 10 bar). After removing the microwave, water (10 mL) and EA (100 mL) were added into the reaction mixture. The organic phases were washed with saturated sodium chloride (10 mL×3), concentrated in vacuo, and the residue was purified by silica gel column chromatography (DCM:MeOH=0-100:3) to give a white solid 36 mg as the objective product (yield: 81.84%). Rf=0.5, (DCM/MeOH=20/1). LC-MS: m/z=624.0 [M+H]$^+$.

Step 6: 6-(1-(difluoromethyl)-1H-pyrazol-4-yl)-4-(6-(3-(4-(((trimethyl silyl) ethynyl)phenoxy))azetidin-1-yl)pyridin-3-yl)pyrazolo[1,5-a]pyridine-3-carbonitrile To a two-necked flask were sequentially added 6-(1-(difluoromethyl)-1H-pyrazol-4-yl)-4-(6-(3-(4-iodophenoxy)azetidin-1-yl)pyridin-3-yl)pyrazolo[1,5-a]pyridine-3-carbonitrile (32 mg, 0.052 mmol), Pd(PPh$_3$)$_2$Cl$_2$ (1.5 mg, 0.002 mmol), triethylamine (2 mL) and THF (2 mL). The reaction mixture was degassed and refilled with nitrogen. After stirring for 15 min, cuprous iodide (1.0 mg, 0.005 mmol) and ethynyl (trimethyl)silane (0.1 mL, 0.7 mmol) were added. The mixture was stirred and reacted at room temperature. After the completion of reaction was monitored by TLC, the reaction mixture was directly concentrated in vacuo, and the residue was purified by silica gel column chromatography (DCM:MeOH=0-100:3) to give a brown solid 30 mg as the target product (the yield was 98.55%). Rf=0.5, (DCM/MeOH=20/1). LC-MS: m/z=580.2[M+H]$^+$.

Step 7: 6-(1-(difluoromethyl)-1H-pyrazol-4-yl)-4-(6-(3-(4-ethynylphenoxy)azetidin-1-yl) pyridin-3-yl) pyrazolo[1,5-a]pyridine-3-carbonitrile To a single-necked flask were sequentially added 6-(1-(difluoromethyl)-1H-pyrazol-4-yl)-4-(6-(3-(4-((trimethylsilyl)ethynyl)phenoxy)azetidine-1-yl)pyridin-3-yl)pyrazole[1,5-a]pyridine-3-carbonitrile (30 mg, 0.052 mmol), potassium carbonate (14 mg, 0.101 mmol) and methanol (3 mL). The mixture was stirred at room temperature for 3 h. The reaction mixture was directly concentrated in vacuo, and the residue was purified by silica gel column chromatography (DCM/MeOH=0-10/3) to give a white solid 10 mg as the target product (the yield was 38.08%). (Rf=0.5, DCM/MeOH=20/1). LC-MS: m/z=508.5[M+H]$^+$. $^1$H NMR (400 MHz, CDCl$_3$) δ 8.72 (s, 1H), 8.36 (s, 1H), 8.30 (s, 1H), 8.15 (s, 1H), 7.97 (s, 1H), 7.75 (dd, J=8.4, 1.4 Hz, 1H), 7.46 (d, J=8.7 Hz, 2H), 7.42 (s, 1H), 7.25 (s, 1H), 6.76 (d, J=8.7 Hz, 2H), 6.50 (d, J=8.7 Hz, 1H), 5.20-5.10 (m, 1H), 4.62-4.50 (m, 2H), 4.22 (dd, J=9.2, 3.4 Hz, 2H), 3.02 (s, 1H).

Example 286: (R)-6-(1-(difluoromethyl)-1H-pyrazol-4-yl)-4-(6-(3-(4-ethynylphenoxy) pyrrolidin-1-yl)pyridin-3-yl)pyrazolo[1,5-a]pyridine-3-carbonitrile

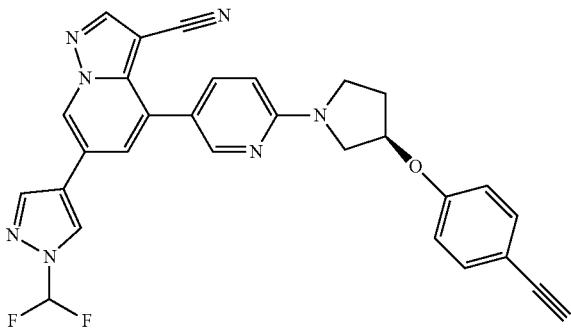

(286)

Step 1: tert-butyl (S)-3-((methyl sulfonyl)oxy)pyrrolidine-1-carboxylate tert-Butyl (3S)-3-hydroxypyrrolidine-1-carboxylate (2.00 g, 10.7 mmol) was dissolved in THF (50 mL) in a double-necked flask under nitrogen, then NaH (0.856 g, 21.4 mmol, 60 mass %) was added. Methanesulfonyl chloride (0.911 mL, 11.8 mmol) was added under ice bath conditions, and the mixture was reacted at room temperature for 4.5 h (the reaction liquid was a white solid suspension). The reaction mixture was added with water (30 mL) and EA (100 mL). The organic phases were separated and the aqueous phase was extracted with EA (50 mL). The combined organic phases were washed with saturated brine (30 mL), dried over anhydrous sodium sulfate, concentrated in vacuo to give colorless transparent liquid 2.84 g as the target product (the yield was 100%). (Rf=0.4, PE/EA=2/1). LC-MS: m/z=210.2 [M-t-Bu+H]$^+$.

Step 2: tert-butyl (R)-3-(4-iodophenoxy)pyrrolidine-1-carboxylate

To a single-necked flask were sequentially added tert-butyl (3S)-3-methylsulfonyloxypyrrolidine-1-carboxylate (470 mg, 1.7714 mmol), 4-iodophenol (300 mg, 1.3636 mmol), potassium carbonate (565 mg, 4.0880 mmol) and DMF (6 mL). The mixture was stirred at 80° C. overnight. To the reaction mixture was added water (10 mL), and the mixture was extracted with EA (100 mL). The organic layers were washed with saturated brine (10 mL×2), dried over anhydrous sodium sulfate and filtered. The filtrate was concentrated in vacuo, and the residue was purified by silica gel column chromatography (PE/EA=0-20/1) to give colorless transparent liquid 424 mg as the target product (the yield was 79.89%). LC-MS: m/z=334.0[M-t-Bu+H]$^+$. $^1$H NMR (600 MHz, CDCl$_3$) δ 7.61-7.51 (m, 2H), 6.64 (d, J=8.6 Hz, 2H), 4.83 (s, 1H), 3.65-3.55 (m, 2H), 3.54-3.40 (m, 2H), 2.19-2.05 (m, 2H), 1.46 (s, 9H).

Step 3: (A)-3-(4-iodophenoxy)pyrrolidine hydrochloride tert-Butyl (R)-3-(4-iodophenoxy)pyrrolidine-1-carboxylate (434 mg, 1.115 mmol) was dissolved in EA (2 mL) in a single-necked flask, then a solution of 4M hydrochloric acid in EA (5 mL, 20 mmol) was added. The mixture was stirred at room temperature for 1 h (the reaction solution was light brown and solid precipitated). The reaction mixture was directly concentrated in vacuo to give a khaki solid 363 mg as the target product (the yield was 99.99%). $^1$H NMR (400 MHz, DMSO-d$_6$) δ 9.39 (s, 2H), 7.63 (d, J=8.8 Hz, 2H), 6.83 (d, J=8.8 Hz, 2H), 5.12 (s, 1H), 3.48-3.40 (m, 1H), 3.31-3.27 (m, 2H), 3.27-3.19 (m, 1H), 2.24-2.05 (m, 2H).

Step 4: (A)-6-(1-(difluoromethyl)-1H-pyrazol-4-yl)-4-(6-(3-(4-iodophenoxy)pyrrolidin-1-yl) pyridin-3-yl)pyrazolo[1,5-a]pyridine-3-carbonitrile To a solution of 6-(1-(difluoromethyl)-1H-pyrazol-4-yl)-4-(6-fluoropyridin-3-yl)pyrazolo[1,5-a]pyridine-3-carbonitrile (see synthesis of intermediate 6, 25 mg, 0.070 mmol) in DMSO (1.5 mL) were added (R)-3-(4-iodophenoxy)pyrrolidine hydrochloride (21 mg, 0.064 mmol) and DIPEA (0.05 mL, 0.3 mmol) at room temperature. The mixture was reacted for 8 h under microwave (100° C., 10 bar). After the reaction was completed, the reaction mixture was cooled to room temperature, then to the mixture were added water (10 mL) and EA (100 mL). The organic layers were washed with saturated brine (10 mL×3) and concentrated in vacuo, and the residue was purified by silica gel column chromatography (DCM:MeOH=0-100:3) to give a yellow-white solid 36 mg as the target product (the yield was 81.84%). (Rf=0.4, DCM/MeOH=20/1). LC-MS: m/z=624.0 [M+H]$^+$.

Step 5: (R)-6-(1-(difluoromethyl)-1H-pyrazol-4-yl)-4-(6-(3-(4-(((trimethylsilyl)ethynyl)phenoxy))pyrrolidin-1-yl)pyridin3-yl)pyrazolo[1,5-a]pyridine-3-carbonitrile To a two-necked flask were sequentially added (R)-6-(1-(difluoromethyl)-1H-pyrazol-4-yl)-4-(6-(3-(4-iodophenoxy)pyrrolidin-1-yl)pyridin-3-yl)pyrazolo[1,5-a]pyridine-3-carbonitrile (36 mg, 0.05775 mmol), Pd(PPh$_3$)$_2$Cl$_2$ (1.5 mg, 0.0021 mmol), triethylamine (2 mL) and THF (2 mL). The reaction mixture was degassed and refilled with nitrogen. After stirring for 15 min, cuprous iodide (1.0 mg, 0.0053 mmol) and ethynyl (trimethyl)silane (0.1 mL, 0.7 mmol) were added. The mixture was stirred at room temperature overnight. The reaction mixture was concentrated in vacuo, and then purified by silica gel column chromatography (DCM/MeOH=0-100/3) to give brown liquid 30.0 mg as the target product (the yield was 87.50%). (Rf=0.4, DCM/MeOH=20/1). LC-MS: m/z=594.4 [M+H]$^+$.

Step 6: (R)-6-(1-(difluoromethyl)-1H-pyrazol-4-yl)-4-(6-(3-(4-ethynylphenoxy)pyrrolidin-1-yl)pyridin-3-yl)pyrazolo[1,5-a]pyridine-3-carbonitrile To a single-necked flask were sequentially added (R)-6-(1-(difluoromethyl)-1H-pyrazol-4-yl)-4-(6-(3-(4-((trimethylsilyl)ethynyl)phenoxy)pyrrolidin-1-yl)pyridin-3-yl)pyrazolo[1,5-a]pyridine-3-carbonitrile (30 mg, 0.050 mmol), potassium carbonate (14 mg, 0.101 mmol) and methanol (3 mL). The mixture was stirred at room temperature overnight. The reaction mixture was directly concentrated in vacuo, and the residue was purified by silica gel column chromatography (DCM/MeOH=0-100/3) to give a yellow-white solid 20 mg as the target product (the yield was 75.90%). (Rf=0.4, DCM/MeOH=20/1). LC-MS: m/z=522.4 [M+H]$^+$. $^1$H NMR (400 MHz, CDCl$_3$) δ 8.70 (s, 1H), 8.36 (s, 1H), 8.29 (s, 1H), 8.13 (s, 1H), 7.96 (s, 1H), 7.74 (dd, J=8.7, 2.2 Hz, 1H), 7.44 (d, J=8.7 Hz, 2H), 7.39 (s, 1H), 7.26 (s, 1H), 6.86 (d, J=8.7 Hz, 2H), 6.56 (d, J=8.6 Hz, 1H), 5.10 (s, 1H), 3.93-3.82 (m, 2H), 3.78-3.68 (m, 2H), 3.01 (s, 1H), 2.42-2.32 (m, 2H). HPLC: 90.05%.

Example 287: 4-(6-(3-((6-ethynylpyridin-3-yl)oxy) azetidin-1-yl)pyridin-3-yl)-6-(1-methyl-1H-pyrazol-4-yl) pyrazolo[1,5-a]pyridine-3-carbonitrile (287)

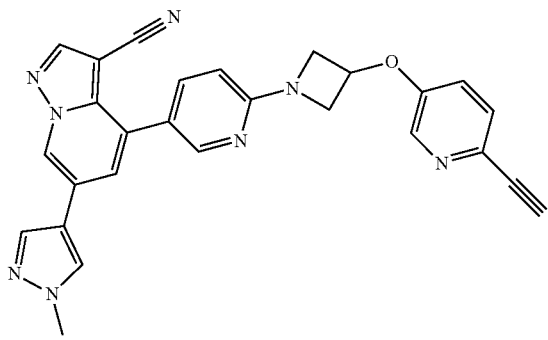

Step 1: tert-butyl 3-hydroxyazetidin-1-carboxylate

To a single-necked flask were added tert-butyl 3-oxoazetidine-1-carboxylate (5.0 g, 29 mmol) and EtOH (50 mL) at room temperature, then NaBH$_4$ (1.1 g, 29 mmol) was added portionwise with stirring. After the completion of reaction was monitored by TLC, a saturated ammonium chloride solution was added to the reaction solution until no bubbles were generated, and a large amount of white solid was precipitated. The mixture was filtered with suction. The filter cake was washed with ethanol (10 mL), and the filtrate was concentrated in vacuo to remove most of the ethanol. To the residue was added with 30 mL of water and the resulting mixture was extracted with EA (100 mL). The combined organic phases were washed with water (20 mL×2) and saturated sodium chloride (20 mL). The organic phases were dried over anhydrous sodium sulfate and filtered. The mother liquid was purified by silica gel column chromatography (eluent EA:PE=1:5) to give colorless oil 5.0 g as the target product. LC-MS: m/z=118.10[M-t-Bu+H]$^+$, $^1$H NMR (400 MHz, CDCl$_3$) δ 4.53 (s, 1H), 4.13-4.09 (m, 2H), 3.78 (dd, J=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask were added tert-butyl 3-hydroxyazetidine-1-carboxylate (500 mg, 2.89 mmol), DCM (15 mL) and NaH (0.14 g, 5.8 mmol) under nitrogen. The mixture was transferred to 0° C. and MsCl (0.25 mL, 3.2 mmol) was added dropwise with stirring. After the addition, the mixture was reacted continuously at this temperature. After the completion of reaction was monitored by TLC, water (20 mL) and DCM (50 mL) were added to the reaction mixture. The organic phase was separated, and the aqueous phase was extracted with EA (50 mL). The combined organic phases were washed with water (20 mL×2) and saturated sodium chloride (20 mL), dried over anhydrous sodium sulfate and filtered. The mother liquid was purified by silica gel column chromatography (eluent EA:PE=1:5) to give colorless oil 566 mg as the target product. LC-MS: m/z=196.10[M-t-Bu+H]$^+$, m/z=152.10[M-Boc+H]$^+$, $^1$H-NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-((6-bromopyridin-3-yl)oxy)azetidin-1-carboxylate

6-Bromopyridin-3-ol (200 mg, 1.15 mmol) was dissolved in DMSO (4 mL) at room temperature, and t-BuOK (168 mg, 1.5 mmol) was added to the solution with stirring. After stirring for 20 min, the temperature was raised to 80° C. tert-Butyl 3-((methylsulfonyl)oxy)azetidin-1-carboxylate (347 mg, 1.4 mmol) dissolved in DMSO (2 mL) was added dropwise slowly. After the addition, the mixture was kept at this temperature with stirring. After the completion of reaction was monitored by TLC, the reaction mixture was poured into water (20 mL). The resulting mixture was extracted with EA (50 mL×2). The combined organic phases were washed with water (20 mL×2) and saturated saline (20 mL). The organic phases were dried over anhydrous sodium sulfate and filtered. The filtrate was concentrated in vacuo, and the residue was purified by silica gel column chromatography (eluent EA:PE=1:20-1:10) to give a light yellow solid 320 mg as the target product. LC-MS: m/z=329.05 [M+H]$^+$.

Step 4: tert-butyl 3-((6-((trimethylsilyl)ethynyl)pyridin-3-yl)oxy)azetidin-1-carboxylate To a two-necked flask were added tert-butyl 3-((6-bromopyridin-3-yl)oxy)azetidin-1-carboxylate (320 mg, 0.97 mmol), CuI (37 mg, 0.19 mmol), PdCl$_2$(PPh$_3$)$_2$ (68 mg, 0.097 mmol), THF (3 mL) and TEA (3 mL) under nitrogen. The mixture was transferred to 50° C. and ethynyl (trimethyl) silane (191 mg, 1.95 mmol) was added dropwise with stirring. After the addition, the mixture was kept at this temperature and reacted. After the completion of reaction was monitored by TLC, the reaction mixture was filtered by suction through a celite pad. The filter cake was washed with a small amount of EA, and the filtrate was concentrated in vacuo, and then purified by silica gel column chromatography (eluent EA:PE=1:20-1:10) to give a brown solid 240 mg as the desired product. LC-MS: m/z=347.25[M+H]$^+$. $^1$H NMR (400 MHz, CDCl$_3$) δ 8.12 (s, 1H), 7.39 (d, J=8.6 Hz, 1H), 6.97 (dd, J=8.6, 2.9 Hz, 1H), 4.92 (ddd, J=10.4, 6.3, 4.0 Hz, 1H), 4.31 (dd, J=9.6, 6.8 Hz, 2H), 4.00 (dd, 7=9.8, 3.4 Hz, 2H), 1.45 (s, 9H), 0.26 (s, 9H).

Step 5: tert-butyl 3-((6-ethynylpyridin-3-yl)oxy) azetidin-1-carboxylate tert-Butyl 3-((6-((trimethylsilyl)ethynyl)pyridin-3-yl) oxy)azetidin-1-carboxylate (240 mg, 0.69 mmol) was dissolved in methanol (2 mL) at room temperature, and then potassium carbonate (194 mg, 1.38 mmol) was added with stirring. The reaction solution was reacted at room temperature. After the completion of reaction was monitored by TLC, the reaction mixture was concentrated in vacuo. To the residue was added water (10 mL) and the resulting mixture was extracted with EA (30 mL×3). The combined organic phases were washed with saturated saline (30 mL), dried over anhydrous sodium sulfate and filtered. The filtrate was concentrated in vacuo, and the residue was purified by silica gel column chromatography (eluent EA:PE=1:20-1:10) to give a light yellow solid 180 mg as the target product. LC-MS: m/z=275.20[M+H]+. 1H NMR (400 MHz, CDCl3) δ 8.14 (d, J=2.8 Hz, 1H), 7.43 (d, J=8.6 Hz, 1H), 6.99 (dd, 7=8.6, 2.9 Hz, 1H), 4.92 (tt, J=6.4, 4.1 Hz, 1H), 4.32 (ddd, 7=9.7, 6.3, 0.6 Hz, 2H), 4.01 (dd, 7=9.9, 3.9 Hz, 2H), 3.09 (s, 1H), 1.45 (s, 9H).

Step 6: 5-(azetidin-3-yloxy)-2-ethynylpyridine hydrochloride tert-Butyl 3-((6-ethynylpyridin-3-yl)oxy)azetidin-1-carboxylate (180 mg, 0.66 mmol) was dissolved in HCl/dioxane (3 mL, 12 mmol, 4 mol/L) with stirring at room temperature. After the completion of reaction was monitored by TLC, the reaction mixture was concentrated in vacuo to give a light yellow solid 158 mg as the target product.

Step 7: 4-(6-(3-((6-ethynylpyridin-3-yl)oxy)azetidin-1-yl)pyridin-3-yl)-6-(1-methyl-1H-pyrazol-4-yl)pyrazolo[1,5-a]pyridine-3-carbonitrile To a microwave tube were sequentially added 4-(6-fluoro-3-pyridyl)-6-(1-methylpyrazol-4-yl)pyrazolo[1,5-a]pyridine-3-carbonitrile (see synthesis of intermediate 1, 60 mg, 0.189 mmol), 5-(azetidin-3-yloxy)-2-ethynylpyridine hydrochloride (80 mg, 0.380 mmol) and DIPEA (0.1 mL, 0.6 mmol). The mixture was reacted at 110° C. for 8 h under microwave. The reaction solution was added to 10 mL of water, and the resulting mixture was extracted with EA (30 mL×3). The organic phases were combined and washed with saturated brine (20 mL×2). The organic phases were separated, dried over anhydrous sodium sulfate and filtered. The filtrate was concentrated in vacuo, and the residue was purified by silica gel column chromatography to give a white solid 28 mg as the target product (yield: 31.44%). LC-MS: m/z=473.10[M+H]+. 1H NMR (400 MHz, DMSO-d6) δ 9.23 (s, 1H), 8.64 (s, 1H), 8.39 (s, 1H), 8.37 (d, 7=1.9 Hz, 1H), 8.28 (d, J=2.7 Hz, 1H), 8.12 (s, 1H), 7.84 (dd, J=8.5, 2.3 Hz, 1H), 7.77 (s, 1H), 7.56 (d, J=8.6 Hz, 1H), 7.37 (dd, J=8.6, 2.9 Hz, 1H), 6.61 (d, J=8.6 Hz, 1H), 5.38-5.30 (m, 1H), 4.54 (dd, J=9.3, 6.3 Hz, 2H), 4.19 (s, 1H), 4.02 (dd, 7=9.6, 3.4 Hz, 2H), 3.88 (s, 3H). HPLC: 94.91%.

Example 288: 1-(4-(5-(6-(1-methyl-1H-pyrazol-4-yl) pyrazolo[1,5-a]pyridin-4-yl)pyridin-2-yl) piperazin-1-yl)-3-phenylprop-2-yn-1-one (288)

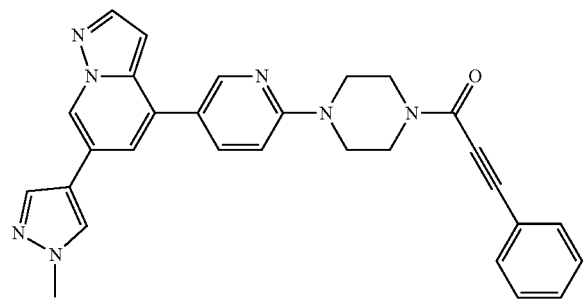

Step 1: 4-bromopyrazolo[1,5-a]pyridine-6-ol

To a 100 mL single-necked flask at room temperature was added 4-bromo-6-methoxy-pyrazolo[1,5-a]pyridine (1600 mg, 7.047 mmol), which was dissolved by adding DCE (50 mL). AlCl3 (2.82 g, 21.1 mmol) was added slowly. After the addition, the mixture was transferred to an oil bath and reacted at 80° C. for 6 h. TLC showed the reaction was completed. The mixture was cooled to room temperature and to the mixture was added a solution of sodium sulfate decahydrate in THF (100 mL). The resulting mixture was stirred at room temperature for 30 min and stratified. The organic phases were washed with saturated saline (30 mL), dried over anhydrous sodium sulfate, filtered, and concentrated in vacuo to give an off-white solid 1.48 g (yield: 98.6%) as the target product. LC-MS (ES-API): m/z=213.00 [M+H]+. 1H NMR (400 MHz, MeOD) δ 8.27 (s, 1H), 7.84 (d, J=2.1 Hz, 1H), 6.68 (d, J=1.6 Hz, 1H), 6.55 (d, 1H).

Step 2: (4-bromopyrazolo[1,5-a]pyridin-6-yl) trifluoromethanesulfonate

To a 50 mL two-necked flask was added 4-bromopyrazolo[1,5-a]pyridine-6-ol (500 mg, 2.347 mmol). The mixture was degassed and refilled with nitrogen. DCM (10 mL) was added to dissolve the solid, and then pyridine (0.45 mL, 5.6 mmol) was added. Trifluoromethanesulfonic anhydride (0.58 mL, 2.8 mmol) was slowly added dropwise at 0° C. After the addition, the mixture was reacted at 0° C. for 2 h. TLC showed the reaction was completed. To the reaction mixture was added water (30 mL), then the resulting mixture was extracted with DCM (80 mL×2). The combined organic phases were washed with saturated saline (30 mL), dried over anhydrous sodium sulfate, filtered, and concentrated in vacuo. The residue was purified by silica gel column chromatography (eluent PE:EA=50:1-10:1) to give a gray soft solid 669.7 mg (the yield was 82.68%), which was the target product. LC-MS (ES-API): m/z=345.90[M+H]+. 1H NMR (400 MHz, CDCl3) δ 8.65 (s, 1H), 8.01 (d, J=2.3 Hz, 1H), 7.24 (d, J=1.0 Hz, 1H), 6.72 (d, J=1.8 Hz, 1H).

Step 3: 4-bromo-6-(1-methylpyrazol-4-yl) pyrazolo[1,5-a]pyridine

To a 25 mL two-necked flask were added (4-bromopyrazolo[1,5-a]pyridin-6-yl) trifluoromethanesulfonate (644 mg, 1.866 mmol), 1-methyl-4-(4,4,5,5-tetramethyl-1,3,2-dioxaborolane-2-yl)-1H-pyrazole (408 mg, 1.961 mmol) and PdCl2(dppf)CH2Cl2 (154 mg, 0.187 mmol). The reaction mixture was degassed and refilled with nitrogen for several times. 1,4-Dioxane (13 mL) was added to dissolve the solids, then an aqueous solution of potassium acetate (3.732 mL, 3.732 mmol, 1 mmol/mL) was added in an ice bath. The mixture was heated to 80° C. and reacted overnight. TLC showed the reaction was completed. To the resulting mixture was added water (10 mL) and the resulting mixture was extracted with EA (30 mL×2). The organic phases were washed with saturated saline (15 mL), dried over anhydrous sodium sulfate, filtered, concentrated in vacuo, and then purified by silica gel column chromatography (eluent PE:EA=6: 1-1:2) to give a brown solid 174 mg as the target product (yield: 33.6%). LC-MS (ES-API): m/z=277.10[M+H]+. 1H NMR (400 MHz, CDCl3) δ 8.55 (s, 1H), 7.96 (d, J=2.2 Hz, 1H), 7.88 (s, 1H), 7.78 (s, 1H), 7.24 (d, J=1.3 Hz, 1H), 6.71 (d, J=1.5 Hz, 1H).

Step 4: 4-(6-fluoro-3-pyridyl)-6-(1-methylpyrazol-4-yl) pyrazolo[1,5-a]pyridine

To a 25 mL two-necked flask were added 4-bromo-6-(1-methylpyrazol-4-yl) pyrazolo[1,5-a]pyridine (155 mg, 0.559 mmol), potassium acetate (165 mg, 1.681 mmol), 2-fluoro-5-(4,4,5,5-tetramethyl-1,3,2-dioxaborolane-2-yl)pyridine (0.188 g, 0.843 mmol) and PdCl$_2$(dppf)CH$_2$Cl$_2$ (46 mg, 0.056 mmol). The reaction mixture was degassed and refilled with nitrogen. 1,4-Dioxane (12 mL) was then added, and the mixture was heated to 90° C. and reacted overnight. TLC showed the reaction was completed. To the reaction mixture was added water (15 mL) and the resulting mixture was extracted with EA (40 mL×2). The organic phases were washed with saturated saline (20 mL), dried over anhydrous sodium sulfate, filtered, and the filtrate was concentrated in vacuo, and then purified by silica gel column chromatography (eluent PE:EA=6:1-1:3) to give a yellow-white solid 150 mg as the target product (yield: 91%). LC-MS (ES-API): m/z=294.20[M+H]$^+$. $^1$H NMR (400 MHz, CDCl$_3$) δ 8.59 (s, 1H), 8.47 (s, 1H), 8.04 (d, J=4.9 Hz, 1H), 8.00 (dd, J=7.9, 2.2 Hz, 1H), 7.94 (s, 1H), 7.84 (s, 1H), 7.32 (s, 1H), 7.07 (dd, J=8.4, 2.9 Hz, 1H), 6.75 (s, 1H).

Step 5: tert-butyl 4-(3-phenylpropioloyl) piperazine-1-carboxylate

To a 25 mL single-necked flask was added 3-phenylprop-2-ynoic acid (500 mg, 3.422 mmol), which was dissolved by adding DMF (5 mL). Then tert-butyl piperazine-1-carboxylate (637 mg, 3.420 mmol) was added at 0° C. N,N-dicyclohexylcarbodiimide (706 mg, 3.422 mmol) was added in portions. The resulting mixture was reacted for 4 h at 0° C. TLC showed the reaction was completed. To the reaction mixture was added with water (25 mL), then the resulting mixture was extracted with EA (100 mL×2). The combined organic phases were washed with saturated saline (40 mL), dried over anhydrous sodium sulfate, filtered, and concentrated in vacuo. The mixture was purified by silica gel column chromatography (eluent PE:EA=8:1-2:1) to give a yellow-white solid 0.985 g as the target product (the yield was 91.6%). LC-MS (ES-API): m/z=315.3[M+H]$^+$. $^1$H NMR (400 MHz, CDCl$_3$) δ 7.57-7.52 (m, 2H), 7.39 (ddd, J=15.9, 7.2, 1.9 Hz, 3H), 3.84-3.78 (m, 2H), 3.70-3.63 (m, 2H), 3.5-3.50 (m, 2H), 3.48-3.42 (m, 2H), 1.48 (s, 9H).

Step 6: 3-phenyl-1-(piperazin-1-yl)-prop-2-yn-1-one hydrochloride

To a 100 mL single-necked flask were added tert-butyl 4-(3-phenylpropioloyl)piperazine-1-carboxylate (0.985 g, 3.13 mmol) and a solution of hydrogen chloride in ethyl acetate (9.85 mL, 39.4 mmol). The mixture was stirred at room temperature, and the solid was dissolved, then a white solid precipitated. The solution was turned to a white suspension, and the reaction was continued for 3 h. TLC showed the reaction was completed. The reaction solution was directly concentrated in vacuo to give yellow oil, which was dried in an oven at 60° C. to obtain a theoretical amount of yellow white solid 0.785 g as the target product. LC-MS (ES-API): m/z=215.3[M+H]$^+$.

Step 7: 1-(4-(5-(6-(1-methyl-1H-pyrazol-4-yl)pyrazolo[1,5-a]pyridin-4-yl)pyridin-2-yl)piperazin-1-yl)-3-phenylprop-2-yn-1-one To a 10 mL single-necked flask were sequentially added 3-cyano-4-(6-fluoro-pyridin-3-yl)-6-(1-methyl-1H-pyrazol-4-yl) pyrazolo[1,5-a]pyridine (see synthesis of intermediate 1, 55 mg, 0.188 mmol), 3-phenyl-1-piperazin-1-yl-prop-2-yn-1-one hydrochloride (70 mg, 0.279 mmol), potassium carbonate (104 mg, 0.753 mmol) and DMSO (1.7 mL). The mixture was reacted at 140° C. for 3 d. TLC showed the reaction was completed. To the resulting mixture was added water (15 mL) and the resulting mixture was extracted with EA (30 mL×3). The organic phases were washed with saturated saline (30 mL), dried over anhydrous sodium sulfate, filtered and concentrated in vacuo. The residue was purified by silica gel column chromatography (eluent: DCM-DCM:MeOH (v:v)=20:1)) to give an off-white solid 12 mg as the target product (yield: 13%). LC-MS (ES-API): m/z=488.15[M+H]$^+$. $^1$H NMR (400 MHz, CDCl$_3$) δ 8.56 (s, 1H), 8.48 (d, J=2.0 Hz, 1H), 8.01 (d, J=2.1 Hz, 1H), 7.93 (s, 1H), 7.82 (s, 1H), 7.58 (d, J=6.7 Hz, 2H), 7.45-7.34 (m, 5H), 6.80 (d, J=8.6 Hz, 1H), 6.71 (d, J=1.6 Hz, 1H), 4.03 (s, 3H), 4.01-3.98 (m, 2H), 3.87-3.84 (m, 2H), 3.79-3.76 (m, 2H), 3.69-3.66 (m, 2H). HPLC: 90.43%.

Example 289: 4-(6-(3-((5-ethynylpyridin-2-yl)oxy) azetidin-1-yl)pyridin-3-yl)-6-(1-methyl-1H-pyrazol-4-yl)pyrazolo[1,5-a]pyridine-3-carbonitrile

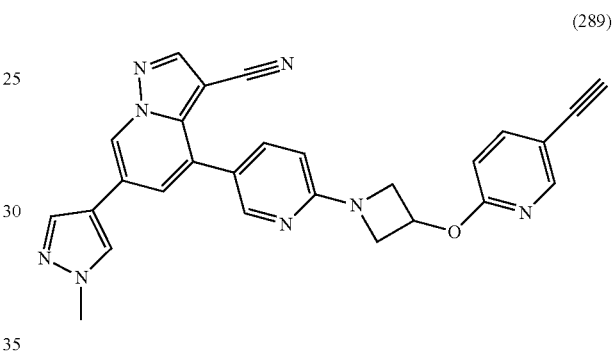

(289)

Step 1: tert-butyl 3-hydroxyazetidin-1-carboxylate

To a 100 mL single-necked flask were added tert-butyl 3-oxoazetidine-1-carboxylate (2.0 g, 12 mmol) and EtOH (20 mL) at room temperature, then NaBH$_4$ (0.88 g, 23 mmol) was added portionwise with stirring. The mixture was stirred at room temperature for reaction. After the completion of reaction was monitored by TLC, a saturated ammonium chloride solution was added to the reaction solution until no bubbles were generated. The mixture was filtered with suction. The filter cake was washed with ethanol (10 mL), and the filtrate was concentrated in vacuo to remove most of the ethanol. To the mixture was added 30 mL of water and the resulting mixture was extracted with EA (100 mL×2). The combined organic phases were washed with water (20 mL×2) and saturated sodium chloride (20 mL). The organic phases were dried over anhydrous sodium sulfate and filtered. The mother liquor was concentrated in vacuo, and the residue was purified by silica gel column chromatography (eluent EA:PE=1:5) to give colorless oil 2.0 g as the target product. LC-MS: m/z=118.10[M-t-Bu+H]$^+$, $^1$H NMR (400 MHz, CDCl$_3$) δ 4.53 (s, 1H), 4.13-4.09 (m, 2H), 3.78 (dd, J=9.9, 4.1 Hz, 2H), 3.54-3.45 (m, 1H), 1.41 (s, 9H).

Step 2: tert-butyl 3-((methylsulfonyl)oxy)azetidin-1-carboxylate

To a two-necked flask were added tert-butyl 3-hydroxyazetidine-1-carboxylate (500 mg, 2.89 mmol), DCM (15 mL) and NaH (0.14 g, 5.8 mmol) under nitrogen. The mixture was transferred to 0° C. and MsCl (0.25 mL, 3.2 mmol) was added dropwise with stirring. After the addition, the mixture was reacted continuously at this temperature. After the completion of reaction was monitored by TLC, the reaction solution was quenched with water (20 mL) and then DCM (50 mL) were added. The organic phase was separated, and the aqueous phase was extracted with DCM (50 mL). The combined organic phases were washed with water (20 mL×2) and saturated sodium chloride (20 mL). The organic phases were dried over anhydrous sodium sulfate and filtered. The mother liquor was concentrated in vacuo and purified by silica gel column chromatography (eluent EA:PE=1:5) to give colorless oil 680 mg as the target product. LC-MS: m/z=196.10[M-t-Bu+H]$^+$, m/z=152.10 [M-Boc+H]$^+$; $^1$H-NMR (400 MHz, CDCl$_3$) δ 5.18 (tt, J=6.7, 4.2 Hz, 1H), 4.26 (ddd, J=10.3, 6.7, 1.0 Hz, 2H), 4.11-4.04 (m, 2H), 3.05 (s, 3H), 1.43 (s, 9H).

Step 3: tert-butyl 3-((5-iodopyridin-2-yl)oxy)azetidin-1-carboxylate

To a 25 mL single-necked flask were added tert-butyl 3-methylsulfonyloxyazetidine-1-carboxylate (410 mg, 1.63 mmol), 5-iodo-2-olpyridine (300 mg, 1.36 mmol) and potassium tert-butoxide (195 mg, 1.65 mmol). DMF (5 mL) was added to dissolve the solids, and the mixture was reacted in an oil bath at 100° C. After the completion of reaction was monitored by TLC, to the reaction solution was added water (10 mL) and the resulting mixture was extracted with EA (40 mL×2). The organic phases were washed with water (15 mL×6) and saturated saline (15 mL), dried over anhydrous sodium sulfate and filtered. The filtrate was purified by silica gel column chromatography (eluent PE:EA=10:1) to give a white solid 283 mg as the target product. LC-MS: m/z=377.10[M+H]$^+$. $^1$H NMR (400 MHz, CDCl$_3$) δ 8.29 (d, J=1.9 Hz, 1H), 7.82 (dd, J=8.7, 2.3 Hz, 1H), 6.62 (d, J=8.7 Hz, 1H), 5.26 (tt, J=6.6, 4.3 Hz, 1H), 4.34-4.24 (m, 2H), 3.95 (dd, J=10.0, 4.1 Hz, 2H), 1.44 (s, 9H).

Step 4: tert-butyl 3-((5-((trimethylsilyl)ethynyl)pyridin-2-yl)oxy)azetidin-1-carboxylate To a 50 mL double-necked flask were added tert-butyl 3-((5-iodopyridin-2-yl)oxy) azetidine-1-carboxylate (283 mg, 0.75 mmol), Pd(PPh$_3$)C$_{1-2}$ (15 mg, 0.021 mmol), triethylamine (1.5 mL, 11.0 mmol) and THF (8 mL). The reaction mixture was degassed and refilled with nitrogen. Then cuprous iodide (40 mg, 0.21 mmol), trimethylchlorosilane (1.5 mL, 11.0 mmol) were added. The mixture was reacted at room temperature. After the completion of reaction was monitored by TLC, the reaction mixture was directly concentrated in vacuo, and the residue was purified by silica gel column chromatography (eluent PE/EA=100/1) to give colorless transparent liquid 250 mg, which was the target product. LC-MS: m/z=347.20[M+H]$^+$.

Step 5: tert-butyl 3-((5-ethynylpyridin-2-yl)oxy) azetidin-1-carboxylate

To a 25 mL single-necked flask was added tert-Butyl 3-((5-((trimethylsilyl)ethynyl)pyridin-2-yl)oxy)azetidin-1-carboxylate (250 mg, 0.72 mmol), which was dissolved by adding methanol (3 mL). Then potassium carbonate (300 mg, 2.17 mmol) was added at room temperature. The mixture was reacted at room temperature. After the completion of reaction was monitored by TLC, the reaction mixture was directly concentrated in vacuo, and the residue was purified by silica gel column chromatography (eluent PE/EA=20/1) to give a pale yellow solid 146 mg, which was the target product. LC-MS: m/z=275.20[M+H]$^+$.

Step 6: 2-(azetidin-3-oxy)-5-ethynylpyridine hydrochloride

To a 25 mL single-necked flask was added tert-Butyl 3-((5-ethynylpyridin-2-yl)oxy)azetidin-1-carboxylate (146 mg, 0.53 mmol), then HCl/EA (5 mL, 4N) was added with stirring. The mixture was stirred at room temperature for reaction. After the completion of reaction was monitored by TLC, the reaction solution was concentrated in vacuo to remove the solvent and dried in a vacuum drying oven at 60° C. to obtain an off-white solid 112 mg as the target product. LC-MS: m/z=211.20[M+H]$^+$, m/z=175.20[M+H-HCl]$^+$.

Step 7: 4-(6-(3-((5-ethynylpyridin-2-yl)oxy)azetidin-1-yl)pyridin-3-yl)-6-(1-methyl-1H-pyrazol-4-yl) pyrazolo[1,5-a]pyridine-3-carbonitrile To a 10 mL single-necked flask were added 4-(6-fluoro-3-pyridyl)-6-(1-methylpyrazol-4-yl)pyrazolo[1,5-a]pyridine-3-carbonitrile (see synthesis of intermediate 1, 80 mg, 0.25 mmol), 2-(azetidin-3-yloxy)-5-ethynylpyridine hydrochloride (170 mg, 0.81 mmol), 4-dimethylaminopyridine (4 mg, 0.03 mmol), triethylamine (0.4 mL, 3 mmol) and DMSO (1 mL). The mixture was reacted at 90° C. After the completion of reaction was monitored by TLC, to the reaction solution was added water (15 mL) and the resulting mixture was extracted with EA (60 mL×2). The organic phases were separated, washed with water (15 mL×5) and saturated saline (15 mL×2), dried over anhydrous sodium sulfate and filtered. The filtrate was concentrated in vacuo, and the residue was purified by silica gel column chromatography (eluent DCM:MeOH=150: 1-50:1) to give a white solid 38 mg as the target product. LC-MS: m/z=473.60[M+H]$^+$. $^1$H NMR (400 MHz, CDCl$_3$) δ 8.63 (s, 1H), 8.31 (dd, J=18.9, 1.7 Hz, 2H), 8.25 (s, 1H), 7.79 (s, 1H), 7.74-7.66 (m, 3H), 7.38 (s, 1H), 6.78 (d, J=8.6 Hz, 1H), 6.46 (d, J=8.5 Hz, 1H), 5.61-5.54 (m, 1H), 4.59-4.52 (m, 2H), 4.16 (dd, 7=9.8, 3.9 Hz, 2H), 3.99 (s, 3H), 3.13 (s, 1H). HPLC: 97.05%.

Example 290: 6-(1-(difluoromethyl)-1H-pyrazol-4-yl)-4-(6-(3-((5-ethynylpyridin-2-yl)oxy) azetidin-1-yl)pyridin-3-yl)pyrazolo[1,5-a]pyridine-3-carbonitrile (290)

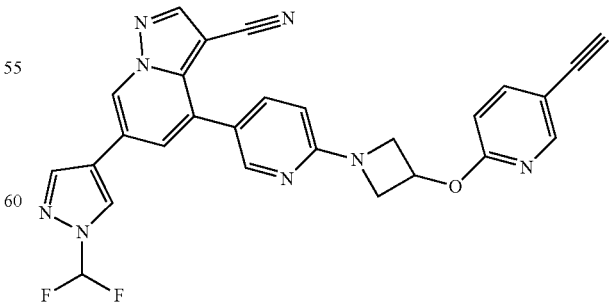

To a 10 mL single-necked flask were added 6-[1-(difluoromethyl)pyrazol-4-yl]-4-(6-fluoro-3-pyridyl)pyrazolo[1,5- a]pyridine-3-carbonitrile (see synthesis of intermediate 6, 80 mg, 0.23 mmol), 2-(azetidin-3-yloxy)-5-ethynylpyridine hydrochloride (see the synthesis of step 6 in Example 289, 144 mg, 0.68 mmol), 4-dimethylaminopyridine (5 mg, 0.04 mmol), triethylamine (0.4 mL, 3 mmol) and DMSO (1 mL). The mixture was reacted at 90° C. After the completion of reaction was monitored by TLC, to the reaction solution was added water (15 mL) and the resulting mixture was extracted with EA (100 mL×2). The organic phases were washed with water (20 mL×5) and saturated saline (20 mL×2), dried over anhydrous sodium sulfate and filtered. The filtrate was purified by silica gel column chromatography (eluent DCM: MeOH=150: 1-50:1) to give a white solid 19 mg as the target product. LC-MS: m/z=509.20[M+H]+. $^1$H NMR (400 MHz, DMSO-d$_6$) δ 9.43 (s, 1H), 9.01 (s, 1H), 8.69 (s, 1H), 8.53 (s, 1H), 8.43-8.32 (m, 2H), 7.93 (s, 1H), 7.89-7.82 (m, 2H), 7.66-7.60 (m, 1H), 6.97 (d, J=8.6 Hz, 1H), 6.61 (d, J=8.6 Hz, 1H), 5.60-5.51 (m, 1H), 4.49 (dd, J=9.4, 6.5 Hz, 2H), 4.29 (s, 1H), 4.02 (dd, J=9.7, 3.7 Hz, 2H). HPLC: purity 93.79%.

Example 291: 6-(1-methyl-1H-pyrazol-4-yl)-4-(6-(3-(4-(((trimethylsilyl)ethynyl)phenoxy))azetidin-1-yl)pyridin-3-yl)pyrazolo[5-a]pyridine-3-carbonitrile

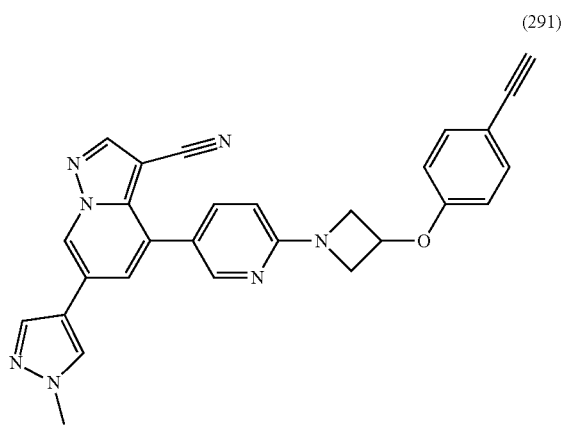 [SMILES: C#Cc1ccc(OC2CN(c3ccc(-c4cc(-c5cnn(C)c5)cn5ncc(C#N)c45)cn3)C2)cc1]

(291)

Step 1: tert-butyl 3-(4-iodophenoxy)azetidin-1-carboxylate p-iodophenol (550 mg, 2.5 mmol) was dissolved in DMF (4 mL) at room temperature, and t-BuOK (320 mg, 2.85 mmol) was added to the solution with stirring. After stirring for 20 min, the temperature was raised to 80° C. tert-Butyl 3-((methylsulfonyl)oxy)azetidin-1-carboxylate (680 mg, 2.75 mmol) dissolved in DMF (1.5 mL) was added dropwise slowly. After the addition, the mixture was kept at this temperature with stirring. After the completion of reaction was monitored by TLC, the reaction mixture was poured into water (20 mL). The resulting mixture was extracted with EA (50 mL×2). The combined organic phases were washed with water (20 mL×2) and saturated saline (20 mL). The organic phases were dried over anhydrous sodium sulfate and filtered. The mother liquor was concentrated in vacuo, and the residue was purified by silica gel column chromatography (eluent EA:PE=1:20-1:10) to give a white solid 615 mg as the target product. LC-MS: m/z=319.9[M-56+H]+. $^1$H NMR (400 MHz, CDCl$_3$) δ 7.56 (d, J=8.8 Hz, 2H), 6.52 (d, J=8.8 Hz, 2H), 4.83 (ddd, J=10.4, 6.3, 4.1 Hz, 1H), 4.28 (dd, J=9.6, 6.5 Hz, 2H), 3.98 (dd, J=9.7, 4.0 Hz, 2H), 1.44 (s, 9H).

Step 2: 3-(4-iodophenoxy)azetidine hydrochloride tert-Butyl 3-(4-iodophenoxy)azetidin-1-carboxylate (615 mg, 1.64 mmol) was dissolved in HCl/EA (3 mL, 12 mmol, 4 mol/L) with stirring at room temperature. After the completion of reaction was monitored by TLC, the reaction mixture was concentrated in vacuo to give a white solid 510 mg as the target product. $^1$H NMR (400 MHz, DMSO-d$_6$) δ 11.96 (s, 1H), 7.64 (d, J=8.9 Hz, 2H), 6.73 (d, J=8.9 Hz, 2H), 5.11-5.02 (m, 1H), 4.41 (dd, J=12.3, 6.6 Hz, 2H), 3.96 (dd, J=12.3, 4.7 Hz, 2H), 1.91 (s, 1H).

Step 3: 4-(6-(3-(4-iodophenoxy)azetidin-1-yl)pyridin-3-yl)-6-(1-methyl-1H-pyrazol-4-yl)pyrazolo[1,5-a]pyridine-3-carbonitrile To a solution of 4-(6-fluoro-3-pyridyl)-6-(1-methylpyrazol-4-yl)pyrazolo[1,5-a]pyridine-3-carbonitrile (see synthesis of intermediate 1, 50 mg, 0.1571 mmol) in DMSO (2 mL) were added 3-(4-iodophenoxy)azetidine hydrochloride (59 mg, 0.18938 mmol) and DIPEA (0.1 mL, 0.6 mmol) at room temperature. The mixture was reacted for 8 h under microwave (110° C., 10 bar). After the reaction was completed, to the reaction mixture were added water (20 mL) and EA (200 mL). The organic layers were washed with saturated brine (30 mL×3) and concentrated in vacuo, and the residue was purified by silica gel column chromatography (DCM: MeOH=0-100:3) to give a yellow solid 90 mg as the target product (the yield was 99.92%). (Rf=0.5, DCM/MeOH=20/1). LC-MS: m/z=574.0[M+H]+.

Step 4: 6-(1-methyl-1H-pyrazol-4-yl)-4-(6-(3-(4-(((trimethylsilyl)ethynyl)phenoxy))azetidin-1-yl)pyridin-3-yl)pyrazolo[1,5-a]pyridine-3-carbonitrile To a two-necked flask were sequentially added 4-[6-[3-(4-iodophenoxy) azetidin-1-yl]-3-pyridyl]-6-(1-methylpyrazol-4-yl)pyrazolo[1,5-a]pyridine-3-carbonitrile (90 mg, 0.1570 mmol), Pd(PPh$_3$)$_2$Cl$_2$ (2.2 mg, 0.0031 mmol), triethylamine (2 mL) and THF (4 mL). The reaction mixture was degassed and refilled with nitrogen. After stirring for 15 min, cuprous iodide (2.0 mg, 0.011 mmol) and ethynyl (trimethyl)silane (0.1 mL, 0.7 mmol) were added. The mixture was stirred at room temperature overnight. The reaction mixture was concentrated in vacuo, and the residue was purified by silica gel column chromatography (DCM/MeOH=0-100/3) to give a brown solid 70 mg as the target product (the yield was 82.03%). (Rf=0.5, DCM/MeOH=20/1). LC-MS: m/z=544.2 [M+H]+.

Step 7: 4-(6-(3-(4-ethynylphenoxy) azetidin-1-yl) pyridin-3-yl)-6-(1-methyl-1H-pyrazol-4-yl)pyrazolo [1,5-a]pyridine-3-carbonitrile To a single-necked flask were sequentially added 6-(1-methylpyrazol-4-yl)-4-[6-[3-[4-[2-(2-trimethylsilylethynyl) phenoxy]azetidine-1-yl]-3-pyridyl]pyrazolo[1,5-a]pyridine-3carbonitrile (80 mg, 0.1471 mmol), potassium carbonate (98 mg, 0.70907 mmol) and methanol (5 mL). The mixture was stirred at room temperature for 3 h. The reaction mixture was directly concentrated in vacuo, and the residue was purified by silica gel column chromatography (DCM/MeOH=0-100/4) to give a white solid 16 mg as the target product (the yield was 23.06%). (Rf=0.5, DCM/MeOH=20/1). LC-MS: m/z=472.6[M+H]+. 1H NMR (400 MHz, CDCl3) δ 8.64 (s, 1H), 8.35 (s, 1H), 8.26 (s, 1H), 7.79 (s, 1H), 7.75 (dd, J=8.6, 2.0 Hz, 1H), 7.69 (s, 1H), 7.46 (d, J=8.7 Hz, 2H), 7.39 (s, 1H), 6.76 (d, J=8.7 Hz, 2H), 6.49 (d, J=8.6 Hz, 1H), 5.18-5.10 (m, 1H), 4.56 (dd, 7=8.6, 6.7 Hz, 2H), 4.20 (dd, 7=9.2, 3.9 Hz, 2H), 3.99 (s, 3H), 3.02 (s, 1H). HPLC: 93.88%.

Example 292: 4-(6-(3-(4-ethynyl-3-fluorophenoxy) azetidin-1-yl)pyridine3-yl)-6-(1-methyl-1H-pyrazol-4-yl)pyrazolo[1,5-a]pyridine-3-carbonitrile

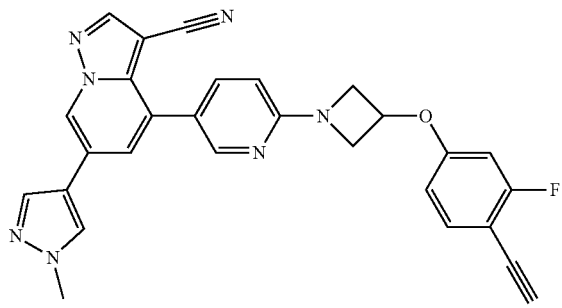

(292)

Step 1: tert-butyl 3-(3-fluoro-4-iodo-phenoxy)azetidin-1-carboxylate

To a 10 mL single-necked flask were added 3-fluoro-4-iodo-phenol (400 mg, 1.681 mmol), tert-butyl 3-((methylsulfonyl)oxy)azetidin-1-carboxylate (507 mg, 2.018 mmol) and t-BuOK (377.2 mg, 3.361 mmol). Then DMF (6 mL) was added to dissolve the solids. The mixture was reacted in an oil bath at 100° C. overnight. TLC showed the reaction was completed. To the mixture was added water (25 mL) and to the resulting mixture was extracted with EA (50 mL×2). The organic phases were washed with saturated saline (30 mL), dried over anhydrous sodium sulfate and filtered. The filtrate was concentrated in vacuo, and then purified by silica gel column chromatography (pure PE-PE:EA(v:v=10:1)) to give a white crystalline solid (yield: 69%) as the target product. LC-MS (ES-API): m/z=338.00[M-56+H]+. 1H NMR (400 MHz, CDCl3) δ 7.60 (dd, J=8.6, 7.4 Hz, 1H), 6.50 (dd, 7=9.4, 2.7 Hz, 1H), 6.36 (dd, 7=8.7, 2.3 Hz, 1H), 4.83 (qd, 7=6.4, 4.1 Hz, 1H), 4.29 (dd, 7=9.6, 6.8 Hz, 2H), 3.98 (dd, 7=9.9, 3.8 Hz, 2H), 1.45 (s, 9H).

Step 2: tert-butyl 3-(3-fluoro-4-(2-trimethylsilylethynyl) phenoxy)azetidin-1-carboxylate To a 25 mL two-necked flask were added tert-butyl 3-(3-fluoro-4-iodo-phenoxy) azetidine-1-carboxylate (450 mg, 1.144 mmol), CuI (22 mg, 0.116 mmol) and PdCl2(PPh3)2 (41 mg, 0.058 mmol). The reaction mixture was degassed and refilled with nitrogen. Then anhydrous THF (4.5 mL) and TEA (4.5 mL, 32 mmol) were added. After the dissolution, ethynyl (trimethyl)silane (0.323 mL, 2.29 mmol) was added. The mixture was stirred for reaction at room temperature overnight. TLC showed the reaction was completed. The resulting mixture was filtered by suction through a celite pad. The filter cake was washed with EA (60 mL) several times, and the filtrate was washed with saturated brine (20 mL), dried over anhydrous sodium sulfate and filtered. The filtrate was concentrated in vacuo, and then purified by silica gel column chromatography (eluent PE:EA=100: 1-10:1) to give a brown solid 0.398 g (yield: 95.7%) as the target product. LC-MS (ES-API): m/z=308.10 [M-56+H]+. 1H NMR (400 MHz, CDCl3) δ 7.36 (t, J=8.5 Hz, 1H), 6.51-6.41 (m, 2H), 4.88-4.81 (m, 1H), 4.29 (dd, J=9.6, 6.7 Hz, 2H), 3.98 (dd, J=9.9, 3.9 Hz, 2H), 1.45 (s, 9H), 0.25 (s, 9H).

Step 3: tert-butyl 3-(4-ethynyl-3-fluorophenoxy) azetidin-1-carboxylate

To a 10 mL single-necked flask were sequentially added tert-butyl 3-(3-fluoro-4-(2-trimethylsilylethynyl) phenoxy) azetidine-1-carboxylate (400 mg, 1.100 mmol), K2CO3 (305 mg, 2.207 mmol) and MeOH (3 mL). The mixture was stirred to react at room temperature overnight. After TLC showed the reaction was completed, the mixture was quenched by adding 10 mL of saturated ammonium chloride dropwise and then concentrated in vacuo to remove part of methanol. The resulting mixture was extracted with EA (30 mL×2). The organic phases were washed with saturated saline (15 mL), dried over anhydrous sodium sulfate and filtered. The filtrate was concentrated in vacuo, and then purified by silica gel column chromatography (eluent PE:EA=100:1-5:1) to give a white solid 0.364 g (the yield was 82.3%), which was the target product. LC-MS (ES-API): m/z=236.10[M-56+H]+. 1H NMR (400 MHz, CDCl3) δ 7.39 (t, J=8.4 Hz, 1H), 6.51-6.45 (m, 2H), 4.89-4.82 (m, 1H), 4.30 (dd, 7=9.4, 6.8 Hz, 2H), 3.99 (dd, 7=9.9, 3.7 Hz, 2H), 3.23 (s, 1H), 1.45 (s, 9H).

Step 4: 3-(4-ethynyl-3-fluoro-phenoxy)azetidine hydrochloride

To a 10 mL single-necked flask were added tert-butyl 3-(4-ethynyl-3-fluorophenoxy) azetidine-1-carboxylate (254 mg, 0.872 mmol) and a solution of hydrogen chloride in ethyl acetate (6 mL, 24 mmol, 4 mol/L). The mixture was reacted with stirring at room temperature for 1 h. TLC showed the reaction was completed. The reaction solution was directly concentrated in vacuo, dried in an oven at 60° C. to obtain a theoretical amount of yellow white solid. LC-MS (ES-API): m/z=192.15 [M+H]+.

Step 5: 4-(6-(3-(4-ethynyl-3-fluorophenoxy) azetidin-1-yl)pyridin-3-yl)-6-(1-methyl-1H-pyrazol-4-yl) pyrazolo[1,5-a]pyridine-3-carbonitrile To a 10 mL single-necked flask were sequentially added 4-(6-fluoro-3-pyridyl)-6-(1-methylpyrazol-4-yl)pyrazolo[1,5-a]pyridine-3-carbonitrile (see synthesis of intermediate 1, 30 mg, 0.094 mmol) and 3-(4-ethynyl-3-fluoro-phenoxy) azetidine hydrochloride (65 mg, 0.286 mmol), which were dissolved by adding DMSO (1 mL). Then DIPEA (0.1 mL, 0.6 mmol) and DMAP (1.2 mg, 0.01 mmol) were added. The mixture was reacted at 90° C. in an oil bath overnight. TLC showed the reaction was completed. The reaction solution was cooled to room temperature, then to the resulting mixture was added water (15 mL) and the resulting mixture was extracted with EA (30 mL×3). The organic phases were washed with saturated saline (30 mL), dried over anhydrous sodium sulfate and filtered. The filtrate was concentrated in vacuo. The residue was purified by silica gel column chromatography (eluent: DCM-DCM:MeOH (v:v=10:1)) to give a white solid 0.015 g (yield: 33%) as the target product.

LC-MS (ES-API): m/z=490.60[M+H]⁺. ¹H NMR (400 MHz, DMSO-$d_6$) δ 9.23 (s, 1H), 8.64 (s, 1H), 8.38 (d, J=6.9 Hz, 2H), 8.12 (s, 1H), 7.86-7.82 (m, 1H), 7.77 (s, 1H), 7.51 (t, J=8.5 Hz, 1H), 6.94 (dd, J=11.5, 2.1 Hz, 1H), 6.80 (dd, J=8.6, 2.0 Hz, 1H), 6.61 (d, J=8.6 Hz, 1H), 5.33-5.27 (m, 1H), 4.52 (dd, J=9.3, 6.2 Hz, 2H), 4.36 (s, 1H), 3.99 (dd, 7=9.5, 3.3 Hz, 2H), 3.88 (s, 3H). HPLC: 87.58%.

Example 293: 4-(6-(3-(4-ethynyl-2-fluorophenoxy) azetidin-1-yl)pyridin-3-yl)-6-(1-methyl-1H-pyrazol-4-yl)pyrazolo[1,5-a]pyridine-3-carbonitrile

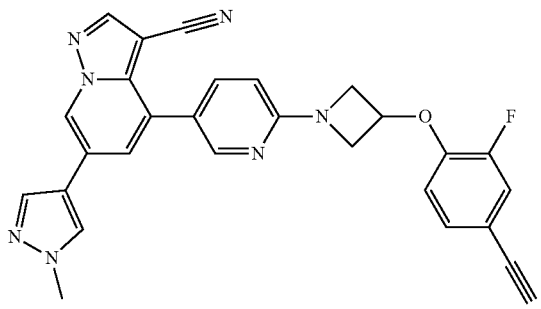

(293)

Step 1: tert-butyl 3-(2-fluoro-4-iodo-phenoxy)azetidin-1-carboxylate

To a 10 mL single-necked flask were added 2-fluoro-4-iodo-phenol (400 mg, 1.681 mmol), tert-butyl 3-methyl-sulfonyloxyazetidin-1-carboxylate (507 mg, 2.018 mmol) and t-BuOK (377.2 mg, 3.361 mmol). Then DMF (6 mL) was added to dissolve the solids. The mixture was reacted in an oil bath at 100° C. overnight. TLC showed the reaction was completed. To the mixture was added water (25 mL) and to the resulting mixture was extracted with EA (50 mL×2). The organic phases were washed with saturated saline (30 mL), dried over anhydrous sodium sulfate and filtered. The filtrate was concentrated in vacuo, and the residue was purified by silica gel column chromatography (pure PE-PE:EA(v:v=10:1)) to give a white crystalline solid (yield: 70%) as the target product. LC-MS (ES-API): m/z=338.00[M-56+H]⁺. ¹H NMR (400 MHz, CDCl₃) δ 7.42 (dd, J=10.4, 1.9 Hz, 1H), 7.35 (d, J=8.6 Hz, 1H), 6.43 (t, J=8.5 Hz, 1H), 4.87 (ddd, J=10.4, 6.3, 4.2 Hz, 1H), 4.28 (dd, J=9.8, 6.5 Hz, 2H), 4.04 (dd, J=9.9, 4.0 Hz, 2H), 1.44 (s, 9H).

Step 2: tert-butyl 3-(2-fluoro-4-(2-trimethylsilyl-ethynyl) phenoxy)azetidine-1-carboxylate To a 25 mL two-necked flask were added tert-butyl 3-(3-fluoro-4-iodo-phenoxy)azetidine-1-carboxylate (450 mg, 1.144 mmol), CuI (22 mg, 0.116 mmol) and PdCl₂(PPh₃)₂ (41 mg, 0.058 mmol). The reaction mixture was degassed and refilled with nitrogen. Then anhydrous THF (4.5 mL) and TEA (4.5 mL, 32 mmol) were added. After the dissolution, ethynyl (trimethyl)silane (0.323 mL, 2.29 mmol) was added. The mixture was stirred for reaction at room temperature overnight. TLC showed the reaction was completed. The resulting mixture was filtered by suction through a celite pad. The filter cake was washed with EA (60 mL) several times, and the filtrate was washed with saturated brine (20 mL), dried over anhydrous sodium sulfate and filtered. The filtrate was concentrated in vacuo, and the residue was purified by silica gel column chromatography (eluent PE:EA=100: 1-10:1) to give a brown solid 0.398 g (yield: 78.1%) as the target product. LC-MS (ES-API): m/z=308.10[M-56+H]⁺. ¹H NMR (400 MHz, CDCl₃) δ 7.20 (dd, J=11.7, 1.8 Hz, 1H), 7.15 (d, J=8.4 Hz, 1H), 6.57 (t, J=8.4 Hz, 1H), 4.95-4.86 (m, 1H), 4.29 (dd, 7=9.6, 6.8 Hz, 2H), 4.05 (dd, 7=9.9, 3.6 Hz, 2H), 1.44 (s, 9H), 0.23 (s, 9H).

Step 3: tert-butyl 3-(4-ethynyl-2-fluorophenoxy) azetidine-1-carboxylate

To a 10 mL single-necked flask were sequentially added tert-butyl 3-(3-fluoro-4-(2-trimethylsilylethynyl) phenoxy) azetidine-1-carboxylate (400 mg, 1.100 mmol), K₂CO₃ (305 mg, 2.207 mmol) and MeOH (3 mL). The mixture was stirred to react at room temperature overnight. After TLC showed the reaction was completed, the mixture was quenched by adding 10 mL of saturated ammonium chloride dropwise and then concentrated in vacuo to remove part of methanol. The resulting mixture was extracted with EA (30 mL×2). The organic phases were washed with saturated saline (15 mL), dried over anhydrous sodium sulfate and filtered. The filtrate was concentrated in vacuo, and then purified by silica gel column chromatography (eluent PE:EA=100:1-5:1) to give a white solid 0.364 g (the yield was 91.1%), which was the target product. LC-MS (ES-API): m/z=236.10[M-56+H]⁺. ¹H NMR (400 MHz, CDCl₃) δ 7.23 (dd, J=11.5, 1.8 Hz, 1H), 7.21-7.16 (m, 1H), 6.60 (t, J=8.4 Hz, 1H), 4.95-4.88 (m, 1H), 4.29 (dd, J=10.0, 6.7 Hz, 2H), 4.06 (dd, J=10.1, 4.0 Hz, 2H), 3.03 (s, 1H), 1.45 (s, 9H).

Step 4: 3-(4-ethynyl-2-fluoro-phenoxy)azetidine hydrochloride

To a 10 mL single-necked flask were added tert-butyl 3-(4-ethynyl-3-fluorophenoxy) azetidine-1-carboxylate (254 mg, 0.872 mmol) and a solution of hydrogen chloride in ethyl acetate (6 mL, 24 mmol, 4 mol/L). The mixture was reacted with stirring at room temperature for 1 h. TLC showed the reaction was completed. The reaction solution was directly concentrated in vacuo, dried in an oven at 60° C. to obtain a theoretical amount of yellow white solid. LC-MS (ES-API): m/z=192.15 [M+H]⁺.

Step 5: 4-(6-(3-(4-ethynyl-2-fluorophenoxy) azetidin-1-yl)pyridin-3-yl)-6-(1-methyl-1H-pyrazol-4-yl) pyrazolo[1,5-a]pyridine-3-carbonitrile To a 10 mL single-necked flask were sequentially added 4-(6-fluoro-3-pyridyl)-6-(2-hydroxy-2-methyl-propoxy) pyrazolo[1,5-a]pyridine-3-carbonitrile (see synthesis of intermediate 1, 30 mg, 0.092 mmol) and 3-(4-ethynyl-2-fluoro-phenoxy) azetidine hydrochloride (63 mg, 0.277 mmol), which were dissolved by adding DMSO (1 mL). Then DIPEA (0.1 mL, 0.6 mmol) and DMAP (1.2 mg, 0.01 mmol) were added. The mixture was reacted at 90° C. in an oil bath overnight. TLC showed the reaction was completed. The reaction solution was cooled to room temperature, then to the resulting mixture was added water (15 mL) and the resulting mixture was extracted with EA (30 mL×3). The organic phases were washed with saturated saline (30 mL), dried over anhydrous sodium sulfate and filtered. The filtrate was concentrated in vacuo, and then purified by silica gel column chromatography (eluent pure DCM-DCM:MeOH (v:v=10:1)) to give a white solid 0.008 g (yield: 20%) as the target product. LC-MS (ES-API): m/z=498.20[M+H]+. 1H NMR (400 MHz, CDCl3) δ 8.64 (s, 1H), 8.35 (s, 1H), 8.25 (s, 1H), 7.79 (s, 1H), 7.74 (d, J=8.4 Hz, 1H), 7.69 (s, 1H), 7.39 (s, 1H), 7.23 (d, J=7.7 Hz, 2H), 6.71 (t, J=8.5 Hz, 1H), 6.49 (d, J=8.6 Hz, 1H), 5.21-5.14 (m, 1H), 4.54 (dd, J=8.6, 6.7 Hz, 2H), 4.25 (dd, J=9.2, 3.9 Hz, 2H), 3.99 (s, 3H), 3.04 (s, 1H). HPLC: 85.60%.

Example 294: 6-(1-(difluoromethyl)-1H-pyrazol-4-yl)-4-(6-(3-(4-ethynyl-3-fluorophenoxy) azetidine-1-yl) pyridin-3-yl) pyrazolo[1,5-a]pyridine-3-carbonitrile (294)

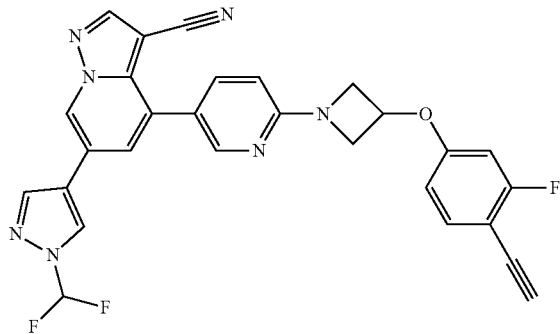

To a single-necked flask were sequentially added 6-[1-(difluoromethyl) pyrazol-4-yl]-4-(6-fluoro-3-pyridyl) pyrazolo[1,5-a]pyridine-3-carbonitrile (see synthesis of intermediate 6, 30 mg, 0.085 mmol) and 3-(4-ethynyl-3-fluorophenoxy) azetidine hydrochloride (see the synthesis of step 4 in Example 292, 58 mg, 0.255 mmol), which were dissolved by adding DMSO (1 mL). Then K2CO3 (26.5 mg, 0.192 mmol) and DMAP (1.2 mg, 0.01 mmol) were added. The mixture was reacted at 90° C. in an oil bath overnight. The reaction mixture was cooled to room temperature, added with water (15 mL), then extracted with EA (30 mL×2). The combined organic phases were washed with saturated saline (30 mL), dried over anhydrous sodium sulfate and filtered. The filtrate was concentrated in vacuo and the residue was purified by silica gel column chromatography (eluent: pure DCM-DCM:MeOH (v:v=10:1)) to give a white solid 0.015 g (yield: 33%) as the target product. LC-MS (ES-API): m/z=526.10[M+H]+. 1H NMR (400 MHz, DMSO-d6) δ 9.43 (s, 1H), 9.01 (s, 1H), 8.69 (s, 1H), 8.53 (s, 1H), 8.39 (d, J=1.8 Hz, 1H), 7.93 (s, 1H), 7.90-7.82 (m, 2H), 7.51 (t, J=8.5 Hz, 1H), 6.95 (dd, J=11.4, 2.1 Hz, 1H), 6.81 (dd, J=8.5, 2.0 Hz, 1H), 6.62 (d, J=8.6 Hz, 1H), 5.34-5.24 (m, 1H), 4.53 (dd, J=9.2, 6.4 Hz, 2H), 4.36 (s, 1H), 3.99 (dd, 7=9.5, 3.2 Hz, 2H). HPLC: 88.58%.

Example 295: 4-(6-(3-((2-ethynylpyridin-4-yl)oxy) azetidin-1-yl)pyridin-3-yl)-6-(1-methyl-1H-pyrazol-4-yl) pyrazolo[1,5-a]pyridine-3-carbonitrile (295)

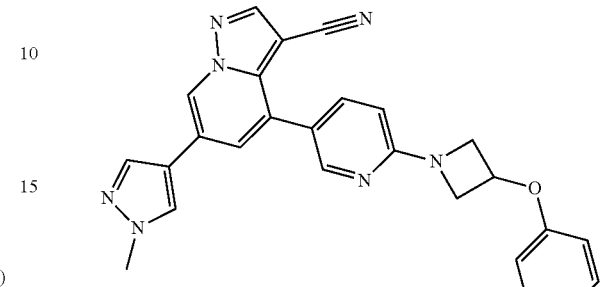

Step 1: tert-butyl 3-((2-bromo-4-pyridyl)oxy) azetidine-1-carboxylate ' '

To a 25 mL single-necked flask were added 2-bromopyridin-4-ol (1 g, 5.74 mmol), tert-butyl 3-methylsulfonyloxyazetidin-1-carboxylate (1.74 g, 6.92 mmol), tert-Butyl potassium (815 mg, 6.90 mmol) and DMF (10 mL). The mixture was reacted in an oil bath at 100° C. overnight. The reaction solution was cooled to room temperature, added with water (50 mL) and extracted with EA (150 mL×2). The combined organic phases were washed with water (50 mL×4) and saturated saline (50 mL×2), dried over anhydrous sodium sulfate and filtered. The filtrate was concentrated in vacuo, and then purified by silica gel column chromatography (eluent PE:EA=4:1) to give colorless liquid 490 mg as the target product.

Step 2: 4-(azetidin-3-yloxy)-2-bromopyridine hydrochloride

To a single-necked flask were sequentially added tert-butyl 3-((2-bromo-4-pyridyl)oxy) azetidine-1-carboxylate (140 mg, 0.425 mmol) and a solution of hydrochloric acid in EA (4 mL, 16 mmol, 4 mol/L). The mixture was stirred at room temperature for 1 h. The reaction mixture was directly filtered to give a white solid 113 mg as the target product (the yield was 99.98%). LC-MS: m/z=228.9[M+H]+, 231.0[M+2H]+. 1H NMR (400 MHz, DMSO-d6) δ 9.54 (s, 1H), 9.45 (s, 1H), 8.24 (d, J=5.7 Hz, 1H), 7.21 (d, J=2.2 Hz, 1H), 7.02 (dd, J=5.7, 2.3 Hz, 1H), 5.28-5.19 (m, 1H), 4.53-4.40 (m, 2H), 4.00-3.94 (m, 2H).

Step 3: 4-(6-(3-((2-bromopyridin-4-yl)oxy) azetidin-1-yl) pyridin-3-yl)-6-(1-methyl-1H-pyrazol-4-yl) pyrazolo[1,5-a]pyridine-3-carbonitrile To a flask were added 4-(6-fluoro-3-pyridyl)-6-(1-methylpyrazol-4-yl)pyrazolo[1,5-a]pyridine-3-carbonitrile (see synthesis of intermediate 1, 51 mg, 0.16 mmol), 4-(azetidin-3-yloxy)-2-bromopyridine hydrochloride (65 mg, 0.24 mmol), potassium carbonate (45 mg, 0.33 mmol), DMAP (2 mg, 0.016 mmol) and DMSO (2 mL). The mixture was reacted with stirring at 90° C. overnight. To the mixture were added water (20 mL) and EA (200 mL). The organic phases were separated, washed with saturated brine (30 mL×3) and concentrated in vacuo, and the residue was purified by silica gel column chromatography (DCM:MeOH=0-100:3) to give a yellow-white solid 44 mg (the yield was 52.07%) and recycled raw materials 21.6 mg. MS (ESI, pos.ion) m/z=582.1 [M+H]$^+$. $^1$H NMR (400 MHz, DMSO-d$_6$) δ 9.24 (s, 1H), 8.65 (s, 1H), 8.39 (s, 1H), 8.37 (d, J=1.5 Hz, 1H), 8.25 (d, J=5.7 Hz, 1H), 8.12 (s, 1H), 7.85 (dd, 7=8.5, 2.1 Hz, 1H), 7.78 (s, 1H), 7.23 (d, J=1.8 Hz, 1H), 7.05 (dd, 7=5.7, 1.9 Hz, 1H), 6.62 (d, J=8.6 Hz, 1H), 5.41-5.34 (m, 1H), 4.54 (dd, J=9.5, 5.9 Hz, 2H), 4.02 (dd, J=9.4, 3.1 Hz, 2H), 3.88 (s, 3H).

Step 4: 6-(1-methyl-1H-pyrazol-4-yl)-4-(6-(3-((2-(2-(2-(trimethylsilylethynyl)pyridin-4-yl)oxy)azetidin-1-yl)pyridin-3-yl)pyrazolo[1,5-a]pyridine-3-carbonitrile To a 10 mL double-necked flask were added 4-(6-(3-((2-bromopyridin-4-yl)oxy) azetidin-1-yl) pyridin-3-yl)-6-(1-methyl-1H-pyrazol-4-yl) pyrazolo[1,5-a]pyridine-3-carbonitrile (44 mg, 0.083 mmol), cuprous iodide (2 mg, 0.010 mmol,), triphenylphosphine (3 mg, 0.011 mmol), Pd(PPh$_3$)$_2$Cl$_2$ (12 mg, 0.017 mmol), DMF (1 mL), triethylamine (0.06 mL, 0.4 mmol) and ethynyl (trimethyl) silane (0.1 mL, 0.7 mmol) under nitrogen. The mixture was stirred for reaction at 80° C. for 6 h. Post-treatment: the resulting mixture was filtered through a celite pad. The filter cake was washed with EA, the filtrate was added with 20 mL of water, and extracted with EA (50 mL×3). The combined organic phases were washed with saturated saline (30 mL×6), dried over anhydrous sodium sulfate and filtered. The filtrate was concentrated in vacuo, and the residue was purified by silica gel column chromatography (eluent DCM:MeOH=0-100:5) to give a light yellow solid 15.8 mg as the target product. MS(ESI, pos.ion) m/z=545.10 [M+H]$^+$.

Step 5: 4-(6-(3-((2-ethynylpyridin-4-yl)oxy)azetidin-1-yl)pyridin-3-yl)-6-(1-methyl-1H-pyrazol-4-yl) pyrazolo[1,5-a]pyridine-3-carbonitrile To a single-necked flask were sequentially added 6-(1-methyl-1H-pyrazol-4-yl)-4-(6-(3-((2-(2-(2-(trimethylsilyl-ethynyl)pyridin-4-yl)oxy)azetidin-1-yl)pyridin-3-yl)pyrazole[1,5-a]pyridine-3-carbonitrile (15 mg, 0.027 mmol), potassium carbonate (10 mg, 0.072 mmol) and methanol (2 mL). The mixture was stirred for reaction at room temperature for 5 h. The reaction mixture was directly concentrated in vacuo, and the residue was purified by silica gel column chromatography (DCM/MeOH=0-100/4) to give a white solid 12.3 mg as the target product (the yield was 82%). $^1$H NMR (400 MHz, CDCl$_3$) δ 8.64 (s, 1H), 8.44 (d, J=5.6 Hz, 1H), 8.35 (s, 1H), 8.26 (s, 1H), 7.79 (s, 1H), 7.76 (d, J=8.5 Hz, 1H), 7.69 (s, 1H), 7.39 (s, 1H), 6.93 (d, 7=1.5 Hz, 1H), 6.74 (d, J=3.9 Hz, 1H), 6.50 (d, J=8.2 Hz, 1H), 5.20-5.15 (m, 1H), 4.62-4.52 (m, 2H), 4.24-4.16 (m, 2H), 3.99 (s, 3H), 3.16 (s, 1H). HPLC: 96.75%.

Example 296: 6-(1-(difluoromethyl)-1H-pyrazol-4-yl)-4-(6-(3-(4-ethynyl-2-fluorophenoxy) azetidine-1-yl) pyridin-3-yl) pyrazolo[1,5-a]pyridine-3-carbonitrile

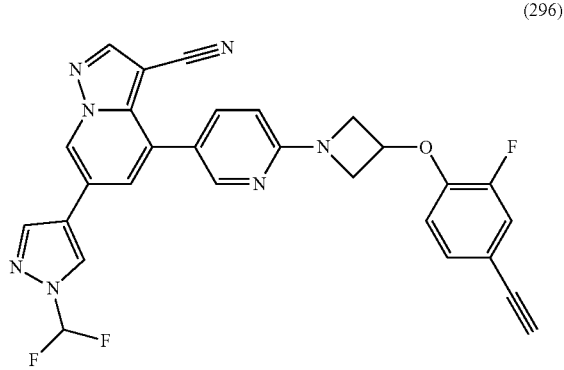 [SMILES: C#Cc1ccc(OC2CN(c3ccc(-c4cc(-c5cnn(C(F)F)c5)cn5ncc(C#N)c45)cn3)C2)c(F)c1]

(296)

Step 1: 3-(2-fluoro-4-iodo-phenoxy) azetidine hydrochloride

To a 10 mL single-necked flask were added tert-butyl 3-(2-fluoro-4-iodo-phenoxy) azetidine-1-carboxylate (see the synthesis of Step 1 in Example 293, 434 mg, 1.104 mmol) and a solution of hydrogen chloride in ethyl acetate (6 mL, 24 mmol, 4 mol/L). The mixture was reacted with stirring at room temperature for 1.5 h. TLC showed the reaction was completed. The reaction solution was directly concentrated in vacuo to obtain a theoretical amount of white solid. LC-MS (ES-API): m/z=294.00[M+H]$^+$.

Step 2: 6-(1-(difluoromethyl) pyrazol-4-yl)-4-(6-(3-(2-fluoro-4-iodo-phenoxy) azetidin-1-yl)-3-pyridyl) pyrazolo[1,5-a]pyridine-3-carbonitrile To a 5 mL single-necked flask were sequentially added 6-[1-(difluoromethyl) pyrazol-4-yl]-4-(6-fluoro-3-pyridyl) pyrazolo[1,5-a]pyridine-3-carbonitrile (see synthesis of intermediate 6, 70 mg, 0.198 mmol) and 3-(2-fluoro-4-iodo-phenoxy) azetidine hydrochloride (98 mg, 0.297 mmol), which were dissolved by adding DMSO (2 mL). Then K$_2$CO$_3$ (61.5 mg, 0.445 mmol) and DMAP (2.5 mg, 0.020 mmol) were added. The mixture was reacted at 90° C. in an oil bath overnight. TLC showed the reaction was completed. The reaction solution was cooled to room temperature, then to the resulting mixture was added water (15 mL) and the resulting mixture was extracted with EA (15 mL×2). The organic phases were washed with saturated saline (30 mL), dried over anhydrous sodium sulfate and filtered. The filtrate was concentrated in vacuo. The residue was purified by silica gel column chromatography (eluent pure DCM-DCM:MeOH=20:1) to give a white solid 0.052 g (yield: 42%) as the target product. LC-MS (ES-API): m/z=628.00[M-56+H]$^+$. $^1$H NMR (400 MHz, DMSO-d$_6$) δ 9.42 (s, 1H), 9.01 (s, 1H), 8.69 (s, 1H), 8.53 (s, 1H), 8.39 (s, 1H), 7.93 (s, 1H), 7.86 (d, J=11.8 Hz, 2H), 7.67 (d, J=10.1 Hz, 1H), 7.50 (d, J=8.3 Hz, 1H), 6.88 (t, J=8.6 Hz, 1H), 6.62 (d, J=8.5 Hz, 1H), 5.32-5.23 (m, 1H), 4.55-4.48 (m, 2H), 4.06-4.00 (m, 2H).

Step 3: 6-(1-(difluoromethyl)-1H-pyrazol-4-yl)-4-(6-(3-(2-fluoro-4-((trimethylsilyl) ethynyl) phenoxy))azetidin-1-yl)pyridin-3-yl)pyrazolo[1,5-a]pyridine-3-carbonitrile To a 25 mL two-necked flask were added 6-(1-(difluoromethyl) pyrazol-4-yl)-4-(6-(3-(2-fluoro-4-iodo-phenoxy) azetidin-1-yl)-3-pyridyl) pyrazolo[1,5-a]pyridine-3-carbonitrile (52 mg, 0.083 mmol), CuI (2 mg, 0.011 mmol) and Bis (triphenylphosphine) palladium (II) dichloride (3 mg, 0.004 mmol). The reaction mixture was degassed and refilled with nitrogen. Then anhydrous THF (2 mL) and TEA (2 mL, 14.3 mmol) were added. After the dissolution, ethynyl (trimethyl)silane (0.025 mL, 0.18 mmol) was added. The mixture was stirred for reaction at room temperature overnight. TLC showed the reaction was completed. The resulting mixture was filtered by suction through a celite pad. The filter cake was washed with EA (60 mL) several times, and the filtrate was washed with saturated brine (30 mL), dried over anhydrous sodium sulfate and filtered. The filtrate was concentrated in vacuo, and then purified by silica gel column chromatography (eluent DCM:MeOH=100:1-15:1) to give a yellow-white solid 0.042 g (yield: 84%) as the target product. LC-MS (ES-API): m/z=598.20[M+H]$^+$. $^1$H NMR (400 MHz, DMSO-d$_6$) δ 9.43 (s, 1H), 9.01 (s, 1H), 8.70 (s, 1H), 8.53 (s, 1H), 8.40 (d, J=2.0 Hz, 1H), 7.94 (s, 1H), 7.87 (dd, J=9.1, 2.9 Hz, 2H), 7.41 (dd, J=11.8, 1.8 Hz, 1H), 7.29 (d, J=8.3 Hz, 1H), 7.04 (t, J=8.7 Hz, 1H), 6.63 (d, J=8.7 Hz, 1H), 5.36-5.29 (m, 1H), 4.53 (dd, 7=9.3, 6.1 Hz, 2H), 4.04 (dd, 7=9.7, 3.5 Hz, 2H), 0.23 (s, 9H).

Step 4: 6-(1-(difluoromethyl)-1H-pyrazol-4-yl)-4-(6-(3-(4-ethynyl-2-fluorophenoxy)azetidin-1-yl)pyridin-3-yl)pyrazolo[1,5-a]pyridine-3-carbonitrile To a 10 mL single-necked flask were sequentially added 6-(1-(difluoromethyl)-1H-pyrazol-4-yl)-4-(6-(3-(2-fluoro-4-((trimethylsilyl)ethynyl)phenoxy)azetidine-1-yl)pyridin-3-yl) pyrazolo[1,5-a]pyridine-3-carbonitrile (41 mg, 0.069 mmol), potassium carbonate (19 mg, 0.137 mmol) and methanol (3 mL). The mixture was stirred at room temperature for 2 h. After TLC showed the reaction was completed, the mixture was quenched by adding 10 mL of saturated ammonium chloride dropwise and then concentrated in vacuo to remove part of methanol. The resulting turbid liquid was extracted with EA (30 mL×2). The combined organic phases were washed with saturated saline (15 mL), dried over anhydrous sodium sulfate and filtered. The filtrate was concentrated in vacuo, The residue was purified by silica gel column chromatography (eluent: pure DCM-DCM:MeOH (v:v=30:1)) to give a white solid 0.02 g (the yield was 60%), which was the target product. LC-MS (ES-API): m/z=526.10[M+H]$^+$. $^1$H NMR (400 MHz, CDCl$_3$) δ 8.71 (s, 1H), 8.35 (s, 1H), 8.29 (s, 1H), 8.14 (s, 1H), 7.97 (s, 1H), 7.74 (d, J=8.4 Hz, 1H), 7.40 (s, 1H), 7.26-7.08 (m, 3H), 6.69 (t, J=8.5 Hz, 1H), 6.48 (d, J=8.6 Hz, 1H), 5.20-5.13 (m, 1H), 4.58-4.50 (m, 2H), 4.36 (s, 1H), 4.28-4.22 (m, 2H). HPLC: 98.69%.

Example 297: 4-(6-(4-((3-ethynylphenyl)sulfonyl) piperazin-1-yl)pyridin-3-yl)-6-(1-methyl-1H-pyrazol-4-yl)pyrazolo[1,5-a]pyridine-3-carbonitrile

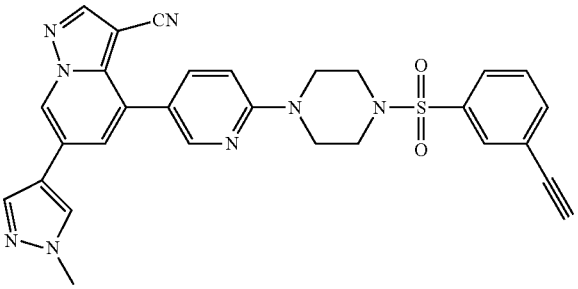

(297)

Step 1: 4-(6-(4-((3-bromophenyl) sulfonyl) piperazin-1-yl)pyridin-3-yl)-6-(1-methyl-1H-pyrazol-4-yl)pyrazolo[1,5-a]pyridine-3-carbonitrile To a 5 mL single-necked flask were added 6-(1-methyl-1H-pyrazol-4-yl)-4-(6-(piperazin-1-yl)pyridin-3-yl)pyrazolo[1,5-a]pyridine-3-carbonitrile dihydrochloride (see synthesis of intermediate 2, 72 mg, 0.15 mmol) and potassium carbonate (100 mg, 0.72 mmol), which were dissolved by adding DMF (1 mL). Then 3-bromobenzenesulfonyl chloride (0.1 mL, 0.75 mmol) was added. The mixture was reacted in an oil bath at 60° C. After the completion of reaction was monitored by TLC, to the reaction solution was added water (15 mL) and the resulting mixture was extracted with EA (20 mL×2). The organic phases were washed with water (5 mL×3) and saturated saline (5 mL×2), dried over anhydrous sodium sulfate and filtered. The filtrate was concentrated in vacuo and the residue was purified by silica gel column chromatography (eluent: PE:EA(v:v=1:1)-EA) to give a yellow solid 35 mg as the target product. LC-MS: m/z=604.08[M+H]$^+$.

Step 2: 6-(1-methyl-1H-pyrazol-4-yl)-4-(6-(4-(3-(((trimethylsilyl)ethynyl)phenyl)sulfonyl) piperazin-1-yl)pyridin-3-yl)pyrazolo[1,5-a]pyridine-3-carbonitrile To a 10 mL double-necked flask was added Pd(PPh$_3$)$_2$Cl$_2$ (12 mg, 0.017 mmol). The reaction flask was degassed and refilled with nitrogen. Then a solution of 4-(6-(4-((3-bromophenyl) sulfonyl)piperazin-1-yl)pyridin-3-yl)-6-(1-methyl-1H-pyrazol-4-yl)pyrazolo[1,5-a]pyridine-3-carbonitrile (35 mg, 0.057 mmol) in THF (2 mL) and triethylamine (0.1 mL, 0.7 mmol) were added. Cuprous iodide (6 mg, 0.03 mmol) and ethynyltrimethylsilane (0.1 mL, 0.7 mmol) were added with stirring. After the addition, the mixture was reacted at 40° C. in an oil bath. After the completion of reaction was monitored by TLC, the reaction mixture was directly concentrated in vacuo, and the residue was purified by silica gel column chromatography (eluent: PE:EA(v:v=1:1)-EA) to give a yellow solid 15 mg, which was the target product. LC-MS: m/z=621.21 [M+H]$^+$.

Step 3: 4-(6-(4-(((3-ethynylphenyl) sulfonyl)piperazin-1-yl)pyridin-3-yl)-6-(1-methyl-1H-pyrazol-4-yl)pyrazolo[1,5-a]pyridine-3-carbonitrile To a 5 mL single-necked flask was added 6-(1-methyl-1H-pyrazol-4-yl)-4-(6-(4-((3-((((trimethylsilyl)ethynyl)phenyl)sulfonyl)piperazin-1-yl)pyridin-3-yl)pyrazole[1,5-a]pyridine-3-carbonitrile (15 mg, 0.024 mmol), which was dissolved by adding methanol. Then potassium carbonate (12 mg, 0.087 mmol) was added. The mixture was reacted at room temperature. After the completion of reaction was monitored by TLC, the reaction mixture was directly concentrated in vacuo, and the residue was purified by silica gel column chromatography to give a white solid 4 mg, which was the target product. LC-MS: m/z=548.21 [M+H]$^+$. $^1$H NMR (400 MHz, CDCl$_3$) δ 8.65 (d, J=1.0 Hz, 1H), 8.38 (d, J=2.4 Hz, 1H), 8.28 (s, 1H), 7.87 (s, 1H), 7.83 (s, 1H), 7.79 (dd, J=8.8, 2.5 Hz, 1H), 7.76-7.73 (m, 1H), 7.70 (s, 1H), 7.49-7.47 (m, 2H), 7.14 (s, 1H), 6.79 (d, J=8.8 Hz, 1H), 4.01 (s, 3H), 3.83-3.74 (m, 4H), 3.22 (s, 1H), 3.20-3.12 (m, 4H).

Examples 6-30, Examples 32-48

Using suitable raw materials, the target compounds (6)-(30) of Examples 6-30 and the target compounds (32)-(48) of Examples 32-48 can be prepared by referring to the synthetic route of Example 5, Example 1 or synthesis scheme 3. The specific structures and characterization data are described in Table 1 below:

TABLE 1

Structures and characterization data of compounds (6)-(30) and compounds (32)-(48)

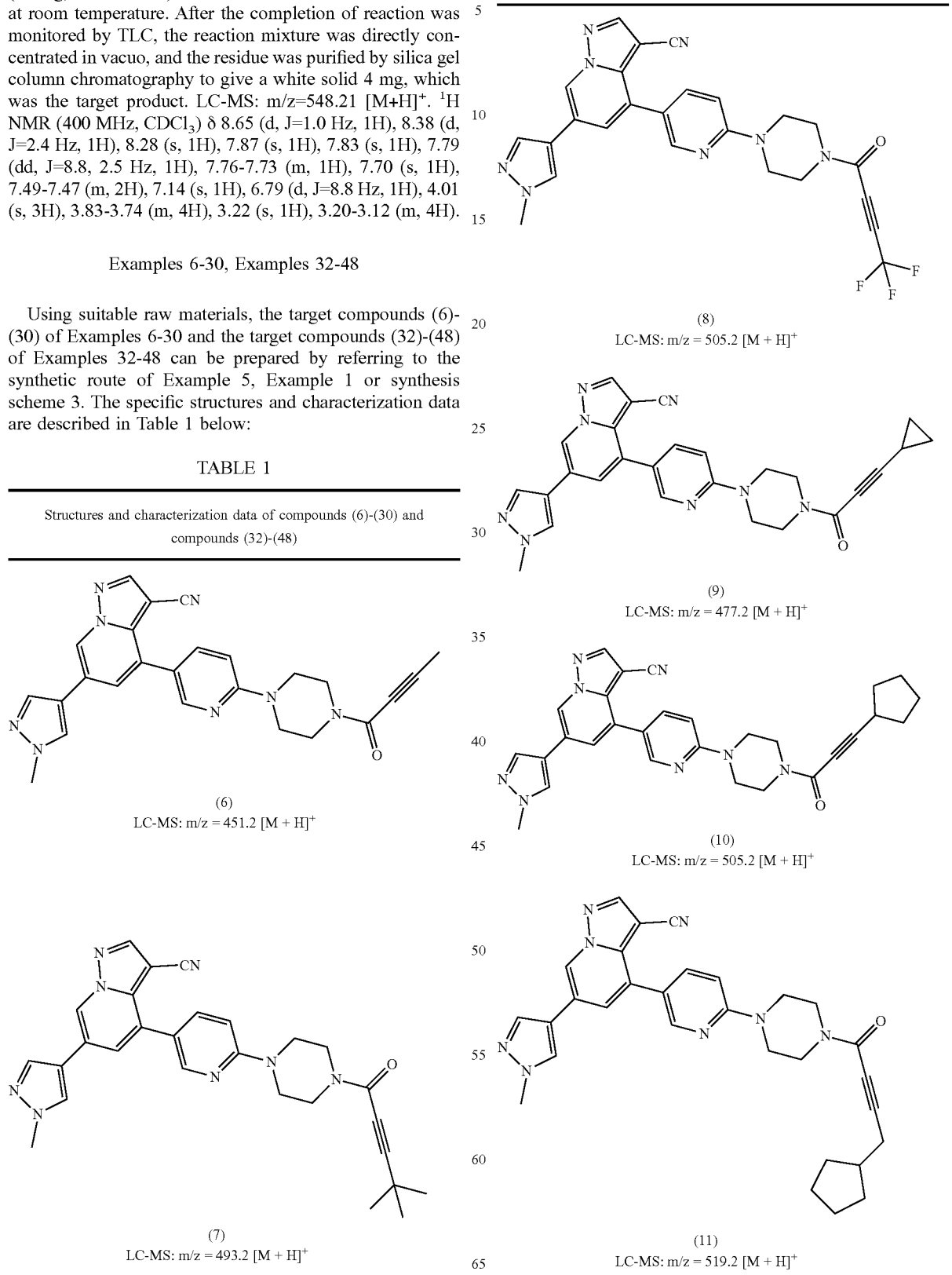

TABLE 1-continued
Structures and characterization data of compounds (6)-(30) and compounds (32)-(48)
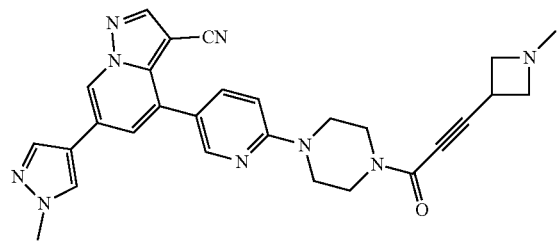
(12)
LC-MS: m/z = 506.2 [M + H]+
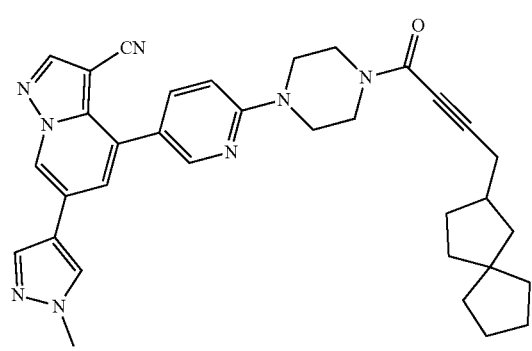
(13)
LC-MS: m/z = 573.3 [M + H]+
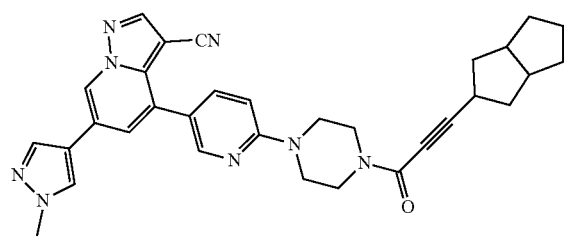
(14)
LC-MS: m/z = 545.2 [M + H]+
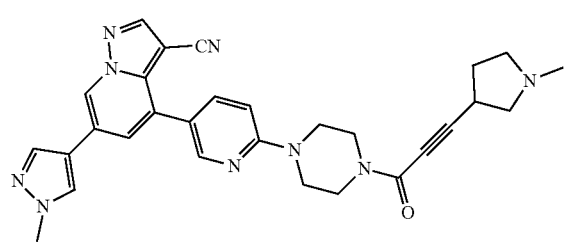
(15)
LC-MS: m/z = 520.2 [M + H]+
TABLE 1-continued
Structures and characterization data of compounds (6)-(30) and compounds (32)-(48)
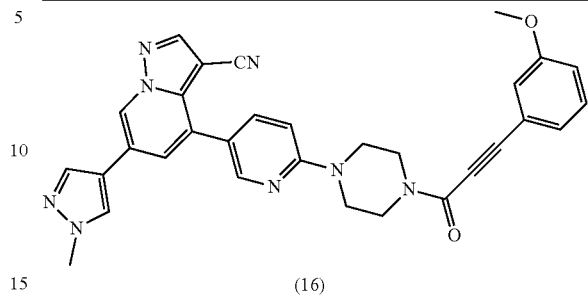
(16)
LC-MS: m/z = 543.2 [M + H]+
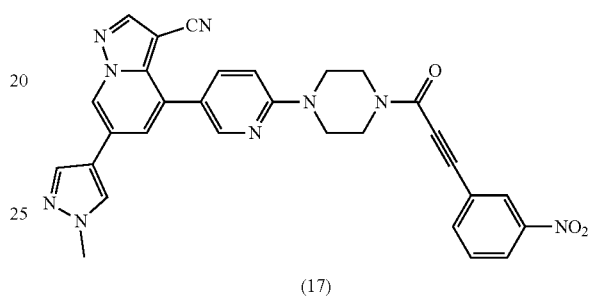
(17)
LC-MS: m/z = 558.2 [M + H]+
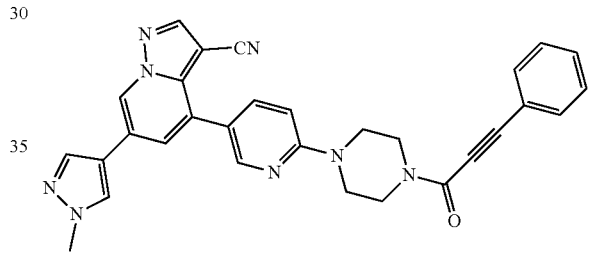
(18)
LC-MS: m/z = 513.21 [M + H]+
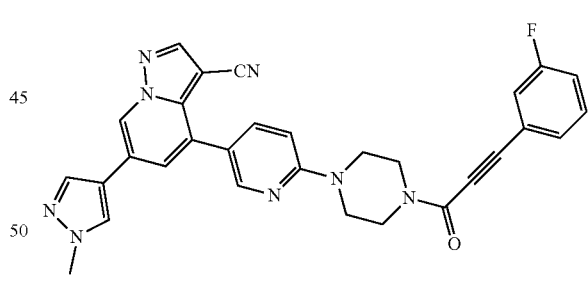
(19)
LC-MS: m/z = 531.2 [M + H]+
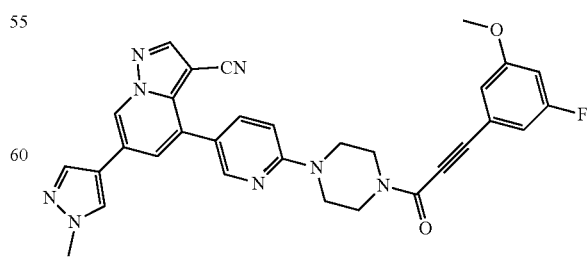
(20)
LC-MS: m/z = 561.2 [M + H]+

TABLE 1-continued
Structures and characterization data of compounds (6)-(30) and compounds (32)-(48)
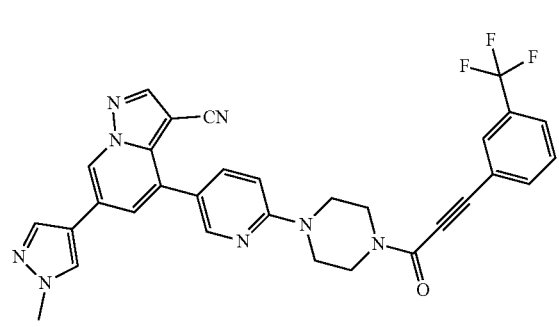
(21)
LC-MS: m/z = 581.2 [M + H]+
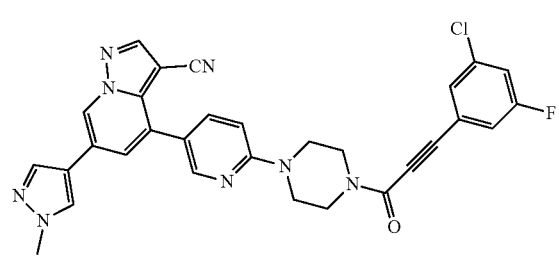
(22)
LC-MS: m/z = 551.1 [M + H]+
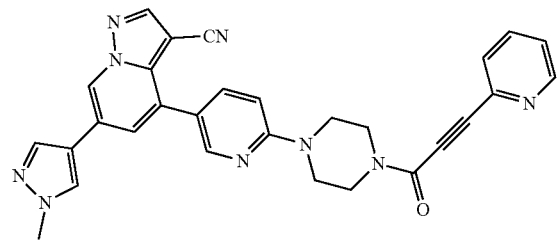
(23)
LC-MS: m/z = 514.2 [M + H]+
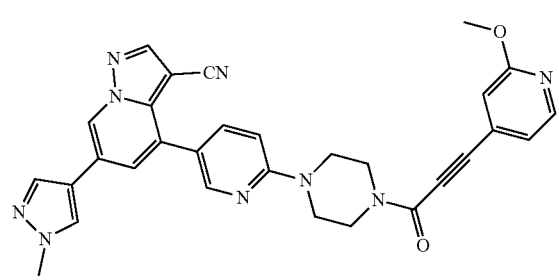
(24)
LC-MS: m/z = 544.2 [M + H]+
TABLE 1-continued
Structures and characterization data of compounds (6)-(30) and compounds (32)-(48)
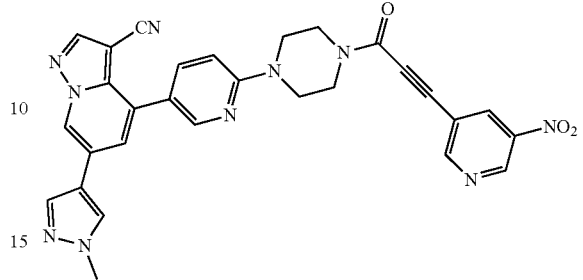
(25)
LC-MS: m/z = 559.2 [M + H]+
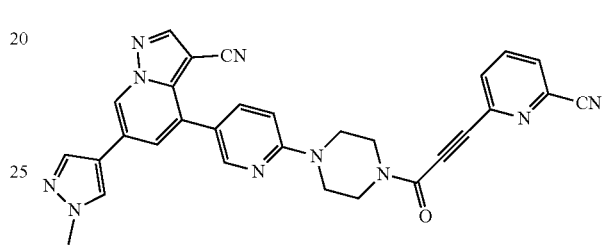
(26)
LC-MS: m/z = 539.2 [M + H]+
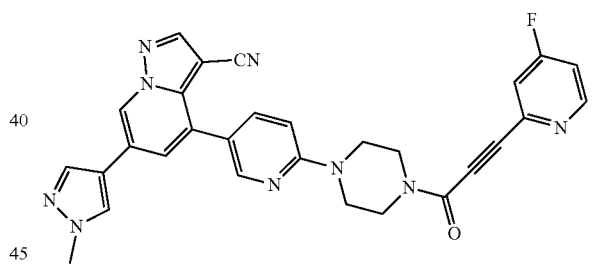
(27)
LC-MS: m/z = 532.2 [M + H]+
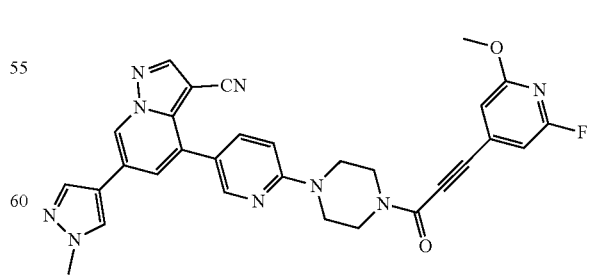
(28)
LC-MS: m/z = 562.2 [M + H]+

TABLE 1-continued
Structures and characterization data of compounds (6)-(30) and compounds (32)-(48)
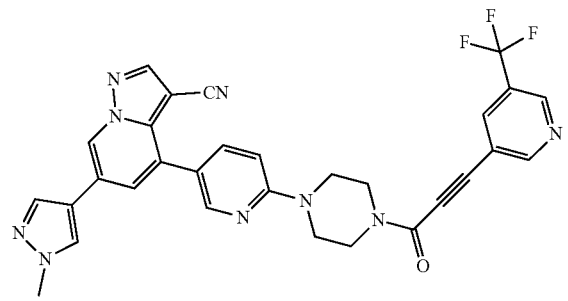
(29)
LC-MS: m/z = 582.2 [M + H]⁺
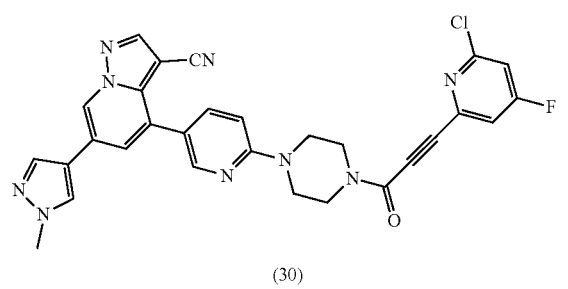
(30)
LC-MS: m/z = 567.2 [M + H]⁺
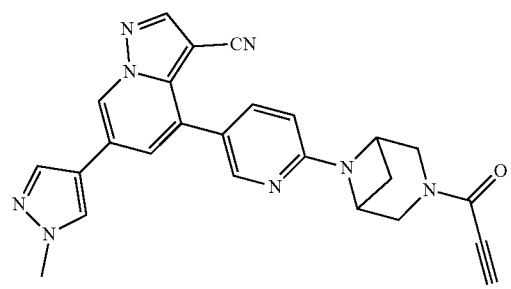
(32)
LC-MS: m/z = 449.2 [M + H]⁺
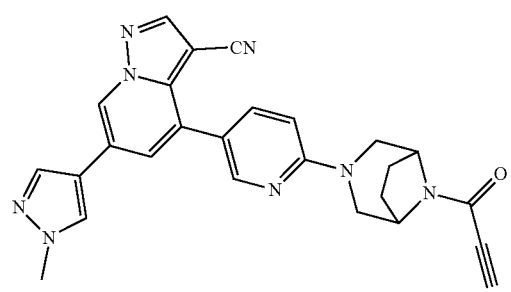
(33)
LC-MS: m/z = 463.2 [M + H]⁺
TABLE 1-continued
Structures and characterization data of compounds (6)-(30) and compounds (32)-(48)
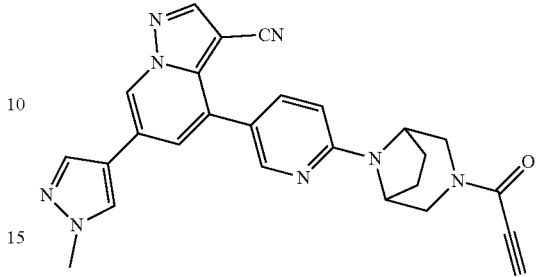
(34)
LC-MS: m/z = 463.2 [M + H]⁺
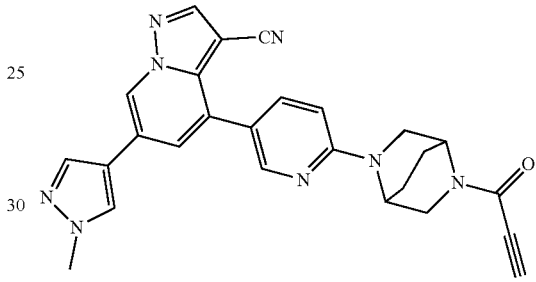
(35)
LC-MS: m/z = 463.3 [M + H]⁺
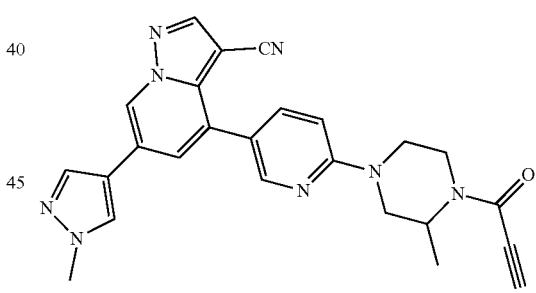
(36)
LC-MS: m/z = 451.2 [M + H]⁺
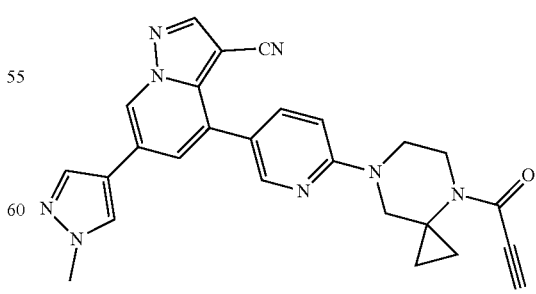
(37)
LC-MS: m/z = 463.2 [M + H]⁺

TABLE 1-continued
Structures and characterization data of compounds (6)-(30) and compounds (32)-(48)
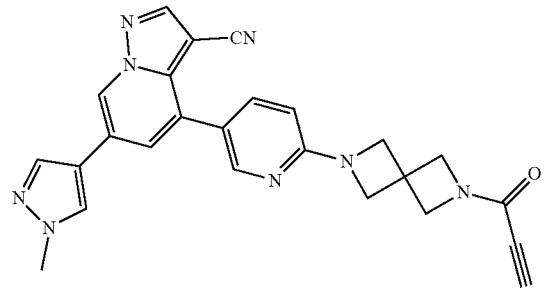
(38)
LC-MS: m/z = 449.2 [M + H]$^+$
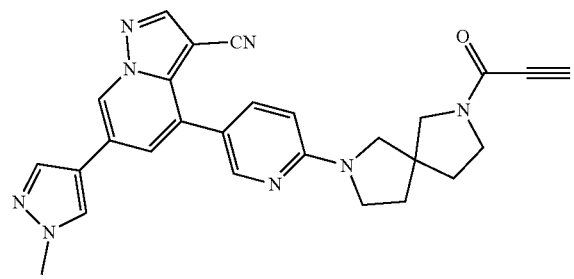
(39)
LC-MS: m/z = 477.2 [M + H]$^+$
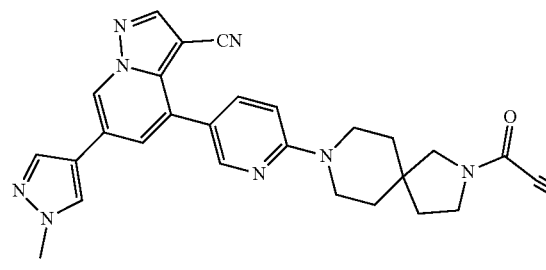
(40)
LC-MS: m/z = 491.2 [M + H]$^+$
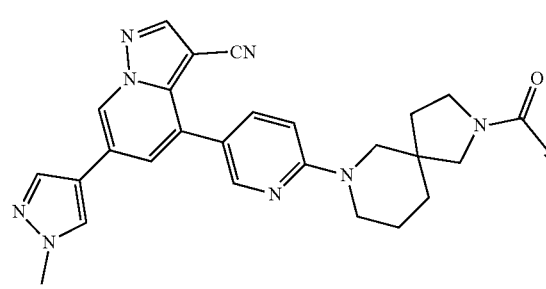
(41)
LC-MS: m/z = 491.2 [M + H]$^+$
TABLE 1-continued
Structures and characterization data of compounds (6)-(30) and compounds (32)-(48)
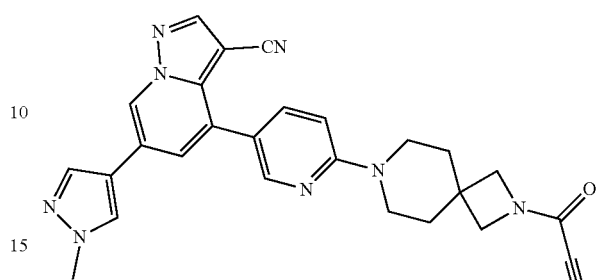
(42)
LC-MS: m/z = 477.2 [M + H]$^+$
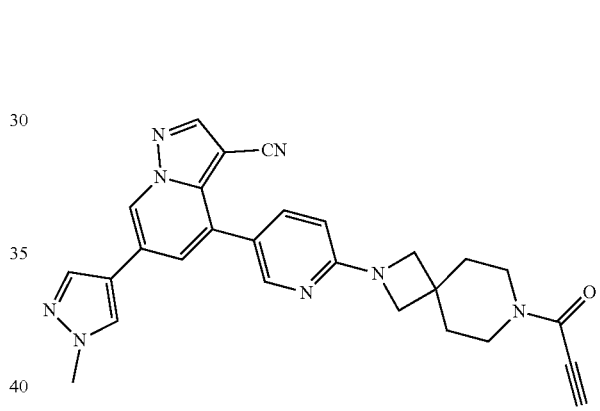
(43)
LC-MS: m/z = 477.2 [M + H]$^+$
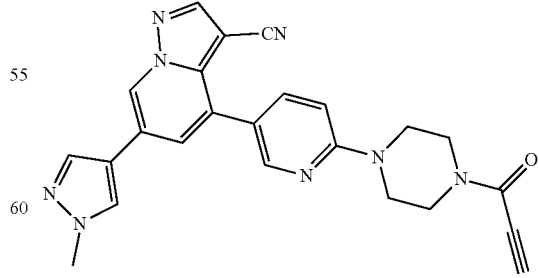
(44)
LC-MS: m/z = 436.2 [M + H]$^+$ TABLE 1-continued Structures and characterization data of compounds (6)-(30) and compounds (32)-(48)

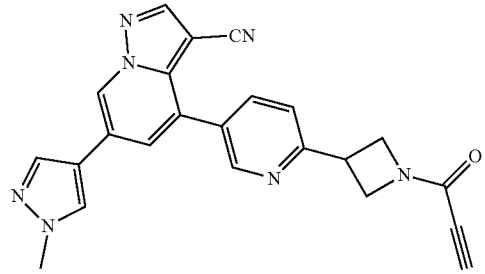

(45)
LC-MS: m/z = 408.2 [M + H]+

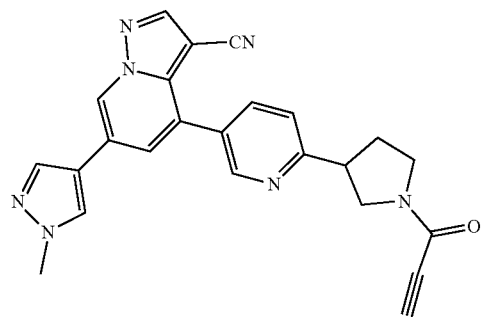

(46)
LC-MS: m/z = 422.2 [M + H]+

TABLE 1-continued

Structures and characterization data of compounds (6)-(30) and compounds (32)-(48)

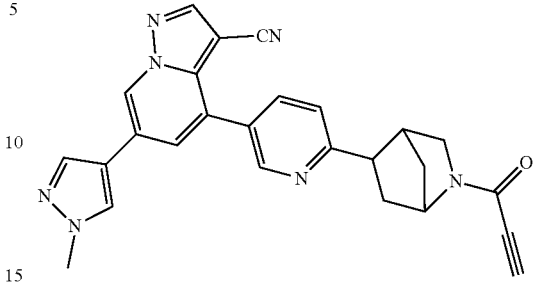

(47)
LC-MS: m/z = 448.2 [M + H]+

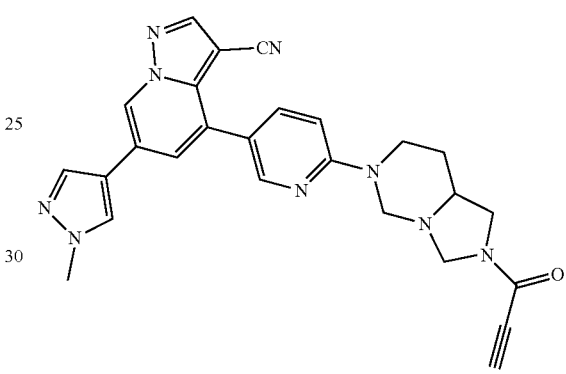

(48)
LC-MS: m/z = 478.2 [M + H]+

Examples 49-84

Using suitable raw materials, the target compounds (49)-(84) of Examples 49-84 can be prepared by referring to the synthetic route of Example 5, Example 1 or synthesis scheme 3. The specific structures and characterization data are described in Table 2 below:

TABLE 2

Structures and characterization data of compounds (49)-(84)

(49)

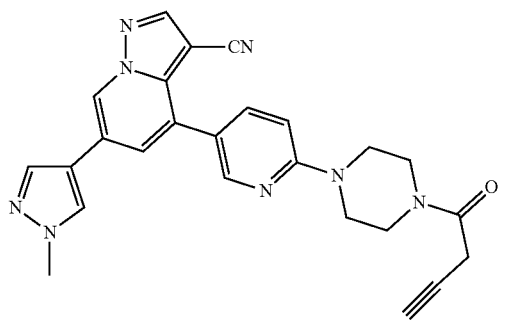

LC-MS: m/z = 451.2[M + H]+

TABLE 2-continued
Structures and characterization data of compounds (49)-(84)
(50)
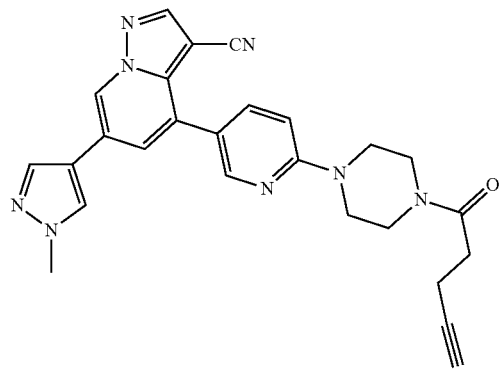
LC-MS: m/z = 465.2[M + H]+
(51)
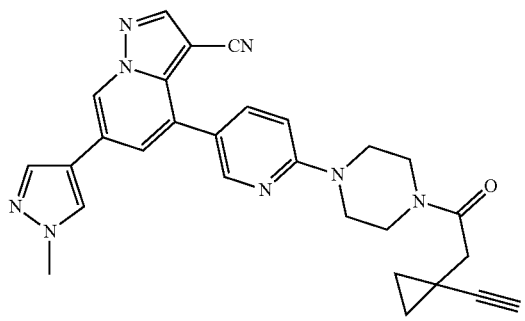
LC-MS: m/z = 491.2[M + H]+
(52)
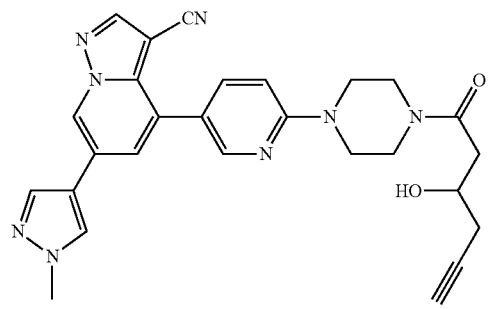
LC-MS: m/z = 495.2[M + H]+
(53)
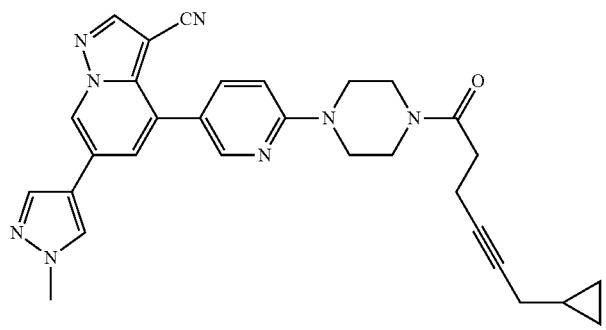
LC-MS: m/z = 519.3[M + H]+

TABLE 2-continued
Structures and characterization data of compounds (49)-(84)
(54)
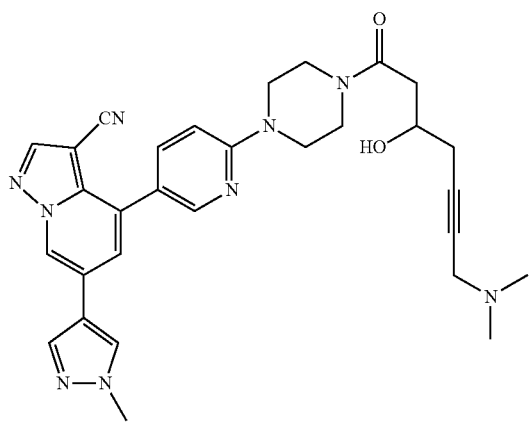
LC-MS: m/z = 552.3[M + H]⁺
(55)
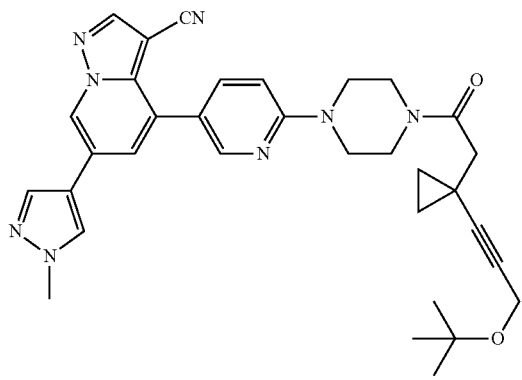
LC-MS: m/z = 577.3[M + H]⁺
(56)
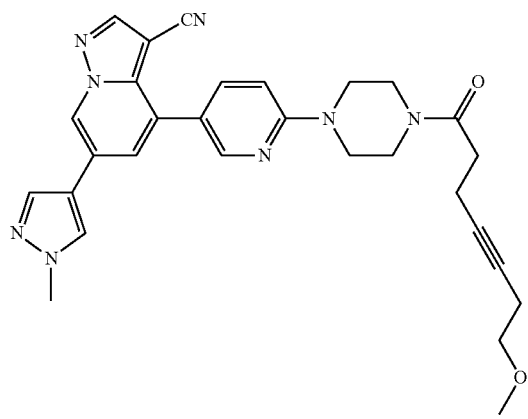
LC-MS: m/z = 523.2[M + H]⁺

TABLE 2-continued
Structures and characterization data of compounds (49)-(84)
(57)
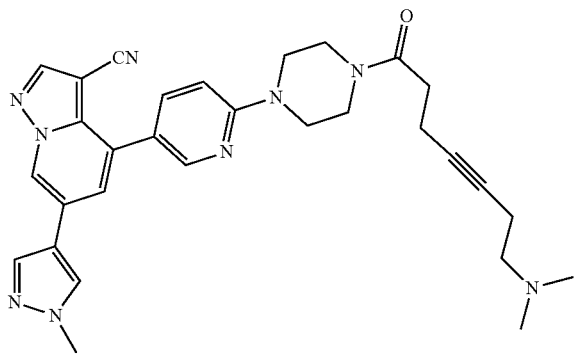
LC-MS: m/z = 536.3[M + H]+
(58)
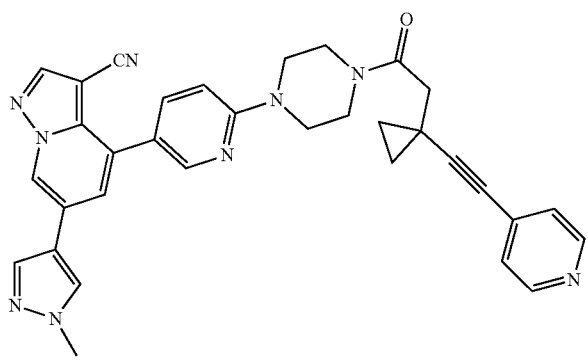
LC-MS: m/z = 568.2[M + H]+
(59)
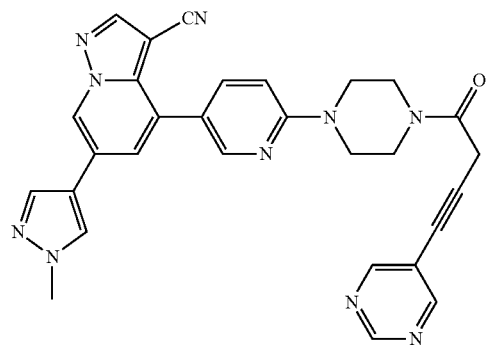
LC-MS: m/z = 529.2[M + H]+
(60)
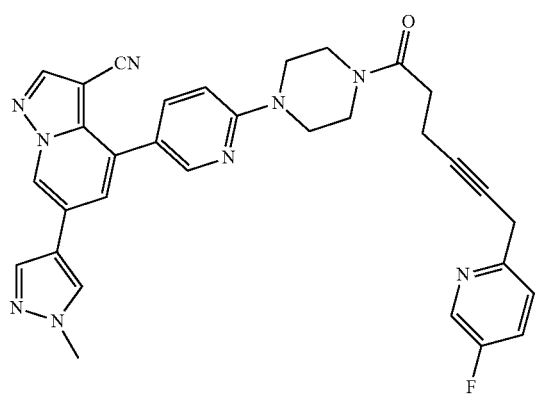
LC-MS: m/z = 574.2[M + H]+

TABLE 2-continued
Structures and characterization data of compounds (49)-(84)
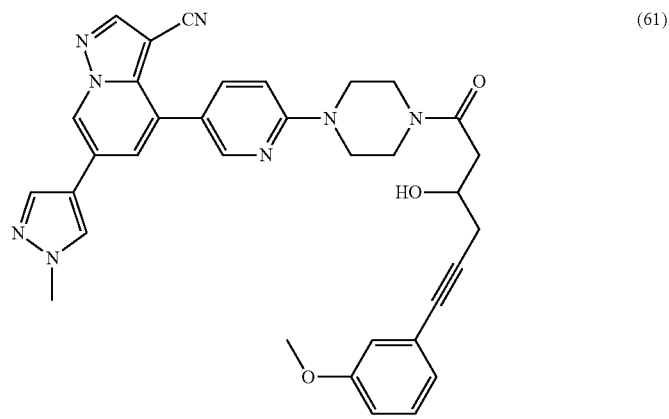
(61)
LC-MS: m/z = 601.2[M + H]+
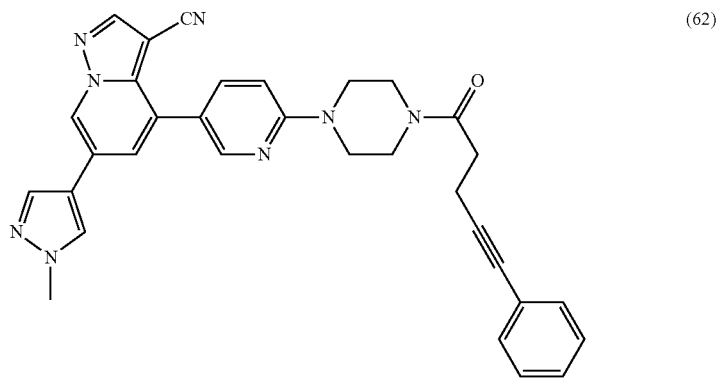
(62)
LC-MS: m/z = 541.2[M + H]+
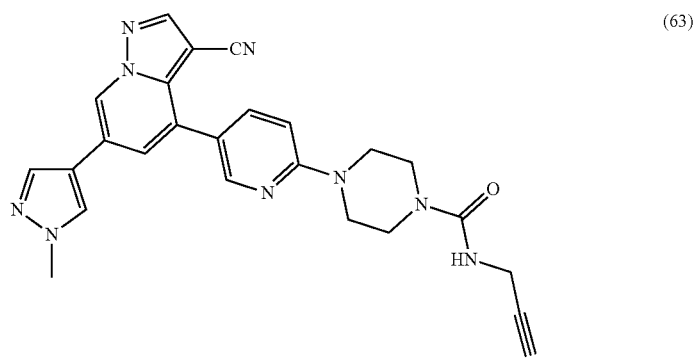
(63)
LC-MS: m/z = 466.2[M + H]+

TABLE 2-continued
Structures and characterization data of compounds (49)-(84)
(64)
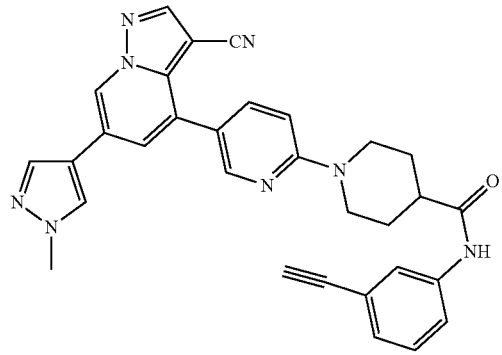
LC-MS: m/z = 527.2[M + H]$^+$
(65)
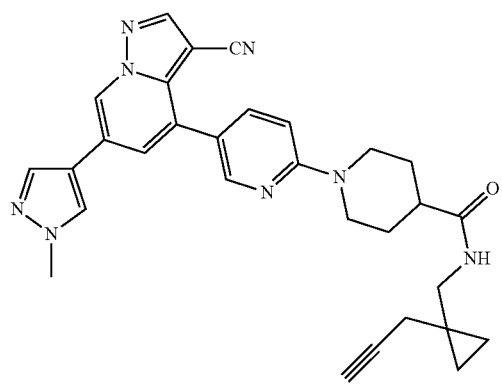
LC-MS: m/z = 519.2[M + H]$^+$
(66)
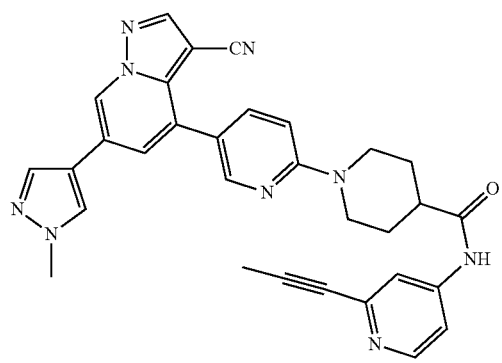
LC-MS: m/z = 542.2[M + H]$^+$
(67)
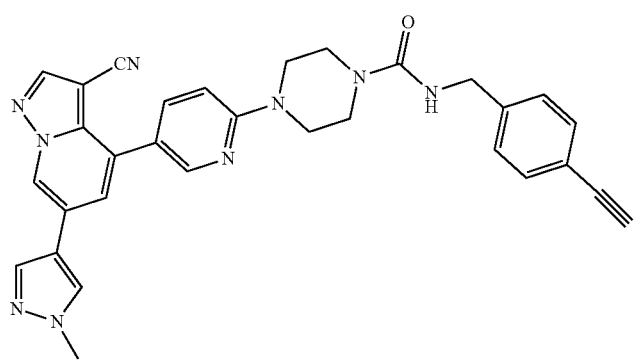
LC-MS: m/z = 542.2[M + H]$^+$ TABLE 2-continued
Structures and characterization data of compounds (49)-(84)
(68)
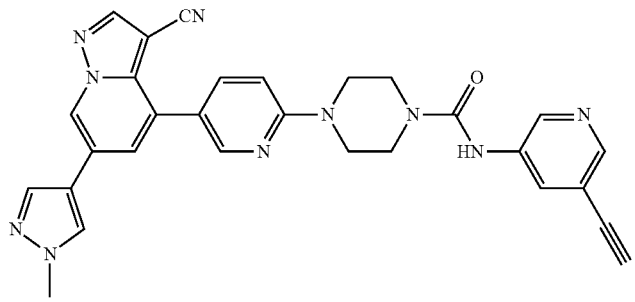
LC-MS: m/z = 529.2[M + H]⁺
(69)
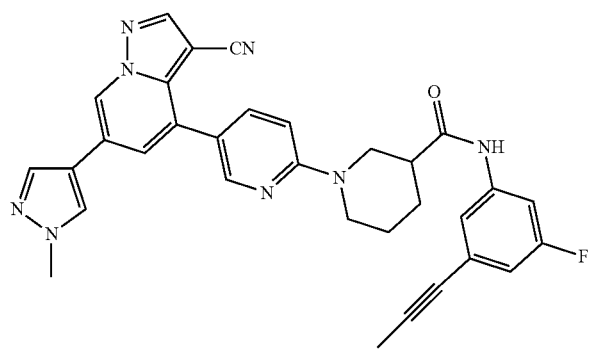
LC-MS: m/z = 559.23[M + H]⁺
(70)
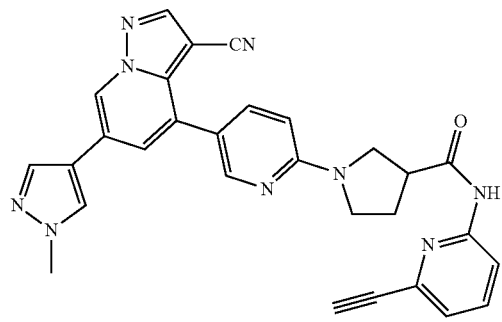
LC-MS: m/z = 514.2[M + H]⁺
(71)
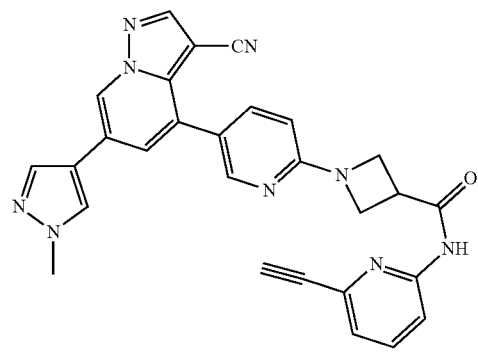
LC-MS: m/z = 500.19[M + H]⁺

TABLE 2-continued
Structures and characterization data of compounds (49)-(84)
(72)
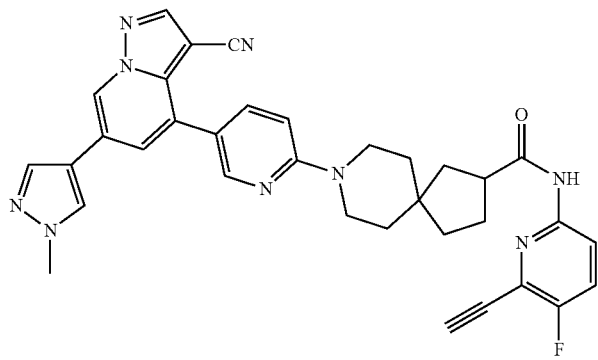
LC-MS: m/z = 600.2[M + H]$^+$
(73)
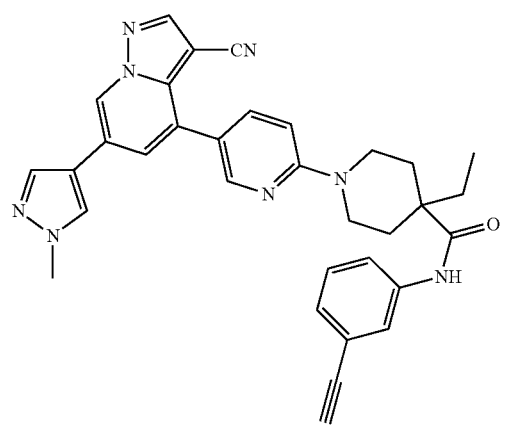
LC-MS: m/z = 555.2[M + H]$^+$
(74)
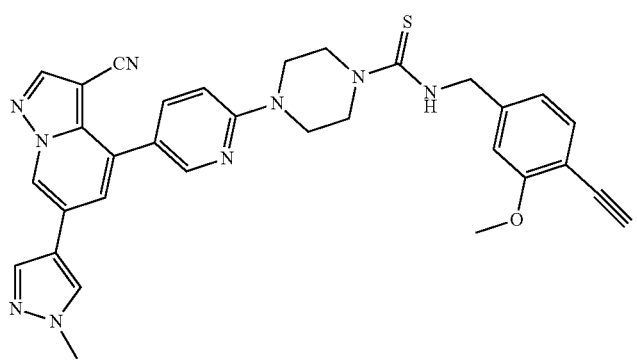
LC-MS: m/z = 588.2[M + H]$^+$
(75)
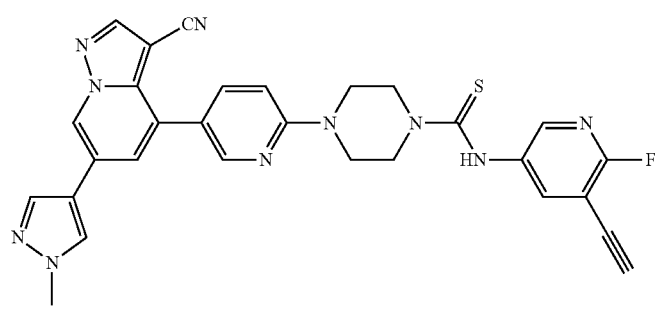
LC-MS: m/z = 563.2[M + H]$^+$ TABLE 2-continued
Structures and characterization data of compounds (49)-(84)
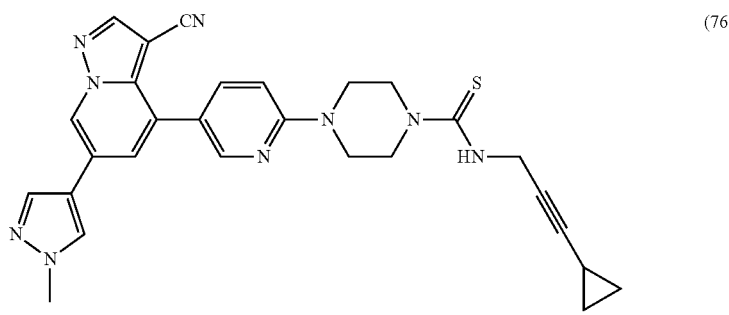
(76)
LC-MS: m/z = 522.2[M + H]+
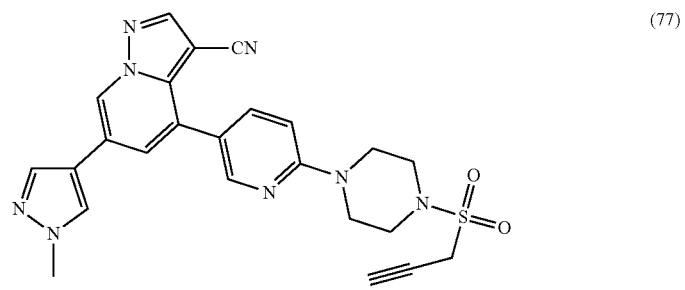
(77)
LC-MS: m/z = 487.2[M + H]+
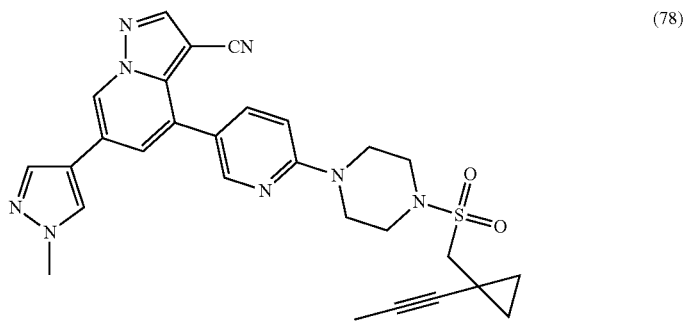
(78)
LC-MS: m/z = 541.2[M + H]+
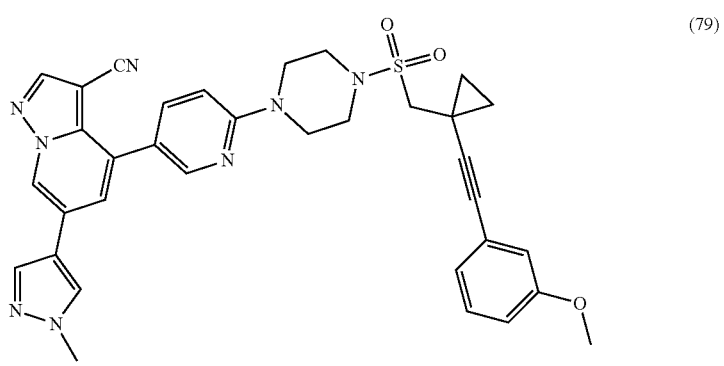
(79)
LC-MS: m/z = 633.2[M + H]+

TABLE 2-continued
Structures and characterization data of compounds (49)-(84)
(80)
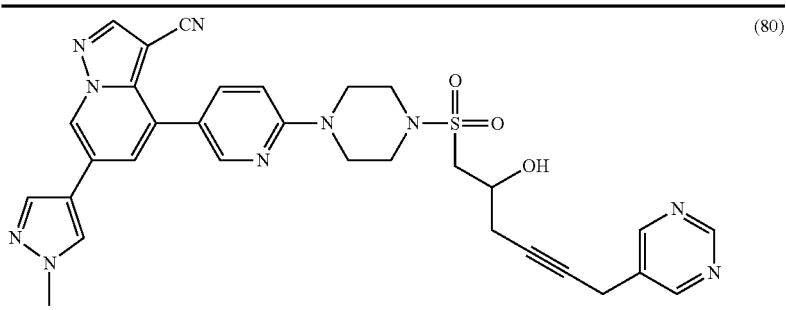
LC-MS: m/z = 623.2[M + H]$^+$
(81)
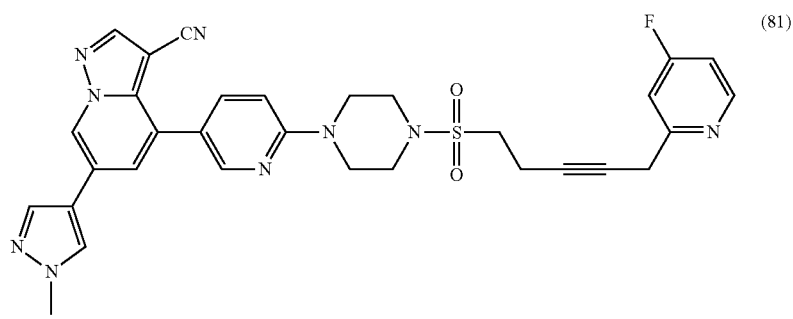
LC-MS: m/z = 610.2[M + H]$^+$
(82)
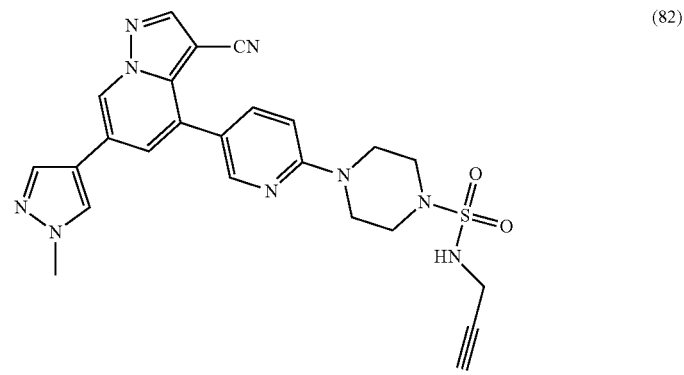
LC-MS: m/z = 502.2[M + H]$^+$
(83)
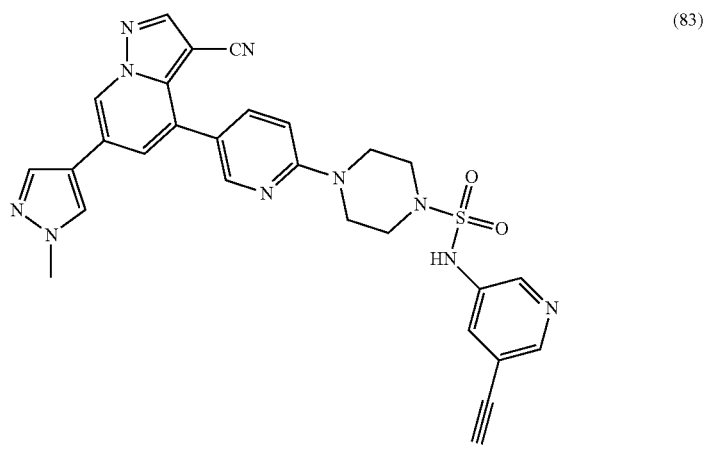
LC-MS: m/z = 565.2[M + H]$^+$ TABLE 2-continued Structures and characterization data of compounds (49)-(84)

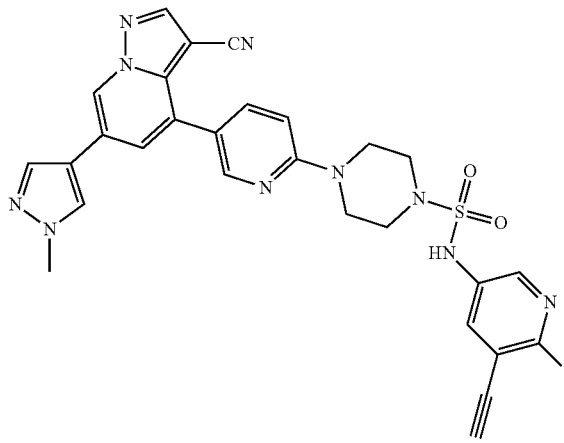

(84)

LC-MS: m/z = 583.2[M + H]⁺

Examples 85-113

Using suitable raw materials, the target compounds (85)-(113) of Examples 85-113 can be prepared by referring to the synthetic route of Example 2, Example 268, Example 277 or synthesis scheme 3. The specific structures and characterization data are described in Table 3 below:

TABLE 3

Structures and characterization data of compounds (85)-(113)

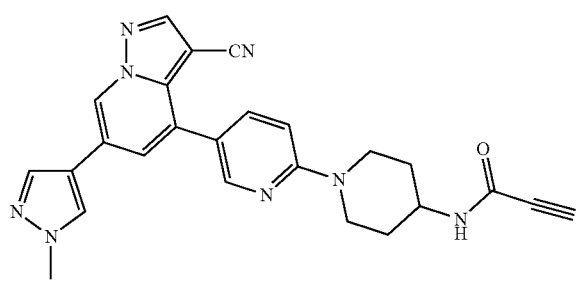

(85)

LC-MS: m/z = 451.2[M + H]⁺

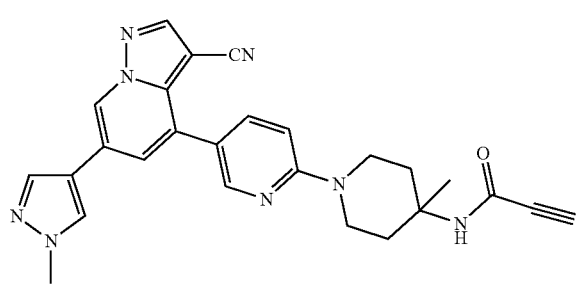

(86)

LC-MS: m/z = 465.2[M + H]⁺

TABLE 3-continued
Structures and characterization data of compounds (85)-(113)
(87)
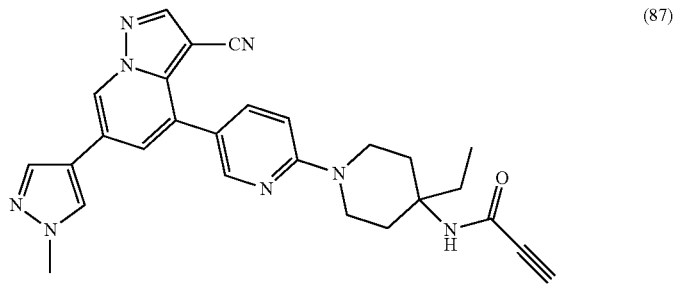
LC-MS: m/z = 479.2[M + H]$^+$
(88)
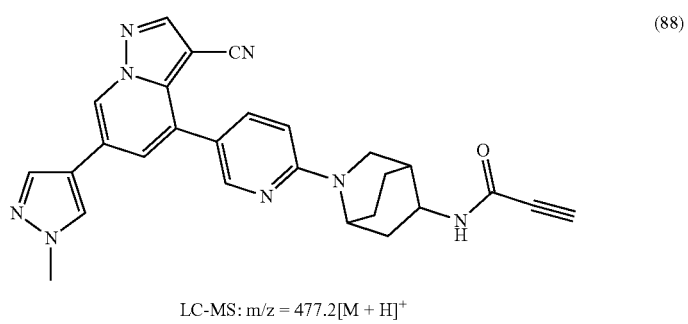
LC-MS: m/z = 477.2[M + H]$^+$
(89)
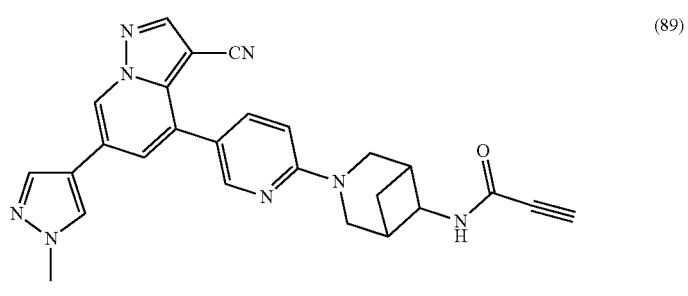
LC-MS: m/z = 463.2[M + H]$^+$
(90)
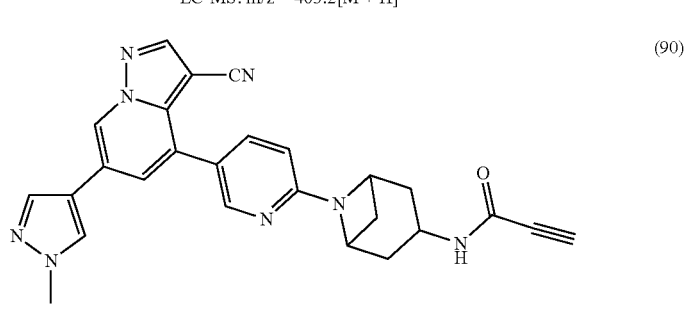
LC-MS: m/z = 463.2[M + H]$^+$
(91)
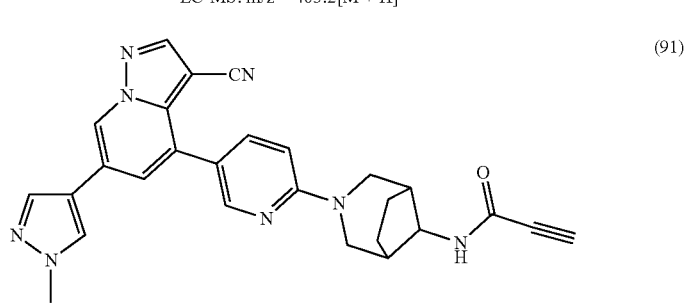
LC-MS: m/z = 477.2[M + H]$^+$ TABLE 3-continued
Structures and characterization data of compounds (85)-(113)
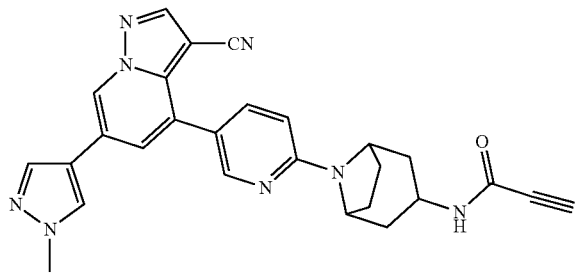
(92)
LC-MS: m/z = 477.2[M + H]$^+$
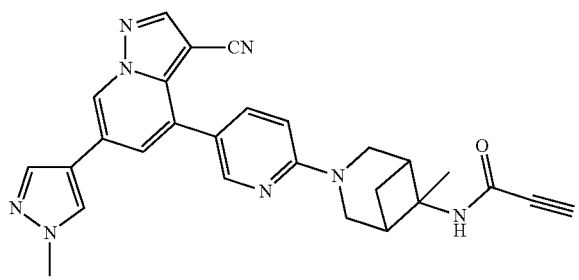
(93)
LC-MS: m/z = 477.2[M + H]$^+$
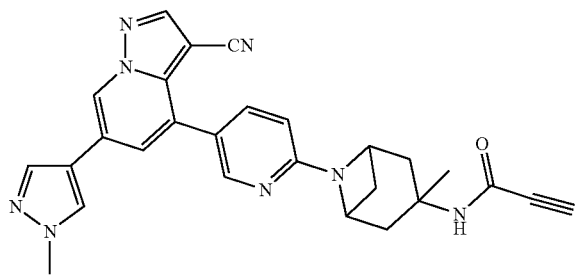
(94)
LC-MS: m/z = 477.2[M + H]$^+$
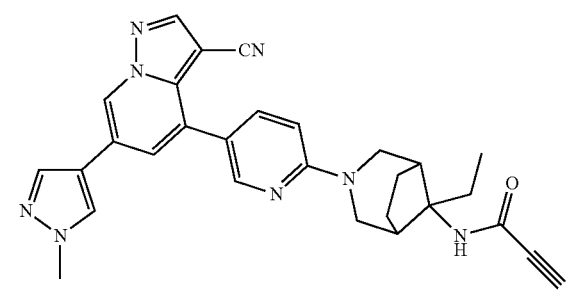
(95)
LC-MS: m/z = 505.2[M + H]$^+$ TABLE 3-continued
Structures and characterization data of compounds (85)-(113)
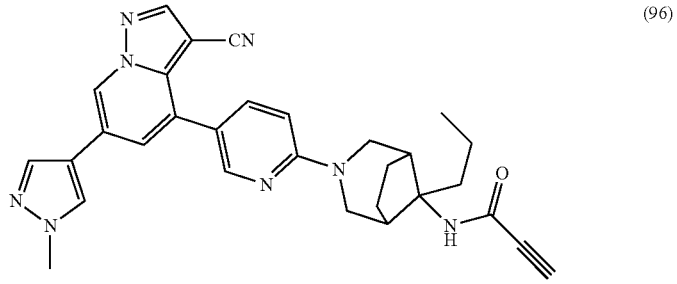
(96)
LC-MS: m/z = 519.2[M + H]+
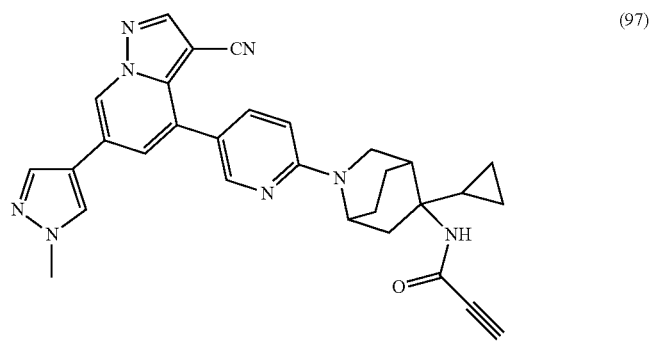
(97)
LC-MS: m/z = 517.2[M + H]+
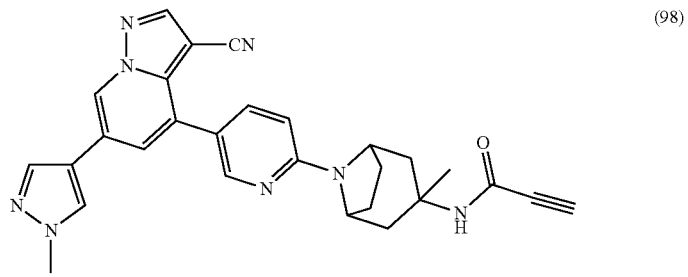
(98)
LC-MS: m/z = 491.2[M + H]+
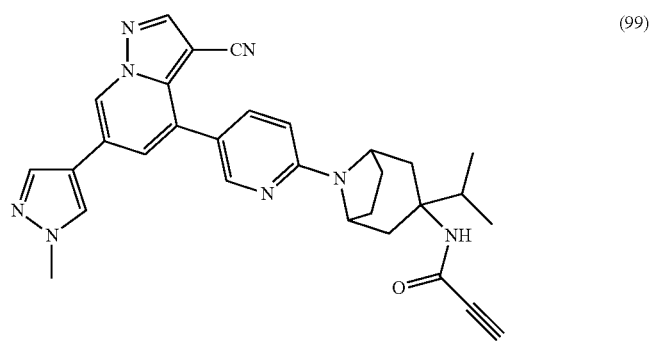
(99)
LC-MS: m/z = 519.2[M + H]+

TABLE 3-continued
Structures and characterization data of compounds (85)-(113)
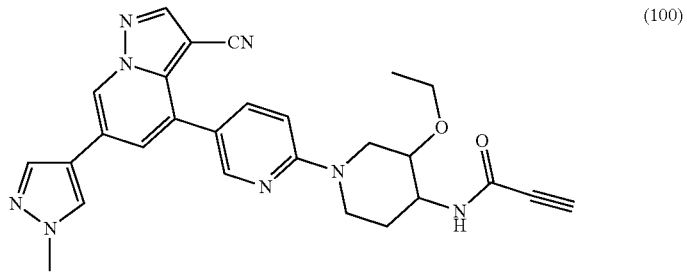
(100)
LC-MS: m/z = 495.2[M + H]+
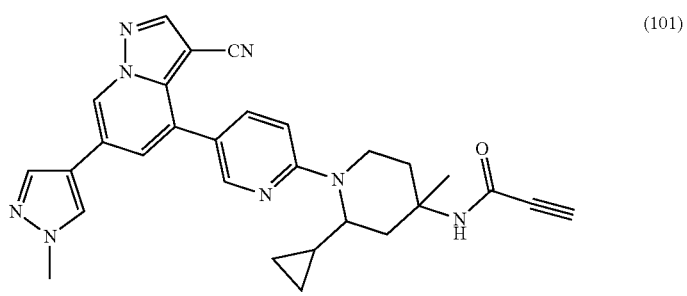
(101)
LC-MS: m/z = 502.2[M + H]+
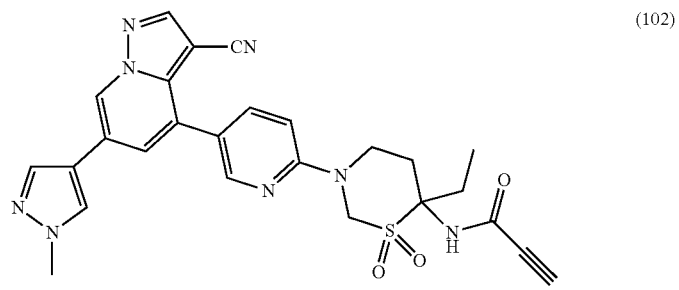
(102)
LC-MS: m/z = 529.2[M + H]+
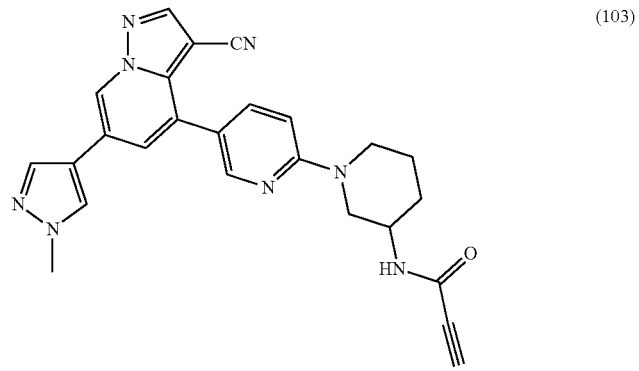
(103)
LC-MS: m/z = 451.2[M + H]+

TABLE 3-continued
Structures and characterization data of compounds (85)-(113)
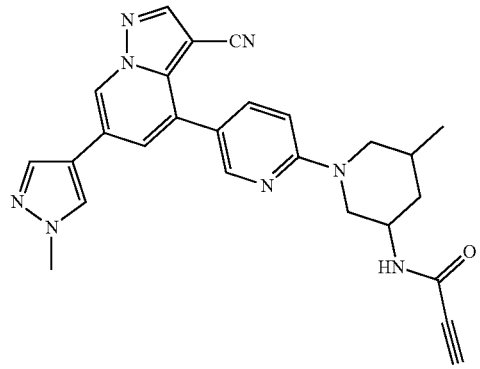
(104)
LC-MS: m/z = 465.2[M + H]⁺
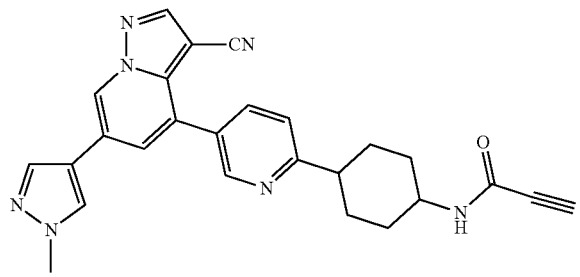
(105)
LC-MS: m/z = 450.2[M + H]⁺
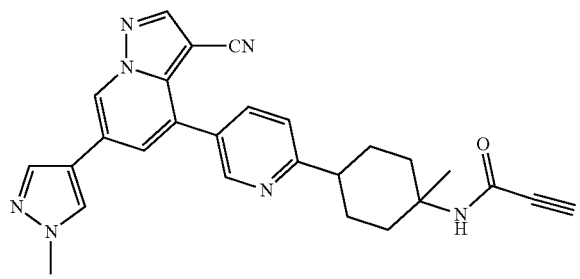
(106)
LC-MS: m/z = 464.2[M + H]⁺
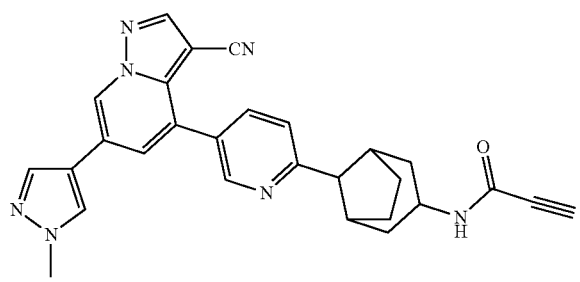
(107)
LC-MS: m/z = 476.2[M + H]⁺

TABLE 3-continued
Structures and characterization data of compounds (85)-(113)
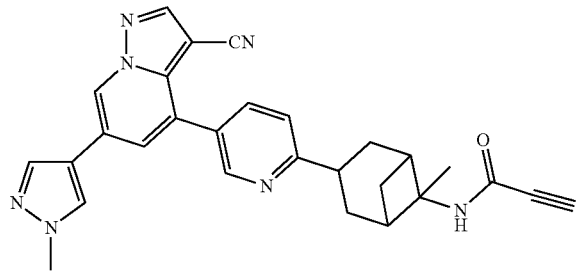
(108)
LC-MS: m/z = 476.2[M + H]+
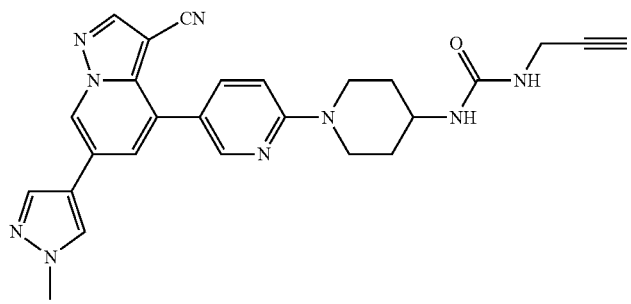
(109)
LC-MS: m/z = 480.2[M + H]+
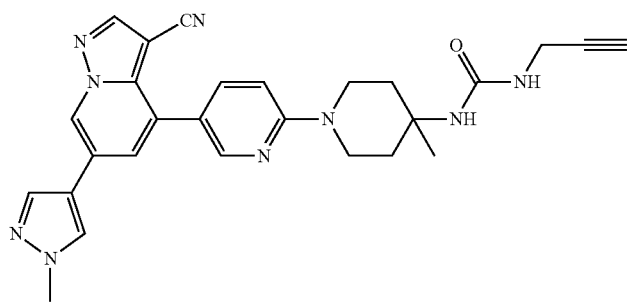
(110)
LC-MS: m/z = 494.2[M + H]+
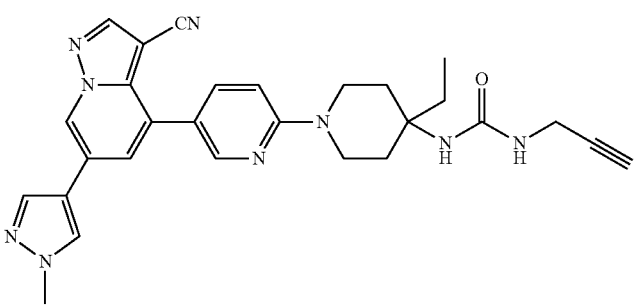
(111)
LC-MS: m/z = 508.2[M + H]+

TABLE 3-continued

Structures and characterization data of compounds (85)-(113)

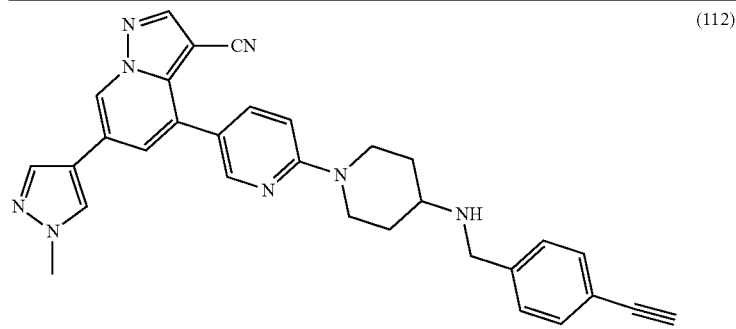

(112)

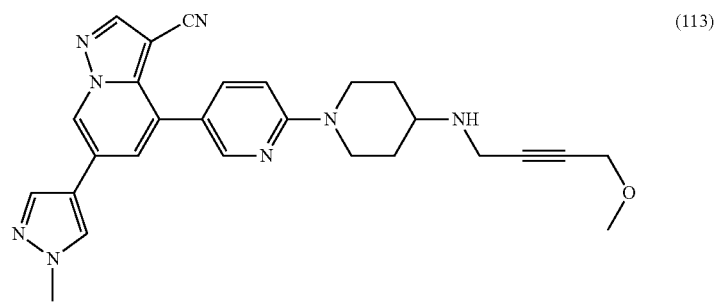

(113)

LC-MS: m/z = 481.2[M + H]+

Examples 114-132

Using suitable raw materials, the target compounds (114)-(132) of Examples 114-132 can be prepared by referring to the synthetic route of synthesis scheme 2. The specific structures and characterization data are described in Table 4 below:

TABLE 4

Structures and characterization data of compounds (114)-(132)

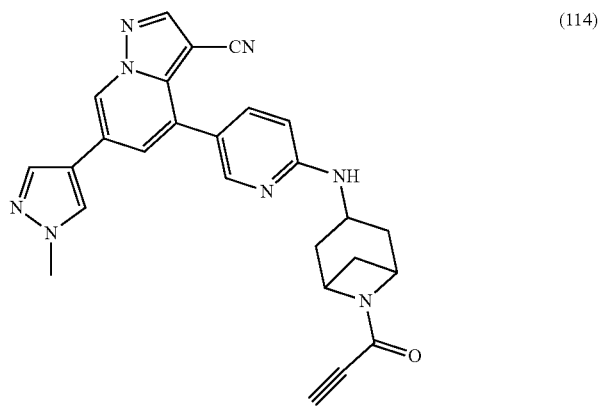

(114)

LC-MS: m/z = 463.2[M + H]+

TABLE 4-continued
Structures and characterization data of compounds (114)-(132)
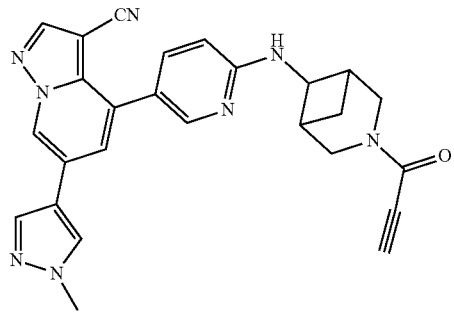
(115)
LC-MS: m/z = 463.2[M + H]$^+$
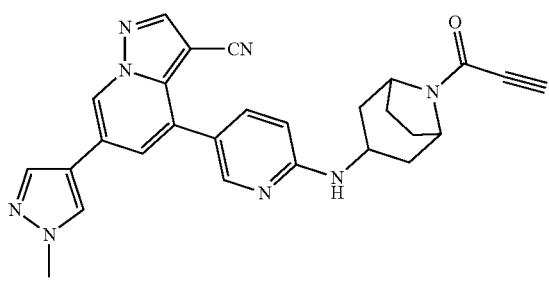
(116)
LC-MS: m/z = 477.2[M + H]$^+$
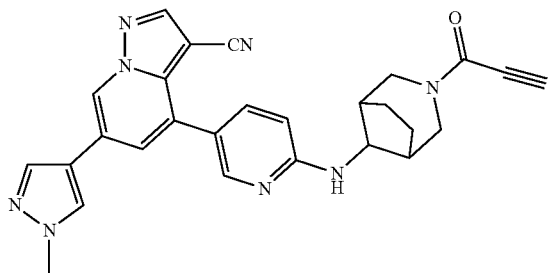
(117)
LC-MS: m/z = 477.2[M + H]$^+$
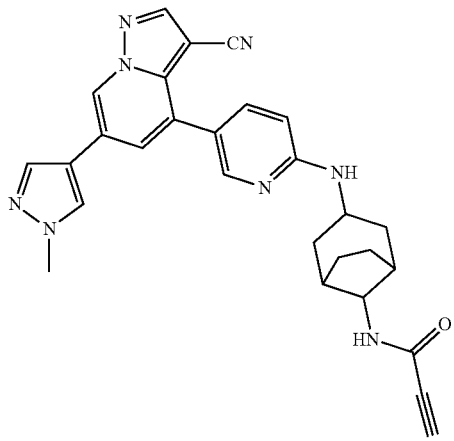
(118)
LC-MS: m/z = 491.2[M + H]$^+$ TABLE 4-continued
Structures and characterization data of compounds (114)-(132)
(119)
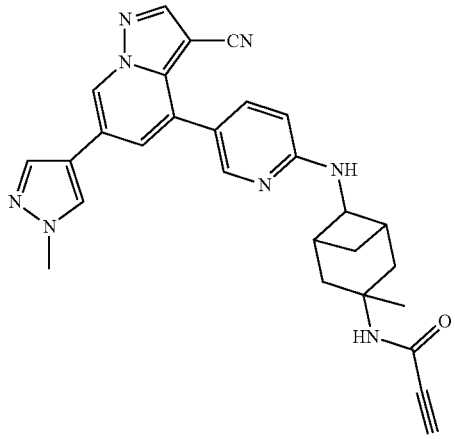
LC-MS: m/z = 491.2[M + H]+
(120)
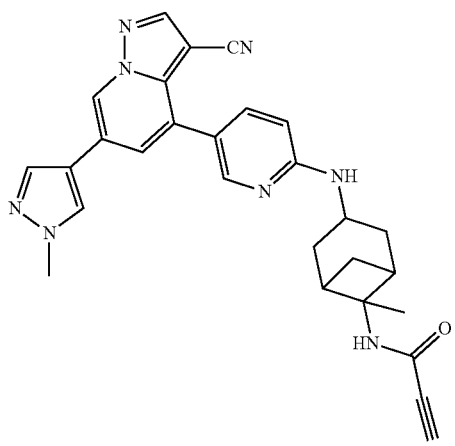
LC-MS: m/z = 491.2[M + H]+
(121)
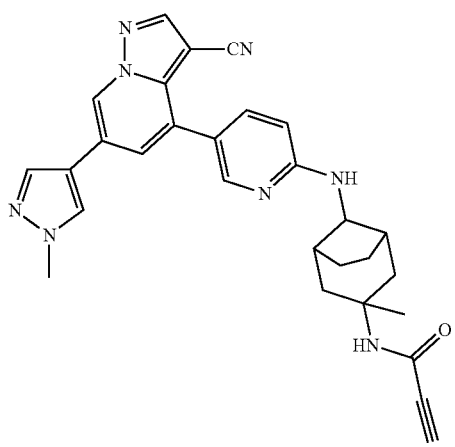
LC-MS: m/z = 505.2[M + H]+

TABLE 4-continued
Structures and characterization data of compounds (114)-(132)
(122)
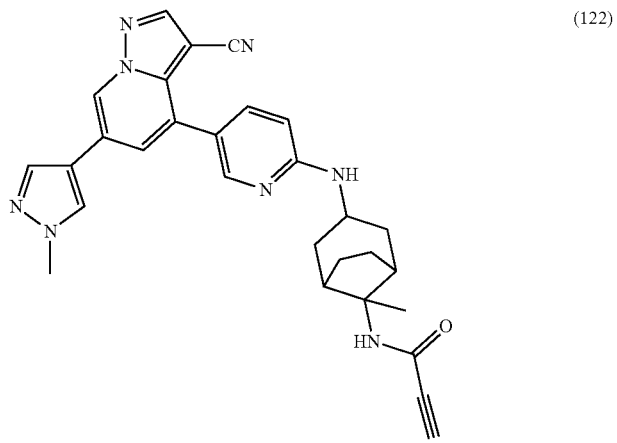
LC-MS: m/z = 505.2[M + H]+
(123)
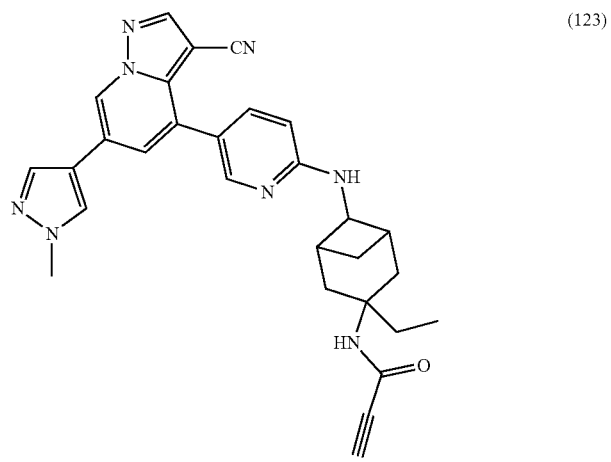
LC-MS: m/z = 505.2[M + H]+
(124)
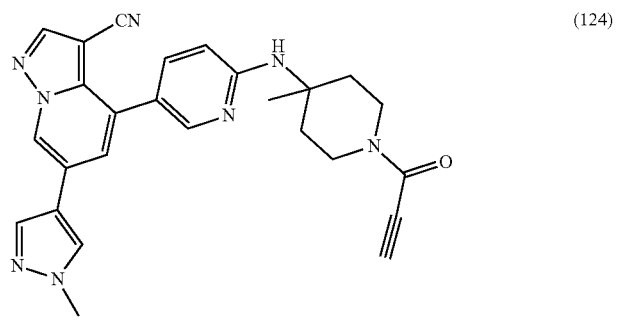
LC-MS: m/z = 465.2[M + H]+

TABLE 4-continued
Structures and characterization data of compounds (114)-(132)
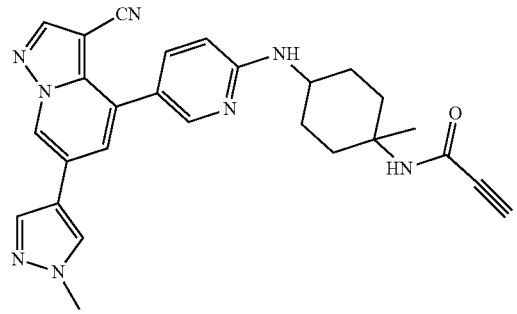
(125)
LC-MS: m/z = 479.2[M + H]+
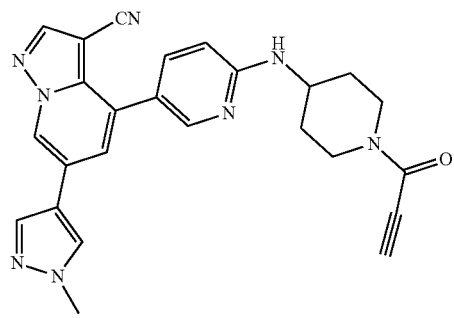
(126)
LC-MS: m/z = 451.2[M + H]+
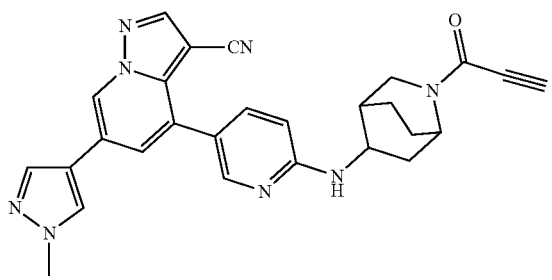
(127)
LC-MS: m/z = 477.2[M + H]+
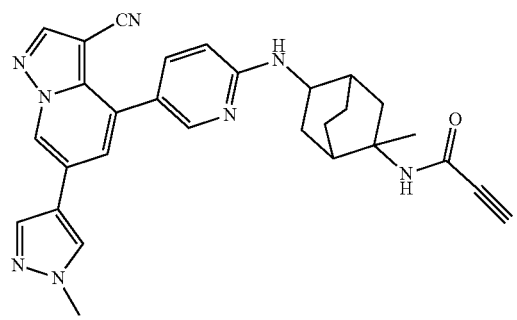
(128)
LC-MS: m/z = 505.2[M + H]+

TABLE 4-continued
Structures and characterization data of compounds (114)-(132)
(129)
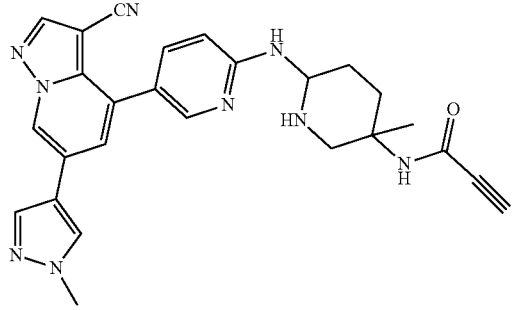
LC-MS: m/z = 480.2[M + H]+
(130)
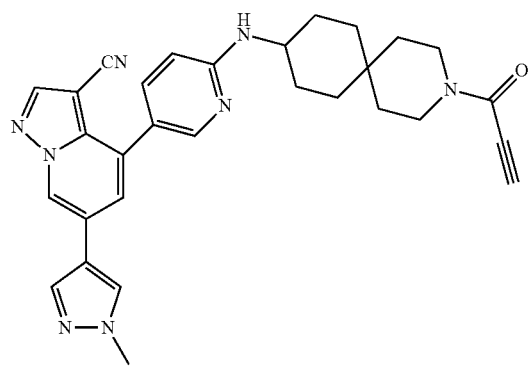
LC-MS: m/z = 519.2[M + H]+
(131)
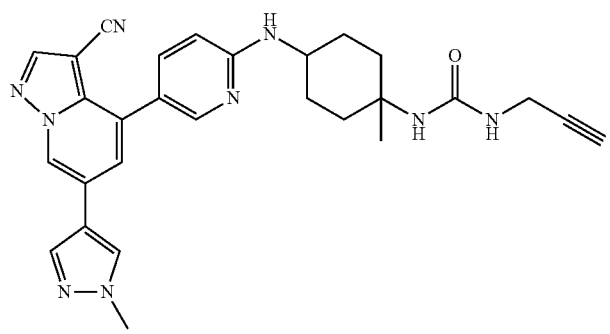
LC-MS: m/z = 508.2[M + H]+
(132)
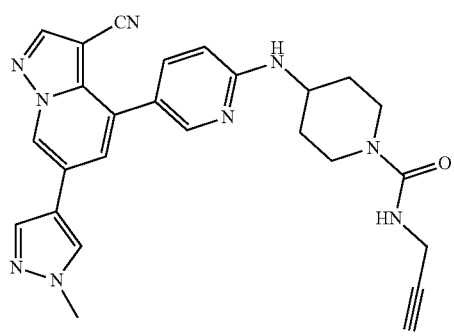
LC-MS: m/z = 480.2[M + H]+

Examples 133-141

Using suitable raw materials, the target compounds (133)-(141) of Examples 133-141 can be prepared by referring to the synthetic route of Example 281 or synthesis scheme 3. The specific structures and characterization data are described in Table 5 below:

TABLE 5

Structures and characterization data of compounds (133)-(141)

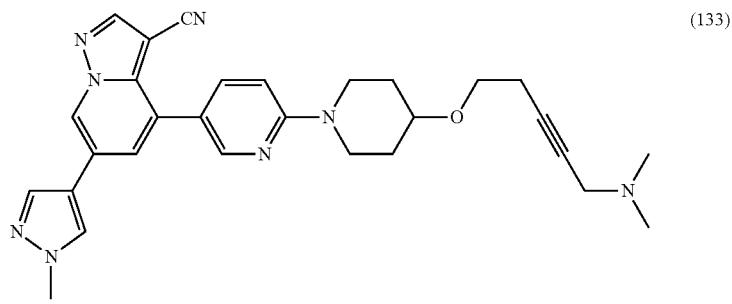

(133)

LC-MS: m/z = 509.2[M + H]$^+$

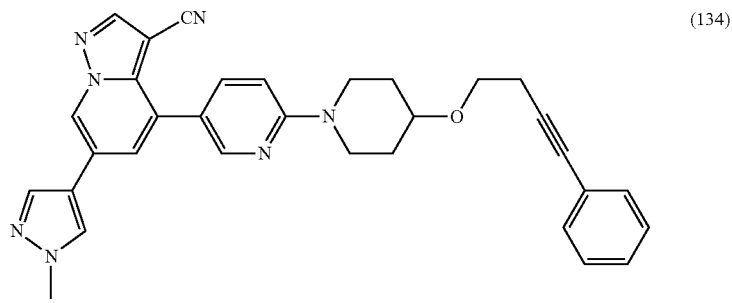

(134)

LC-MS: m/z = 528.2[M + H]$^+$

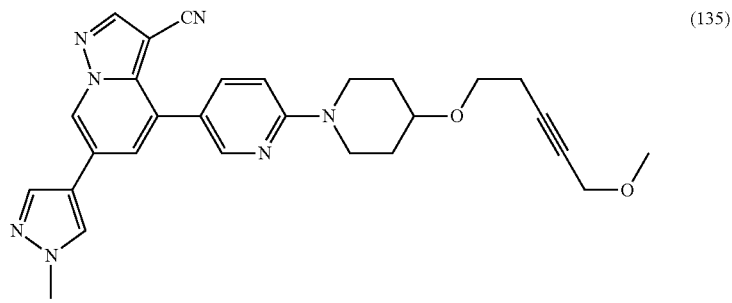

(135)

LC-MS: m/z = 496.2[M + H]$^+$

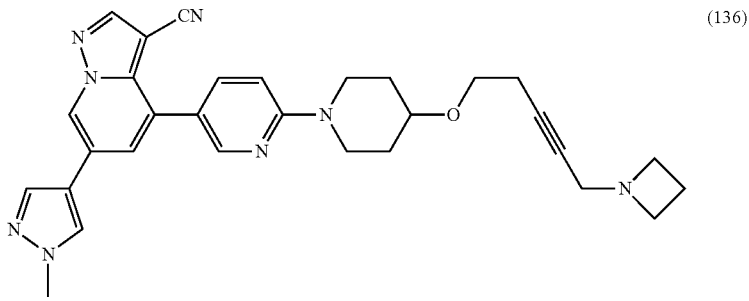

(136)

LC-MS: m/z = 521.3[M + H]$^+$

TABLE 5-continued
Structures and characterization data of compounds (133)-(141)
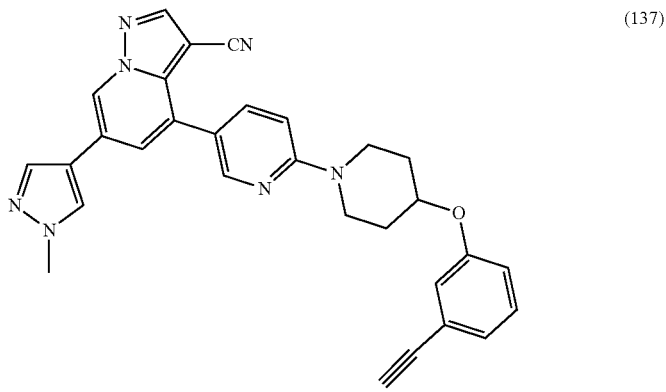
(137)
LC-MS: m/z = 500.2[M + H]+
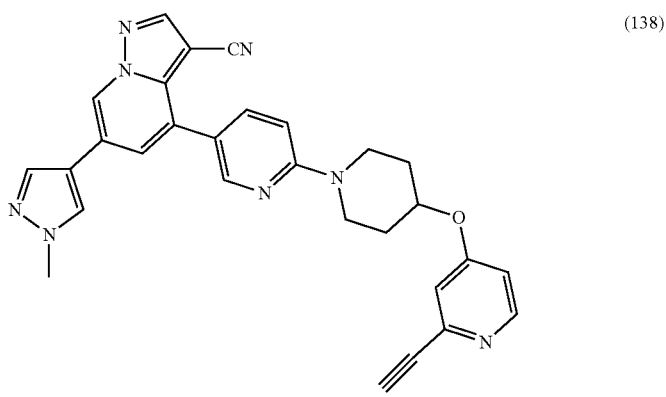
(138)
LC-MS: m/z = 501.2[M + H]+
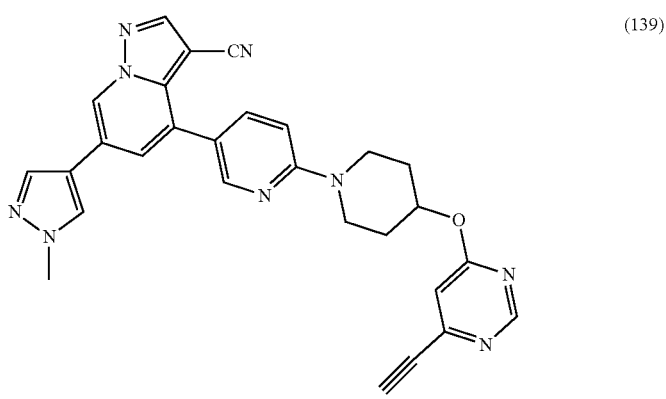
(139)
LC-MS: m/z = 502.2[M + H]+

TABLE 5-continued
Structures and characterization data of compounds (133)-(141)
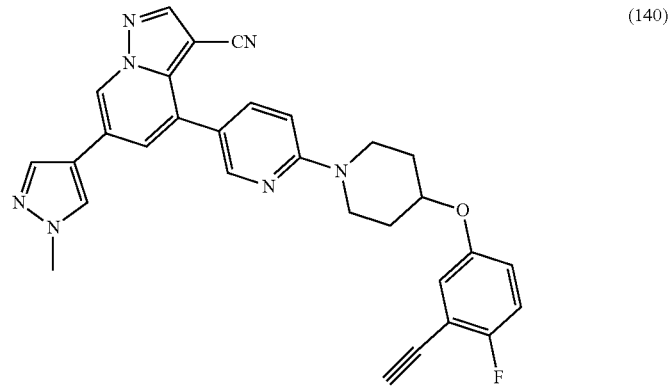
(140)
LC-MS: m/z = 518.2[M + H]⁺
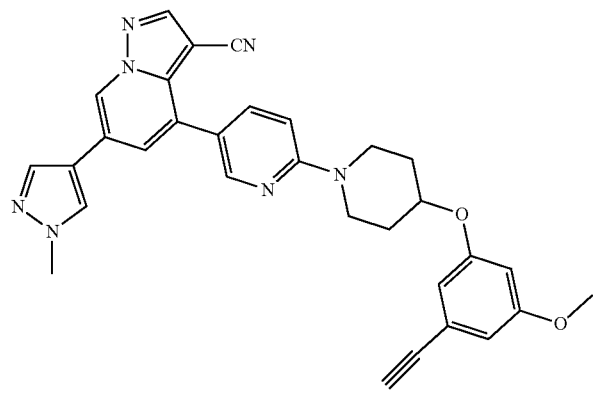
(141)
LC-MS: m/z = 530.2[M + H]⁺

Examples 142-185

Using suitable raw materials, the target compounds (142)-(185) of Examples 142-185 can be prepared by referring to the synthetic route of Example 5 or synthesis scheme 3. The specific structures and characterization data are described in Table 6 below:

TABLE 6

Structures and characterization data of compounds (142)-(185)

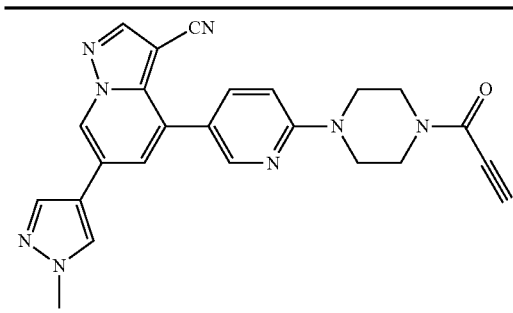

(142)

LC-MS: m/z = 412.2[M + H]⁺

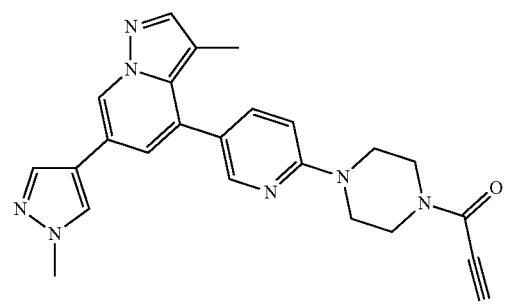

(143)

LC-MS: m/z = 426.2[M + H]⁺

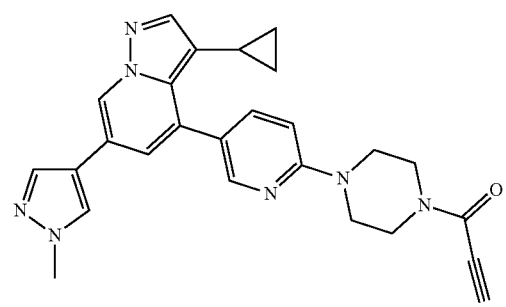

(144)

LC-MS: m/z = 452.2[M + H]⁺

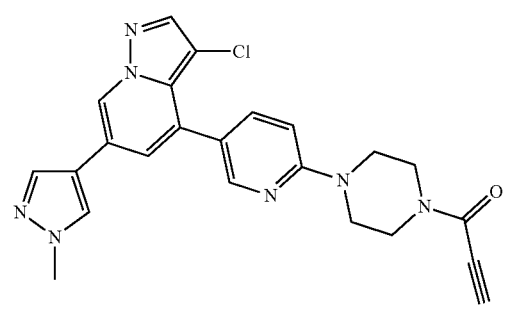

(145)

LC-MS: m/z = 447.1[M + H]⁺

TABLE 6-continued

Structures and characterization data of compounds (142)-(185)

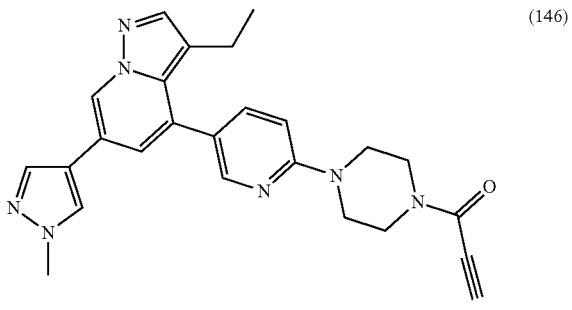

(146)

LC-MS: m/z = 440.2[M + H]⁺

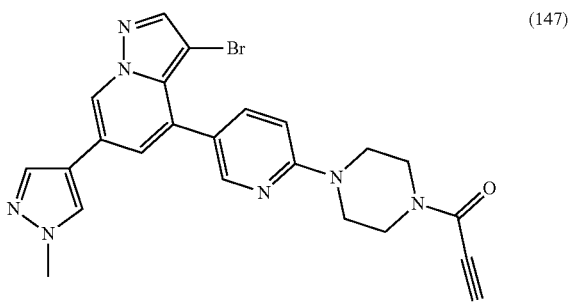

(147)

LC-MS: m/z = 491.1[M + H]⁺

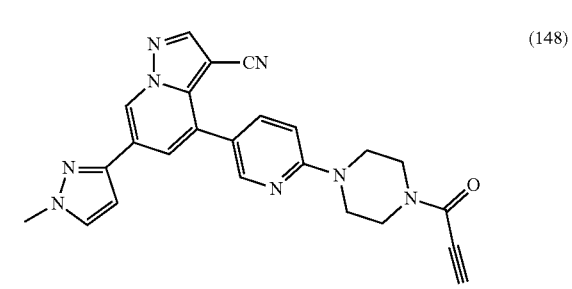

(148)

LC-MS: m/z = 437.2[M + H]⁺

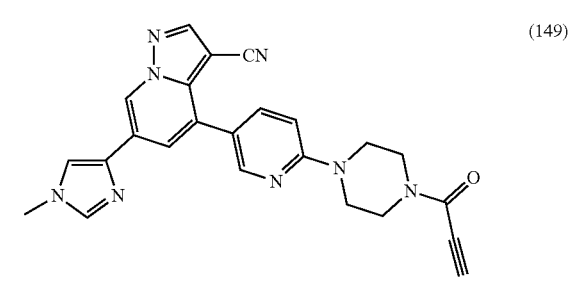

(149)

LC-MS: m/z = 437.2[M + H]⁺

TABLE 6-continued
Structures and characterization data of compounds (142)-(185)
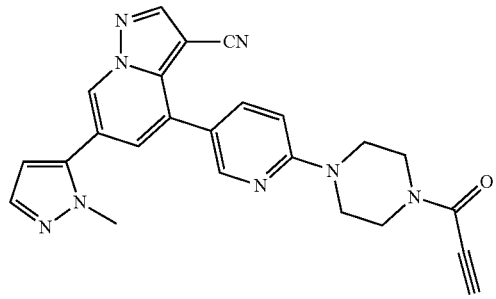
(150)
LC-MS: m/z = 437.2[M + H]+
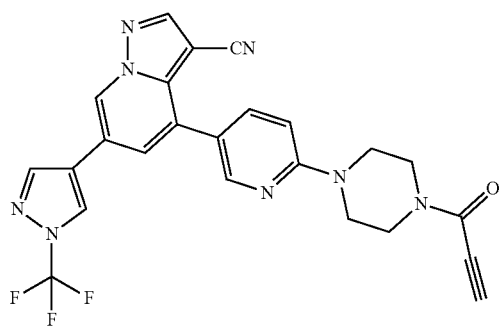
(151)
LC-MS: m/z = 491.2[M + H]+
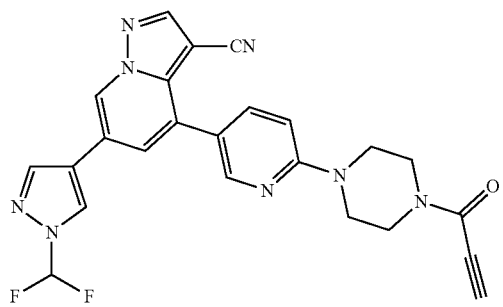
(152)
LC-MS: m/z = 473.2[M + H]+
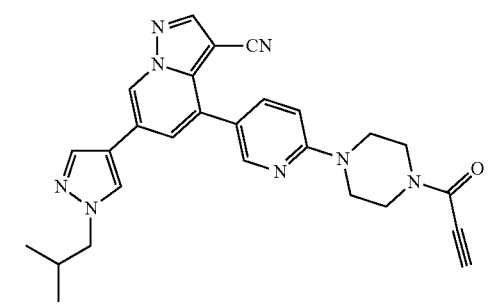
(153)
LC-MS: m/z = 479.2[M + H]+
TABLE 6-continued
Structures and characterization data of compounds (142)-(185)
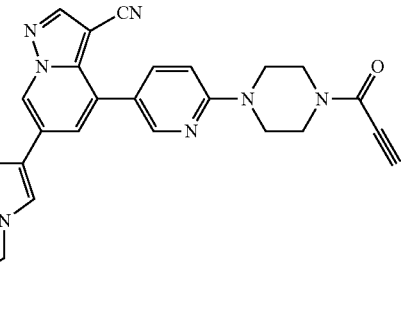
(154)
LC-MS: m/z = 481.2[M + H]+
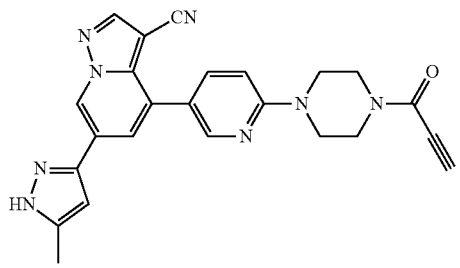
(155)
LC-MS: m/z = 437.2[M + H]+
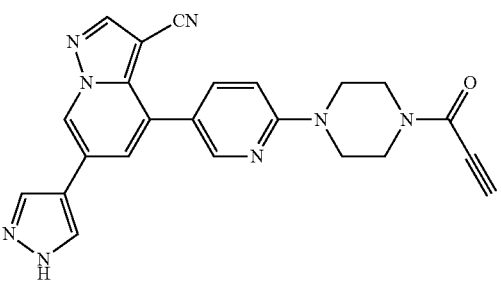
(156)
LC-MS: m/z = 423.2[M + H]+
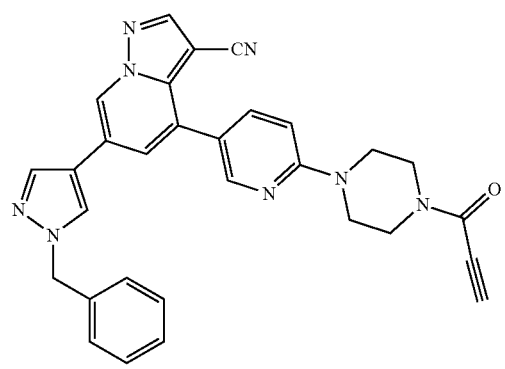
(157)
LC-MS: m/z = 513.2[M + H]+

TABLE 6-continued
Structures and characterization data of compounds (142)-(185)
(158)
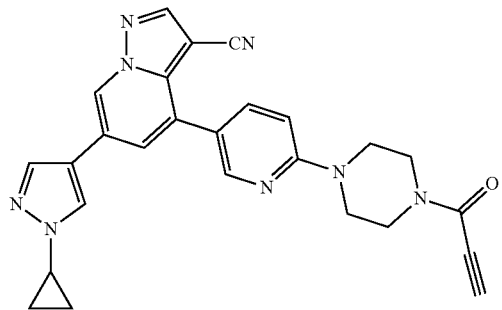
LC-MS: m/z = 463.2[M + H]+
(159)
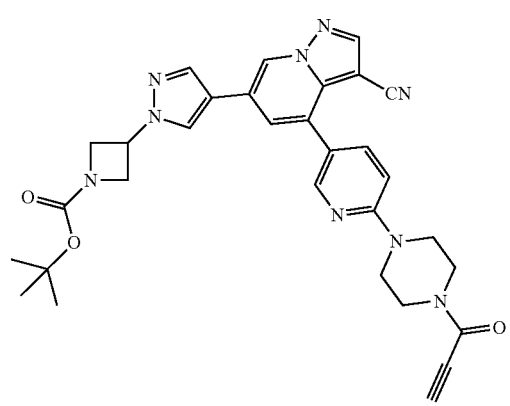
LC-MS: m/z = 578.2[M + H]+
(160)
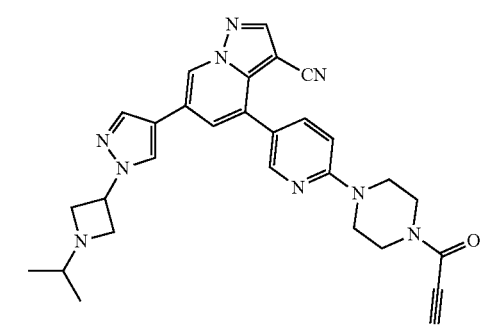
LC-MS: m/z = 520.2[M + H]+
(161)
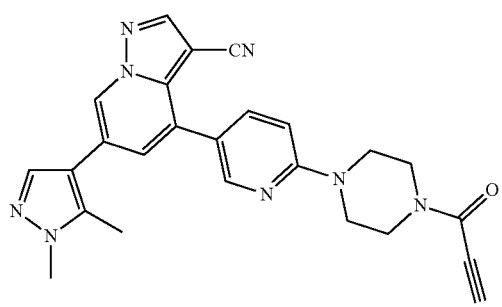
LC-MS: m/z = 451.2[M + H]+
TABLE 6-continued
Structures and characterization data of compounds (142)-(185)
(162)
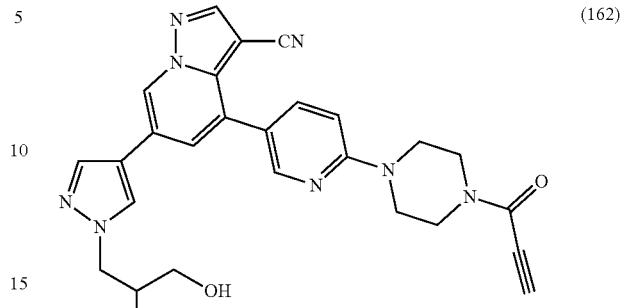
LC-MS: m/z = 495.2[M + H]+
(163)
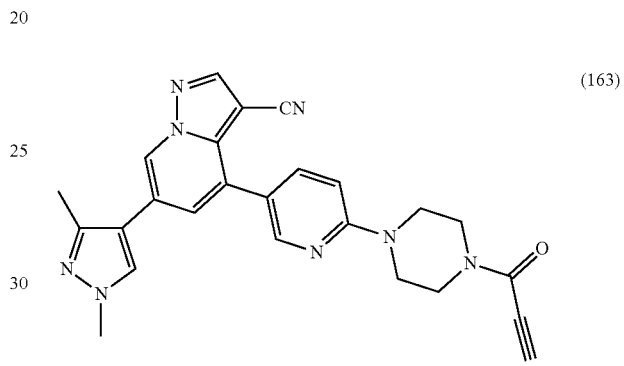
LC-MS: m/z = 451.2[M + H]+
(164)
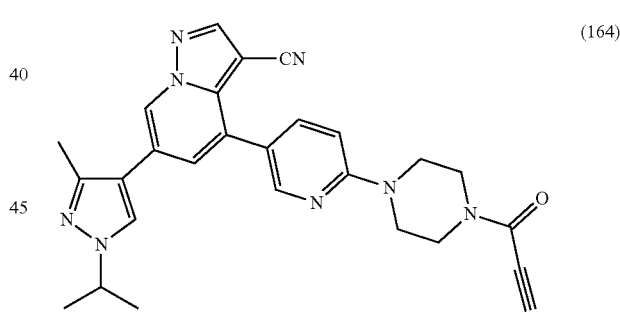
LC-MS: m/z = 479.2[M + H]+
(165)
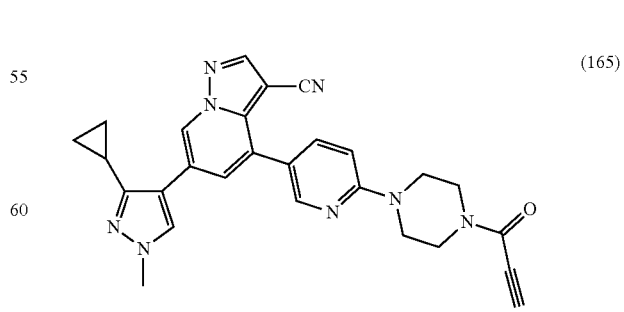
LC-MS: m/z = 477.2[M + H]+

TABLE 6-continued
Structures and characterization data of compounds (142)-(185)
(166)
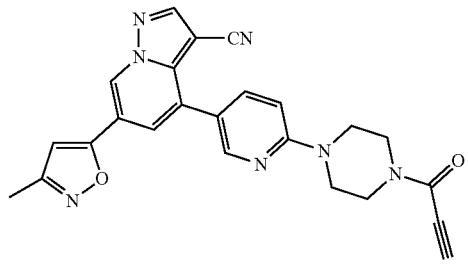
LC-MS: m/z = 438.2[M + H]+
(167)
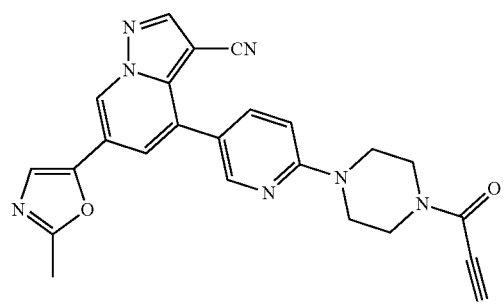
LC-MS: m/z = 438.2[M + H]+
(168)
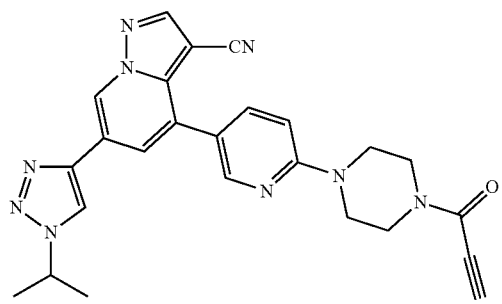
LC-MS: m/z = 466.2[M + H]+
(169)
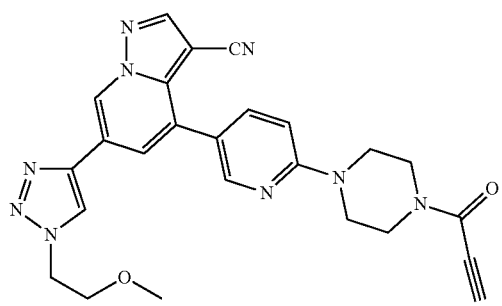
LC-MS: m/z = 482.2[M + H]+
(170)
LC-MS: m/z = 468.2[M + H]+
(171)
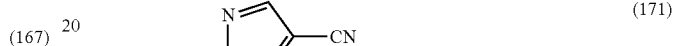
LC-MS: m/z = 506.2[M + H]+
(172)
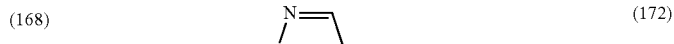
LC-MS: m/z = 543.2[M + H]+
(173)
LC-MS: m/z = 438.2[M + H]+

TABLE 6-continued
Structures and characterization data of compounds (142)-(185)
(174)
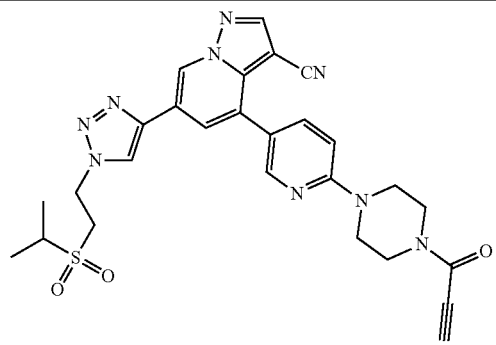
LC-MS: m/z = 558.2[M + H]+
(175)
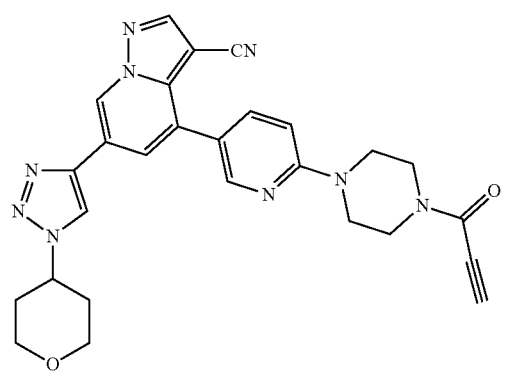
LC-MS: m/z = 508.2[M + H]+
(176)
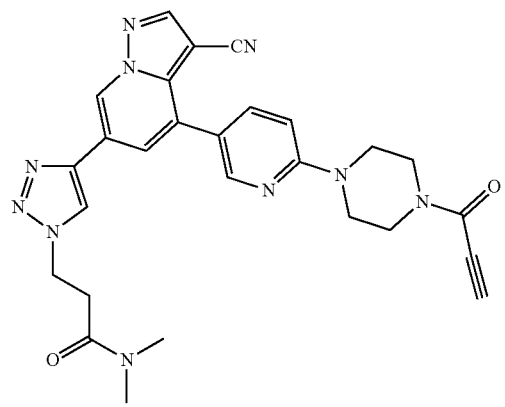
LC-MS: m/z = 523.2[M + H]+
(177)
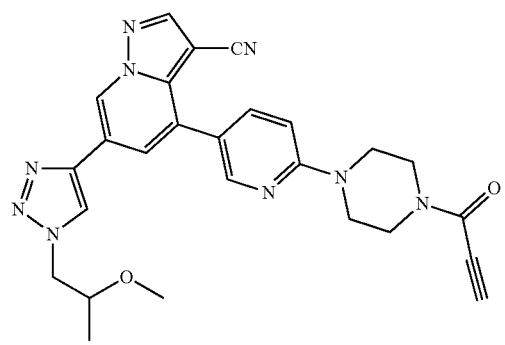
LC-MS: m/z = 496.2[M + H]+
TABLE 6-continued
Structures and characterization data of compounds (142)-(185)
(178)
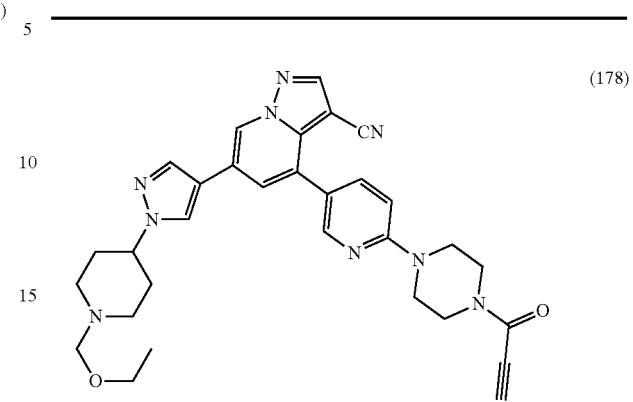
LC-MS: m/z = 564.2[M + H]+
(179)
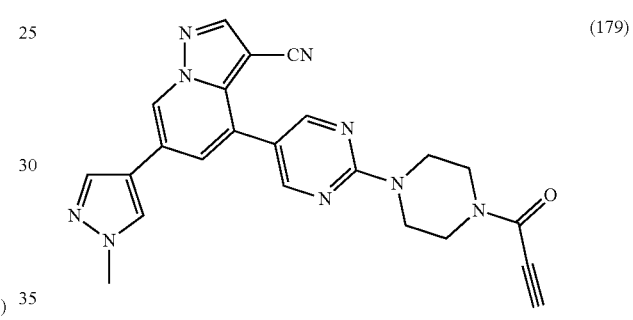
LC-MS: m/z = 438.2[M + H]+
(180)
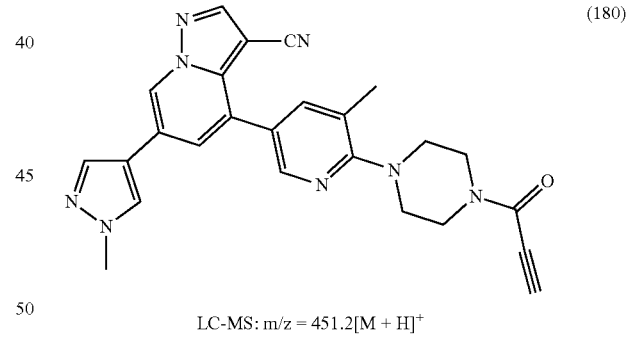
LC-MS: m/z = 451.2[M + H]+
(181)
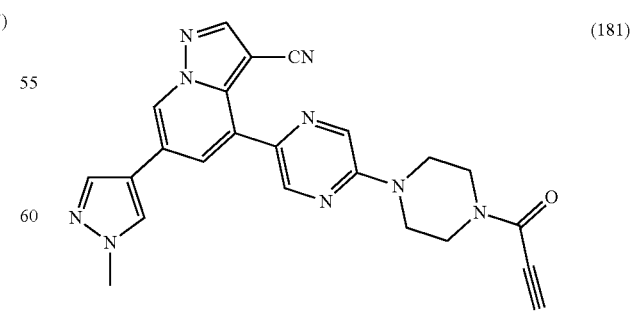
LC-MS: m/z = 438.2[M + H]+

TABLE 6-continued

Structures and characterization data of compounds (142)-(185)

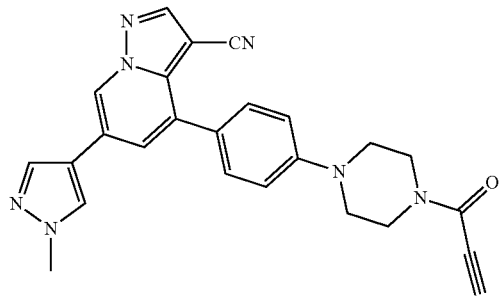

(182)

LC-MS: m/z = 436.2[M + H]⁺

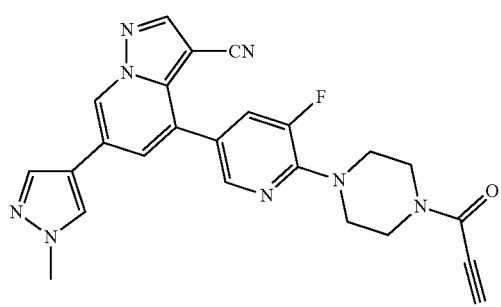

(183)

LC-MS: m/z = 455.2[M + H]⁺

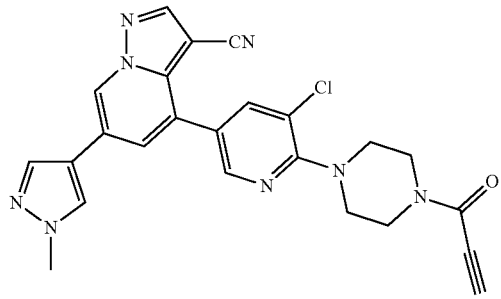

(184)

LC-MS: m/z = 472.1[M + H]⁺

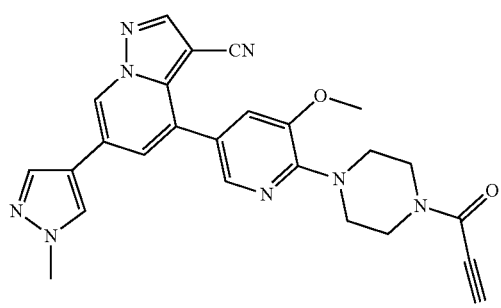

(185)

LC-MS: m/z = 467.2[M + H]⁺

Biological Activities Test Example

Test Example 1

1. Experimental Purpose:
   The inhibitory activities of the series of compounds against Ret wt, VEGFR2, CCDC6-RET, Ret M918T, Ret V804L, and Ret V804M were tested by HTRF method, and $IC_{50}$ values were determined.
2. The assay agents and consumables used are as shown below:
   1) HTRF KinEASE-TK kit (Cisbio, 62TK0PEC)
   2) Ret wt (Invitrogen, PV3082)
   3) VEGFR2 (invitrogeon, PV3660)
   4) CCDC6-RET (Signalchem, R02-19BG-10)
   5) RetM918T (Signalchem, R02-12JG-10)
   6) Ret V804L (Signalchem, R02-12BG-10)
   7) Ret V804M (Signalchem, R02-12GG-10)
   8) MgCl2 (Sigma, M1028)
   9) ATP (Promega, V910B)
   10) DTT (Invitrogen, P2325)
   11) DMSO (Sigma, D8418)
   12) 384-well plate, white, low volume, round-bottom (Greiner, 784075)
   13) 384-Well Polypropylene microplate, Clear, Flatt Bottom, Bar Code (Labcyte, P-05525-BC)
   14) 96-well polypropylene plate (Nunc, 249944)
   15) Plate shaker (Thermo, 4625-1 CECN/THZ Q)
   16) Centrifuge (Eppendorf, 5810R)
   17) Envision 2104 multi-label Reader (PerkinElmer, 2104 Oct. 1)
   18) Echo (Labcyte, 550)
3. Experimental procedure
   3.1 Preparation of 1× Kinase Reaction Buffer:
      1 volume of 5× kinase reaction buffer and 4 volumes of water; 5 mM $MgCl_2$; 1 mM DTT;
      1 mM $MnCl_2$.
   3.2 10 nl of diluted compound was transferred to per well in the Echo 550 reaction plate (784075, Greiner);
   3.3 The reaction plate was sealed with a sealing film and centrifuged at 1000 g for 1 minute.
   3.4 1× Enzyme reaction buffer was used to prepare 2× Kinase.
   3.5 5 µl of kinase was added to each well in the reaction plate (prepared in step 3). The plate was sealed with a sealing film, centrifuged at 1000 g for 30 seconds, and then left at room temperature for 10 minutes.
   3.6 4×TK-substrate-biotin and 4×ATP were prepared with 1× enzyme reaction buffer, and then mixed uniformly. To the reaction plate was added 5 µl of the mixture of K-substrate-biotin/ATP.
   3.7 The plate was sealed with a sealing film, centrifuged at 1000 g for 30 seconds, and then left for reaction at room temperature for 40 minutes.
   3.8 4× Sa-XL 665 (250 nM) was prepared using HTRF assay buffer.
   3.9 5 µl of Sa-XL 665 and 5 µl of TK-antibody-Cryptate were added to each well, centrifuged at 1000 g for 30 seconds, and reacted at room temperature for 1 hour.
   3.10 Fluorescence signals at 615 nm (Cryptate) and 665 nm (XL665) were read with Envision 2104.
4. Data Analysis
   4.1 Calculation of the ratio of each well (Ratio_665/615 nm)
   4.2 The inhibition rate was calculated as follows:

The inhibition rate of the compound (% inhibition) =

$$\left[1 - \frac{Ratio_{compound} - Ratio_{positive\ control}}{Ratio_{negative\ control} - Ratio_{positive\ control}}\right] \times 100$$

Ratio$_{positive\ control}$: average of CEP-32496 readings in all positive control wells
Ratio$_{negative\ control}$: average of DMSO readings in all negative control wells
Wherein, the chemical name of CEP-32496 is: N-[3-[(6,7-dimethoxy-4-quinazolinyl)oxy]phenyl]-N'-[5-(2,2,2-trifluoro-1,1-dimethylethyl)-3-isoxazolyl]urea.
4.3 Calculation of the IC$_{50}$ and Drawing of the inhibition curve of the compound:
The IC$_{50}$ (half inhibitory concentration) of the compound was obtained using the following non-linear fitting formula: Data analysis was performed using Graphpad 6.0 software.

$$Y=\text{Bottom}+(\text{Top}-\text{Bottom})/(1+10^{((\log \text{IC50}-X)*\text{Hill Slope})})$$

X: compound concentration log value Y: inhibition, %
5. Results were as shown in Table A-1 to Table A-3.

TABLE A-1

Kinase inhibitory activity of the compounds of the invention

| Example | IC$_{50}$ (nM), Ret wt | IC$_{50}$ (nM), Ret CCDC6 | IC$_{50}$ (nM), Ret M918T | IC$_{50}$ (nM), Ret V804L | IC$_{50}$ (nM), Ret V804M |
|---|---|---|---|---|---|
| Example 1 | 0.61 | 0.87 | 0.97 | 0.95 | 5.53 |
| Example 3 | 0.27 | 0.8 | 0.7 | 0.3 | 16.55 |
| Example 4 | 0.27 | 0.6 | 2.8 | 0.2 | 2.3 |
| Example 215 | 0.16 | 0.16 | 0.183 | 0.06 | 0.42 |
| Example 194 | 0.68 | 0.26 | 0.62 | 0.23 | 7.07 |
| Example 214 | 0.30 | 0.60 | 0.30 | 0.10 | 3.50 |
| Example 268 | 2.69 | 3.16 | 1.92 | 2.35 | 30.82 |

TABLE A-2

Kinase inhibitory activity of the compounds of the invention

| Example | IC$_{50}$ (nM), Ret wt | IC$_{50}$ (nM), Ret V804M |
|---|---|---|
| Example 5 | 0.39 | 8.20 |
| Example 31 | 1.95 | 44.30 |
| Example 186 | 0.17 | 0.76 |
| Example 221 | 0.55 | 12.44 |
| Example 222 | 0.43 | 4.35 |
| Example 223 | 0.48 | 3.23 |
| Example 224 | 0.57 | 20.98 |
| Example 225 | 0.39 | 2.22 |
| Example 226 | 0.81 | 5.04 |
| Example 227 | 0.13 | 0.30 |
| Example 232 | 0.37 | 1.79 |
| Example 233 | 0.50 | 8.92 |
| Example 234 | 4.00 | 62.30 |
| Example 235 | 0.40 | 10.01 |
| Example 236 | 1.57 | 19.68 |
| Example 237 | 0.39 | 2.06 |
| Example 238 | 0.30 | 2.75 |
| Example 239 | 0.62 | 12.26 |
| Example 243 | 3.51 | 37.79 |
| Example 244 | 0.15 | 0.27 |
| Example 245 | 0.65 | 10.69 |
| Example 246 | 7.06 | 198.50 |
| Example 247 | 0.15 | 1.94 |
| Example 248 | 0.58 | 5.76 |
| Example 249 | 0.39 | 1.77 |
| Example 250 | 0.14 | 0.88 |
| Example 251 | 2.41 | 27.87 |
| Example 252 | 0.25 | 3.21 |
| Example 253 | 0.91 | 5.47 |
| Example 254 | 3.57 | 18.27 |
| Example 255 | 0.57 | 4.11 |
| Example 256 | 0.14 | 0.44 |
| Example 257 | 0.17 | 0.74 |
| Example 258 | 0.15 | 0.21 |
| Example 259 | 0.16 | 0.91 |
| Example 261 | 3.1 | 5.1 |
| Example 262 | 0.20 | 1.92 |
| Example 263 | 2.50 | 31.41 |
| Example 265 | 3.65 | 69.61 |
| Example 270 | 1.1 | 4.9 |
| Example 271 | 5.82 | 74.08 |
| Example 272 | 0.72 | 5.26 |
| Example 273 | 4.28 | 82.64 |
| Example 275 | 0.58 | 8.22 |
| Example 276 | 0.39 | 1.08 |
| Example 277 | 1.38 | 10.3 |
| Example 280 | 0.43 | 0.92 |
| Example 281 | 3.47 | 38.8 |
| Example 282 | 2.9 | 60.8 |
| Example 283 | 0.39 | 2.29 |
| Example 284 | 1.63 | 23.04 |
| Example 285 | 0.56 | 0.71 |
| Example 286 | 0.85 | 0.85 |
| Example 287 | 0.13 | 0.20 |

TABLE A-3

Kinase inhibitory activity of the compounds of the invention

| Example | IC$_{50}$ (nM), Ret wt |
|---|---|
| Example 2 | 0.35 |
| Example 187 | 0.28 |
| Example 195 | 0.29 |
| Example 217 | 0.35 |
| Example 218 | 0.52 |
| Example 219 | 2.90 |
| Example 220 | 0.22 |
| Example 229 | 25.06 |
| Example 230 | 1.05 |
| Example 231 | 3.75 |
| Example 242 | 1.72 |
| Example 269 | 26.97 |

It can be seen from Table A-1 to Table A-3 that the compounds of the present invention have a good inhibitory effect on Ret wt. In addition, the compounds of the present invention have good inhibitory effects on Ret CCDC-6, Ret M918T, Ret V804L, and Ret V804M.

In addition to the compounds of the examples in Table A1 to Table A3, the other compounds of the present invention also have a good inhibitory effect on Ret wt, with IC$_{50}$ values ranging from 0 to 10 nM; In addition, the other compounds of the present invention have good inhibitory effects on Ret CCDC-6, Ret M918T, Ret V804L, and Ret V804M, with IC$_{50}$ values ranging from 0 to 50 nM.

Reference throughout this specification to "an embodiment", "some embodiments", "one embodiment", "another example," "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples" in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure. The scope of the present invention is defined by the appended claims and their equivalents.

The invention claimed is:

1. A compound having Formula (I) or a stereoisomer, a geometric isomer, a tautomer, an N-oxide, a solvate, or a pharmaceutically acceptable salt thereof,

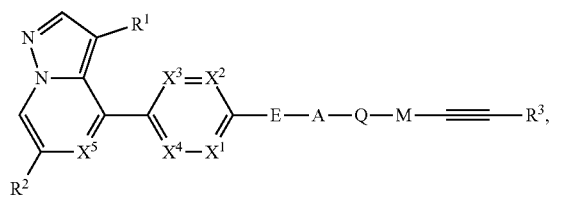

(I)

wherein, each of $X^1$, $X^2$, $X^3$, $X^4$ and $X^5$ is independently $CR^4$ or N, wherein 0, 1, or 2 of $X^1$, $X^2$, $X^3$, $X^4$ are N;

E is a bond, $-NR^6-$ or $-O-$;

A is Cyc or hetCyc, wherein each of Cyc and hetCyc is independently and optionally substituted by 1, 2, 3 or 4 substituents selected from F, Cl, Br, oxo, $NR^5R^6$, $R^5O-$, $R^5(C=O)NR^6-$, $NR^5R^6$ alkyl, $NR^5R^6(C=O)$ alkoxyalkyl, $NR^6R^7$ alkoxy, $NR^6R^7$ alkoxyalkyl, alkyl, haloalkyl, hydroxyalkyl, Cyc, hetCyc, hetCyc-alkyl, alkoxyalkyl, hetCyc-alkoxyalkyl, cycloalkylidene and heterocyclylidene;

Q is $-(C=O)-$, $-O-$, $-(C=O)NR^5-$, $-(C=S)NR^5-$, $-S(=O)_2-$, $-S(=O)_2NR^5-$, $-NR^5(C=O)-$, $-NR^5(C=O)O-$, $-NR^5(C=O)NR^5-$, $-NR^5-$, $-(C=O)O-$ or a bond;

M is $-(C=O)-$, alkylene, alkenylene, alkynylene, alkylarylene, alkylheteroarylene, alkenylarylene, alkynylarylene, alkenylheteroarylene, alkynylheteroarylene, arylene, heteroarylene, Cyc, hetCyc, arylalkylene, heteroarylalkylene, Cyc-alkyl, hetCyc-alkyl, wherein each of alkylene, alkenylene, alkynylene, alkylarylene, alkylheteroarylene, alkenylarylene, alkynylarylene, alkenylheteroarylene, alkynylheteroarylene, arylene, heteroarylene, Cyc, hetCyc, arylalkylene, heteroarylalkylene, Cyc-alkyl and hetCyc-alkyl is independently and optionally substituted by 1, 2, 3 or 4 substituents selected from F, Cl, Br, OH, CF3, $NR^5R^6$, oxo, alkoxy, cycloalkylidene, heterocyclylidene, hydroxyalkyl, alkyl, cycloalkyl and heterocyclic group $R^1$ is H, D, CN, F, Cl, Br, alkyl or cycloalkyl, wherein each of alkyl and cycloalkyl is independently and optionally substituted by 1, 2, 3 or 4 substituents selected from F, Cl, Br, CN, $NH_2$, OH and $NO_2$;

$R^2$ is a 5-membered heteroaryl group, wherein the 5-membered heteroaryl group can be independently and optionally substituted by 1, 2, 3 or 4 substituents selected from F, Cl, Br, alkyl, Cyc, hetCyc, arylalkyl, heteroarylalkyl and alkyl hetCyc; wherein each of alkyl, Cyc, hetCyc, arylalkyl and alkyl hetCyc can be further independently and optionally substituted by 1, 2, 3 or 4 substituents selected from F, Cl, Br, CN, $R^5O-$, $R^5(C=O)-$, $R^5O(C=O)-$, $NR^5R^6$, $NR^5R^6(C=O)-$, $R^5S(=O)_2-$, alkyl, Cyc, hetCyc and alkoxy;

$R^3$ is H, D, alkyl, alkynyl, Cyc, hetCyc, aryl, heteroaryl, Cyc-alkyl, hetCyc-alkyl, alkoxyalkyl, arylalkyl, heteroarylalkyl or aminoalkyl, wherein each of alkyl, alkynyl, Cyc, hetCyc, aryl, heteroaryl, Cyc-alkyl, hetCyc-alkyl, alkoxyalkyl, arylalkyl, heteroarylalkyl and aminoalkyl is independently and optionally substituted by 1, 2, 3 or 4 substituents selected from F, Cl, Br, $NR^5R^6$, $R^5O-$, $R^5O(C=O)-$, $R^5(C=O)-$, $NR^5R^6(C=O)NR^5-$, $R^5S(=O)_2-$, $NO_2$, CN, $CF_3$, alkyl and cycloalkyl;

$R^4$ is H, D, alkyl, F, Cl, Br or alkoxy, wherein each of alkyl and alkoxy can be independently and optionally substituted by 1, 2, 3 or 4 substituents selected from F, Cl, Br, CN, $NH_2$, OH and $NO_2$;

$R^5$ is H, D, alkyl, Cyc, hetCyc, aryl, heteroaryl, arylalkyl, heteroarylalkyl, alkoxyalkyl, aryloxyalkyl, aminoalkyl, alkylaminoalkyl, dialkylaminoalkyl, Cyc-alkyl or hetCyc-alkyl, wherein each of alkyl, Cyc, hetCyc, aryl, heteroaryl, arylalkyl, heteroarylalkyl, alkoxyalkyl, aryloxyalkyl, aminoalkyl, alkylaminoalkyl, dialkylaminoalkyl, Cyc-alkyl and hetCyc-alkyl is independently and optionally substituted by 1, 2, 3 or 4 substituents selected from F, Cl, Br, OH, $NR^6R^7$, alkyl, alkylsulfonyl, alkoxy, aryl and heteroaryl;

$R^6$ is H or alkyl;

$R^7$ is alkyl, arylalkyl or heteroarylalkyl;

each Cyc is independently cycloalkyl, bridged carbocyclyl or spirocarbocyclyl; and each hetCyc is independently heterocyclyl, bridged heterocyclyl or spiroheterocyclyl.

2. The compound of claim 1, wherein $R^2$ is one of the following sub-formulae:

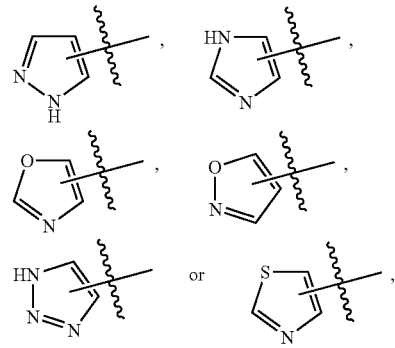

wherein each sub-formula of $R^2$ can be independently and optionally substituted by F, Cl, Br, $C_{1-6}$ alkyl, 3-12 membered Cyc, 3-12 membered hetCyc, $C_{6-12}$ aryl $C_{1-6}$ alkyl, (5-10 membered heteroaryl)-$C_{1-6}$ alkyl and $C_{1-6}$ alkyl-(3-12 membered hetCyc); wherein each of $C_{1-6}$ alkyl, 3-12 membered Cyc, 3-12 membered hetCyc, $C_{6-12}$ aryl $C_{1-6}$ alkyl, (5-10 membered heteroaryl)-$C_{1-6}$ alkyl and $C_{1-6}$ alkyl-(3-12 membered hetCyc) can be further independently and optionally substituted by 1, 2, 3 or 4 substituents selected from F, Cl, Br, CN, R⁵O—, R⁵(C=O)—, R⁵O(C=O)—, NR⁵R⁶, NR⁵R⁶(C=O)—, R⁵S(=O)₂—, C₁₋₆ alkyl, 3-12 membered Cyc, 3-12 membered hetCyc and C₁₋₆ alkoxy.

3. The compound of claim 1, wherein
R² is one of the following sub-formulae:

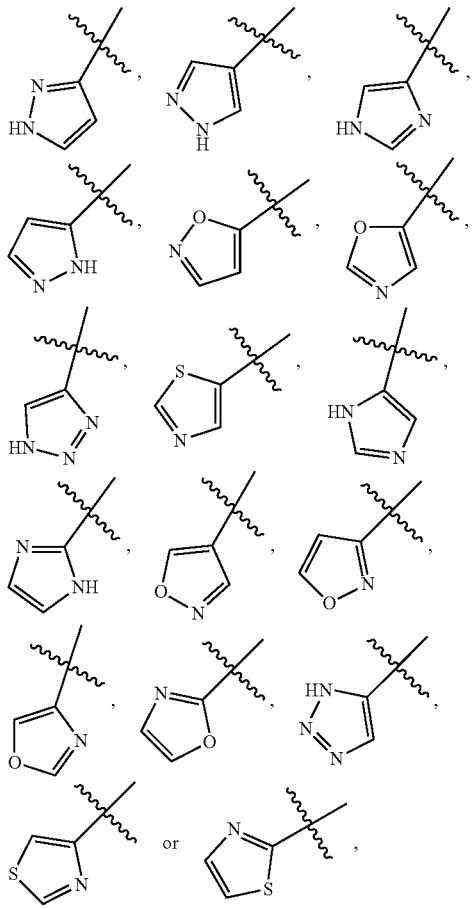

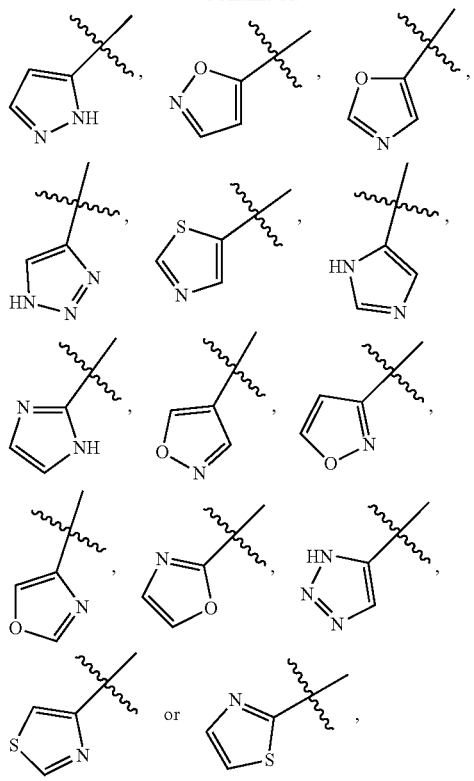

wherein each sub-formula of R² can be independently and optionally substituted by F, Cl, Br, C₁₋₄ alkyl, 3-10 membered Cyc, 3-10 membered hetCyc, phenyl C₁₋₄ alkyl, (5-10 membered heteroaryl)-C₁₋₄ alkyl and C₁₋₄ alkyl-(3-10 membered hetCyc); wherein each of C₁₋₄ alkyl, 3-10 membered Cyc, 3-10 membered hetCyc, phenyl C₁₋₄ alkyl, (5-10 membered heteroaryl)-C₁₋₄ alkyl and C₁₋₄ alkyl-(3-10 membered hetCyc) can be further independently and optionally substituted by 1, 2, 3 or 4 substituents selected from F, Cl, Br, CN, R⁵O—, R⁵(C=O)—, R⁵O(C=O)—, NR⁵R⁶, NR⁵R⁶(C=O)—, R⁵S(=O)₂—, C₁₋₄ alkyl, 3-10 membered Cyc, 3-10 membered hetCyc and C₁₋₄ alkoxy; or,
R is one of the following sub-formulae:

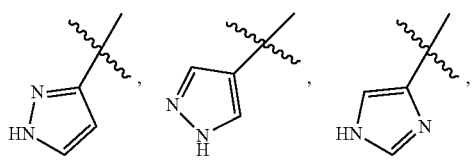

wherein each sub-formula of R² can be independently optionally substituted by 1, 2, 3 or 4 substituents selected from F, Cl, Br, methyl, ethyl, n-propyl, isopropyl trifluoromethyl, difluoromethyl, 2-methylpropyl, 2-hydroxypropyl, benzyl, cyclopropyl, tert-butoxycarbonylazetidinyl, isopropylazetidinyl, 2-hydroxymethylpropyl, methoxymethyl, methoxyethyl, ethoxymethyl, piperidinyl, methoxybenzyl, isopropylsulfonylethyl, isopropylsulfonylmethyl, tetrahydropyranyl, aminocarbonylethyl, dimethylaminocarbonylethyl, 2-methoxypropyl, ethoxymethylpiperidinyl.

4. The compound of claim 1, wherein
A is 3-12 membered Cyc or 3-12 membered hetCyc, wherein each of 3-12 membered Cyc and 3-12 membered hetCyc is independently and optionally substituted by 1, 2, 3 or 4 substituents selected from F, Cl, Br, oxo, NR⁵R⁶, R⁵O—, R⁵(C=O)NR⁶—, NR⁵R⁶C₁₋₆ alkyl, NR⁵R⁶(C=O)C₁₋₆ alkoxy C₁₋₆ alkyl, NR⁶R⁷C₁₋₆ alkoxy, NR⁶R⁷C₁₋₆ alkoxy C₁₋₆ alkyl, C₁₋₆alkyl, C₁₋₆ haloalkyl, C₁₋₆ hydroxyalkyl, 3-12 membered Cyc, 3-12 membered hetCyc, 3-12 membered hetCyc-C₁₋₆ alkyl, C₁₋₆ alkoxy C₁₋₆ alkyl, 3-12 membered hetCyc-C₁₋₆ alkoxy C₁₋₆ alkyl, C₃₋₆ cycloalkylidene and 3-6 membered heterocyclylidene; or, A is one of the following sub-formulae:

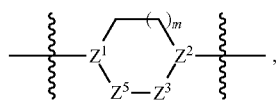

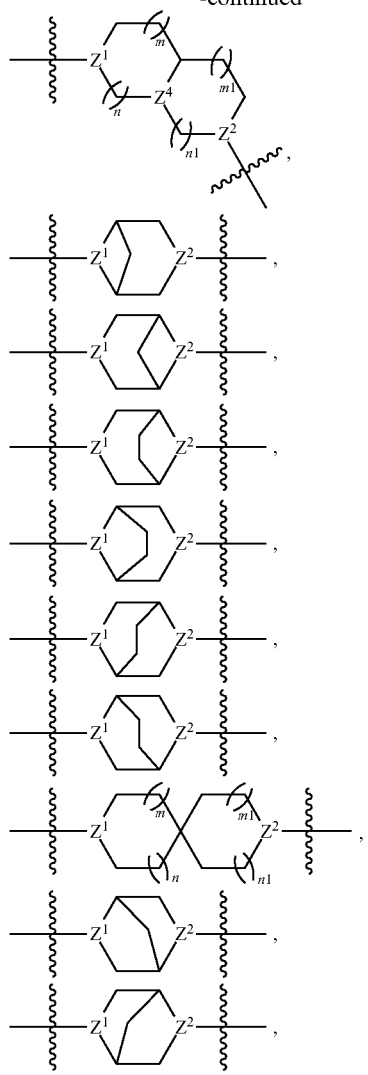

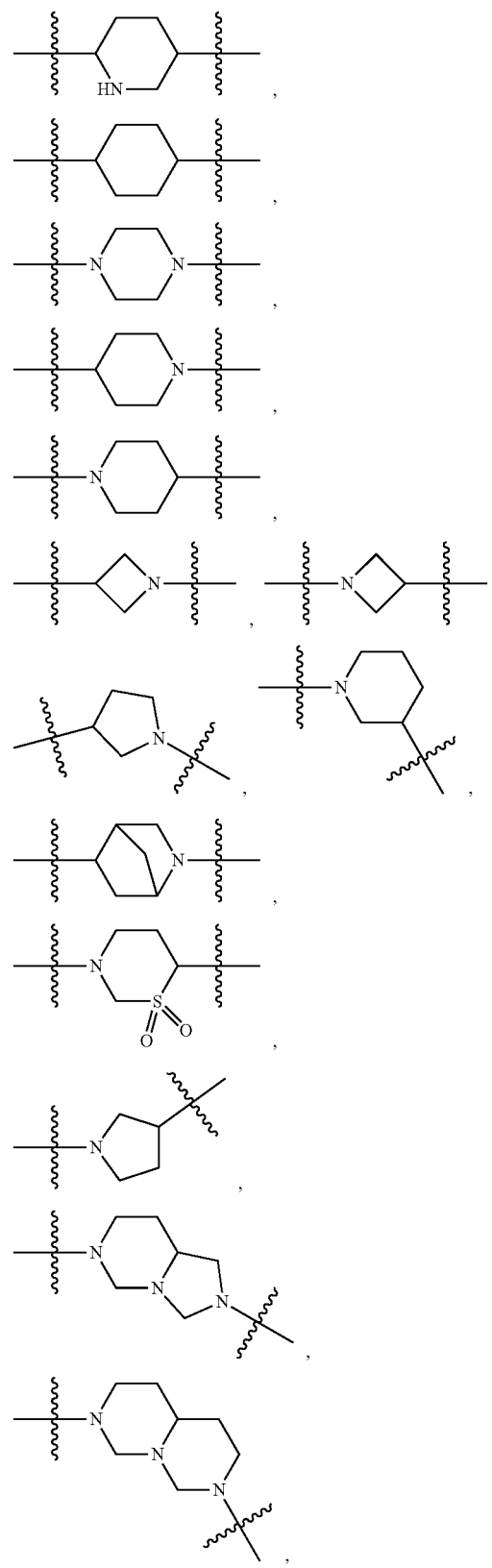

wherein each $Z^1$, $Z^2$ and $Z^4$ is independently CH or N;
each of $Z^3$ and $Z^5$ is independently a bond, $CH_2$, O, S, NH, C=O, S=O or $S(=O)_2$;
each m is 0, 1, or 2;
each n, m1 and n1 is independently 0 or 1;
each sub-formula of A is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene and 3-6 membered heterocyclylidene; or,
each sub-formula of A is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-4}$alkyl, $NR^5R^6(C=O)C_{1-4}$ alkoxy $C_{1-4}$ alkyl, $NR^6R^7C_{1-4}$ alkoxy, $NR^6R^7C_{1-4}$ alkoxy $C_{1-4}$ alkyl, $C_{1-4}$alkyl, $C_{1-4}$ haloalkyl, $C_{1-4}$ hydroxyalkyl, 3-10 membered Cyc, 3-10 membered hetCyc, 3-10 membered hetCyc-$C_{1-4}$ alkyl, $C_{1-4}$ alkoxy $C_{1-4}$ alkyl, 3-10 membered hetCyc-$C_{1-4}$ alkoxy $C_{1-4}$ alkyl, $C_{3-6}$ cycloalkylidene and 3-6 membered heterocyclylidene.

5. The compound of claim 1, wherein
A is a one of the following sub-formulae:

-continued
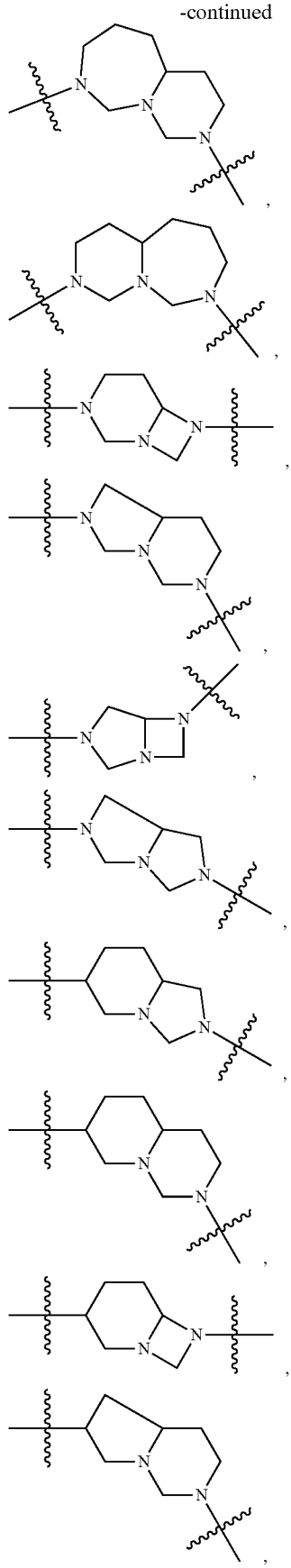
-continued
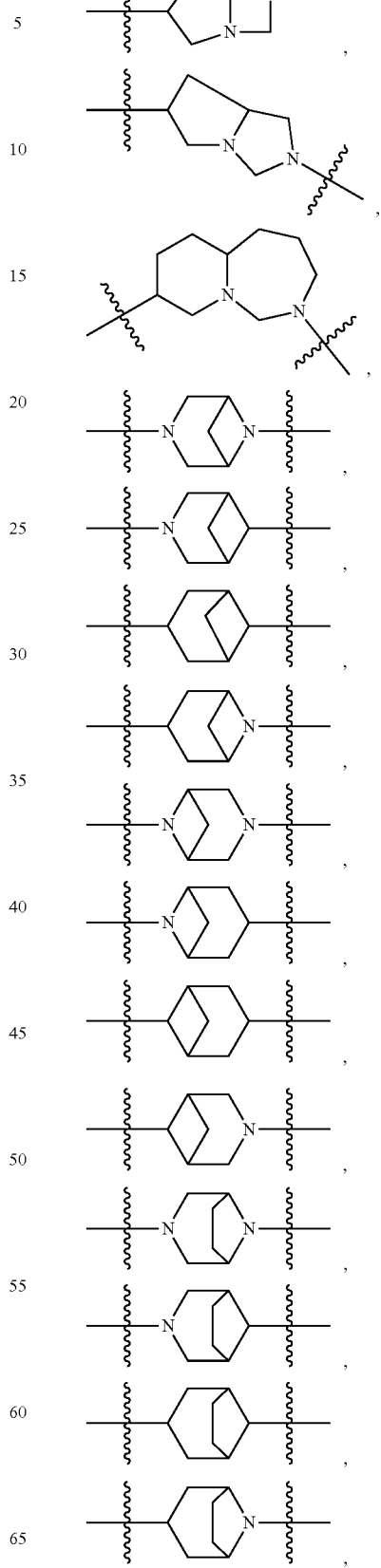

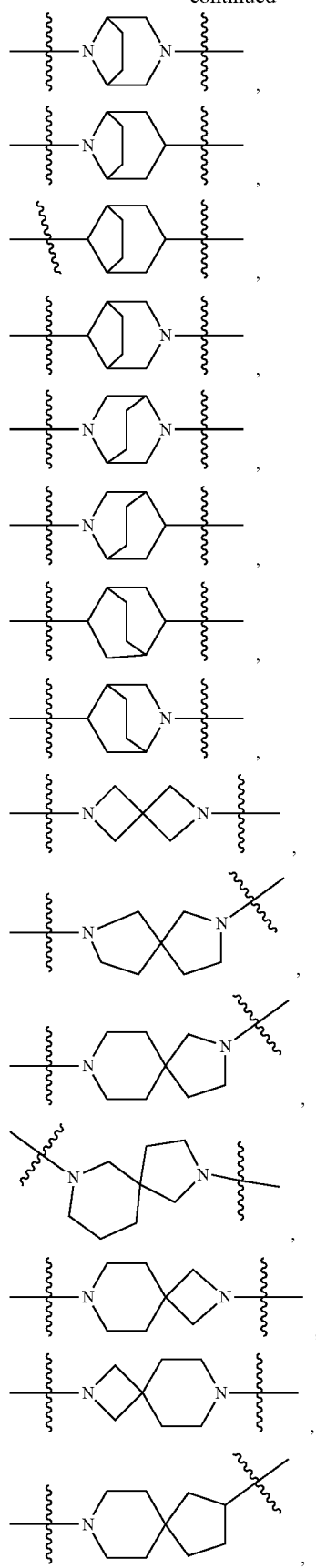
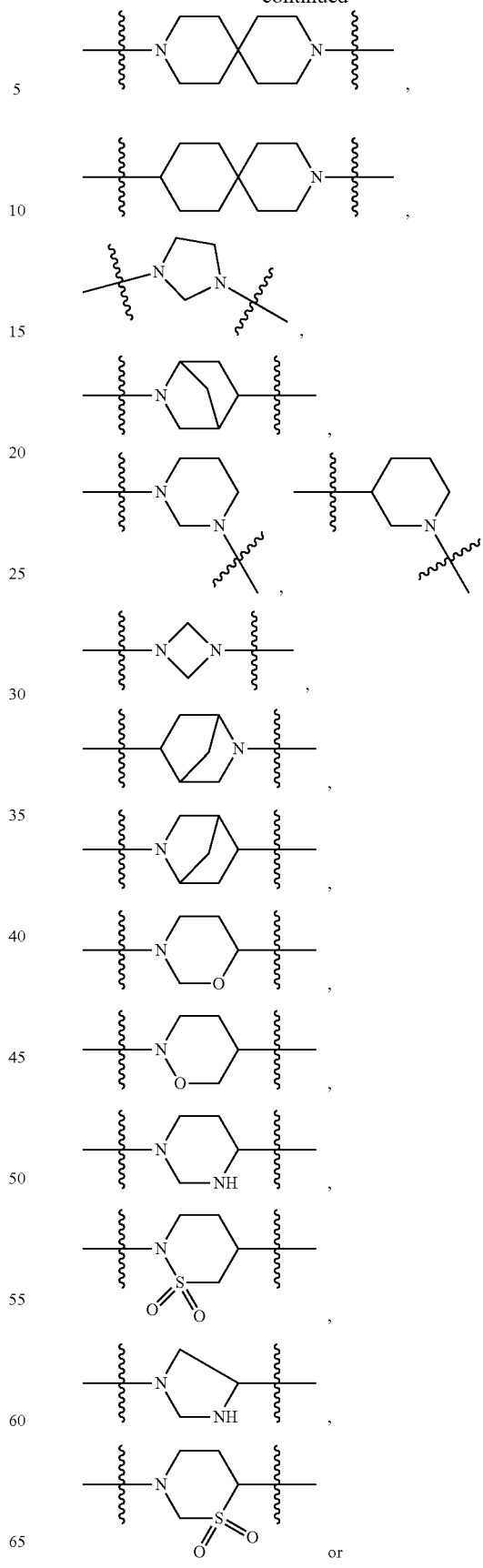

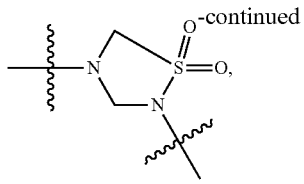

wherein each sub-formula of A is independently and optionally substituted by 1, 2, 3 or 4 substituents selected from F, Cl, Br, oxo, $NR^5R^6$, $R^5O$—, $R^5(C=O)NR^6$—, $NR^5R^6C_{1-4}$ alkyl, $NR^6R^7C_{1-4}$ alkoxy, $C_{1-4}$ alkyl, $C_{1-4}$ haloalkyl, 3-10 membered Cyc, 3-10 membered hetCyc, 3-10 membered hetCyc-$C_{1-4}$ alkyl, 3-10 membered hetCyc-$C_{1-4}$ alkoxy $C_{1-4}$ alkyl, $C_{3-6}$ cycloalkylidene and 3-6 membered heterocyclylidene; or, each sub-formula of A is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH$—, benzyl $(C=O)NH$—, pyridylmethyl $(C=O)NH$—, $CH_3CH_2(C=O)NH$—, methoxy, ethoxy, n-propoxy, isopropoxy, n-butoxy, isobutoxy, phenoxy-$(CH_2)_2O$—, $NH_2(CH_2)_2O$—, $N(CH_3)_2(CH_2)_2$ O—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, methoxymethyl, methoxyethyl, ethoxymethyl, cyclopropylidene, cyclobutylidene, cyclopentylidene, cyclohexylidene, azetidinylidene, oxetanylidene, pyrrolidinylidene or pyrazolidinylidene.

6. The compound of claim 1, wherein

M is —(C=O)—, $C_{1-6}$ alkyl, $C_{2-6}$ alkenyl, $C_{2-6}$ alkynyl, $C_{1-6}$ alkyl-$C_{6-10}$ aryl, $C_{1-6}$ alkyl-(5-10 membered heteroaryl), $C_{2-6}$ alkenyl-$C_{6-10}$ aryl, $C_{2-6}$ alkynyl-$C_{6-10}$ aryl, $C_{2-6}$ alkenyl-(5-10 membered heteroaryl), $C_{2-6}$ alkynyl-(5-10 membered heteroaryl), $C_{6-10}$ aryl, 5-10 membered heteroaryl, 3-12 membered hetCyc, 3-12 membered Cyc, $C_{6-10}$ aryl-$C_{1-6}$ alkyl, (5-10 membered heteroaryl)-$C_{1-6}$ alkyl, (3-12 membered hetCyc)-$C_{1-6}$ alkyl or (3-12 membered Cyc)-$C_{1-6}$ alkyl, wherein each of $C_{1-6}$ alkyl, $C_{2-6}$ alkenyl, $C_{2-6}$ alkynyl, $C_{1-6}$ alkyl-$C_{6-10}$ aryl, $C_{1-6}$ alkyl-(5-10 membered heteroaryl), $C_{2-6}$ alkenyl-$C_{6-10}$ aryl, $C_{2-6}$ alkynyl-$C_{6-10}$ aryl, $C_{2-6}$ alkenyl-(5-10 membered heteroaryl), $C_{2-6}$ alkynyl-(5-10 membered heteroaryl), $C_{6-10}$ aryl, 5-10 membered heteroaryl, 3-12 membered hetCyc, 3-12 membered Cyc, $C_{6-10}$ aryl-$C_{1-6}$ alkyl, (5-10 membered heteroaryl)-$C_{1-6}$ alkyl, (3-12 membered hetCyc)-$C_{1-6}$ alkyl and (3-12 membered Cyc)-$C_{1-6}$ alkyl is independently and optionally substituted by 1, 2, 3 or 4 substituents selected from F, Cl, Br, OH, $NR^5R^6$, oxo, $C_{1-6}$ alkoxy, $C_{3-6}$ cycloalkylidene, 3-6 membered heterocyclylidene, hydroxy $C_{1-6}$ alkyl, $C_{1-6}$ alkyl, $C_{3-6}$ cycloalkyl and 3-7 membered heterocyclyl; or, M is —(C=O)—, $C_{1-4}$ alkyl, $C_{2-4}$ alkenyl, $C_{2-4}$ alkynyl, $C_{1-4}$ alkylphenyl, $C_{1-4}$ alkyl-(5-10 membered heteroaryl), $C_{2-4}$ alkenylphenyl, $C_{2-4}$ alkynylphenyl, $C_{2-4}$ alkenyl-(5-10 membered heteroaryl), $C_{2-4}$ alkynyl-(5-10 membered heteroaryl), phenyl, 5-10 membered heteroaryl, 3-10 membered hetCyc, 3-10 membered Cyc, phenyl-$C_{1-4}$ alkyl, (5-10 membered heteroaryl)-$C_{1-4}$ alkyl, (3-10 membered hetCyc)-$C_{1-4}$ alkyl or (3-10 membered Cyc)-$C_{1-4}$ alkyl, wherein each of $C_{1-4}$ alkyl, $C_{2-4}$ alkenyl, $C_{2-4}$ alkynyl, $C_{1-4}$ alkylphenyl, $C_{1-4}$ alkyl-(5-10 membered heteroaryl), $C_{2-4}$ alkenylphenyl, $C_{2-4}$ alkynylphenyl, $C_{2-4}$ alkenyl-(5-10 membered heteroaryl), $C_{2-4}$ alkynyl-(5-10 membered heteroaryl), phenyl, 5-10 membered heteroaryl, 3-10 membered hetCyc, 3-10 membered Cyc, phenyl-$C_{1-4}$ alkyl, (5-10 membered heteroaryl)-$C_{1-4}$ alkyl, (3-10 membered hetCyc)-$C_{1-4}$ alkyl and (3-10 membered Cyc)-$C_{1-4}$ alkyl is independently and optionally substituted by 1, 2, 3 or 4 substituents selected from F, Cl, Br, OH, $CF_3$, $NR^5R^6$, oxo, $C_{1-4}$ alkoxy, $C_{3-6}$ cycloalkylidene, 3-6 membered heterocyclylidene, hydroxy $C_{1-4}$ alkyl, $C_{1-4}$ alkyl, $C_{3-6}$ cycloalkyl and 3-6 membered heterocyclyl; or, M is —(C=O)—, —$CH_2$—, —$(CH_2)_2$—, —$(CH_2)_3$—, —$(CH_2)_4$—, —CH=CH—, —$CH_2$CH=CH—, —$CH_2$CH=CH$CH_2$—, —C≡C—, —$CH_2$CH≡C—, —$CH_2$CH≡C$CH_2$—, —CH=CH-phenyl, —$CH_2$CH=CH-phenyl, —$CH_2$CH=CH—$CH_2$-phenyl, —C≡C-phenyl, —$CH_2$C≡C-phenyl, —$CH_2$C≡C—$CH_2$-phenyl, —CH=CH-pyridyl, —$CH_2$CH=CH-pyridyl, —$CH_2$CH=CH—$CH_2$-pyridyl, —CH=CH-pyrazolyl, —$CH_2$CH=CH-pyrazolyl, —CH=CH-pyrimidinyl, —CH=CH-pyrazinyl, —CH=CH-benzimidazolyl, —CH=CH-benzopyrazolyl, —C≡C-pyridyl, —$CH_2$C≡C-pyridyl, —$CH_2$C≡C—$CH_2$-pyridyl, —C≡C-pyrazolyl, —$CH_2$C≡C-pyrazolyl, —C≡C-pyrimidinyl, —C≡C-pyrazinyl, —C≡C-benzimidazolyl, —C≡C-benzopyrazolyl, phenyl, pyridyl, pyrimidinyl, pyrazinyl, imidazolyl, pyrazolyl, —$CH_2$-pyridyl, —$CH_2CH_2$-pyridyl, —$CH_2$-phenyl, —$CH_2CH_2$-phenyl, —$CH_2$-pyrimidinyl, —$CH_2$-pyrazinyl, —$CH_2$-imidazolyl, —$CH_2$-pyrazolyl, phenyl-$CH_2$—, phenyl-$CH_2CH_2$—, pyridyl-$CH_2$—, pyridyl-$CH_2CH_2$—, pyrimidinyl-$CH_2$—, pyrazinyl-$CH_2$—, imidazolyl-$CH_2$— or pyrazolyl-$CH_2$—, wherein each of —$CH_2$—, —$(CH_2)_2$—, —$(CH_2)_3$—, —$(CH_2)_4$—, —CH=$CH_2$—, —$CH_2$CH=CH—, —$CH_2$CH=CH$CH_2$—, —C≡C—, —$CH_2$CH≡C—, —$CH_2$CH≡CH$CH_2$—, —CH=CH-phenyl, —$CH_2$CH=CH-phenyl, —$CH_2$CH=CH—$CH_2$-phenyl, —C≡C-phenyl, —$CH_2$C≡C—phenyl, —$CH_2$C≡C—$CH_2$-phenyl, —CH=CH-pyridyl, —$CH_2$CH=CH-pyridyl, —$CH_2$CH=CH—$CH_2$-pyridyl, —CH=CH-pyrazolyl, —$CH_2$CH=CH-pyrazolyl, —CH=CH-pyrimidinyl, —CH=CH— pyrazinyl, —CH=CH-benzimidazolyl, —CH=CH-benzopyrazolyl, —C≡C-pyridyl, —$CH_2$C≡C-pyridyl, —$CH_2$C≡C—$CH_2$-pyridyl, —C≡C-pyrazolyl, —$CH_2$C≡C-pyrazolyl, —C≡C-pyrimidinyl, —C≡C-pyrazinyl, —C≡C-benzimidazolyl, —C≡C-benzopyrazolyl, phenyl, pyridyl, pyrimidinyl, pyrazinyl, imidazolyl, pyrazolyl, —$CH_2$-pyridyl, —$CH_2CH_2$-pyridyl, —$CH_2$-phenyl, —$CH_2CH_2$-phenyl, —$CH_2$-pyrimidinyl, —$CH_2$-pyrazinyl, —$CH_2$-imidazolyl, —$CH_2$-pyrazolyl, phenyl-$CH_2$—, phenyl-$CH_2CH_2$—, pyridyl-$CH_2$—, pyridyl-$CH_2CH_2$—, pyrimidinyl-$CH_2$—, pyrazinyl-$CH_2$—, imidazolyl-$CH_2$— and pyrazolyl-$CH_2$— is independently and optionally substituted by 1, 2, 3 or 4 substituents selected from F, Cl, Br, OH, $CF_3$, $NH_2$, oxo, methoxy, ethoxy, n-propoxy, isopropoxy, cyclopropylidene, cyclobutylidene, cyclopentylidene, azetidinylidene, hydroxymethyl, hydroxyethyl, 2-hydroxy-2-propyl, methyl, ethyl, n-propyl, isopropyl, n-butyl, isobutyl, tert-butyl, cyclopropyl, cyclobutyl, cyclopentyl, pyrrolidinyl and morpholinyl.

7. The compound of claim 1, wherein
$R^3$ is H, D, $C_{1-6}$ alkyl, $C_{2-6}$ alkynyl, 3-12 membered Cyc, 3-12 membered hetCyc, $C_{6-10}$ aryl, 5-10 membered heteroaryl, (3-12 membered Cyc)-$C_{1-6}$ alkyl, (3-12 membered hetCyc)-$C_{1-6}$ alkyl, $C_{1-6}$ alkoxy $C_{1-6}$ alkyl, $C_{6-10}$ aryl $C_{1-6}$ alkyl, (5-10 membered heteroaryl) $C_{1-6}$ alkyl or amino $C_{1-6}$ alkyl, wherein each of $C_{1-6}$ alkyl, $C_{2-6}$ alkynyl, 3-12 membered Cyc, 3-12 membered hetCyc, $C_{6-10}$ aryl, 5-10 membered heteroaryl, (3-12 membered Cyc)-$C_{1-6}$ alkyl, (3-12 membered hetCyc)-$C_{1-6}$ alkyl, $C_{1-6}$ alkoxy $C_{1-6}$ alkyl, $C_{6-10}$ aryl $C_{1-6}$ alkyl, (5-10 membered heteroaryl) $C_{1-6}$ alkyl and amino $C_{1-6}$ alkyl is independently and optionally substituted by 1, 2, 3 or 4 substituents selected from F, Cl, Br, $NR^5R^6$, $R^5O$—, $R^5O(C=O)$—, $R^5(C=O)$—, $NR^5R^6(C=O)NR^5$—, $R^5S(=O)_2$—, $NO_2$, CN, $CF_3$, $C_{1-6}$ alkyl and $C_{3-6}$ cycloalkyl; or,
$R^3$ is H, D, $C_{1-4}$ alkyl, $C_{2-4}$ alkynyl, 3-10 membered Cyc, 3-10 membered hetCyc, phenyl, 5-10 membered heteroaryl, (3-10 membered Cyc)-$C_{1-4}$ alkyl, (3-10 membered hetCyc)-$C_{1-4}$ alkyl, $C_{1-4}$ alkoxy $C_{1-4}$ alkyl, phenyl $C_{1-4}$ alkyl, (5-10 membered heteroaryl)-$C_{1-4}$ alkyl or amino $C_{1-4}$ alkyl, wherein each of $C_{1-4}$ alkyl, $C_{2-4}$ alkynyl, 3-10 membered Cyc, 3-10 membered hetCyc, phenyl, 5-10 membered heteroaryl, (3-10 membered Cyc)-$C_{1-4}$ alkyl, (3-10 membered hetCyc)-$C_{1-4}$ alkyl, $C_{1-4}$ alkoxy $C_{1-4}$ alkyl, phenyl $C_{1-4}$ alkyl, (5-10 membered heteroaryl)-$C_{1-4}$ alkyl or amino $C_{1-4}$ alkyl is independently and optionally substituted by 1, 2, 3 or 4 substituents selected from F, Cl, Br, $NR^5R^6$, $R^5O$—, $R^5O(C=O)$—, $R^5(C=O)$—, $NR^5R^6(C=O)NR^5$—, $R^5S(=O)_2$—, $NO_2$, CN, $CF_3$, $C_{1-4}$ alkyl and $C_{3-6}$ cycloalkyl; or,
$R^3$ is H, D, methyl, ethyl, n-propyl, isopropyl, n-butyl, isobutyl, tert-butyl, ethynyl, trifluoromethyl, cyclopropyl, cyclobutyl, cyclopentyl, cyclohexyl, cyclopentylmethyl, cyclopropylmethyl, cyclobutylmethyl, cyclohexylmethyl, spiro[4.4]decylmethyl, bicyclo[3.3.0]octyl, pyrrolidinyl, azetidinyl, piperidinyl, morpholinyl, azetidinylmethyl, piperidinylmethyl, morpholinylmethyl, methoxymethyl, methoxyethyl, ethoxymethyl, ethoxyethyl, n-propoxymethyl, isopropoxymethyl, isopropoxyethyl, n-butoxymethyl, isobutoxymethyl, tert-butoxymethyl, tert-butoxyethyl, phenyl, pyridyl, imidazolyl, pyrazolyl, pyrimidinyl, 3H-indolyl, indolyl, benzimidazolyl, 3,8a-dihydroindolizinyl, phenylmethyl, 3,8a-dihydroindolizinylmethyl, pyridylmethyl, imidazolylmethyl, pyrazolylmethyl, pyrimidinylmethyl, 3H-indolylmethyl, indolylmethyl, benzimidazolylmethyl, $NH_2CH_2$—, $NH(CH_3)CH_2$—, $N(CH_3)_2CH_2$—, $NH_2(CH_2)_2$—, $NH(CH_3)CH_2$—, $NH(CH_3)(CH_2)_2$— or $N(CH_3)_2(CH_2)_2$—, wherein each of methyl, ethyl, n-propyl, isopropyl, n-butyl, isobutyl, tert-butyl, ethynyl, trifluoromethyl, cyclopropyl, cyclobutyl, cyclopentyl, cyclohexyl, cyclopentylmethyl, cyclopropylmethyl, cyclobutylmethyl, cyclohexylmethyl, spiro[4.4]decylmethyl, bicyclo[3.3.0]octyl, pyrrolidinyl, azetidinyl, piperidinyl, morpholinyl, azetidinylmethyl, piperidinylmethyl, morpholinylmethyl, methoxymethyl, methoxyethyl, ethoxymethyl, ethoxyethyl, n-propoxymethyl, isopropoxymethyl, isopropoxyethyl, n-butoxymethyl, isobutoxymethyl, tert-butoxymethyl, tert-butoxyethyl, phenyl, pyridyl, imidazolyl, pyrazolyl, pyrimidinyl, 3H-indolyl, indolyl, benzimidazolyl, 3,8a-dihydroindolizinyl, phenylmethyl, 3,8a-dihydroindolizinylmethyl, pyridylmethyl, imidazolylmethyl, pyrazolylmethyl, pyrimidinylmethyl, 3H-indolylmethyl, indolylmethyl, benzimidazolylmethyl, $NH_2CH_2$—, $NH(CH_3)CH_2$—, $N(CH_3)_2CH_2$—, $NH_2(CH_2)_2$—, $NH(CH_3)CH_2$—, $NH(CH_3)(CH_2)_2$— and $N(CH_3)_2(CH_2)_2$— is independently and optionally substituted by 1, 2, 3 or 4 substituents selected from F, Cl, Br, OH, $NH_2$, $NO_2$, CN, $CF_3$, $C(CH_3)_3O(C=O)$—, $CH_3(C=O)$—, $NH_2(C=O)NH$—, $NHCH_3(C=O)NH$—, $CH_3S(=O)_2$—, methyl, methoxy, ethoxy, n-propoxy, isopropoxy, phenoxy, pyridyloxy, cyclopropyl, cyclobutyl, cyclopentyl, cyclohexyl.

8. The compound of claim 1, wherein
$R^1$ is H, D, CN, F, Cl, Br, methyl, ethyl, n-propyl, isopropyl, n-butyl, isobutyl, tert-butyl, cyclopropyl, cyclobutyl, cyclopentyl or cyclohexyl, wherein each of methyl, ethyl, n-propyl, isopropyl, n-butyl, isobutyl, tert-butyl, cyclopropyl, cyclobutyl, cyclopentyl and cyclohexyl is independently and optionally substituted by 1, 2, 3 or 4 substituents selected from F, Cl, Br, CN, $NH_2$, OH and $NO_2$; and
$R^4$ is H, D, F, Cl, Br, CN, methyl, ethyl, n-propyl, isopropyl, n-butyl, isobutyl, tert-butylmethoxy, ethoxy, n-propoxy, isopropoxy, n-butoxy, isobutoxy or tert-butoxy, wherein each of methyl, ethyl, n-propyl, isopropyl, n-butyl, isobutyl, tert-butylmethoxy, ethoxy, n-propoxy, isopropoxy, n-butoxy, isobutoxy and tert-butoxy is independently and optionally substituted by 1, 2, 3 or 4 substituents selected from F, Cl, Br, CN, $NH_2$, OH and $NO_2$.

9. The compound of claim 1, wherein
$R^5$ is H, $C_{1-6}$ alkyl, 3-12 membered Cyc, 3-12 membered hetCyc, $C_{6-10}$ aryl, 5-10 membered heteroaryl, $C_{6-10}$ aryl $C_{1-6}$ alkyl, (5-10 membered heteroaryl)-$C_{1-6}$ alkyl, $C_{1-6}$ alkoxy $C_{1-6}$ alkyl, $C_{6-10}$ aryloxy $C_{1-6}$ alkyl, amino $C_{1-6}$ alkyl, $C_{1-6}$ alkylamino $C_{1-6}$ alkyl, di($C_{1-6}$ alkyl) amino $C_{1-6}$ alkyl, (3-12 membered Cyc)-$C_{1-6}$ alkyl or (3-12 membered hetCyc)-$C_{1-6}$ alkyl, wherein each of $C_{1-6}$ alkyl, 3-12 membered Cyc, 3-12 membered hetCyc, $C_{6-10}$ aryl, 5-10 membered heteroaryl, $C_{6-10}$ aryl $C_{1-6}$ alkyl, (5-10 membered heteroaryl)-$C_{1-6}$ alkyl, $C_{1-6}$ alkoxy $C_{1-6}$ alkyl, $C_{6-10}$ aryloxy $C_{1-6}$ alkyl, amino $C_{1-6}$ alkyl, $C_{1-6}$ alkylamino $C_{1-6}$ alkyl, di($C_{1-6}$ alkyl)amino $C_{1-6}$ alkyl, (3-12 membered Cyc)-$C_{1-6}$ alkyl and (3-12 membered hetCyc)-$C_{1-6}$ alkyl is independently and optionally substituted by 1, 2, 3 or 4 substituents selected from F, Cl, Br, OH, $NR^6R^7$, $C_{1-6}$ alkyl, $C_{1-6}$ alkylsulfonyl, $C_{1-6}$ alkoxy, $C_{6-10}$ aryl and 5-10 membered heteroaryl;
$R^6$ is H or $C_{1-6}$ alkyl; and
$R^7$ is $C_{1-6}$ alkyl, $C_{6-10}$ aryl $C_{1-6}$ alkyl or (5-10 membered heteroaryl) $C_{1-6}$ alkyl;
or,
$R^5$ is H, $C_{1-4}$ alkyl, 3-10 membered Cyc, 3-10 membered hetCyc, phenyl, 5-10 membered heteroaryl, phenyl $C_{1-4}$ alkyl, (5-10 membered heteroaryl)-$C_{1-4}$ alkyl, $C_{1-4}$ alkoxy $C_10.4$ alkyl, phenoxy $C_{1-4}$ alkyl, amino $C_{1-4}$ alkyl, $C_{1-4}$ alkylamino $C_{1-4}$ alkyl, di($C_{1-4}$ alkyl)amino $C_{1-4}$ alkyl, (3-10 membered Cyc)-$C_{1-4}$ alkyl or hetCyc-$C_{1-4}$ alkyl, wherein each of $C_{1-4}$ alkyl, 3-10 membered Cyc, 3-10 membered hetCyc, phenyl, 5-10 membered heteroaryl, phenyl $C_{1-4}$ alkyl, (5-10 membered heteroaryl)-$C_{1-4}$ alkyl, $C_{1-4}$ alkoxy $C_{1-4}$ alkyl, phenoxy $C_{1-4}$ alkyl, amino $C_{1-4}$ alkyl, $C_{1-4}$ alkylamino $C_{1-4}$ alkyl, di($C_{1-4}$ alkyl)amino $C_{1-4}$ alkyl, (3-10 membered Cyc)-$C_{1-4}$ alkyl and hetCyc-$C_{1-4}$ alkyl is independently and optionally substituted by 1, 2, 3 or 4 substituents selected from F, Cl, Br, OH, NR⁶R⁷, C₁₋₆ alkyl, C₁₋₄ alkylsulfonyl, C₁₋₄ alkoxy, phenyl and 5-10 membered heteroaryl;

R⁶ is H or C₁₋₄ alkyl; and

R⁷ is C₁₋₄ alkyl, phenyl C₁₋₄ alkyl or (5-10 membered heteroaryl) C₁₋₄ alkyl;

or,

R⁵ is H, NH₂CH₂—, NH₂(CH₂)₂—, NH(CH₃)CH₂—, NH(CH₃)(CH₂)₂—, N(CH₃)₂CH₂—, NH(CH₃)₂(CH₂)₂—, methyl, ethyl, n-propyl, isopropyl, n-butyl, isobutyl, tert-butyl, cyclopropyl, cyclobutyl, cyclopentyl, cyclohexyl, cyclopropylmethyl, cyclopropylethyl, cyclobutylethyl, cyclobutylmethyl, cyclopentylmethyl, cyclopentylethyl, cyclohexylmethyl, cyclohexylethyl, methoxymethyl, methoxyethyl, ethoxyethyl, phenylmethyl, phenylethyl, phenyl-n-propyl, pyridylmethyl, pyridylethyl, pyridyl-n-propyl, phenoxymethyl, phenoxyethyl, phenoxy-n-propyl, azetidinyl, oxetanyl or tetrahydropyranyl, wherein each of NH₂CH₂—, NH₂(CH₂)₂—, NH(CH₃)CH₂—, NH(CH₃)(CH₂)₂—, N(CH₃)₂CH₂—, NH(CH₃)₂(CH₂)₂—, methyl, ethyl, n-propyl, isopropyl, n-butyl, isobutyl, tert-butyl, cyclopropyl, cyclobutyl, cyclopentyl, cyclohexyl, cyclopropylmethyl, cyclopropylethyl, cyclobutylethyl, cyclobutylmethyl, cyclopentylmethyl, cyclopentylethyl, cyclohexylmethyl, cyclohexylethyl, methoxymethyl, methoxyethyl, ethoxyethyl, phenylmethyl, phenylethyl, phenyl-n-propyl, pyridylmethyl, pyridylethyl, pyridyl-n-propyl, phenoxymethyl, phenoxyethyl, phenoxy-n-propyl, azetidinyl, oxetanyl and tetrahydropyranyl is independently and optionally substituted by 1, 2, 3 or 4 substituents selected from F, Cl, Br, OH, NH₂, NH(CH₃), CH₃S(=O)₂—, CH₃CH₂S(=O)₂—, CH(CH₃)₂S(=O)₂—, C(CH₃)₃S(=O)₂—, methyl, ethyl, n-propyl, isopropyl, n-butyl, isobutyl, tert-butyl, methoxy, ethoxy, n-propoxy, phenyl, pyridyl, pyrazolyl, pyrimidinyl;

R⁶ is H, methyl, ethyl, n-propyl, isopropyl, n-butyl, isobutyl or tert-butyl; and R⁷ is methyl, ethyl, n-propyl, isopropyl, n-butyl, isobutyl, tert-butyl, phenylmethyl, phenylethyl, phenyl-n-propyl, imidazolylmethyl, pyrazolylmethyl, pyridylmethyl, pyridylethyl, pyrimidinylmethyl or pyrimidinylethyl.

10. The compound of claim 1 having Formula (I-1), or a stereoisomer, a geometric isomer, a tautomer, an N-oxide, a solvate, or a pharmaceutically acceptable salt thereof,

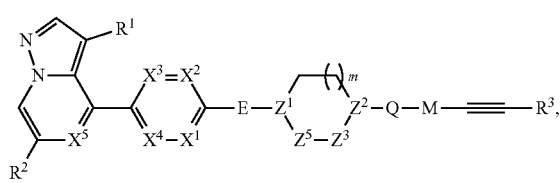

(I-1)

wherein, each of Z and Z² is independently CH or N;

each of Z³, Z⁵ is independently a bond, CH₂, O, S, NH, C=O, S=O or S(=O)₂;

m is 0, 1 or 2;

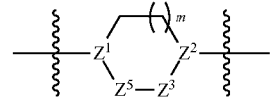

is optionally substituted by 1, 2, 3 or 4 substituents selected from F, Cl, Br, oxo, NR⁵R⁶, R⁵O—, R⁵(C=O)NR⁶—, NR⁵R⁶C₁₋₆ alkyl, NR⁵R⁶(C=O)C₁₋₆ alkoxy C₁₋₆ alkyl, NR⁶R⁷C₁₋₆ alkoxy, NR⁶R⁷C₁₋₆ alkoxy C₁₋₆ alkyl, C₁₋₆ alkyl, C₁₋₆ haloalkyl, C₁₋₆ hydroxyalkyl, 3-10 membered Cyc, 3-10 membered hetCyc, 3-10 membered hetCyc-C₁₋₆ alkyl, C₁₋₆ alkoxy C₁₋₆ alkyl, 3-10 membered hetCyc-C₁₋₆ alkoxy C₁₋₆ alkyl, C₃₋₆ cycloalkylidene, 3-6 membered heterocyclylidene.

11. The compound of claim 10, wherein

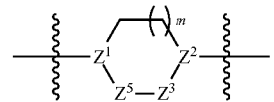

is one of the following-subformulae:

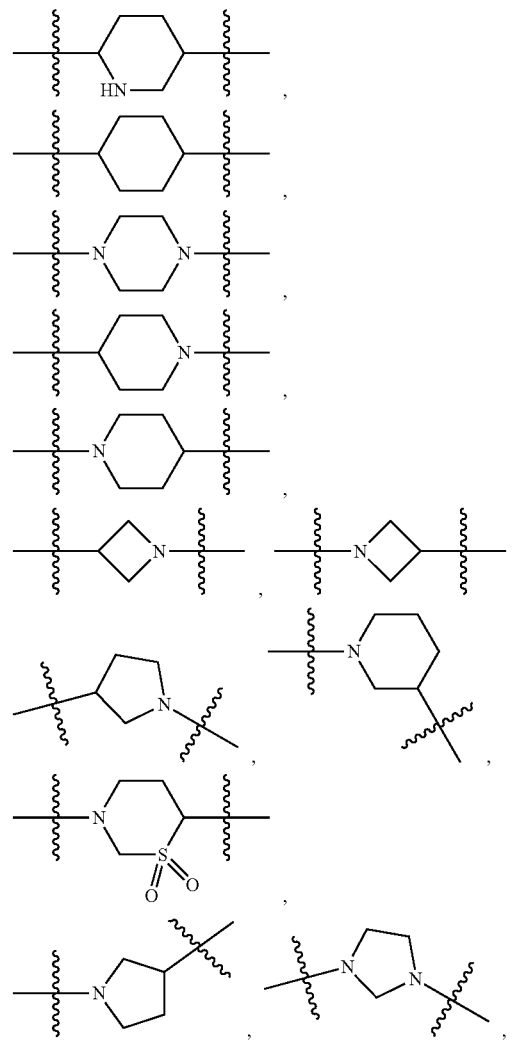

-continued

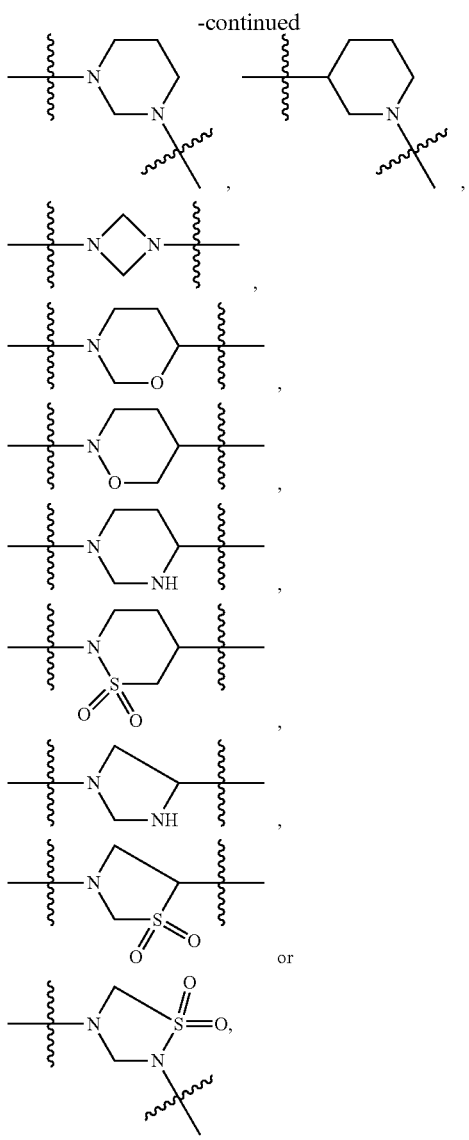

wherein each sub-formula of

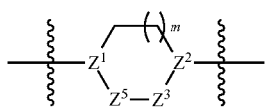

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl (C=O)NH—, pyridylmethyl(C=O)NH—, $CH_3CH_2$(C=O)NH—, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene or pyrazolylidene.

12. The compound of claim 1 having formula (I-2), or a stereoisomer, a geometric isomer, a tautomer, an N-oxide, a solvate, or a pharmaceutically acceptable salt thereof,

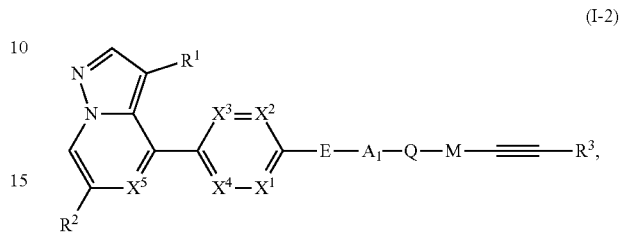

(I-2)

wherein, $A_1$ is one of the following sub-formulae:

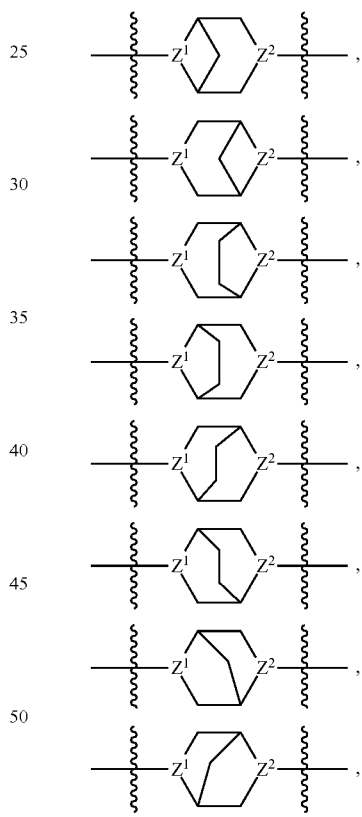

each Z and $Z^2$ is independently CH or N;

each sub-formulae of $A_1$ is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene, 3-6 membered heterocyclylidene.

13. The compound of claim 12, wherein A₁ is a one of the following sub-formulae:

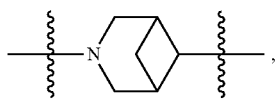

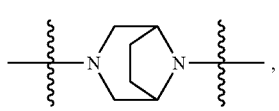

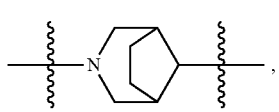

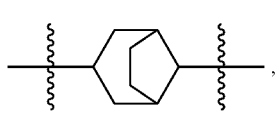

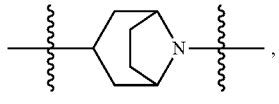

-continued

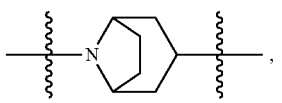

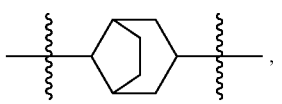

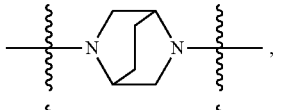

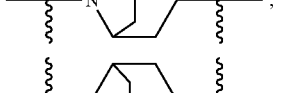

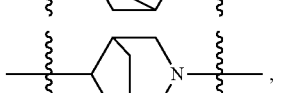

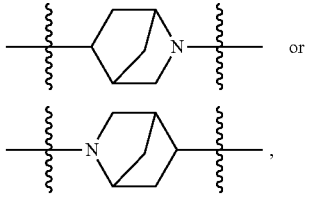 or wherein each sub-formula of A₁ is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH$—, benzyl (C=O)NH—, pyridylmethyl (C=O)NH—, $CH_3CH_2$(C=O)NH—, methoxy, ethoxy, n-propoxy, isopropoxy, n-butoxy, isobutoxy, phenoxy-$(CH_2)_2O$—, $NH_2(CH_2)_2O$—, $N(CH_3)_2(CH_2)_2O$—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene or pyrazolidinylidene.

14. The compound claim 1 having Formula (I-3) or (I-4), or a stereoisomer, a geometric isomer, a tautomer, an N-oxide, a solvate, or a pharmaceutically acceptable salt thereof,

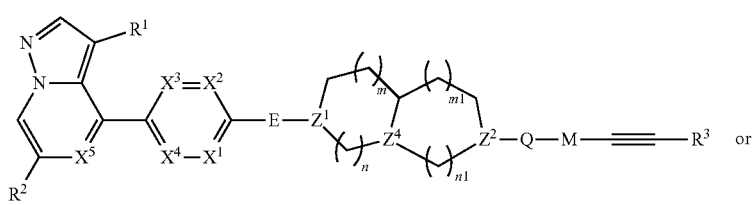

(I-3)

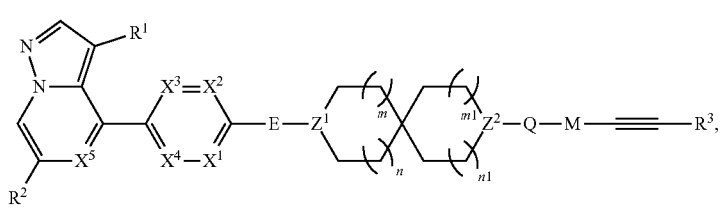

(I-4)

wherein each $Z^1$, $Z^2$ and $Z^4$ is independently CH or N;
each m is 0, 1, or 2;
each n, m1 and n1 is independently 0 or 1;
each of

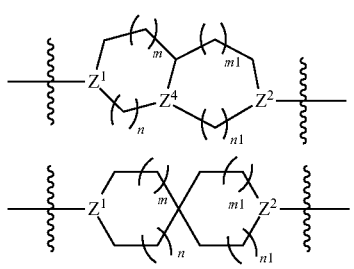

is independently and optionally substituted by 1, 2, 3 or 4 substituents selected from F, Cl, Br, oxo, $NR^5R^6$, $R^5O-$, $R^5(C=O)NR^6-$, $NR^5R^6C_{1-6}$ alkyl, $NR^5R^6(C=O)C_{1-6}$ alkoxy $C_{1-6}$ alkyl, $NR^6R^7C_{1-6}$ alkoxy, $NR^6R^7C_{1-6}$ alkoxy $C_{1-6}$ alkyl, $C_{1-6}$ alkyl, $C_{1-6}$ haloalkyl, $C_{1-6}$ hydroxyalkyl, 3-10 membered Cyc, 3-10 membered hetCyc, 3-10 membered hetCyc-$C_{1-6}$ alkyl, $C_{1-6}$ alkoxy $C_{1-6}$ alkyl, 3-10 membered hetCyc-$C_{1-6}$ alkoxy $C_{1-6}$ alkyl, $C_{3-6}$ cycloalkylidene, 3-6 membered heterocyclylidene.

15. The compound of claim 14, wherein

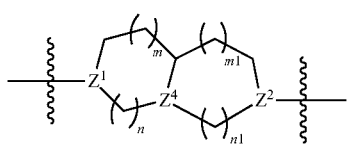

is one of the following sub-formulae:

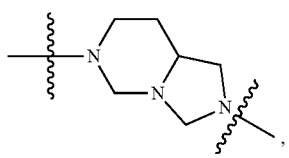

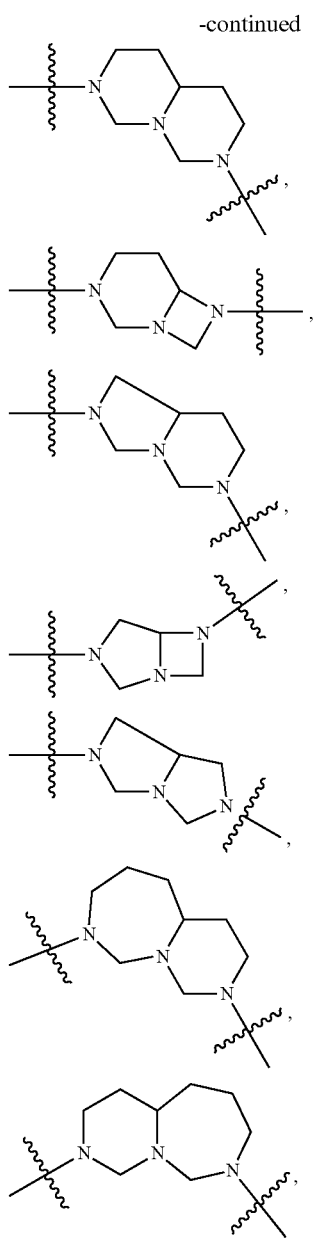

-continued

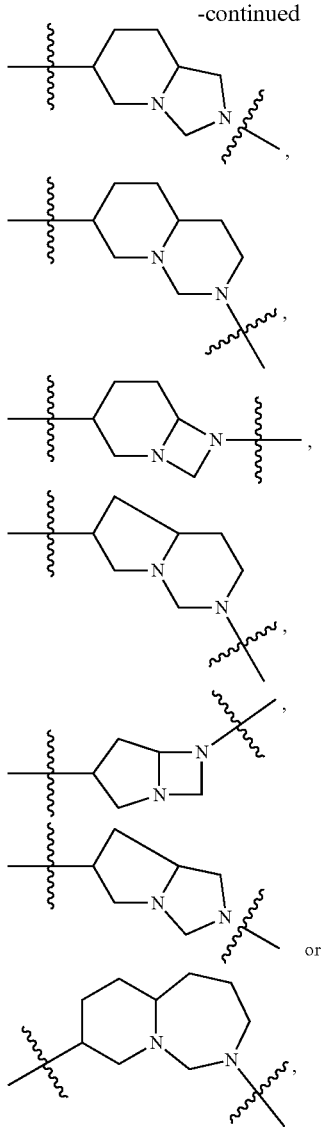

Wherein each sub-formulae of

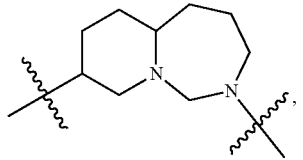

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl $(C=O)NH-$, pyridylmethyl $(C=O)NH-$, $CH_3CH_2(C=O)NH-$, methoxy, ethoxy, n-propoxy, isopropoxy, n-butoxy, isobutoxy, phenoxy-$(CH_2)_2O-$, $NH_2(CH_2)_2O-$, $N(CH_3)_2(CH_2)_2O-$, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene and pyrazolylidene;

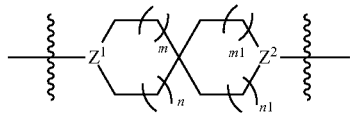

is one of the following sub-formulae:

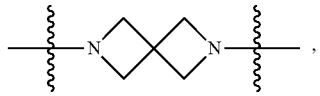

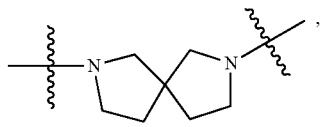

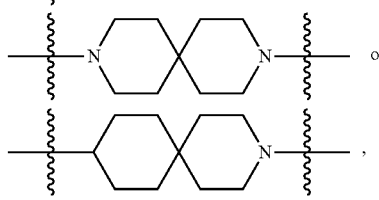

or

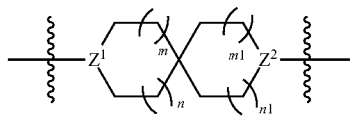

wherein each sub-formulae of

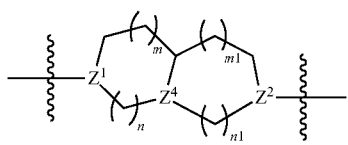

is independently and optionally substituted by 1, 2, 3 or 4 substituents selected from F, Cl, Br, oxo, $NH_2$, $NHCH_3$, $NH(CH_2)_3CH_3$, $N(CH_3)_2$, benzyl $OCH_2NH-$, benzyl $(C=O)NH-$, pyridylmethyl $(C=O)NH-$, $CH_3CH_2(C=O)NH-$, methoxy, ethoxy, n-propoxy, isopropoxy, n-butoxy, isobutoxy, phenoxy-(CH$_2$)$_2$O—, NH$_2$(CH$_2$)$_2$O—, N(CH$_3$)$_2$(CH$_2$)$_2$O—, 1-ethylcyclopropylmethyl, fluoropyridylethyl, cyclopropyl, cyclobutyl, cyclopentyl, cyclohexyl, pyrrolidinyl, pyrazolidinyl, piperidinyl, morpholinyl, piperazinyl, methyl, ethyl, propyl, monofluoromethyl, difluoromethyl, trifluoromethyl, monochloromethyl, dichloromethyl, trichloromethyl, 1,2-dichloroethyl, 1,2-difluoroethyl, hydroxymethyl, hydroxyethyl, pyrrolidinylidene, methoxymethyl, methoxyethyl, ethoxymethyl, cyclopropylidene, cyclobutylidene, cyclopentylidene, cyclohexylidene, azetidinylidene, oxetanylidene or pyrazolylidene.

16. The compound of claim 1 having one of the following structures, or a stereoisomer, a geometric isomer, a tautomer, an N-oxide, a solvate, or a pharmaceutically acceptable salt thereof,

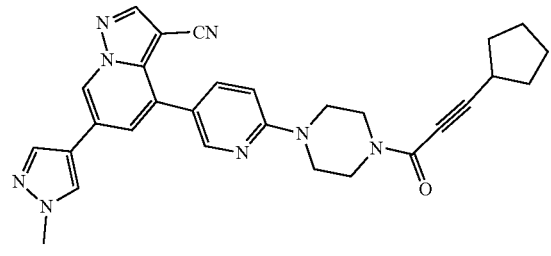
(10)
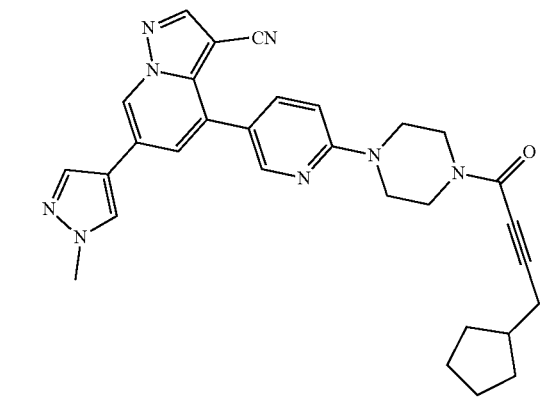
(11)
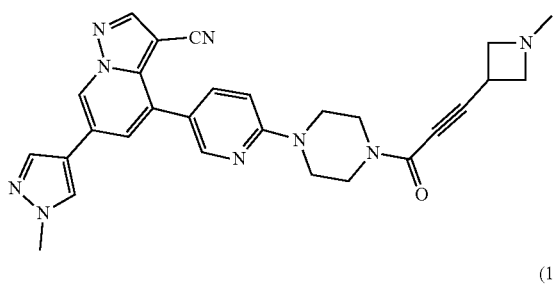
(12)
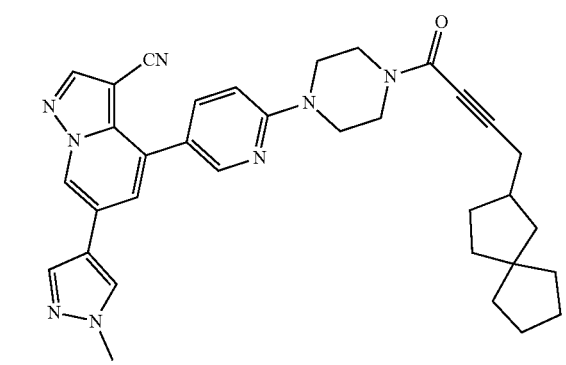
(13)
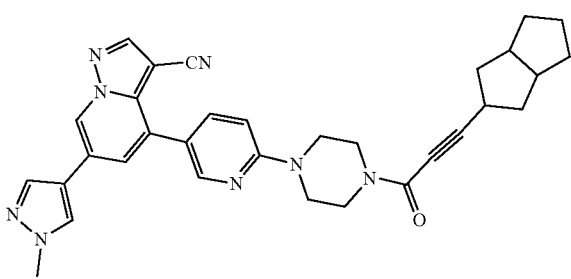
(14)
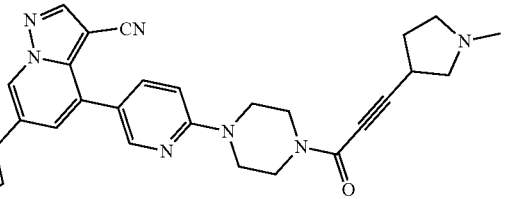
(15)
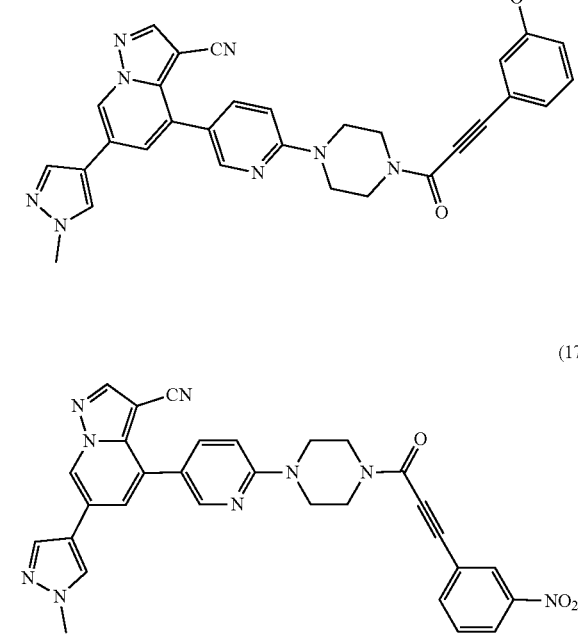
(16)
(17)
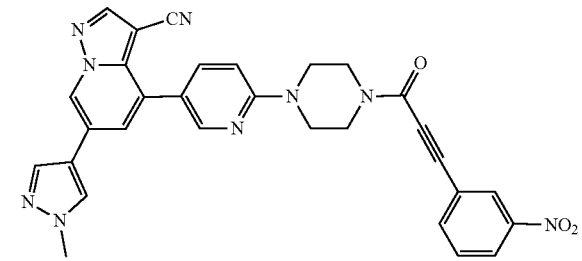
(18)
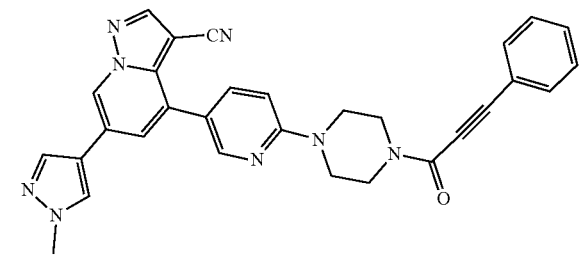
(19)
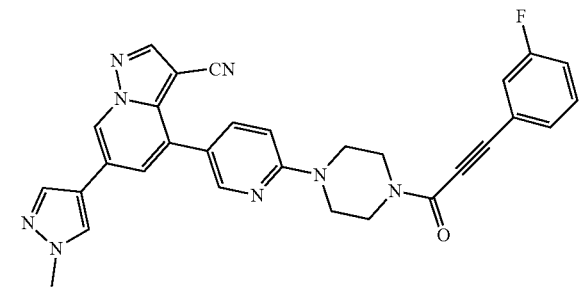

-continued
(20)
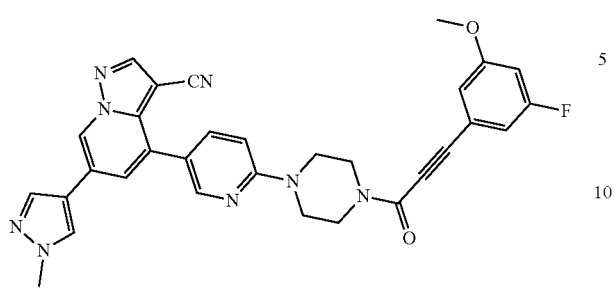
(21)
(22)
(23)
(24)
-continued
(25)
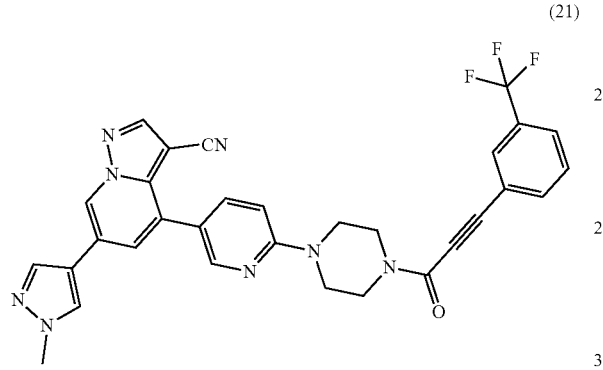
(26)
(27)
(28)
(29)

(30)
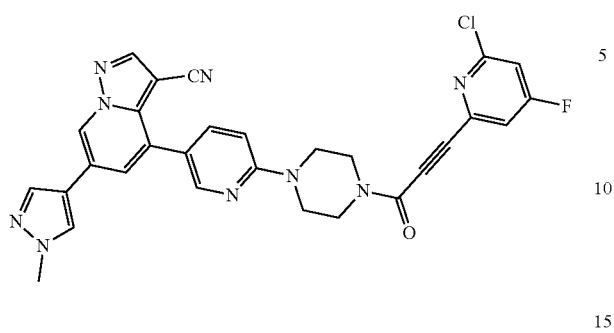
(35)
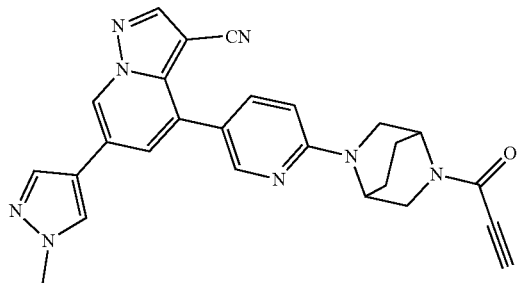
(31)
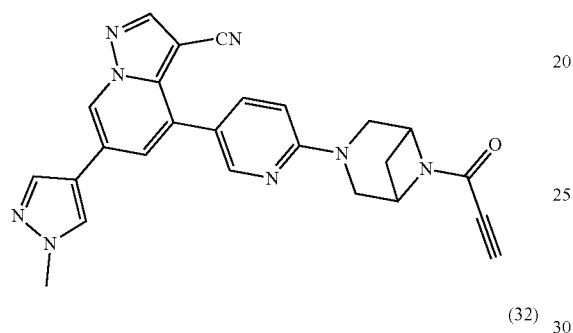
(36)
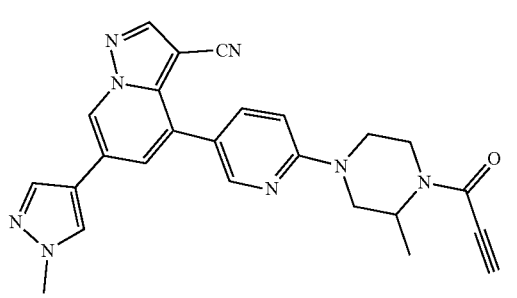
(32)
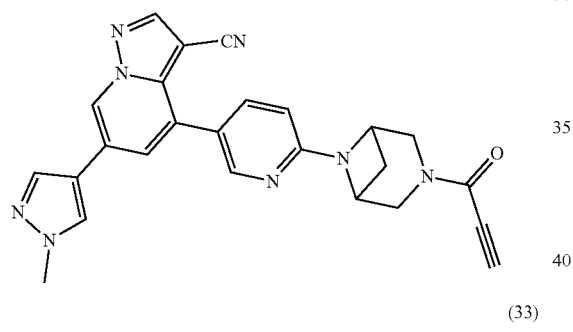
(37)
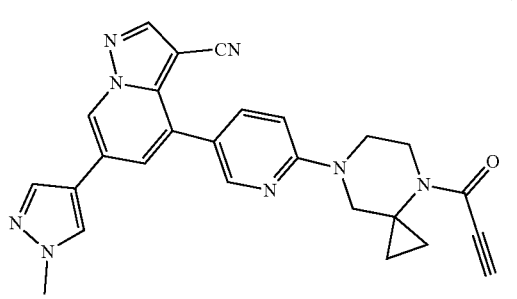
(33)
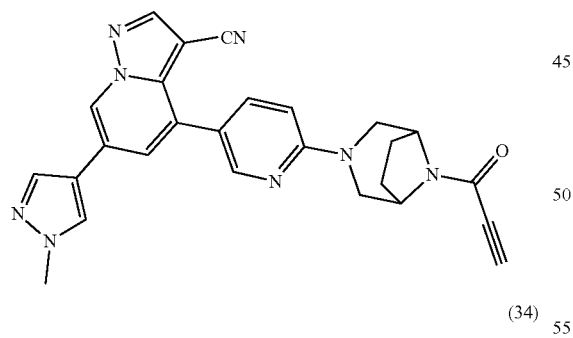
(38)
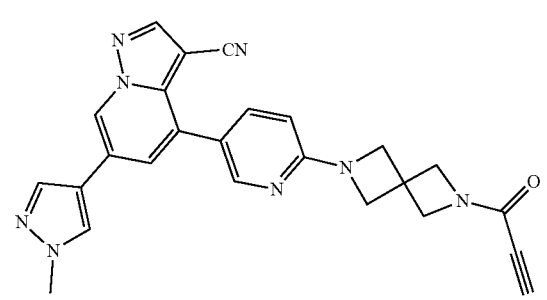
(34)
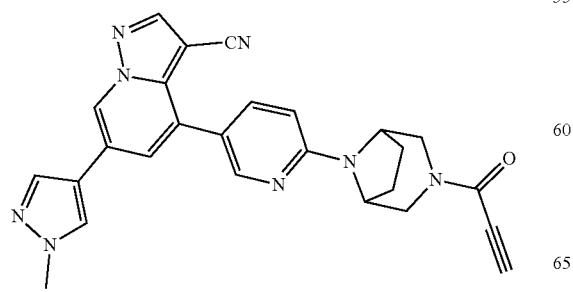
(39)
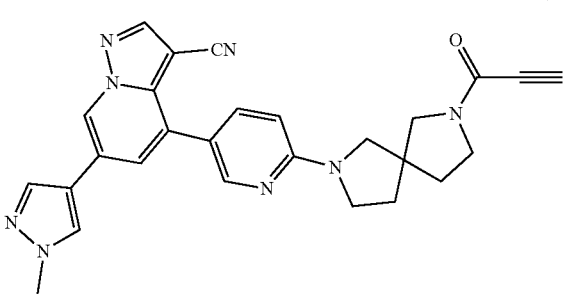

-continued
(40)
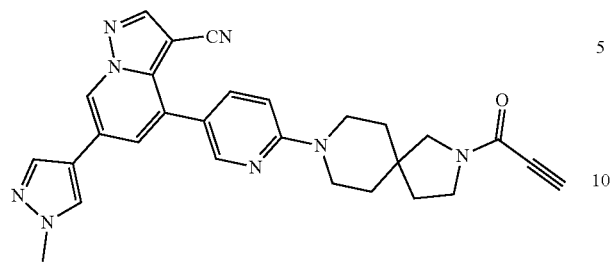
(41)
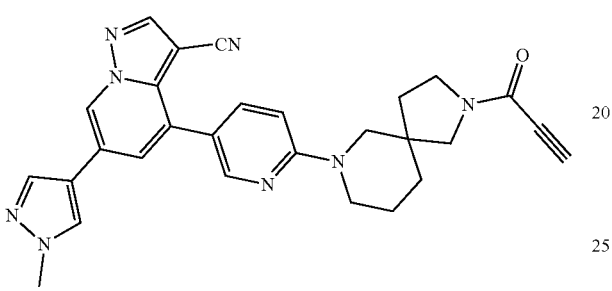
(42)
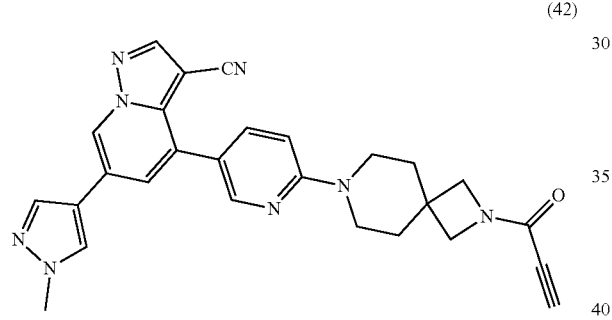
(43)
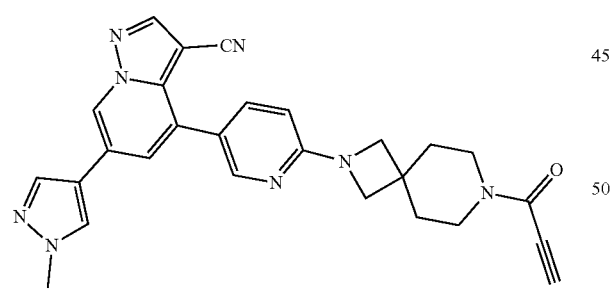
(44)
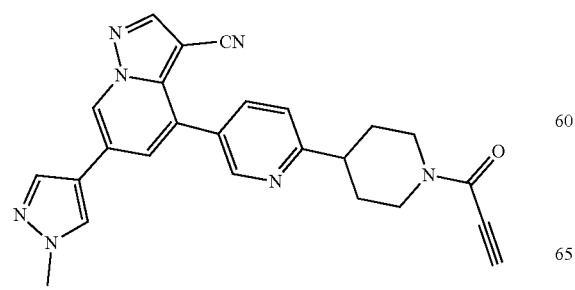
-continued
(45)
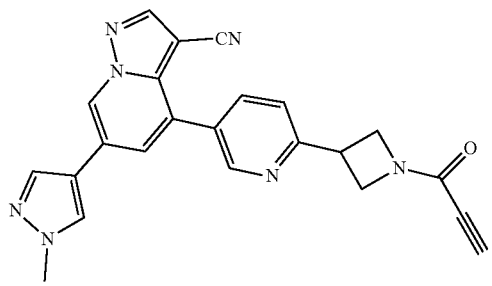
(46)
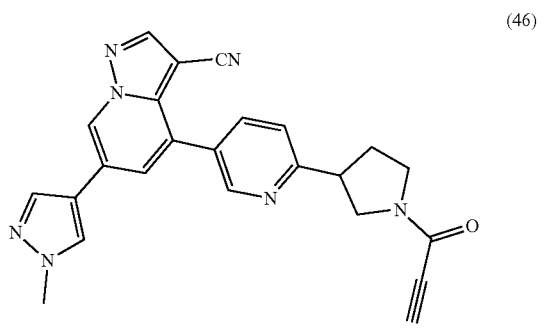
(47)
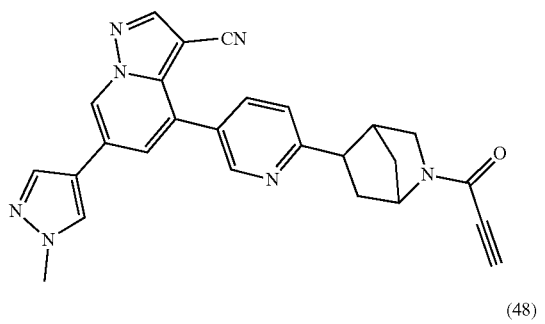
(48)
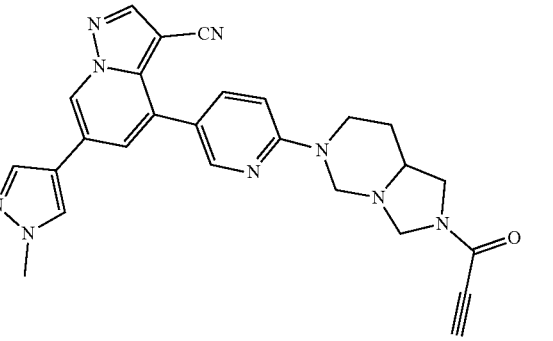
(49)
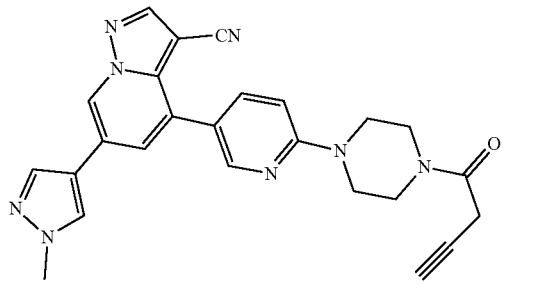

-continued
(50)
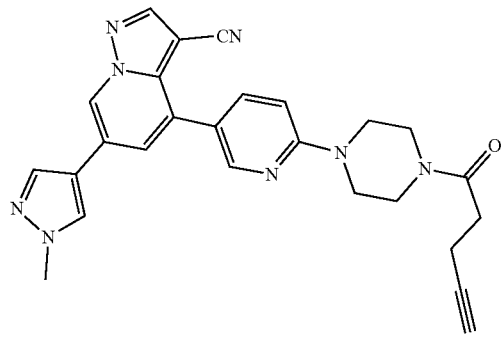
(51)
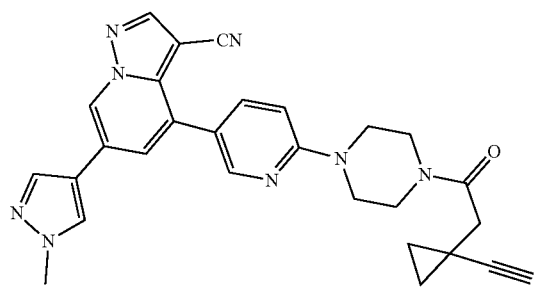
(52)
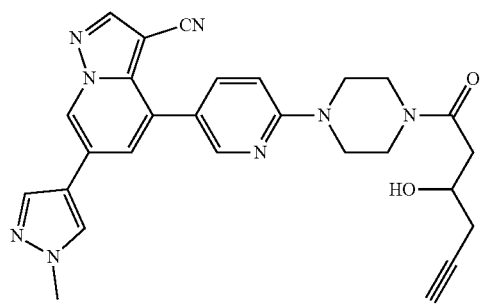
(53)
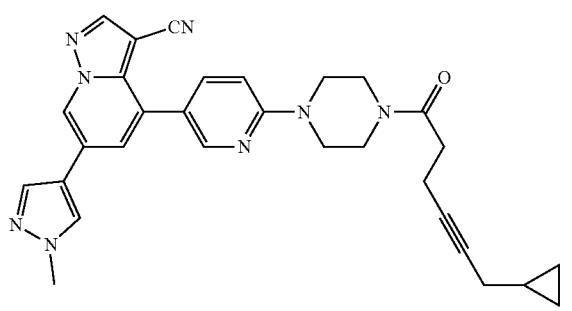
-continued
(54)
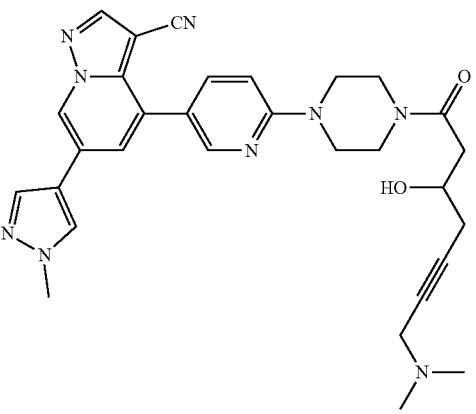
(55)
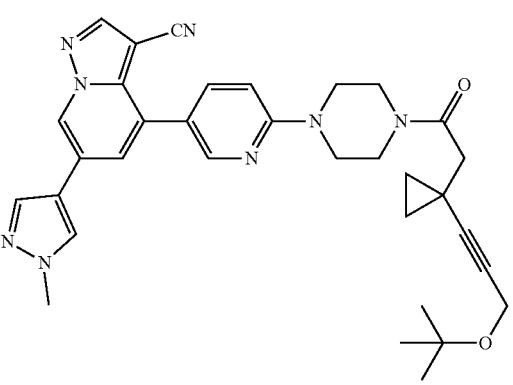
(56)
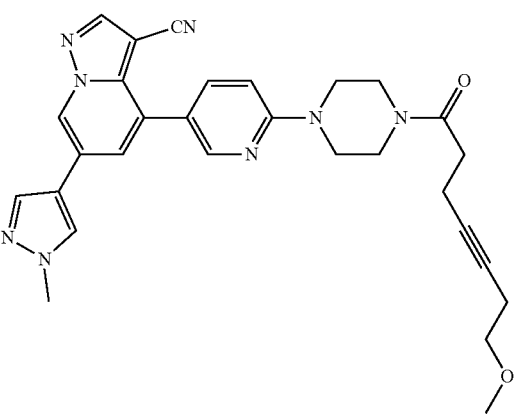

-continued
(57)
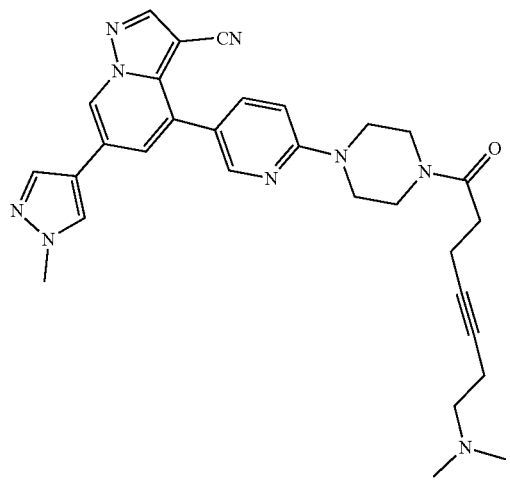
(58)
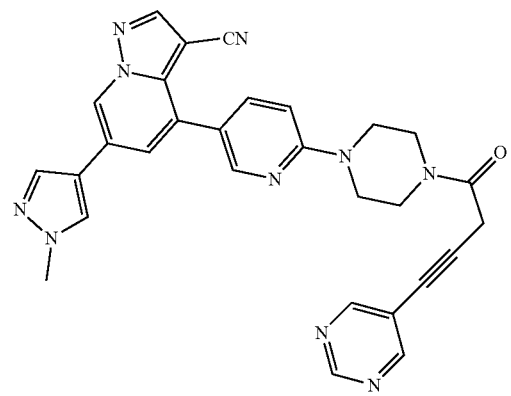
(59)
(60)
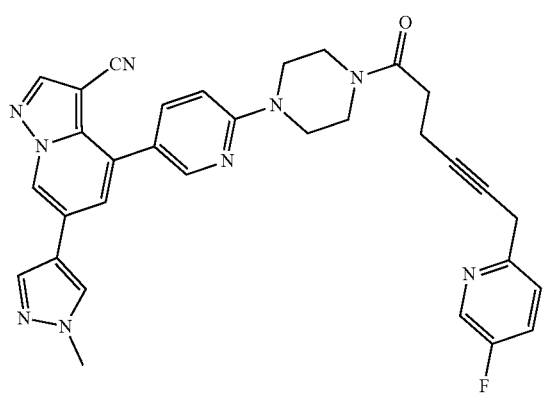
(61)
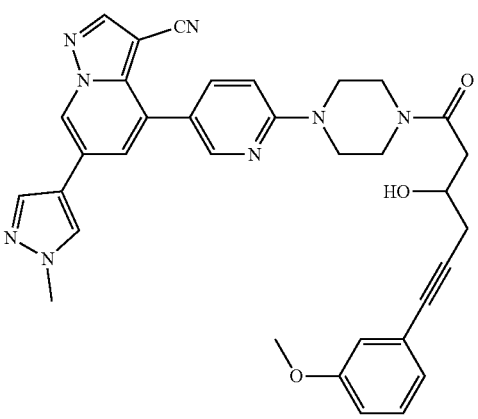
(62)
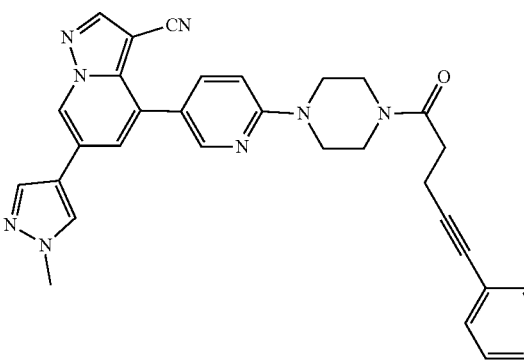
(63)
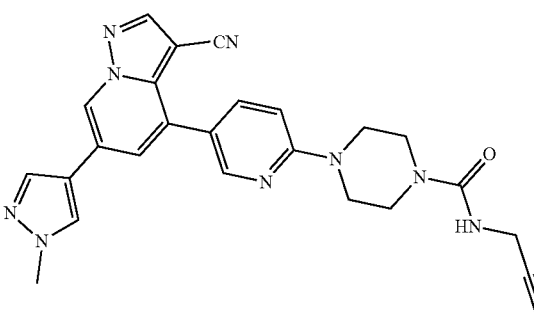

(64)
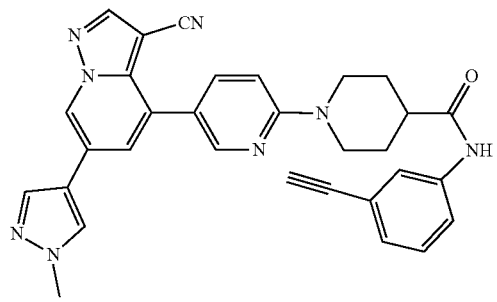
(65)
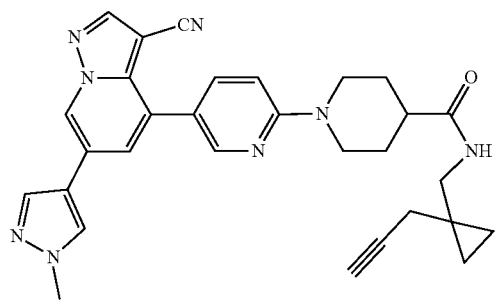
(66)
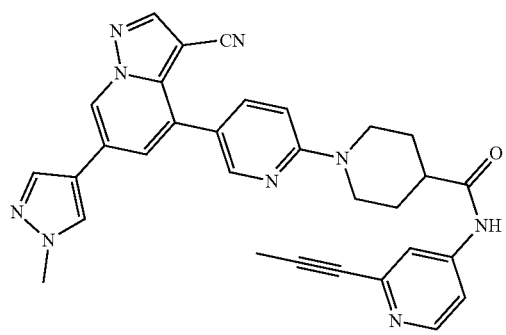
(67)
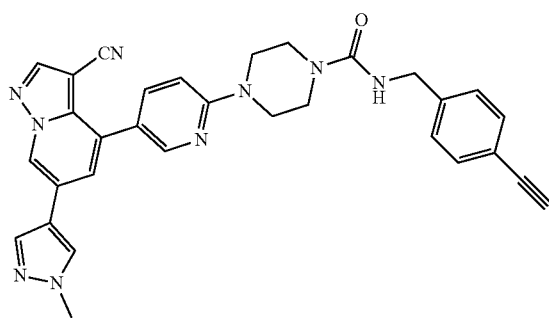
(68)
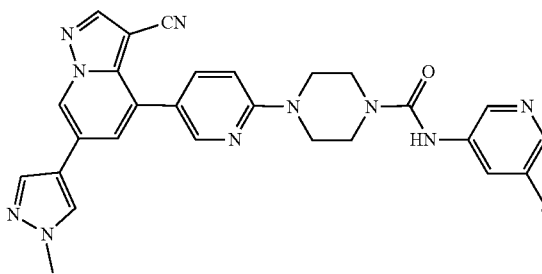
(69)
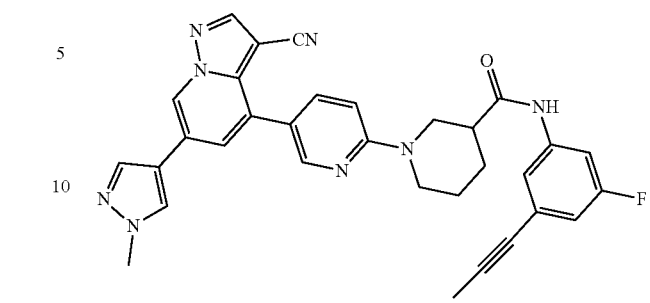
(70)
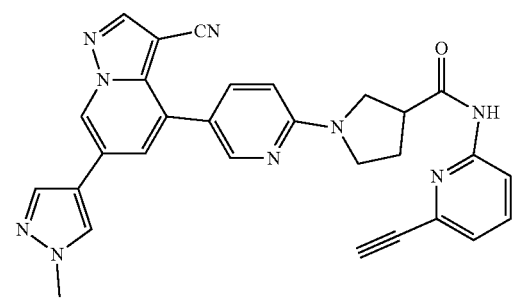
(71)
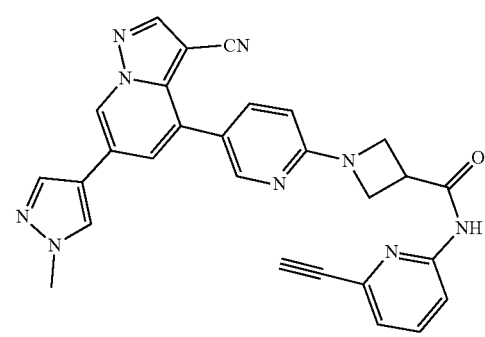
(72)
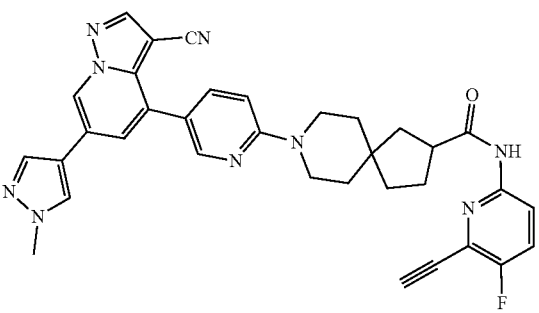

-continued

(73)
(74)
(75)
(76)
(77)
(78)
(79)
(80)
(81)
(82)

(83)
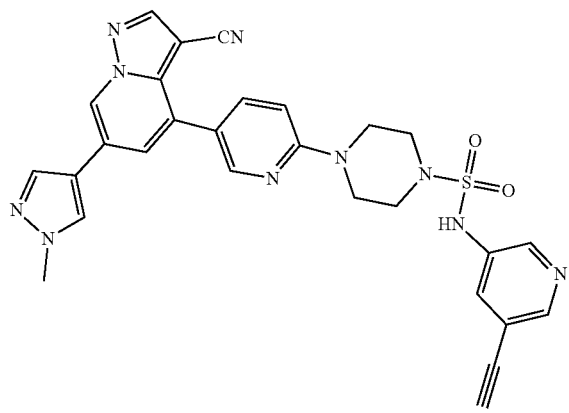
(84)
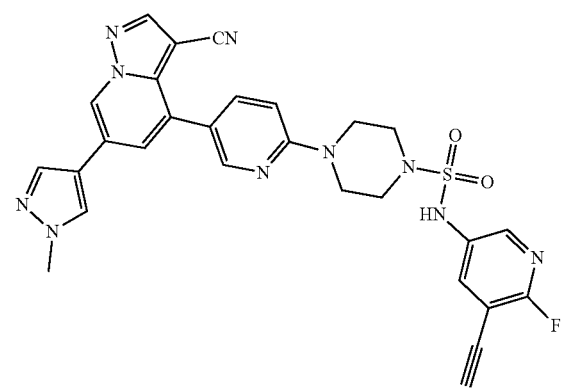
(85)
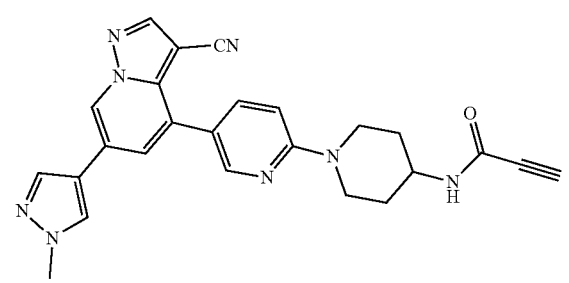
(86)
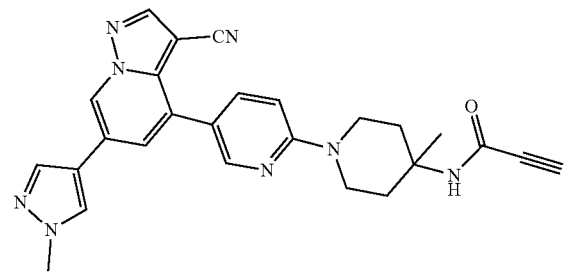
(87)
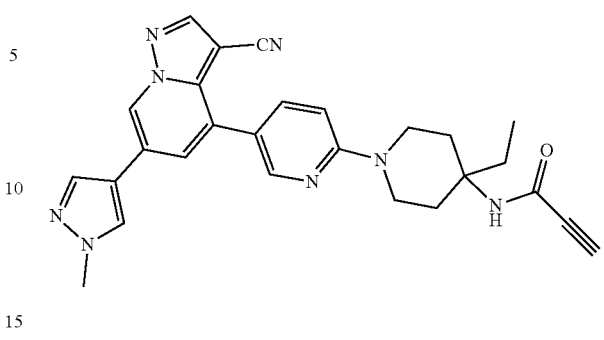
(88)
(89)
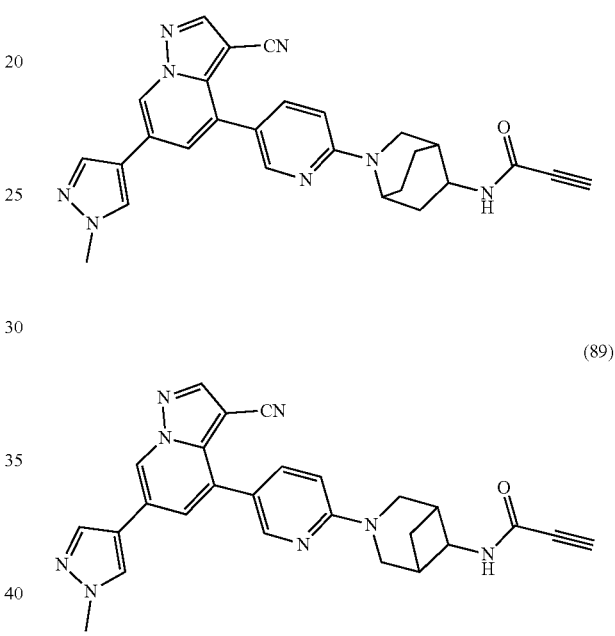
(90)
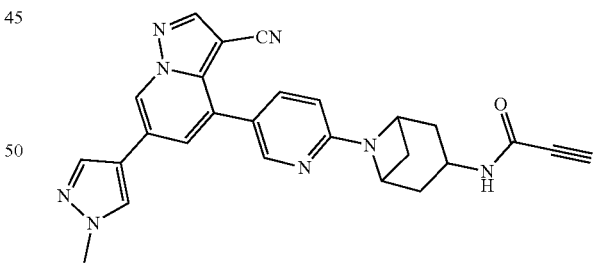
(91)
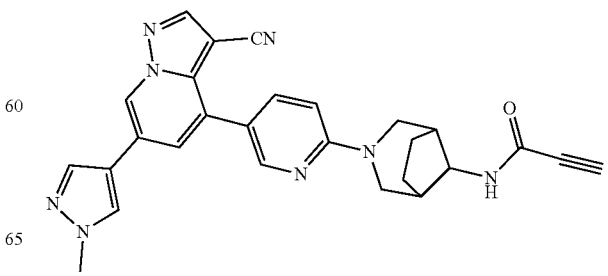

-continued
(92)
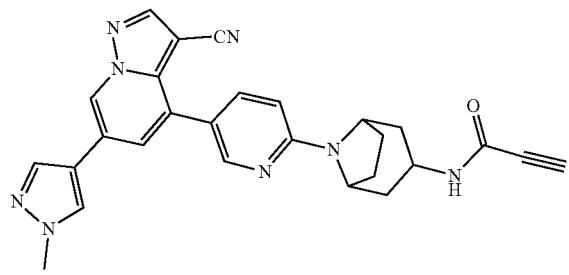
(93)
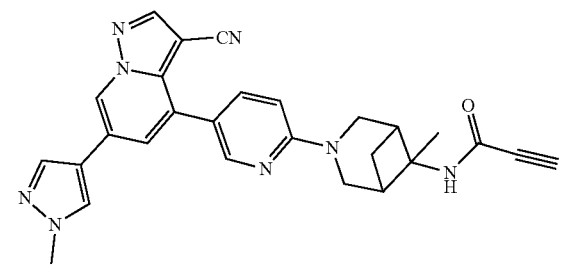
(94)
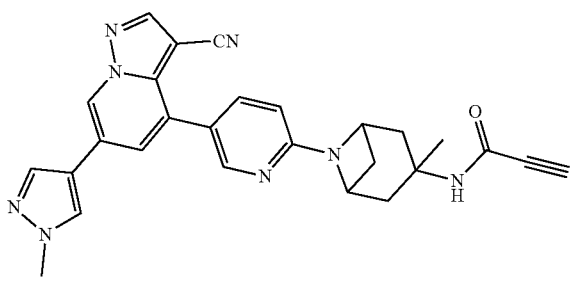
(95)
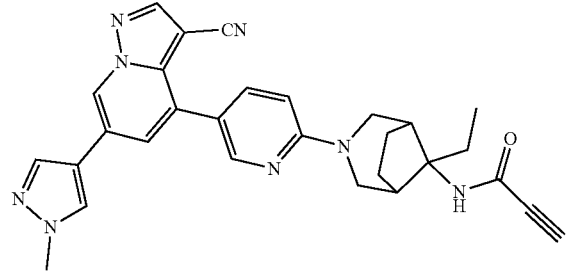
(96)
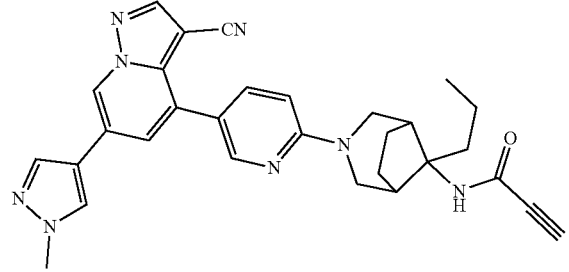
-continued
(97)
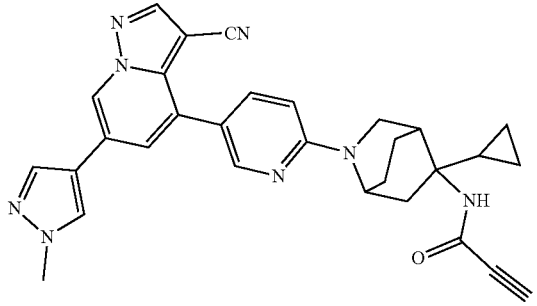
(98)
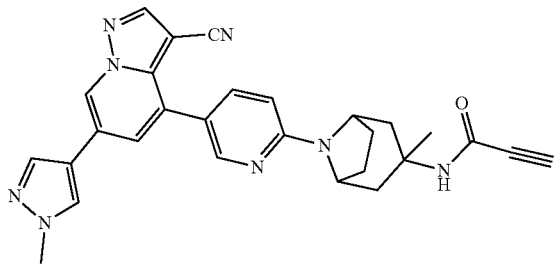
(99)
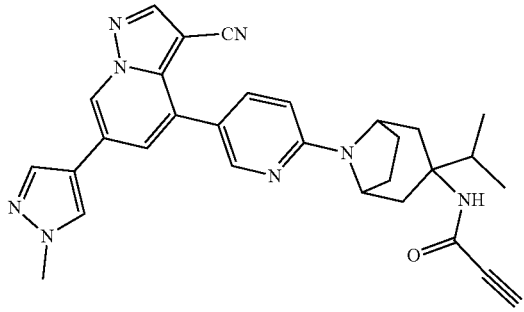
(100)
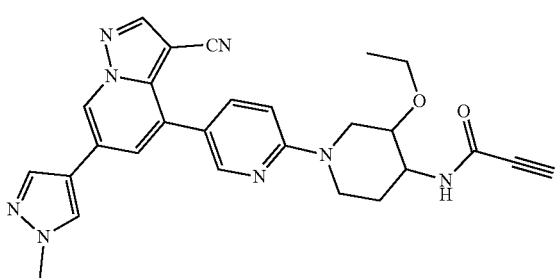
(101)
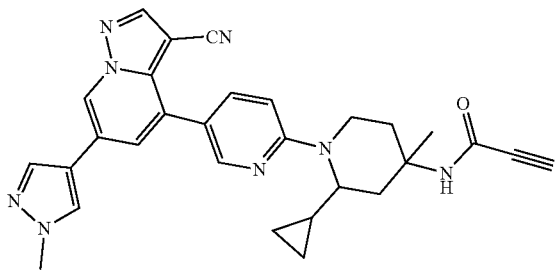

-continued
(102)
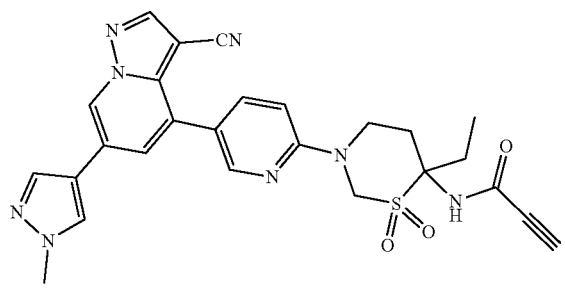
(103)
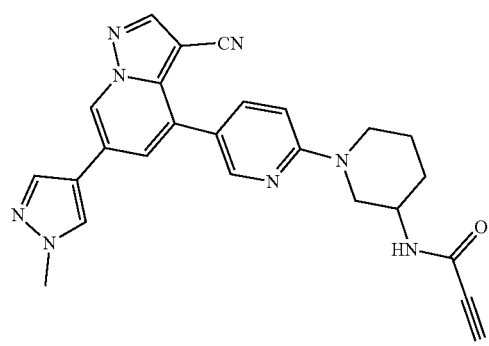
(104)
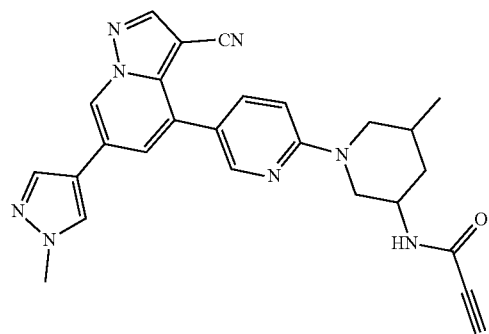
(105)
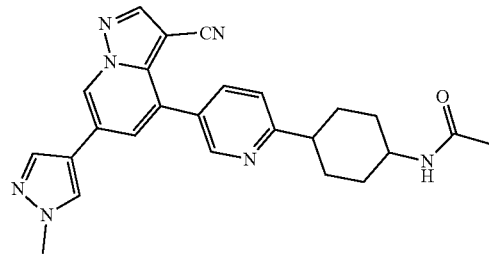
(106)
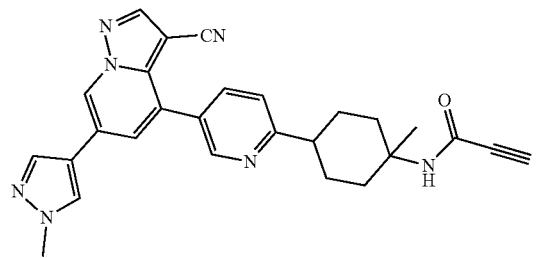
-continued
(107)
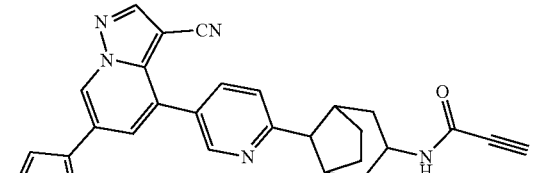
(108)
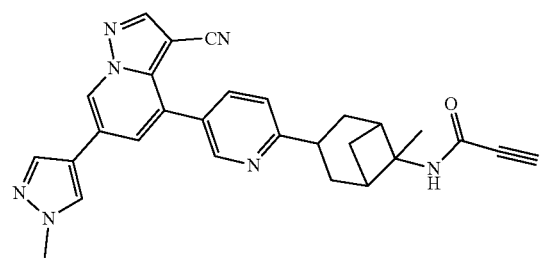
(109)
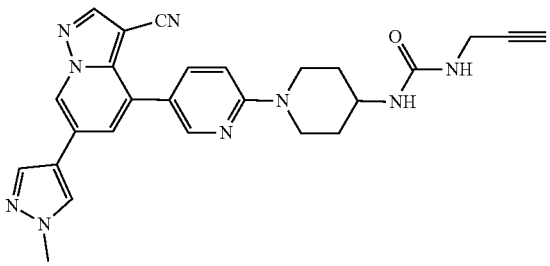
(110)
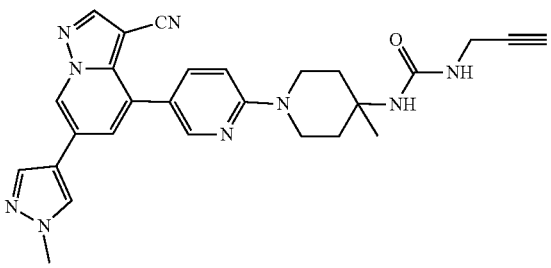
(111)
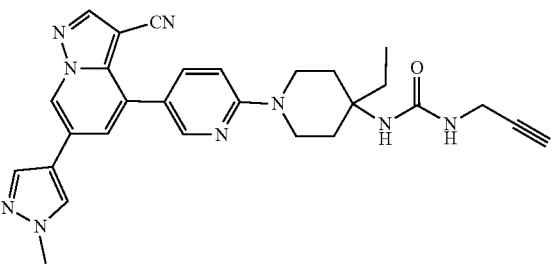

421
-continued
(112)
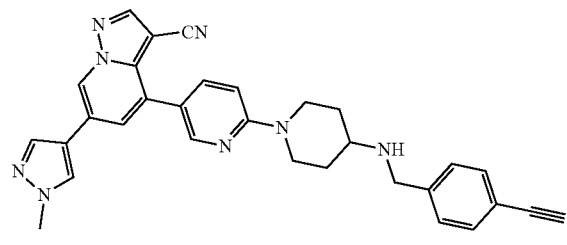
(113)
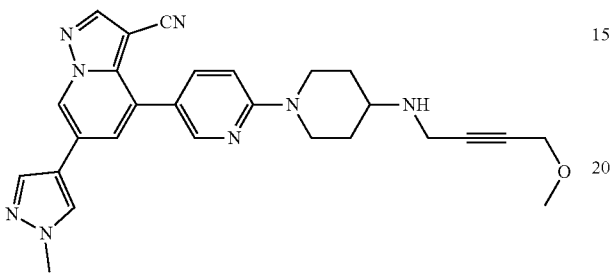
(114)
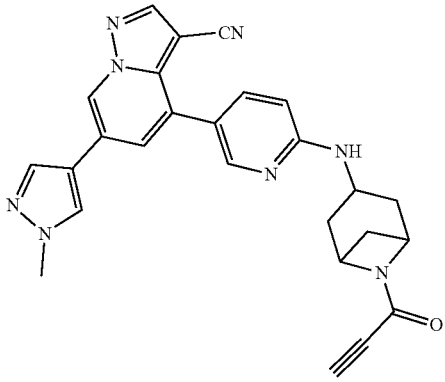
(115)
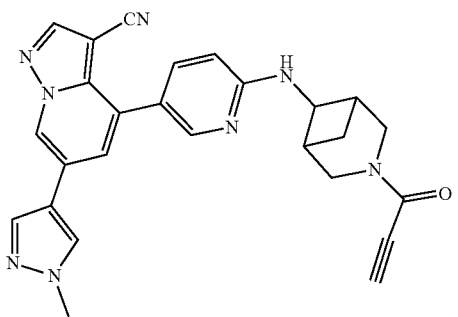
(116)
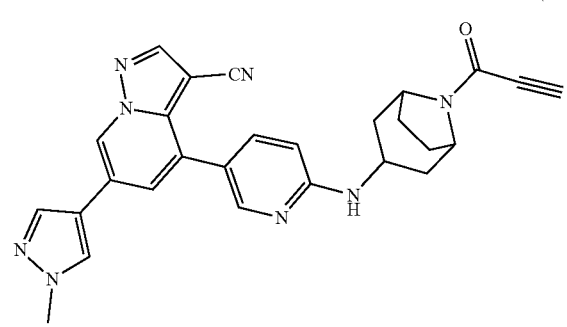
422
-continued
(117)
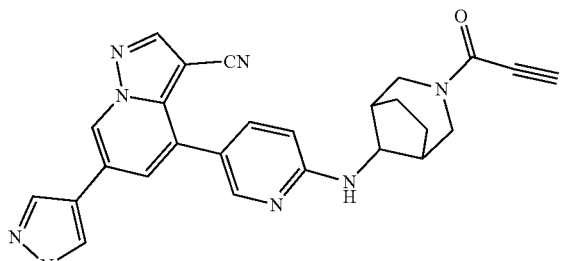
(118)
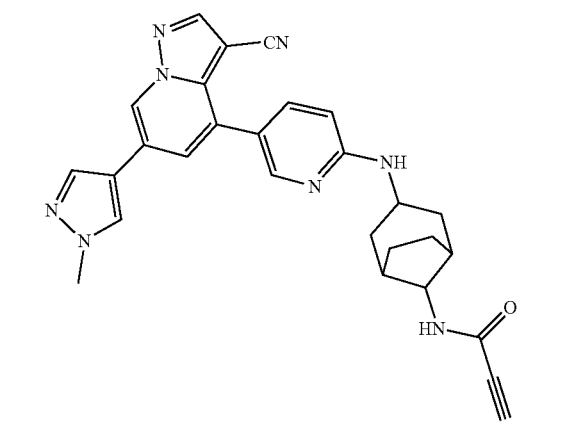
(119)
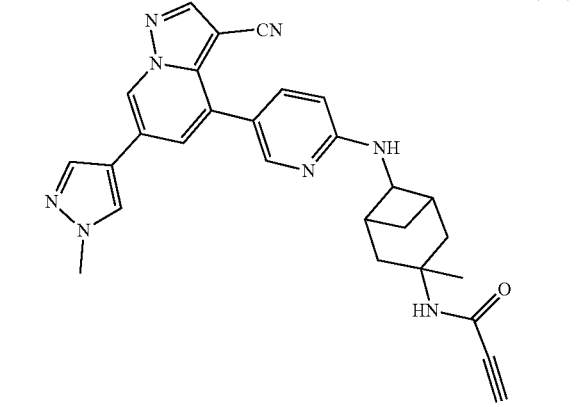
(120)
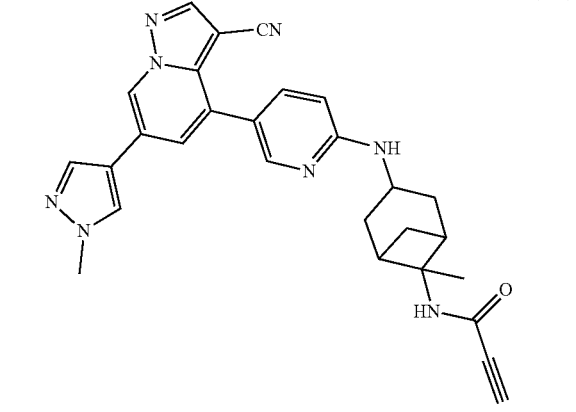

(121)
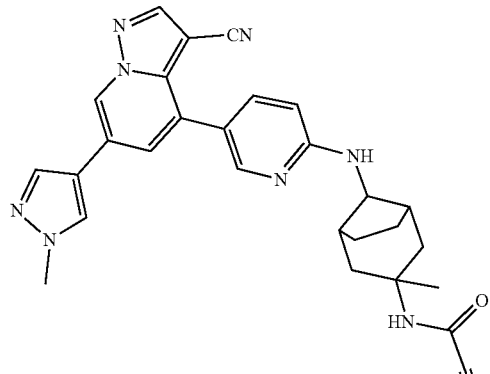
(122)
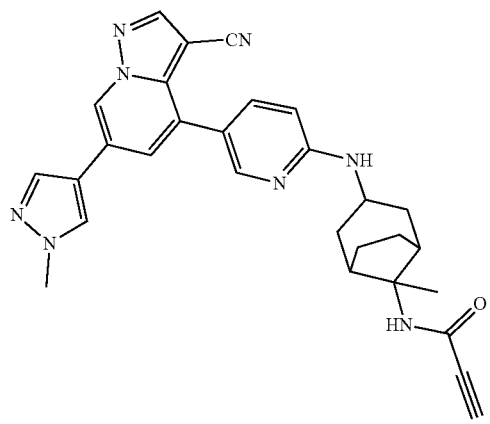
(123)
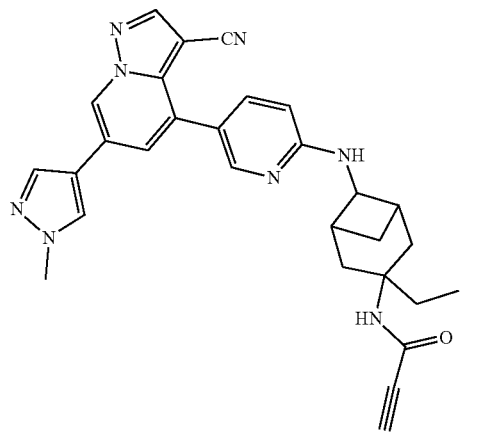
(124)
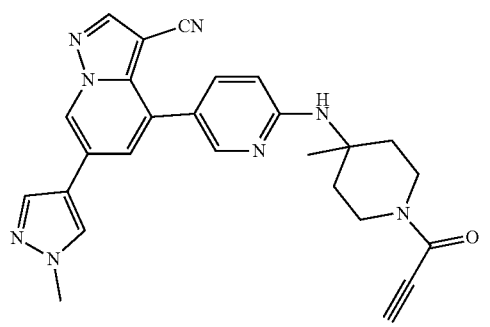
(125)
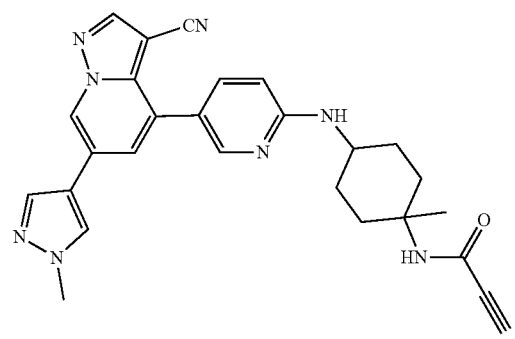
(126)
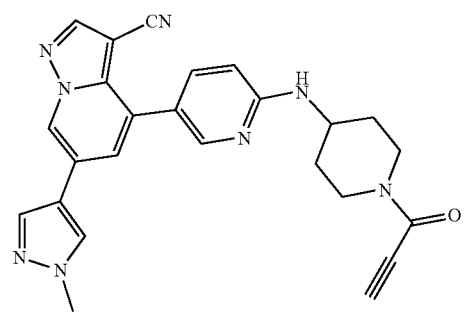
(127)
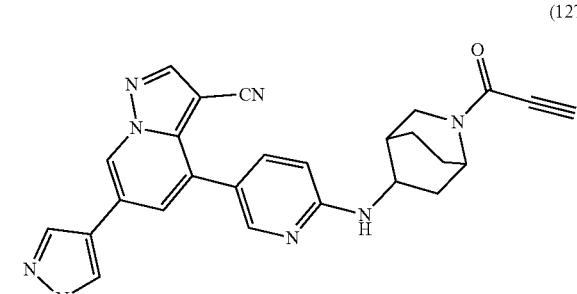
(128)
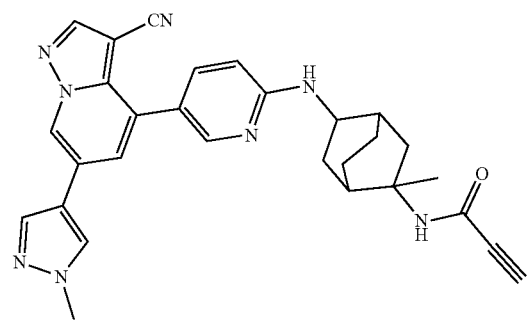

-continued
(129)
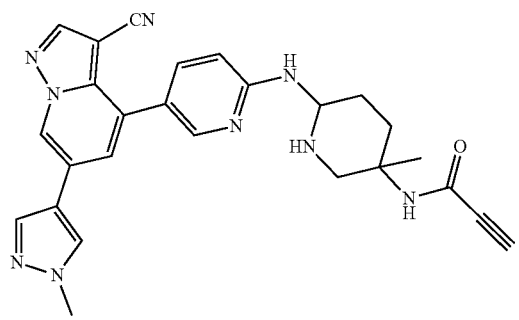
(130)
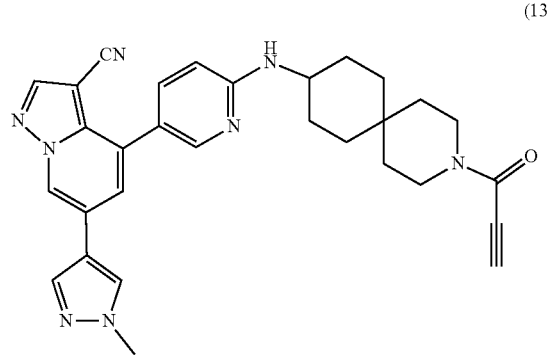
(131)
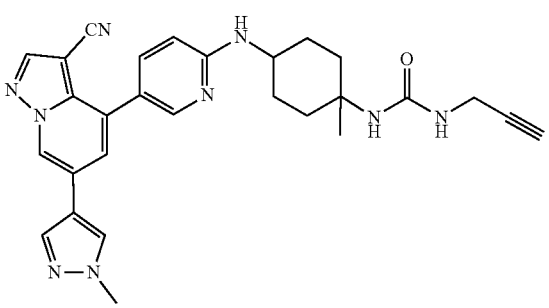
(132)
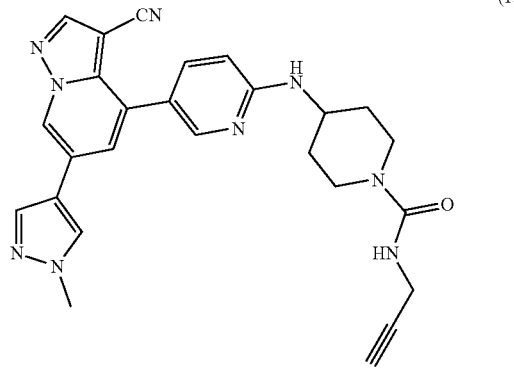
-continued
(133)
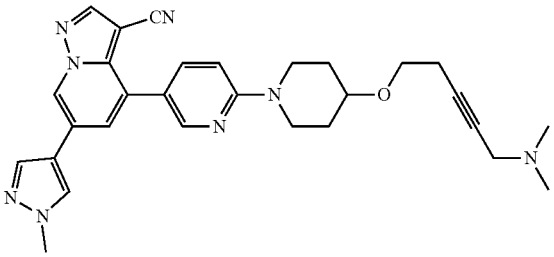
(134)
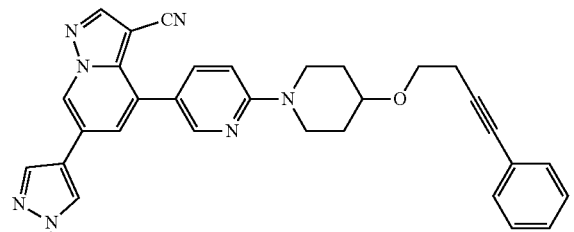
(135)
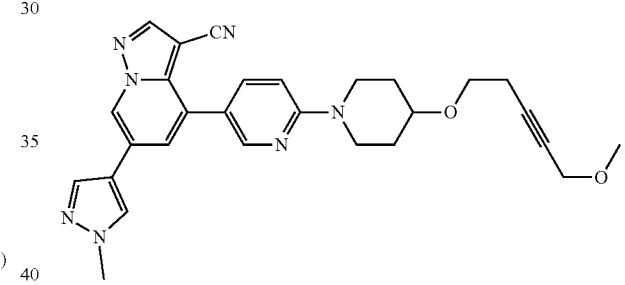
(136)
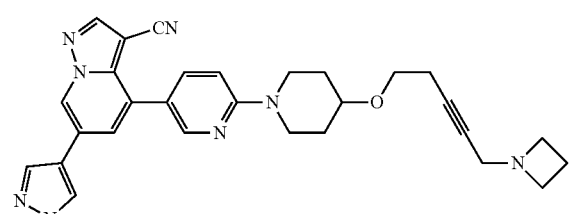
(137)
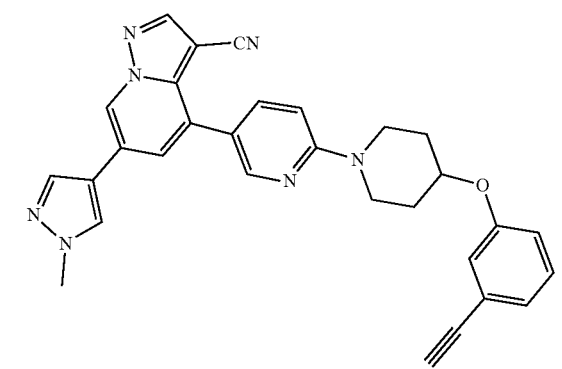

(138)
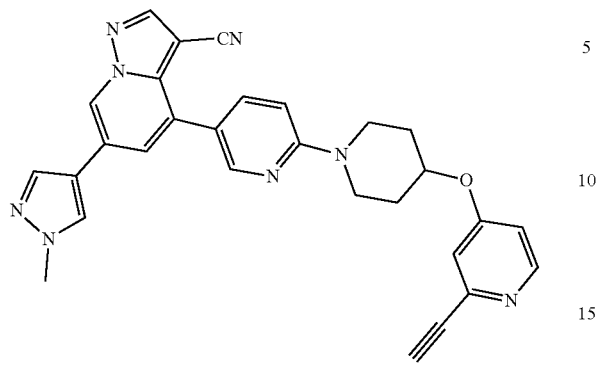
(139)
(140)
(141)
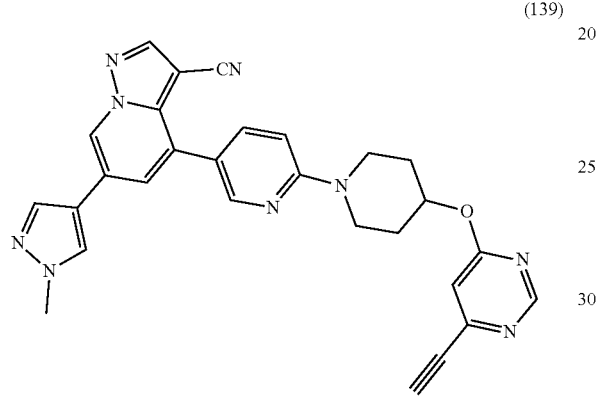
(142)
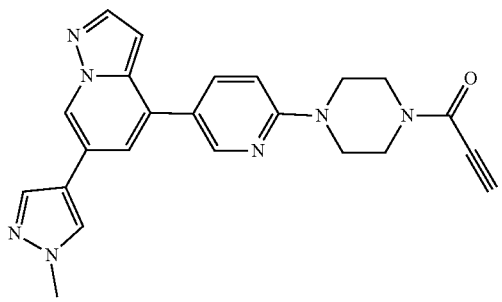
(143)
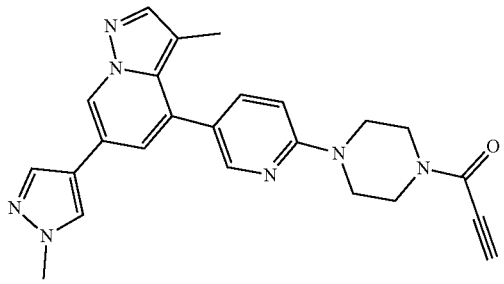
(144)
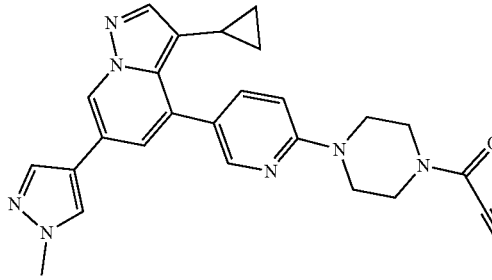
(145)
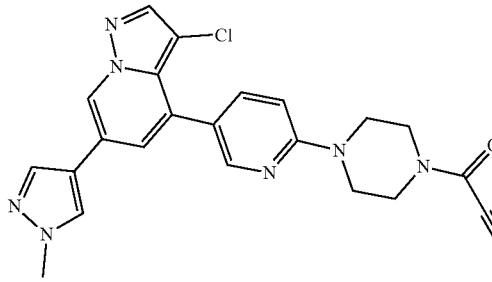
(146)
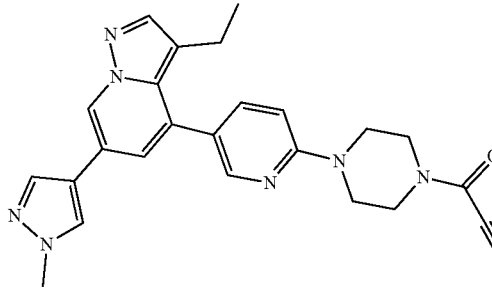

-continued
(147)
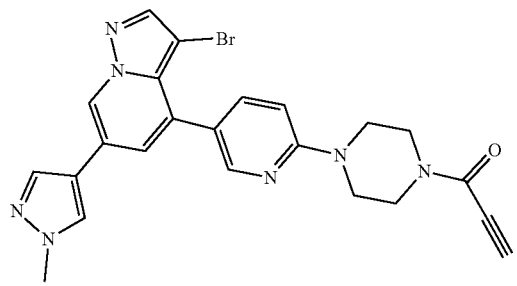
(148)
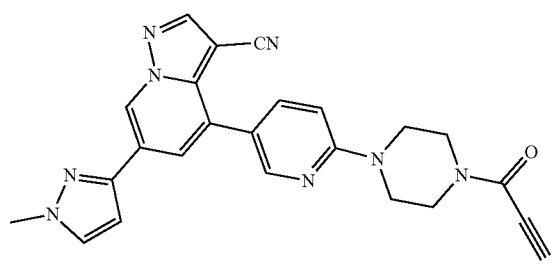
(149)
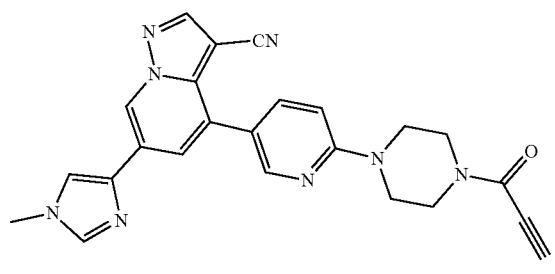
(150)
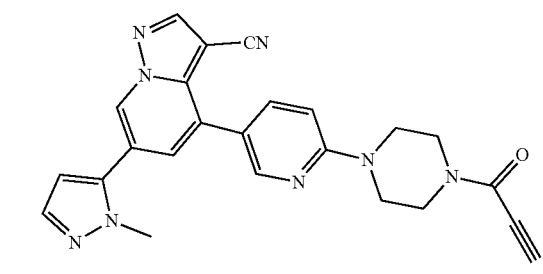
(151)
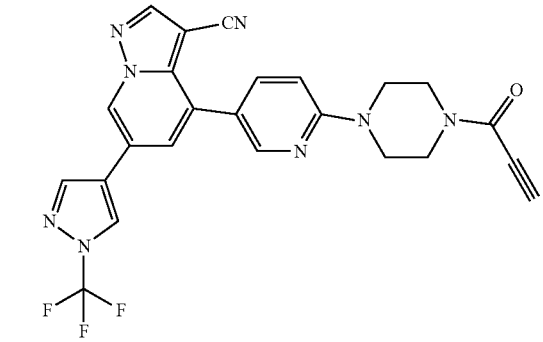
-continued
(152)
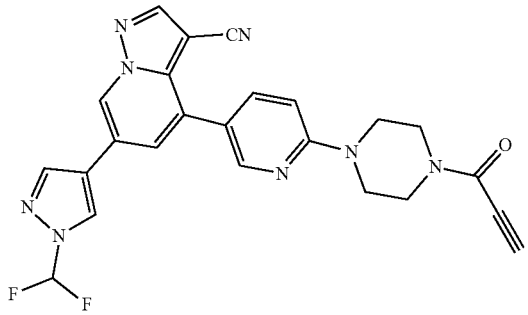
(153)
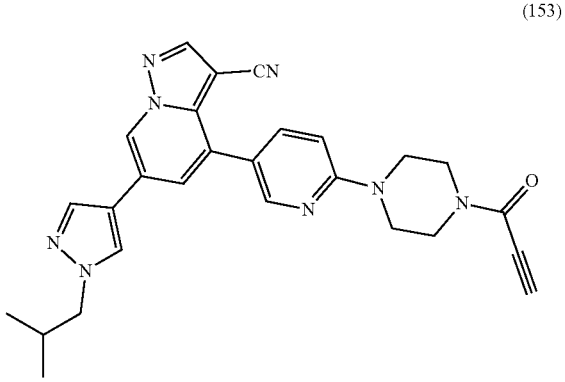
(154)
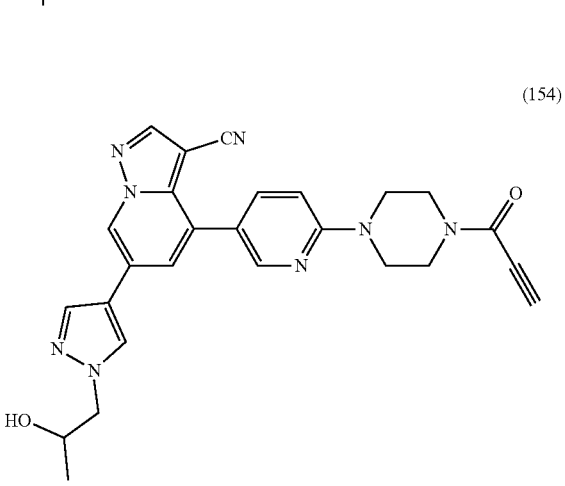
(155)
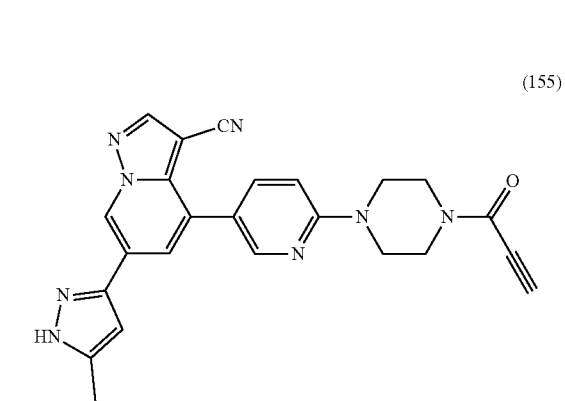

(156)
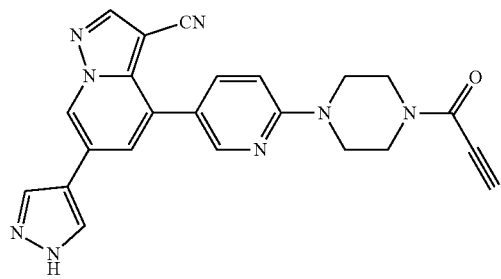
(157)
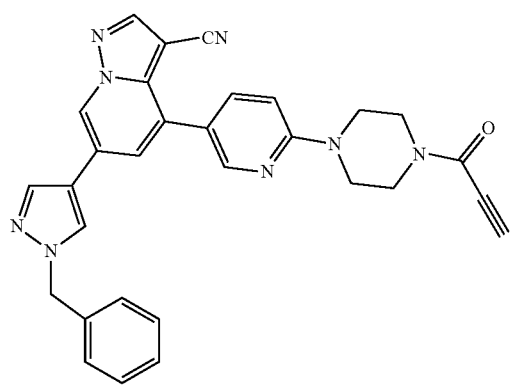
(158)
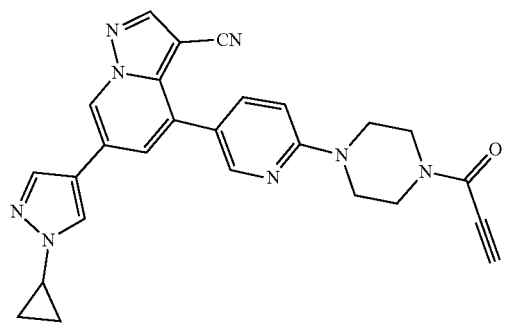
(159)
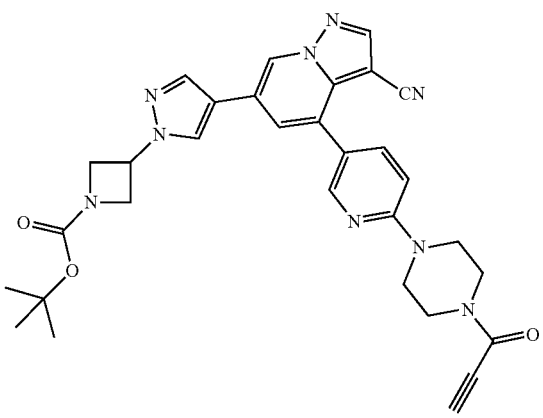
(160)
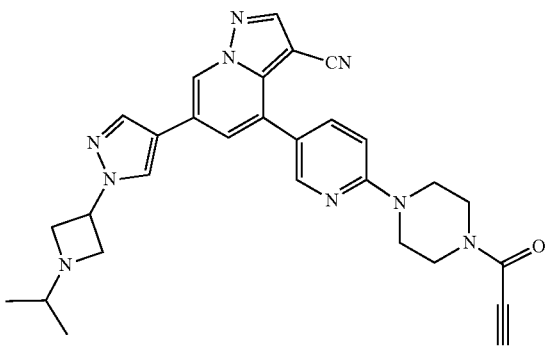
(161)
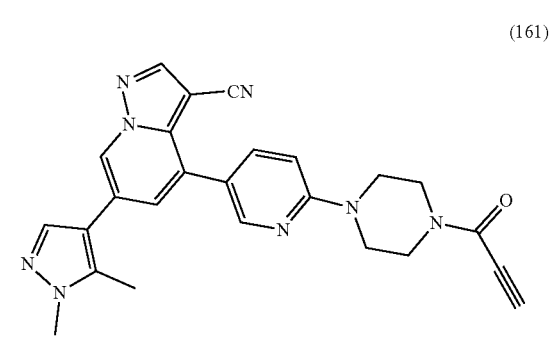
(162)
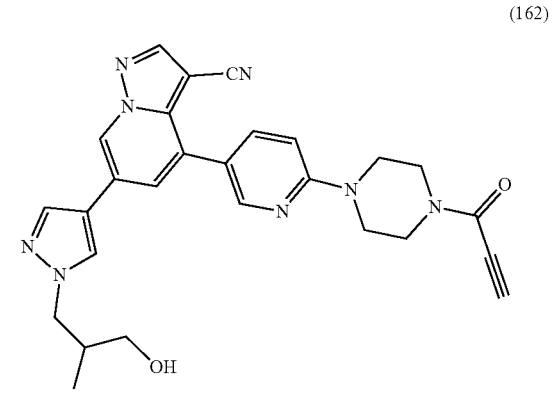
(163)
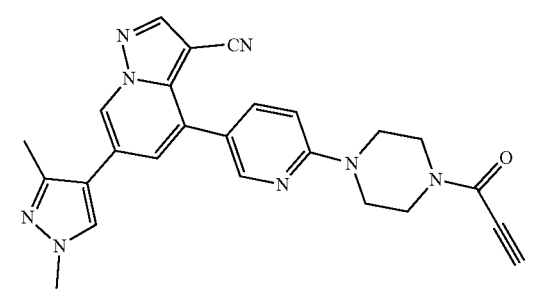

(164)
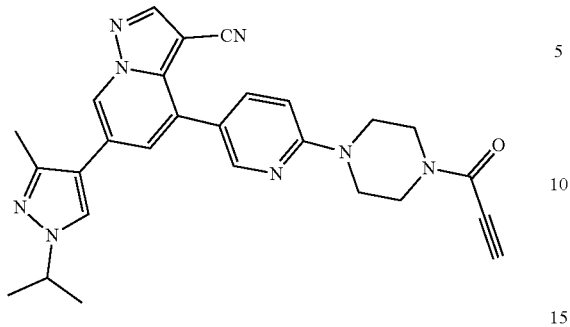
(165)
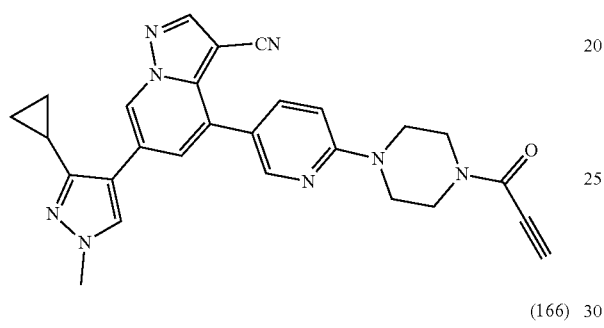
(166)
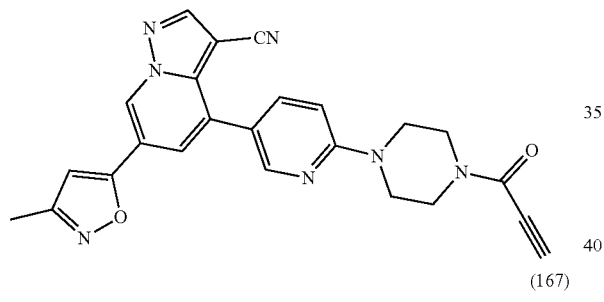
(167)
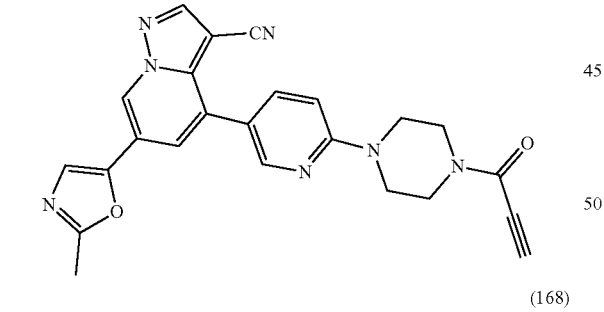
(168)
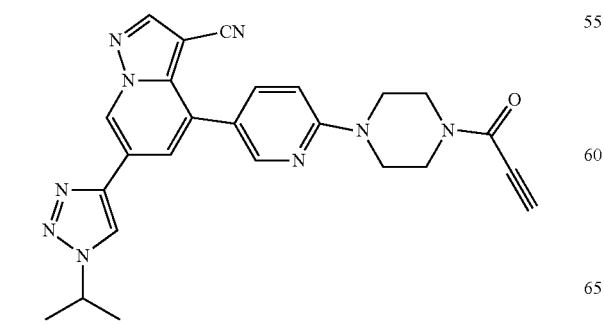
(169)
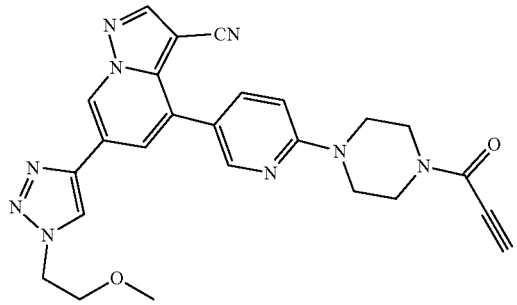
(170)
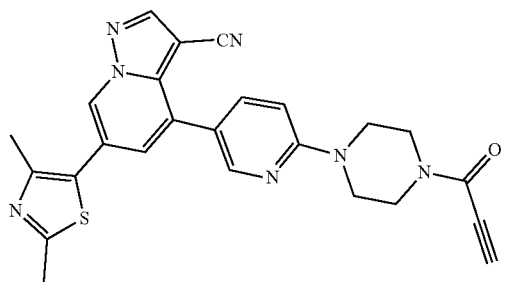
(171)
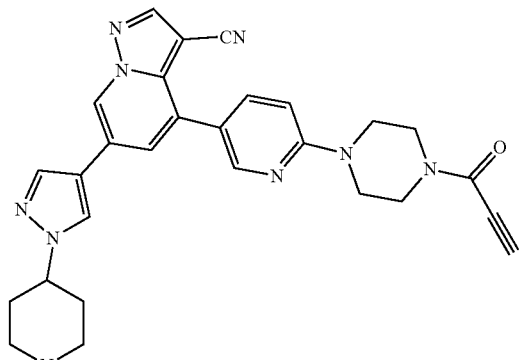
(172)
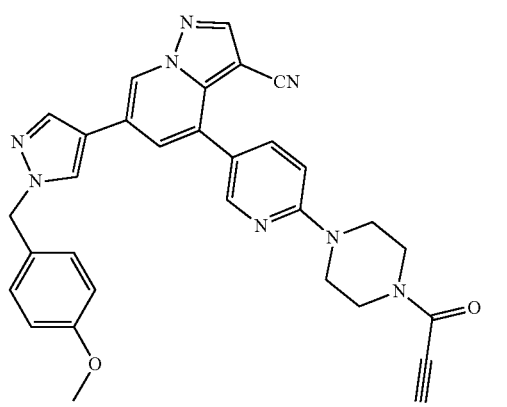

-continued
(173)
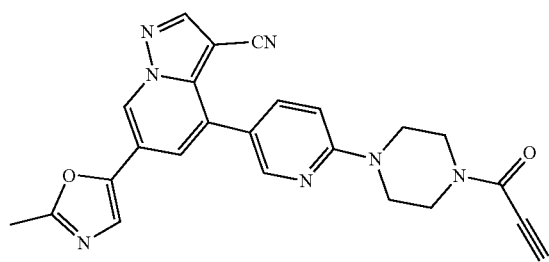
(174)
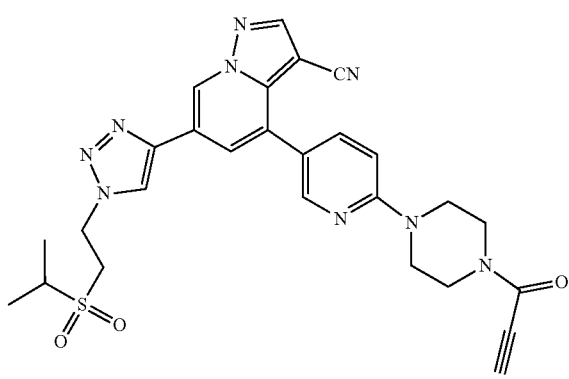
(175)
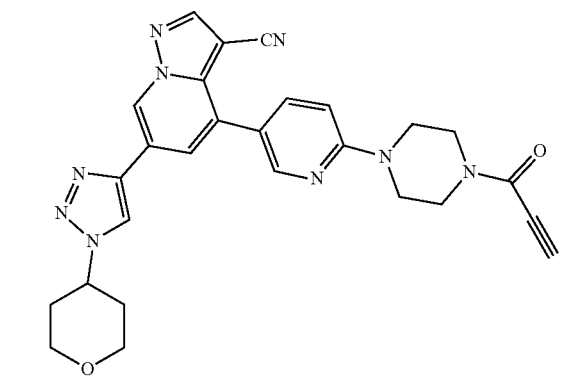
(176)
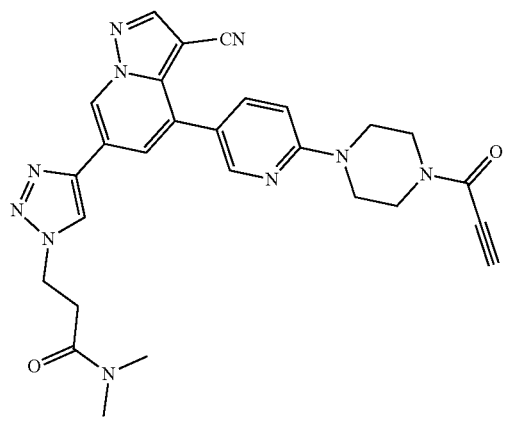
-continued
(177)
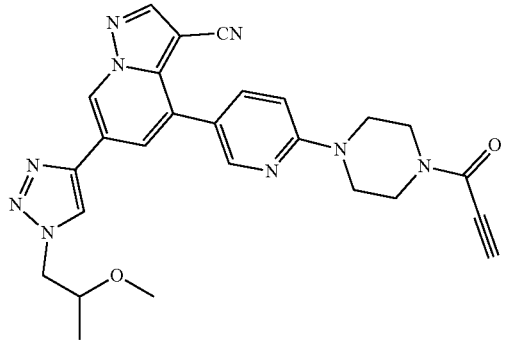
(178)
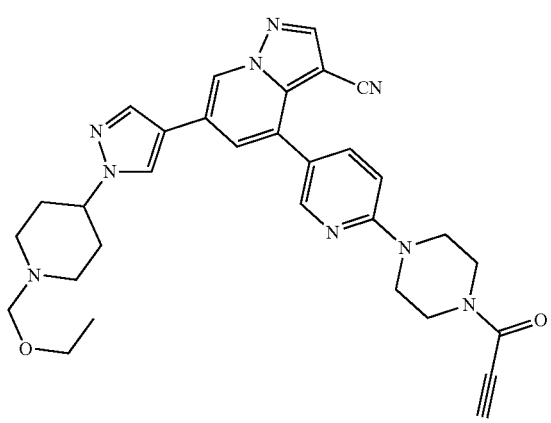
(179)
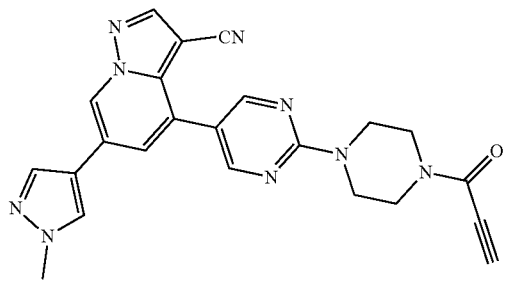
(180)
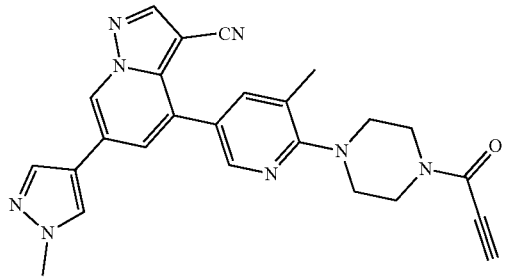

(181)
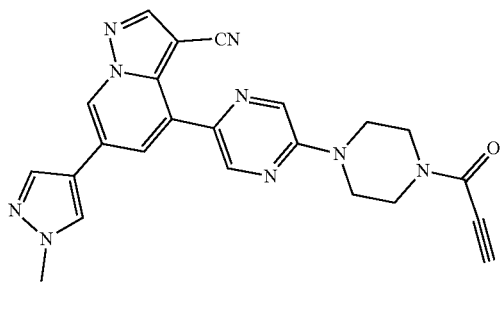
(182)
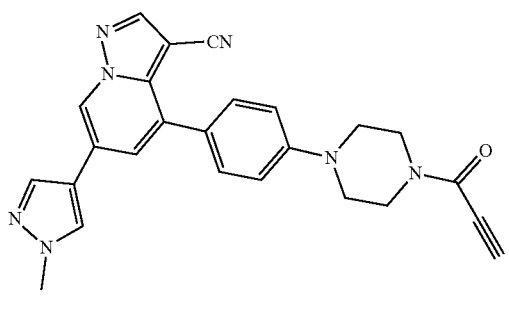
(183)
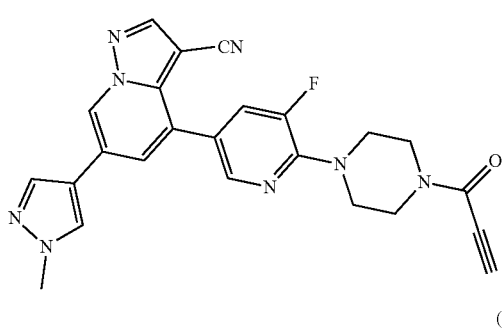
(184)
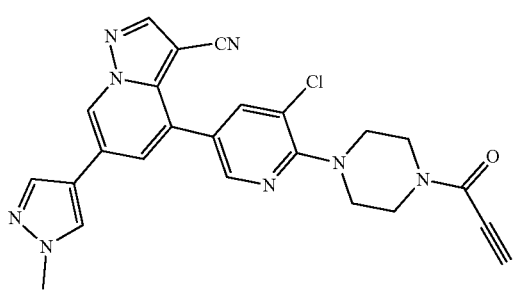
(185)
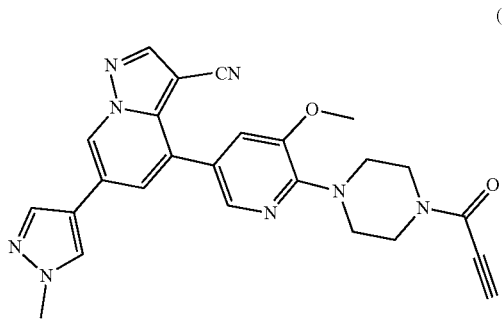
(186)
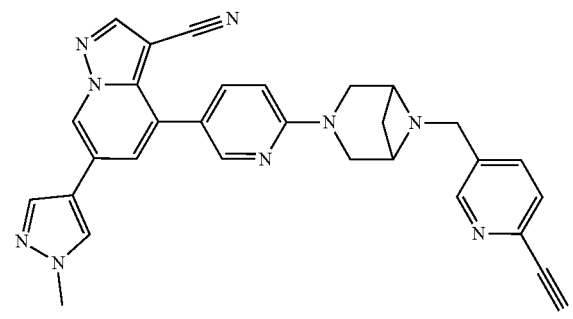
(187)
(188)
(189)
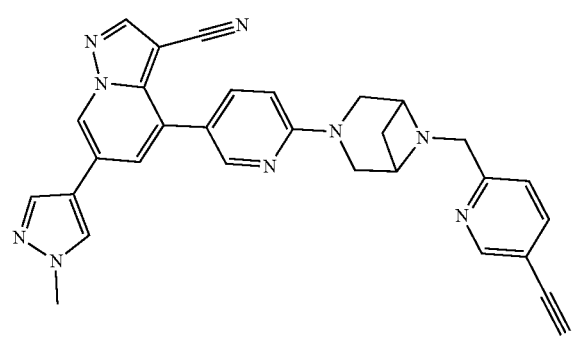

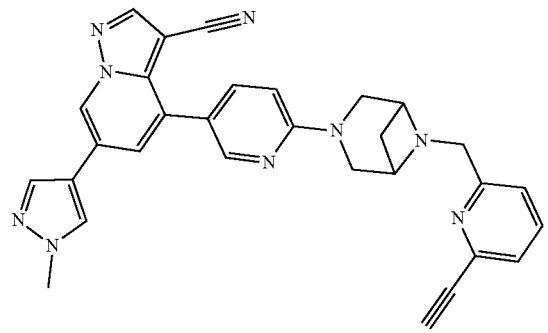
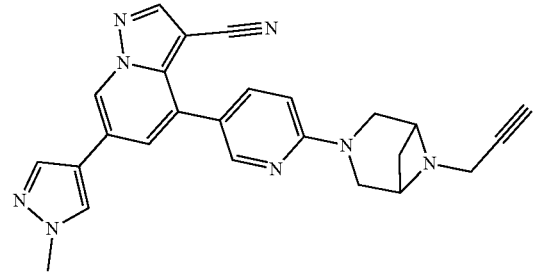
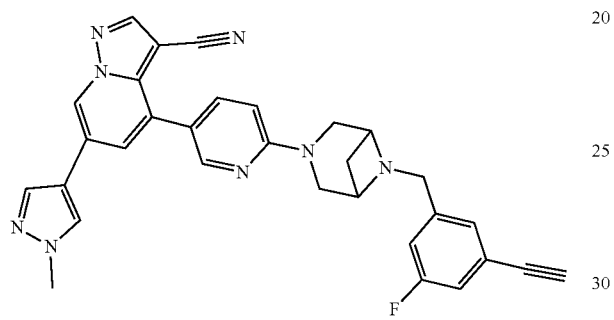
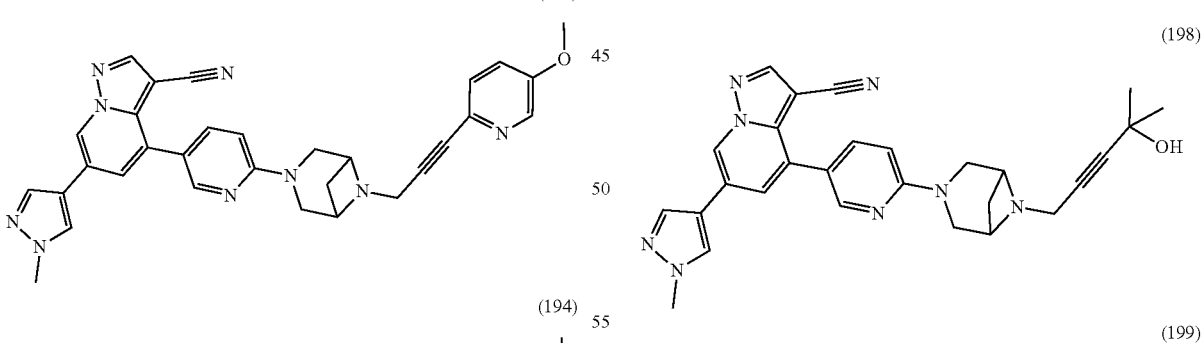
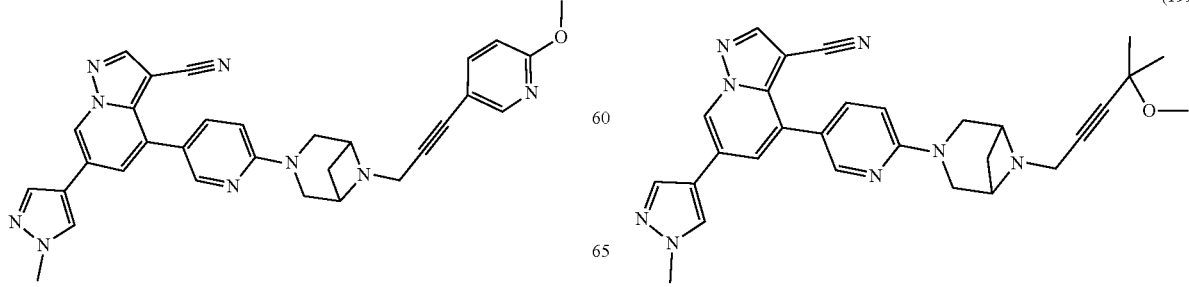

(200)
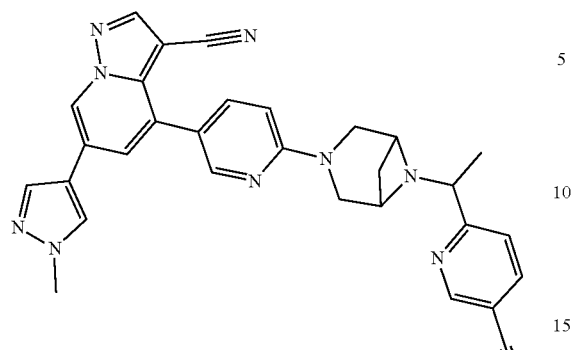
(201)
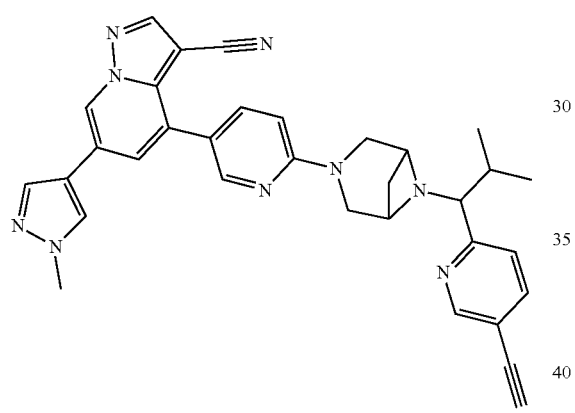
(202)
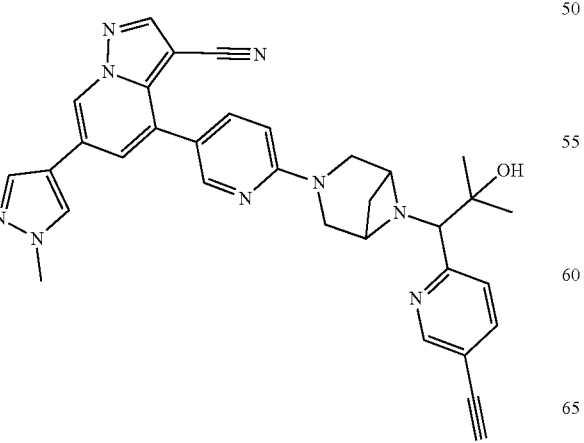
(203)
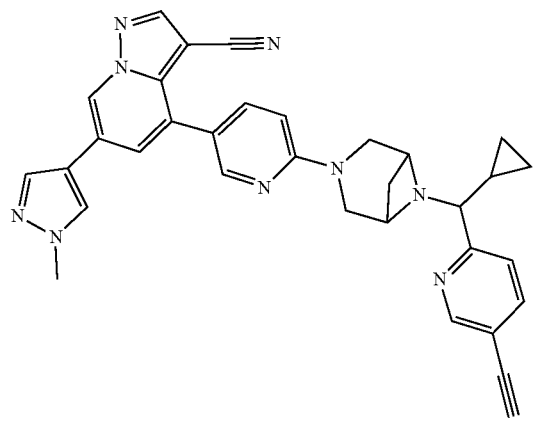
(204)
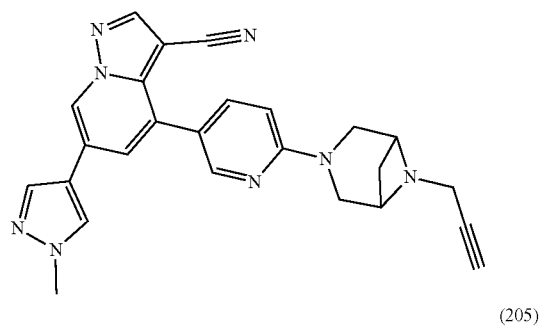
(205)
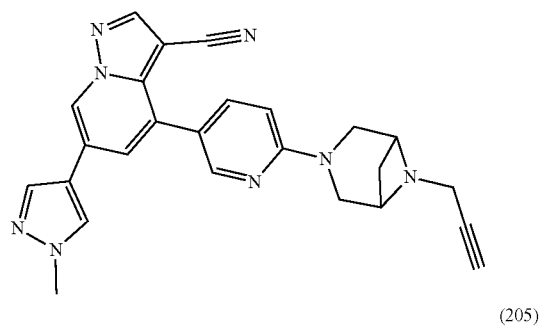
(206)
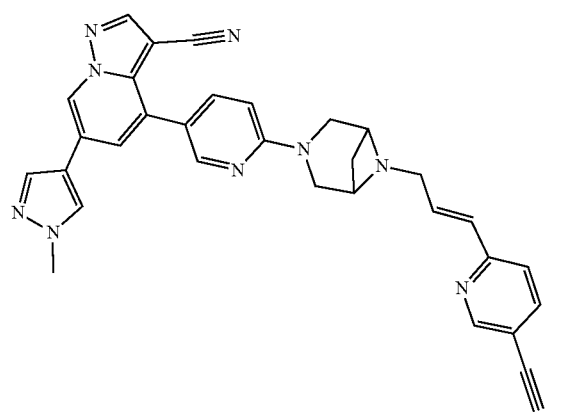

443
-continued
(207)
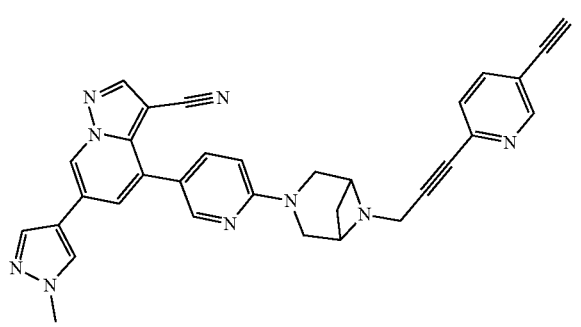
(208)
(210)
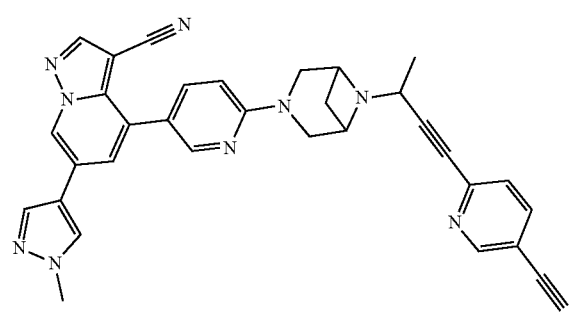
(211)
(212)
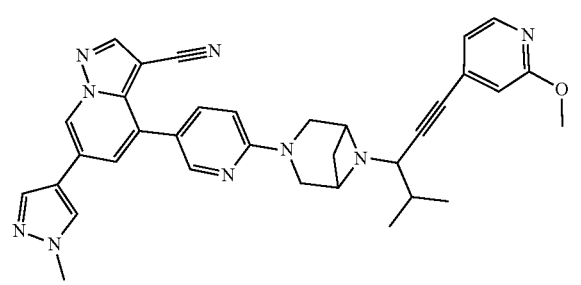
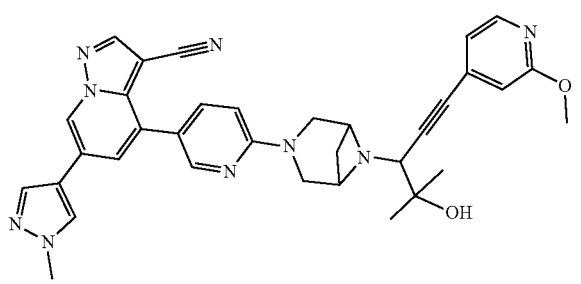
444
-continued
(213)
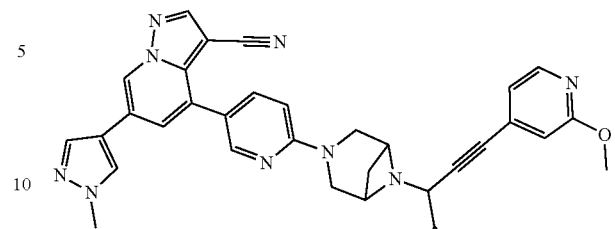
(214)
(215)
(216)
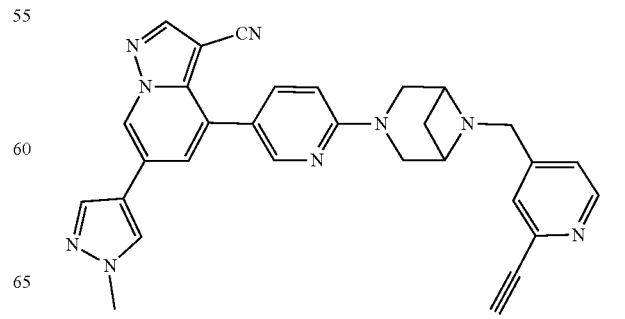
(217)

-continued
(218)
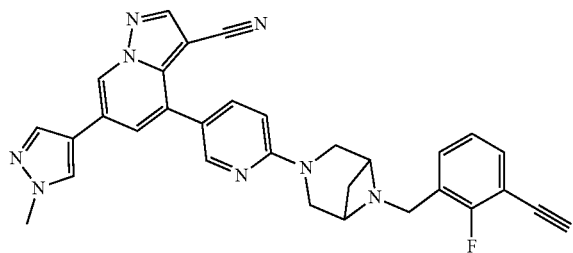
(219)
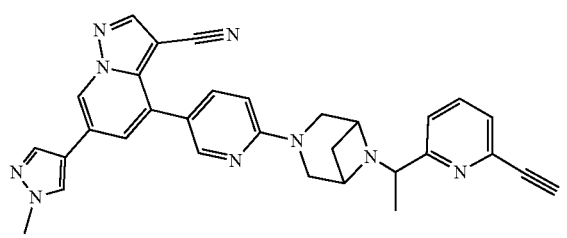
(220)
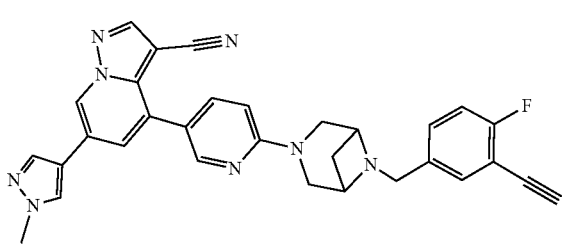
(221)
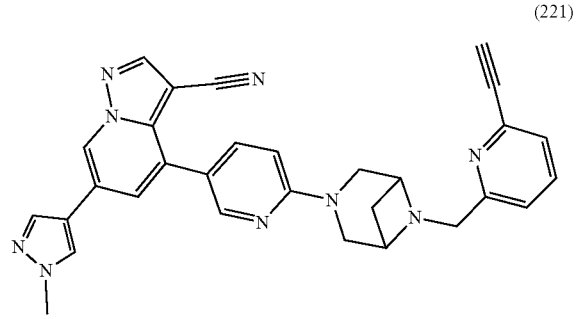
(222)
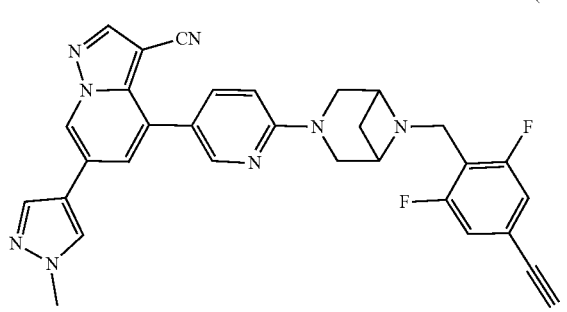
-continued
(223)
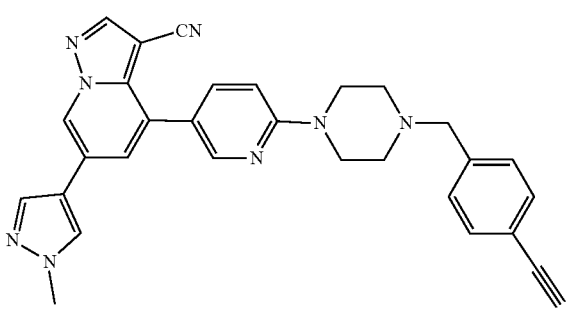
(224)
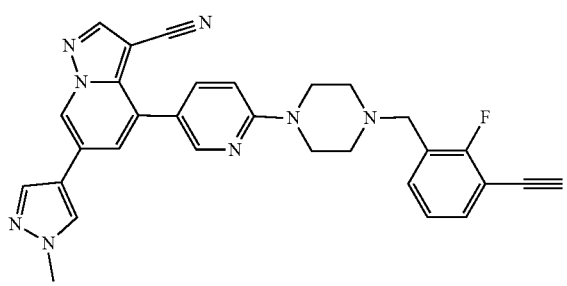
(225)
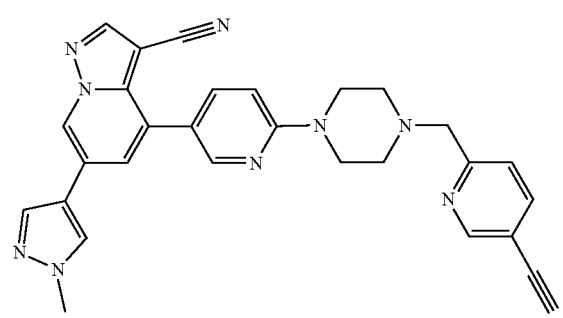
(226)
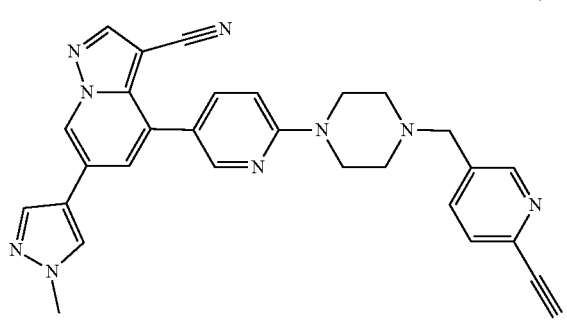
(227)
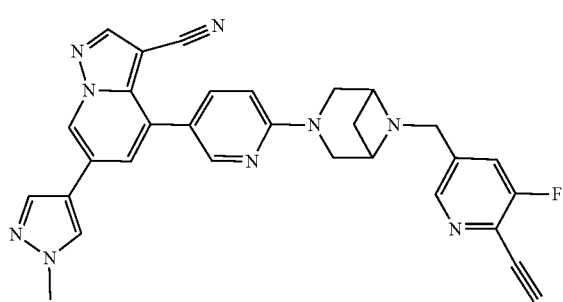

-continued
(228)
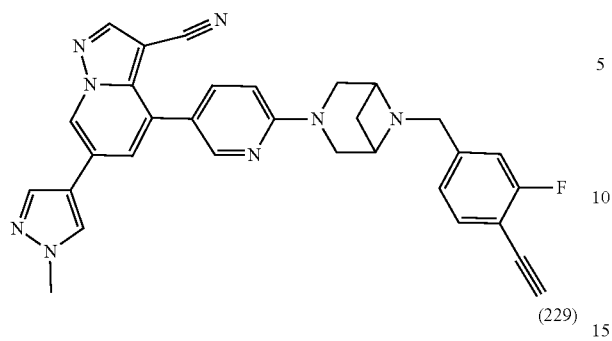
(229)
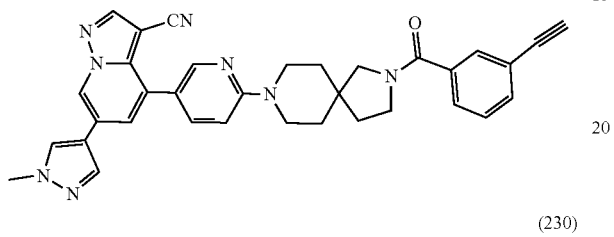
(230)
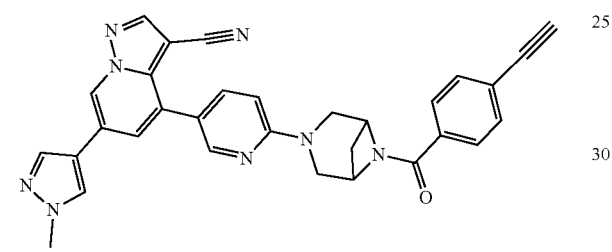
(231)
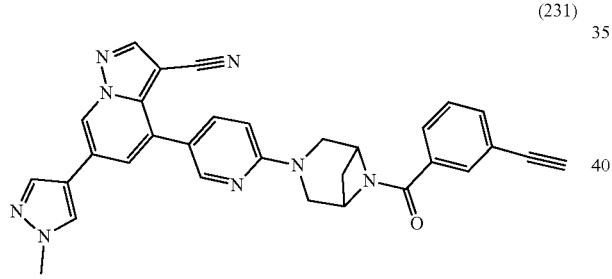
(232)
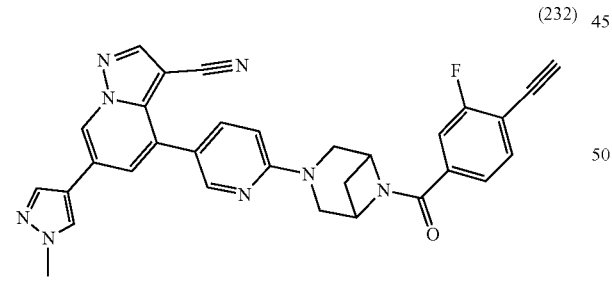
(233)
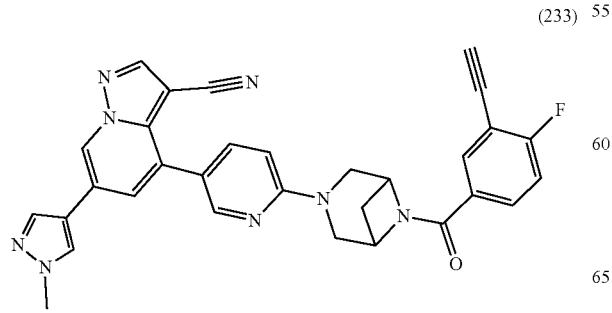
-continued
(234)
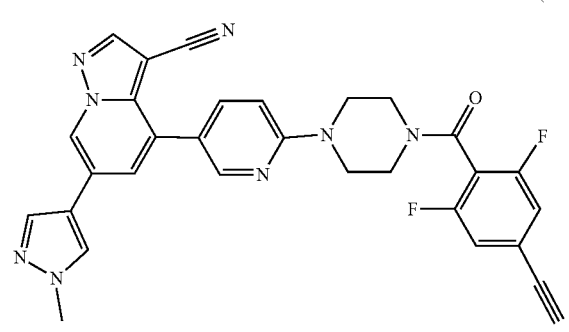
(235)
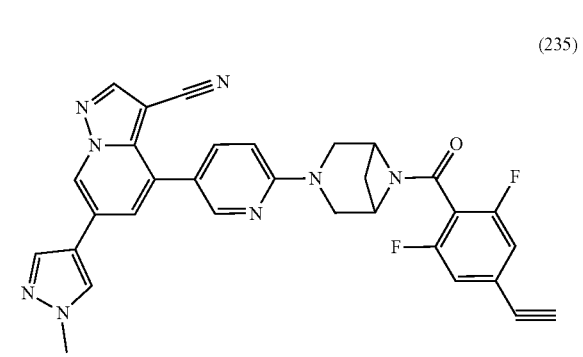
(236)
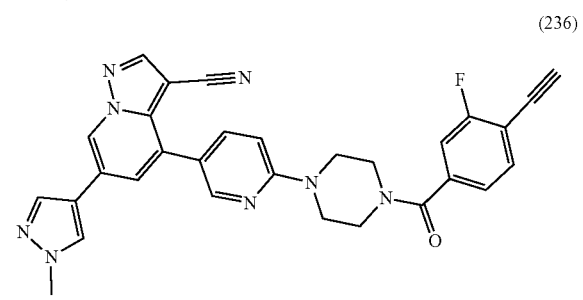
(237)
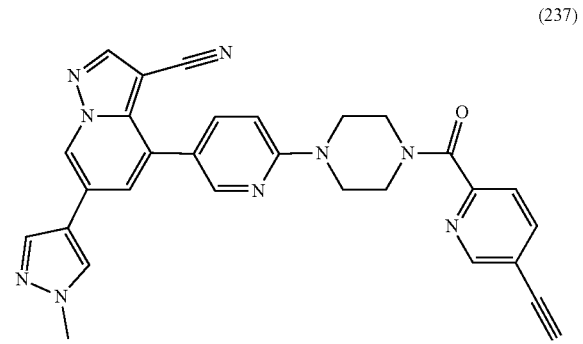
(238)
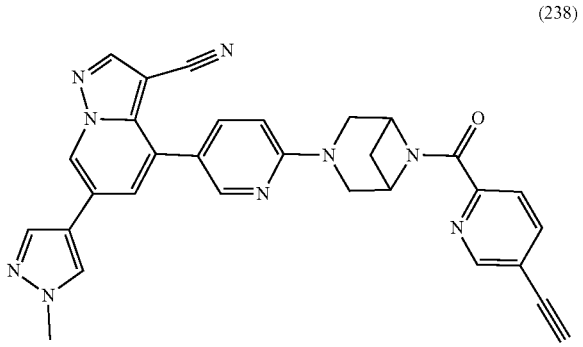

449
-continued
(239)
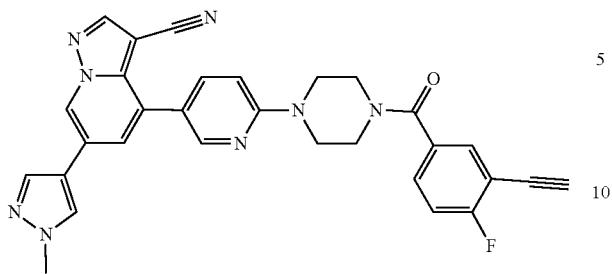
(240)
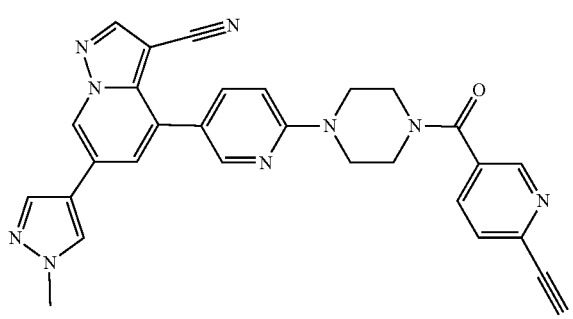
(241)
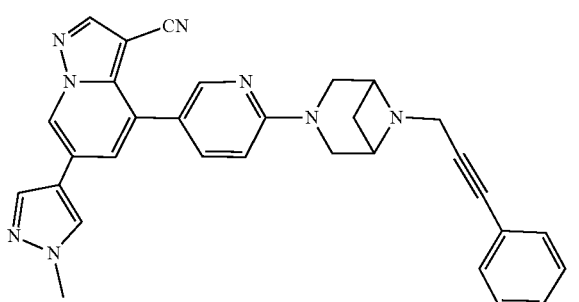
(242)
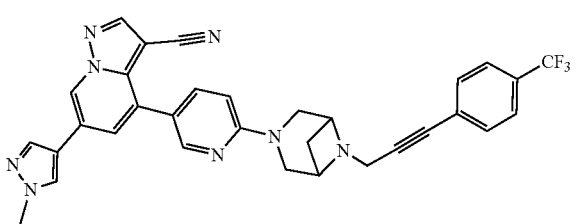
(243)
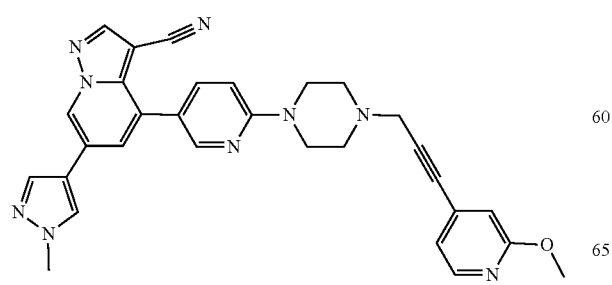
450
-continued
(244)
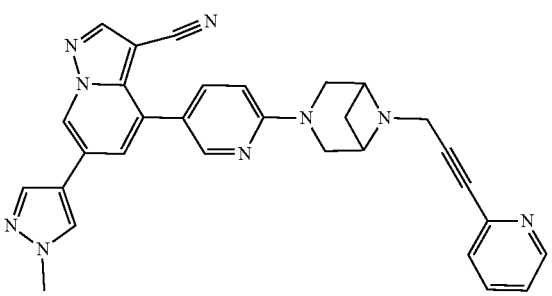
(245)
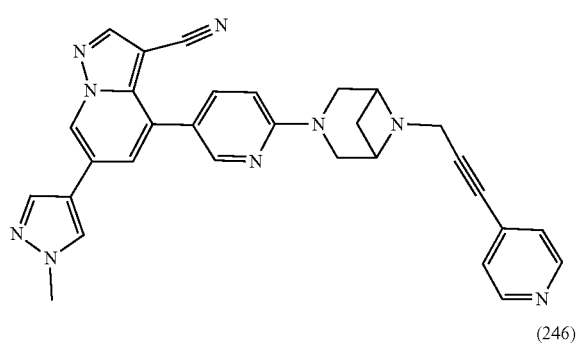
(246)
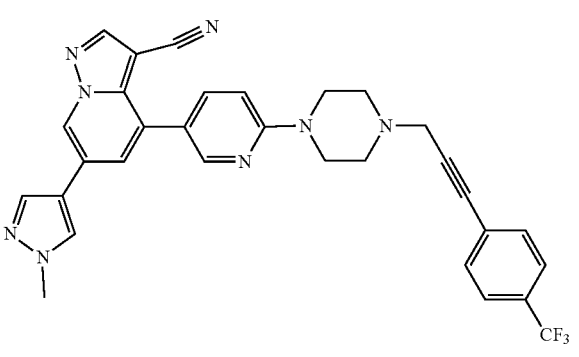
(247)
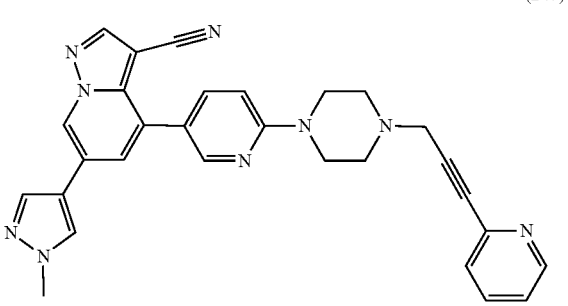
(248)
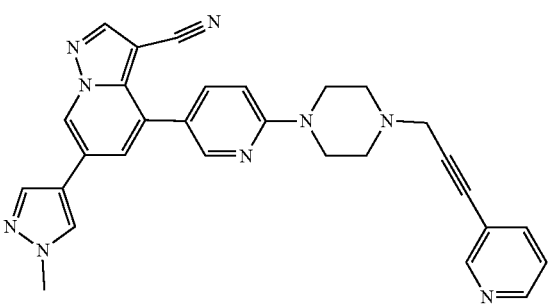

(249)
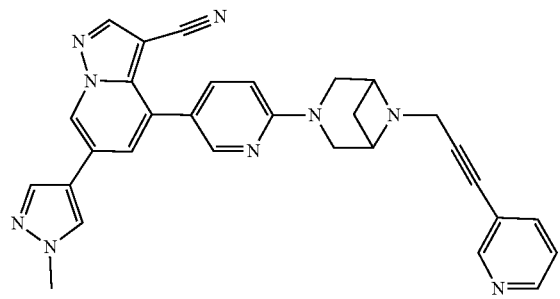
(250)
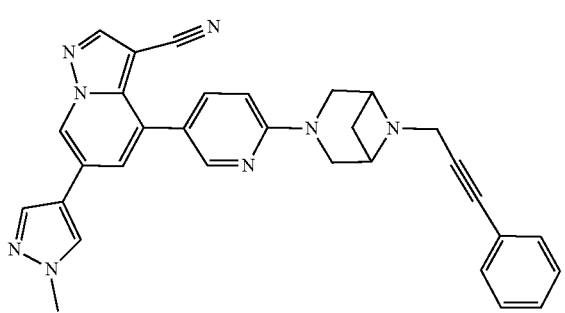
(251)
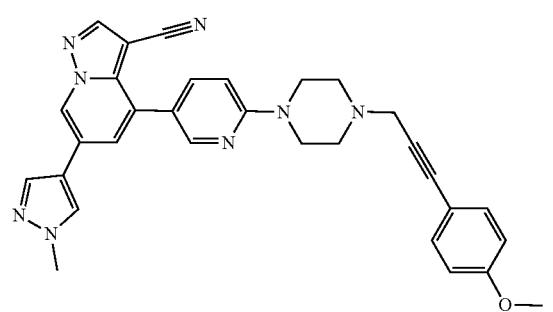
(252)
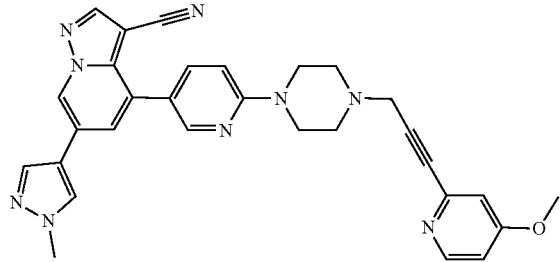
(253)
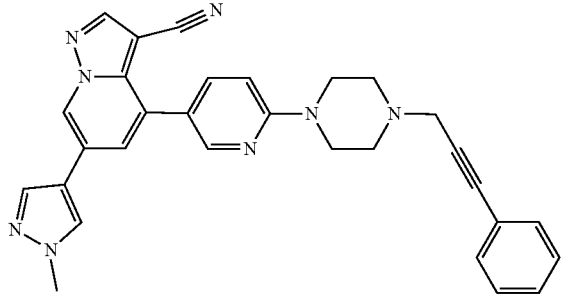
(254)
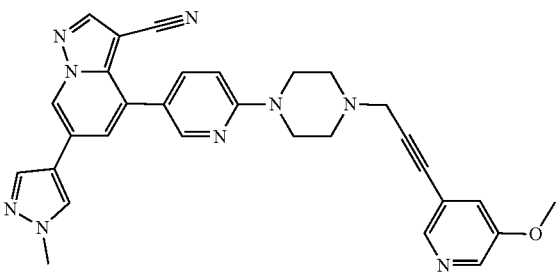
(255)
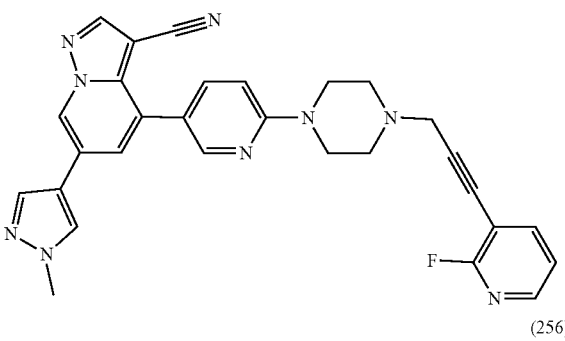
(256)
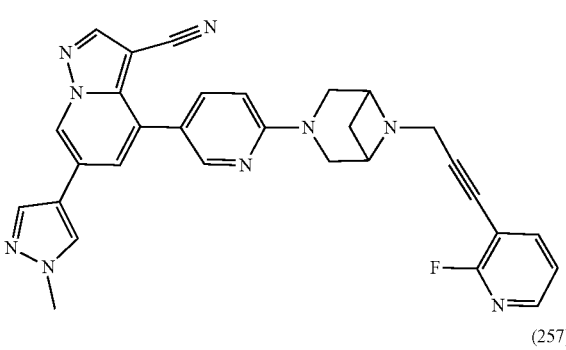
(257)
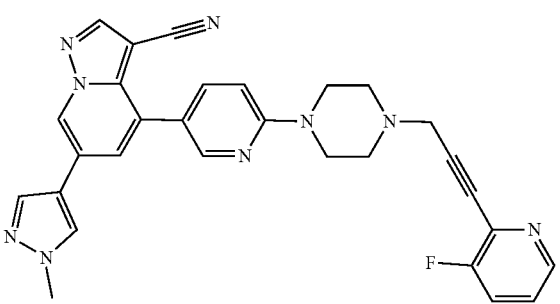
(258)
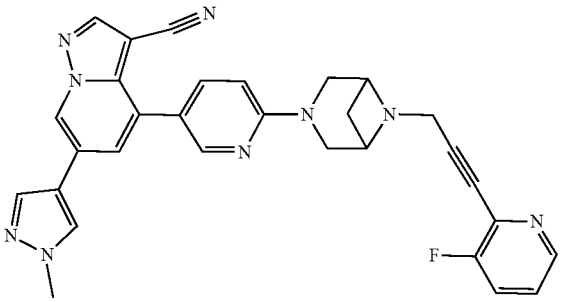

(259)
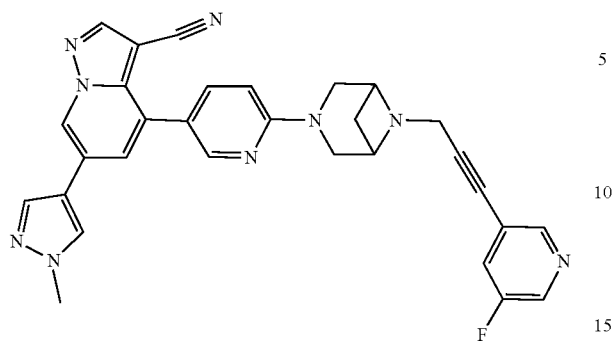
(263)
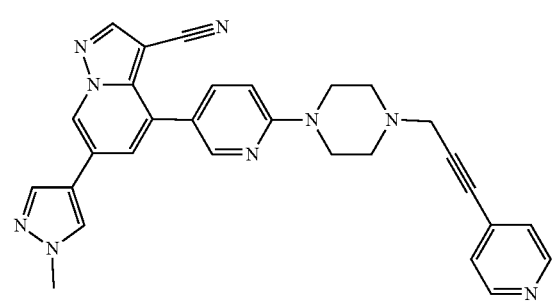
(260)
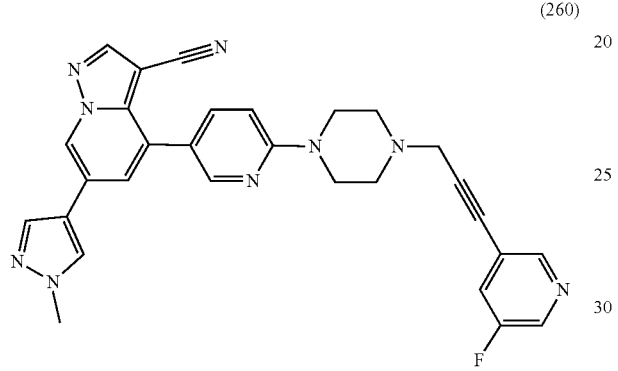
(264)
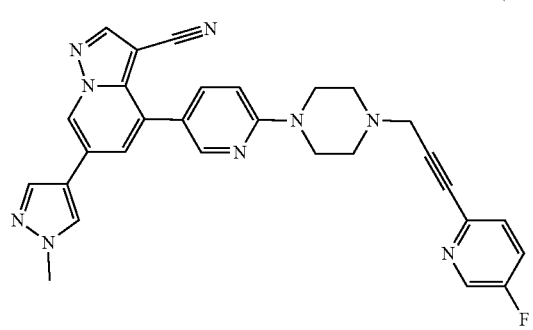
(261)
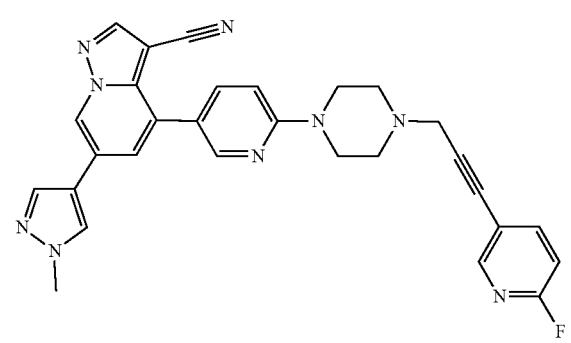
(265)
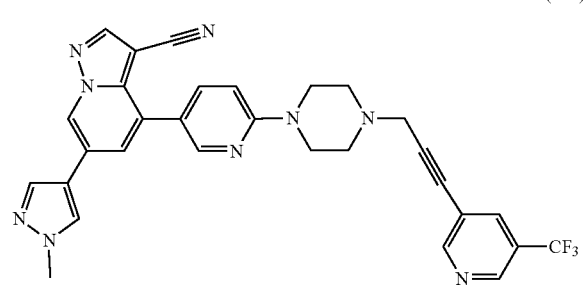
(262)
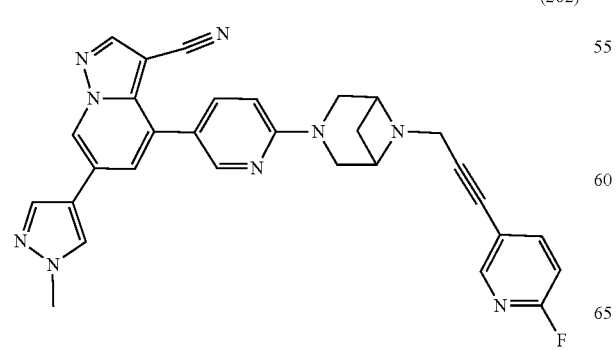
(266)
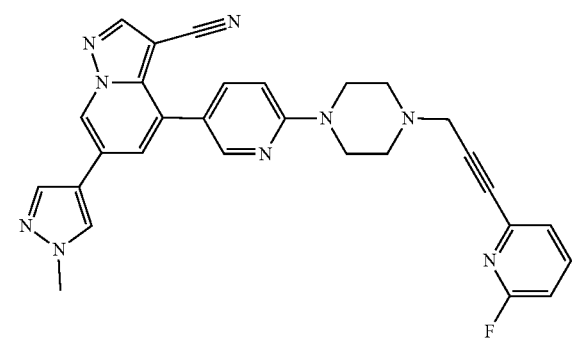

(267)
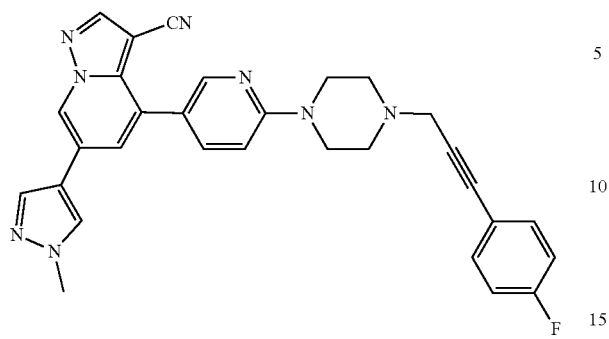
(272)
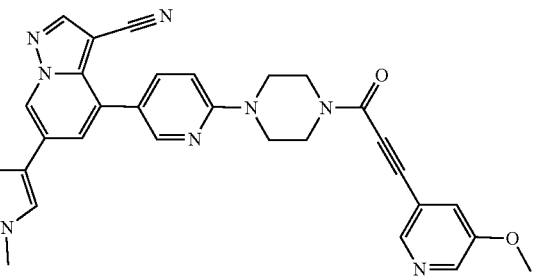
(268)
(273)
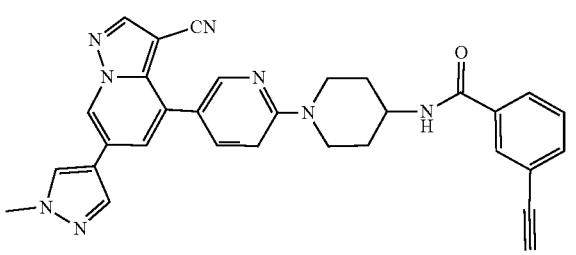
(269)
(274)
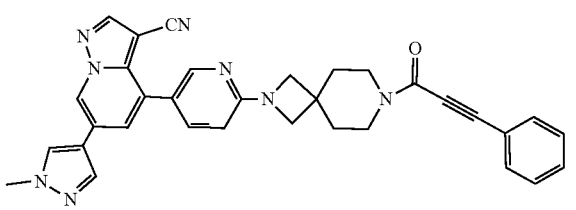
(270)
(275)
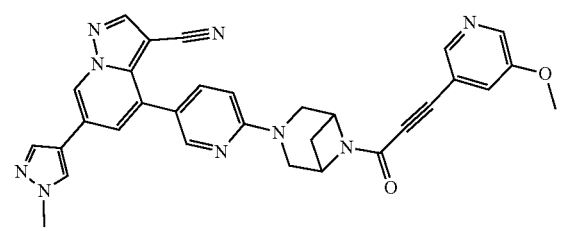
(271)
(276)
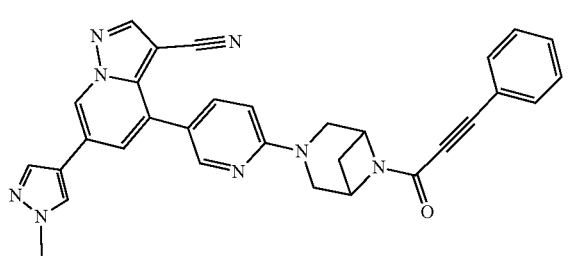

457
-continued
(277)
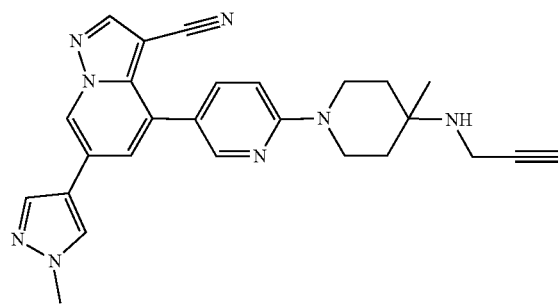
(278)
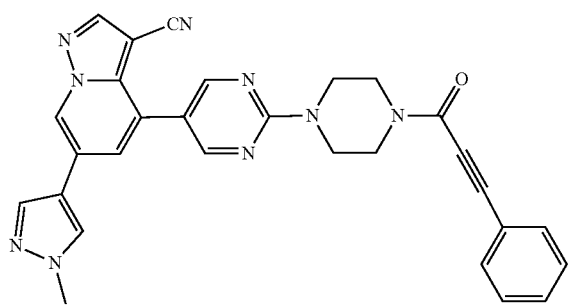
(279)
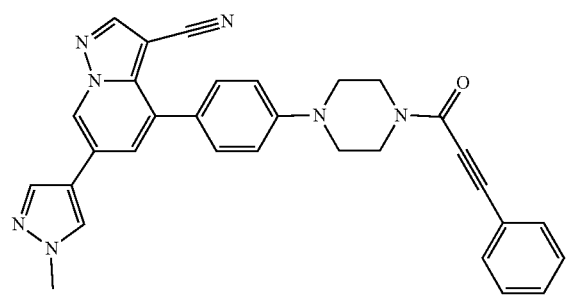
(280)
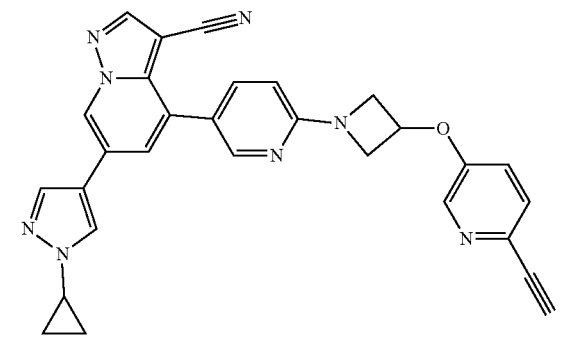
458
-continued
(281)
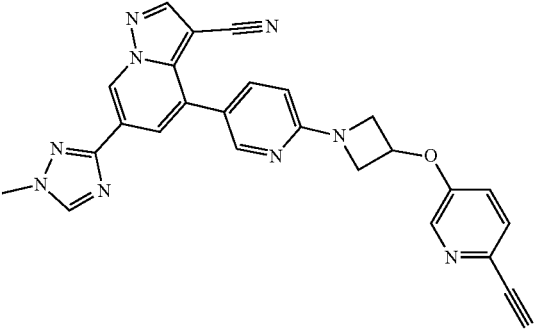
(282)
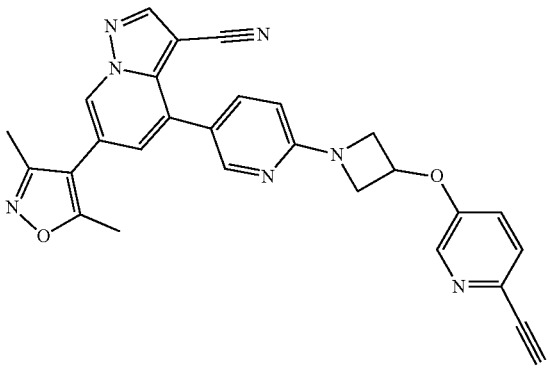
(283)
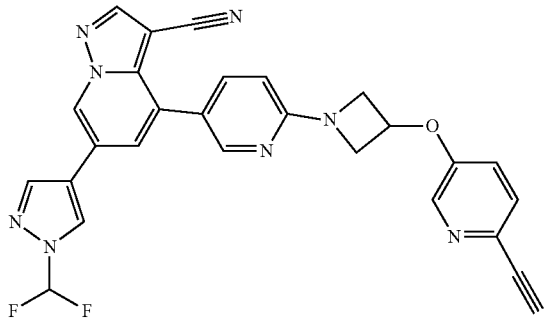
(284)
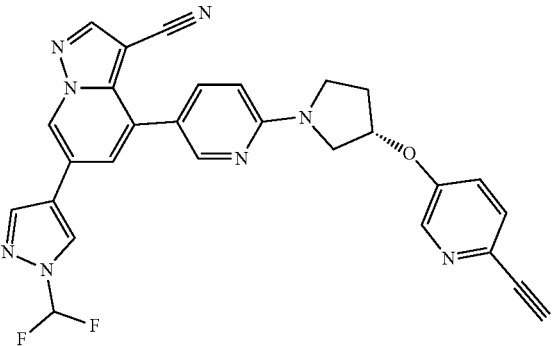

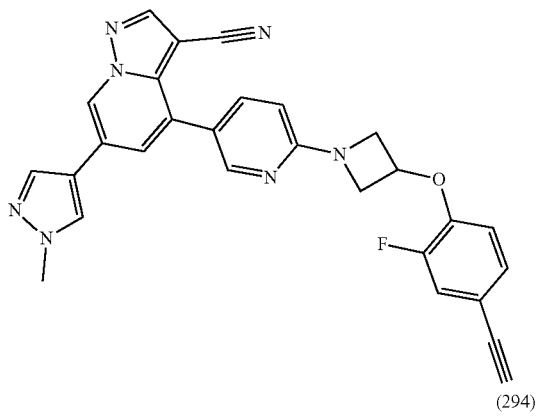

17. A pharmaceutical composition comprising the compound of claim 1 and pharmaceutically acceptable adjuvants.

18. A method of treating non-s mall cell lung cancer or thyroid cancer, the method comprising:
administering to a patient a therapeutically effective amount of the compound of claim 1.

19. A method of treating non-small cell lung cancer or thyroid cancer, the method comprising:
administering to a patient a therapeutically effective amount of the pharmaceutical composition of claim 17.

* * * * *